United States Patent
Wang et al.

(10) Patent No.: US 9,296,741 B2
(45) Date of Patent: Mar. 29, 2016

(54) BROMODOMAIN INHIBITORS

(71) Applicant: AbbVie Inc., North Chicago, IL (US)

(72) Inventors: Le Wang, Vernon Hills, IL (US); John K Pratt, Kenosha, WI (US); Keith F McDaniel, Wauconda, IL (US); Yujia Dai, Gurnee, IL (US); Steven D Fidanze, Grayslake, IL (US); Lisa Hasvold, Grayslake, IL (US); James H Holms, Gurnee, IL (US); Warren M Kati, Gurnee, IL (US); Dachun Liu, Vernon Hills, IL (US); Robert A Mantei, Franklin, WI (US); William J McClellan, Waukegan, IL (US); George S Sheppard, Wilmette, IL (US); Carol K Wada, Evanston, IL (US)

(73) Assignee: AbbVie Inc., North Chicago, IL (US)

( * ) Notice: Subject to any disclaimer, the term of this patent is extended or adjusted under 35 U.S.C. 154(b) by 11 days.

(21) Appl. No.: 13/828,285

(22) Filed: Mar. 14, 2013

(65) Prior Publication Data

US 2014/0162971 A1 Jun. 12, 2014

Related U.S. Application Data

(63) Continuation of application No. PCT/CN2012/086357, filed on Dec. 11, 2012.

(51) Int. Cl.
| | | |
|---|---|---|
| C07D 471/04 | (2006.01) | |
| C07D 487/04 | (2006.01) | |
| A61K 31/437 | (2006.01) | |
| A61K 31/5377 | (2006.01) | |
| A61K 31/541 | (2006.01) | |
| A61K 31/5025 | (2006.01) | |
| A61K 45/06 | (2006.01) | |

(52) U.S. Cl.
CPC ............ *C07D 471/04* (2013.01); *A61K 31/437* (2013.01); *A61K 31/5025* (2013.01); *A61K 31/5377* (2013.01); *A61K 31/541* (2013.01); *A61K 45/06* (2013.01); *C07D 487/04* (2013.01)

(58) Field of Classification Search
CPC .. C07D 471/04; C07D 487/04; A61K 31/437; A61K 31/5377; A61K 31/541; A61K 31/5025; A61K 45/06
USPC .................. 514/49, 210.21, 228.2, 234.5, 43; 544/127, 236; 546/113
See application file for complete search history.

(56) References Cited

U.S. PATENT DOCUMENTS

| | | | |
|---|---|---|---|
| 4,004,012 A | 1/1977 | Lesher et al. | |
| 4,072,746 A | 2/1978 | Lesher et al. | |
| 4,093,812 A | 6/1978 | Rainer | |
| 4,107,315 A | 8/1978 | Lesher et al. | |
| 4,137,233 A | 1/1979 | Lesher et al. | |
| 4,199,586 A | 4/1980 | Lesher et al. | |
| 4,225,715 A | 9/1980 | Lesher et al. | |
| 4,289,774 A | 9/1981 | Schacht et al. | |
| 4,298,609 A | 11/1981 | Lesher et al. | |
| 4,304,776 A | 12/1981 | Lesher et al. | |
| 4,305,943 A | 12/1981 | Lesher et al. | |
| 4,337,253 A | 6/1982 | Lesher et al. | |
| 4,338,446 A | 7/1982 | Lesher et al. | |
| 4,346,221 A | 8/1982 | Lesher et al. | |
| 4,353,905 A | 10/1982 | Sircar et al. | |

(Continued)

FOREIGN PATENT DOCUMENTS

| | | | |
|---|---|---|---|
| DE | 10010423 A1 | 9/2001 | |
| EP | 0010156 A1 | 4/1980 | |

(Continued)

OTHER PUBLICATIONS

Banerjee C., et al., "BET Bromodomain Inhibition as a Novel Strategy for Reactivation of HIV-1," Journal of Leukocyte Biology, 2012, vol. 92 (6), pp. 1147-1154.
Best O.G., et al., "The Novel Hsp-90 Inhibitor SNX7081 is Significantly More Potent than 17-AAG Against Primary CLL Cells and a Range of Haematological Cell Lines, Irrespective of Lesions in the TP53 Pathway," British Journal of Haematalogy, 2010, vol. 151 (2), pp. 185-188.
Chandarlapaty S., et al., "SNX2112, A Synthetic Heat Shock Protein 90 Inhibitor, has Potent Antitumor Activity against HER Kinase-Dependent Cancers," Clinical Cancer Research, 2008, vol. 14 (1), pp. 240-248.
Chung C.W., et al., "Discovery and Characterization of Small Molecule Inhibitors of the BET Family Bromodomains," Journal of Medicinal Chemistry, 2011, vol. 54 (11), pp. 3827-3838.

(Continued)

*Primary Examiner* — Mark Shibuya
*Assistant Examiner* — Yih-Horng Shiao
(74) *Attorney, Agent, or Firm* — Glen J. Gesicki

(57) ABSTRACT

The present invention provides for compounds of formula (I)

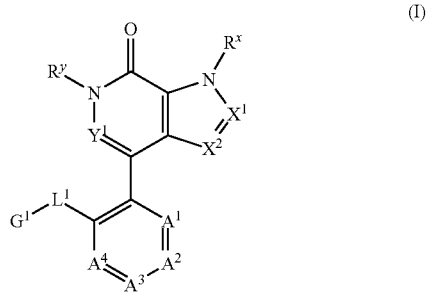

(I)

wherein $A^1$, $A^2$, $A^3$, $A^4$, $X^1$, $X^2$, $Y^1$, $L^1$, $G^1$, $R^x$, and $R^y$ have any of the values defined thereof in the specification, and pharmaceutically acceptable salts thereof, that are useful as agents in the treatment of diseases and conditions, including inflammatory diseases, cancer, and AIDS. Also provided are pharmaceutical compositions comprising one or more compounds of formula (I).

61 Claims, No Drawings

(56) References Cited

U.S. PATENT DOCUMENTS

| | | |
|---|---|---|
| 4,397,854 A | 8/1983 | Sircar |
| 4,404,203 A | 9/1983 | Sircar |
| 4,465,686 A | 8/1984 | Lesher et al. |
| 4,486,431 A | 12/1984 | Lesher et al. |
| 4,515,797 A | 5/1985 | Lesher et al. |
| 4,559,352 A | 12/1985 | Lesher et al. |
| 4,599,423 A | 7/1986 | Lesher et al. |
| 4,643,998 A | 2/1987 | Hilboll et al. |
| 4,666,902 A | 5/1987 | Zoller et al. |
| 4,667,033 A | 5/1987 | Hilboll et al. |
| 4,678,786 A | 7/1987 | Roe et al. |
| 4,734,415 A | 3/1988 | Sircar et al. |
| 4,816,454 A | 3/1989 | Zoller et al. |
| 4,820,819 A | 4/1989 | Roe et al. |
| 4,863,745 A | 9/1989 | Zibell |
| 4,919,941 A | 4/1990 | Zibell |
| 5,112,625 A | 5/1992 | Zibell et al. |
| 5,192,563 A | 3/1993 | Patel et al. |
| 5,217,735 A | 6/1993 | Zibell |
| 5,221,543 A | 6/1993 | Zibell et al. |
| 5,385,925 A | 1/1995 | Narr et al. |
| 5,401,738 A | 3/1995 | Mederski et al. |
| 5,418,233 A | 5/1995 | Linz et al. |
| 5,455,348 A | 10/1995 | Austel et al. |
| 5,466,697 A | 11/1995 | Wilhelm et al. |
| 5,552,409 A | 9/1996 | Michelotti et al. |
| 5,563,268 A | 10/1996 | Linz et al. |
| 5,587,393 A | 12/1996 | Narr et al. |
| 5,631,254 A | 5/1997 | Michelotti et al. |
| 5,635,494 A | 6/1997 | Ross et al. |
| 5,668,279 A | 9/1997 | Chakravarty et al. |
| 5,684,029 A | 11/1997 | Narr et al. |
| 5,698,554 A | 12/1997 | Ishida et al. |
| 5,716,954 A | 2/1998 | Wilhelm et al. |
| 5,726,162 A | 3/1998 | Michelotti et al. |
| 5,726,176 A | 3/1998 | Michelotti et al. |
| 5,728,694 A | 3/1998 | Michelotti et al. |
| 5,728,698 A | 3/1998 | Michelotti et al. |
| 5,728,715 A | 3/1998 | Michelotti et al. |
| 5,741,793 A | 4/1998 | Young et al. |
| 5,753,642 A | 5/1998 | Michelotti et al. |
| 5,763,440 A | 6/1998 | Ross et al. |
| 5,808,065 A | 9/1998 | Ishida et al. |
| 5,814,651 A | 9/1998 | Duplantier et al. |
| 5,855,654 A | 1/1999 | Willingham et al. |
| 5,935,961 A | 8/1999 | Ross et al. |
| 5,958,925 A | 9/1999 | Ross et al. |
| 6,143,751 A | 11/2000 | Cheshire et al. |
| 6,245,804 B1 | 6/2001 | Lehmann et al. |
| 6,271,380 B1 | 8/2001 | Gilligan et al. |
| 6,307,047 B1 | 10/2001 | Black et al. |
| 6,344,454 B1 | 2/2002 | Lehmann et al. |
| 6,348,468 B1 | 2/2002 | Ohkuchi et al. |
| 6,403,586 B1 | 6/2002 | Ohkuchi et al. |
| 6,420,367 B1 | 7/2002 | Ueda et al. |
| 6,518,271 B1 | 2/2003 | Gilligan et al. |
| 6,548,534 B2 | 4/2003 | Lehmann et al. |
| 7,001,895 B2 | 2/2006 | Black et al. |
| 7,115,591 B2 | 10/2006 | Black et al. |
| 7,132,424 B2 | 11/2006 | Picard |
| 7,226,920 B2 | 6/2007 | Arnost et al. |
| 7,273,877 B2 | 9/2007 | Black et al. |
| 7,435,735 B2 | 10/2008 | Wai et al. |
| 7,459,453 B2 | 12/2008 | Dal Piaz et al. |
| 7,595,316 B2 | 9/2009 | Ohtake et al. |
| 7,598,245 B2 | 10/2009 | Arnost et al. |
| 7,838,523 B2 | 11/2010 | Blomgren et al. |
| 7,884,108 B2 | 2/2011 | Blomgren et al. |
| 7,915,267 B2 | 3/2011 | Nara et al. |
| 7,943,618 B2 | 5/2011 | Dewdney et al. |
| 7,994,325 B2 | 8/2011 | Paone et al. |
| 2002/0013318 A1 | 1/2002 | Black et al. |
| 2002/0016365 A1 | 2/2002 | Lehmann et al. |
| 2002/0028938 A1 | 3/2002 | Black et al. |
| 2002/0099055 A1 | 7/2002 | Bantick et al. |
| 2002/0123496 A1 | 9/2002 | Ohkuchi et al. |
| 2003/0203902 A1 | 10/2003 | Lehmann et al. |
| 2003/0225276 A1 | 12/2003 | Black et al. |
| 2004/0043979 A1 | 3/2004 | Picard |
| 2004/0063673 A1 | 4/2004 | Johnson |
| 2004/0147516 A1 | 7/2004 | Ohkuchi et al. |
| 2004/0158064 A1 | 8/2004 | Black et al. |
| 2005/0026964 A1 | 2/2005 | Black et al. |
| 2005/0065155 A1 | 3/2005 | Ohkuchi et al. |
| 2005/0222034 A1 | 10/2005 | Hsu et al. |
| 2005/0261268 A1 | 11/2005 | Arnost et al. |
| 2005/0267113 A1 | 12/2005 | Ohkuchi et al. |
| 2006/0002379 A1 | 1/2006 | Koyama |
| 2006/0160804 A1 | 7/2006 | Ohkuchi et al. |
| 2006/0178375 A1 | 8/2006 | Ohtake et al. |
| 2007/0049595 A1 | 3/2007 | Ohkuchi et al. |
| 2007/0093496 A1 | 4/2007 | Wai et al. |
| 2007/0208025 A1 | 9/2007 | Ohkuchi et al. |
| 2008/0027041 A1 | 1/2008 | Hudkins et al. |
| 2008/0090827 A1 | 4/2008 | Taylor et al. |
| 2008/0096901 A1 | 4/2008 | Arnost et al. |
| 2008/0119457 A1 | 5/2008 | Huang et al. |
| 2008/0119474 A1 | 5/2008 | Ohkuchi et al. |
| 2008/0153834 A1 | 6/2008 | Blomgren et al. |
| 2008/0261972 A1 | 10/2008 | Paone et al. |
| 2008/0269235 A1 | 10/2008 | Dal Piaz et al. |
| 2008/0269287 A1 | 10/2008 | Ohtake et al. |
| 2009/0042888 A1 | 2/2009 | Black et al. |
| 2009/0069332 A1 | 3/2009 | Ohkuchi et al. |
| 2009/0082330 A1 | 3/2009 | Blomgren et al. |
| 2009/0105209 A1 | 4/2009 | Dewdney et al. |
| 2009/0111824 A1 | 4/2009 | Bratt et al. |
| 2009/0137603 A1 | 5/2009 | Nara et al. |
| 2009/0163545 A1 | 6/2009 | Goldfarb |
| 2009/0181983 A1 | 7/2009 | Corte |
| 2009/0270399 A1 | 10/2009 | Ohkuchi et al. |
| 2010/0210637 A1 | 8/2010 | Ohtake et al. |
| 2010/0256363 A1 | 10/2010 | Xu |
| 2010/0273779 A1 | 10/2010 | Bacon et al. |
| 2010/0280007 A1 | 11/2010 | Bacon et al. |
| 2010/0286127 A1 | 11/2010 | Miyoshi et al. |
| 2010/0331320 A1 | 12/2010 | Renz et al. |
| 2011/0009402 A1 | 1/2011 | Himmelsbach |
| 2011/0015157 A1 | 1/2011 | Claremon et al. |
| 2011/0021512 A1 | 1/2011 | Claremon et al. |
| 2011/0059944 A1 | 3/2011 | Blomgren et al. |
| 2011/0098269 A1 | 4/2011 | Becknell et al. |
| 2011/0124635 A1 | 5/2011 | Claremon et al. |
| 2011/0224198 A1 | 9/2011 | Kuduk et al. |

FOREIGN PATENT DOCUMENTS

| | | |
|---|---|---|
| EP | 0316279 A2 | 5/1989 |
| EP | 0612321 A1 | 8/1994 |
| EP | 0634404 A1 | 1/1995 |
| EP | 0634413 A1 | 1/1995 |
| EP | 0652218 A1 | 5/1995 |
| EP | 0711759 A1 | 5/1996 |
| EP | 0760208 A2 | 3/1997 |
| EP | 0856255 A2 | 8/1998 |
| EP | 0934933 A1 | 8/1999 |
| EP | 0984961 A1 | 3/2000 |
| EP | 0989131 A1 | 3/2000 |
| EP | 1887008 A1 | 2/2008 |
| EP | 2239264 A1 | 10/2010 |
| FR | 2478640 A1 | 9/1981 |
| JP | H08337583 A | 12/1996 |
| JP | 2003313169 A | 11/2003 |
| JP | 2008156311 A | 7/2008 |
| WO | 9112251 A1 | 8/1991 |
| WO | 9206087 A1 | 4/1992 |
| WO | 9701551 A1 | 1/1997 |
| WO | 0138377 A1 | 5/2001 |
| WO | 0172812 A1 | 10/2001 |
| WO | 0201935 A1 | 1/2002 |
| WO | 2006032470 A1 | 3/2006 |
| WO | 2006038734 A1 | 4/2006 |
| WO | 2006129623 A1 | 12/2006 |
| WO | 2007008144 A1 | 1/2007 |

(56) References Cited

FOREIGN PATENT DOCUMENTS

| | | |
|---|---|---|
| WO | 2007008145 A1 | 1/2007 |
| WO | 2008064018 A1 | 5/2008 |
| WO | 2009084693 A1 | 7/2009 |
| WO | 2009134387 A1 | 11/2009 |
| WO | 2010069504 A1 | 6/2010 |
| WO | 2011054553 A1 | 5/2011 |
| WO | 2011054843 A1 | 5/2011 |
| WO | 2011054844 A1 | 5/2011 |
| WO | 2011054845 A1 | 5/2011 |
| WO | 2011054846 A1 | 5/2011 |
| WO | 2011054848 A1 | 5/2011 |
| WO | 2011054851 A1 | 5/2011 |
| WO | 2011060067 A2 | 5/2011 |
| WO | 2011143669 A2 | 11/2011 |
| WO | 2011161031 A1 | 12/2011 |
| WO | 2012075456 A1 | 6/2012 |

OTHER PUBLICATIONS

Chung C.W., "Small Molecule Bromodomain Inhibitors: Extending the Druggable Genome," Progress in Medicinal Chemistry, 2012, vol. 51, pp. 1-55.

Dal Piaz V., et al., "Synthesis and Evaluation of Noval Pyrrolo[2,3-d] and Thieno[2,3-d]Pyridazinones as in Vitro Antiproliferative Agents," Acta Chimica Slovenica, 2009, vol. 56 (3), pp. 571-579.

Dawson M.A., et al., "Inhibition of BET Recruitment to Chromatin as an Effective Treatment for MLL-fusion Leukaemia," Nature, 2011, vol. 478 (7370), pp. 529-533.

Delmore J.E., et al., "BET Bromodomain Inhibition as a Therapeutic Strategy to Target c-Myc," Cell, 2011, vol. 146 (6), pp. 904-917.

Denis G.V., "Bromodomain Coactivators in Cancer, Obesity, type 2 Diabetes, and Inflammation," Discovery Medicine, 2010, vol. 10 (55), pp. 489-499.

Filippakopoulos P., et al., "Selective Inhibition of BET Bromodomains," Nature, 2010, vol. 468 (7327), pp. 1067-1073.

Greene T.W., et al., in: Protective Groups in Organic Synthesis, 3rd Edition, John Wiley and Sons, Inc., 1999, Preface, Table of Contents, Abbreviations.

Hewings D.S., et al., "Progress in the Development and Application of Small Molecule Inhibitors of Bromodomain-acetyl-lysine Interactions," Journal of Medicinal Chemistry, 2012, vol. 55 (22), pp. 9393-9413.

Huang B., et al., "Brd4 Coactivates Transcriptional Activation of NF-kappaB Via Specific Binding to Acetylated RelA," Molecular and Cellular Biology, 2009, vol. 29 (5), pp. 1375-1387.

Ikeura Y., et al., "Potent NK1 Receptor Antagonists: Synthesis and Antagonistic Activity of Various Heterocycles with an N-[3,5-bis(trifluoromethyl)benzyl]-N-methylcarbamoyl Substituent," Chemical and Pharmaceutical Bulletin, 1997, vol. 45 (10), pp. 1642-1652.

International Search Report and Written Opinion for Application No. PCT/CN2011/002224, mailed on Oct. 25, 2012, 16 pages.

International Search Report and Written Opinion for Application No. PCT/CN2012/076748, mailed on Mar. 21, 2013, 14 pages.

International Search Report and Written Opinion for Application No. PCT/CN2012/086357, mailed on Mar. 21, 2013, 13 pages.

International Search Report for Application No. PCT/EP2010/066695, mailed on Feb. 7, 2011, 2 pages.

Jang M.K., et al., "The Bromodomain Protein Brd4 is a Positive Regulatory Component of P-TEFb and Stimulates RNA Polymerase II-dependent Transcription," Molecular Cell, 2005, vol. 19 (4), pp. 523-534.

Leroy G., et al., "The Double Bromodomain Proteins Brd2 and Brd3 Couple Histone Acetylation to Transcription," Molecular Cell, 2008, vol. 30 (1), pp. 51-60.

Matzuk M.M., et al., "Small-molecule Inhibition of BRDT for Male Contraception," Cell, 2012, vol. 150 (4), pp. 673-684.

Mertz J.A., et al., "Targeting MYC Dependence in Cancer by Inhibiting BET Bromodomains," Proceedings of the National Academy of Sciences, 2011, vol. 108 (40), pp. 16669-16674.

Miyaura N., et al., "Palladium-Catalyzed Cross-Coupling Reactions of Organoboron Compounds," Chemical Reviews, 1995, vol. 95 (7), pp. 2457-2483.

Nicodeme E., et al., "Suppression of Inflammation by a Synthetic Histone Mimic," Nature, 2010, vol. 468 (7327), pp. 1119-1123.

Prescott D.M., "Methods in Cell Biology", Academic Press, 1976, Table of Contents.

Prinjha R.K., et al., "Place your BETs: the Therapeutic Potential of Bromodomains," Trends in Pharmacological Sciences, 2012, vol. 33 (3), pp. 146-153.

Suzuki A., "Recent Advances in the Cross-Coupling Reactions of organoboron Derivates with organic Electrophiles, 1995-1998," Journal of Organometallic Chemistry, 1999, vol. 576, pp. 147-168.

Wang F., et al., "Brd2 Disruption in Mice Causes Severe Obesity without Type 2 Diabetes," Biochemical Journal, 2010, vol. 425, pp. 71-83.

Yang Z., et al., "Brd4 Recruits P-TEFb to Chromosomes at Late Mitosis to Promote G1 Gene Expression and Cell Cycle Progression," Molecular and Cellular Biology, 2008, vol. 28 (3), pp. 967-976.

Zhang G., et al., "Down-regulation of NF-κB Transcriptional Activity in HIV-associated Kidney Disease by BRD4 Inhibition," Journal of Biological Chemistry, 2012, vol. 287 (34), pp. 28840-28851.

Zuber J., et al., "RNAi Screen Identifies Brd4 as a Therapeutic Target in Acute Myeloid Leukaemia," Nature, 2011, vol. 478 (7370), pp. 524-528.

BROMODOMAIN INHIBITORS

CROSS-REFERENCE TO RELATED APPLICATIONS

This present application is a continuation of International PCT Application No. PCT/CN2012/086357, filed on Dec. 11, 2012, which claims the benefit of priority to International PCT Application No. PCT/CN2011/002224, filed on Dec. 30, 2011, the teachings of which are each herein incorporated by reference in their entirety

BACKGROUND

Bromodomains refer to conserved protein structural folds which bind to N-acetylated lysine residues that are found in some proteins. The BET family of bromodomain containing proteins is comprised of four members (BRD2, BRD3, BRD4 and BRDt). Each member of the BET family employs two bromodomains to recognize N-acetylated lysine residues found primarily, but not exclusively, on the amino-terminal tails of histone proteins. These interactions modulate gene expression by recruiting transcription factors to specific genome locations within chromatin. For example, histone-bound BRD4 recruits the transcription factor P-TEFb to promoters, resulting in the expression of a subset of genes involved in cell cycle progression (Yang et al., Mol. Cell. Biol. 28: 967-976 (2008)). BRD2 and BRD3 also function as transcriptional regulators of growth promoting genes (LeRoy et al., Mol. Cell 30: 51-60 (2008)). BET family members were recently established as being important for the maintenance of several cancer types (Zuber et al., Nature 478: 524-528 (2011); Mertz et al; Proc. Nat'l. Acad. Sci. 108: 16669-16674 (2011); Delmore et al., Cell 146: 1-14, (2011); Dawson et al., Nature 478: 529-533 (2011)). BET family members have also been implicated in mediating acute inflammatory responses through the canonical NF-KB pathway (Huang et al., Mol. Cell. Biol. 29: 1375-1387 (2009)) resulting in the upregulation of genes associated with the production of cytokines (Nicodeme et al., Nature 468: 1119-1123, (2010)). In addition, bromodomain function has been implicated in kidney disease (Zhang, et al., J. Biol. Chem. 287: 28840-28851 (2012)). BRD2 function has also been linked to a predisposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). BET bromodomain inhibitors have also been shown to reactivate HIV transcription in models of latent T cell infection and latent monocyte infection (Banerjee, et al, J. Leukocyte Biol. doi:10.1189/jlb.0312165). BRDt has an important role in spermatogenesis (Matzuk, et al., Cell 150: 673-684 (2012)). Accordingly, there is an ongoing medical need to develop new drugs to treat diseases and indications involving bromodomain function, including BET bromodomain function.

SUMMARY

In one aspect the present invention provides for compounds of formula (I) or pharmaceutically acceptable thereof,

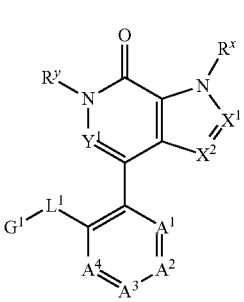

(I)

wherein
$R^x$ is hydrogen or $C_1$-$C_3$ alkyl;
$R^y$ is $C_1$-$C_3$ alkyl, —($C_2$-$C_3$ alkylenyl)-OH, or $C_1$-$C_3$ haloalkyl;
$X^1$ is N or $CR^{x1}$ wherein
  $R^{x1}$ is hydrogen, $C_2$-$C_6$ alkenyl, $C_2$-$C_6$ alkynyl, —C(O)OR$^{ax1}$, —C(O)NR$^{bx1}$R$^{cx1}$, —C(O)R$^{dx1}$, S(O)$_2$R$^{dx1}$, —S(O)$_2$NR$^{bx1}$R$^{cx1}$, G$^{x1}$, $C_1$-$C_6$ haloalkyl, or $C_1$-$C_6$ alkyl; wherein the $C_1$-$C_6$ alkyl is optionally substituted with one substituent selected from the group consisting of OR$^{ax1}$, SR$^{ax1}$, S(O)R$^{dx1}$, S(O)$_2$R$^{dx1}$, NR$^{bx1}$R$^{cx1}$, —C(O)R$^{ax1}$, —C(O)OR$^{ax1}$, —C(O)NR$^{bx1}$R$^{cx1}$, —S(O)$_2$NR$^{bx1}$R$^{cx1}$, and G$^{x1}$;
  $R^{ax1}$, $R^{bx1}$ and $R^{cx1}$, at each occurrence, are each independently hydrogen, $C_1$-$C_6$ alkyl, $C_1$-$C_6$ haloalkyl, G$^a$, or —($C_1$-$C_6$ alkylenyl)-G$^a$;
  $R^{dx1}$, at each occurrence, are each independently $C_1$-$C_6$ alkyl, $C_1$-$C_6$ haloalkyl, G$^a$, or —($C_1$-$C_6$ alkylenyl)-G$^a$;
$X^2$ is N or $CR^{x2}$; wherein
  $R^{x2}$ is hydrogen, $C_2$-$C_6$ alkenyl, $C_2$-$C_6$ alkynyl, —C(O)OR$^{ax2}$, —C(O)NR$^{bx2}$R$^{cx2}$, —C(O)R$^{dx2}$, —C(O)H, S(O)$_2$R$^{dx2}$, —S(O)$_2$NR$^{bx2}$R$^{cx2}$, G$^{x2}$, $C_1$-$C_6$ haloalkyl, or $C_1$-$C_6$ alkyl; wherein the $C_1$-$C_6$ alkyl is optionally substituted with one substituent selected from the group consisting of OR$^{ax2}$, SR$^{ax2}$, S(O)R$^{dx2}$, S(O)$_2$R$^{dx2}$, NR$^{bx2}$R$^{cx2}$, —C(O)R$^{ax2}$, —C(O)OR$^{ax2}$, —C(O)NR$^{bx2}$R$^{cx2}$, —S(O)$_2$NR$^{bx2}$R$^{cx2}$, and G$^{x2}$;
  $R^{ax2}$, $R^{bx2}$, and $R^{cx2}$, at each occurrence, are each independently hydrogen, $C_1$-$C_6$ alkyl, $C_1$-$C_6$ haloalkyl, G$^b$, or —($C_1$-$C_6$ alkylenyl)-G$^b$;
  $R^{dx2}$, at each occurrence, is independently $C_1$-$C_6$ alkyl, $C_1$-$C_6$ haloalkyl, G$^b$, or —($C_1$-$C_6$ alkylenyl)-G$^b$;
$Y^1$ is N or $CR^u$; wherein $R^u$ is hydrogen, $C_1$-$C_6$ alkyl, halogen, or $C_1$-$C_6$ haloalkyl;
$A^1$ is N or $CR^1$, $A^2$ is N or $CR^2$, $A^3$ is N or $CR^3$; and $A^4$ is N or $CR^4$; with the proviso that zero, one, two, or three of $A^1$, $A^2$, $A^3$, and $A^4$ are N;
$R^1$, $R^3$, and $R^4$ are each independently hydrogen, $C_1$-$C_6$ alkyl, $C_2$-$C_6$ alkenyl, $C_2$-$C_6$ alkynyl, halogen, $C_1$-$C_6$ haloalkyl, CN, or NO$_2$;
$R^2$ is hydrogen, $C_1$-$C_6$ alkyl, $C_2$-$C_6$ alkenyl, $C_2$-$C_6$ alkynyl, halogen, $C_1$-$C_6$ haloalkyl, —CN, NO$_2$, G$^{2a}$, —OR$^{2a}$, —OC(O)R$^{2d}$, —OC(O)NR$^{2b}$R$^{2c}$, —SR$^{2a}$, —S(O)$_2$R$^{2d}$, —S(O)$_2$NR$^{2b}$R$^{2c}$, —C(O)R$^{2d}$, —C(O)OR$^{2a}$, —C(O)NR$^{2b}$R$^{2c}$, —NR$^{2b}$R$^{2c}$, —N(R$^{2e}$)C(O)R$^{2d}$, —N(R$^{2e}$)S(O)$_2$R$^{2d}$, —N(R$^{2e}$)C(O)O(R$^{2d}$), —N(R$^{2e}$)C(O)NR$^{2b}$R$^{2c}$, —N(R$^{2e}$)S(O)$_2$NR$^{2b}$R$^{2c}$, —($C_1$-$C_6$ alkylenyl)-G$^{2a}$, —($C_1$-$C_6$ alkylenyl)-OR$^{2a}$, —($C_1$-$C_6$ alkylenyl)-OC(O)R$^{2d}$, —($C_1$-$C_6$ alkylenyl)-OC(O)NR$^{2b}$R$^{2c}$, —($C_1$-$C_6$ alkylenyl)-S(O)$_2$R$^{2d}$, —($C_1$-$C_6$ alkylenyl)-S(O)$_2$NR$^{2b}$R$^{2c}$, —($C_1$-$C_6$ alkylenyl)-C(O)R$^{2d}$, —($C_1$-$C_6$ alkylenyl)-C(O)OR$^{2a}$, —($C_1$-$C_6$ alkylenyl)-C(O)NR$^{2b}$R$^{2c}$, —(C$_1$-C$_6$ alkylenyl)-NR$^{2b}$R$^{2c}$, —(C$_1$-C$_6$ alkylenyl)-N(R$^{2e}$)C(O)R$^{2d}$, —(C$_1$-C$_6$ alkylenyl)-N(R$^{2e}$)S(O)$_2$R$^{2d}$, —(C$_1$-C$_6$ alkylenyl)-N(R$^{2e}$)C(O)O(R$^{2a}$), —(C$_1$-C$_6$ alkylenyl)-N(R$^{2e}$)C(O)NR$^{2b}$R$^{2c}$, —(C$_1$-C$_6$ alkylenyl)-N(R$^{2e}$)S(O)$_2$NR$^{2b}$R$^{2c}$, and —(C$_1$-C$_6$ alkylenyl)-CN;

R$^{2a}$, R$^{2b}$, R$^{2c}$, and R$^{2e}$, at each occurrence, are each independently hydrogen, C$_2$-C$_6$ alkenyl, C$_2$-C$_6$ alkynyl, C$_1$-C$_6$ haloalkyl, G$^{2b}$, or C$_1$-C$_6$ alkyl wherein the C$_1$-C$_6$ alkyl is optionally substituted with one substituent selected from the group consisting of —OR$^{z1}$, NR$^{z1}$R$^{z2}$, —C(O)OR$^{z1}$, —C(O)NR$^{z1}$R$^{z2}$, —S(O)$_2$R$^{z1}$, —S(O)$_2$NR$^{z1}$R$^{z2}$, and G$^{2b}$;

R$^{2d}$, at each occurrence, is independently C$_2$-C$_6$ alkenyl, C$_2$-C$_6$ alkynyl, C$_1$-C$_6$ haloalkyl, G$^{2b}$, or C$_1$-C$_6$ alkyl wherein the C$_1$-C$_6$ alkyl is optionally substituted with one substituent selected from the group consisting of —OR$^{z1}$, NR$^{z1}$R$^{z2}$, —C(O)OR$^{z1}$, —C(O)NR$^{z1}$R$^{z2}$, —S(O)$_2$R$^{z1}$, —S(O)$_2$NR$^{z1}$R$^{z2}$, and G$^{2b}$;

R$^{z1}$ and R$^{z2}$, at each occurrence, are each independently hydrogen, C$_1$-C$_6$ alkyl, or C$_1$-C$_6$ haloalkyl;

G$^{x1}$, G$^{x2}$, G$^{a}$, G$^{b}$, G$^{2a}$, and G$^{2b}$, at each occurrence, are each independently aryl, heteroaryl, heterocycle, cycloalkyl, or cycloalkenyl, and each of which is independently unsubstituted or substituted with 1, 2, 3, 4, or 5 of R$^{v}$;

L$^1$ is absent, CH$_2$, C(O), C(H)(OH), (CH$_2$)$_m$O, (CH$_2$)$_m$S(O)$_n$ wherein n is 0, 1, or 2; or (CH$_2$)$_m$N(R$^z$) wherein R$^z$ is hydrogen, C$_1$-C$_3$ alkyl, C$_1$-C$_3$ haloalkyl, (C$_2$-C$_3$ alkylenyl)-OH, or unsubstituted cyclopropyl;

m is 0 or 1;

G$^1$ is C$_1$-C$_6$ alkyl, alkoxyalkyl, G$^{1a}$ or —(C$_1$-C$_6$ alkylenyl)-G$^{1a}$; wherein each G$^{1a}$ is independently aryl, heteroaryl, heterocycle, cycloalkyl, or cycloalkenyl, and each G$^{1a}$ is independently unsubstituted or substituted with 1, 2, 3, 4, or 5 of R$^{w}$;

R$^v$ and R$^w$, at each occurrence, are each independently C$_1$-C$_6$ alkyl, C$_2$-C$_6$ alkenyl, C$_2$-C$_6$ alkynyl, halogen, C$_1$-C$_6$ haloalkyl, —CN, oxo, —OR$^h$, —OC(O)R$^i$, —OC(O)NR$^j$R$^k$, —SR$^h$, —S(O)$_2$R$^h$, —S(O)$_2$NR$^j$R$^k$, —C(O)R$^h$, —C(O)-monocyclic heterocycle, —C(O)-monocyclic heteroaryl, —C(O)OR$^h$, —C(O)NR$^j$R$^k$, —NR$^j$R$^k$, —N(R$^h$)C(O)R$^i$, —N(R$^h$)S(O)$_2$R$^i$, —N(R$^h$)C(O)O(R$^i$), —N(R$^h$)C(O)NR$^j$R$^k$, —(C$_1$-C$_6$ alkylenyl)-OR$^h$, —(C$_1$-C$_6$ alkylenyl)-OC(O)R$^i$, —(C$_1$-C$_6$ alkylenyl)-OC(O)NR$^j$R$^k$, —(C$_1$-C$_6$ alkylenyl)-S(O)$_2$R$^h$, —(C$_1$-C$_6$ alkylenyl)-S(O)$_2$NR$^j$R$^k$, —(C$_1$-C$_6$ alkylenyl)-C(O)R$^h$, —(C$_1$-C$_6$ alkylenyl)-C(O)OR$^h$, —(C$_1$-C$_6$ alkylenyl)-C(O)NR$^j$R$^k$, —(C$_1$-C$_6$ alkylenyl)-NR$^j$R$^k$, —(C$_1$-C$_6$ alkylenyl)-N(R$^h$)C(O)R$^i$, —(C$_1$-C$_6$ alkylenyl)-N(R$^h$)S(O)$_2$R$^i$, —(C$_1$-C$_6$ alkylenyl)-N(R$^h$)C(O)O(R$^i$), —(C$_1$-C$_6$ alkylenyl)-N(R$^h$)C(O)NR$^j$R$^k$, or —(C$_1$-C$_6$ alkylenyl)-CN;

R$^h$, R$^j$, R$^k$, at each occurrence, are each independently hydrogen, C$_1$-C$_6$ alkyl, or C$_1$-C$_6$ haloalkyl; and R$^i$, at each occurrence, is independently C$_1$-C$_6$ alkyl or C$_1$-C$_6$ haloalkyl.

In one aspect the present invention provides for compounds of formula (I) or pharmaceutically acceptable thereof,

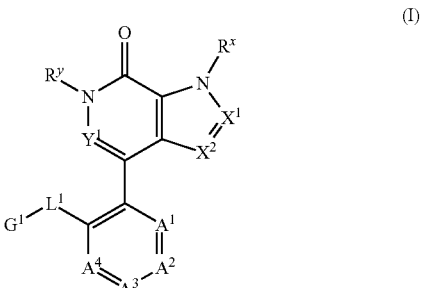

(I)

wherein

R$^x$ is hydrogen or C$_1$-C$_3$ alkyl;

R$^y$ is C$_1$-C$_3$ alkyl, —(C$_2$-C$_3$ alkylenyl)-OH, or C$_1$-C$_3$ haloalkyl;

X$^1$ is N or CR$^{x1}$ wherein

R$^{x1}$ is hydrogen, C$_2$-C$_6$ alkenyl, C$_2$-C$_6$ alkynyl, —C(O)OR$^{ax1}$, —C(O)NR$^{bx1}$R$^{cx1}$, —C(O)R$^{dx1}$, S(O)$_2$R$^{dx1}$, —S(O)$_2$NR$^{bx1}$R$^{cx1}$, G$^{x1}$, C$_1$-C$_6$ haloalkyl, or C$_1$-C$_6$ alkyl; wherein the C$_1$-C$_6$ alkyl is optionally substituted with one substituent selected from the group consisting of OR$^{ax1}$, SR$^{ax1}$, S(O)R$^{dx1}$, S(O)$_2$R$^{dx1}$, NR$^{bx1}$R$^{cx1}$, —C(O)R$^{ax1}$, —C(O)OR$^{ax1}$, —C(O)NR$^{bx1}$R$^{cx1}$, —S(O)$_2$NR$^{bx1}$R$^{cx1}$, and G$^{x1}$;

R$^{ax1}$, R$^{bx1}$, and R$^{cx1}$, at each occurrence, are each independently hydrogen, C$_1$-C$_6$ alkyl, C$_1$-C$_6$ haloalkyl, G$^a$, or —(C$_1$-C$_6$ alkylenyl)-G$^a$;

R$^{dx1}$, at each occurrence, are each independently C$_1$-C$_6$ alkyl, C$_1$-C$_6$ haloalkyl, G$^a$, or —(C$_1$-C$_6$ alkylenyl)-G$^a$;

X$^2$ is N or CR$^{x2}$; wherein

R$^{x2}$ is hydrogen, C$_2$-C$_6$ alkenyl, C$_2$-C$_6$ alkynyl, —C(O)OR$^{ax2}$, —C(O)NR$^{bx2}$R$^{cx2}$, —C(O)R$^{dx2}$, S(O)$_2$R$^{dx2}$, —S(O)$_2$NR$^{bx2}$R$^{cx2}$, G$^{x2}$, C$_1$-C$_6$ haloalkyl, or C$_1$-C$_6$ alkyl; wherein the C$_1$-C$_6$ alkyl is optionally substituted with one substituent selected from the group consisting of OR$^{ax2}$, SR$^{ax2}$, S(O)R$^{dx2}$, S(O)$_2$R$^{dx2}$, NR$^{bx2}$R$^{cx2}$, —C(O)R$^{ax2}$, —C(O)OR$^{ax2}$, —C(O)NR$^{bx2}$R$^{cx2}$, —S(O)$_2$NR$^{bx2}$R$^{cx2}$, and G$^{x2}$, R$^{ax2}$, R$^{bx2}$, and R$^{cx2}$, at each occurrence, are each independently hydrogen, C$_1$-C$_6$ alkyl, C$_1$-C$_6$ haloalkyl, G$^b$, or —(C$_1$-C$_6$ alkylenyl)-G$^b$;

R$^{dx2}$, at each occurrence, is independently C$_1$-C$_6$ alkyl, C$_1$-C$_6$ haloalkyl, G$^b$, or —(C$_1$-C$_6$ alkylenyl)-G$^b$;

Y$^1$ is N or CR$^u$; wherein R$^u$ is hydrogen, C$_1$-C$_6$ alkyl, halogen, or C$_1$-C$_6$ haloalkyl;

A$^1$ is N or CR$^1$, A$^2$ is N or CR$^2$, A$^3$ is N or CR$^3$; and A$^4$ is N or CR$^4$; with the proviso that zero, one, two, or three of A$^1$, A$^2$, A$^3$, and A$^4$ are N;

R$^1$, R$^3$, and R$^4$ are each independently hydrogen, C$_1$-C$_6$ alkyl, C$_2$-C$_6$ alkenyl, C$_2$-C$_6$ alkynyl, halogen, C$_1$-C$_6$ haloalkyl, CN, or NO$_2$;

R$^2$ is hydrogen, C$_1$-C$_6$ alkyl, C$_2$-C$_6$ alkenyl, C$_2$-C$_6$ alkynyl, halogen, C$_1$-C$_6$ haloalkyl, —CN, NO$_2$, G$^{2a}$, —OR$^{2a}$, —OC(O)R$^{2d}$, —OC(O)NR$^{2b}$R$^{2c}$, —SR$^{2a}$, —S(O)$_2$R$^{2d}$, —S(O)$_2$NR$^{2b}$R$^{2c}$, —C(O)R$^{2d}$, —C(O)OR$^{2a}$, —C(O)NR$^{2b}$R$^{2c}$, —NR$^{2b}$R$^{2c}$, —N(R$^{2e}$)C(O)R$^{2d}$, —N(R$^{2e}$)S(O)$_2$R$^{2d}$, —N(R$^{2e}$)C(O)O(R$^{2d}$), —N(R$^{2e}$)C(O)NR$^{2b}$R$^{2c}$, —N(R$^{2e}$)S(O)$_2$NR$^{2b}$R$^{2c}$, —(C$_1$-C$_6$ alkylenyl)-G$^{2a}$, —(C$_1$-C$_6$ alkylenyl)-OR$^{2a}$, —(C$_1$-C$_6$ alkylenyl)-OC(O)R$^{2d}$, —(C$_1$-C$_6$ alkylenyl)-OC(O)NR$^{2b}$R$^{2c}$, —(C$_1$-C$_6$ alkylenyl)-S(O)$_2$R$^{2d}$, —(C$_1$-C$_6$ alkylenyl)-S(O)$_2$NR$^{2b}$R$^{2c}$, —(C$_1$-C$_6$ alkylenyl)-C(O)R$^{2d}$, —(C$_1$-C$_6$ alkylenyl)-C(O)OR$^{2a}$, —(C$_1$-C$_6$ alkylenyl)-C(O)NR$^{2b}$R$^{2c}$, —(C$_1$-C$_6$ alkylenyl)-NR$^{2b}$R$^{2c}$, —(C$_1$-C$_6$ alkylenyl)-N(R$^{2e}$)C(O)R$^{2d}$, —(C$_1$-C$_6$ alkylenyl)-N(R$^{2e}$)S(O)$_2$R$^{2d}$, —(C$_1$-C$_6$ alkylenyl)-N(R$^{2e}$)C(O)O(R$^{2a}$), —(C$_1$-C$_6$ alkylenyl)-N(R$^{2e}$)C(O)NR$^{2b}$R$^{2c}$, —(C$_1$-C$_6$ alkylenyl)-N(R$^{2e}$)S(O)$_2$NR$^{2b}$R$^{2c}$, and —(C$_1$-C$_6$ alkylenyl)-CN;

R$^{2a}$, R$^{2b}$, R$^{2c}$, and R$^{2e}$, at each occurrence, are each independently hydrogen, C$_2$-C$_6$ alkenyl, C$_2$-C$_6$ alkynyl, C$_1$-C$_6$ haloalkyl, G$^{2b}$, or C$_1$-C$_6$ alkyl wherein the C$_1$-C$_6$ alkyl is optionally substituted with one substituent selected from the group consisting of —OR$^{z1}$, NR$^{z1}$R$^{z2}$, —C(O)OR$^{z1}$, —C(O)NR$^{z1}$R$^{z2}$, —S(O)$_2$R$^{z1}$, —S(O)$_2$NR$^{z1}$R$^{z2}$, and G$^{2b}$;

R$^{2d}$, at each occurrence, is independently C$_2$-C$_6$ alkenyl, C$_2$-C$_6$ alkynyl, C$_1$-C$_6$ haloalkyl, G$^{2b}$, or C$_1$-C$_6$ alkyl wherein the C$_1$-C$_6$ alkyl is optionally substituted with one substituent selected from the group consisting of —OR$^{z1}$, NR$^{z1}$R$^{z2}$, —C(O)OR$^{z1}$, —C(O)NR$^{z1}$R$^{z2}$, —S(O)$_2$R$^{z1}$, —S(O)$_2$NR$^{z1}$R$^{z2}$, and G$^{2b}$;

R$^{z1}$ and R$^{z2}$, at each occurrence, are each independently hydrogen, C$_1$-C$_6$ alkyl, or C$_1$-C$_6$ haloalkyl;

G$^{x1}$, G$^{x2}$, G$^a$, G$^b$, G$^{2a}$, and G$^{2b}$, at each occurrence, are each independently aryl, heteroaryl, heterocycle, cycloalkyl, or cycloalkenyl, and each of which is independently unsubstituted or substituted with 1, 2, 3, 4, or 5 of R$^v$;

L$^1$ is absent, CH$_2$, C(O), (CH$_2$)$_m$O, (CH$_2$)$_m$S(O)$_n$ wherein n is 0, 1, or 2; or (CH$_2$)$_m$N(R$^z$) wherein R$^z$ is hydrogen, C$_1$-C$_3$ alkyl, C$_1$-C$_3$ haloalkyl, (C$_2$-C$_3$ alkylenyl)-OH, or unsubstituted cyclopropyl;

m is 0 or 1;

G$^1$ is G$^{1a}$ or —(C$_1$-C$_6$ alkylenyl)-G$^{1a}$; wherein each G$^{1a}$ is independently aryl, heteroaryl, heterocycle, cycloalkyl, or cycloalkenyl, and each G$^{1a}$ is independently unsubstituted or substituted with 1, 2, 3, 4, or 5 of R$^w$;

R$^v$ and R$^w$, at each occurrence, are each independently C$_1$-C$_6$ alkyl, C$_2$-C$_6$ alkenyl, C$_2$-C$_6$ alkynyl, halogen, C$_1$-C$_6$ haloalkyl, —CN, oxo, —OR$^h$, —OC(O)R$^i$, —OC(O)NR$^j$R$^k$, —SR$^h$, —S(O)$_2$R$^h$, —S(O)$_2$NR$^j$R$^k$, —C(O)R$^h$, —C(O)OR$^h$, —C(O)NR$^j$R$^k$, —NR$^j$R$^k$, —N(R$^h$)C(O)R$^i$, —N(R$^h$)S(O)$_2$R$^i$, —N(R$^h$)C(O)O(R$^i$), —N(R$^h$)C(O)NR$^j$R$^k$, —(C$_1$-C$_6$ alkylenyl)-OR$^h$, —(C$_1$-C$_6$ alkylenyl)-OC(O)R$^i$, —(C$_1$-C$_6$ alkylenyl)-OC(O)NR$^j$R$^k$, —(C$_1$-C$_6$ alkylenyl)-S(O)$_2$R$^h$, —(C$_1$-C$_6$ alkylenyl)-S(O)$_2$NR$^j$R$^k$, —(C$_1$-C$_6$ alkylenyl)-C(O)R$^h$, —(C$_1$-C$_6$ alkylenyl)-C(O)OR$^h$, —(C$_1$-C$_6$ alkylenyl)-C(O)NR$^j$R$^k$, —(C$_1$-C$_6$ alkylenyl)-NR$^j$R$^k$, —(C$_1$-C$_6$ alkylenyl)-N(R$^h$)C(O)R$^i$, —(C$_1$-C$_6$ alkylenyl)-N(R$^h$)S(O)$_2$R$^i$, —(C$_1$-C$_6$ alkylenyl)-N(R$^h$)C(O)O(R$^i$), —(C$_1$-C$_6$ alkylenyl)-N(R$^h$)C(O)NR$^j$R$^k$, or —(C$_1$-C$_6$ alkylenyl)-CN;

R$^h$, R$^j$, R$^k$, at each occurrence, are each independently hydrogen, C$_1$-C$_6$ alkyl, or C$_1$-C$_6$ haloalkyl; and R$^i$, at each occurrence, is independently C$_1$-C$_6$ alkyl or C$_1$-C$_6$ haloalkyl.

In another aspect, the present invention provides for methods for treating or preventing disorders that are ameliorated by inhibition of BET. Such methods comprise of administering to the subject a therapeutically effective amount of a compound of formula (I), alone, or in combination with a pharmaceutically acceptable carrier.

Some of the methods are directed to treating or preventing an inflammatory disease or cancer or AIDS.

In another aspect, the present invention relates to methods of treating cancer in a subject comprising administering a therapeutically effective amount of a compound of formula (I) or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor. In certain embodiments, the methods further comprise administering a therapeutically effective amount of at least one additional therapeutic agent. In certain embodiments, the additional therapeutic agent is an anti-cancer agent. In particular embodiments, the additional therapeutic agents are selected from the group consisting of cytarabine, bortezomib, and 5-azacitidine.

In another aspect, the present invention relates to methods of treating a disease or condition in a subject comprising administering a therapeutically effective amount of a compound of formula (I) or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating a chronic kidney disease or condition in a subject comprising administering a therapeutically effective amount of a compound of formula (I) or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating an acute kidney injury or disease or condition in a subject comprising administering a therapeutically effective amount of a compound of formula (I) or a pharmaceutically acceptable salt thereof, to a subject in need thereof, wherein said acute kidney injury or disease or condition is selected from the group consisting of: ischemia-reperfusion induced, cardiac and major surgery induced, percutaneous coronary intervention induced, radio-contrast agent induced, sepsis induced, pneumonia induced, and drug toxicity induced. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating AIDS in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity, dyslipidemia, hypercholesterolemia, Alzheimer's disease, metabolic syndrome, hepatic steatosis, type II diabetes, insulin resistance, diabetic retinopathy or diabetic neuropathy in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

In another aspect, the present invention relates to methods of preventing conception by inhibiting spermatogenesis in a subject comprising administering a therapeutically effective amount of a compound of formula (I) or a pharmaceutically acceptable salt thereof, to a subject in need thereof. In certain embodiments, the methods further comprise administering a therapeutically effective amount of at least one additional therapeutic agent.

A further aspect of the invention provides the use of a compound of formula (I), alone or in combination with a second active pharmaceutical agent, in the manufacture of a medicament for treating or preventing conditions and disorders disclosed herein, with or without a pharmaceutically acceptable carrier.

Pharmaceutical compositions comprising a compound of formula (I), or a pharmaceutically acceptable salt, alone or in combination with a second active pharmaceutical agent, are also provided.

DETAILED DESCRIPTION

Disclosed herein are compounds of formula (I)

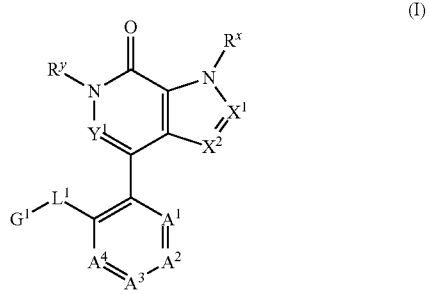

wherein $A^1$, $A^2$, $A^3$, $A^4$, $X^1$, $X^2$, $Y^1$, $L^1$, $G^1$, $R^x$, and $R^y$ are defined above in the Summary of the Invention and below in the Detailed Description. Further, compositions comprising such compounds and methods for treating conditions and disorders using such compounds and compositions are also disclosed.

Compounds disclosed herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. DEFINITIONS

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond, optionally substituted with 1, 2, or 3 halogen atoms. The term "$C_2$-$C_6$ alkenyl" means an alkenyl group containing 2-6 carbon atoms. Non-limiting examples of alkenyl include buta-1, 3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. Representative examples of alkenylene include, but are not limited to, —CH═CH— and —CH$_2$CH═CH—.

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" refers to an alkyl substituent containing from 1 to 6 carbon atoms and "$C_1$-$C_3$ alkyl" refers to an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms or of 2 to 3 carbon atoms ($C_2$-$C_3$ alkylenyl). Examples of alkylene and alkylenyl include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" as used herein, means a straight or branched chain hydrocarbon radical containing from 2 to 10 carbon atoms and containing at least one carbon-carbon triple bond, optionally substituted with 1, 2, or 3 halogen atoms. The term "$C_2$-$C_6$ alkynyl" means an alkynyl group of 2 to 6 carbon atoms. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl, indenyl, naphthyl, dihydronaphthalenyl, and tetrahydronaphthalenyl. The bicyclic aryls are attached to the parent molecular moiety through any carbon atom contained within the bicyclic ring systems and can be unsubstituted or substituted.

The term "cycloalkyl" as used herein, refers to a radical that is a monocyclic cyclic alkyl, a bicyclic cycloalkyl, or a spiro cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. The monocyclic and the bicyclic cycloalkyl groups may contain one or two alkylene bridges, each consisting of one, two, three, or four carbon atoms in length, and each bridge links two non-adjacent carbon atoms of the ring system. Non-limiting examples of bicyclic ring systems include bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, tricyclo[3.3.1.0$^{3,7}$] nonane (octahydro-2,5-methanopentalene or noradamantane), and tricyclo[3.3.1.1$^{3,7}$]decane (adamantane). A spiro cycloalkyl is a monocyclic cycloalkyl wherein two substituents on the same carbon atom of the monocyclic cycloalkyl ring together with said carbon atom form a second monocyclic cycloalkyl ring. The monocyclic, the bicyclic, and the spiro cycloalkyl groups can be unsubstituted or substituted, and are attached to the parent molecular moiety through any substitutable atom contained within the ring system.

The term "cycloalkenyl" as used herein, refers to a monocyclic or a bicyclic hydrocarbon ring radical. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, or three carbon atoms, and each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyls can be attached to the parent molecular moiety through any substitutable atom contained within the ring systems, and can be unsubstituted or substituted.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five or six hydrogen atoms are replaced by halogen. The term "$C_1$-$C_3$ haloalkyl" means a $C_1$-$C_3$ alkyl group, as defined herein, in which one, two, or three hydrogen atoms are replaced by halogen. Representative examples of haloalkyl include, but are not limited to, chloromethyl, 2-fluoroethyl, 2,2-difluoroethyl, 2,2,2-trifluoroethyl, trifluoromethyl, difluoromethyl, pentafluoroethyl, 2-chloro-3-fluoropentyl, trifluorobutyl, and trifluoropropyl.

The term "heterocycle" or "heterocyclic" as used herein, means a radical of a monocyclic heterocycle, a bicyclic heterocycle, and a spiro heterocycle. A monocyclic heterocycle is a three-, four-, five-, six-, seven-, or eight-membered carbocyclic ring also containing at least one heteroatom independently selected from the group consisting of O, N, and S. A three- or four-membered ring contains zero or one double bond, and one heteroatom selected from the group consisting of O, N, and S. When two O atoms or one O atom and one S atom are present in a heterocyclic ring, then the two O atoms or one O atom and one S atom are not bonded directly to each other. A five-membered ring contains zero or one double bond and one, two, or three heteroatoms selected from the group consisting of O, N, and S. Examples of five-membered heterocyclic rings include those containing in the ring: 1O; 1S; 1N; 2N; 3N; 1S and 1N; 1S, and 2N; 1O and 1N; or 1O and 2N. Examples of 5-membered heterocyclic groups include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl. A six-membered ring contains zero, one, or two double bonds and one, two, or three heteroatoms selected from the group consisting of O, N, and S. Examples of six-membered heterocyclic rings include those containing in the ring: 1 O; 2O; 1S; 2S; 1N; 2N; 3N; 1S, 1O, and 1N; 1S and 1N; 1S and 2N; 1S and 1O; 1S and 2O; 1Q and 1N; and 1O and 2N. Examples of 6-membered heterocyclic groups include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6- tetrahydropyridinyl, tetrahydrothiopyranyl, 1,1-dioxohexahydro-1-thiopyranyl, 1,1-dioxo-1λ⁶-thiomorpholinyl, thiomorpholinyl, thioxanyl, and trithianyl. Seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Representative examples of bicyclic heterocycles include, but are not limited to, benzopyranyl, benzothiopyranyl, 2,3-dihydrobenzofuranyl, 2,3-dihydrobenzothienyl, 2,3-dihydro-1H-indolyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1 (5H)-yl. The monocyclic heterocycle and the bicyclic heterocycle may contain one or two alkylene bridges or an alkenylene bridge, or mixture thereof, each consisting of no more than four carbon atoms and each linking two non adjacent atoms of the ring system. Examples of such bridged heterocycle include, but are not limited to, azabicyclo[2.2.1] heptyl (including 2-azabicyclo[2.2.1]hept-2-yl), 8-azabicyclo[3.2.1]oct-8-yl, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1³,⁷]decane), and oxa-adamantane (2-oxatricyclo[3.3.1.1³,⁷]decane). A spiro heterocycle is a monocyclic heterocycle wherein two substituents on the same carbon atom of the monocyclic heterocycle ring together with said carbon atom form a second ring system selected from a monocyclic cycloalkyl, a bicyclic cycloalkyl, a monocyclic heterocycle, or a bicyclic heterocycle. Examples of spiro heterocycle include, but not limited to, 6-azaspiro[2.5]oct-6-yl, 1'H,4H-spiro[1,3-benzodioxine-2,4'-piperidin]-1'-yl, 1'H,3H-spiro[2-benzofuran-1,4'-piperidin]-1'-yl, and 1,4-dioxa-8-azaspiro[4.5]dec-8-yl. The monocyclic, the bicyclic, and the spiro heterocycles can be unsubstituted or substituted. The monocyclic, the bicyclic and the spiro heterocycles are connected to the parent molecular moiety through any carbon atom or any nitrogen atom contained within the ring systems. The nitrogen and sulfur heteroatoms in the heterocycle rings may optionally be oxidized (e.g. 1,1-dioxidotetrahydrothienyl, 1,1-dioxido-1,2-thiazolidinyl, 1,1-dioxidothiomorpholinyl)) and the nitrogen atoms may optionally be quarternized.

The term "heteroaryl" as used herein, means a monocyclic heteroaryl and a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems. The nitrogen atom in the heteroaryl rings may optionally be oxidized and may optionally be quarternized.

The term "heteroatom" as used herein, means a nitrogen, oxygen, and sulfur.

The term "oxo" as used herein, means a =O group.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another pharmaceutical agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, horses, dogs, cats, rabbits, rats, mice and the like. In preferred embodiments, the subject is a human.

b. COMPOUNDS

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

In compounds of formula (I), $R^x$ is as defined in the Summary. For example, in certain embodiments, $R^x$ is hydrogen or methyl. In certain embodiments, $R^x$ is hydrogen.

$R^y$, in compounds of formula (I), is as disclosed in the Summary. For example, in certain embodiments, $R^y$ is $C_1$-$C_3$ alkyl (e.g. methyl, ethyl). In certain embodiments, $R^y$ is methyl.

$X^1$ is as disclosed in the Summary. For example, in certain embodiments, $X^1$ is N. In certain embodiments, $X^1$ is $CR^{x1}$. $R^{x1}$ is as defined in the Summary or embodiments herein. In certain embodiments, $R^{x1}$ is hydrogen, $C_2$-$C_6$ alkenyl, —C(O)$OR^{ax1}$, —C(O)$NR^{bx1}R^{cx1}$, —C(O)$R^{dx1}$, $G^{x1}$, or $C_1$-$C_6$ alkyl wherein the $C_1$-$C_6$ alkyl is optionally substituted with one substituent selected from the group consisting of $OR^{ax1}$, $NR^{bx1}R^{cx1}$, and $G^{x1}$. In certain embodiments, $R^{x1}$ is hydrogen, —C(O)$OR^{ax1}$, —C(O)$NR^{bx1}R^{cx1}$, $G^{x1}$, or $C_1$-$C_6$ alkyl wherein the $C_1$-$C_6$ alkyl is optionally substituted with $OR^{ax1}$ In certain embodiments, $R^{x1}$ is hydrogen, —C(O)$OR^{ax1}$, —C(O)$NR^{bx1}R^{cx1}$, optionally substituted phenyl, or $C_1$-$C_6$ alkyl wherein the $C_1$-$C_6$ alkyl is optionally substituted with $OR^{ax1}$ In certain embodiments, $R^{x1}$ is hydrogen, —C(O)$OR^{ax1}$, or —C(O)$NR^{bx1}R^{cx1}$. In certain embodiments, $R^{x1}$ is hydrogen or unsubstituted $C_1$-$C_6$ alkyl. In certain embodiments, $R^{x1}$ is —C(O)$OR^{ax1}$, —C(O)$NR^{bx1}R^{cx1}$, or $C_1$-$C_6$ alkyl substituted with $OR^{ax1}$. In certain embodiments, $R^{x1}$ is hydrogen or —C(O)$NR^{bx1}R^{cx1}$. In certain embodiments, $R^{x1}$ is hydrogen. $R^{ax1}$, $R^{bx1}$, $R^{cx1}$, $R^{dx1}$, and $G^{x1}$, are as disclosed in the Summary. For example, $R^{ax1}$ and $R^{bx1}$, are each independently hydrogen, $C_1$-$C_6$ alkyl (e.g. methyl, ethyl, isopropyl), or $C_1$-$C_6$ haloalkyl (e.g. trifluoromethyl). In certain embodiments, $R^{ax1}$ and $R^{bx1}$, are each independently hydrogen or $C_1$-$C_6$ alkyl (e.g. methyl, ethyl, isopropyl). In certain embodiments, $R^{ax1}$ and $R^{bx1}$, are each independently hydrogen, methyl, or ethyl. $R^{cx1}$, for example, is hydrogen, $C_1$-$C_6$ alkyl (e.g. methyl, ethyl, isopropyl), or $C_1$-$C_6$ haloalkyl (e.g. trifluoromethyl, 2,2,2 trifluoroethyl), wherein the $C_1$-$C_6$ alkyl is optionally substituted with $G^{x1}$. In certain embodiments, $R^{cx1}$, for example, is hydrogen or $C_1$-$C_6$ alkyl (e.g. methyl, ethyl, isopropyl). In certain embodiments, $R^{cx1}$, for example, is $G^{x1}$ or $C_1$-$C_6$ alkyl substituted with $G^{x1}$; wherein $G^{x1}$ is thiazolyl, morpholinyl, piperazinyl, tetrahydrofuranyl, or phenyl, each of which is optionally substituted with 1, 2, or 3 substituents selected from the group consisting of $C_1$-$C_3$ alkyl and $C_1$-$C_3$ haloalkyl.

$X^2$ is as disclosed in the Summary. For example, in certain embodiments, $X^2$ is N. In certain embodiments, $X^2$ is $CR^{x2}$. $R^{x2}$ is as defined in the Summary or embodiments herein. In certain embodiments, $X^2$ is C(O)H or $C_1$-$C_6$ alkyl substituted with one $G^{x2}$. In certain embodiments, $X^2$ is C(O)H or $C_1$-$C_3$ alkyl substituted with one $G^{x2}$ wherein $G^{x2}$ is piperidinyl, piperazinyl, or morpholinyl, each of which is optionally substituted with 1, 2, or 3 $C_1$-$C_3$ alkyl. In certain embodiments, $R^{x2}$ is hydrogen or unsubstituted $C_1$-$C_6$ alkyl (e.g. methyl). In certain embodiments, $R^{x2}$ is hydrogen.

$Y^1$ is N or $CR^u$. For example, in certain embodiments, $Y^1$ is N. In certain embodiments, $Y^1$ is $CR^u$. $R^u$ is as defined in the Summary and embodiments herein. For example, in certain embodiments, $R^u$ is hydrogen or $C_1$-$C_6$ alkyl (e.g. methyl). In certain embodiments, $R^u$ is hydrogen or $C_1$-$C_3$ alkyl (e.g. methyl). In certain embodiments, $R^u$ is hydrogen or methyl. In certain embodiments, $R^u$ is hydrogen.

$A^1$, $A^2$, $A^3$, and $A^4$ are as defined in the Summary. In certain embodiments, $A^1$ is $CR^1$, $A^2$ is $CR^2$, $A^3$ is $CR^3$, and $A^4$ is $CR^4$; or one of $A^1$, $A^2$, $A^3$, and $A^4$ is N. In certain embodiments, $A^1$ is $CR^1$, $A^2$ is $CR^2$, $A^3$ is $CR^3$, and $A^4$ is $CR^4$. In certain embodiments, one of $A^1$, $A^2$, $A^3$, and $A^4$ is N. In the embodiments that one of $A^1$, $A^2$, $A^3$, and $A^4$ is N, example of a group of compound includes, but is not limited to, those wherein $A^1$ is $CR^1$, $A^2$ is $CR^2$, $A^3$ is $CR^3$, and $A^4$ is N. In certain embodiments, two of $A^1$, $A^2$, $A^3$, and $A^4$ are N, for example, $A^1$ is N, $A^2$ is $CR^2$, $A^3$ is N, and $A^4$ is $CR^4$; or for example, $A^1$ is N, $A^2$ is $CR^2$, $A^3$ is $CR^3$, and $A^4$ is N. In certain embodiments, three of $A^1$, $A^2$, $A^3$, and $A^4$ are N, for example, $A^1$ is N, $A^2$ is $CR^2$, $A^3$ is N, and $A^4$ is N.

$R^1$, $R^3$, and $R^4$, are as defined in the Summary. For example, in certain embodiments, $R^1$, $R^3$, and $R^4$, are each independently hydrogen, $C_1$-$C_6$ alkyl (e.g. methyl, ethyl), halogen (e.g. Br, F, or Cl), or CN. For example, in certain embodiments, $R^1$, $R^3$, and $R^4$, are each independently hydrogen, $C_1$-$C_6$ alkyl (e.g. methyl, ethyl), or $C_1$-$C_6$ haloalkyl (e.g. trifluoromethyl). In certain embodiments, $R^1$, $R^3$, and $R^4$, are each independently hydrogen or methyl. In certain embodiments, $R^1$, $R^3$, and $R^4$ are hydrogen.

$R^2$ is as disclosed in the Summary. In certain embodiment, $R^2$, for example, is halogen, haloalkyl (e.g. $CF_3$), or —($C_1$-$C_3$ alkylenyl)-CN. In certain embodiments, $R^2$, for example, is hydrogen, $C_1$-$C_6$ alkyl, $NO_2$, $G^{2a}$, —S(O)$_2R^{2d}$, —S(O)$_2NR^{2b}R^{2c}$, —C(O)$R^{2d}$, —C(O)$OR^{2a}$, —C(O)$NR^{2b}R^{2c}$, —$NR^{2b}R^{2c}$, —N($R^{2e}$)C(O)$R^{2d}$, —N($R^{2e}$)S(O)$_2R^{2d}$, —N($R^{2e}$)S(O)$_2NR^{2b}R^{2c}$, —($C_1$-$C_6$ alkylenyl)-$G^{2a}$, —($C_1$-$C_6$ alkylenyl)-$OR^{2a}$, —($C_1$-$C_6$ alkylenyl)-S(O)$_2R^{2d}$, —($C_1$-$C_6$ alkylenyl)-S(O)$_2NR^{2b}$, —($C_1$-$C_6$ alkylenyl)-C(O)$R^{2d}$, —($C_1$-$C_6$ alkylenyl)-C(O)$OR^{2a}$, —($C_1$-$C_6$ alkylenyl)-C(O)$NR^{2b}R^{2c}$, —($C_1$-$C_6$ alkylenyl)-$NR^{2b}R^{2c}$, —($C_1$-$C_6$ alkylenyl)-N($R^{2e}$)C(O)$R^{2d}$, —($C_1$-$C_6$ alkylenyl)-N($R^{2e}$)S(O)$_2R^{2d}$, or —($C_1$-$C_6$ alkylenyl)-N($R^{2e}$)S(O)$_2NR^{2b}R^{2c}$. In certain embodiments, $R^2$, for example, is hydrogen, or $NO_2$. In certain embodiments, $R^2$, for example, is $G^{2a}$, —S(O)$_2R^{2d}$, —S(O)$_2NR^{2b}R^{2c}$, —C(O)$R^{2d}$, —C(O)$OR^{2a}$, —C(O)$NR^{2b}R^{2c}$, —$NR^{2b}R^{2c}$, —N($R^{2e}$)C(O)$R^{2d}$, —N($R^{2e}$)S(O)$_2R^{2d}$, —N($R^{2e}$)S(O)$_2NR^{2b}R^2$, —($C_1$-$C_6$ alkylenyl)-$G^{2a}$, —($C_1$-$C_6$ alkylenyl)-$OR^{2a}$, —($C_1$-$C_6$ alkylenyl)-S(O)$_2R^{2d}$, —($C_1$-$C_6$ alkylenyl)-S(O)$_2NR^{2b}R^{2c}$, —($C_1$-$C_6$ alkylenyl)-C(O)$R^{2d}$, —($C_1$-$C_6$ alkylenyl)-C(O)$OR^{2a}$, —($C_1$-$C_6$ alkylenyl)-C(O)$NR^{2b}R^{2c}$, —($C_1$-$C_6$ alkylenyl)-$NR^{2b}R^{2c}$, —($C_1$-$C_6$ alkylenyl)-N($R^{2e}$)C(O)$R^{2d}$, —($C_1$-$C_6$ alkylenyl)-N($R^{2e}$)S(O)$_2R^{2d}$, or —($C_1$-$C_6$ alkylenyl)-N($R^{2e}$)S(O)$_2NR^{2b}R^{2c}$. In certain embodiments, $R^2$, for example, is —S(O)$_2R^{2d}$, —S(O)$_2$NR$^{2b}$R$^{2c}$, —C(O)R$^{2d}$, —C(O)NR$^{2b}$R$^{2c}$, —N(R$^{2e}$)C(O)R$^{2d}$, —N(R$^{2e}$)S(O)$_2$R$^{2d}$, —N(R$^{2e}$)S(O)$_2$NR$^{2b}$R$^{2c}$, —(C$_1$-C$_6$ alkylenyl)-S(O)$_2$R$^{2d}$, —(C$_1$-C$_6$ alkylenyl)-S(O)$_2$NR$^{2b}$R$^{2c}$, —(C$_1$-C$_6$ alkylenyl)-C(O)R$^{2d}$, —(C$_1$-C$_6$ alkylenyl)-C(O)NR$^{2b}$R$^2$, —(C$_1$-C$_6$ alkylenyl)-N(R$^{2e}$)C(O)R$^{2d}$, —(C$_1$-C$_6$ alkylenyl)-N(R$^{2e}$)S(O)$_2$R$^{2d}$, or —(C$_1$-C$_6$ alkylenyl)-N(R$^{2e}$)S(O)$_2$NR$^{2b}$R$^{2c}$. In certain embodiments, R$^2$, for example, is —S(O)$_2$R$^{2d}$, —S(O)$_2$NR$^{2b}$R$^{2c}$, —N(R$^{2e}$)S(O)$_2$R$^{2d}$, or —N(R$^{2e}$)S(O)$_2$NR$^{2b}$R$^{2c}$. In certain embodiment, R$^2$, for example, is —S(O)$_2$R$^{2d}$, —S(O)$_2$NR$^{2b}$R$^{2c}$, —N(R$^{2e}$)S(O)$_2$R$^{2d}$, or —(C$_1$-C$_6$ alkylenyl)-S(O)$_2$R$^{2d}$. In certain embodiment, R$^2$, for example, is —(C$_1$-C$_3$ alkylenyl)-S(O)$_2$R$^{2d}$ wherein R$^{2d}$ is C$_1$-C$_3$ alkyl. In certain embodiment, R$^2$, for example, is —(CH$_2$)—S(O)$_2$R$^{2d}$ wherein R$^{2d}$ is methyl or ethyl.

G$^{2a}$, R$^{2a}$, R$^{2b}$, R$^{2c}$, R$^{2d}$, and R$^{2e}$ are as disclosed in the Summary and embodiments herein below.

In the embodiments wherein R$^2$ is G$^{2a}$, G$^{2a}$ is as disclosed in the Summary and embodiments herein. For example, in certain embodiments, G$^{2a}$ is an optionally substituted heterocycle. In certain embodiments, G$^{2a}$ is an optionally substituted monocyclic heterocycle. In certain embodiments, G$^{2a}$ is 1,2-dioxido-1,2-thiazolidin-2-yl or tetrahydropyridinyl, each of which is optionally substituted. In certain embodiments, G$^{2a}$ is optionally substituted 1,2-dioxido-1,2-thiazolidin-2-yl. In certain embodiment, G$^{2a}$ is aryl or heteroaryl, each of which is optionally substituted. In certain embodiments, G$^{2a}$ is optionally substituted phenyl. In certain embodiments, G$^{2a}$ is pyridinyl or pyrazolyl, each of which is optionally substituted. In certain embodiments, G$^{2a}$ is unsubstituted.

In the embodiments wherein R$^2$ is —(C$_1$-C$_6$ alkylenyl)-G$^{2a}$, G$^{2a}$ is as disclosed in the Summary and embodiments herein. For example, in certain embodiments, G$^{2a}$ is a heterocycle or a heteroaryl, each of which is optionally substituted. In certain embodiments, G$^{2a}$ is a monocyclic heterocycle or a monocyclic heteroaryl, each of which is optionally substituted. In certain embodiments, G$^{2a}$ is 1,1-dioxido-1,2-thiazolidin-2-yl, pyrrolidinyl, morpholinyl, or pyrazolyl, each of which is optionally substituted. In certain embodiments, G$^{2a}$ is unsubstituted. In certain embodiments, G$^{2a}$ is optionally substituted phenyl.

Where G$^{2a}$ group is optionally substituted, it is, for example, optionally substituted with 1, 2, 3, 4, or 5 R$^v$. R$^v$ is as described in the Summary and herein, for example, R$^v$ is C$_1$-C$_6$ alkyl (e.g. methyl), halogen (e.g. F, Cl), C$_1$-C$_6$ haloalkyl, —CN, —NR$^j$R$^k$, or —C(O)OR$^h$; or for example, R$^v$ is C$_1$-C$_6$ alkyl (e.g. methyl), halogen (e.g. F, Cl), or C$_1$-C$_6$ haloalkyl.

In the embodiments wherein R$^2$ is —S(O)$_2$R$^{2d}$, R$^{2d}$ is as disclosed in the Summary and embodiments herein. In certain embodiments, R$^{2d}$ is C$_1$-C$_6$ haloalkyl (e.g. CF$_3$), G$^{2b}$, unsubstituted C$_1$-C$_6$ alkyl (e.g. methyl, ethyl, isopropyl), or C$_1$-C$_6$ alkyl substituted with one G$^{2b}$ group; wherein G$^{2b}$ is phenyl, monocyclic cycloalkyl, or monocyclic heterocycle, each of which is optionally substituted. In some such embodiments, the G$^{2b}$ group is optionally substituted with 1, 2, or 3 R$^v$ groups wherein R$^v$ is as described in the Summary and herein, for example, each R$^v$ is independently C$_1$-C$_6$ alkyl (e.g. methyl), halogen (e.g. F, Cl), C$_1$-C$_6$ haloalkyl, —OR$^h$, —CN, or —NR$^j$R$^k$. In certain embodiments, R$^{2d}$ is C$_1$-C$_6$ haloalkyl or unsubstituted C$_1$-C$_6$ alkyl. In certain embodiments, R$^{2d}$ is methyl or ethyl.

In the embodiments wherein R$^2$ is —S(O)$_2$NR$^{2b}$R$^{2c}$, R$^{2b}$ and R$^{2c}$ are as disclosed in the Summary and embodiments herein. For example, in certain embodiments, R$^{2b}$ is hydrogen or unsubstituted C$_1$-C$_6$ alkyl (e.g. methyl, ethyl), and R$^{2c}$ is hydrogen, unsubstituted C$_1$-C$_6$ alkyl (e.g. methyl, ethyl), or C$_1$-C$_6$ haloalkyl (e.g. 2,2,2-trifluoroethyl, 2-fluoroethyl). In certain embodiments, R$^{2b}$ is hydrogen, and R$^{2c}$ is optionally substituted phenyl, or R$^{2c}$ is —C$_1$-C$_3$ alkyl substituted with one G$^{2b}$ group wherein G$^{2b}$ is optionally substituted pyridinyl.

In the embodiments wherein R$^2$ is —C(O)R$^{2d}$, R$^{2d}$ is as disclosed in the Summary and embodiments herein. For example, in certain embodiments, R$^{2d}$ is G$^{2b}$ wherein G$^{2b}$ is as disclosed in the Summary and embodiments herein. For example, in certain embodiments, G$^{2b}$ is an optionally substituted heterocycle. In certain embodiments, G$^{2b}$ is an optionally substituted monocyclic heterocycle. In certain embodiments, G$^{2b}$ is 1,1-dioxidothiomorpholin-4-yl, piperazinyl, piperidinyl, pyrrolidin-1-yl, or morpholin-4-yl, each of which is optionally substituted. Each G$^{2b}$ is optionally substituted as described in the Summary and embodiments herein. For example, each G$^{2b}$ is independently unsubstituted or substituted with 1, 2, or 3 R$^v$. R$^v$ is as described in the Summary and embodiments herein. For example, each R$^v$ is independently C$_1$-C$_6$ alkyl (e.g. methyl), oxo, N(H)C(O)O(C$_1$-C$_6$ alkyl), —CH$_2$—C(O)NR$^j$R$^k$, —C(O)-monocyclic heterocycle, or —C(O)-monocyclic heteroaryl. In certain embodiments, each R$^v$ is independently C$_1$-C$_6$ alkyl (e.g. methyl), oxo, or N(H)C(O)O(C$_1$-C$_6$ alkyl).

In the embodiments wherein R$^2$ is —C(O)OR$^{2a}$, R$^{2a}$ is as disclosed in the Summary and embodiments herein. For example, in certain embodiments, R$^{2a}$ is hydrogen or unsubstituted C$_1$-C$_6$ alkyl (e.g. methyl, ethyl).

In the embodiments wherein R$^2$ is —C(O)NR$^{2b}$R$^{2c}$, R$^{2b}$ and R$^{2c}$ are as disclosed in the Summary and embodiments herein. For example, in certain embodiments, R$^{2b}$ is hydrogen or unsubstituted C$_1$-C$_6$ alkyl (e.g. methyl), and R$^{2c}$ is hydrogen, G$^{2b}$, C$_1$-C$_6$ haloalkyl (e.g. 2,2-difluoroethyl), C$_1$-C$_6$ alkyl (e.g. methyl, ethyl) wherein the C$_1$-C$_6$ alkyl is optionally substituted with one substituent selected from the group consisting of —OR$^{z1}$, NR$^{z1}$R$^{z2}$, and G$^{2b}$. R$^{z1}$, R$^{z2}$, and G$^{2b}$ are as defined in the Summary and embodiments herein. For example, in certain embodiments, G$^{2b}$ is optionally substituted phenyl. In certain embodiments, G$^{2b}$ is a cycloalkyl, a heteroaryl, or a heterocycle, each of which is optionally substituted. In certain embodiments, G$^{2b}$ is a monocyclic cycloalkyl, a monocyclic heteroaryl, or a monocyclic heterocycle, each of which is optionally substituted. In certain embodiments, G$^{2b}$ is pyridinyl, pyrimidinyl, indazolyl, indolyl, cyclopentyl, thiazolyl, 1,1-dioxidotetrahydrothienyl, tetrahydrofuranyl, piperazinyl, piperidinyl, or pyrrolidinyl, each of which is optionally substituted. Each G$^{2b}$ is optionally substituted as described in the Summary and embodiments herein. For example, each G$^{2b}$ is independently unsubstituted or substituted with 1, 2, or 3 R$^v$. R$^v$ is as described in the Summary and embodiments herein. For example, each R$^v$ is independently C$_1$-C$_6$ alkyl (e.g. methyl), C$_1$-C$_6$ haloalkyl, —OR$^h$, —C(O)OR$^h$, —S(O)$_2$R$^h$, halogen, or oxo. In certain embodiments, each R$^v$ is independently C$_1$-C$_6$ alkyl (e.g. methyl) or oxo.

In the embodiments wherein R$^2$ is —NR$^{2b}$R$^{2c}$, R$^{2b}$ and R$^{2c}$ are as disclosed in the Summary and embodiments herein. For example, in certain embodiments, R$^{2b}$ and R$^{2c}$ are each independently hydrogen or unsubstituted C$_1$-C$_6$ alkyl (e.g. methyl, ethyl).

In the embodiments wherein R$^2$ is —N(R$^{2e}$)C(O)R$^{2d}$, R$^{2d}$ and R$^{2e}$ are as disclosed in the Summary and embodiments herein. For example, in certain embodiments, R$^{2e}$ hydrogen or unsubstituted C$_1$-C$_6$ alkyl (e.g. methyl, ethyl), and R$^{2d}$ is unsubstituted C$_1$-C$_6$ alkyl (e.g. methyl, ethyl, tert-butyl) or C$_1$-C$_6$ haloalkyl (e.g. 2,2,2-trifluoroethyl).

In the embodiments wherein $R^2$ is —N($R^{2e}$)S(O)$_2R^{2d}$, $R^{2d}$ and $R^{2e}$ are as disclosed in the Summary and embodiments herein. For example, in certain embodiments, $R^{2e}$ is hydrogen or unsubstituted $C_1$-$C_6$ alkyl (e.g. methyl, ethyl), and $R^{2d}$ is unsubstituted $C_1$-$C_6$ alkyl (e.g. methyl, ethyl) or $C_1$-$C_6$ haloalkyl (e.g. 2,2,2-trifluoroethyl, 2-fluoroethyl, 2,2-dfluoroethyl). In certain embodiments, $R^{2e}$ is hydrogen and $R^{2d}$ is unsubstituted $C_1$-$C_6$ alkyl (e.g. methyl, ethyl). In certain embodiments, $R^{2e}$ is $C_1$-$C_6$ haloalkyl, or $C_1$-$C_6$ alkyl substituted with one substituent selected from the group consisting of —$OR^{z1}$, —$NR^{z1}R^{z2}$, and $G^{2b}$, and $R^{2d}$ is unsubstituted $C_1$-$C_6$ alkyl (e.g. methyl, ethyl). In certain embodiments, $R^{2e}$ is $C_1$-$C_6$ haloalkyl (e.g. 3,3,3-trifluoropropyl), or $C_1$-$C_3$ alkyl substituted with one substituent selected from the group consisting of —$OR^{z1}$, —$NR^{z1}R^{z2}$, and $G^{2b}$, and $R^{2d}$ is unsubstituted $C_1$-$C_6$ alkyl (e.g. methyl, ethyl), wherein $G^{2b}$ is monocyclic cycloalkyl (e.g. cyclopropyl), monocyclic heterocycle (e.g. pyrrolidinyl or tetrahydrofuranyl), or monocyclic heteroaryl (e.g. pyridinyl), each of which is optionally substituted.

In the embodiments wherein $R^2$ is —N($R^{2e}$)S(O)$_2$N$R^{2b}R^{2c}$, $R^{2b}$, $R^{2c}$, and $R^{2e}$ are as disclosed in the Summary and embodiments herein. For example, in certain embodiments, $R^{2b}$, $R^{2c}$, and $R^{2e}$ are each independently hydrogen or unsubstituted $C_1$-$C_6$ alkyl (e.g. methyl, ethyl).

In the embodiments wherein $R^2$ is —($C_1$-$C_6$ alkylenyl)-O$R^{2a}$, $R^{2a}$ is as described in the Summary and embodiments herein. In certain embodiments $R^{2a}$ is hydrogen. In certain embodiments, $R^2$ is —CH$_2$—OH or —CH$_2$CH$_2$—OH.

In the embodiments wherein $R^2$ is —($C_1$-$C_6$ alkylenyl)-C(O)O$R^{2a}$, $R^{2a}$ is as described in the Summary and embodiments herein. For example, $R^{2a}$ is hydrogen or unsubstituted $C_1$-$C_6$ alkyl (e.g. methyl, ethyl).

In the embodiments wherein $R^2$ is —($C_1$-$C_6$ alkylenyl)-C(O)N$R^{2b}R^{2c}$, $R^{2b}$ and $R^{2c}$ are as disclosed in the Summary and embodiments herein. For example, in certain embodiments, $R^{2b}$ and $R^{2c}$ are each independently hydrogen or unsubstituted $C_1$-$C_6$ alkyl (e.g. methyl, ethyl).

In the embodiments wherein $R^2$ is —($C_1$-$C_6$ alkylenyl)-N($R^{2e}$)C(O)$R^{2d}$, $R^{2d}$ and $R^{2e}$ are as disclosed in the Summary and embodiments herein. For example, in certain embodiments, $R^{2e}$ is hydrogen or unsubstituted $C_1$-$C_6$ alkyl (e.g. methyl, ethyl), and $R^{2d}$ is $C_1$-$C_6$ alkyl (e.g. methyl) optionally substituted with C(O)O$R^{z1}$.

In the embodiments wherein $R^2$ is —($C_1$-$C_6$ alkylenyl)-S(O)$_2R^{2d}$, $R^{2d}$ is as disclosed in the Summary and embodiments herein. For example, in certain embodiments, $R^{2d}$ is optionally substituted phenyl or unsubstituted $C_1$-$C_6$ alkyl. In certain embodiments, $R^{2d}$ is unsubstituted $C_1$-$C_3$ alkyl. In certain embodiments, $R^{2d}$ is methyl or ethyl. In certain embodiments, $R^{2d}$ is optionally substituted phenyl.

$L^1$ is as set forth in the Summary and embodiments herein. For example, in certain embodiments, $L^1$ is absent, CH$_2$, C(H)(OH), C(O), (CH$_2$)$_m$O, or (CH$_2$)$_m$N($R^z$). For example, in certain embodiments, $L^1$ is CH$_2$, C(O), (CH$_2$)$_m$O, or (CH$_2$)$_m$N($R^z$). In certain embodiments, $L^1$ is (CH$_2$)$_m$O or (CH$_2$)$_m$N($R^z$). In certain embodiments, $L^1$ is (CH$_2$)$_m$O. In certain embodiments, $L^1$ is (CH$_2$)$_m$N($R^z$).

The variable, m, is 0 or 1. In certain embodiments, m is 0. In certain embodiments, m is 1.

$R^z$, is as set forth in the Summary and embodiments herein. For example, $R^z$ is hydrogen or $C_1$-$C_3$ alkyl. In certain embodiments, $R^z$ is hydrogen.

$G^1$ is as set forth in the Summary and embodiments herein. For example, $G^1$ is $G^{1a}$. In certain embodiments, $G^1$ is —($C_1$-$C_6$ alkylenyl)-$G^{1a}$. In certain embodiments, $G^1$ is $C_1$-$C_6$ alkyl or alkoxyalkyl. In certain embodiments, $G^1$ is $C_1$-$C_6$ alkyl (e.g. methyl, ethyl, isobutyl, or 2,2-dimethylpropyl). In certain embodiments, $G^1$ is alkoxyalkyl.

$G^{1a}$ is as defined in the Summary and embodiments herein. For example, in certain embodiments $G^{1a}$ is aryl, heterocycle, or cycloalkyl, each of which is optionally substituted. In certain embodiments $G^{1a}$ is aryl, heterocycle, heteroaryl, or cycloalkyl, each of which is optionally substituted. In certain embodiments $G^{1a}$ is optionally substituted aryl. In certain embodiments $G^{1a}$ is optionally substituted heterocycle. In certain embodiments $G^{1a}$ is optionally substituted heteroaryl. In certain embodiments $G^{1a}$ is optionally substituted cycloalkyl.

In the embodiments wherein $G^{1a}$ is optionally substituted aryl, $G^{1a}$, for example, is phenyl, naphthyl, or indanyl, each of which is optionally substituted. In certain embodiments, $G^{1a}$, for example, is optionally substituted phenyl. In certain embodiments, $G^{1a}$, for example, is phenyl optionally substituted with one or two halogen (e.g. F). In certain embodiments, $G^{1a}$ is

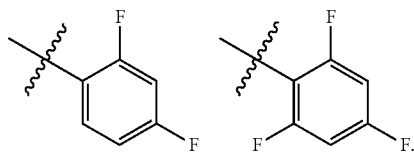 [SMILES: *c1ccc(F)cc1F ; *c1c(F)cc(F)cc1F]

In certain embodiments, $G^{1a}$ is unsubstituted phenyl or

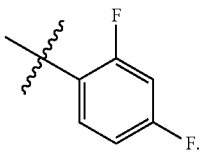 [SMILES: *c1ccc(F)cc1F]

In the embodiments wherein $G^{1a}$ is optionally substituted heterocycle, examples of the heterocycle include, but are not limited to, oxetanyl, tetrahydrofuranyl (e.g. tetrahydrofuran-2-yl, tetrahydrofuran-3-yl), pyrrolidinyl, morpholinyl, piperidinyl, tetrahydrothiopyranyl, and tetrahydropyranyl (e.g. tetrahydropyran-4-yl, tetrahydropyran-3-yl), each of which (including the exemplary rings) is optionally substituted.

In the embodiments wherein $G^{1a}$ is optionally substituted heteroaryl, $G^{1a}$, for example, is pyrazolyl, pyridinyl, pyrimidinyl, 2,1,3-benzothiadiazolyl, quinolinyl, or isoquinolinyl, each of which is optionally substituted.

In the embodiments wherein $G^{1a}$ is optionally substituted cycloalkyl (e.g. optionally substituted monocyclic cycloalkyl), examples of the cycloalkyl include, but are not limited to, cyclopropyl, cyclobutyl, cyclopentyl, cyclohexyl, cycloheptyl, bicyclo[2.2.1]heptyl, and adamantyl, each of which is optionally substituted. In certain embodiments, $G^{1a}$ is optionally substituted cycloalkyl. In certain embodiments, $G^{1a}$ is unsubstituted cycloalkyl. In certain embodiments, $G^{1a}$ is a substituted cycloalkyl. In certain embodiments, $G^{1a}$ is cyclohexyl optionally substituted with 1 or two substituents selected from the group consisting of $C_1$-$C_3$ alkyl (e.g. methyl), O($C_1$-$C_3$ alkyl), and halogen. In certain embodiments, $G^{1a}$ is cyclohexyl optionally substituted with 1 or two substituents selected from the group consisting of methyl and O(CH$_3$). In certain embodiments, $G^{1a}$ is 4,4-difluorocyclohexyl. In certain embodiments, $G^{1a}$ is optionally substituted cyclopropyl. In certain embodiments, $G^{1a}$ is unsubstituted cyclopropyl.

The optional substituents of $G^{1a}$ are as set forth in the Summary and embodiments herein. For example, each $G^{1a}$ is independently unsubstituted or substituted with 1, 2, 3, 4, or 5 $R^w$. In certain embodiments, $R^w$ is, for example, $C_1$-$C_6$ alkyl—CN, halogen (e.g. F, Cl), oxo, $C_1$-$C_6$ haloalkyl (e.g. trifluoromethyl), —$OR^h$, $NR^jR^k$, —$S(O)_2R^h$, —$C(O)R^h$, —$C(O)OR^h$, —$C(O)NR^jR^k$, —($C_1$-$C_3$ alkylenyl)-$OR^h$, or —($C_1$-$C_3$ alkylenyl)$C(O)NR^jR^k$. In certain embodiments, $R^w$ is, for example, $C_1$-$C_6$ alkyl, —CN, halogen (e.g. F, Cl), or $C_1$-$C_6$ haloalkyl (e.g. trifluoromethyl). In certain embodiments, $R^w$ is halogen, —$OR^h$, or $C_1$-$C_6$ alkyl. In certain embodiments, $R^w$ is halogen. In certain embodiments, $R^w$ is F.

It is appreciated that compounds of formula (I) with combinations of the above embodiments, including particular, more particular and preferred embodiments are contemplated. All embodiments of compounds of formula (I) formed by combining the substituent embodiments discussed above are within the scope of Applicants' invention, and some illustrative embodiments of the compounds of formula (I) are provided below.

Accordingly, one aspect of the invention is directed to a group of compounds of formula (I) wherein L is $(CH_2)_mO$ and $G^1$ is $G^{1a}$ and $G^{1a}$ is as disclosed in the Summary and embodiments herein above.

Other examples of a group of compounds of formula (I) is directed to those wherein $Y^1$ is N; $X^1$ is $CR^{x1}$; and $X^2$ is $CR^{x2}$.

Yet other examples of a group of compounds of formula (I) is directed to those wherein $Y^1$ is N; $X^1$ is $CR^{x1}$; $X^2$ is $CR^{x2}$, and $R^y$ is methyl.

Other examples of a group of compounds of formula (I) is directed to those wherein $Y^1$ is N; $X^1$ is $CR^{x1}$; $X^2$ is $CR^{x2}$, $R^y$ is methyl, and $L^1$ is $CH_2$, $C(O)$, $(CH_2)_mO$, or $(CH_2)_mN(R^z)$. In certain embodiments, $L^1$ is $(CH_2)_mO$. In yet other embodiments, $L^1$ is $(CH_2)_mO$ and m is 0. In yet other embodiments, $L^1$ is $(CH_2)_mO$ and m is 1. In certain embodiments, $L^1$ is $(CH_2)_mN(R^z)$. In certain embodiments, $L^1$ is $(CH_2)_mN(R^z)$ and m is 0. In yet other embodiments, $L^1$ is $(CH_2)_mN(R^z)$ and m is 1. $R^z$ has values as described in the Summary and embodiments herein above.

Other examples of a group of compounds of formula (I) is directed to those wherein $Y^1$ is N; $X^1$ is $CR^{x1}$; $X^2$ is $CR^{x2}$, $R^y$ is methyl, $L^1$ is $(CH_2)_mO$, and $G^1$ is —($C_1$-$C_6$ alkylenyl)-$G^{1a}$ wherein $G^{1a}$ is optionally substituted phenyl.

Other examples of a group of compounds of formula (I) is directed to those wherein $Y^1$ is N; $X^1$ is $CR^{x1}$; $X^2$ is $CR^{x2}$, $R^y$ is methyl, $L^1$ is $(CH_2)_mO$, and $G^1$ is —($C_1$-$C_6$ alkylenyl)-$G^{1a}$ wherein $G^{1a}$ is optionally substituted cycloalkyl. In some embodiments, $G^{1a}$ is unsubstituted cyclopropyl.

Other examples of a group of compounds of formula (I) is directed to those wherein $Y^1$ is N; $X^1$ is $CR^{x1}$; $X^2$ is $CR^{x2}$, $R^y$ is methyl, $L^1$ is $(CH_2)_mO$, and $G^1$ is $G^{1a}$.

Other examples of a group of compounds of formula (I) is directed to those wherein $Y^1$ is N; $X^1$ is $CR^{x1}$; $X^2$ is $CR^{x2}$, $R^y$ is methyl, $L^1$ is $(CH_2)_mO$, $G^1$ is $G^{1a}$, and $G^{1a}$ is optionally substituted aryl.

Other examples of a group of compounds of formula (I) is directed to those wherein $Y^1$ is N; $X^1$ is $CR^{x1}$; $X^2$ is $CR^{x2}$, $R^y$ is methyl, $L^1$ is $(CH_2)_mO$, $G^1$ is $G^{1a}$, and $G^{1a}$ is optionally substituted phenyl.

Other examples of a group of compounds of formula (I) is directed to those wherein $Y^1$ is N; $X^1$ is $CR^{x1}$; $X^2$ is $CR^{x2}$, $R^y$ is methyl, $L^1$ is $(CH_2)_mO$, $G^1$ is $G^{1a}$, and $G^{1a}$ is optionally substituted cycloalkyl (e.g. optionally substituted monocyclic cycloalkyl).

Other examples of a group of compounds of formula (I) is directed to those wherein $Y^1$ is N; $X^1$ is $CR^{x1}$; $X^2$ is $CR^{x2}$, $R^y$ is methyl, $L^1$ is $(CH_2)_mO$, $G^1$ is $G^{1a}$, and $G^{1a}$ is optionally substituted heterocycle (e.g. optionally substituted monocyclic heterocycle).

Other examples of a group of compounds of formula (I) is directed to those wherein $Y^1$ is $CR^u$; $X^1$ is $CR^{x1}$; and $X^2$ is $CR^{x2}$.

Yet other examples of a group of compounds of formula (I) is directed to those wherein $Y^1$ is $CR^u$; $X^1$ is $CR^{x1}$; $X^2$ is $CR^{x2}$, and $R^y$ is methyl.

Other examples of a group of compounds of formula (I) is directed to those wherein $Y^1$ is $CR^u$; $X^1$ is $CR^{x1}$; $X^2$ is $CR^{x2}$, $R^y$ is methyl, and $L^1$ is $CH_2$, $C(O)$, $(CH_2)_mO$, or $(CH_2)_mN(R^z)$. In certain embodiments, $L^1$ is $(CH_2)_mO$. In yet other embodiments, $L^1$ is $(CH_2)_mO$ and m is 0. In yet other embodiments, $L^1$ is $(CH_2)_mO$ and m is 1. In certain embodiments, $L^1$ is $(CH_2)_mN(R^z)$. In certain embodiments, $L^1$ is $(CH_2)_mN(R^z)$ and m is 0. In yet other embodiments, $L^1$ is $(CH_2)_mN(R^z)$ and m is 1. $R^z$ has meaning as described in the Summary and embodiments herein above.

Other examples of a group of compounds of formula (I) is directed to those wherein $Y^1$ is $CR^u$; $X^1$ is $CR^{x1}$; $X^2$ is $CR^{x2}$, $R^y$ is methyl, $L^1$ is $(CH_2)_mN(R^z)$, and $G^1$ is $G^{1a}$ or —($C_1$-$C_6$ alkylenyl)-$G^{1a}$ wherein $G^{1a}$ is phenyl, monocyclic heterocycle (e.g. tetrahydrofuranyl), or monocyclic cycloalkyl (e.g. cyclopropyl, cyclopentyl, cyclohexyl), each of which (including the exemplary rings) is optionally substituted.

Other examples of a group of compounds of formula (I) is directed to those wherein $Y^1$ is $CR^u$; $X^1$ is $CR^{x1}$; $X^2$ is $CR^{x2}$, $R^y$ is methyl, $L^1$ is $(CH_2)_mN(R^z)$, m is 0, $R^z$ is hydrogen, and $G^1$ is $G^{1a}$ wherein $G^{1a}$ is phenyl, monocyclic heterocycle (e.g. tetrahydrofuranyl), or monocyclic cycloalkyl (e.g. cyclopropyl, cyclopentyl, cyclohexyl), each of which (including the exemplary rings) is optionally substituted.

Other examples of a group of compounds of formula (I) is directed to those wherein $Y^1$ is $CR^u$; $X^1$ is $CR^{x1}$; $X^2$ is $CR^{x2}$, $R^y$ is methyl, $L^1$ is $(CH_2)_mN(R^z)$, m is 0, $R^z$ is hydrogen, and $G^1$ is —($C_1$-$C_6$ alkylenyl)-$G^{1a}$ wherein $G^{1a}$ is monocyclic heterocycle (e.g. tetrahydrofuranyl), or monocyclic cycloalkyl (e.g. cyclopropyl, cyclopentyl, cyclohexyl), each of which (including the exemplary rings) is optionally substituted. In some embodiments, $G^1$ is —($C_1$-$C_3$ alkylenyl)-$G^{1a}$ wherein $G^{1a}$ is optionally substituted monocyclic cycloalkyl (e.g. cyclopropyl, cyclopentyl, cyclohexyl, each of which is optionally substituted). In some embodiments, $G^1$ is —($CH_2$)-$G^{1a}$ wherein $G^{1a}$ is optionally substituted monocyclic cycloalkyl (e.g. cyclopropyl, cyclopentyl, cyclohexyl, each of which is optionally substituted). In certain embodiments, $G^{1a}$ is optionally substituted is monocyclic heterocycle (e.g. optionally substituted tetrahydrofuranyl). In certain embodiments, $G^{1a}$ is optionally substituted cyclopropyl. In some embodiments, $G^{1a}$ is unsubstituted cyclopropyl.

Other examples of a group of compounds of formula (I) is directed to those wherein $Y^1$ is $CR^u$; $X^1$ is $CR^{x1}$; $X^2$ is $CR^{x2}$, $R^y$ is methyl, $L^1$ is $(CH_2)_mO$, and $G^1$ is $C_1$-$C_6$ alkyl or alkoxyalkyl. In certain embodiments, $G^1$ is $C_1$-$C_6$ alkyl (e.g. methyl, ethyl, isobutyl, or 2,2-dimethylpropyl). In certain embodiments, $G^1$ is alkoxyalkyl.

Other examples of a group of compounds of formula (I) is directed to those wherein $Y^1$ is $CR^u$; $X^1$ is $CR^{x1}$; $X^2$ is $CR^{x2}$, $R^y$ is methyl, $L^1$ is $(CH_2)_mO$, and $G^1$ is —($C_1$-$C_6$ alkylenyl)-$G^{1a}$ wherein $G^{1a}$ is optionally substituted phenyl.

Other examples of a group of compounds of formula (I) is directed to those wherein $Y^1$ is $CR^u$; $X^1$ is $CR^{x1}$; $X^2$ is $CR^{x2}$, $R^y$ is methyl, $L^1$ is $(CH_2)_mO$, and $G^1$ is —($C_1$-$C_6$ alkylenyl)-$G^{1a}$ wherein $G^{1a}$ is optionally substituted cycloalkyl. In some embodiments, $G^{1a}$ is optionally substituted cyclopropyl. In some embodiments, $G^{1a}$ is unsubstituted cyclopropyl.

Other examples of a group of compounds of formula (I) is directed to those wherein $Y^1$ is $CR^u$; $X^1$ is $CR^{x1}$; $X^2$ is $CR^{x2}$, $R^y$ is methyl, $L^1$ is $(CH_2)_mO$, and $G^1$ is $G^{1a}$.

Other examples of a group of compounds of formula (I) is directed to those wherein $Y^1$ is $CR^u$; $X^1$ is $CR^{x1}$; $X^2$ is $CR^{x2}$, $R^y$ is methyl, $L^1$ is $(CH_2)_mO$, $G^1$ is $G^{1a}$, and $G^{1a}$ is optionally substituted aryl.

Other examples of a group of compounds of formula (I) is directed to those wherein $Y^1$ is $CR^u$; $X^1$ is $CR^{x1}$; $X^2$ is $CR^{x2}$, $R^y$ is methyl, $L^1$ is $(CH_2)_mO$, $G^1$ is $G^{1a}$, and $G^{1a}$ is optionally substituted phenyl.

Other examples of a group of compounds of formula (I) is directed to those wherein $Y^1$ is $CR^u$; $X^1$ is $CR^{x1}$; $X^2$ is $CR^{x2}$, $R^y$ is methyl, $L^1$ is $(CH_2)_mO$, $G^1$ is $G^{1a}$, and $G^{1a}$ is optionally substituted cycloalkyl (e.g. optionally substituted monocyclic cycloalkyl).

Other examples of a group of compounds of formula (I) is directed to those wherein $Y^1$ is $CR^u$; $X^1$ is $CR^{x1}$; $X^2$ is $CR^{x2}$, $R^y$ is methyl, $L^1$ is $(CH_2)_mO$, $G^1$ is $G^{1a}$, and $G^{1a}$ is optionally substituted heterocycle (e.g. optionally substituted monocyclic heterocycle).

Yet other examples of a group of compounds of formula (I) is directed to those wherein $Y^1$ is $CR^u$; $X^1$ is N; $X^2$ is $CR^{x2}$, and $R^y$ is methyl.

Other examples of a group of compounds of formula (I) is directed to those wherein $Y^1$ is $CR^u$; $X^1$ is N; $X^2$ is $CR^{x2}$, $R^y$ is methyl, and $L^1$ is $CH_2$, $C(O)$, $(CH_2)_mO$, or $(CH_2)_mN(R^z)$. In certain embodiments, $L^1$ is $(CH_2)_mO$. In yet other embodiments, $L^1$ is $(CH_2)_mO$ and m is 0. In yet other embodiments, $L^1$ is $(CH_2)_mO$ and m is 1. In certain embodiments, $L^1$ is $(CH_2)_mN(R^z)$. In certain embodiments, $L^1$ is $(CH_2)_mN(R^z)$ and m is 0. In yet other embodiments, $L^1$ is $(CH_2)_mN(R^z)$ and m is 1. $R^z$ has meaning as described in the Summary and embodiments herein above.

Other examples of a group of compounds of formula (I) is directed to those wherein $Y^1$ is $CR^u$; $X^1$ is N; $X^2$ is $CR^{x2}$, $R^y$ is methyl, $L^1$ is $(CH_2)_mO$, and $G^1$ is $G^{1a}$.

Other examples of a group of compounds of formula (I) is directed to those wherein $Y^1$ is $CR^u$; $X^1$ is N; $X^2$ is $CR^{x2}$, $R^y$ is methyl, $L^1$ is $(CH_2)_mO$, $G^1$ is $G^{1a}$, and $G^{1a}$ is optionally substituted aryl.

Other examples of a group of compounds of formula (I) is directed to those wherein $Y^1$ is $CR^u$; $X^1$ is N; $X^2$ is $CR^{x2}$, $R^y$ is methyl, $L^1$ is $(CH_2)_mO$, $G^1$ is $G^{1a}$, and $G^{1a}$ is optionally substituted phenyl.

Other examples of a group of compounds of formula (I) is directed to those wherein $Y^1$ is $CR^u$; $X^1$ is N; $X^2$ is $CR^{x2}$, $R^y$ is methyl, $L^1$ is $(CH_2)_mO$, $G^1$ is $G^{1a}$, and $G^{1a}$ is optionally substituted cycloalkyl (e.g. optionally substituted monocyclic cycloalkyl).

Other examples of a group of compounds of formula (I) is directed to those wherein $Y^1$ is $CR^u$; $X^1$ is N; $X^2$ is $CR^{x2}$, $R^y$ is methyl, $L^1$ is $(CH_2)_mO$, $G^1$ is $G^{1a}$, and $G^{1a}$ is optionally substituted heterocycle (e.g. optionally substituted monocyclic heterocycle).

Other examples of a group of compounds of formula (I) is directed to those wherein $Y^1$ is $CR^u$; $X^1$ is N; $X^2$ is $CR^{x2}$, $R^y$ is methyl, $L^1$ is $(CH_2)_mO$, and $G^1$ is $-(C_1-C_6 \text{ alkylenyl})-G^{1a}$ wherein $G^{1a}$ is optionally substituted cycloalkyl. In some embodiments, $G^{1a}$ is optionally substituted cyclopropyl. In some embodiments, $G^{1a}$ is unsubstituted cyclopropyl.

Within each group of compounds of formula (I) described herein above, $A^1$, $A^2$, $A^3$, and $A^4$ have meanings as disclosed in the Summary and embodiments herein above.

For example, within each group of compounds of formula (I) described herein above, examples of a subgroup include those wherein $A^1$ is $CR^1$, $A^2$ is $CR^2$, $A^3$ is $CR^3$, and $A^4$ is $CR^4$; or one of $A^1$, $A^2$, $A^3$, and $A^4$ is N.

Other examples of a subgroup include, but are not limited to, those wherein $A^1$ is $CR^1$, $A^2$ is $CR^2$, $A^3$ is $CR^3$, and $A^4$ is $CR^4$.

Other examples of a subgroup include, but are not limited to, those wherein one of $A^1$, $A^2$, $A^3$, and $A^4$ is N.

Yet other examples of a subgroup include, but are not limited to, those wherein $A^1$ is $CR^1$, $A^2$ is $CR^2$, $A^3$ is $CR^3$, and $A^4$ is N.

Yet other examples of a subgroup include, but are not limited to, those wherein two of $A^1$, $A^2$, $A^3$, and $A^4$ are N.

Yet other examples of a subgroup include, but are not limited to, those wherein $A^1$ is N, $A^2$ is $CR^2$, $A^3$ is N, and $A^4$ is $CR^4$.

Yet other examples of a subgroup include, but are not limited to, those wherein $A^1$ is N, $A^2$ is $CR^2$, $A^3$ is $CR^3$, and $A^4$ is N.

Yet other examples of a subgroup include, but are not limited to, those wherein three of $A^1$, $A^2$, $A^3$, and $A^4$ are N.

Yet other examples of a subgroup include, but are not limited to, those wherein $A^1$ is N, $A^2$ is $CR^2$, $A^3$ is N, and $A^4$ is N.

Of all the groups and subgroups of compounds of formula (I) disclosed in the preceding paragraphs, $R^1$, $R^2$, $R^3$, $R^4$, $R^x$, $R^u$; $R^{x1}$, $R^{x2}$, m, and the optional substituents of $G^1$ are as described in the Summary and embodiments herein above.

For example, of all the groups and subgroups of compounds of formula (I) disclosed in the preceding paragraphs, $R^2$ is hydrogen, $C_1-C_6$ alkyl, $NO_2$, $G^{2a}$, $-S(O)_2R^{2d}$, $-S(O)_2NR^{2b}R^{2c}$, $-C(O)R^{2d}$, $-C(O)OR^{2a}$, $-C(O)NR^{2b}R^{2c}$, $-NR^{2b}R^{2c}$, $-N(R^{2e})C(O)R^{2d}$, $-N(R^{2e})S(O)_2R^{2d}$, $-N(R^{2e})S(O)_2NR^{2b}R^{2c}$, $-(C_1-C_6 \text{ alkylenyl})-G^{2a}$, $-(C_1-C_6 \text{ alkylenyl})-OR^{2a}$, $-(C_1-C_6 \text{ alkylenyl})-S(O)_2R^{2d}$, $-(C_1-C_6 \text{ alkylenyl})-S(O)_2NR^{2b}R^{2c}$, $-(C_1-C_6 \text{ alkylenyl})-C(O)R^{2d}$, $-(C_1-C_6 \text{ alkylenyl})-C(O)OR^{2a}$, $-(C_1-C_6 \text{ alkylenyl})-C(O)NR^{2b}R^{2c}$, $-(C_1-C_6 \text{ alkylenyl})-NR^{2b}R^{2c}$, $-(C_1-C_6 \text{ alkylenyl})-N(R^{2e})C(O)R^{2d}$, $-(C_1-C_6 \text{ alkylenyl})-N(R^{2e})S(O)_2R^{2d}$, or $-(C_1-C_6 \text{ alkylenyl})-N(R^{2e})S(O)_2NR^{2b}R^{2c}$. In certain embodiments, $R^2$ is $-S(O)_2R^{2d}$, $-S(O)_2NR^{2b}R^{2c}$, $-N(R^{2e})S(O)_2R^{2d}$, or $-N(R^{2e})S(O)_2NR^{2b}R^{2c}$. In some embodiments, $R^2$ is $-S(O)_2R^{2d}$, $-S(O)_2NR^{2b}R^{2c}$, $-N(R^{2e})S(O)_2R^{2d}$, or $-(C_1-C_6 \text{ alkylenyl})-S(O)_2R^{2d}$.

For example, of all the groups and subgroups of compounds of formula (I) disclosed in the preceding paragraphs, $R^2$ is $-S(O)_2R^{2d}$, $-S(O)_2NR^{2b}R^{2c}$, $-N(R^{2e})S(O)_2R^{2d}$, or $-N(R^{2e})S(O)_2NR^{2b}R^{2c}$, and $R^x$ is hydrogen or methyl. In certain embodiments, $R^x$ is hydrogen.

For example, of all the groups and subgroups of compounds of formula (I) disclosed in the preceding paragraphs, $R^2$ is $-S(O)_2R^{2d}$, $-S(O)_2NR^{2b}R^{2c}$, $-N(R^{2e})S(O)_2R^{2d}$, or $-N(R^{2e})S(O)_2NR^{2b}R^{2c}$, $R^x$ is hydrogen, and $R^{x1}$ is hydrogen, $-C(O)OR^{ax1}$, $-C(O)NR^{bx1}R^{cx1}$, $G^{x1}$, or $C_1-C_6$ alkyl wherein the $C_1-C_6$ alkyl is optionally substituted with $OR^{ax1}$. In certain embodiments, $R^{x1}$ is hydrogen, $-C(O)OR^{ax1}$, or $-C(O)NR^{bx1}R^{cx1}$.

For example, of all the groups and subgroups of compounds of formula (I) disclosed in the preceding paragraphs, $R^2$ is $-S(O)_2R^{2d}$, $-S(O)_2NR^{2b}R^{2c}$, $-N(R^{2e})S(O)_2R^{2d}$, or $-N(R^{2e})S(O)_2NR^{2b}R^{2c}$, $R^x$ is hydrogen, $R^{x1}$ is hydrogen, $-C(O)OR^{ax1}$, or $-C(O)NR^{bx1}R^{cx1}$, and $R^{x2}$ is hydrogen.

For example, of all the groups and subgroups of compounds of formula (I) disclosed in the preceding paragraphs, $R^2$ is $-S(O)_2R^{2d}$, $-S(O)_2NR^{2b}R^{2c}$, $-N(R^{2e})S(O)_2R^{2d}$, or $-(C_1-C_6 \text{ alkylenyl})S(O)_2R^{2d}$, $R^x$ is hydrogen, $R^{x1}$ is hydrogen or $-C(O)NR^{bx1}R^{cx1}$, and $R^{x2}$ is hydrogen.

One aspect of the invention is directed to compounds of formula (I) or pharmaceutically acceptable salts thereof, wherein
$R^x$ is hydrogen;
$R^y$ is methyl;
$Y^1$ is $CR^u$ wherein $R^u$ is hydrogen;
$X^1$ is $CR^{x1}$ wherein $R^{x1}$ is hydrogen or $-C(O)NR^{bx1}R^{cx1}$;
$X^2$ is $CR^{x2}$ wherein $R^{x2}$ is hydrogen;
$L^1$ is $(CH_2)_mO$ wherein m is 0;
$G^1$ is $G^{1a}$ or $-(C_1-C_6$ alkylenyl)-$G^{1a}$, wherein $G^{1a}$ is optionally substituted phenyl or optionally substituted cycloalkyl; and
$R^2$ is $-S(O)_2R^{2d}$, $-S(O)_2NR^{2b}R^{2c}$, $-N(R^{2e})S(O)_2R^{2d}$, or $-(C_1-C_6$ alkylenyl)-$S(O)_2R^{2d}$.

In some such embodiments, $A^1$ is $CR^1$, $A^2$ is $CR^2$, $A^3$ is $CR^3$, and $A^4$ is $CR^4$. In some further embodiments, $A^1$ is $CR^1$, $A^2$ is $CR^2$, $A^3$ is $CR^3$, and $A^4$ is N.

Another aspect of the invention is directed to compounds of formula (I) or pharmaceutically acceptable salts thereof, wherein
$R^x$ is hydrogen;
$R^y$ is methyl;
$Y^1$ is $CR^u$ wherein $R^u$ is hydrogen;
$X^1$ is $CR^{x1}$ wherein $R^{x1}$ is hydrogen;
$X^2$ is $CR^{x2}$ wherein $R^{x2}$ is hydrogen;
$L^1$ is $(CH_2)_mN(R^z)$ or wherein m is 0 and $R^z$ is hydrogen;
$G^1$ is $-(C_1-C_6$ alkylenyl)-$G^{1a}$, wherein $G^{1a}$ is optionally substituted cycloalkyl; and
$R^2$ is $-S(O)_2R^{2d}$, $-S(O)_2NR^{2b}R^{2c}$, $-N(R^{2e})S(O)_2R^{2d}$, or $-(C_1-C_6$ alkylenyl)-$S(O)_2R^{2d}$.

In some such embodiments, $A^1$ is $CR^1$, $A^2$ is $CR^2$, $A^3$ is $CR^3$, and $A^4$ is $CR^4$. In some further embodiments, $A^1$ is $CR^1$, $A^2$ is $CR^2$, $A^3$ is $CR^3$, and $A^4$ is N.

In one aspect the present invention provides for compounds of formula (I) or pharmaceutically acceptable thereof,

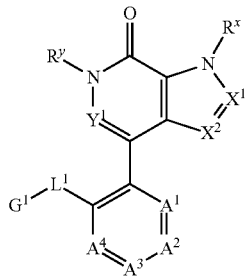

(I)

wherein
$R^x$ is hydrogen or $C_1-C_3$ alkyl;
$R^y$ is $C_1-C_3$ alkyl, $-(C_2-C_3$ alkylenyl)-OH, or $C_1-C_3$ haloalkyl;
$X^1$ is N or $CR^{x1}$ wherein
$R^{x1}$ is hydrogen, $C_2-C_6$ alkenyl, $C_2-C_6$ alkynyl, $-C(O)OR^{ax1}$, $-C(O)NR^{bx1}R^{cx1}$, $-C(O)R^{dx1}$, $S(O)_2R^{dx1}$, $-S(O)_2NR^{bx1}R^{cx1}$, $G^{x1}$, $C_1-C_6$ haloalkyl, or $C_1-C_6$ alkyl; wherein the $C_1-C_6$ alkyl is optionally substituted with one substituent selected from the group consisting of $OR^{ax1}$, $SR^{ax1}$, $S(O)R^{dx1}$, $S(O)_2R^{dx1}$, $NR^{bx1}R^{cx1}$, $-C(O)R^{ax1}$, $-C(O)OR^{ax1}$, $-C(O)NR^{bx1}R^{cx1}$, $-S(O)_2NR^{bx1}R^{cx1}$, and $G^{x1}$;
$R^{ax1}$, $R^{bx1}$, and $R^{cx1}$, at each occurrence, are each independently hydrogen, $C_1-C_6$ alkyl, $C_1-C_6$ haloalkyl, $G^a$, or $-(C_1-C_6$ alkylenyl)-$G^a$;

$R^{dx1}$, at each occurrence, are each independently $C_1-C_6$ alkyl, $C_1-C_6$ haloalkyl, $G^a$, or $-(C_1-C_6$ alkylenyl)-$G^a$;
$X^2$ is N or $CR^{x2}$; wherein
$R^{x2}$ is hydrogen, $C_2-C_6$ alkenyl, $C_2-C_6$ alkynyl, $-C(O)OR^{ax2}$, $-C(O)NR^{bx2}R^{cx2}$, $-C(O)R^{dx2}$, $S(O)_2R^{dx2}$, $-S(O)_2NR^{bx2}R^{cx2}$, $G^{x2}$, $C_1-C_6$ haloalkyl, or $C_1-C_6$ alkyl; wherein the $C_1-C_6$ alkyl is optionally substituted with one substituent selected from the group consisting of $OR^{ax2}$, $SR^{ax2}$, $S(O)R^{dx2}$, $S(O)_2R^{dx2}$, $NR^{bx2}R^{cx2}$, $-C(O)R^{ax2}$, $-C(O)OR^{ax2}$, $-C(O)NR^{bx2}R^{cx2}$, $-S(O)_2NR^{bx2}R^{cx2}$, and $G^{x2}$;
$R^{ax2}$, $R^{bx2}$, and $R^{cx2}$, at each occurrence, are each independently hydrogen, $C_1-C_6$ alkyl, $C_1-C_6$ haloalkyl, $G^b$, or $-(C_1-C_6$ alkylenyl)-$G^b$;
$R^{dx2}$, at each occurrence, is independently $C_1-C_6$ alkyl, $C_1-C_6$ haloalkyl, $G^b$, or $-(C_1-C_6$ alkylenyl)-$G^b$;
$Y^1$ is N or $CR^u$; wherein $R^u$ is hydrogen, $C_1-C_6$ alkyl, halogen, or $C_1-C_6$ haloalkyl;
$A^1$ is N or $CR^1$, $A^2$ is N or $CR^2$, $A^3$ is N or $CR^3$; and $A^4$ is N or $CR^4$; with the proviso that zero, one, two, or three of $A^1$, $A^2$, $A^3$, and $A^4$ are N;
$R^1$, $R^3$, and $R^4$ are each independently hydrogen, $C_1-C_6$ alkyl, $C_2-C_6$ alkenyl, $C_2-C_6$ alkynyl, halogen, $C_1-C_6$ haloalkyl, CN, or $NO_2$;
$R^2$ is hydrogen, $C_1-C_6$ alkyl, $C_2-C_6$ alkenyl, $C_2-C_6$ alkynyl, halogen, $C_1-C_6$ haloalkyl, $-CN$, $NO_2$, $G^{2a}$, $-OR^{2a}$, $-OC(O)R^{2d}$, $-OC(O)NR^{2b}R^{2c}$, $-SR^{2a}$, $-S(O)_2R^{2d}$, $-S(O)_2NR^{2b}R^{2c}$, $-C(O)R^{2d}$, $-C(O)OR^{2a}$, $-C(O)NR^{2b}R^{2c}$, $-NR^{2b}R^{2c}$, $-N(R^{2e})C(O)R^{2d}$, $-N(R^{2e})S(O)_2R^{2d}$, $-N(R^{2e})C(O)O(R^{2d})$, $-N(R^{2e})C(O)NR^{2b}R^{2c}$, $-N(R^{2e})S(O)_2NR^{2b}R^{2c}$, $-(C_1-C_6$ alkylenyl)-$G^{2a}$, $-(C_1-C_6$ alkylenyl)-$OR^{2a}$, $-(C_1-C_6$ alkylenyl)-$OC(O)R^{2d}$, $-(C_1-C_6$ alkylenyl)-$OC(O)NR^{2b}R^{2c}$, $-(C_1-C_6$ alkylenyl)-$S(O)_2R^{2d}$, $-(C_1-C_6$ alkylenyl)-$S(O)_2NR^{2b}R^{2c}$, $-(C_1-C_6$ alkylenyl)-$C(O)R^{2d}$, $-(C_1-C_6$ alkylenyl)-$C(O)OR^{2a}$, $-(C_1-C_6$ alkylenyl)-$C(O)NR^{2b}R^{2c}$, $-(C_1-C_6$ alkylenyl)-$NR^{2b}R^{2c}$, $-(C_1-C_6$ alkylenyl)-$N(R^{2e})C(O)R^{2d}$, $-(C_1-C_6$ alkylenyl)-$N(R^{2e})S(O)_2R^{2d}$, $-(C_1-C_6$ alkylenyl)-$N(R^{2e})C(O)O(R^{2a})$, $-(C_1-C_6$ alkylenyl)-$N(R^{2e})C(O)NR^{2b}R^{2c}$, $-(C_1-C_6$ alkylenyl)-$N(R^{2e})S(O)_2NR^{2b}R^{2c}$, and $-(C_1-C_6$ alkylenyl)-CN;
$R^{2a}$, $R^{2b}$, $R^{2c}$, and $R^{2e}$, at each occurrence, are each independently hydrogen, $C_2-C_6$ alkenyl, $C_2-C_6$ alkynyl, $C_1-C_6$ haloalkyl, $G^{2b}$, or $C_1-C_6$ alkyl wherein the $C_1-C_6$ alkyl is optionally substituted with one substituent selected from the group consisting of $-OR^{z1}$, $NR^{z1}R^{z2}$, $-C(O)OR^{z1}$, $-C(O)NR^{z1}R^{z2}$, $-S(O)_2R^{z1}$, $-S(O)_2NR^{z1}R^{z2}$, and $G^{2b}$;
$R^{2d}$, at each occurrence, is independently $C_2-C_6$ alkenyl, $C_2-C_6$ alkynyl, $C_1-C_6$ haloalkyl, $G^{2b}$, or $C_1-C_6$ alkyl wherein the $C_1-C_6$ alkyl is optionally substituted with one substituent selected from the group consisting of $-OR^{z1}$, $NR^{z1}R^{z2}$, $-C(O)OR^{z1}$, $-C(O)NR^{z1}R^{z2}$, $-S(O)_2R^{z1}$, $-S(O)_2NR^{z1}R^{z2}$, and $G^{2b}$;
$R^{z1}$ and $R^{z2}$, at each occurrence, are each independently hydrogen, $C_1-C_6$ alkyl, or $C_1-C_6$ haloalkyl;
$G^{x1}$, $G^{x2}$, $G^a$, $G^b$, $G^{2a}$, and $G^{2b}$, at each occurrence, are each independently aryl, heteroaryl, heterocycle, cycloalkyl, or cycloalkenyl, and each of which is independently unsubstituted or substituted with 1, 2, 3, 4, or 5 of $R^v$;
$L^1$ is absent, $CH_2$, $C(O)$, $(CH_2)_mO$, $(CH_2)_mS(O)_n$ wherein n is 0, 1, or 2; or $(CH_2)_mN(R^z)$ wherein $R^z$ is hydrogen, $C_1-C_3$ alkyl, $C_1-C_3$ haloalkyl, $(C_2-C_3$ alkylenyl)-OH, or unsubstituted cyclopropyl;

m is 0 or 1;
G$^1$ is G$^{1a}$ or —(C$_1$-C$_6$ alkylenyl)-G$^{1a}$; wherein each G$^{1a}$ is independently aryl, heteroaryl, heterocycle, cycloalkyl, or cycloalkenyl, and each G$^{1a}$ is independently unsubstituted or substituted with 1, 2, 3, 4, or 5 of R$^w$;
R$^v$ and R$^w$, at each occurrence, are each independently C$_1$-C$_6$ alkyl, C$_2$-C$_6$ alkenyl, C$_2$-C$_6$ alkynyl, halogen, C$_1$-C$_6$ haloalkyl, —CN, oxo, —OR$^h$, —OC(O)R$^i$, —OC(O)NR$^j$R$^k$, —SR$^h$, —S(O)$_2$R$^h$, —S(O)$_2$NR$^j$R$^k$, —C(O)R$^h$, —C(O)OR$^h$, —C(O)NR$^j$R$^k$, —NR$^j$R$^k$, —N(R$^h$)C(O)R$^i$, —N(R$^h$)S(O)$_2$R$^i$, —N(R$^h$)C(O)O(R$^i$), —N(R$^h$)C(O)NR$^j$R$^k$, —(C$_1$-C$_6$ alkylenyl)-OR$^h$, —(C$_1$-C$_6$ alkylenyl)-OC(O)R$^i$, —(C$_1$-C$_6$ alkylenyl)-OC(O)NR$^j$R$^k$, —(C$_1$-C$_6$ alkylenyl)-S(O)$_2$R$^h$, —(C$_1$-C$_6$ alkylenyl)-S(O)$_2$NR$^j$R$^k$, —(C$_1$-C$_6$ alkylenyl)-C(O)R$^h$, —(C$_1$-C$_6$ alkylenyl)-C(O)OR$^h$, —(C$_1$-C$_6$ alkylenyl)-C(O)NR$^j$R$^k$, —(C$_1$-C$_6$ alkylenyl)-NR$^j$R$^k$, —(C$_1$-C$_6$ alkylenyl)-N(R$^h$)C(O)R$^i$, —(C$_1$-C$_6$ alkylenyl)-N(R$^h$)S(O)$_2$R$^i$, —(C$_1$-C$_6$ alkylenyl)-N(R$^h$)C(O)O(R$^i$), —(C$_1$-C$_6$ alkylenyl)-N(R$^h$)C(O)NR$^j$R$^k$, or —(C$_1$-C$_6$ alkylenyl)-CN;
R$^h$, R$^j$, R$^k$, at each occurrence, are each independently hydrogen, C$_1$-C$_6$ alkyl, or C$_1$-C$_6$ haloalkyl; and
R$^i$, at each occurrence, is independently C$_1$-C$_6$ alkyl or C$_1$-C$_6$ haloalkyl.

Compounds of formula (I) may contain one or more asymmetrically substituted atoms. Compounds of formula I may also exist as individual stereoisomers (including enantiomers and diastereomers) and mixtures thereof. Individual stereoisomers of compounds of formula I may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Compounds of formula I may also include the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or heterocycle are designated as being of cis or trans configuration.

Within the present invention it is to be understood that compounds disclosed herein may exhibit the phenomenon of tautomerism and all tautomeric isomers are included in the scope of the invention.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Exemplary compounds of formula (I) include, but are not limited to:
6-methyl-4-(2-phenoxyphenyl)-1,6-dihydro-7H-pyrrolo[2,3-c]pyridin-7-one;
6-methyl-4-(5-nitro-2-phenoxyphenyl)-1,6-dihydro-7H-pyrrolo[2,3-c]pyridin-7-one;
4-(5-amino-2-phenoxyphenyl)-6-methyl-1,6-dihydro-7H-pyrrolo[2,3-c]pyridin-7-one;
N-[3-(6-methyl-7-oxo-6,7-dihydro-1H-pyrrolo[2,3-c]pyridin-4-yl)-4-phenoxyphenyl]methanesulfonamide;
2,2,2-trifluoro-N-[3-(6-methyl-7-oxo-6,7-dihydro-1H-pyrrolo[2,3-c]pyridin-4-yl)-4-phenoxyphenyl]ethanesulfonamide;
N-[3-(6-methyl-7-oxo-6,7-dihydro-1H-pyrrolo[2,3-c]pyridin-4-yl)-4-phenoxyphenyl]acetamide;
N-methyl-N-[3-(6-methyl-7-oxo-6,7-dihydro-1H-pyrrolo[2,3-c]pyridin-4-yl)-4-phenoxyphenyl]methanesulfonamide;
ethyl 3-(6-methyl-7-oxo-6,7-dihydro-1H-pyrrolo[2,3-c]pyridin-4-yl)-4-phenoxybenzoate;
3-(6-methyl-7-oxo-6,7-dihydro-1H-pyrrolo[2,3-c]pyridin-4-yl)-4-phenoxybenzoic acid;
N-[3-(6-methyl-7-oxo-6,7-dihydro-1H-pyrrolo[2,3-c]pyridin-4-yl)-4-(pyridin-3-yloxy)phenyl]methanesulfonamide;
6-methyl-4-[2-(morpholin-4-ylmethyl)phenyl]-1,6-dihydro-7H-pyrrolo[2,3-c]pyridin-7-one;
N-ethyl-3-(6-methyl-7-oxo-6,7-dihydro-1H-pyrrolo[2,3-c]pyridin-4-yl)-4-phenoxybenzamide;
3-(6-methyl-7-oxo-6,7-dihydro-1H-pyrrolo[2,3-c]pyridin-4-yl)-4-phenoxy-N-(tetrahydrofuran-2-ylmethyl)benzamide;
N-cyclopentyl-3-(6-methyl-7-oxo-6,7-dihydro-1H-pyrrolo[2,3-c]pyridin-4-yl)-4-phenoxybenzamide;
N-(2,2-difluoroethyl)-3-(6-methyl-7-oxo-6,7-dihydro-1H-pyrrolo[2,3-c]pyridin-4-yl)-4-phenoxybenzamide;
3-(6-methyl-7-oxo-6,7-dihydro-1H-pyrrolo[2,3-c]pyridin-4-yl)-4-phenoxy-N-(1,3-thiazol-2-yl)benzamide;
N-(1,1-dioxidotetrahydrothiophen-3-yl)-3-(6-methyl-7-oxo-6,7-dihydro-1H-pyrrolo[2,3-c]pyridin-4-yl)-4-phenoxybenzamide;
3-(6-methyl-7-oxo-6,7-dihydro-1H-pyrrolo[2,3-c]pyridin-4-yl)-4-phenoxybenzamide;
4-[5-(hydroxymethyl)-2-phenoxyphenyl]-6-methyl-1,6-dihydro-7H-pyrrolo[2,3-c]pyridin-7-one;
N-[3-(6-methyl-7-oxo-6,7-dihydro-1H-pyrrolo[2,3-c]pyridin-4-yl)-4-phenoxyphenyl]ethanesulfonamide;
N,N-dimethyl-N'-[3-(6-methyl-7-oxo-6,7-dihydro-1H-pyrrolo[2,3-c]pyridin-4-yl)-4-phenoxyphenyl]sulfuric diamide;
N-[5-(6-methyl-7-oxo-6,7-dihydro-1H-pyrrolo[2,3-c]pyridin-4-yl)-6-phenoxypyridin-3-yl]methanesulfonamide;
N-[3-fluoro-5-(6-methyl-7-oxo-6,7-dihydro-1H-pyrrolo[2,3-c]pyridin-4-yl)-4-phenoxyphenyl]methanesulfonamide;
N-[4-(2-cyanophenoxy)-3-(6-methyl-7-oxo-6,7-dihydro-1H-pyrrolo[2,3-c]pyridin-4-yl)phenyl]methanesulfonamide;
N-[4-(4-fluorophenoxy)-3-(6-methyl-7-oxo-6,7-dihydro-1H-pyrrolo[2,3-c]pyridin-4-yl)phenyl]methanesulfonamide;
N-[4-(2,4-difluorophenoxy)-3-(6-methyl-7-oxo-6,7-dihydro-1H-pyrrolo[2,3-c]pyridin-4-yl)phenyl]methanesulfonamide;
N-[3-chloro-5-(6-methyl-7-oxo-6,7-dihydro-1H-pyrrolo[2,3-c]pyridin-4-yl)-4-phenoxyphenyl]methanesulfonamide;
N-[3-(6-methyl-7-oxo-6,7-dihydro-1H-pyrrolo[2,3-c]pyridin-4-yl)-4-(tetrahydro-2H-pyran-4-yloxy)phenyl]methanesulfonamide;
6-methyl-4-[2-phenoxy-5-(1H-pyrazol-1-ylmethyl)phenyl]-1,6-dihydro-7H-pyrrolo[2,3-c]pyridin-7-one;

N-[3-(6-methyl-7-oxo-6,7-dihydro-1H-pyrrolo[2,3-c]pyridin-4-yl)-4-(tetrahydrofuran-3-yloxy)phenyl]methanesulfonamide;

N-{3-(6-methyl-7-oxo-6,7-dihydro-1H-pyrrolo[2,3-c]pyridin-4-yl)-4-[2-(trifluoromethyl)phenoxy]phenyl}methanesulfonamide;

N-[4-(4-cyanophenoxy)-3-(6-methyl-7-oxo-6,7-dihydro-1H-pyrrolo[2,3-c]pyridin-4-yl)phenyl]methanesulfonamide;

N-[4-(2-chloro-4-fluorophenoxy)-3-(6-methyl-7-oxo-6,7-dihydro-1H-pyrrolo[2,3-c]pyridin-4-yl)phenyl]methanesulfonamide;

[4-(benzyloxy)-3-(6-methyl-7-oxo-6,7-dihydro-1H-pyrrolo[2,3-c]pyridin-4-yl)phenyl]acetic acid;

N-[4-(2,4-difluorophenoxy)-3-(6-methyl-7-oxo-6,7-dihydro-1H-pyrrolo[2,3-c]pyridin-4-yl)phenyl]ethanesulfonamide;

N-[4-(2,4-difluorophenoxy)-3-(6-methyl-7-oxo-6,7-dihydro-1H-pyrrolo[2,3-c]pyridin-4-yl)phenyl]acetamide;

N-[4-(2,4-difluorophenoxy)-3-(6-methyl-7-oxo-6,7-dihydro-1H-pyrrolo[2,3-c]pyridin-4-yl)phenyl]-3,3,3-trifluoropropanamide;

N-[4-(2,4-difluorophenoxy)-3-(6-methyl-7-oxo-6,7-dihydro-1H-pyrrolo[2,3-c]pyridin-4-yl)phenyl]-2,2-dimethylpropanamide;

ethyl 4-(cyclopentylamino)-3-(6-methyl-7-oxo-6,7-dihydro-1H-pyrrolo[2,3-c]pyridin-4-yl)benzoate;

4-{5-[(1,1-dioxido-1,2-thiazolidin-2-yl)methyl]-2-phenoxyphenyl}-6-methyl-1,6-dihydro-7H-pyrrolo[2,3-c]pyridin-7-one;

4-{[3-(6-methyl-7-oxo-6,7-dihydro-1H-pyrrolo[2,3-c]pyridin-4-yl)-4-phenoxybenzyl]amino}-4-oxobutanoic acid;

4-[2-(2,4-difluorophenoxy)-5-(1,1-dioxido-1,2-thiazolidin-2-yl)phenyl]-6-methyl-1,6-dihydro-7H-pyrrolo[2,3-c]pyridin-7-one;

4-[2-(benzyloxy)-5-(2-hydroxyethyl)phenyl]-6-methyl-1,6-dihydro-7H-pyrrolo[2,3-c]pyridin-7-one;

methyl[4-(benzyloxy)-3-(6-methyl-7-oxo-6,7-dihydro-1H-pyrrolo[2,3-c]pyridin-4-yl)phenyl]acetate;

2-[4-(benzyloxy)-3-(6-methyl-7-oxo-6,7-dihydro-1H-pyrrolo[2,3-c]pyridin-4-yl)phenyl]-N-ethylacetamide;

2-[4-(benzyloxy)-3-(6-methyl-7-oxo-6,7-dihydro-1H-pyrrolo[2,3-c]pyridin-4-yl)phenyl]-N,N-dimethylacetamide;

N-[4-(3,4-difluorophenoxy)-3-(6-methyl-7-oxo-6,7-dihydro-1H-pyrrolo[2,3-c]pyridin-4-yl)phenyl]methanesulfonamide;

N-[3-(6-methyl-7-oxo-6,7-dihydro-1H-pyrrolo[2,3-c]pyridin-4-yl)-4-(2,4,6-trifluorophenoxy)phenyl]methanesulfonamide;

4-(2,4-difluorophenoxy)-3-(6-methyl-7-oxo-6,7-dihydro-1H-pyrrolo[2,3-c]pyridin-4-yl)benzamide;

4-(2,4-difluorophenoxy)-3-(6-methyl-7-oxo-6,7-dihydro-1H-pyrrolo[2,3-c]pyridin-4-yl)-N-(tetrahydrofuran-3-yl)benzamide;

4-{2-(2,4-difluorophenoxy)-5-[(1,1-dioxidothiomorpholin-4-yl)carbonyl]phenyl}-6-methyl-1,6-dihydro-7H-pyrrolo[2,3-c]pyridin-7-one;

4-(2,4-difluorophenoxy)-3-(6-methyl-7-oxo-6,7-dihydro-1H-pyrrolo[2,3-c]pyridin-4-yl)-N-(1-methyl-2-oxopyrrolidin-3-yl)benzamide;

tert-butyl {1-[4-(2,4-difluorophenoxy)-3-(6-methyl-7-oxo-6,7-dihydro-1H-pyrrolo[2,3-c]pyridin-4-yl)benzoyl]pyrrolidin-3-yl}carbamate;

4-[2-(2,4-difluorophenoxy)-5-(pyrrolidin-1-ylcarbonyl)phenyl]-6-methyl-1,6-dihydro-7H-pyrrolo[2,3-c]pyridin-7-one;

4-[2-(2,4-difluorophenoxy)-5-(morpholin-4-ylcarbonyl)phenyl]-6-methyl-1,6-dihydro-7H-pyrrolo[2,3-c]pyridin-7-one;

N-[4-(cyclohexyloxy)-3-(6-methyl-7-oxo-6,7-dihydro-1H-pyrrolo[2,3-c]pyridin-4-yl)phenyl]methanesulfonamide;

N-[4-(cyclopentyloxy)-3-(6-methyl-7-oxo-6,7-dihydro-1H-pyrrolo[2,3-c]pyridin-4-yl)phenyl]methanesulfonamide;

N-{4-[(4,4-difluorocyclohexyl)oxy]-3-(6-methyl-7-oxo-6,7-dihydro-1H-pyrrolo[2,3-c]pyridin-4-yl)phenyl}methanesulfonamide;

N-[3-(6-methyl-7-oxo-6,7-dihydro-1H-pyrrolo[2,3-c]pyridin-4-yl)-4-(tetrahydro-2H-pyran-3-yloxy)phenyl]methanesulfonamide;

6-methyl-4-[2-(morpholin-4-ylcarbonyl)phenyl]-1,6-dihydro-7H-pyrrolo[2,3-c]pyridin-7-one;

N-[3-(6-methyl-7-oxo-6,7-dihydro-1H-pyrrolo[2,3-c]pyridin-4-yl)-4-(2,4,6-trifluorophenoxy)phenyl]ethanesulfonamide;

N-[4-(benzyloxy)-3-(6-methyl-7-oxo-6,7-dihydro-1H-pyrrolo[2,3-c]pyridin-4-yl)phenyl]methanesulfonamide;

N-[4-(2,4-difluorophenoxy)-3-(6-methyl-7-oxo-6,7-dihydro-1H-pyrrolo[2,3-c]pyridin-4-yl)phenyl]-2-fluoroethanesulfonamide;

N-[4-(2,4-difluorophenoxy)-3-(6-methyl-7-oxo-6,7-dihydro-1H-pyrrolo[2,3-c]pyridin-4-yl)phenyl]-N'-methylsulfuric diamide;

N-[3-(6-methyl-7-oxo-6,7-dihydro-1H-pyrrolo[2,3-c]pyridin-4-yl)-4-(tetrahydrofuran-3-yloxy)phenyl]ethanesulfonamide;

methyl 6-methyl-7-oxo-4-(2-phenoxyphenyl)-6,7-dihydro-1H-pyrrolo[2,3-c]pyridine-2-carboxylate;

methyl 1,6-dimethyl-7-oxo-4-(2-phenoxyphenyl)-6,7-dihydro-1H-pyrrolo[2,3-c]pyridine-2-carboxylate;

ethyl 4-(5-amino-2-phenoxyphenyl)-6-methyl-7-oxo-6,7-dihydro-1H-pyrrolo[2,3-c]pyridine-2-carboxylate;

6-methyl-4-(5-(methylsulfonamido)-2-phenoxyphenyl)-7-oxo-6,7-dihydro-1H-pyrrolo[2,3-c]pyridine-2-carboxylic acid;

ethyl 6-methyl-4-{5-[(methylsulfonyl)amino]-2-phenoxyphenyl}-7-oxo-6,7-dihydro-1H-pyrrolo[2,3-c]pyridine-2-carboxylate;

N-ethyl-6-methyl-4-{5-[(methylsulfonyl)amino]-2-phenoxyphenyl}-7-oxo-6,7-dihydro-1H-pyrrolo[2,3-c]pyridine-2-carboxamide;

6-methyl-4-{5-[(methylsulfonyl)amino]-2-phenoxyphenyl}-7-oxo-6,7-dihydro-1H-pyrrolo[2,3-c]pyridine-2-carboxamide;

ethyl 4-(5-amino-2-phenoxyphenyl)-6-methyl-7-oxo-6,7-dihydro-1H-pyrrolo[2,3-d]pyridazine-2-carboxylate;

ethyl 4-[5-(ethylamino)-2-phenoxyphenyl]-6-methyl-7-oxo-6,7-dihydro-1H-pyrrolo[2,3-d]pyridazine-2-carboxylate;

ethyl 4-{5-[ethyl(methylsulfonyl)amino]-2-phenoxyphenyl}-6-methyl-7-oxo-6,7-dihydro-1H-pyrrolo[2,3-d]pyridazine-2-carboxylate;

6-methyl-4-{5-[(methylsulfonyl)amino]-2-phenoxyphenyl}-7-oxo-6,7-dihydro-1H-pyrrolo[2,3-d]pyridazine-2-carboxylic acid;

6-methyl-4-{5-[(methylsulfonyl)amino]-2-phenoxyphenyl}-7-oxo-6,7-dihydro-1H-pyrrolo[2,3-d]pyridazine-2-carboxamide;

6-methyl-N-[2-(4-methylpiperazin-1-yl)ethyl]-4-{5-[(methylsulfonyl)amino]-2-phenoxyphenyl}-7-oxo-6,7-dihydro-1H-pyrrolo[2,3-d]pyridazine-2-carboxamide;

N-[3-(6-methyl-7-oxo-6,7-dihydro-1H-pyrrolo[2,3-d]pyridazin-4-yl)-4-phenoxyphenyl]methanesulfonamide;

N-ethyl-6-methyl-4-{5-[(methylsulfonyl)amino]-2-phenoxyphenyl}-7-oxo-6,7-dihydro-1H-pyrrolo[2,3-d]pyridazine-2-carboxamide;

6-methyl-4-(2-phenoxyphenyl)-1,6-dihydro-7H-pyrrolo[2,3-d]pyridazin-7-one;

N-ethyl-N,6-dimethyl-4-{5-[(methylsulfonyl)amino]-2-phenoxyphenyl}-7-oxo-6,7-dihydro-1H-pyrrolo[2,3-d]pyridazine-2-carboxamide;

4-{4-[(ethylsulfonyl)amino]-2-(6-methyl-7-oxo-6,7-dihydro-1H-pyrrolo[2,3-c]pyridin-4-yl)phenoxy}benzamide;

6-methyl-4-[5-(methylsulfonyl)-2-phenoxyphenyl]-1,6-dihydro-7H-pyrrolo[2,3-c]pyridin-7-one;

5-(6-methyl-7-oxo-6,7-dihydro-1H-pyrrolo[2,3-c]pyridin-4-yl)-6-(tetrahydrofuran-3-yloxy)pyridine-3-sulfonamide;

N-methyl-5-(6-methyl-7-oxo-6,7-dihydro-1H-pyrrolo[2,3-c]pyridin-4-yl)-6-(tetrahydrofuran-3-yloxy)pyridine-3-sulfonamide;

6-methyl-4-(2-phenoxyphenyl)-2-phenyl-1,6-dihydro-7H-pyrrolo[2,3-c]pyridin-7-one;

N-{3-[2-(hydroxymethyl)-6-methyl-7-oxo-6,7-dihydro-1H-pyrrolo[2,3-c]pyridin-4-yl]-4-phenoxyphenyl}methanesulfonamide;

N-[4-(4-cyanophenoxy)-3-(6-methyl-7-oxo-6,7-dihydro-1H-pyrrolo[2,3-c]pyridin-4-yl)phenyl]ethanesulfonamide;

2-fluoro-N-[3-(6-methyl-7-oxo-6,7-dihydro-1H-pyrrolo[2,3-c]pyridin-4-yl)-4-(tetrahydrofuran-3-yloxy)phenyl]ethanesulfonamide;

N-[3-(6-methyl-7-oxo-6,7-dihydro-1H-pyrrolo[2,3-c]pyridin-4-yl)-4-(tetrahydrofuran-3-yloxy)phenyl]propane-1-sulfonamide;

N-[4-(4-cyanophenoxy)-3-(6-methyl-7-oxo-6,7-dihydro-1H-pyrrolo[2,3-c]pyridin-4-yl)phenyl]propane-1-sulfonamide;

N-[3-(6-methyl-7-oxo-6,7-dihydro-1H-pyrrolo[2,3-c]pyridin-4-yl)-4-(2,4,6-trifluorophenoxy)phenyl]propane-1-sulfonamide;

3-(6-methyl-7-oxo-6,7-dihydro-1H-pyrrolo[2,3-c]pyridin-4-yl)-4-phenoxybenzenesulfonamide;

6-(cyclohexylamino)-5-(6-methyl-7-oxo-6,7-dihydro-1H-pyrrolo[2,3-c]pyridin-4-yl)pyridine-3-sulfonamide;

6-(cyclohexylamino)-N-methyl-5-(6-methyl-7-oxo-6,7-dihydro-1H-pyrrolo[2,3-c]pyridin-4-yl)pyridine-3-sulfonamide;

N-methyl-N'-[3-(6-methyl-7-oxo-6,7-dihydro-1H-pyrrolo[2,3-c]pyridin-4-yl)-4-(2,4,6-trifluorophenoxy)phenyl]sulfuric diamide;

N-[3-(6-methyl-7-oxo-6,7-dihydro-1H-pyrrolo[2,3-c]pyridin-4-yl)-4-(tetrahydro-2H-pyran-4-yloxy)phenyl]propane-1-sulfonamide;

2,2,2-trifluoro-N-[3-(6-methyl-7-oxo-6,7-dihydro-1H-pyrrolo[2,3-c]pyridin-4-yl)-4-(tetrahydro-2H-pyran-4-yloxy)phenyl]ethanesulfonamide;

N-{4-[(4,4-difluorocyclohexyl)oxy]-3-(6-methyl-7-oxo-6,7-dihydro-1H-pyrrolo[2,3-c]pyridin-4-yl)phenyl}ethanesulfonamide;

N-{4-[(4,4-difluorocyclohexyl)oxy]-3-(6-methyl-7-oxo-6,7-dihydro-1H-pyrrolo[2,3-c]pyridin-4-yl)phenyl}propane-1-sulfonamide;

N-{4-[(4,4-difluorocyclohexyl)oxy]-3-(6-methyl-7-oxo-6,7-dihydro-1H-pyrrolo[2,3-c]pyridin-4-yl)phenyl}-2,2,2-trifluoroethanesulfonamide;

N-{4-[(4,4-difluorocyclohexyl)oxy]-3-(6-methyl-7-oxo-6,7-dihydro-1H-pyrrolo[2,3-c]pyridin-4-yl)phenyl}-N'-methylsulfuric diamide;

N-[3-(6-methyl-7-oxo-6,7-dihydro-1H-pyrrolo[2,3-c]pyridin-4-yl)-4-(tetrahydro-2H-pyran-3-yloxy)phenyl]ethanesulfonamide;

N-[3-(6-methyl-7-oxo-6,7-dihydro-1H-pyrrolo[2,3-c]pyridin-4-yl)-4-(tetrahydro-2H-pyran-3-yloxy)phenyl]propane-1-sulfonamide;

2,2,2-trifluoro-N-[3-(6-methyl-7-oxo-6,7-dihydro-1H-pyrrolo[2,3-c]pyridin-4-yl)-4-(tetrahydro-2H-pyran-3-yloxy)phenyl]ethanesulfonamide;

N-methyl-N'-[3-(6-methyl-7-oxo-6,7-dihydro-1H-pyrrolo[2,3-c]pyridin-4-yl)-4-(tetrahydro-2H-pyran-3-yloxy)phenyl]sulfuric diamide;

N-[3-(6-methyl-7-oxo-6,7-dihydro-1H-pyrrolo[2,3-c]pyridin-4-yl)-4-(tetrahydro-2H-pyran-4-yloxy)phenyl]ethanesulfonamide;

N,N-dimethyl-5-(6-methyl-7-oxo-6,7-dihydro-1H-pyrrolo[2,3-c]pyridin-4-yl)-6-(tetrahydrofuran-3-yloxy)pyridine-3-sulfonamide;

5-(6-methyl-7-oxo-6,7-dihydro-1H-pyrrolo[2,3-c]pyridin-4-yl)-6-(phenylamino)pyridine-3-sulfonamide;

N-methyl-5-(6-methyl-7-oxo-6,7-dihydro-1H-pyrrolo[2,3-c]pyridin-4-yl)-6-(phenylamino)pyridine-3-sulfonamide;

N-[4-(4-cyanophenoxy)-3-(6-methyl-7-oxo-6,7-dihydro-1H-pyrrolo[2,3-c]pyridin-4-yl)phenyl]-2-fluoroethanesulfonamide;

2-fluoro-N-[3-(6-methyl-7-oxo-6,7-dihydro-1H-pyrrolo[2,3-c]pyridin-4-yl)-4-(2,4,6-trifluorophenoxy)phenyl]ethanesulfonamide;

N-[4-(2,4-difluorophenoxy)-3-(6-methyl-7-oxo-6,7-dihydro-1H-pyrrolo[2,3-c]pyridin-4-yl)phenyl]propane-1-sulfonamide;

4-(2,4-difluorophenoxy)-3-(6-methyl-7-oxo-6,7-dihydro-1H-pyrrolo[2,3-c]pyridin-4-yl)-N-(pyrimidin-2-yl)benzamide;

4-(2,4-difluorophenoxy)-N-(2,6-dimethoxypyridin-3-yl)-3-(6-methyl-7-oxo-6,7-dihydro-1H-pyrrolo[2,3-c]pyridin-4-yl)benzamide;

4-(2,4-difluorophenoxy)-N-(1H-indazol-6-yl)-3-(6-methyl-7-oxo-6,7-dihydro-1H-pyrrolo[2,3-c]pyridin-4-yl)benzamide;

4-[2-(2,4-difluorophenoxy)-5-{[4-(pyrrolidin-1-ylcarbonyl)piperazin-1-yl]carbonyl}phenyl]-6-methyl-1,6-dihydro-7H-pyrrolo[2,3-c]pyridin-7-one;

4-(2,4-difluorophenoxy)-N-[4-(dimethylamino)phenyl]-3-(6-methyl-7-oxo-6,7-dihydro-1H-pyrrolo[2,3-c]pyridin-4-yl)benzamide;

4-(2,4-difluorophenoxy)-3-(6-methyl-7-oxo-6,7-dihydro-1H-pyrrolo[2,3-c]pyridin-4-yl)-N-(pyridin-4-ylmethyl)benzamide;

4-(2,4-difluorophenoxy)-3-(6-methyl-7-oxo-6,7-dihydro-1H-pyrrolo[2,3-c]pyridin-4-yl)-N-[2-(2-oxopyrrolidin-1-yl)ethyl]benzamide;

4-(2,4-difluorophenoxy)-N-(2-hydroxy-2-methylpropyl)-3-(6-methyl-7-oxo-6,7-dihydro-1H-pyrrolo[2,3-c]pyridin-4-yl)benzamide;

4-(2,4-difluorophenoxy)-N-[2-(5-methoxy-1H-indol-3-yl)ethyl]-3-(6-methyl-7-oxo-6,7-dihydro-1H-pyrrolo[2,3-c]pyridin-4-yl)benzamide;

N-(3,4-difluorobenzyl)-4-(2,4-difluorophenoxy)-3-(6-methyl-7-oxo-6,7-dihydro-1H-pyrrolo[2,3-c]pyridin-4-yl)benzamide;

4-(2,4-difluorophenoxy)-3-(6-methyl-7-oxo-6,7-dihydro-1H-pyrrolo[2,3-c]pyridin-4-yl)-N-[4-(trifluoromethoxy)benzyl]benzamide;

2-{4-[4-(2,4-difluorophenoxy)-3-(6-methyl-7-oxo-6,7-dihydro-1H-pyrrolo[2,3-c]pyridin-4-yl)benzoyl]piperazin-1-yl}-N,N-dimethylacetamide;

4-(2,4-difluorophenoxy)-3-(6-methyl-7-oxo-6,7-dihydro-1H-pyrrolo[2,3-c]pyridin-4-yl)-N-(pyridin-3-ylmethyl)benzamide;

4-(2,4-difluorophenoxy)-3-(6-methyl-7-oxo-6,7-dihydro-1H-pyrrolo[2,3-c]pyridin-4-yl)-N-(pyridin-2-ylmethyl)benzamide;

4-(2,4-difluorophenoxy)-3-(6-methyl-7-oxo-6,7-dihydro-1H-pyrrolo[2,3-c]pyridin-4-yl)-N-(3,4,5-trimethoxybenzyl)benzamide;

4-(2,4-difluorophenoxy)-N-[2-(dimethylamino)ethyl]-3-(6-methyl-7-oxo-6,7-dihydro-1H-pyrrolo[2,3-c]pyridin-4-yl)benzamide;

N-[2-(1,3-benzodioxol-5-yl)ethyl]-4-(2,4-difluorophenoxy)-3-(6-methyl-7-oxo-6,7-dihydro-1H-pyrrolo[2,3-c]pyridin-4-yl)benzamide;

4-(2,4-difluorophenoxy)-N-[2-(1H-indol-3-yl)ethyl]-3-(6-methyl-7-oxo-6,7-dihydro-1H-pyrrolo[2,3-c]pyridin-4-yl)benzamide;

4-[2-(2,4-difluorophenoxy)-5-{[4-(furan-2-ylcarbonyl)piperazin-1-yl]carbonyl}phenyl]-6-methyl-1,6-dihydro-7H-pyrrolo[2,3-c]pyridin-7-one;

tert-butyl {1-[4-(2,4-difluorophenoxy)-3-(6-methyl-7-oxo-6,7-dihydro-1H-pyrrolo[2,3-c]pyridin-4-yl)benzoyl]piperidin-4-yl}carbamate;

tert-butyl 4-{[4-(2,4-difluorophenoxy)-3-(6-methyl-7-oxo-6,7-dihydro-1H-pyrrolo[2,3-c]pyridin-4-yl)benzoyl]amino}piperidine-1-carboxylate;

4-[2-(2,4-difluorophenoxy)-5-{[4-(ethylsulfonyl)piperazin-1-yl]carbonyl}phenyl]-6-methyl-1,6-dihydro-7H-pyrrolo[2,3-c]pyridin-7-one;

4-[2-(2,4-difluorophenoxy)-5-(methylsulfonyl)phenyl]-6-methyl-1,6-dihydro-7H-pyrrolo[2,3-c]pyridin-7-one;

4-[2-(4-chlorobenzoyl)phenyl]-6-methyl-1,6-dihydro-7H-pyrrolo[2,3-c]pyridin-7-one;

4-{2-[(4-chlorophenyl)(hydroxy)methyl]phenyl}-6-methyl-1,6-dihydro-7H-pyrrolo[2,3-c]pyridin-7-one;

N-[3-(6-methyl-7-oxo-6,7-dihydro-1H-pyrrolo[2,3-c]pyridin-4-yl)-4-(pyrimidin-5-yloxy)phenyl]ethanesulfonamide;

N-{3-(6-methyl-7-oxo-6,7-dihydro-1H-pyrrolo[2,3-c]pyridin-4-yl)-4-[(1-methyl-1H-pyrazol-5-yl)methoxy]phenyl}ethanesulfonamide;

N-{4-[(1,3-dimethyl-1H-pyrazol-5-yl)methoxy]-3-(6-methyl-7-oxo-6,7-dihydro-1H-pyrrolo[2,3-c]pyridin-4-yl)phenyl}ethanesulfonamide;

N-[4-(2,2-dimethylpropoxy)-3-(6-methyl-7-oxo-6,7-dihydro-1H-pyrrolo[2,3-c]pyridin-4-yl)phenyl]ethanesulfonamide;

N-[4-(cyclopropylmethoxy)-3-(6-methyl-7-oxo-6,7-dihydro-1H-pyrrolo[2,3-c]pyridin-4-yl)phenyl]ethanesulfonamide;

4-(2,4-difluorophenoxy)-3-(6-methyl-7-oxo-6,7-dihydro-1H-pyrrolo[2,3-c]pyridin-4-yl)benzenesulfonamide;

4-[2-(cyclohexylamino)-5-(methylsulfonyl)phenyl]-6-methyl-1,6-dihydro-7H-pyrrolo[2,3-c]pyridin-7-one;

4-[5-amino-2-(2,4-difluorophenoxy)phenyl]-6-methyl-1,6-dihydro-7H-pyrrolo[2,3-d]pyridazin-7-one;

4-[2-(2-fluorophenoxy)-5-(methylsulfonyl)phenyl]-6-methyl-1,6-dihydro-7H-pyrrolo[2,3-c]pyridin-7-one;

4-[2-(3-fluorophenoxy)-5-(methylsulfonyl)phenyl]-6-methyl-1,6-dihydro-7H-pyrrolo[2,3-c]pyridin-7-one;

4-[2-(4-fluorophenoxy)-5-(methylsulfonyl)phenyl]-6-methyl-1,6-dihydro-7H-pyrrolo[2,3-c]pyridin-7-one;

4-[2-(2-chlorophenoxy)-5-(methylsulfonyl)phenyl]-6-methyl-1,6-dihydro-7H-pyrrolo[2,3-c]pyridin-7-one;

4-[2-(3-chlorophenoxy)-5-(methylsulfonyl)phenyl]-6-methyl-1,6-dihydro-7H-pyrrolo[2,3-c]pyridin-7-one;

4-[2-(4-chlorophenoxy)-5-(methylsulfonyl)phenyl]-6-methyl-1,6-dihydro-7H-pyrrolo[2,3-c]pyridin-7-one;

3-[2-(6-methyl-7-oxo-6,7-dihydro-1H-pyrrolo[2,3-c]pyridin-4-yl)-4-(methylsulfonyl)phenoxy]benzonitrile;

4-[2-(6-methyl-7-oxo-6,7-dihydro-1H-pyrrolo[2,3-c]pyridin-4-yl)-4-(methylsulfonyl)phenoxy]benzonitrile;

6-methyl-4-{5-(methylsulfonyl)-2-[3-(trifluoromethyl)phenoxy]phenyl}-1,6-dihydro-7H-pyrrolo[2,3-c]pyridin-7-one;

4-[2-(cyclopropylmethoxy)-5-(methylsulfonyl)phenyl]-6-methyl-1,6-dihydro-7H-pyrrolo[2,3-c]pyridin-7-one;

N-[4-(2,4-difluorophenoxy)-3-(6-methyl-7-oxo-6,7-dihydro-1H-pyrrolo[2,3-d]pyridazin-4-yl)phenyl]methanesulfonamide;

N-[4-(2,4-difluorophenoxy)-3-(6-methyl-7-oxo-6,7-dihydro-1H-pyrrolo[2,3-d]pyridazin-4-yl)phenyl]ethanesulfonamide;

4-[2-(isoquinolin-5-yloxy)-5-(methylsulfonyl)phenyl]-6-methyl-1,6-dihydro-7H-pyrrolo[2,3-c]pyridin-7-one;

6-methyl-4-[5-(methylsulfonyl)-2-(quinolin-6-yloxy)phenyl]-1,6-dihydro-7H-pyrrolo[2,3-c]pyridin-7-one;

4-{2-[2-chloro-5-(trifluoromethyl)phenoxy]-5-(methylsulfonyl)phenyl}-6-methyl-1,6-dihydro-7H-pyrrolo[2,3-c]pyridin-7-one;

4-{2-[2-fluoro-5-(trifluoromethyl)phenoxy]-5-(methylsulfonyl)phenyl}-6-methyl-1,6-dihydro-7H-pyrrolo[2,3-c]pyridin-7-one;

2-{4-[2-(6-methyl-7-oxo-6,7-dihydro-1H-pyrrolo[2,3-c]pyridin-4-yl)-4-(methylsulfonyl)phenoxy]phenyl}acetamide;

4-[2-(3-aminophenoxy)-5-(methylsulfonyl)phenyl]-6-methyl-1,6-dihydro-7H-pyrrolo[2,3-c]pyridin-7-one;

6-methyl-4-[5-(methylsulfonyl)-2-(tetrahydrofuran-3-ylamino)phenyl]-1,6-dihydro-7H-pyrrolo[2,3-c]pyridin-7-one;

4-[2-(2,4-difluorophenoxy)-5-(ethylsulfonyl)phenyl]-6-methyl-1,6-dihydro-7H-pyrrolo[2,3-c]pyridin-7-one;

4-{2-[(4,4-difluorocyclohexyl)oxy]-5-(ethylsulfonyl)phenyl}-6-methyl-1,6-dihydro-7H-pyrrolo[2,3-c]pyridin-7-one;

4-{5-(ethylsulfonyl)-2-[(1-methylpiperidin-4-yl)oxy]phenyl}-6-methyl-1,6-dihydro-7H-pyrrolo[2,3-c]pyridin-7-one;

4-[2-(2,1,3-benzothiadiazol-4-yloxy)-5-(methylsulfonyl)phenyl]-6-methyl-1,6-dihydro-7H-pyrrolo[2,3-c]pyridin-7-one;

4-[2-(isoquinolin-7-yloxy)-5-(methylsulfonyl)phenyl]-6-methyl-1,6-dihydro-7H-pyrrolo[2,3-c]pyridin-7-one;

4-[2-(2,5-difluorophenoxy)-5-(methylsulfonyl)phenyl]-6-methyl-1,6-dihydro-7H-pyrrolo[2,3-c]pyridin-7-one;

4-[2-(3,4-difluorophenoxy)-5-(methylsulfonyl)phenyl]-6-methyl-1,6-dihydro-7H-pyrrolo[2,3-c]pyridin-7-one;

6-methyl-4-{5-(methylsulfonyl)-2-[(1-oxo-2,3-dihydro-1H-inden-4-yl)oxy]phenyl}-1,6-dihydro-7H-pyrrolo[2,3-c]pyridin-7-one;

4-[2-(3,5-difluorophenoxy)-5-(methylsulfonyl)phenyl]-6-methyl-1,6-dihydro-7H-pyrrolo[2,3-c]pyridin-7-one;

6-methyl-4-[2-(4-methylphenoxy)-5-(methylsulfonyl)phenyl]-1,6-dihydro-7H-pyrrolo[2,3-c]pyridin-7-one;

4-[2-(2-methoxyphenoxy)-5-(methylsulfonyl)phenyl]-6-methyl-1,6-dihydro-7H-pyrrolo[2,3-c]pyridin-7-one;

6-methyl-4-{2-[(2-methylpyridin-3-yl)oxy]-5-(methylsulfonyl)phenyl}-1,6-dihydro-7H-pyrrolo[2,3-c]pyridin-7-one;

4-{2-[3-(dimethylamino)phenoxy]-5-(methylsulfonyl)phenyl}-6-methyl-1,6-dihydro-7H-pyrrolo[2,3-c]pyridin-7-one;

6-methyl-4-{5-(methylsulfonyl)-2-[(1-oxo-2,3-dihydro-1H-inden-5-yl)oxy]phenyl}-1,6-dihydro-7H-pyrrolo[2,3-c]pyridin-7-one;
6-methyl-4-{5-(methylsulfonyl)-2-[(3-oxo-2,3-dihydro-1H-inden-5-yl)oxy]phenyl}-1,6-dihydro-7H-pyrrolo[2,3-c]pyridin-7-one;
2-[2-(6-methyl-7-oxo-6,7-dihydro-1H-pyrrolo[2,3-c]pyridin-4-yl)-4-(methylsulfonyl)phenoxy]benzonitrile;
4-[2-(3-chloro-2-fluorophenoxy)-5-(methylsulfonyl)phenyl]-6-methyl-1,6-dihydro-7H-pyrrolo[2,3-c]pyridin-7-one;
6-methyl-4-[5-(methylsulfonyl)-2-(naphthalen-1-yloxy)phenyl]-1,6-dihydro-7H-pyrrolo[2,3-c]pyridin-7-one;
4-[2-(2-fluoro-5-methylphenoxy)-5-(methylsulfonyl)phenyl]-6-methyl-1,6-dihydro-7H-pyrrolo[2,3-c]pyridin-7-one;
4-[2-(5-fluoro-2-methylphenoxy)-5-(methylsulfonyl)phenyl]-6-methyl-1,6-dihydro-7H-pyrrolo[2,3-c]pyridin-7-one;
6-methyl-4-[5-(methylsulfonyl)-2-(quinolin-7-yloxy)phenyl]-1,6-dihydro-7H-pyrrolo[2,3-c]pyridin-7-one;
4-[2-(4-chloro-3-fluorophenoxy)-5-(methylsulfonyl)phenyl]-6-methyl-1,6-dihydro-7H-pyrrolo[2,3-c]pyridin-7-one;
6-methyl-4-[5-(methylsulfonyl)-2-(pyridin-3-yloxy)phenyl]-1,6-dihydro-7H-pyrrolo[2,3-c]pyridin-7-one;
4-[2-(2,3-dihydro-1H-inden-5-yloxy)-5-(methylsulfonyl)phenyl]-6-methyl-1,6-dihydro-7H-pyrrolo[2,3-c]pyridin-7-one;
6-methyl-4-{5-(methylsulfonyl)-2-[4-(propan-2-yl)phenoxy]phenyl}-1,6-dihydro-7H-pyrrolo[2,3-c]pyridin-7-one;
4-[2-(isoquinolin-8-yloxy)-5-(methylsulfonyl)phenyl]-6-methyl-1,6-dihydro-7H-pyrrolo[2,3-c]pyridin-7-one;
6-methyl-4-[5-(methylsulfonyl)-2-(3,4,5-trifluorophenoxy)phenyl]-1,6-dihydro-7H-pyrrolo[2,3-c]pyridin-7-one;
4-(2-benzylphenyl)-6-methyl-1,6-dihydro-7H-pyrrolo[2,3-c]pyridin-7-one;
4-(biphenyl-2-yl)-6-methyl-1,6-dihydro-7H-pyrrolo[2,3-c]pyridin-7-one;
4-[2-(1,4-dioxaspiro[4.5]dec-8-yloxy)-5-(ethylsulfonyl)phenyl]-6-methyl-1,6-dihydro-7H-pyrrolo[2,3-c]pyridin-7-one;
4-[2-(cyclopropylmethoxy)-5-(ethylsulfonyl)phenyl]-6-methyl-1,6-dihydro-7H-pyrrolo[2,3-c]pyridin-7-one;
4-{5-(ethylsulfonyl)-2-[(4-oxocyclohexyl)oxy]phenyl}-6-methyl-1,6-dihydro-7H-pyrrolo[2,3-c]pyridin-7-one;
4-{2-[(cyclopropylmethyl)amino]-5-(ethylsulfonyl)phenyl}-6-methyl-1,6-dihydro-7H-pyrrolo[2,3-c]pyridin-7-one;
6-methyl-4-{5-(methylsulfonyl)-2-[(tetrahydrofuran-3-ylmethyl)amino]phenyl}-1,6-dihydro-7H-pyrrolo[2,3-c]pyridin-7-one;
4-{5-(ethylsulfonyl)-2-[(cis-4-hydroxycyclohexyl)oxy]phenyl}-6-methyl-1,6-dihydro-7H-pyrrolo[2,3-c]pyridin-7-one;
4-{5-(ethylsulfonyl)-2-[(trans-4-hydroxycyclohexyl)oxy]phenyl}-6-methyl-1,6-dihydro-7H-pyrrolo[2,3-c]pyridin-7-one;
4-[2-(cyclopropylmethoxy)-5-(ethylsulfonyl)phenyl]-6-methyl-1,6-dihydro-7H-pyrrolo[2,3-d]pyridazin-7-one;
6-methyl-4-[5-(methylsulfonyl)-2-(tetrahydrofuran-3-yloxy)phenyl]-1,6-dihydro-7H-pyrrolo[2,3-c]pyridin-7-one;
4-{2-[(3-fluorooxetan-3-yl)methoxy]-5-(methylsulfonyl)phenyl}-6-methyl-1,6-dihydro-7H-pyrrolo[2,3-c]pyridin-7-one;
6-(cyclopropylmethoxy)-5-(6-methyl-7-oxo-6,7-dihydro-1H-pyrrolo[2,3-c]pyridin-4-yl)pyridine-3-sulfonamide;
6-(cyclopropylmethoxy)-N-methyl-5-(6-methyl-7-oxo-6,7-dihydro-1H-pyrrolo[2,3-c]pyridin-4-yl)pyridine-3-sulfonamide;
6-[(cyclopropylmethyl)amino]-5-(6-methyl-7-oxo-6,7-dihydro-1H-pyrrolo[2,3-c]pyridin-4-yl)pyridine-3-sulfonamide;
6-[(cyclopropylmethyl)amino]-N-methyl-5-(6-methyl-7-oxo-6,7-dihydro-1H-pyrrolo[2,3-c]pyridin-4-yl)pyridine-3-sulfonamide;
4-{5-(ethylsulfonyl)-2-[(cis-4-hydroxy-4-methylcyclohexyl)oxy]phenyl}-6-methyl-1,6-dihydro-7H-pyrrolo[2,3-c]pyridin-7-one;
4-{5-(ethylsulfonyl)-2-[(trans-4-hydroxy-4-methylcyclohexyl)oxy]phenyl}-6-methyl-1,6-dihydro-7H-pyrrolo[2,3-c]pyridin-7-one;
4-[2-(cyclobutyloxy)-5-(methylsulfonyl)phenyl]-6-methyl-1,6-dihydro-7H-pyrrolo[2,3-c]pyridin-7-one;
4-[2-(cyclopentylmethoxy)-5-(methylsulfonyl)phenyl]-6-methyl-1,6-dihydro-7H-pyrrolo[2,3-c]pyridin-7-one;
4-[2-(cyclohexyloxy)-5-(methylsulfonyl)phenyl]-6-methyl-1,6-dihydro-7H-pyrrolo[2,3-c]pyridin-7-one;
4-[2-(cyclopentyloxy)-5-(methylsulfonyl)phenyl]-6-methyl-1,6-dihydro-7H-pyrrolo[2,3-c]pyridin-7-one;
6-methyl-4-[5-(methylsulfonyl)-2-(tetrahydrofuran-3-ylmethoxy)phenyl]-1,6-dihydro-7H-pyrrolo[2,3-c]pyridin-7-one;
6-methyl-4-{5-(methylsulfonyl)-2-[2-(2-oxoimidazolidin-1-yl)ethoxy]phenyl}-1,6-dihydro-7H-pyrrolo[2,3-c]pyridin-7-one;
4-[2-(2-cyclopropylethoxy)-5-(methylsulfonyl)phenyl]-6-methyl-1,6-dihydro-7H-pyrrolo[2,3-c]pyridin-7-one;
4-[2-(cycloheptyloxy)-5-(methylsulfonyl)phenyl]-6-methyl-1,6-dihydro-7H-pyrrolo[2,3-c]pyridin-7-one;
6-methyl-4-[2-(2-methylpropoxy)-5-(methylsulfonyl)phenyl]-1,6-dihydro-7H-pyrrolo[2,3-c]pyridin-7-one;
6-methyl-4-[2-{[(2S)-1-methylpyrrolidin-2-yl]methoxy}-5-(methylsulfonyl)phenyl]-1,6-dihydro-7H-pyrrolo[2,3-c]pyridin-7-one;
6-methyl-4-{2-[(2-methylcyclopropyl)methoxy]-5-(methylsulfonyl)phenyl}-1,6-dihydro-7H-pyrrolo[2,3-c]pyridin-7-one;
4-[2-(cyclohexylmethoxy)-5-(methylsulfonyl)phenyl]-6-methyl-1,6-dihydro-7H-pyrrolo[2,3-c]pyridin-7-one;
6-methyl-4-{2-[2-(1-methylpyrrolidin-2-yl)ethoxy]-5-(methylsulfonyl)phenyl}-1,6-dihydro-7H-pyrrolo[2,3-c]pyridin-7-one;
6-methyl-4-[5-(methylsulfonyl)-2-{[(2R)-5-oxopyrrolidin-2-yl]methoxy}phenyl]-1,6-dihydro-7H-pyrrolo[2,3-c]pyridin-7-one;
6-methyl-4-{5-(methylsulfonyl)-2-[2-(morpholin-4-yl)ethoxy]phenyl}-1,6-dihydro-7H-pyrrolo[2,3-c]pyridin-7-one;
6-methyl-4-[5-(methylsulfonyl)-2-{[(2S)-5-oxopyrrolidin-2-yl]methoxy}phenyl]-1,6-dihydro-7H-pyrrolo[2,3-c]pyridin-7-one;
4-{2-[(1-tert-butoxypropan-2-yl)oxy]-5-(methylsulfonyl)phenyl}-6-methyl-1,6-dihydro-7H-pyrrolo[2,3-c]pyridin-7-one;
4-{2-[(1S,4R)-bicyclo[2.2.1]hept-2-ylmethoxy]-5-(methylsulfonyl)phenyl}-6-methyl-1,6-dihydro-7H-pyrrolo[2,3-c]pyridin-7-one;
6-methyl-4-{2-[(1-methylcyclopropyl)methoxy]-5-(methylsulfonyl)phenyl}-1,6-dihydro-7H-pyrrolo[2,3-c]pyridin-7-one;

6-methyl-4-{5-(methylsulfonyl)-2-[2-(2-oxopyrrolidin-1-yl)ethoxy]phenyl}-1,6-dihydro-7H-pyrrolo[2,3-c]pyridin-7-one;

6-methyl-4-{2-[(4-methylcyclohexyl)oxy]-5-(methylsulfonyl)phenyl}-1,6-dihydro-7H-pyrrolo[2,3-c]pyridin-7-one;

4-[2-(cyclobutylmethoxy)-5-(methylsulfonyl)phenyl]-6-methyl-1,6-dihydro-7H-pyrrolo[2,3-c]pyridin-7-one;

N-[4-(2,4-difluorophenoxy)-3-(6-methyl-7-oxo-6,7-dihydro-1H-pyrrolo[2,3-c]pyridin-4-yl)phenyl]cyclopropanesulfonamide;

N-[4-(2,4-difluorophenoxy)-3-(6-methyl-7-oxo-6,7-dihydro-1H-pyrrolo[2,3-c]pyridin-4-yl)phenyl]-2-methoxyethanesulfonamide;

6-methyl-4-{5-(methylsulfonyl)-2-[tricyclo[3.3.1.1$^{3,7}$]dec-2-yloxy]phenyl}-1,6-dihydro-7H-pyrrolo[2,3-c]pyridin-7-one;

4-[(cyclopropylmethyl)amino]-3-(6-methyl-7-oxo-6,7-dihydro-1H-pyrrolo[2,3-c]pyridin-4-yl)benzenesulfonamide;

4-[(cyclopropylmethyl)amino]-N-methyl-3-(6-methyl-7-oxo-6,7-dihydro-1H-pyrrolo[2,3-c]pyridin-4-yl)benzenesulfonamide;

4-{2-[(2,2-difluorocyclopropyl)methoxy]-5-(ethylsulfonyl)phenyl}-6-methyl-1,6-dihydro-7H-pyrrolo[2,3-c]pyridin-7-one;

4-(4-bromo-2-methoxyphenyl)-6-methyl-1,6-dihydro-7H-pyrrolo[2,3-c]pyridin-7-one;

6-(2,4-difluorophenoxy)-5-(6-methyl-7-oxo-6,7-dihydro-1H-pyrrolo[2,3-c]pyridin-4-yl)pyridine-3-sulfonamide;

4-{2-(cyclopropylmethoxy)-5-[(trifluoromethyl)sulfonyl]phenyl}-6-methyl-1,6-dihydro-7H-pyrrolo[2,3-c]pyridin-7-one;

4-{2-[(cyclopropylmethyl)amino]-5-[(trifluoromethyl)sulfonyl]phenyl}-6-methyl-1,6-dihydro-7H-pyrrolo[2,3-c]pyridin-7-one;

6-[(cyclopropylmethyl)amino]-N,N-dimethyl-5-(6-methyl-7-oxo-6,7-dihydro-1H-pyrrolo[2,3-c]pyridin-4-yl)pyridine-3-sulfonamide;

6-(2,4-difluorophenoxy)-N-methyl-5-(6-methyl-7-oxo-6,7-dihydro-1H-pyrrolo[2,3-c]pyridin-4-yl)pyridine-3-sulfonamide;

4-[2-(cyclopropylmethoxy)-6-methylphenyl]-6-methyl-1,6-dihydro-7H-pyrrolo[2,3-c]pyridin-7-one;

4-{5-(ethylsulfonyl)-2-[(cis-4-methoxycyclohexyl)oxy]phenyl}-6-methyl-1,6-dihydro-7H-pyrrolo[2,3-c]pyridin-7-one;

4-(cyclopropylmethoxy)-3-(6-methyl-7-oxo-6,7-dihydro-1H-pyrrolo[2,3-c]pyridin-4-yl)benzenesulfonamide;

4-(cyclopropylmethoxy)-N-methyl-3-(6-methyl-7-oxo-6,7-dihydro-1H-pyrrolo[2,3-c]pyridin-4-yl)benzenesulfonamide;

N-[4-(cyclopropylmethoxy)-2-methyl-3-(6-methyl-7-oxo-6,7-dihydro-1H-pyrrolo[2,3-c]pyridin-4-yl)phenyl]ethanesulfonamide;

4-[2-(2,4-difluorophenoxy)-5-(methylsulfonyl)phenyl]-6-methyl-7-oxo-6,7-dihydro-1H-pyrrolo[2,3-c]pyridine-2-carboxamide;

4-[2-(2,4-difluorophenoxy)-5-(methylsulfonyl)phenyl]-N-ethyl-6-methyl-7-oxo-6,7-dihydro-1H-pyrrolo[2,3-c]pyridine-2-carboxamide;

4-[2-(2,4-difluorophenoxy)-5-(methylsulfonyl)phenyl]-6-methyl-7-oxo-N-(2,2,2-trifluoroethyl)-6,7-dihydro-1H-pyrrolo[2,3-c]pyridine-2-carboxamide;

4-[2-(2,4-difluorophenoxy)-5-(methylsulfonyl)phenyl]-6-methyl-2-(morpholin-4-ylcarbonyl)-1,6-dihydro-7H-pyrrolo[2,3-c]pyridin-7-one;

4-[2-(2,4-difluorophenoxy)-5-(methylsulfonyl)phenyl]-6-methyl-2-[(4-methylpiperazin-1-yl)carbonyl]-1,6-dihydro-7H-pyrrolo[2,3-c]pyridin-7-one;

4-[2-(2,4-difluorophenoxy)-5-(methylsulfonyl)phenyl]-6-methyl-7-oxo-N-(1,3-thiazol-2-yl)-6,7-dihydro-1H-pyrrolo[2,3-c]pyridine-2-carboxamide;

ethyl 4-[2-(6-methyl-7-oxo-6,7-dihydro-1H-pyrrolo[2,3-c]pyridin-4-yl)-4-(methylsulfonyl)phenoxy]piperidine-1-carboxylate;

4-[2-ethoxy-5-(methylsulfonyl)phenyl]-6-methyl-1,6-dihydro-7H-pyrrolo[2,3-c]pyridin-7-one;

4-{5-(ethylsulfonyl)-2-[(trans-4-methoxycyclohexyl)oxy]phenyl}-6-methyl-1,6-dihydro-7H-pyrrolo[2,3-c]pyridin-7-one;

4-{2-[(cyclopropylmethyl)amino]-5-(propan-2-ylsulfonyl)phenyl}-6-methyl-1,6-dihydro-7H-pyrrolo[2,3-c]pyridin-7-one;

N-[4-(cyclopropylmethoxy)-2-methyl-3-(6-methyl-7-oxo-6,7-dihydro-1H-pyrrolo[2,3-c]pyridin-4-yl)phenyl]methanesulfonamide;

N-[4-(cyclopropylmethoxy)-2-methyl-5-(6-methyl-7-oxo-6,7-dihydro-1H-pyrrolo[2,3-c]pyridin-4-yl)phenyl]methanesulfonamide;

4-[5-(ethylsulfonyl)-2-(tetrahydro-2H-thiopyran-4-yloxy)phenyl]-6-methyl-1,6-dihydro-7H-pyrrolo[2,3-c]pyridin-7-one;

4-{2-[(1,1-dioxidotetrahydro-2H-thiopyran-4-yl)oxy]-5-(ethylsulfonyl)phenyl}-6-methyl-1,6-dihydro-7H-pyrrolo[2,3-c]pyridin-7-one;

6-(2,4-difluorophenoxy)-N,N-dimethyl-5-(6-methyl-7-oxo-6,7-dihydro-1H-pyrrolo[2,3-c]pyridin-4-yl)pyridine-3-sulfonamide;

4-[2-(cyclopropylamino)-5-(ethylsulfonyl)phenyl]-6-methyl-1,6-dihydro-7H-pyrrolo[2,3-c]pyridin-7-one;

4-(5-(ethylsulfonyl)-2-(cis-4-methoxy-4-methylcyclohexyloxy)phenyl)-6-methyl-1H-pyrrolo[2,3-c]pyridin-7(6H)-one;

4-[2-(2,4-difluorophenoxy)-5-(methylsulfonyl)phenyl]-N,N,6-trimethyl-7-oxo-6,7-dihydro-1H-pyrrolo[2,3-c]pyridine-2-carboxamide;

6-methyl-4-{5-(methylsulfonyl)-2-[4-(methylsulfonyl)phenoxy]phenyl}-1,6-dihydro-7H-pyrrolo[2,3-c]pyridin-7-one;

4-[2-(2,4-difluorophenoxy)-5-(propan-2-ylsulfonyl)phenyl]-6-methyl-1,6-dihydro-7H-pyrrolo[2,3-c]pyridin-7-one;

6-(cyclopropylmethoxy)-N,N-diethyl-5-(6-methyl-7-oxo-6,7-dihydro-1H-pyrrolo[2,3-c]pyridin-4-yl)pyridine-3-sulfonamide;

4-(cyclopropylmethoxy)-N,N-dimethyl-3-(6-methyl-7-oxo-6,7-dihydro-1H-pyrrolo[2,3-c]pyridin-4-yl)benzenesulfonamide;

4-[2-(cyclopropylmethoxy)-5-fluorophenyl]-6-methyl-1,6-dihydro-7H-pyrrolo[2,3-c]pyridin-7-one;

4-[2-(2,4-difluorophenoxy)-5-(trifluoromethyl)phenyl]-6-methyl-1,6-dihydro-7H-pyrrolo[2,3-c]pyridin-7-one;

4-[2-(2,4-difluorophenoxy)-5-(methylsulfonyl)phenyl]-2-(hydroxymethyl)-6-methyl-1,6-dihydro-7H-pyrrolo[2,3-c]pyridin-7-one;

4-[2-(2,3-dihydro-1H-inden-2-yloxy)-5-(methylsulfonyl)phenyl]-6-methyl-1,6-dihydro-7H-pyrrolo[2,3-c]pyridin-7-one;

4-[2-(2,4-difluorophenoxy)-5-(methylsulfonyl)phenyl]-2-(1-hydroxyethyl)-6-methyl-1,6-dihydro-7H-pyrrolo[2,3-c]pyridin-7-one;

4-[2-(2,4-difluorophenoxy)-5-(methylsulfonyl)phenyl]-2-[(dimethylamino)methyl]-6-methyl-1,6-dihydro-7H-pyrrolo[2,3-c]pyridin-7-one;

4-[2-(2,4-difluorophenoxy)-5-(methylsulfonyl)phenyl]-6-methyl-2-(morpholin-4-ylmethyl)-1,6-dihydro-7H-pyrrolo[2,3-c]pyridin-7-one;

4-[2-(2,4-difluorophenoxy)-5-(methylsulfonyl)phenyl]-6-methyl-2-[(4-methylpiperazin-1-yl)methyl]-1,6-dihydro-7H-pyrrolo[2,3-c]pyridin-7-one;

4-[2-(2,4-difluorophenoxy)-5-(methylsulfonyl)phenyl]-6-methyl-2-[(phenylamino)methyl]-1,6-dihydro-7H-pyrrolo[2,3-c]pyridin-7-one;

4-[2-(2,4-difluorophenoxy)-5-(methylsulfonyl)phenyl]-6-methyl-2-[(1,3-thiazol-2-ylamino)methyl]-1,6-dihydro-7H-pyrrolo[2,3-c]pyridin-7-one;

4-[2-(2,4-difluorophenoxy)-5-(methylsulfonyl)phenyl]-6-methyl-2-[(tetrahydrofuran-3-ylamino)methyl]-1,6-dihydro-7H-pyrrolo[2,3-c]pyridin-7-one;

4-[2-(cyclopropylmethoxy)-5-(phenylsulfonyl)phenyl]-6-methyl-1,6-dihydro-7H-pyrrolo[2,3-c]pyridin-7-one;

4-[2-(cyclopropylmethoxy)-5-(morpholin-4-ylsulfonyl)phenyl]-6-methyl-1,6-dihydro-7H-pyrrolo[2,3-c]pyridin-7-one;

4-{2-(2,4-difluorophenoxy)-5-[(methylsulfonyl)methyl]phenyl}-6-methyl-1,6-dihydro-7H-pyrrolo[2,3-c]pyridin-7-one;

4-[2-(2,4-difluorophenoxy)-5-(methylsulfonyl)pyridin-3-yl]-6-methyl-1,6-dihydro-7H-pyrrolo[2,3-c]pyridin-7-one;

4-[2-(2,4-difluorophenoxy)-5-(methylsulfonyl)phenyl]-6-methyl-2-[(pyridin-3-yloxy)methyl]-1,6-dihydro-7H-pyrrolo[2,3-c]pyridin-7-one;

4-[5-(cyclopropylsulfonyl)-2-(2,4-difluorophenoxy)phenyl]-6-methyl-1,6-dihydro-7H-pyrrolo[2,3-c]pyridin-7-one;

4-[2-(2,4-difluorophenoxy)-5-(methylsulfonyl)phenyl]-6-methyl-2-(prop-1-en-2-yl)-1,6-dihydro-7H-pyrrolo[2,3-c]pyridin-7-one;

4-[2-(2,4-difluorophenoxy)-5-(methylsulfonyl)phenyl]-6-methyl-2-(phenoxymethyl)-1,6-dihydro-7H-pyrrolo[2,3-c]pyridin-7-one;

4-[2-(2,4-difluorophenoxy)-5-(morpholin-4-ylsulfonyl)phenyl]-6-methyl-1,6-dihydro-7H-pyrrolo[2,3-c]pyridin-7-one;

4-[2-(2,4-difluorophenoxy)-5-(ethylsulfonyl)pyridin-3-yl]-6-methyl-1,6-dihydro-7H-pyrrolo[2,3-c]pyridin-7-one;

N-[4-(2,4-difluorophenoxy)-3-(6-methyl-7-oxo-6,7-dihydro-1H-pyrrolo[2,3-c]pyridin-4-yl)phenyl]-2-(morpholin-4-yl)ethanesulfonamide;

N-[4-(2,4-difluorophenoxy)-3-(6-methyl-7-oxo-6,7-dihydro-1H-pyrrolo[2,3-c]pyridin-4-yl)phenyl]-N-[2-(dimethylamino)ethyl]ethanesulfonamide;

4-{2-(2,4-difluorophenoxy)-5-[(ethylsulfonyl)methyl]phenyl}-6-methyl-1,6-dihydro-7H-pyrrolo[2,3-c]pyridin-7-one;

4-{2-(2,4-difluorophenoxy)-5-[2-(ethylsulfonyl)propan-2-yl]phenyl}-6-methyl-1,6-dihydro-7H-pyrrolo[2,3-c]pyridin-7-one;

4-[2-(2,4-difluorophenoxy)-5-(pyrrolidin-1-ylsulfonyl)phenyl]-6-methyl-1,6-dihydro-7H-pyrrolo[2,3-c]pyridin-7-one;

N-[4-(2,4-difluorophenoxy)-3-(6-methyl-7-oxo-6,7-dihydro-1H-pyrrolo[2,3-c]pyridin-4-yl)phenyl]-2-(dimethylamino)ethanesulfonamide;

ethyl 4-[4-(ethylsulfonyl)-2-(6-methyl-7-oxo-6,7-dihydro-1H-pyrrolo[2,3-c]pyridin-4-yl)phenoxy]piperidine-1-carboxylate;

4-[2-(cyclopropylmethoxy)-5-(pyrrolidin-1-ylsulfonyl)phenyl]-6-methyl-1,6-dihydro-7H-pyrrolo[2,3-c]pyridin-7-one;

4-{2-[(1-acetylpiperidin-4-yl)oxy]-5-(ethylsulfonyl)phenyl}-6-methyl-1,6-dihydro-7H-pyrrolo[2,3-c]pyridin-7-one;

4-[4-(ethylsulfonyl)-2-(6-methyl-7-oxo-6,7-dihydro-1H-pyrrolo[2,3-c]pyridin-4-yl)phenoxy]benzonitrile;

4-[2-(cyclopropylmethoxy)-5-(2,3-dihydro-1H-indol-1-ylsulfonyl)phenyl]-6-methyl-1,6-dihydro-7H-pyrrolo[2,3-c]pyridin-7-one;

4-{2-(2,4-difluorophenoxy)-5-[(phenylsulfonyl)methyl]phenyl}-6-methyl-1,6-dihydro-7H-pyrrolo[2,3-c]pyridin-7-one;

4-{2-[(2,2-difluorocyclopropyl)methoxy]-5-(pyrrolidin-1-ylsulfonyl)phenyl}-6-methyl-1,6-dihydro-7H-pyrrolo[2,3-c]pyridin-7-one;

4-{2-(cyclopropylmethoxy)-5-[(3,3-difluoroazetidin-1-yl)sulfonyl]phenyl}-6-methyl-1,6-dihydro-7H-pyrrolo[2,3-c]pyridin-7-one;

4-{2-[2-(2-hydroxyethyl)phenoxy]-5-(methylsulfonyl)phenyl}-6-methyl-1,6-dihydro-7H-pyrrolo[2,3-c]pyridin-7-one;

4-[2-(cyclopropylmethoxy)-5-{[3-(dimethylamino)pyrrolidin-1-yl]sulfonyl}phenyl]-6-methyl-1,6-dihydro-7H-pyrrolo[2,3-c]pyridin-7-one;

4-{2-(2,4-difluorophenoxy)-5-[(methylsulfonyl)methyl]pyridin-3-yl}-6-methyl-1,6-dihydro-7H-pyrrolo[2,3-c]pyridin-7-one;

tert-butyl 4-[4-(ethylsulfonyl)-2-(6-methyl-7-oxo-6,7-dihydro-1H-pyrrolo[2,3-c]pyridin-4-yl)phenoxy]piperidine-1-carboxylate;

4-(cyclopropylmethoxy)-3-(6-methyl-7-oxo-6,7-dihydro-1H-pyrrolo[2,3-c]pyridin-4-yl)-N-phenylbenzenesulfonamide;

4-[2-(cyclopropylmethoxy)-5-(pyrrolidin-1-ylmethyl)phenyl]-6-methyl-1,6-dihydro-7H-pyrrolo[2,3-c]pyridin-7-one;

4-[2-(cyclopropylmethoxy)-5-(pyridin-3-yl)phenyl]-6-methyl-1,6-dihydro-7H-pyrrolo[2,3-c]pyridin-7-one;

4-[2-(cyclopropylmethoxy)-5-(morpholin-4-ylmethyl)phenyl]-6-methyl-1,6-dihydro-7H-pyrrolo[2,3-c]pyridin-7-one;

4-{5-(ethylsulfonyl)-2-[3-(hydroxymethyl)phenoxy]phenyl}-6-methyl-1,6-dihydro-7H-pyrrolo[2,3-c]pyridin-7-one;

4-[2-(cyclopropylmethoxy)-5-(1-methyl-1H-pyrazol-4-yl)phenyl]-6-methyl-1,6-dihydro-7H-pyrrolo[2,3-c]pyridin-7-one;

4-[2-(2,4-difluorophenoxy)-5-(2,3-dihydro-1H-indol-1-ylsulfonyl)phenyl]-6-methyl-1,6-dihydro-7H-pyrrolo[2,3-c]pyridin-7-one;

N-[4-(2,4-difluorophenoxy)-3-(6-methyl-7-oxo-6,7-dihydro-1H-pyrazolo[3,4-c]pyridin-4-yl)phenyl]ethanesulfonamide;

4-{2-(2,4-difluorophenoxy)-5-[(methylsulfonyl)methyl]phenyl}-6-methyl-1,6-dihydro-7H-pyrazolo[3,4-c]pyridin-7-one;

4-[2-(2,4-difluorophenoxy)-5-(ethylsulfonyl)phenyl]-6-methyl-1,6-dihydro-7H-pyrazolo[3,4-c]pyridin-7-one;

4-[2-(cyclopropylmethoxy)-5-(ethylsulfonyl)phenyl]-6-methyl-1,6-dihydro-7H-pyrazolo[3,4-c]pyridin-7-one;

N-[2-cyano-4-(2,4-difluorophenoxy)-5-(6-methyl-7-oxo-6,7-dihydro-1H-pyrrolo[2,3-c]pyridin-4-yl)phenyl]ethanesulfonamide;

tert-butyl 4-[4-(cyclopropylmethoxy)-3-(6-methyl-7-oxo-6,7-dihydro-1H-pyrrolo[2,3-c]pyridin-4-yl)phenyl]-3,6-dihydropyridine-1(2H)-carboxylate;

4-[5-(6-aminopyridin-3-yl)-2-(cyclopropylmethoxy)phenyl]-6-methyl-1,6-dihydro-7H-pyrrolo[2,3-c]pyridin-7-one;

4-{2-[(2,2-difluorocyclopropyl)methoxy]-5-(ethylsulfonyl)phenyl}-6-methyl-7-oxo-N-(2,2,2-trifluoroethyl)-6,7-dihydro-1H-pyrrolo[2,3-c]pyridine-2-carboxamide;

4-{2-[(cyclopropylmethyl)amino]-5-[(methylsulfonyl)methyl]phenyl}-6-methyl-1,6-dihydro-7H-pyrrolo[2,3-c]pyridin-7-one;

4-{2-[(cyclopropylmethyl)amino]-5-(methylsulfonyl)phenyl}-6-methyl-1,6-dihydro-7H-pyrrolo[2,3-c]pyridin-7-one;

4-[5-(ethylsulfonyl)-2-(pyrrolidin-1-yl)phenyl]-6-methyl-1,6-dihydro-7H-pyrrolo[2,3-c]pyridin-7-one;

4-[5-(ethylsulfonyl)-2-(4-methylpiperazin-1-yl)phenyl]-6-methyl-1,6-dihydro-7H-pyrrolo[2,3-c]pyridin-7-one;

4-{2-[(4-fluorophenyl)amino]-5-(methylsulfonyl)phenyl}-6-methyl-1,6-dihydro-7H-pyrrolo[2,3-c]pyridin-7-one;

4-(cyclopropylmethoxy)-3-(6-methyl-7-oxo-6,7-dihydro-1H-pyrrolo[2,3-c]pyridin-4-yl)-N-(pyridin-3-ylmethyl)benzenesulfonamide;

4-[4-(cyclopropylmethoxy)-3'-fluorobiphenyl-3-yl]-6-methyl-1,6-dihydro-7H-pyrrolo[2,3-c]pyridin-7-one;

4-{2-[(4-fluorophenyl)amino]-5-[(methylsulfonyl)methyl]phenyl}-6-methyl-1,6-dihydro-7H-pyrrolo[2,3-c]pyridin-7-one;

[4-(cyclopropylmethoxy)-3-(6-methyl-7-oxo-6,7-dihydro-1H-pyrrolo[2,3-c]pyridin-4-yl)phenyl]acetonitrile;

N-{4-(2,4-difluorophenoxy)-3-[2-(hydroxymethyl)-6-methyl-7-oxo-6,7-dihydro-1H-pyrrolo[2,3-c]pyridin-4-yl]phenyl}ethanesulfonamide;

N-[4-(2,4-difluorophenoxy)-3-{6-methyl-2-[(4-methylpiperazin-1-yl)carbonyl]-7-oxo-6,7-dihydro-1H-pyrrolo[2,3-c]pyridin-4-yl}phenyl]ethanesulfonamide;

N-[4-(2,4-difluorophenoxy)-3-{6-methyl-2-[(4-methylpiperazin-1-yl)methyl]-7-oxo-6,7-dihydro-1H-pyrrolo[2,3-c]pyridin-4-yl}phenyl]ethanesulfonamide;

4-[2-(cyclopropylmethoxy)-5-(1,2,3,6-tetrahydropyridin-4-yl)phenyl]-6-methyl-1,6-dihydro-7H-pyrrolo[2,3-c]pyridin-7-one;

N-[4-(2,4-difluorophenoxy)-3-(6-methyl-7-oxo-6,7-dihydro-1H-pyrrolo[2,3-c]pyridin-4-yl)phenyl]-N-(2-methoxyethyl)ethanesulfonamide;

N-[4-(2,4-difluorophenoxy)-3-(6-methyl-7-oxo-6,7-dihydro-1H-pyrrolo[2,3-c]pyridin-4-yl)phenyl]-N-(pyridin-2-ylmethyl)ethanesulfonamide;

N-(cyclopropylmethyl)-N-[4-(2,4-difluorophenoxy)-3-(6-methyl-7-oxo-6,7-dihydro-1 H-pyrrolo[2,3-c]pyridin-4-yl)phenyl]ethanesulfonamide;

N-[4-(2,4-difluorophenoxy)-3-(6-methyl-7-oxo-6,7-dihydro-1H-pyrrolo[2,3-c]pyridin-4-yl)phenyl]-N-[2-(2-oxopyrrolidin-1-yl)ethyl]ethanesulfonamide;

N-[4-(2,4-difluorophenoxy)-3-(6-methyl-7-oxo-6,7-dihydro-1H-pyrrolo[2,3-c]pyridin-4-yl)phenyl]-N-(tetrahydrofuran-2-ylmethyl)ethanesulfonamide;

N-[4-(2,4-difluorophenoxy)-3-(6-methyl-7-oxo-6,7-dihydro-1H-pyrrolo[2,3-c]pyridin-4-yl)phenyl]-N-(3,3,3-trifluoropropyl)ethanesulfonamide;

4-(cyclopropylmethoxy)-N-(4-fluorophenyl)-3-(6-methyl-7-oxo-6,7-dihydro-1H-pyrrolo[2,3-c]pyridin-4-yl)benzenesulfonamide;

4-[2-(cyclopropylmethoxy)-5-(6-fluoropyridin-3-yl)phenyl]-6-methyl-1,6-dihydro-7H-pyrrolo[2,3-c]pyridin-7-one;

N-[4-(2,4-difluorophenoxy)-3-(3-formyl-6-methyl-7-oxo-6,7-dihydro-1H-pyrrolo[2,3-c]pyridin-4-yl)phenyl]ethanesulfonamide;

N-{4-(2,4-difluorophenoxy)-3-[6-methyl-3-(morpholin-4-ylmethyl)-7-oxo-6,7-dihydro-1H-pyrrolo[2,3-c]pyridin-4-yl]phenyl}ethanesulfonamide;

N-[4-(2,4-difluorophenoxy)-3-{6-methyl-3-[(4-methylpiperazin-1-yl)methyl]-7-oxo-6,7-dihydro-1H-pyrrolo[2,3-c]pyridin-4-yl}phenyl]ethanesulfonamide;

4-{2-[(cyclopropylmethyl)amino]phenyl}-6-methyl-1,6-dihydro-7H-pyrrolo[2,3-c]pyridin-7-one;

4'-(cyclopropylmethoxy)-3'-(6-methyl-7-oxo-6,7-dihydro-1H-pyrrolo[2,3-c]pyridin-4-yl)biphenyl-3-carbonitrile; and 4-{2-(cyclopropylmethoxy)-5-[(4-hydroxypiperidin-1-yl)sulfonyl]phenyl}-6-methyl-1,6-dihydro-7H-pyrrolo[2,3-c]pyridin-7-one.

In certain embodiments, a compound of formula I is selected from the group consisting of:

N-[4-(2,4-difluorophenoxy)-3-(6-methyl-7-oxo-6,7-dihydro-1H-pyrrolo[2,3-c]pyridin-4-yl)phenyl]ethanesulfonamide;

N-[4-(2,4-difluorophenoxy)-3-(6-methyl-7-oxo-6,7-dihydro-1H-pyrrolo[2,3-c]pyridin-4-yl)phenyl]methanesulfonamide;

6-methyl-4-[5-(methylsulfonyl)-2-phenoxyphenyl]-1,6-dihydro-7H-pyrrolo[2,3-c]pyridin-7-one;

N-methyl-5-(6-methyl-7-oxo-6,7-dihydro-1H-pyrrolo[2,3-c]pyridin-4-yl)-6-(tetrahydrofuran-3-yloxy)pyridine-3-sulfonamide;

N-[4-(2-chloro-4-fluorophenoxy)-3-(6-methyl-7-oxo-6,7-dihydro-1H-pyrrolo[2,3-c]pyridin-4-yl)phenyl]methanesulfonamide;

6-methyl-4-{5-[(methylsulfonyl)amino]-2-phenoxyphenyl}-7-oxo-6,7-dihydro-1H-pyrrolo[2,3-c]pyridine-2-carboxamide;

N-[3-(6-methyl-7-oxo-6,7-dihydro-1H-pyrrolo[2,3-c]pyridin-4-yl)-4-phenoxyphenyl]methanesulfonamide;

N-[3-(6-methyl-7-oxo-6,7-dihydro-1H-pyrrolo[2,3-c]pyridin-4-yl)-4-(2,4,6-trifluorophenoxy)phenyl]ethanesulfonamide;

N-{4-[(4,4-difluorocyclohexyl)oxy]-3-(6-methyl-7-oxo-6,7-dihydro-1H-pyrrolo[2,3-c]pyridin-4-yl)phenyl}methanesulfonamide; and N-[4-(4-fluorophenoxy)-3-(6-methyl-7-oxo-6,7-dihydro-1H-pyrrolo[2,3-c]pyridin-4-yl)phenyl]methanesulfonamide; or a pharmaceutically acceptable salt thereof.

In certain embodiments, a compound of formula I is selected from the group consisting of:

4-{2-(2,4-difluorophenoxy)-5-[(methylsulfonyl)methyl]pyridin-3-yl}-6-methyl-1,6-dihydro-7H-pyrrolo[2,3-c]pyridin-7-one;

N-[4-(2,4-difluorophenoxy)-3-(6-methyl-7-oxo-6,7-dihydro-1H-pyrrolo[2,3-c]pyridin-4-yl)phenyl]ethanesulfonamide;

4-(cyclopropylmethoxy)-N-methyl-3-(6-methyl-7-oxo-6,7-dihydro-1H-pyrrolo[2,3-c]pyridin-4-yl)benzenesulfonamide;

4-{2-[(4,4-difluorocyclohexyl)oxy]-5-(ethylsulfonyl)phenyl}-6-methyl-1,6-dihydro-7H-pyrrolo[2,3-c]pyridin-7-one;

4-(5-(ethylsulfonyl)-2-(cis-4-methoxy-4-methylcyclohexyloxy)phenyl)-6-methyl-1H-pyrrolo[2,3-c]pyridin-7(6H)-one;

6-methyl-4-{5-[(methylsulfonyl)amino]-2-phenoxyphenyl}-7-oxo-6,7-dihydro-1H-pyrrolo[2,3-c]pyridine-2-carboxamide;

4-{2-(2,4-difluorophenoxy)-5-[(methylsulfonyl)methyl]phenyl}-6-methyl-1,6-dihydro-7H-pyrrolo[2,3-c]pyridin-7-one;

4-[2-(2,4-difluorophenoxy)-5-(ethylsulfonyl)phenyl]-6-methyl-1,6-dihydro-7H-pyrrolo[2,3-c]pyridin-7-one;

4-{5-(ethylsulfonyl)-2-[(trans-4-methoxycyclohexyl)oxy]phenyl}-6-methyl-1,6-dihydro-7H-pyrrolo[2,3-c]pyridin-7-one;

4-{2-[(cyclopropylmethyl)amino]-5-(ethylsulfonyl)phenyl}-6-methyl-1,6-dihydro-7H-pyrrolo[2,3-c]pyridin-7-one;

4-[(cyclopropylmethyl)amino]-3-(6-methyl-7-oxo-6,7-dihydro-1H-pyrrolo[2,3-c]pyridin-4-yl)benzenesulfonamide;

4-(2,4-difluorophenoxy)-3-(6-methyl-7-oxo-6,7-dihydro-1H-pyrrolo[2,3-c]pyridin-4-yl)benzenesulfonamide;

4-[2-(cyclopropylmethoxy)-5-(methylsulfonyl)phenyl]-6-methyl-1,6-dihydro-7H-pyrrolo[2,3-c]pyridin-7-one;

4-[2-(cyclohexyloxy)-5-(methylsulfonyl)phenyl]-6-methyl-1,6-dihydro-7H-pyrrolo[2,3-c]pyridin-7-one; and N-[3-(6-methyl-7-oxo-6,7-dihydro-1H-pyrrolo[2,3-c]pyridin-4-yl)-4-phenoxyphenyl]ethanesulfonamide;

or a pharmaceutically acceptable salt thereof.

In certain embodiments, a compound of the present invention is N-[4-(2,4-difluorophenoxy)-3-(6-methyl-7-oxo-6,7-dihydro-1H-pyrrolo[2,3-c]pyridin-4-yl)phenyl]ethanesulfonamide, or a pharmaceutically acceptable salt thereof.

Compounds of formula I can be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds described herein, including compounds of general formula (I) and specific examples, may be prepared, for example, through the reaction routes depicted in schemes 1-5. The variables $A^1, A^2, A^3, A^4, X^1, X^2, Y^1, L^1, G^1, R^x$, and $R^y$ used in the following schemes have the meanings as set forth in the summary and detailed description sections unless otherwise noted.

Abbreviations used in the descriptions of the schemes and the specific examples have the following meanings: n-BuLi or BuLi for n-butyl lithium, DBU for 1,8-diazabicyclo[5.4.0]undec-7-ene, DIAD for diisopropyl azodicarboxylate; DME for 1,2-dimethoxyethane, DMF for dimethylformamide, DMSO for dimethyl sulfoxide, EtOAc for ethyl acetate; mCPBA for 3-chloroperbenzoic acid, MeOH for methanol; $Pd(PPh_3)_4$ for tetrakis(triphenylphosphine)palladium(0), Preparative HPLC for preparative HPLC; THF for tetrahydrofuran, TFA for trifluoroacetic acid, and HPLC for high performance liquid chromatography.

Compounds of general formula (I) may be prepared (a) by treating an aryl halide, an aryl mesylate, or an aryl triflate with an aryl boronic acid or derivatives thereof (e.g. boronic esters) under Suzuki coupling condition (N. Miyama and A. Suzuki, Chem. Rev. 1995, 95:2457-2483, J. Organomet. Chem. 1999, 576:147-148), and (b) removal of the protecting group (PG), as illustrated in Scheme 1. Thus coupling of compounds of formula (1) wherein $R^{101}$ is Br, Cl, mesylate, or triflate with compounds of formula (2) wherein $R^{102}$ is boronic acid or derivatives thereof (e.g. boronic esters), or coupling of (1) wherein $R^{101}$ is boronic acid or derivatives thereof (e.g. boronic esters) with compounds (2) wherein $R^{102}$ is Br, Cl, mesylate, or triflate, provides intermediates of formula (3). Generally, the coupling reaction is effected in the presence of a palladium catalyst and a base, and optionally in the presence of a ligand, and in a suitable solvent at elevated temperature (for example, at about 80° C. to about 150° C.). The reaction may be facilitated by microwave irradiation. Examples of the palladium catalyst include, but are not limited to, tetrakis (triphenylphosphine)palladium(0), tris(dibenzylideneacetone)dipalladium(0), and palladium(II)acetate. Examples of suitable bases that may be employed include, but are not limited to, carbonates or phosphates of sodium, potassium, and cesium; and cesium fluoride. Examples of suitable ligands include, but are not limited to, 1,3,5,7-tetramethyl-6-phenyl-2,4,8-trioxa-6-phosphaadamante, 2-dicyclohexylphosphino-2',4',6'-triisopropylbiphenyl (X-phos), and 1,1'-bis(diphenylphosphanyl) ferrocene. Non-limiting examples of suitable solvent include methanol, dimethoxyethane, N,N-dimethylformamide, dimethylsulfoxide, dioxane, tetrahydropyran, and water, or a mixture thereof.

Alternatively, treatment of formula (1) wherein $R^{101}$ is Br, Cl, or triflate with boronic acid of formula (4), followed by displacement of the fluoride atom in (4) with an appropriate alcohol or amine of formula $G^1$-$L^1$-H wherein $L^1$ is O or NH, provides compounds of formula (3) or formula (I) wherein $R^x$ is hydrogen.

Displacement of the fluorine with an alcohol or amine may be achieved in a solvent such as, but not limited to, dimethylsulfoxide, dimethylformamide, dioxane, or tetrahydrofuran, and in the presence of a base such as, but not limited to, cesium carbonate, potassium carbonate, or sodium hydride and at a temperature from about 40° C. to about 120° C.

The protecting group (PG) may be removed in situ during the displacement reaction or the coupling conditions described above.

Alternatively, removal of the protecting group (PG) to afford compounds of general formula (I) wherein $R^x$ is hydrogen can be accomplished using reaction conditions known generally to one skilled in the art, or modifications thereof. For example, the tosyl protecting group can be removed in the presence of a base such as, but not limited to, cesium carbonate, sodium hydroxide, or sodium hydride. The reaction is generally performed in the presence of a suitable solvent such as, but not limited to, dimethylsulfoxide, methanol, or tetrahydrofuran, and at a temperature of about 40° C. to about 120° C. The benzyl protecting group may be removed by hydrogenation in the presence of a catalyst such as, but not limited to, palladium on carbon and under hydrogen atmosphere. The reaction is typically performed in the presence of a solvent such as, but not limited to, methanol or ethyl acetate, and at about room temperature.

Removal of the (trimethylsilyl)ethoxy)methyl protecting group can be achieved by treatment with a base such as, but not limited to, cesium carbonate or sodium hydride, or with a fluoride reagent such as, but not limited to, TBAF (tetrabutylammonium fluoride). The reaction is generally performed in the presence of a suitable solvent such as, but not limited to, dimethylsulfoxide, ethanol, or tetrahydrofuran, and at a temperature of about 40° C. to about 120° C. Removal of the (trimethylsilyl)ethoxy)methyl protecting group can also be achieved by treatment with an mild acid such as but not limited to, aqueous hydrochloric acid. The reaction is generally performed in the presence of a suitable solvent such as, but not limited to, ethanol, or methanol, and at a temperature of about 25° C. to about 80° C.

Conversion of compounds of formula (I) wherein $R^x$ is hydrogen to (I) wherein $R^x$ is $C_1$-$C_3$ alkyl can be achieved with an alkylating agent of formula $R^xR^{103}$ wherein $R^{103}$ is halogen, triflate, or mesylate. Generally, the reaction may be conducted in the presence of a base such as, but not limited to, sodium hydride or potassium carbonate, and in a solvent such as, but not limited to, tetrahydrofuran or dimethylformamide, and at a temperature of about 40° C. to about 120° C.

Scheme 1

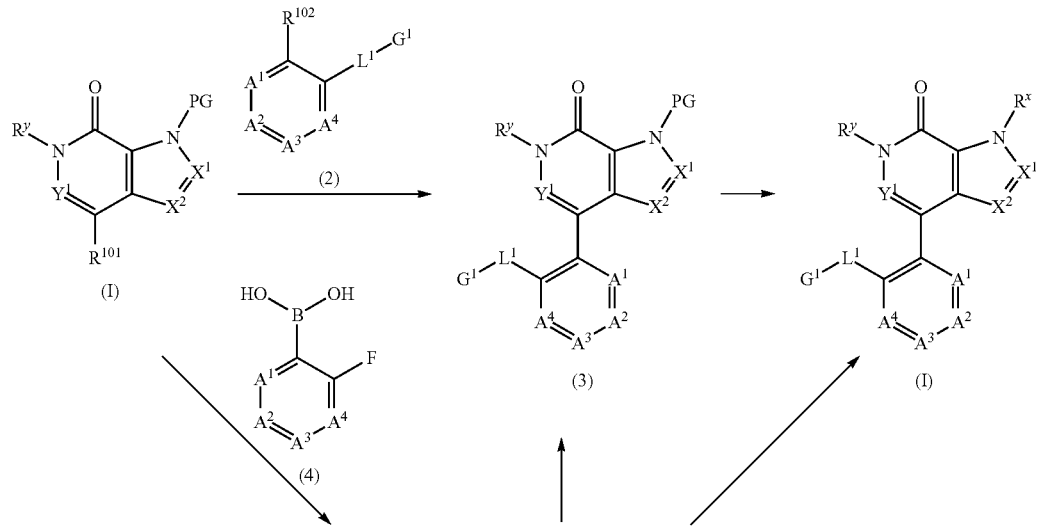

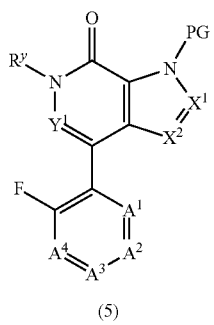

(5)

Compounds of formula (1) wherein $Y^1$ is $CR^u$, $X^1$ and $X^2$ are CH, and $R^u$ is hydrogen, $C_1$-$C_6$ alkyl, or $C_1$-$C_6$ haloalkyl may be prepared by general synthetic methods as shown in Scheme 2.

Treatment of compounds of formula (6) wherein halo is Br, Cl, or I, with 1,1-dimethoxy-N,N-dimethylmethanamine at elevated temperature (e.g. about 60° C. to about 100° C.), in the absence or presence of a base, and in a solvent such as, but not limited to, DMF, provide compounds of formula (7). Examples of suitable bases include, but not limited to, lithium or sodium methanolate. Catalytic hydrogenation of (7) in the presence of a catalyst such as, but not limited to, Raney-Nickel and under hydrogen atmosphere (about 30 psi) and in a solvent such as, but not limited to, ethyl acetate, at about room temperature generally affords compounds of formula (8). Protection of the nitrogen atom with protecting group such as, but not limited to, benzyl, tosyl, and (trimethylsilyl) ethoxy)methyl group can be derived from reaction with an appropriate halide in the presence of a strong base such as, but not limited to, sodium hydride, to provide compounds of formula (9).

Treatment of (9) with an acid such as, but not limited to, hydrochloric acid or hydrobromic acid and in a solvent such as, but not limited to, dioxane or water, at about 40° C. to about 100° C., typically provides compounds of formula (10).

Alkylation of (10) with a halide or mesylate, in the presence of a base such as, but not limited to, sodium hydride, cesium carbonate, or potassium carbonate, and in a solvent such as, but not limited to, dimethylformamide or dimethylsulfoxide at a temperature of about 0° C. to about 50° C. typically provides compounds of formula (11).

Treatment of the compounds of formula (11) with 4,4,4', 4',5,5,5',5'-octamethyl-2,2'-bi(1,3,2-dioxaborolane) generally affords compounds of formula (12). In general, the conversion may be facilitated by a palladium catalyst such as, but not limited to, tetrakis(triphenylphosphine)palladium(0), tris (dibenzylideneacetone)dipalladium(0), or palladium(II)acetate, an optional ligand such as, but not limited to, 2-dicyclohexylphosphino-2',4',6'-triisopropylbiphenyl, 2-dicyclohexylphosphino-2',4',6'-triisopropylbiphenyl (X-phos), or 1,1'-bis(diphenylphosphanyl) ferrocene, and a base such as, but not limited to, carbonates, acetates, or phosphates. of sodium, potassium, and cesium; and cesium fluoride. Non-limiting examples of suitable solvents include methanol, dimethoxyethane, N,N-dimethylformamide, dimethylsulfoxide, dioxane, tetrahydropyran, and water, or a mixture thereof.

Scheme 2

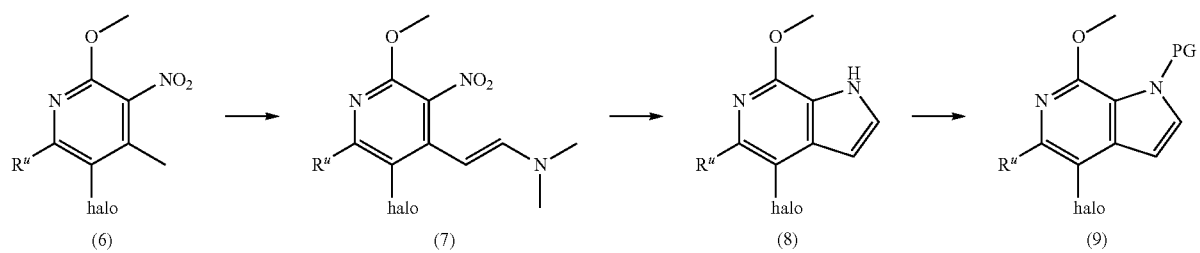

-continued

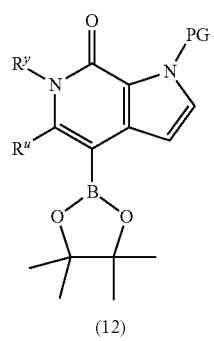 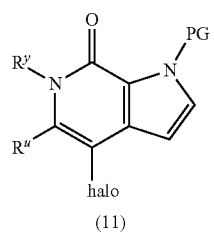 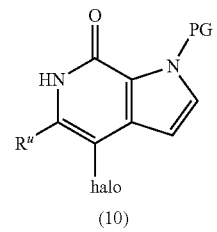

An approach to prepare compounds of formula (1) wherein $Y^1$ is N, $R^{101}$ is Cl, and $X^1$ and $X^2$ are CH, is outlined in Scheme 3.

Treatment of (13) with ammonium hydroxide at about 100° C. to about 150° C. can afford amines of formula (14).

Iodination of (14) with N-iodosuccinimide in a solvent such as, but not limited to, acetonitrile or acetone, at a temperature of about 40° C. to about 85° C., typically yields compounds of formula (15). Subsequent coupling with (E)-2-(2-ethoxyvinyl)-4,4,5,5-tetramethyl-1,3,2-dioxaborolane utilizing Suzuki coupling reaction conditions as described in Scheme 1 provides compounds of formula (16). Cyclization of (16) followed by protection of the nitrogen atom typically affords compounds of formula (17).

Cyclization of (16) may be accomplished in the presence of an acid such as, but not limited to, acetic acid or hydrochloric acid and at an elevated temperature (e.g. about 50° C. to about 100° C.).

Scheme 3

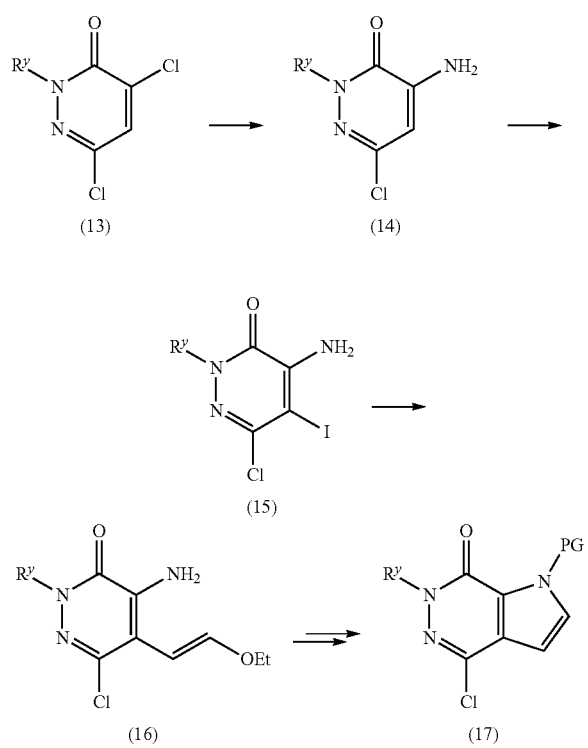

Compounds of formula (1) wherein $Y^1$ is N, $R^{101}$ is Cl, $X^1$ is —COOR$^{ax1}$ or —C(O)NR$^{bx1}$R$^{cx1}$, R$^{ax1}$, R$^{bx1}$, and R$^{cx1}$ are hydrogen or $C_1$-$C_6$ alkyl, and $X^2$ is CH may be prepared using the synthetic route exemplified in Scheme 4.

Treatment of (15) with pyruvic acid in the presence of a palladium catalyst such as, but not limited to, palladium(II) acetate, and a base such as, but not limited to, DBU, and in a solvent such as, but not limited to, DMF and at elevated temperature (e.g. at about 80° C. to about 150° C.) generally results in acids of formula (18). Esterification of (18) to (19) may be accomplished by reaction conditions known to one skilled in the art, for example, by treatment with an alcohol under acidic condition. Subsequent protection of (19) using reaction conditions described in Scheme 2 for the conversion of (8) to (9) can provide for compounds of formula (20). Transformation of (20) to (21) may be accomplished by stepwise reaction of (a) hydrolysis of the ester to the corresponding acid and (b) conversion of the acid to the corresponding amides.

The acid can be transformed to the appropriate acid chloride by treatment with oxalyl chloride in the presence of catalytic amount of DMF at about room temperature, and in a suitable solvent such as, but not limited to, tetrahydrofuran or dichloromethane.

The resulting acid chloride may be converted to amides of formula (21) by treatment with an amine of formula HNR$^{bx1}$R$^{cx1}$ in a solvent such as, but not limited to, tetrahydrofuran, dimethylformamide, or dichloromethane at a temperature from about room temperature to about 50° C., optionally in the presence of a base such as, but not limited to, triethylamine, diisopropylethylamine, or potassium carbonate, and optionally in the presence of a catalyst such as 4-dimethylaminopyridine. Alternatively, the acid can be reacted with the amine of formula HNR$^{bx1}$R$^{cx1}$ in a solvent such as, but not limited to, tetrahydrofuran or dimethylformamide in the presence of a coupling reagent such as 1,1'-carbonyldiimidazole (CDI), bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), or O-benzotriazol-1-yl-N,N,N',N'-tetramethyluronium tetrafluoroborate (TBTU), in the presence or absence of a coupling auxiliary such as, but not limited to, 1-hydroxy-7-azabenzotriazole (HOAT) or 1-hydroxybenzotriazole hydrate (HOBT). The reaction may be generally conducted in the presence or absence of a base such as, but not limited to, N-methyl morpholine, triethylamine, or diisopropylethylamine.

Scheme 4

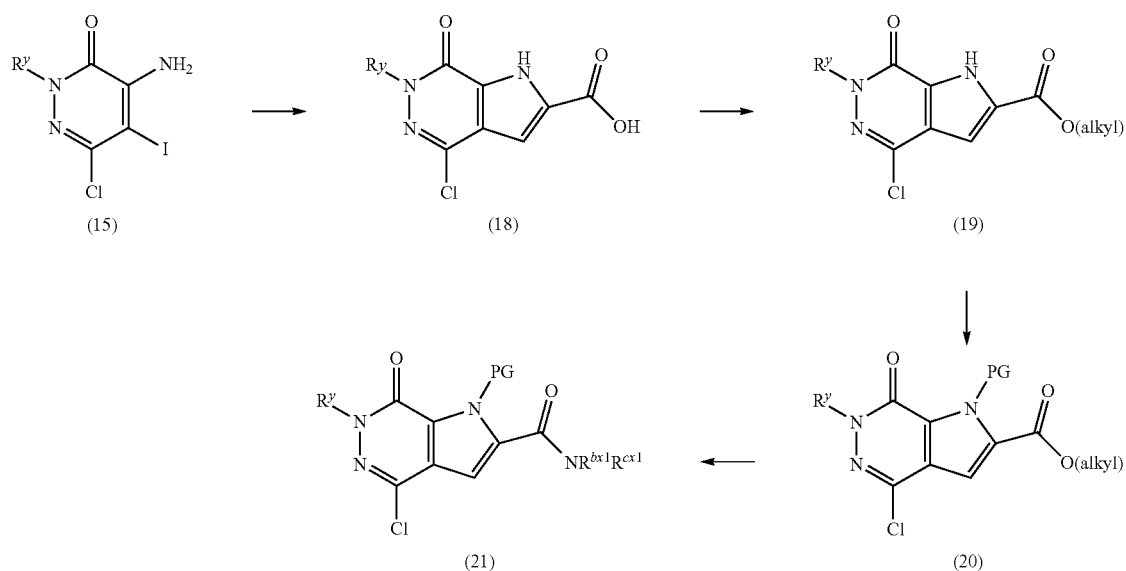

Scheme 5 demonstrates a general approach to the preparation of compounds of formula (1) wherein $Y^1$ is $CR^u$, $R^{101}$ is halogen, $X^1$ is —$COOR^{ax1}$ or —$C(O)NR^{bx1}R^{cx1}$, $R^{ax1}$, $R^{bx1}$, and $R^{cx1}$ are hydrogen or $C_1$-$C_6$ alkyl, and $X^2$ is CH.

An ester of formula (23) may be obtained from (a) treatment of (6) with diethyl oxalate in the presence of a base such as, but not limited to, potassium ethoxide or sodium ethoxide, in a solvent such as, but not limited to, potassium ethoxide or sodium ethoxide, in a solvent such as, but not limited to, ethanol, dioxane, or diethyl ether, and at a temperature of about 40° C. to about 80° C.; and (b) cyclization of the resulting (22) in the presence of iron and in ethanol and acetic acid, at a temperature of about 80° C. to about 100° C. Conversion of (23) to (26) can be achieved by employing reaction conditions discussed above.

An ethyl ester of formula (26) may subsequently be hydrolysed to the corresponding acids. The resulting acids may be transformed to an appropriate ester or amide as described in Scheme 4.

Scheme 5

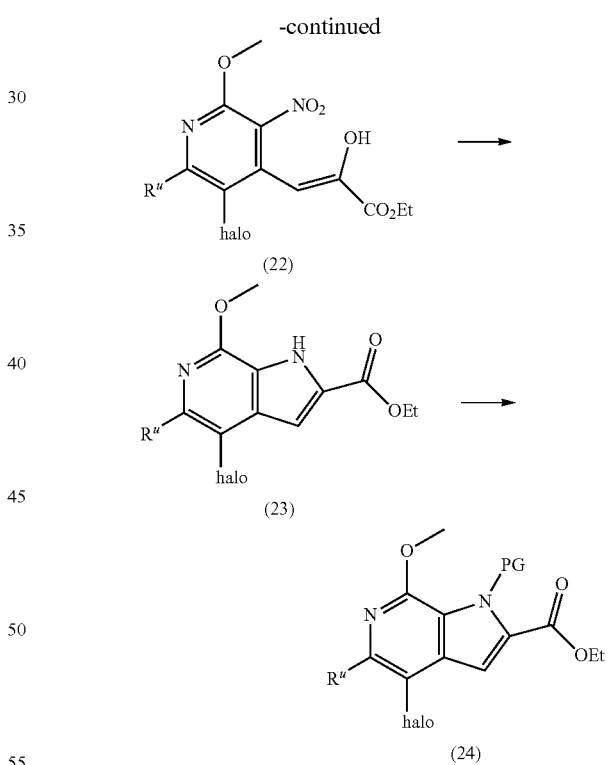

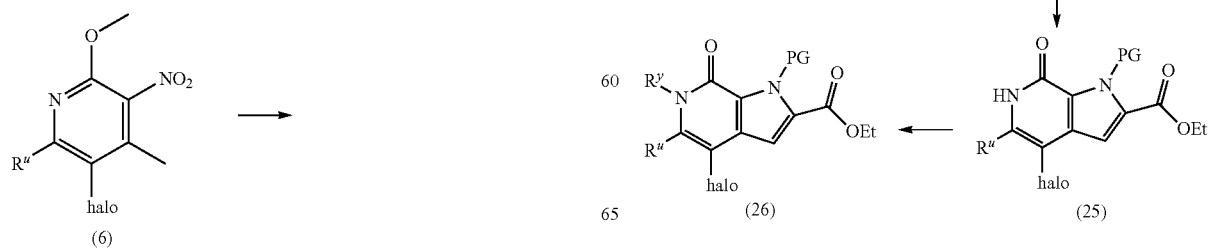

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be further processed in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Pharmaceutical Compositions

This invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula I. In certain embodiments, the compound of formula I may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the formula I can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula I may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds of formula I, or pharmaceutically acceptable salts thereof, and pharmaceutical compositions comprising a compound of formula I, or a pharmaceutically acceptable salt thereof, can be administered to a subject suffering from a bromodomain-mediated disorder or condition. The term "administering" refers to the method of contacting a compound with a subject. Thus, the compounds of formula I can be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of formula I can be administered transdermally, topically, via implantation, transdermally, topically, and via implantation. In certain embodiments, the compounds of the formula I may be delivered orally. The compounds can also be delivered rectally, bucally, intravaginally, ocularly, andially, or by insufflation. Bromodomain-mediated disorders and conditions can be treated prophylactically, acutely, and chronically using compounds of formula I, depending on the nature of the disorder or condition. Typically, the host or subject in each of these methods is human, although other mammals can also benefit from the administration of a compound of formula I.

A "bromodomain-mediated disorder or condition" is characterized by the participation of one or more bromodomains (e.g., BRD4) in the inception, manifestation of one or more symptoms or disease markers, severity, or progression of a disorder or condition. Accordingly, compounds of formula I may be used to treat cancer, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

Further, compounds of formula I may be used to treat inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

Compounds of formula I, or pharmaceutically acceptable salts thereof, may be used to treat AIDS.

Compounds of formula I, or pharmaceutically acceptable salts thereof, may be used to treat chronic kidney disease or condition including, but are not limited to: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis.

Compounds of formula I, or pharmaceutically acceptable salts thereof, may be used to treat acute kidney injury or disease or condition including, but are not limited to: ischemia-reperfusion induced, cardiac and major surgery induced, percutaneous coronary intervention induced, radiocontrast agent induced, sepsis induced, pneumonia induced, and drug toxicity induced.

Compounds of formula I, or pharmaceutically acceptable salts thereof, may be used to treat obesity, dyslipidemia, hypercholesterolemia, Alzheimer's disease, metabolic syndrome, hepatic steatosis, type II diabetes, insulin resistance, diabetic retinopathy or diabetic neuropathy.

Compounds of formula I, or pharmaceutically acceptable salts thereof, may be used to provide for male contraception in a male subject comprising administering a therapeutically effective amount of a compound of formula (I) or a pharmaceutically acceptable salt thereof, to a male subject in need thereof.

The compounds of formula I can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN®(melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax), ABT-199, and the like.

Bcr-Abl kinase inhibitors include DASATINIB® (BMS-354825), GLEEVEC®(imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951 f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT®(AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS®(trabectedin), ZD-6126, ZINECARD® (dexrazoxane), ZOMETA® (zolendronic acid), zorubicin and the like.

The compounds of the invention can also be co-administered with a therapeutically effective amount of one or more agents to treat an inflammatory disease or condition, or autoimmune disease, where examples of the agents include, such as methotrexate, tofacitinib, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNF or IL-1 (e.g., NIK, IKK, p38 or MAP kinase inhibitors), IL-1 converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (etanercept) and p55TNFRIgG (Lenercept), sIL-1RI, sIL-1RII, sIL-6R), antiinflammatory cytokines (e.g. IL-4, IL-10, IL-11, IL-13 and TGF), celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. In certain embodiments, combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention may be co-administered include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1 monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNF or IL-1 (e.g. NIK, IKK, or MAP kinase inhibitors); IL-1 converting enzyme inhibitors; TNF converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGF). Preferred examples of therapeutic agents for Crohn's disease with which a compound of Formula (I) can be combined include the following: TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1 converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) may be co-administered include the following: corticosteroids; prednisolone; methylprednisolone; azathioprine; cyclophosphamide; cyclosporine; methotrexate; 4-aminopyridine; tizanidine; interferon-1a (AVONEX®; Biogen); interferon-1b (BETASERON®; Chiron/Berlex); interferon-n3) (Interferon Sciences/Fujimoto), interferon- (Alfa Wassermann/J&J), interferon 1A-IF (Serono/Inhale Therapeutics), Peginterferon 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNF or IL-1 (e.g., NIK, IKK, p38 or MAP kinase inhibitors), IL-1 converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGF).

A compound of Formula (I) may also be co-administered with agents, such as alemtuzumab, dronabinol, daclizumab, mitoxantrone, xaliproden hydrochloride, fampridine, glatiramer acetate, natalizumab, sinnabidol, -immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be co-administered include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (HUMIRA®), CA2 (infliximab), CDP 571, TNFR-Ig constructs, (p75TNFRIgG (ENBREL®) and p55TNFRIgG (LENERCEPT®).

Non-limiting examples of therapeutic agents for asthma with which a compound of Formula (I) may be co-administered include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) may be co-administered include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for psoriasis with which a compound of Formula (I) may be co-administered include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) may be co-administered include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), and efalizumab.

Preferred examples of therapeutic agents for SLE (Lupus) with which a compound of Formula (I) may be co-administered include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1 converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™).

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

The compounds of the invention can be co-administered with a therapeutically effective amount of one or more agents to prevent or treat type II diabetes, hepatic steatosis, insulin resistance, metabolic syndrome and related disorders, where examples of the agents include, but are not limited to, insulin and insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide and tolbutamide; agents that are glucagon-like peptide agonists such as exanatide, liraglutide and taspoglutide; agents that inhibit dipeptidyl-peptidase IV such as vildagliptin, sitagliptin, saxagliptin, linagliptin, allogliptin and septagliptin; agents that bind to the peroxisome proliferator-activated receptor gamma such as rosiglitazone and pioglitazone; agents that decrease insulin resistance such as metformin; agents that reduce glucose absorbance in the small intestine such as acarbose, miglitol and voglibose.

The compounds of the invention can be co-administered with a therapeutically effective amount of one or more agents to prevent or treat acute kidney disorders and chronic kidney diseases, where examples of the agents include, but are not limited to, dopamine, diuretics such as furosemide, bumetanide, thiazide and the like, mannitol, calcium gluconate, sodium bicarbonate, albuterol, paricalcitol, doxercalciferol, cinacalcet and bardoxalone methyl.

The compounds of the invention can be co-administered with a therapeutically effective amount of one or more agents to a male subject to provide for male contraception.

The following Examples may be used for illustrative purposes and should not be deemed to narrow the scope of the invention.

EXAMPLES

Example 1

6-methyl-4-(2-phenoxyphenyl)-1,6-dihydro-7H-pyrrolo[2,3-c]pyridin-7-one

Example 1a (E)-2-(5-bromo-2-methoxy-3-nitropyridin-4-yl)-N,N-dimethylethenamine 5-Bromo-2-methoxy-4-methyl-3-nitropyridine (15.0 g, 60.7 mmol) was dissolved in dimethylformamide (300 mL), and lithium methanolate (6.07 mL, 6.07 mmol, 1 M) was added. The reaction mixture was heated to 100° C. To this mixture was added 1,1-dimethoxy-N,N-dimethylmethanamine (64.5 mL, 486 mmol) over 10 minutes. The reaction mixture was stirred at 95° C. for 16 hours. The reaction mixture was cooled to room temperature and water was added carefully (300 mL, exothermic). The resulting precipitate was collected by vacuum filtration, washed with water, and dried to provide the title compound (13.9 g, 45.9 mmol, 76% yield).

Example 1b 4-bromo-7-methoxy-1H-pyrrolo[2,3-c]pyridine

Example 1a (13.9 g, 45.8 mmol) and ethyl acetate (150 mL) were added to Ra—Ni 2800 (pre-washed with ethanol), water slurry (6.9 g, 118 mmol) in a stainless steel pressure bottle and stirred for 30 minutes at 30 psi and room temperature. The reaction mixture was filtered, and concentrated. The residue was triturated with dichloromethane, and the solid filtered to provide the title compound (5.82 g). The mother liquor was evaporated and the residue triturated again with dichloromethane and filtered to provide an additional 1.63 g of the title compound. Total yield=7.45 g, 72% yield.

Example 1c 4-bromo-7-methoxy-1-tosyl-1H-pyrrolo[2,3-c]pyridine

A solution of Example 1b (7.42 g, 32.7 mmol) in dimethylformamide (235 mL) was stirred at room temperature. To this solution was added sodium hydride (1.18 g, 1.96 g of 60% dispersion in oil, 49.0 mmol), and the reaction mixture was stirred for 10 min. P-toluenesulfonyl chloride (9.35 g, 49.0 mmol) was then added portion-wise, and the mixture was stirred at room temperature under nitrogen for 16 hours. The reaction mixture was quenched carefully with water and the resulting beige solid collected by vacuum filtration on a Buchner funnel, and washed with water. The solid was collected and dried in a vacuum oven at 50° C. to provide 12.4 g (100%) of the title compound.

Example 1d 4-bromo-1-tosyl-1H-pyrrolo[2,3-c]pyridin-7(6H)-one

A solution of Example 1c (12.4 g, 32.6 mmol) in dioxane (140 mL) was stirred at room temperature. To this solution was added 4M HCl in dioxane (140 mL). The reaction mixture was stirred at 40° C. for 16 hours. The reaction mixture was cooled to room temperature and concentrated. The residue was triturated with diethylether, filtered, and rinsed with additional diethylether and dried to provide the title compound (11.23 g, 30.6 mmol, 94% yield) as a beige solid.

Example 1e 4-bromo-6-methyl-1-tosyl-1H-pyrrolo[2,3-c]pyridin-7(6H)-one

Sodium hydride (0.875 g, 36.5 mmol, 1.46 g of a 60% in oil dispersion) was added to a stirring solution of Example 1d (11.2 g, 30.4 mmol) in dimethylformamide (217 mL) under nitrogen. After 30 minutes, iodomethane (2.27 mL, 36.5 mmol) was added and the solution was stirred at room temperature for 3 h. Upon addition of water (250 mL) a precipitate formed. The precipitate was collected by vacuum filtration, rinsed with water (50 mL) and dried in a vacuum oven at 55° C. overnight to provide 11.2 g of the title compound (96%).

Example 1f 6-methyl-4-(2-phenoxyphenyl)-1,6-dihydro-7H-pyrrolo[2,3-c]pyridin-7-one A mixture of Example 1e (152 mg, 0.40 mmol), 2-phenoxyphenylboronic acid (0.111 g, 0.520 mmol, 1.3 equivalents), Pd(PPh$_3$)$_4$ (0.023 g, 5 mol %) and cesium fluoride (0.182 g, 1.2 mmol) in DME (3 mL) and methanol (1.5 mL) was heated under microwave condition (120° C., 30 minutes). To this mixture was added potassium carbonate (0.055 g, 0.40 mmol) and water (1 mL) and the reaction mixture was reheated in the microwave oven at 120° C. for another 2 hours. The organic layer was separated and purified by flash chromatography (silica gel, ethyl acetate). The resulting material was triturated with acetone and filtered to provide 0.075 g of the title compound (59%). $^1$H NMR (500 MHz, DMSO-d$_6$) δ 3.50 (s, 3H), 6.21-6.23 (m, 1H), 6.88 (d, J=7.62 Hz, 2H), 6.99-7.04 (m, 2H), 7.24-7.30 (m, 5H), 7.36-7.40 (m, 1H), 7.50 (dd, J=7.48, 1.68 Hz, 1H), 11.98 (s, 1H). MS (ESI+) m/z 317 (M+H)$^+$.

Example 2

6-methyl-4-(5-nitro-2-phenoxyphenyl)-1,6-dihydro-7H-pyrrolo[2,3-c]pyridin-7-one

Example 2a 4-(2-fluoro-5-nitrophenyl)-6-methyl-1-tosyl-1H-pyrrolo[2,3-c]pyridin-7(6H)-one Method A:
Example 1e (0.687 g, 1.802 mmol), 2-fluoro-5-nitrophenylboronic acid (0.500 g, 2.70 mmol), Pd(PPh$_3$)$_4$ (0.104 g, 0.090 mmol) and sodium carbonate (2.70 mL, 5.41 mmol) were combined in DME (7 mL) and water (7 mL) in a 20 mL microwave tube, sealed, sparged with nitrogen and heated under microwave at 120° C. for 30 minutes. The mixture was partitioned between EtAOc and water. The organic layer was washed with brine, dried (Na$_2$SO$_4$), filtered and concentrated. The crude product was purified by flash chromatography (silica gel, 0-100% ethyl acetate in hexanes) to provide 0.41 g (52%) of the title compound.
Method B:
Example 1e (6.00 g, 15.7 mmol), 2-fluoro-5-nitrophenylboronic acid (5.82 g, 31.5 mmol), Pd(PPh$_3$)$_4$ (0.909 g, 0.787 mmol) and sodium carbonate (3.34 g, 31.5 mmol) were combined in toluene (60 mL), ethanol (15 mL) and water (15 mL) and the mixture was degassed and left under nitrogen. The reaction mixture was heated at 90° C. overnight, and then cooled to room temperature. The mixture was partitioned between ethyl acetate and water. The organic layer was washed with brine, dried (MgSO$_4$), filtered and concentrated. The crude product was purified by flash chromatography (silica gel, 20-50% ethyl acetate in hexanes) to provide 6.95 g (61%) of the title compound.

Example 2b 6-methyl-4-(5-nitro-2-phenoxyphenyl)-1,6-dihydro-7H-pyrrolo[2,3-c]pyridin-7-one Phenol (0.094 g, 0.997 mmol), Example 2a (0.4 g, 0.906 mmol) and cesium carbonate (0.325 g, 0.997 mmol) were combined in DMSO (4.53 mL) and heated at 100° C. for 2 hours. The reaction mixture was partitioned between ethyl acetate and water and pH was adjusted to pH 7. The organic layer was washed with brine, dried (Na$_2$SO$_4$), filtered and concentrated. Purification by flash chromatography (silica gel, 0-4% methanol in dichloromethane) afforded 0.28 g (84%) of the title compound. $^1$H NMR (300 MHz, DMSO-d$_6$) δ 3.57 (s, 3H) 6.28-6.34 (m, 1H) 6.98 (d, J=9.12 Hz, 1H) 7.16 (d, J=7.54 Hz, 2H) 7.21-7.32 (m, 2H) 7.40-7.49 (m, 3H) 8.22 (dd, J=9.12, 2.78 Hz, 1H) 8.32 (d, J=2.78 Hz, 1H) 12.07-12.11 (m, 1H). MS (ESI+) m/z 362 [M+H]$^+$ Example 3

4-(5-amino-2-phenoxyphenyl)-6-methyl-1,6-dihydro-7H-pyrrolo[2,3-c]pyridin-7-one

Example 2b (0.25 g, 0.692 mmol), iron powder (0.193 g, 3.46 mmol), and ammonium chloride (0.056 g, 1.038 mmol) were combined in tetrahydrofuran (6 mL), ethanol (6 mL) and water (2 mL). The mixture was heated at 95° C. with vigorous stirring for 1.5 hours. The reaction mixture was cooled to room temperature and filtered through a plug of Celite to remove solids. The plug was rinsed repeatedly with methanol and tetrahydrofuran. The filtrate was concentrated and the residue partitioned between ethyl acetate and water. The ethyl acetate layer was washed with brine, dried (Na$_2$SO$_4$), filtered, and concentrated. The residue was purified by flash chromatography (silica gel, 1-4% methanol in dichloromethane) to afford 0.21 g (82%) of the title compound. $^1$H NMR (300 MHz, DMSO-d$_6$) δ 3.43 (s, 3H) 5.07 (s, 2H) 6.22-6.25 (m, 1H) 6.59 (dd, J=8.48, 2.71 Hz, 1H) 6.68 (d, J=7.80 Hz, 2H) 6.74 (d, J=2.71 Hz, 1H) 6.80-6.88 (m, 2H) 7.11-7.19 (m, 3H) 7.24 (t, J=2.71 Hz, 1H) 11.91 (s, 1H). MS (ESI+) m/z 362 [M+H]$^+$.

Example 4

N-[3-(6-methyl-7-oxo-6,7-dihydro-1H-pyrrolo[2,3-c]pyridin-4-yl)-4-phenoxyphenyl]methanesulfonamide Method A:
To a solution of Example 3 (0.125 g, 0.377 mmol) and triethylamine (0.131 mL, 0.943 mmol) in dichloromethane (3.0 mL) was added dropwise methanesulfonyl chloride (0.064 mL, 0.830 mmol). The reaction mixture was stirred for 2 hours at ambient temperature and then concentrated. The residue was dissolved in a mixture of dioxane (5 mL) and 1M sodium hydroxide (2 mL) and heated for 1 hour at 90° C. The reaction mixture was cooled and diluted with ethyl acetate, brought to pH 7 with 1 M HCl and partitioned. The organic layer was washed with brine, dried (Na$_2$SO$_4$), filtered, and concentrated. The residue was purified by flash chromatography (silica gel, 0-4% methanol in dichloromethane) to afford 0.20 g (77%) of the title compound. $^1$H NMR (300 MHz, DMSO-d$_6$) δ 3.02 (s, 3H) 3.48 (s, 3H) 6.23-6.30 (m, 1H) 6.85 (d, J=7.46 Hz, 2H) 6.99 (t, J=7.29 Hz, 1H) 7.04 (d, J=8.82 Hz, 1H) 7.20-7.29 (m, 5H) 7.39 (d, J=2.71 Hz, 1H) 9.72 (s, 1H) 12.01 (s, 1H). MS (ESI+) m/z 410 [M+H]$^+$.
Method B:
The product of Example 7d (1.127 g, 2 mmol), potassium hydroxide (1.82 g, 52.5 mmol) and cetyltrimethylammonium bromide (0.036 g, 0.100 mmol) were combined in tetrahydrofuran (15.00 mL) and water (5.00 mL) and the mixture heated at 100° C. for 14 hours. The reaction mixture was partitioned between equal volumes of EtOAc and water and the pH was adjusted to pH 7 by careful addition of concentrated HCl. The organic layer was separated, washed three times with saturated brine, dried (Na$_2$SO$_4$) and concentrated.

Purification by trituration in dichloromethane afforded the title compound (0.76 g, 93%).

Example 5

2,2,2-trifluoro-N-[3-(6-methyl-7-oxo-6,7-dihydro-1H-pyrrolo[2,3-c]pyridin-4-yl)-4-phenoxyphenyl]ethanesulfonamide To a solution of Example 3 (0.05 g, 0.151 mmol) and triethylamine (0.053 mL, 0.377 mmol) in dichloromethane (1.0 mL) was added dropwise 2,2,2-trifluoroethanesulfonyl chloride (0.036 g, 0.196 mmol). The reaction mixture was stirred for 1 hour at room temperature and then purified by flash chromatography (silica gel, 0-5% methanol in dichloromethane) to afford 0.050 g (68%) of the title compound. $^1$H NMR (300 MHz, DMSO-$d_6$) δ 3.49 (s, 3H) 4.55 (q, J=9.91 Hz, 2H) 6.28 (t, J=2.38 Hz, 1H) 6.86 (d, J=7.54 Hz, 2H) 6.95-7.07 (m, 2H) 7.20-7.31 (m, 5H) 7.40 (d, J=2.78 Hz, 1H) 10.43 (s, 1H) 12.02 (s, 1H). MS (APCI+) m/z 478 [M+H]$^+$.

Example 6

N-[3-(6-methyl-7-oxo-6,7-dihydro-1H-pyrrolo[2,3-c]pyridin-4-yl)-4-phenoxyphenyl]acetamide

Example 6a 6-methyl-4-(4,4,5,5-tetramethyl-1,3,2-dioxaborolan-2-yl)-1-tosyl-1H-pyrrolo[2,3-c]pyridin-7(6H)-one Example 1e (6.55 g, 17.2 mmol), 4,4,4',4',5,5,5',5'-octamethyl-2,2'-bi(1,3,2-dioxaborolane) (8.73 g, 34.4 mmol), potassium acetate (3.71 g, 37.8 mmol), tris(dibenzylideneacetone)dipalladium(0) (0.393 g, 0.430 mmol) and 2-dicyclohexylphosphino-2',4',6'-triisopropylbiphenyl (X-PHOS, 0.819 g, 1.72 mmol) were combined and sparged with argon for 1 hour with stirring. Dioxane (86 mL) was sparged with nitrogen for 1 hour, transferred via canula under nitrogen to the solid components, and the mixture was heated under argon at 80° C. for 5 hours. The reaction mixture was cooled to room temperature, partitioned between ethyl acetate and water, and filtered through Celite. The ethyl acetate layer was washed twice with brine, dried (Na$_2$SO$_4$), filtered and concentrated. The residue was purified by chromatography (silica gel, 25-80% ethyl acetate in hexane). The resulting material from chromatography was triturated with a minimal amount of hexanes (30 mL) and the particulate solid was collected by filtration, rinsed with a minimal amount of hexanes and dried to constant mass to afford the title compound (5.4 g, 73%).

Example 6b

N-(3-bromo-4-phenoxyphenyl)acetamide

Example 7b (0.2 g, 0.757 mmol), and acetic anhydride (1 mL, 10.60 mmol) were combined in a 5 mL microwave tube, sealed and heated under microwave at 100° C. for 30 minutes. The mixture was concentrated and the residue was purified by chromatography (silica gel, 0-50% ethyl acetate in hexanes) to afford the title compound (0.22 g, 95%).

Example 6c

N-(3-(6-methyl-7-oxo-1-tosyl-6,7-dihydro-1H-pyrrolo[2,3-c]pyridin-4-yl)-4-phenoxyphenyl)acetamide Example 6a (0.07 g, 0.163 mmol), Example 6b (0.075 g, 0.245 mmol), tetrakis(triphenylphosphine)palladium(0) (9.44 mg, 8.17 μmol) and sodium carbonate (2.0 M, 0.245 mL, 0.490 mmol) were combined in DME (0.817 mL) and water (0.817 mL) in a 5 mL microwave tube, sealed, sparged with nitrogen and heated under microwave at 120° C. for 30 minutes. The mixture was partitioned between ethyl acetate and water. The organic layer was washed with brine, dried (Na$_2$SO$_4$), filtered and concentrated. Purification by chromatography (silica gel, 0-5% methanol in dichloromethane) afforded the title compound (0.048 g, 56%).

Example 6d

N-[3-(6-methyl-7-oxo-6,7-dihydro-1H-pyrrolo[2,3-c]pyridin-4-yl)-4-phenoxyphenyl]acetamide Example 6c (0.048 g, 0.091 mmol) and potassium carbonate (0.044 g, 0.318 mmol were combined in methanol (2 mL) and water (0.200 mL) in a 2 mL microwave tube, sealed, and heated under microwave at 110° C. for 30 minutes. The reaction mixture was concentrated and the residue partitioned between ethyl acetate and water, adjusting the pH to 6 with 1M HCl. The organic layer was separated and concentrated. Purification by flash chromatography (silica gel, 0-4% methanol in dichloromethane) afforded 0.018 g (53%) of the title compound. $^1$H NMR (300 MHz, DMSO-$d_6$) δ 2.05 (s, 3H) 3.48 (s, 3H) 6.25-6.30 (m, 1H) 6.80 (d, J=7.46 Hz, 2H) 6.96 (t, J=7.29 Hz, 1H) 7.01 (d, J=8.82 Hz, 1H) 7.18-7.31 (m, 4H) 7.56 (dd, J=8.65, 2.54 Hz, 1H) 7.79 (d, J=2.71 Hz, 1H) 10.04 (s, 1H) 11.97 (s, 1H). MS (ESI+) m/z 374 [M+H]$^+$.

Example 7

N-(3-{6-methyl-1-[(4-methylphenyl)sulfonyl]-7-oxo-6,7-dihydro-1H-pyrrolo[2,3-c]pyridin-4-yl}-4-phenoxyphenyl)methanesulfonamide

Example 7a 2-bromo-4-nitro-1-phenoxybenzene

2-Bromo-1-fluoro-4-nitrobenzene (2.5 g, 11.4 mmol), phenol (1.28 g, 13.6 mmol), and cesium carbonate (4.44 g, 13.6 mmol) were combined in dimethylsulfoxide (140 mL) and heated to 110° C. for 1 hour. The reaction mixture was partitioned between ethyl acetate and brine. The combined organics were washed with brine, dried (MgSO$_4$), filtered and concentrated to afford the title compound.

Example 7b 3-bromo-4-phenoxyaniline

Example 7a (3.43 g, 11.7 mmol), iron powder (3.26 g, 58.4 mmol), and ammonium chloride (1.25 g, 23.4 mmol) were combined in ethanol (50 mL), tetrahydrofuran (50 mL), and water (16.7 mL), and heated at 100° C. for 2 hour. The reaction mixture was cooled to just below reflux, vacuum filtered through diatomaceous earth, the filter cake washed with warm methanol (3×35 mL), and the filtrate concentrated under reduced pressure. The residue was partitioned between saturated aqueous NaHCO$_3$ and ethyl acetate (3×125 mL). The combined organics were washed with brine, dried (MgSO$_4$), gravity filtered then concentrated to afford the title compound.

Example 7c

N-(3-bromo-4-phenoxyphenyl)methanesulfonamide

Example 7b (2.86 g, 10.8 mmol) and triethylamine (6.03 mL, 43.3 mmol) were stirred in dichloromethane (48.1 mL) at ambient temperature. Methanesulfonyl chloride (2.53 mL, 32.4 mmol) was added dropwise and the solution stirred at ambient temperature for 1 hour. The reaction mixture was concentrated under reduced pressure, dioxane (24 mL) and sodium hydroxide (10% w/v, 12 mL, 0.427 mmol) were added, and the solution was heated to 70° C. for 1 h. The solution was neutralized to a pH of 7 with saturated aqueous $NH_4Cl$ (200 mL). The aqueous phase was extracted with ethyl acetate (3×125 mL). The combined organics were washed with brine, dried ($MgSO_4$), filtered, then concentrated. The residue was purified by flash chromatography (silica gel, 0-25% ethyl acetate/hexane gradient) to afford the title compound.

Example 7d

N-(3-{6-methyl-1-[(4-methylphenyl)sulfonyl]-7-oxo-6,7-dihydro-1H-pyrrolo[2,3-c]pyridin-4-yl}-4-phenoxyphenyl)methanesulfonamide Example 6a (0.670 g, 1.564 mmol), Example 7c (0.562 g, 1.643 mmol), tris(dibenzylideneacetone)dipalladium(0) (0.036 g, 0.039 mmol), 1,3,5,7-tetramethyl-6-phenyl-2,4,8-trioxa-6-phosphaadamante (0.023 g, 0.078 mmol) and potassium phosphate tribasic (1.03 g, 4.85 mmol) were combined and sparged with argon for 30 minutes. A solution of 4:1 dioxane/water (10 mL total volume) was sparged with nitrogen for 30 minutes and transferred by syringe into the reaction vessel under argon. The reaction mixture was stirred at 60° C. for 2 hours, cooled to room temperature and partitioned between ethyl acetate and water. The organic layer was washed with brine, dried ($Na_2SO_4$), treated with 3-mercaptopropyl functionalized silica gel (Aldrich, 538086-100G) for 45 minutes, filtered and concentrated. Purification by chromatography (silica gel, 20-100% ethyl acetate in hexanes) afforded 0.68 g (74%) of the title compound. $^1$H NMR (300 MHz, DMSO-$d_6$) δ 2.38 (s, 3H) 3.02 (s, 3H) 3.38 (s, 3H) 6.52 (d, J=3.39 Hz, 1H) 6.82 (d, J=7.80 Hz, 2H) 6.96-7.04 (m, 2H) 7.19-7.28 (m, 4H) 7.41 (d, J=8.14 Hz, 2H) 7.48 (s, 1H) 7.89-7.97 (m, 3H) 9.73 (s, 1H). MS (ESI+) m/z 564 [M+H]$^+$.

Example 8

N-methyl-N-[3-(6-methyl-7-oxo-6,7-dihydro-1H-pyrrolo[2,3-c]pyridin-4-yl)-4-phenoxyphenyl]methanesulfonamide A mixture of Example 7d (0.113 g, 0.2 mmol) and potassium carbonate (0.111 g, 0.800 mmol) in methanol (0.9 mL) and water (0.1 mL) was heated at 100° C. for 1 hour. The reaction was partitioned between ethyl acetate and water adjusting the pH to 7. The organic layer was separated, dried ($Na_2SO_4$), filtered and concentrated. The residue was purified by reverse phase HPLC (C18, 10-100% $CH_3CN$/water (0.1% TFA)) to afford the title compound (0.012 g, 14%). $^1$H NMR (300 MHz, DMSO-$d_6$) δ 2.99 (s, 3H) 3.27 (s, 3H) 3.51 (s, 3H) 6.27-6.32 (m, 1H) 6.93 (d, J=7.80 Hz, 2H) 6.99 (d, J=8.82 Hz, 1H) 7.03-7.10 (m, 1H) 7.25-7.34 (m, 4H) 7.40 (dd, J=8.65, 2.88 Hz, 1H) 7.55 (d, J=2.71 Hz, 1H) 12.01 (s, 1H). MS (ESI+) m/z 424 [M+H]$^+$.

Example 9 ethyl 3-(6-methyl-7-oxo-6,7-dihydro-1H-pyrrolo[2,3-c]pyridin-4-yl)-4-phenoxybenzoate

Example 9a ethyl 4-fluoro-3-(6-methyl-7-oxo-1-tosyl-6,7-dihydro-1H-pyrrolo[2,3-c]pyridin-4-yl)benzoate A mixture of Example 1e (1.33 g, 3.5 mmol), 5-(ethoxycarbonyl)-2-fluorophenylboronic acid (1.04 g, 4.9 mmol), Pd(PPh$_3$)$_4$ (0.20 g, 5 mol %), and sodium carbonate (0.742 g, 7.0 mmol) in toluene (12 mL), ethanol (3 mL) and water (3 mL) was degassed and stirred under a nitrogen atmosphere. The reaction mixture was heated at 90° C. for 24 hours. The reaction mixture was cooled to room temperature and partitioned between water and ethyl acetate. The aqueous layer was extracted with additional ethyl acetate twice. The combined organic layers were washed with brine, dried over $MgSO_4$, filtered, and concentrated. The residue was purified by flash chromatography (silica gel, 20-50% ethyl acetate in hexanes) to afford 1.43 g (87%) of the title compound.

Example 9b ethyl 3-(6-methyl-7-oxo-6,7-dihydro-1H-pyrrolo[2,3-c]pyridin-4-yl)-4-phenoxybenzoate A mixture of Example 9a (1.43 g, 3.05 mmol), phenol (0.0344 g, 3.66 mmol) and cesium carbonate (0.995, 3.05 mmol), in DMSO (15 mL) was heated at 110° C. for 12 hours. After cooling to room temperature, the reaction mixture was partitioned between water and ethyl acetate. The aqueous layer was extracted with additional ethyl acetate twice. The combined organic layers were washed with brine, dried over $MgSO_4$, filtered, and concentrated. The residue was purified by flash chromatography (silica gel, 30-80% ethyl acetate/hexane) to afford 0.85 g (72%) of the title compound. $^1$H NMR (500 MHz, DMSO-$d_6$) δ 1.31 (t, J=7.02 Hz, 3H), 3.55 (s, 3H), 4.32 (q, J=7.22 Hz, 2H), 6.23 (t, J=2.29 Hz, 1H), 6.97 (d, J=8.54 Hz, 1H), 7.06 (d, J=8.24 Hz, 2H), 7.17 (t, J=7.32 Hz, 1H), 7.28 (t, J=2.75 Hz, 1H), 7.36-7.51 (m, 3H), 7.94 (dd, J=8.7, 2.29 Hz, 1H), 8.04 (d, J=2.14 Hz, 1H), 12.02 (s, 1H). MS (ESI+) m/z 389.2 (M+H)$^+$.

Example 10

3-(6-methyl-7-oxo-6,7-dihydro-1H-pyrrolo[2,3-c]pyridin-4-yl)-4-phenoxybenzoic acid A mixture of Example 9b (0.23 g, 0.59 mmol) and sodium hydroxide (0.89 mL of 2.0 M aqueous solution) in dioxane (10 mL) was heated at 60° C. for 2 hours. The reaction mixture was cooled to room temperature and poured into water (100 mL). After addition of concentrated HCl (5 mL), the mixture was extracted with ethyl acetate (3×40 mL). The combined organic layers were washed with brine, dried over $MgSO_4$, filtered, and concentrated to afford 0.21 g (98%) of the title compound. $^1$H NMR (500 MHz, DMSO-$d_6$) δ 3.55 (s, 3H), 6.24-6.25 (m, 1H), 6.94 (d, J=8.54 Hz, 1H), 7.05 (d, J=7.63 Hz, 2H), 7.16 (t, J=7.32 Hz, 1H), 7.27 (t, J=2.9 Hz, 1H), 7.35-7.40 (m, 3H), 7.92 (dd, J=8.7, 2.29 Hz, 1H), 8.04 (d, J=2.14 Hz, 1H), 12.03 (s, 1H). MS (ESI+) m/z 361.2 (M+H)$^+$.

Example 11

N-[3-(6-methyl-7-oxo-6,7-dihydro-1H-pyrrolo[2,3-c]pyridin-4-yl)-4-(pyridin-3-yloxy)phenyl]methanesulfonamide

Example 11a 6-methyl-4-(5-nitro-2-(pyridin-3-yloxy)phenyl)-1H-pyrrolo[2,3-c]pyridin-7(6H)-one Example 11a was prepared according to the procedure used for the preparation of Example 2b, substituting pyridin-3-ol for phenol, to provide the title compound.

Example 11b 4-(5-amino-2-(pyridin-3-yloxy)phenyl)-6-methyl-1H-pyrrolo[2,3-c]pyridin-7(6H)-one Example 11b was prepared according to the procedure used for the preparation of Example 3, substituting Example 11a for Example 2b, to provide the title compound.

Example 11c

N-[3-(6-methyl-7-oxo-6,7-dihydro-1H-pyrrolo[2,3-c]pyridin-4-yl)-4-(pyridin-3-yloxy)phenyl]methanesulfonamide Example 11c was prepared according to the procedure used in method A of Example 4, substituting Example 11b for Example 3, and purified by Preparative HPLC (C18, 10-100% acetonitrile in 0.1% TFA/water) to provide the TFA salt of the title compound. $^1$H NMR (300 MHz, DMSO-$d_6$) δ 3.49 (s, 3H), 3.05 (s, 3H), 6.25 (dd, J=2.8, 1.9 Hz, 1H), 7.16 (d, J=8.7 Hz, 1H), 7.34-7.21 (m, 5H), 7.40 (d, J=2.6 Hz, 1H), 8.23-8.16 (m, 2H), 9.80 (s, 1H), 12.02 (bs, 1H). MS (ESI+) m/z 411.1 (M+H)$^+$.

Example 12

6-methyl-4-[2-(morpholin-4-ylmethyl)phenyl]-1,6-dihydro-7H-pyrrolo[2,3-c]pyridin-7-one Example 12 was prepared according to the procedure used for the preparation of Example 1f, substituting 2-(morpholinomethyl)phenylboronic acid for 2-phenoxyphenylboronic acid, followed by purification by preparative HPLC (C18, 10-100% acetonitrile in 0.1% TFA in water), to provide the TFA salt of the title compound. $^1$H NMR (500 MHz, DMSO-$d_6$) δ 2.85 (br, 2H), 3.09 (br, 2H), 3.56 (s, 3H), 3.74 (br, 2H), 4.26 (br, 2H), 5.89-5.90 (m, 1H), 7.20 (s, 1H), 7.29 (t, J=2.75 Hz, 1H), 7.39-7.43 (m, 1H), 7.53-7.55 (m, 2H), 7.75-7.77 (m, 1H), 9.73 (br, 1H), 12.12 (s, 1H). MS (ESI+) m/z 324.0 (M+H)$^+$.

Example 13

N-ethyl-3-(6-methyl-7-oxo-6,7-dihydro-1H-pyrrolo[2,3-c]pyridin-4-yl)-4-phenoxybenzamide

Example 13a 3-(6-methyl-7-oxo-6,7-dihydro-1H-pyrrolo[2,3-c]pyridin-4-yl)-4-phenoxybenzoyl chloride A solution of Example 10 (0.24 g, 0.67 mmol) in dichloromethane (10 mL) was treated with oxalyl chloride (0.17 g, 1.33 mmol) and dimethylformamide (5 mg, 10 mol %). The reaction mixture was stirred at room temperature for 2 hours. The solvent was removed under reduced pressure to afford the title compound (0.25 g, quantitative).

Example 13b

N-ethyl-3-(6-methyl-7-oxo-6,7-dihydro-1H-pyrrolo[2,3-c]pyridin-4-yl)-4-phenoxybenzamide A solution of Example 13a (0.040 g, 0.11 mmol) in tetrahydrofuran (1 mL) was treated with ethylamine (0.21 mL of a 2 M solution in tetrahydrofuran, 0.42 mmol) for 2 h. The reaction mixture was concentrated and the residue purified by preparative HPLC (C18, 10-90% acetonitrile in 0.1% TFA in water) to afford the title compound (0.025 g, 61%). $^1$H NMR (500 MHz, DMSO-$d_6$) δ 1.12 (t, J=7.32 Hz, 3H), 3.25-3.32 (m, 2H), 3.54 (s, 3H), 6.23-6.24 (m, 1H), 6.95-6.99 (m, 3H), 7.11 (t, J=7.48 Hz, 1H), 7.27 (t, J=2.75 Hz, 1H), 7.31-7.37 (m, 3H), 7.84 (dd, J=8.54, 2.44 Hz, 1H), 7.98 (d, J=2.44 Hz, 1H), 8.46 (t, J=5.49 Hz, 1H), 11.99 (s, 1H). MS (ESI+) m/z 388.2 (M+H)$^+$.

Example 14

3-(6-methyl-7-oxo-6,7-dihydro-1H-pyrrolo[2,3-c]pyridin-4-yl)-4-phenoxy-N-(tetrahydrofuran-2-ylmethyl)benzamide Example 14 was prepared according to the procedure used for the preparation of Example 13b, substituting (tetrahydrofuran-2-yl)methanamine for ethylamine, and dichloromethane for tetrahydrofuran, respectively, to provide the title compound. $^1$H NMR (500 MHz, DMSO-$d_6$) δ 1.56-1.57 (m, 1H), 1.79-1.89 (m, 3H), 3.26-3.32 (m, 3H), 3.53 (s, 3H), 3.58-3.63 (m, 1H), 3.73-3.78 (m, 1H), 3.94-3.97 (m, 1H), 6.21-6.22 (m, 1H), 6.93-6.98 (m, 3H), 7.10 (t, J=7.48 Hz, 1H), 7.25 (t, J=2.9 Hz, 1H), 7.30-7.35 (m, 3H), 7.84 (dd, J=8.54, 2.44 Hz, 1H), 7.98 (d, J=2.14 Hz, 1H), 8.52 (t, J=5.8 Hz, 1H), 12.00 (s, 1H). MS (ESI+) m/z 444.2 (M+H)$^+$.

Example 15

N-cyclopentyl-3-(6-methyl-7-oxo-6,7-dihydro-1H-pyrrolo[2,3-c]pyridin-4-yl)-4-phenoxybenzamide Example 15 was prepared according to the procedure used for the preparation of Example 13b, substituting cyclopentylamine for ethylamine, and dichloromethane for tetrahydrofuran, respectively, to provide the title compound. $^1$H NMR (500 MHz, DMSO-$d_6$) δ 1.49-1.66 (m, 4H), 1.65-1.69 (m, 2H), 1.85-1.91 (m, 2H), 3.54 (s, 3H), 4.20-4.26 (m, 1H), 6.20-6.22 (m, 1H), 6.95-6.98 (m, 3H), 7.01 (t, J=7.32 Hz, 1H), 7.26 (t, J=2.75 Hz, 1H), 7.30-7.36 (m, 3H), 7.85 (dd, J=8.54, 2.14 Hz, 1H), 7.99 (d, J=2.44 Hz, 1H), 8.52 (t, J=5.8 Hz, 1H), 12.01 (s, 1H). MS (ESI+) m/z 428.3 (M+H)$^+$.

Example 16

N-(2,2-difluoroethyl)-3-(6-methyl-7-oxo-6,7-dihydro-1H-pyrrolo[2,3-c]pyridin-4-yl)-4-phenoxybenzamide Example 16 was prepared according to the procedure used for the preparation of Example 13b, substituting 2,2-difluoroethanamine for ethylamine, and dichloromethane for tetrahydrofuran, respectively, to provide the title compound. $^1$H NMR (500 MHz, DMSO-$d_6$) δ 3.55 (s, 3H), 3.62-3.72 (m, 3H), 5.97 (t, J=3.97 Hz, 0.25H), 6.11 (t, J=4.12 Hz, 0.5H), 6.23-6.26 (m, 1.25H), 6.98 (d, J=8.54 Hz, 1H), 7.01 (d, J=7.63 Hz, 2H), 7.13 (t, J=7.48 Hz, 1H), 7.27 (t, J=2.75 Hz, 1H), 7.33-7.36 (m, 3H), 7.88 (dd, J=8.54, 2.44 Hz, 1H), 8.03 (d, J=2.14 Hz, 1H), 8.85 (t, J=5.8 Hz, 1H), 12.03 (s, 1H). MS (ESI+) m/z 424.2 (M+H)$^+$.

Example 17

3-(6-methyl-7-oxo-6,7-dihydro-1H-pyrrolo[2,3-c]pyridin-4-yl)-4-phenoxy-N-(1,3-thiazol-2-yl)benzamide Example 17 was prepared according to the procedure used for the preparation of Example 13b, substituting thiazol-2-amine for ethylamine, and dichloromethane for tetrahydrofuran, respectively, to provide the title compound. $^1$H NMR (500 MHz, DMSO-$d_6$) δ 3.58 (s, 3H), 6.30-6.31 (m, 1H), 6.23-6.26 (m, 1H), 6.98 (d, J=8.54 Hz, 1H), 7.07 (d, J=7.63 Hz, 2H), 7.17 (t, J=7.32 Hz, 1H), 7.27-7.29 (m, 2H), 7.38-7.42 (m, 3H), 7.56 (d, J=3.36 Hz, 1H), 8.09 (dd, J=8.55, 2.44 Hz, 1H), 8.28 (d, J=2.44 Hz, 1H), 12.04 (s, 1H), 12.61 (s, 1H). MS (ESI+) m/z 443.1 (M+H)$^+$.

Example 18

N-(1,1-dioxidotetrahydrothiophen-3-yl)-3-(6-methyl-7-oxo-6,7-dihydro-1H-pyrrolo[2,3-c]pyridin-4-yl)-4-phenoxybenzamide Example 18 was prepared according to the procedure used for the preparation of Example 13b, substituting 1,1-dioxidotetrahydrothien-3-ylamine for ethylamine, and dichloromethane for tetrahydrofuran, respectively, to provide the title compound. $^1$H NMR (500 MHz, DMSO-$d_6$) δ 2.20-2.23 (m, 1H), 2.41-2.45 (m, 1H), 3.04-3.09 (m, 1H), 3.19-3.23 (m, 1H), 3.34-3.37 (m, 1H), 3.48-3.53 (m, 1H), 3.55 (s, 3H), 4.66-4.76 (m, 1H), 6.30-6.31 (m, 1H), 6.21-6.22 (m, 1H), 6.99 (dd, J=8.09, 2.59 Hz, 2H), 7.12 (t, J=7.48 Hz, 1H), 7.27 (t, J=2.75 Hz, 1H), 7.31-7.37 (m, 3H), 7.87 (dd, J=8.54, 2.14 Hz, 1H), 8.02 (d, J=2.14 Hz, 1H), 8.72 (d, J=7.02 Hz, 1H), 12.03 (s, 1H). MS (ESI+) m/z 478.2 (M+H)$^+$.

Example 19

3-(6-methyl-7-oxo-6,7-dihydro-1H-pyrrolo[2,3-c]pyridin-4-yl)-4-phenoxybenzamide

Example 19 was prepared according to the procedure used for the preparation of Example 13b, substituting aqueous ammonium hydroxide for ethylamine to provide the title compound. $^1$H NMR (500 MHz, DMSO-$d_6$) δ 3.54 (s, 3H), 6.23-6.24 (m, 1H), 6.94 (d, J=8.54 Hz, 1H), 6.98-7.00 (m, 2H), 7.11 (t, J=7.48 Hz, 1H), 7.26 (t, J=2.75 Hz, 1H), 7.31-7.37 (m, 4H), 7.86 (dd, J=8.54, 2.44 Hz, 1H), 7.96 (s, 1H), 8.02 (d, J=2.44 Hz, 1H), 12.01 (s, 1H). MS (ESI+) m/z 360.2 (M+H)$^+$.

Example 20

4-[5-(hydroxymethyl)-2-phenoxyphenyl]-6-methyl-1,6-dihydro-7H-pyrrolo[2,3-c]pyridin-7-one

Example 20a ethyl 3-(6-methyl-7-oxo-1-tosyl-6,7-dihydro-1H-pyrrolo[2,3-c]pyridin-4-yl)-4-phenoxybenzoate Example 20a was prepared according to the procedure used for the preparation of Example 1c, substituting Example 9b for Example 1b to provide the title compound.

Example 20b

4-[5-(hydroxymethyl)-2-phenoxyphenyl]-6-methyl-1,6-dihydro-7H-pyrrolo[2,3-c]pyridin-7-one Example 20a (0.32 g, 0.59 mmol) in tetrahydrofuran (5 mL) was cooled to 0° C. To this solution was added 1.0 N aluminum lithium hydride (0.59 mL, 0.59 mmol). The reaction mixture was stirred at room temperature for 1 hour. The reaction mixture was quenched with 2.0 N HCl (5 mL), and then partitioned between water and ethyl acetate. The aqueous layer was extracted with additional ethyl acetate twice. The combined organic layers were washed with brine, dried over MgSO$_4$, filtered, and concentrated. The residue was purified by flash chromatography on silica gel eluting with 50-100% ethyl acetate in hexanes to afford 0.08 g (39%) of the title compound. $^1$H NMR (500 MHz, DMSO-$d_6$) δ 3.49 (s, 3H), 4.54 (d, J=5.49 Hz, 2H), 5.21 (t, J=5.8 Hz, 1H), 6.23-6.24 (m, 1H), 6.94 (d, J=7.93 Hz, 2H), 6.97-7.01 (m, 2H), 7.22-7.28 (m, 4H), 7.32 (dd, J=8.39, 2.29 Hz, 1H), 7.16 (d, J=1.83 Hz, 1H), 11.97 (s, 1H). MS (ESI+) m/z 347.3 (M+H)$^+$.

Example 21

N-[3-(6-methyl-7-oxo-6,7-dihydro-1H-pyrrolo[2,3-c]pyridin-4-yl)-4-phenoxyphenyl]ethanesulfonamide Example 21 was prepared according to the procedure used in method A of Example 4, substituting ethanesulfonyl chloride for methanesulfonyl chloride, to provide the title compound. $^1$H NMR (300 MHz, DMSO-$d_6$) δ 1.24 (t, J=7.3 Hz, 3H), 3.13 (q, J=7.3 Hz, 2H), 3.48 (s, 3H), 6.26 (t, J=2.3 Hz, 1H), 6.88-6.80 (m, 2H), 7.07-6.95 (m, 2H), 7.31-7.18 (m, 5H), 7.40 (d, J=2.7 Hz, 1H), 9.79 (s, 1H), 12.02 (bs, 1H). MS (ESI+) m/z 424.2 (M+H)$^+$.

Example 22

N,N-dimethyl-N'-[3-(6-methyl-7-oxo-6,7-dihydro-1H-pyrrolo[2,3-c]pyridin-4-yl)-4-phenoxyphenyl]sulfuric diamide Example 22 was prepared according to the procedure used in method A of Example 4, substituting dimethylsulfamoyl chloride for methanesulfonyl chloride, to provide the title compound. $^1$H NMR (300 MHz, DMSO-$d_6$) δ 2.74 (s, 6H), 3.48 (s, 3H), 6.28-6.23 (m, 1H), 6.85-6.78 (m, 2H), 7.06-6.93

(m, 2H), 7.31-7.17 (m, 5H), 7.40 (d, J=2.7 Hz, 1H), 9.91 (s, 1H), 12.04-12.00 (m, 1H). MS (ESI+) m/z 439.1 (M+H)$^+$.

Example 23

N-[5-(6-methyl-7-oxo-6,7-dihydro-1H-pyrrolo[2,3-c]pyridin-4-yl)-6-phenoxypyridin-3-yl]methanesulfonamide

Example 23a 3-bromo-5-nitro-2-phenoxypyridine

Phenol (0.416 g, 4.42 mmol), 3-bromo-2-chloro-5-nitropyridine (Combi-Blocks, CAS [5470-17-7], 1 g, 4.21 mmol) and cesium carbonate (1.372 g, 4.21 mmol) were combined in DMSO (8 mL) and heated at 80° C. for 30 minutes. The reaction mixture was cooled and partitioned between ethyl acetate and water. The organic layer was washed with brine, dried (Na$_2$SO$_4$), filtered and concentrated. Purification of the residue by chromatography (silica gel, 0-30% ethyl acetate in hexanes) afforded the title compound (1.13 g, 91%).

Example 23b 6-methyl-4-(5-nitro-2-phenoxypyridin-3-yl)-1-tosyl-1H-pyrrolo[2,3-c]pyridin-7(6H)-one Example 23b was prepared according to the procedure used for the preparation of Example 7d, substituting the product of Example 23a for the product of Example 7c and stirring at 60° C. for 24 hours, to provide the title compound.

Example 23c 4-(5-amino-2-phenoxypyridin-3-yl)-6-methyl-1-tosyl-1H-pyrrolo[2,3-c]pyridin-7(6H)-one Example 23c was prepared according to the procedure used for the preparation of Example 3, substituting the product of Example 23b for the product of Example 2, to provide the title compound.

Example 23d

N-[5-(6-methyl-7-oxo-6,7-dihydro-1H-pyrrolo[2,3-c]pyridin-4-yl)-6-phenoxypyridin-3-yl]methanesulfonamide Example 23d was prepared according to the procedure used in method A of Example 4, substituting the product of Example 23c for the product of Example 3, to provide the title compound (0.035 g, 36%). $^1$H NMR (300 MHz, DMSO-d$_6$) δ 3.05 (s, 3H) 3.57 (s, 3H) 6.28-6.36 (m, 1H) 7.10 (d, J=7.54 Hz, 2H) 7.16 (t, J=7.54 Hz, 1H) 7.28-7.41 (m, 3H) 7.48 (s, 1H) 7.78 (d, J=2.78 Hz, 1H) 7.96 (d, J=2.38 Hz, 1H) 9.79 (s, 1H) 12.11 (s, 1H). MS (ESI+) m/z 411.0 (M+H)$^+$.

Example 24

N-[3-fluoro-5-(6-methyl-7-oxo-6,7-dihydro-1H-pyrrolo[2,3-c]pyridin-4-yl)-4-phenoxyphenyl]methanesulfonamide

Example 24a 4-(2,3-difluoro-5-nitrophenyl)-6-methyl-1-tosyl-1H-pyrrolo[2,3-c]pyridin-7(6H)-one Example 24a was prepared according to the procedure used for the preparation of Example 7d, substituting 1-bromo-2,3-difluoro-5-nitrobenzene (Oakwood Products) for the product of Example 7c, to provide the title compound.

Example 24b 4-(3-fluoro-5-nitro-2-phenoxyphenyl)-6-methyl-1H-pyrrolo[2,3-c]pyridin-7(6H)-one Phenol (0.043 g, 0.457 mmol), Example 24a (0.2 g, 0.435 mmol) and cesium carbonate (0.142 g, 0.435 mmol) were combined in DMSO (2.177 mL) and heated at 80° C. for 30 minutes. The reaction mix was cooled and partitioned between ethyl acetate and water. The organic layer was washed with brine, dried (Na$_2$SO$_4$), filtered and concentrated to afford the title compound.

Example 24c 4-(5-amino-3-fluoro-2-phenoxyphenyl)-6-methyl-1H-pyrrolo[2,3-c]pyridin-7(6H)-one Example 24c was prepared according to the procedure used for the preparation of Example 3, substituting the product of Example 24b for the product of Example 2, to provide the title compound.

Example 24d

N-[3-fluoro-5-(6-methyl-7-oxo-6,7-dihydro-1H-pyrrolo[2,3-c]pyridin-4-yl)-4-phenoxyphenyl]methanesulfonamide Example 24d was prepared according to the procedure used in method A of Example 4, substituting the product of Example 24c for the product of Example 3, to provide the title compound (0.13 g, 67%). $^1$H NMR (300 MHz, DMSO-d$_6$) δ 3.05 (s, 3H) 3.57 (s, 3H) 6.28-6.36 (m, 1H) 7.10 (d, J=7.54 Hz, 2H) 7.16 (t, J=7.54 Hz, 1H) 7.28-7.41 (m, 3H) 7.48 (s, 1H) 7.78 (d, J=2.78 Hz, 1H) 7.96 (d, J=2.38 Hz, 1H) 9.79 (s, 1H) 12.11 (s, 1H).

Example 25

N-[4-(2-cyanophenoxy)-3-(6-methyl-7-oxo-6,7-dihydro-1H-pyrrolo[2,3-c]pyridin-4-yl)phenyl]methanesulfonamide

Example 25a 2-(2-(6-methyl-7-oxo-6,7-dihydro-1H-pyrrolo[2,3-c]pyridin-4-yl)-4-nitrophenoxy)benzonitrile Example 25a was prepared according to the procedure used for the preparation of Example 2b, substituting 2-hydroxybenzonitrile for phenol, to provide the title compound.

Example 25b 2-(4-amino-2-(6-methyl-7-oxo-6,7-dihydro-1H-pyrrolo[2,3-c]pyridin-4-yl)phenoxy)benzonitrile Example 25b was prepared according to the procedure used for the preparation of Example 3, substituting the product of Example 25a for the product of Example 2b, to provide the title compound.

Example 25c

N-[4-(2-cyanophenoxy)-3-(6-methyl-7-oxo-6,7-dihydro-1H-pyrrolo[2,3-c]pyridin-4-yl)phenyl]methanesulfonamide Example 25c was prepared according to the procedure used in method A of Example 4, substituting the product of Example 25b for the product of Example 3, to provide the title compound. $^1$H NMR (300 MHz, DMSO-$d_6$) δ 3.07 (s, 3H), 3.50 (s, 3H), 6.26 (dd, J=2.8, 1.9 Hz, 1H), 6.73 (dd, J=8.6, 0.9 Hz, 1H), 7.07 (td, J=7.6, 0.9 Hz, 1H), 7.34-7.23 (m, 4H), 7.53-7.40 (m, 2H), 7.71 (dd, J=7.7, 1.7 Hz, 1H), 9.89 (s, 1H), 12.03 (bs, 1H). MS (ESI+) m/z 435.2 (M+H)$^+$.

Example 26

N-[4-(4-fluorophenoxy)-3-(6-methyl-7-oxo-6,7-dihydro-1H-pyrrolo[2,3-c]pyridin-4-yl)phenyl]methanesulfonamide

Example 26a 4-(2-(4-fluorophenoxy)-5-nitrophenyl)-6-methyl-1H-pyrrolo[2,3-c]pyridin-7(6H)-one Example 26a was prepared according to the procedure used for the preparation of Example 2b, substituting 4-fluorophenol for phenol, to provide the title compound.

Example 26b 4-(5-amino-2-(4-fluorophenoxy)phenyl)-6-methyl-1H-pyrrolo[2,3-c]pyridin-7(6H)-one Example 26b was prepared according to the procedure used for the preparation of Example 3, substituting the product of Example 26a for the product of Example 2b, to provide the title compound.

Example 26c

N-[4-(4-fluorophenoxy)-3-(6-methyl-7-oxo-6,7-dihydro-1H-pyrrolo[2,3-c]pyridin-4-yl)phenyl]methanesulfonamide Example 26c was prepared according to the procedure used in method A of Example 4, substituting the product of Example 26b for the product of Example 3, to provide the title compound. $^1$H NMR (300 MHz, DMSO-$d_6$) δ 3.02 (s, 3H), 3.50 (s, 3H), 6.29-6.23 (m, 1H), 6.94-6.82 (m, 2H), 7.14-6.96 (m, 3H), 7.21 (dd, J=8.7, 2.7 Hz, 1H), 7.31-7.24 (m, 2H), 7.38 (d, J=2.7 Hz, 1H), 9.71 (s, 1H), 12.02 (bs, 1H). MS (ESI+) m/z 428.1 (M+H)$^+$.

Example 27

N-[4-(2,4-difluorophenoxy)-3-(6-methyl-7-oxo-6,7-dihydro-1H-pyrrolo[2,3-c]pyridin-4-yl)phenyl]methanesulfonamide

Example 27a 4-(2-(2,4-difluorophenoxy)-5-nitrophenyl)-6-methyl-1H-pyrrolo[2,3-c]pyridin-7(6H)-one Example 27a was prepared according to the procedure used for the preparation of Example 2b, substituting 2,4-difluorophenol for phenol, to provide the title compound.

Example 27b 4-(5-amino-2-(2,4-difluorophenoxy)phenyl)-6-methyl-1H-pyrrolo[2,3-c]pyridin-7(6H)-one Example 27b was prepared according to the procedure used for the preparation of Example 3, substituting the product of Example 27a for the product of Example 2b, to provide the title compound.

Example 27c

N-[4-(2,4-difluorophenoxy)-3-(6-methyl-7-oxo-6,7-dihydro-1H-pyrrolo[2,3-c]pyridin-4-yl)phenyl]methanesulfonamide Example 27b (50 mg, 0.136 mmol) and triethylamine (0.057 mL, 0.408 mmol) were combined in $CH_2Cl_2$ (9 mL). Methanesulfonyl chloride (0.042 mL, 0.544 mmol) was added dropwise and the solution stirred at ambient temperature for 1 hour. The solution was concentrated under reduced pressure, dioxane (5 mL) and sodium hydroxide (10% w/v, 3 mL, 0.136 mmol) were added and the solution heated at 70° C. for 1 hour. The mixture was cooled to ambient temperature and then neutralized with saturated $NH_4Cl$ (100 mL) to a pH of 8. The organic layer was separated and the aqueous phase was extracted with ethyl acetate (3×25 mL). The combined organic layers were washed with brine, dried ($MgSO_4$), filtered, and concentrated. Purification by reverse phase HPLC (C18, 10-100% acetonitrile/water, 0.1% TFA) afforded 27.5 mg (45.4%) of the title compound. $^1$H NMR (300 MHz, DMSO-$d_6$) δ 3.01 (s, 3H), 3.53 (s, 3H), 6.29-6.23 (m, 1H), 7.04-6.90 (m, 2H), 7.09 (td, J=9.1, 5.6 Hz, 1H), 7.44-7.14 (m, 5H), 9.70 (s, 1H), 12.04 (bs, 1H). MS (ESI+) m/z 446.1 (M+H)$^+$.

Example 28

N-[3-chloro-5-(6-methyl-7-oxo-6,7-dihydro-1H-pyrrolo[2,3-c]pyridin-4-yl)-4-phenoxyphenyl]methanesulfonamide

Example 28a 4-(3-chloro-2-fluoro-5-nitrophenyl)-6-methyl-1-tosyl-1H-pyrrolo[2,3-c]pyridin-7(6H)-one Example 28a was prepared according to the procedure used for the preparation of Example 6c, substituting 1,3-dichloro-2-fluoro-5-nitrobenzene (0.176 g, 0.841 mmol) for the product of Example 6b, to provide the title compound.

Example 28b

N-[3-chloro-5-(6-methyl-7-oxo-6,7-dihydro-1H-pyrrolo[2,3-c]pyridin-4-yl)-4-phenoxyphenyl]methanesulfonamide Example 28b was prepared according to the procedures used for the preparation of Examples 24b-24d, substituting Example 28a for the product of Example 24a, to provide the title compound. $^1$H NMR (300 MHz, DMSO-$d_6$) δ 3.12 (s, 3H) 3.43 (s, 3H) 6.25-6.29 (m, 1H) 6.63 (d, J=7.93 Hz, 2H) 6.87 (t, J=7.34 Hz, 1H) 7.10-7.18 (m, 2H) 7.27-7.31 (m, 2H) 7.39 (s, 2H) 10.05 (s, 1H) 12.04 (s, 1H). MS (ESI+) m/z 444 (M+H)$^+$.

Example 29

N-[3-(6-methyl-7-oxo-6,7-dihydro-1H-pyrrolo[2,3-c]pyridin-4-yl)-4-(tetrahydro-2H-pyran-4-yloxy)phenyl]methanesulfonamide

Example 29a

6-methyl-4-(5-nitro-2-(tetrahydro-2H-pyran-4-yloxy)phenyl)-1H-pyrrolo[2,3-c]pyridin-7(6H)-one Tetrahydro-2H-pyran-4-ol (0.046 g, 0.453 mmol) in tetrahydrofuran (2 mL) was treated with sodium hydride (0.022 g, 0.906 mmol, 0.036 g of 60% dispersion in oil) at room temperature. The reaction mixture was stirred for 10 minutes. To this solution was added Example 2a (0.1 g. 0.227 mmol). The reaction mixture was heated at 50° C. for 2 hours. After cooling to room temperature, the reaction mixture was partitioned between water and ethyl acetate. The aqueous layer was extracted twice with additional ethyl acetate. The combined organic layers were washed with brine, dried over $MgSO_4$, filtered, and concentrated. The residue was purified by flash chromatography on silica gel eluting with ethyl acetate to afford 0.055 g of the title compound.

Example 29b

4-(5-amino-2-(tetrahydro-2H-pyran-4-yloxy)phenyl)-6-methyl-1H-pyrrolo[2,3-c]pyridin-7(6H)-one A mixture of Example 29b (0.055 g) and 10% palladium on carbon (0.050 g) in ethyl acetate (10 mL) was treated with a balloon of hydrogen overnight. The solid was removed by filtration. The filtrate was concentrated under reduced pressure to provide 0.042 g of the title compound.

Example 29c

N-[3-(6-methyl-7-oxo-6,7-dihydro-1H-pyrrolo[2,3-c]pyridin-4-yl)-4-(tetrahydro-2H-pyran-4-yloxy)phenyl]methanesulfonamide Example 29c was prepared according to the procedure used in method A of Example 4, substituting the product of Example 29b for the product of Example 3, to provide the title compound. $^1$H NMR (500 MHz, DMSO-$d_6$) δ 1.45-1.51 (m, 2H), 1.82-1.87 (m, 2H), 2.94 (s, 3H), 3.35-3.41 (m, 2), 3.56 (s, 3H), 3.60-3.68 (m, 2H), 4.45-4.49 (m, 1H), 6.20 (t, J=2.29 Hz, 1H), 7.14-7.16 (m, 2H), 7.28-7.29 (m, 3H), 9.45 (s, 1H), 12.01 (s, 1H). (ESI+) m/z 418.2 (M+H)$^+$.

Example 30

6-methyl-4-[2-phenoxy-5-(1H-pyrazol-1-ylmethyl)phenyl]-1,6-dihydro-7H-pyrrolo[2,3-c]pyridin-7-one A mixture of Example 20b (0.04 g, 0.115 mmol), 1H-pyrazole (0.016 g, 0.231 mmol), and triphenylphosphine (0.061 g, 0.231 mmol) in tetrahydrofuran (1 mL) was stirred for 2 minutes. To this solution was added di-t-butyl azodicarboxylate (DTBAD, 0.053 g, 0.231 mmol). The reaction mixture was stirred at room temperature for 3 hours. The solvent was removed under reduced pressure, and the residue was purified by preparative HPLC (C18, 10-80% acetonitrile/water with 0.1% TFA) to afford 0.006 g of the title compound. $^1$H NMR (500 MHz, DMSO-$d_6$) δ 3.49 (s, 3H), 5.37 (s, 2H), 5.21 (t, J=5.8 Hz, 1H), 6.17-6.18 (m, 1H), 6.28 (t, J=1.98 Hz, 1H), 6.86 (d, J=7.63 Hz, 2H), 6.97 (d, J=8.24 Hz, 1H), 7.02 (t, J=7.32 Hz, 4H), 7.22-7.29 (m, 5H), 7.39 (d, J=2.14 Hz, 1H), 7.47 (d, J=1.83 Hz, 1H), 7.53-7.46 (m, 3H), 7.86 (d, J=2.44 Hz, 1H), 11.97 (s, 1H). (ESI+) m/z 397.2 (M+H)$^+$.

Example 31

N-[3-(6-methyl-7-oxo-6,7-dihydro-1H-pyrrolo[2,3-c]pyridin-4-yl)-4-(tetrahydrofuran-3-yloxy)phenyl]methanesulfonamide

Example 31a

6-methyl-4-(5-nitro-2-(tetrahydrofuran-3-yloxy)phenyl)-1H-pyrrolo[2,3-c]pyridin-7(6H)-one Example 31a was prepared according to the procedure used for the preparation of Example 29a, substituting tetrahydrofuran-3-ol for tetrahydro-2H-pyran-4-ol, to provide the title compound.

Example 31b

4-(5-amino-2-(tetrahydrofuran-3-yloxy)phenyl)-6-methyl-1H-pyrrolo[2,3-c]pyridin-7(6H)-one Example 31b was prepared according to the procedure used for the preparation of Example 29b, substituting the product of Example 31a for the product of Example 29a, to provide the title compound.

Example 31c

N-[3-(6-methyl-7-oxo-6,7-dihydro-1H-pyrrolo[2,3-c]pyridin-4-yl)-4-(tetrahydrofuran-3-yloxy)phenyl]methanesulfonamide Example 31 was prepared according to the procedure used in method A of Example 4, substituting the product of Example 31b for the product of Example 3, to provide the title compound. $^1$H NMR (500 MHz, DMSO-$d_6$) δ 1.84-1.90 (m, 1H), 2.08-2.17 (m, 1H), 2.95 (s, 3H), 3.35-3.41 (m, 2), 3.56 (s, 3H), 3.62-3.69 (M, 2H), 3.80-3.84 (m, 1H), 4.96-4.98 (m, 1H), 6.17-6.18 (m, 1H), 7.06-7.08 (m, 1H), 7.16-7.18 (m, 1H), 7.25 (s, 1H), 7.27-7.29 (m, 2H), 9.45 (s, 1H), 12.00 (s, 1H). (ESI+) m/z 404.2 (M+H)$^+$.

Example 32

N-{3-(6-methyl-7-oxo-6,7-dihydro-1H-pyrrolo[2,3-c]pyridin-4-yl)-4-[2-(trifluoromethyl)phenoxy]phenyl}methanesulfonamide

Example 32a

6-methyl-4-(5-nitro-2-(2-(trifluoromethyl)phenoxy)phenyl)-1H-pyrrolo[2,3-c]pyridin-7(6H)-one Example 32a was prepared according to the procedure used for the preparation of Example 2b, substituting 2-(trifluoromethyl)phenol for phenol, to provide the title compound.

Example 32b 4-(5-amino-2-(2-(trifluoromethyl)phenoxy)phenyl)-6-methyl-1H-pyrrolo[2,3-c]pyridin-7(6H)-one Example 32b was prepared according to the procedure used for the preparation of Example 3, substituting the product of Example 32a for the product of Example 2b, to provide the title compound.

Example 32c

N-{3-(6-methyl-7-oxo-6,7-dihydro-1H-pyrrolo[2,3-c]pyridin-4-yl)-4-[2-(trifluoromethyl)phenoxy]phenyl}methanesulfonamide Example 32c was prepared according to the procedure used in method A of Example 4, substituting the product of Example 32b for the product of Example 3, to provide the title compound. $^1$H NMR (300 MHz, DMSO-$d_6$) δ 3.05 (s, 3H), 3.44 (s, 3H), 6.32-6.26 (m, 1H), 6.75 (d, J=8.4 Hz, 1H), 7.17-7.07 (m, 2H), 7.34-7.18 (m, 3H), 7.53-7.38 (m, 2H), 7.65 (dd, J=7.8, 1.6 Hz, 1H), 9.84 (s, 1H), 12.09-11.99 (m, 1H). MS (ESI+) m/z 478.1 (M+H)$^+$.

Example 33

N-[4-(4-cyanophenoxy)-3-(6-methyl-7-oxo-6,7-dihydro-1H-pyrrolo[2,3-c]pyridin-4-yl)phenyl]methanesulfonamide

Example 33a 4-(2-(6-methyl-7-oxo-6,7-dihydro-1H-pyrrolo[2,3-c]pyridin-4-yl)-4-nitrophenoxy)benzonitrile Example 33a was prepared according to the procedure used for the preparation of Example 2b, substituting 4-hydroxybenzonitrile for phenol, to provide the title compound.

Example 33b 4-(4-amino-2-(6-methyl-7-oxo-6,7-dihydro-1H-pyrrolo[2,3-c]pyridin-4-yl)phenoxy)benzonitrile Example 33b was prepared according to the procedure used for the preparation of Example 3, substituting the product of Example 33a for the product of Example 2b, to provide the title compound.

Example 33c

N-[4-(4-cyanophenoxy)-3-(6-methyl-7-oxo-6,7-dihydro-1H-pyrrolo[2,3-c]pyridin-4-yl)phenyl]methanesulfonamide Example 33c was prepared according to the procedure used in method A of Example 4, substituting the product of Example 33b for the product of Example 3, to provide the title compound. $^1$H NMR (300 MHz, DMSO-$d_6$) δ 3.07 (s, 3H), 3.46 (s, 3H), 6.27-6.21 (m, 1H), 6.94-6.87 (m, 2H), 7.32-7.20 (m, 4H), 7.42 (d, J=2.5 Hz, 1H), 7.70-7.63 (m, 2H), 9.87 (s, 1H), 12.03 (bs, 1H). MS (ESI+) m/z 435.2 (M+H)$^+$.

Example 34

N-[4-(2-chloro-4-fluorophenoxy)-3-(6-methyl-7-oxo-6,7-dihydro-1H-pyrrolo[2,3-c]pyridin-4-yl)phenyl]methanesulfonamide

Example 34a 4-(2-(2-chloro-4-fluorophenoxy)-5-nitrophenyl)-6-methyl-1H-pyrrolo[2,3-c]pyridin-7(6H)-one Example 34a was prepared according to the procedure used for the preparation of Example 2b, substituting 2-chloro-4-fluorophenol for phenol, to provide the title compound.

Example 34b 4-(5-amino-2-(2-chloro-4-fluorophenoxy)phenyl)-6-methyl-1H-pyrrolo[2,3-c]pyridin-7(6H)-one Example 34b was prepared according to the procedure used for the preparation of Example 3, substituting the product of Example 34a for the product of Example 2b, to provide the title compound.

Example 34c

N-[4-(2-chloro-4-fluorophenoxy)-3-(6-methyl-7-oxo-6,7-dihydro-1H-pyrrolo[2,3-c]pyridin-4-yl)phenyl]methanesulfonamide Example 34c was prepared according to the procedure used in method A of Example 4, substituting the product of Example 34b for the product of Example 3, to provide the title compound. $^1$H NMR (300 MHz, DMSO-$d_6$) δ 3.02 (s, 3H), 3.52 (s, 3H), 6.29 (t, J=2.3 Hz, 1H), 6.99-6.88 (m, 2H), 7.14-7.03 (m, 1H), 7.21 (dd, J=8.7, 2.7 Hz, 1H), 7.28 (t, J=2.8 Hz, 1H), 7.34 (s, 1H), 7.41 (d, J=2.7 Hz, 1H), 7.49 (dd, J=8.3, 3.0 Hz, 1H), 9.75 (s, 1H), 12.05 (bs, 1H). MS (ESI+) m/z 462.1 (M+H)$^+$.

Example 35

[4-(benzyloxy)-3-(6-methyl-7-oxo-6,7-dihydro-1H-pyrrolo[2,3-c]pyridin-4-yl)phenyl]acetic acid

Example 35a ethyl 2-(3-bromo-4-hydroxyphenyl)acetate

To a solution of ethyl 2-(4-hydroxyphenyl)acetate (Alfa, 2.70 g, 15 mmol) in acetic acid (20 mL) was added drop wise over 15 minutes a solution of bromine (0.773 mL, 15.00 mmol) in acetic acid (15 mL). The mixture was stirred at ambient temperature for 30 minutes and evaporated. Purification by chromatography (silica gel, 10-20% ethyl acetate in hexane) afforded the title compound (3.66 g, 94%).

Example 35b ethyl 2-(4-(benzyloxy)-3-bromophenyl)acetate

A solution of Example 35a (2.011 mL, 16.90 mmol), and potassium carbonate (5.84 g, 42.3 mmol) in ethanol (100 mL)

Example 35c ethyl 2-(4-(benzyloxy)-3-(6-methyl-7-oxo-1-tosyl-6,7-dihydro-1H-pyrrolo[2,3-c]pyridin-4-yl)phenyl) acetate Example 35c was prepared according to the procedure used for the preparation of Example 7d, substituting the product of Example 35b for the product of Example 7c to provide the title compound.

Example 35d

[4-(benzyloxy)-3-(6-methyl-7-oxo-6,7-dihydro-1H-pyrrolo[2,3-c]pyridin-4-yl)phenyl]acetic acid Example 35c (0.4 g, 0.701 mmol), potassium hydroxide (0.787 g, 14.02 mmol) and cetyltrimethylammonium bromide (0.013 g, 0.035 mmol) were combined in dioxane (10 mL) and water (5 mL) and heated at 100° C. for 3 hours, cooled and partitioned between equal volumes of ethyl acetate and water (20 mL each). The pH was adjusted to pH 2 by careful addition of concentrated HCl. The organic layer was separated and washed with saturated brine, dried ($Na_2SO_4$), filtered and concentrated. Trituration of the residue in hexane afforded the title compound (0.27 g, 98%). $^1$H NMR (300 MHz, DMSO-$d_6$) δ 3.52 (s, 3H) 3.55 (s, 2H) 5.09 (s, 2H) 6.14-6.21 (m, 1H) 7.10-7.33 (m, 10H) 11.97 (s, 1H) 12.25 (s, 1H). MS (ESI+) m/z 389.0 (M+H)$^+$.

Example 36

N-[4-(2,4-difluorophenoxy)-3-(6-methyl-7-oxo-6,7-dihydro-1H-pyrrolo[2,3-c]pyridin-4-yl)phenyl] ethanesulfonamide

Example 36a 2-bromo-1-(2,4-difluorophenoxy)-4-nitrobenzene

A mixture of 2-bromo-1-fluoro-4-nitrobenzene (15 g, 68 mmol), 2,4-difluorophenol (7.82 ml, 82 mmol), and cesium carbonate (26.7 g, 82 mmol) in dimethylsulfoxide (75 mL) was heated to 110° C. for 1 hour. The reaction mixture was cooled to ambient temperature and water (1000 mL) and saturated aqueous sodium chloride (1000 mL) were added. The mixture was extracted with ethyl acetate (3×200 mL). The combined organics were washed with saturated aqueous sodium chloride, dried (anhydrous magnesium sulfate), filtered, and concentrated under reduced pressure to provide the title compound (22.5 g, quantitative).

Example 36b 3-bromo-4-(2,4-difluorophenoxy)aniline

A mixture of Example 36a (22.5 g, 68.2 mmol), iron powder (19.04 g, 341 mmol), and ammonium chloride (7.30 g, 136 mmol) in tetrahydrofuran (117 mL), ethanol (117 mL), and water (39.0 mL) was heated under reflux at 100° C. for 2 hours. The reaction mixture was cooled to just below reflux temperature, filtered through celite, and the filter cake washed with warm methanol (3×50 mL). The resulting solution was concentrated under reduced pressure and then neutralized to a pH of 8 with saturated sodium hydrogen carbonate (150 mL). The mixture was extracted with ethyl acetate (3×100 mL). The combined organics were washed with saturated aqueous sodium chloride, dried over anhydrous magnesium sulfate, filtered, and concentrated. The residue was purified by flash chromatography (silica gel, ethyl acetate/hexane gradient 0-15%) to provide the title compound (16.8 g, 82% yield).

Example 36c 4-(5-amino-2-(2,4-difluorophenoxy)phenyl)-6-methyl-1-tosyl-1H-pyrrolo[2,3-c]pyridin-7(6H)-one A mixture of Example 6a (5.0 g, 11.67 mmol), Example 36b (3.85 g, 12.84 mmol), 1,3,5,7-tetramethyl-6-phenyl-2,4,8-trioxa-6-phosphaadamantane (0.399 g, 1.366 mmol), tris(dibenzylideneacetone)dipalladium(0) (0.321 g, 0.350 mmol), and potassium phosphate (6.19 g, 29.2 mmol) in dioxane (50 mL) and water (12.5 mL) was degassed and back-filled with nitrogen several times. The reaction mixture was heated at 60° C. for 16 hours and then cooled to ambient temperature. The reaction mixture was partitioned between water and ethyl acetate. The aqueous layer was extracted with additional ethyl acetate three times. The combined organic layers were washed with brine, dried over anhydrous magnesium sulfate, filtered, and concentrated. The residue was purified by flash column chromatography (silica gel, 60% ethyl acetate/hexanes) to provide the title compound (4.40 g, 72.3% yield)

Example 36d

N-(4-(2,4-difluorophenoxy)-3-(6-methyl-7-oxo-1-tosyl-6,7-dihydro-1H-pyrrolo[2,3-c]pyridin-4-yl) phenyl)-N-(ethylsulfonyl)ethanesulfonamide A solution of Example 36c (4.35 g, 8.34 mmol) in dichloromethane (50 mL) was cooled to 0° C. To this solution was added ethanesulfonyl chloride (2.37 mL, 25.0 mmol). The reaction mixture was stirred at room temperature for 2 hours. The solvent was evaporated, and the residue was partitioned between ethyl acetate and water. The aqueous layer was extracted with additional ethyl acetate twice. The combined organic layers were washed with saturated aqueous sodium chloride, dried over anhydrous magnesium sulfate, filtered, and concentrated. The residue was purified by flash chromatography (silica gel, 80% ethyl acetate/hexanes) to provide the title compound (5.34 g, 91% yield).

Example 36e

N-[4-(2,4-difluorophenoxy)-3-(6-methyl-7-oxo-6,7-dihydro-1H-pyrrolo[2,3-c]pyridin-4-yl)phenyl] ethanesulfonamide A mixture of Example 36d (5.3 g, 7.5 mmol), potassium hydroxide (8.43 g, 150 mmol), and N,N,N-trimethylhexadecan-1-aminium bromide (0.137 g, 0.375 mmol) in tetrahydrofuran (60 mL) and water (30 mL) was heated at 90° C. for 16 hours. Tetrahydrofuran was removed under reduced pressure, and the residue was partitioned between water and ethyl acetate. The aqueous layer was neutralized to pH=7 using 10% HCl. The aqueous layer was then extracted with ethyl acetate. The combined organic layers were washed with saturated aqueous sodium chloride, dried over anhydrous magnesium sulfate, filtered, and concentrated. The residue was purified by flash chromatography (silica gel, ethyl acetate). The desired fractions were combined and concentrated. The residue was triturated with 20 mL of acetonitrile to provide the title compound (2.82 g, 82% yield). $^1$H NMR (300 MHz, DMSO-$d_6$) δ 1.23 (t, J=7.3 Hz, 3H), 3.11 (q, J=7.3 Hz, 2H), 3.53 (s, 3H), 6.27-6.22 (m, 1H), 6.91 (d, J=8.7 Hz, 1H), 7.13-6.93 (m, 2H), 7.19 (dd, J=8.8, 2.7 Hz, 1H), 7.32-7.25 (m, 2H), 7.42-7.31 (m, 2H), 9.77 (s, 1H), 12.04 (bs, 1H). MS (ESI+) m/z 460.1 (M+H)$^+$.

Example 37

N-[4-(2,4-difluorophenoxy)-3-(6-methyl-7-oxo-6,7-dihydro-1H-pyrrolo[2,3-c]pyridin-4-yl)phenyl]acetamide Example 27b (50 mg, 0.136 mmol) and triethylamine (56.9 μL, 0.408 mmol) were combined in CH$_2$Cl$_2$ (10 mL). Acetyl chloride (11.6 μL, 0.163 mmol) was added dropwise and the solution stirred for 1 hour at ambient temperature. Water (25 mL) and saturated aqueous sodium bicarbonate (25 mL) were added, and the mixture was extracted with CH$_2$Cl$_2$ (3×25 mL). The combined organics were washed with brine, dried (MgSO$_4$), filtered, and concentrated. Purification of the residue by reverse phase HPLC (C18, 10-100% acetonitrile/water, 0.1% TFA) afforded 15 mg (28%) of the title compound. $^1$H NMR (300 MHz, DMSO-$d_6$) δ 2.04 (s, 3H), 3.52 (s, 3H), 6.29 6.23 (m, 1H), 7.08-6.85 (m, 3H), 7.39-7.25 (m, 3H), 7.53 (dd, J=8.8, 2.6 Hz, 1H), 7.77 (d, J=2.6 Hz, 1H), 10.00 (s, 1H), 12.07-11.96 (m, 1H). MS (ESI+) m/z 410.3 (M+H)$^+$.

Example 38

N-[4-(2,4-difluorophenoxy)-3-(6-methyl-7-oxo-6,7-dihydro-1H-pyrrolo[2,3-c]pyridin-4-yl)phenyl]-3,3,3-trifluoropropanamide Example 38 was prepared according to the procedure used for the preparation of Example 37, substituting 3,3,3-trifluoropropanoyl chloride for acetyl chloride, to provide the title compound. $^1$H NMR (300 MHz, DMSO-$d_6$) δ 3.54-3.46 (m, 2H), 3.53 (s, 3H), 6.27 (t, J=2.3 Hz, 1H), 7.14-6.87 (m, 3H), 7.28 (t, J=2.7 Hz, 1H), 7.31 (s, 1H), 7.37 (ddd, J=11.3, 8.7, 2.8 Hz, 1H), 7.50 (dd, J=8.8, 2.6 Hz, 1H), 7.76 (d, J=2.6 Hz, 1H), 10.38 (s, 1H), 12.03 (bs, 1H). MS (ESI+) m/z 478.2 (M+H)$^+$.

Example 39

N-[4-(2,4-difluorophenoxy)-3-(6-methyl-7-oxo-6,7-dihydro-1H-pyrrolo[2,3-c]pyridin-4-yl)phenyl]-2,2-dimethylpropanamide Example 39 was prepared according to the procedure used for the preparation of Example 37, substituting pivaloyl chloride for acetyl chloride, to provide the title compound. $^1$H NMR (300 MHz, DMSO-$d_6$) δ 1.22 (s, 9H), 3.53 (s, 3H), 6.31-6.25 (m, 1H), 6.88 (d, J=8.8 Hz, 1H), 7.08-6.92 (m, 2H), 7.31-7.24 (m, 2H), 7.40-7.29 (m, 1H), 7.62 (dd, J=8.8, 2.6 Hz, 1H), 7.83 (d, J=2.6 Hz, 1H), 9.28 (s, 1H), 12.00 (bs, 1H). MS (ESI+) m/z 452.3 (M+H)$^+$.

Example 40 ethyl 4-(cyclopentylamino)-3-(6-methyl-7-oxo-6,7-dihydro-1H-pyrrolo[2,3-c]pyridin-4-yl)benzoate A mixture of Example 9a (0.094 g, 0.2 mmol), cyclopentanamine (0.034 g, 0.4 mmol), and triethylamine (0.081 g, 0.8 mmol) in DMSO (2 mL) was heated at 120° C. overnight. The reaction mixture was purified by preparative HPLC (C18, 10-80% acetonitrile in 0.1% TFA/water to afford 0.019 g of the title product. $^1$H NMR (500 MHz, DMSO-$d_6$) δ 1.27 (t, J=7.02 Hz, 3H), 1.32-1.36 (m, 2H), 1.47-1.55 (m, 3H), 1.88-1.93 (m, 2H), 3.55 (s, 3H), 3.83-3.88 (m, 1H), 4.22 (q, J=7.02 Hz, 2H), 5.94 (t, J=2.29 Hz, 1H), 6.77 (d, J=8.85 Hz, 1H), 7.22 (s, 1H), 7.28 (t, J=2.75 Hz, 1H), 7.63 (d, J=1.83 Hz, 1H), 7.82 (dd, J=8.54, 2.14, 1H), 12.01 (s, 1H). MS (ESI+) m/z 380.2 (M+H)$^+$.

Example 41

4-{5-[(1,1-dioxido-1,2-thiazolidin-2-yl)methyl]-2-phenoxyphenyl}-6-methyl-1,6-dihydro-7H-pyrrolo[2,3-c]pyridin-7-one Example 41a 4-(5-(hydroxymethyl)-2-phenoxyphenyl)-6-methyl-1-tosyl-1H-pyrrolo[2,3-c]pyridin-7(6H)-one Example 41a was isolated as a by-product from the preparation of Example 20b.

Example 41b 3-(6-methyl-7-oxo-1-tosyl-6,7-dihydro-1H-pyrrolo[2,3-c]pyridin-4-yl)-4-phenoxybenzyl methanesulfonate A mixture of Example 41a (0.15 g, 0.3 mmol), methanesulfonyl chloride (0.069 g, 0.6 mmol), and triethylamine (0.121 g, 1.2 mmol) in dichloromethane (5 mL) was stirred at room temperature for 2 hours. The solvent was removed, and the residue was purified by flash chromatography on silica gel eluting with 20-40% ethyl acetate in hexanes to afford 0.105 g of the title product.

Example 41c

4-{5-[(1,1-dioxido-1,2-thiazolidin-2-yl)methyl]-2-phenoxyphenyl}-6-methyl-1,6-dihydro-7H-pyrrolo[2,3-c]pyridin-7-one 1,2-thiazolidine 1,1-dioxide (0.031 g, 0.259 mmol) in dimethylformamide (1 mL) was treated with 60% sodium hydride (0.012 g, 0.518 mmol, 0.021 g of a 60% in oil dispersion). The reaction mixture was stirred for 5 min. To this solution was added Example 41b (0.05 g, 0.086 mmol). The reaction mixture was stirred at room temperature for 2 hours. 2 N NaOH (1 mL) was added and the reaction mixture was heated at 65° C. for 2 hours. After cooling to room temperature, the reaction mixture was partitioned between water and ethyl acetate. The aqueous layer was extracted with additional ethyl acetate twice. The combined organic layers were washed with brine, dried over MgSO$_4$, filtered, and concentrated. The residue was purified by preparative HPLC (C18, 10-80% acetonitrile in 0.1% TFA water) to afford 0.025 g (64%) of the title compound. $^1$H NMR (500 MHz, DMSO-$d_6$)

δ 2.21-2.25 (m, 2H), 3.15 (t, J=6.97 Hz, 2H), 3.23-3.27 (m, 2H), 3.50 (s, 3H), 4.13 (s, 2H), 6.25-6.26 (m, 1H), 6.88 (d, J=7.63 Hz, 2H), 7.00 (d, J=8.54 Hz, 1H), 7.03-7.05 (m, 1H), 7.25-7.30 (m, 4H), 7.34 (dd, J=8.39, 2.29, 1H), 7.48 (d, J=2.44 Hz, 1H), 12.00 (s, 1H). MS (ESI+) m/z 450.2 (M+H)+.

Example 42

4-{[3-(6-methyl-7-oxo-6,7-dihydro-1H-pyrrolo[2,3-c]pyridin-4-yl)-4-phenoxybenzyl]amino}-4-oxobutanoic acid Example 42 was prepared according to the procedure used for the preparation of Example 41c, substituting pyrrolidine-2,5-dione for 1,2-thiazolidine 1,1-dioxide, to provide the title compound. $^1$H NMR (500 MHz, DMSO-$d_6$) δ 2.37-2.40 (m, 2H), 2.44-2.48 (m, 2H), 3.50 (s, 3H), 4.31 (d, J=5.8 Hz, 2H), 6.23-6.24 (m, 1H), 6.84 (d, J=7.63 Hz, 2H), 6.96 (d, J=8.24 Hz, 1H), 7.00 (t, J=7.32 Hz, 1H), 7.22-7.29 (m, 5H), 7.40 (d, J=2.14, 1H), 8.40 (t, J=5.95 Hz, 1H), 11.98 (s, 1H). MS (ESI+) m/z 446.1 (M+H)+.

Example 43

4-[2-(2,4-difluorophenoxy)-5-(1,1-dioxido-1,2-thiazolidin-2-yl)phenyl]-6-methyl-1,6-dihydro-7H-pyrrolo[2,3-c]pyridin-7-one

Example 43a 3-chloro-N-(3-chloropropylsulfonyl)-N-(4-(2,4-difluorophenoxy)-3-(6-methyl-7-oxo-6,7-dihydro-1H-pyrrolo[2,3-c]pyridin-4-yl)phenyl)propane-1-sulfonamide A mixture of Example 27b (0.1 g, 0.272 mmol), 3-chloropropane-1-sulfonyl chloride (0.145 g, 0.817 mmol), and triethylamine (0.165 g, 1.633 mmol) in dichloromethane (3 mL) was stirred for 2 hours. The solvent was removed, and the residue was used directly for the next reaction.

Example 43b

4-[2-(2,4-difluorophenoxy)-5-(1,1-dioxido-1,2-thiazolidin-2-yl)phenyl]-6-methyl-1,6-dihydro-7H-pyrrolo[2,3-c]pyridin-7-one Sodium (0.064 g, 2.78 mmol) was dissolved in ethanol (15 mL). To this solution was added Example 43a (0.18 g, 0.278 mmol) in ethanol (5 mL). The reaction mixture was heated at 75° C. for 2 hours. After cooling, the solvent was removed under reduced pressure, and the residue was purified by preparative HPLC (C18, 10-80% acetonitrile in 0.1% TFA/water) to afford 0.055 g of the title compound. $^1$H NMR (500 MHz, DMSO-$d_6$) δ 2.37-2.44 (m, 2H), 3.49-3.53 (m, 2H), 3.54 (s, 3H), 3.76 (t, J=6.56 Hz, 2H), 6.27-6.28 (m, 1H), 6.95 (d, J=8.85 Hz, 1H), 7.00-7.12 (m, 2H), 7.20 (dd, J=8.85, 2.75 Hz, 1H), 7.28 (t, J=2.75 Hz, 1H), 7.32 (s, 1H), 7.35-7.41 (m, 2H), 12.05 (s, 1H). MS (ESI+) m/z 472.2 (M+H)+.

Example 44

4-[2-(benzyloxy)-5-(2-hydroxyethyl)phenyl]-6-methyl-1,6-dihydro-7H-pyrrolo[2,3-c]pyridin-7-one Example 35d (0.039 g, 0.1 mmol) in tetrahydrofuran (2 mL) was treated dropwise with borane-tetrahydrofuran complex (1M, 0.200 mL, 0.200 mmol), and the mixture was stirred at 40° C. for 1 hour, diluted with 5 mL of methanol, heated at 50° C. for 30 minutes and concentrated. Purification by chromatography (silica gel, 0.5-4% methanol in dichloromethane) afforded the title compound (0.03 g, 79%). $^1$H NMR (300 MHz, DMSO-$d_6$) δ 2.70 (t, J=6.94 Hz, 2H) 3.52 (s, 3H) 3.57-3.64 (m, 2H) 4.59-4.63 (m, 1H) 5.06 (s, 2H) 6.14-6.18 (m, 1H) 7.08-7.18 (m, 2H) 7.20-7.32 (m, 8H) 11.95 (s, 1H). MS (ESI+) m/z 375.0 (M+H)+.

Example 45 methyl [4-(benzyloxy)-3-(6-methyl-7-oxo-6,7-dihydro-1H-pyrrolo[2,3-c]pyridin-4-yl)phenyl]acetate

Example 45a 2-(4-(benzyloxy)-3-(6-methyl-7-oxo-6,7-dihydro-1H-pyrrolo[2,3-c]pyridin-4-yl)phenyl)acetyl chloride Example 35d (0.18 g, 0.463 mmol) in tetrahydrofuran (4.63 mL) was treated with one drop of dimethylformamide followed by drop-wise addition of oxalyl chloride (0.122 mL, 1.390 mmol), stirred for twenty minutes and concentrated.

Example 45b methyl [4-(benzyloxy)-3-(6-methyl-7-oxo-6,7-dihydro-1H-pyrrolo[2,3-c]pyridin-4-yl)phenyl]acetate Example 45a (0.058 g, 0.143 mmol) in tetrahydrofuran (4 mL) was treated with methanol (5 mL, 124 mmol), stirred for 1 hour at room temperature and concentrated. Purification by chromatography (silica gel, 0.5-3% methanol in dichloromethane) afforded the title compound (0.048 g, 79%). $^1$H NMR (300 MHz, DMSO-$d_6$) δ 3.52 (s, 3H) 3.62 (s, 3H) 3.66 (s, 2H) 5.09 (s, 2H) 6.15-6.20 (m, 1H) 7.10-7.37 (m, 10H) 11.97 (s, 1H). MS (ESI+) m/z 403.0 (M+H)+.

Example 46

2-[4-(benzyloxy)-3-(6-methyl-7-oxo-6,7-dihydro-1H-pyrrolo[2,3-c]pyridin-4-yl)phenyl]-N-ethylacetamide Example 46 was prepared according to the procedure used for the preparation of Example 45b, substituting ethylamine for methanol, to provide the title compound (0.039 g, 64%). $^1$H NMR (300 MHz, DMSO-$d_6$) δ 1.01 (t, J=7.29 Hz, 3H) 2.99-3.11 (m, 2H) 3.35 (s, 2H) 3.52 (s, 3H) 5.07 (s, 2H) 6.14-6.21 (m, 1H) 7.08-7.35 (m, 10H) 7.98 (t, J=5.43 Hz, 1H) 11.96 (s, 1H). MS (ESI+) m/z 416.0 (M+H)+.

Example 47

2-[4-(benzyloxy)-3-(6-methyl-7-oxo-6,7-dihydro-1H-pyrrolo[2,3-c]pyridin-4-yl)phenyl]-N,N-dimethylacetamide Example 47 was prepared according to the procedure used for the preparation of Example 45b, substituting dimethylamine for methanol, to provide the title compound (0.058 g, 98%). $^1$H NMR (300 MHz, DMSO-$d_6$) δ 2.83 (s, 3H) 3.02 (s, 3H) 3.52 (s, 3H) 3.66 (s, 2H) 5.08 (s, 2H) 6.12-6.24 (m, 1H) 7.06-7.36 (m, 10H) 11.96 (s, 1H). MS (ESI+) m/z 416.0 (M+H)+.

Example 48

N-[4-(3,4-difluorophenoxy)-3-(6-methyl-7-oxo-6,7-dihydro-1H-pyrrolo[2,3-c]pyridin-4-yl)phenyl]methanesulfonamide

Example 48a 4-(2-(3,4-difluorophenoxy)-5-nitrophenyl)-6-methyl-1H-pyrrolo[2,3-c]pyridin-7(6H)-one Example 48a was prepared according to the procedure used for the preparation of Example 2b, substituting 3,4-difluorophenol for phenol, to provide the title compound.

Example 48b 4-(5-amino-2-(3,4-difluorophenoxy)phenyl)-6-methyl-1H-pyrrolo[2,3-c]pyridin-7(6H)-one Example 48b was prepared according to the procedure used for the preparation of Example 3, substituting the product of Example 48a for the product of Example 2b, to provide the title compound.

Example 48c

N-[4-(3,4-difluorophenoxy)-3-(6-methyl-7-oxo-6,7-dihydro-1H-pyrrolo[2,3-c]pyridin-4-yl)phenyl]methanesulfonamide Example 48c was prepared according to the procedure used in method A of Example 4, substituting the product of Example 48b for the product of Example 3, to provide the title compound. $^1$H NMR (300 MHz, DMSO-$d_6$) δ 3.04 (s, 3H), 3.50 (s, 3H), 6.28-6.23 (m, 1H), 6.72-6.62 (m, 1H), 6.97 (ddd, J=11.9, 6.7, 3.0 Hz, 1H), 6.97 (ddd, J=11.9, 6.7, 3.0 Hz, 1H), 7.11 (d, J=8.7 Hz, 1H), 7.41-7.19 (m, 5H), 9.78 (s, 1H), 12.03 (bs, 1H). MS (ESI+) m/z 446.1 (M+H)$^+$.

Example 49

N-[3-(6-methyl-7-oxo-6,7-dihydro-1H-pyrrolo[2,3-c]pyridin-4-yl)-4-(2,4,6-trifluorophenoxy)phenyl]methanesulfonamide

Example 49a 6-methyl-4-(5-nitro-2-(2,4,6-trifluorophenoxy)phenyl)-1H-pyrrolo[2,3-c]pyridin-7(6H)-one Example 49a was prepared according to the procedure used for the preparation of Example 2b, substituting 2,4,6-trifluorophenol for phenol, to provide the title compound.

Example 49b 4-(5-amino-2-(2,4,6-trifluorophenoxy)phenyl)-6-methyl-1H-pyrrolo[2,3-c]pyridin-7(6H)-one Example 49b was prepared according to the procedure used for the preparation of Example 3, substituting the product of Example 49a for the product of Example 2b, to provide the title compound.

Example 49c

N-[3-(6-methyl-7-oxo-6,7-dihydro-1H-pyrrolo[2,3-c]pyridin-4-yl)-4-(2,4,6-trifluorophenoxy)phenyl]methanesulfonamide Example 49c was prepared according to the procedure used in method A of Example 4, substituting the product of Example 49b for the product of Example 3, to provide the title compound. 1H$^1$H NMR NMR (300 MHz, DMSO-$d_6$) δ 2.99 (s, 3H), 3.57 (s, 3H), 6.23 (t, J=2.3 Hz, 1H), 6.80 (d, J=8.8 Hz, 1H), 7.15 (dd, J=8.8, 2.7 Hz, 1H), 7.34-7.27 (m, 3H), 7.45-7.34 (m, 2H), 9.66 (s, 1H), 12.07 (bs, 1H). MS (ESI+) m/z 464.1 (M+H)$^+$.

Example 50

4-(2,4-difluorophenoxy)-3-(6-methyl-7-oxo-6,7-dihydro-1H-pyrrolo[2,3-c]pyridin-4-yl)benzamide

Example 50a ethyl 4-(2,4-difluorophenoxy)-3-(6-methyl-7-oxo-6,7-dihydro-1H-pyrrolo[2,3-c]pyridin-4-yl)benzoate Example 50a was prepared according to the procedure used for the preparation of Example 9b, substituting 2,4-difluorophenol for phenol, to provide the title compound.

Example 50b 4-(2,4-difluorophenoxy)-3-(6-methyl-7-oxo-6,7-dihydro-1H-pyrrolo[2,3-c]pyridin-4-yl)benzoic acid Example 50b was prepared according to the procedure used for the preparation of Example 10, substituting Example 50a for Example 9b, to provide the title compound.

Example 50c 4-(2,4-difluorophenoxy)-3-(6-methyl-7-oxo-6,7-dihydro-1H-pyrrolo[2,3-c]pyridin-4-yl)benzamide Example 50c was prepared according to the procedure used for the preparation of Example 13a, substituting Example 50b for Example 10, to provide the title compound.

Example 50d 4-(2,4-difluorophenoxy)-3-(6-methyl-7-oxo-6,7-dihydro-1H-pyrrolo[2,3-c]pyridin-4-yl)benzamide Example 50d was prepared according to the procedure used for the preparation of Example 13b, substituting Example 50c for Example 13a, and aqueous ammonium hydroxide for ethylamine, respectively, to provide the title compound. $^1$H NMR (500 MHz, DMSO-$d_6$) δ 3.57 (s, 3H), 6.24-6.25 (m, 1H), 6.83 (d, J=8.24 Hz, 1H), 7.07-7.13 (m, 1H), 7.27-7.34 (m, 4H), 7.42-7.48 (m, 1H), 7.85 (dd, J=8.54, 2.44, 1H), 7.96 (s, 1H), 8.00 (d, J=2.44 Hz, 1H), 12.04 (s, 1H). MS (ESI+) m/z 396.3 (M+H)$^+$.

Example 51

4-(2,4-difluorophenoxy)-3-(6-methyl-7-oxo-6,7-dihydro-1H-pyrrolo[2,3-c]pyridin-4-yl)-N-(tetrahydrofuran-3-yl)benzamide Example 51 was prepared according to the procedure used for the preparation of Example 13b, substituting Example 50c for Example 13a, and tetrahydrofuran-3-amine for ethylamine, respectively, to provide the title compound. $^1$H NMR (500 MHz, DMSO-$d_6$) δ 1.87-1.94 (m, 1H), 2.10-2.19 (m, 1H), 3.57 (s, 3H), 3.67-3.73 (m, 2H), 3.81-3.87 (m, 2H), 4.42-4.49 (m, 1H), 6.22-6.23 (m, 1H), 6.85 (d, J=8.54 Hz, 1H), 7.07-7.13 (m, 1H), 7.25-7.34 (m, 3H), 7.42-7.47 (m, 1H), 7.85 (dd, J=8.85, 2.14, 1H), 7.96 (s, 1H), 8.00 (d, J=2.14 Hz, 1H), 8.50 (d, J=6.41 Hz, 1H), 12.03 (s, 1H). MS (ESI+) m/z 466.3 (M+H)$^+$.

Example 52

4-{2-(2,4-difluorophenoxy)-5-[(1,1-dioxidothiomorpholin-4-yl)carbonyl]phenyl}-6-methyl-1,6-dihydro-7H-pyrrolo[2,3-c]pyridin-7-one Example 52 was prepared according to the procedure used for the preparation of Example 13b, substituting 1,1-dioxo-1-thiomorpholine for ethylamine and Example 50c for Example 13a, respectively, to provide the title compound. $^1$H NMR (500 MHz, DMSO-$d_6$) δ 3.25-3.28 (m, 4H), 3.56 (s, 3H), 3.78 (m, 4H), 4.45-4.61 (m, 1H), 3.81-3.87 (m, 2H), 6.26-6.27 (m, 1H), 6.86 (d, J=8.24 Hz, 1H), 7.07-7.12 (m, 1H), 7.27-7.33 (m, 3H), 7.42-7.48 (m, 2H), 7.63 (d, J=2.14, 1H), 12.04 (s, 1H). MS (ESI+) m/z 514.2 (M+H)$^+$.

Example 53

4-(2,4-difluorophenoxy)-3-(6-methyl-7-oxo-6,7-dihydro-1H-pyrrolo[2,3-c]pyridin-4-yl)-N-(1-methyl-2-oxopyrrolidin-3-yl)benzamide Example 53 was prepared according to the procedure used for the preparation of Example 13b, substituting Example 50c for Example 13a, and 3-amino-1-methylpyrrolidin-2-one for ethylamine, respectively, to provide the title compound. 1H NMR (500 MHz, DMSO-$d_6$) δ 1.87-1.97 (m, 1H), 2.29-2.38 (m, 1H), 2.76 (s, 3H), 3.30-3.34 (m, 2H), 3.57 (s, 3H), 4.45-4.61 (m, 1H), 3.81-3.87 (m, 2H), 4.42-4.49 (m, 1H), 6.23-6.24 (m, 1H), 6.87 (d, J=8.54 Hz, 1H), 7.08-7.13 (m, 1H), 7.25-7.34 (m, 3H), 7.43-7.48 (m, 1H), 7.85 (dd, J=8.54, 2.44 Hz, 1H), 7.96 (s, 1H), 7.99 (d, J=2.14 Hz, 1H), 8.73 (d, J=8.85 Hz, 1H), 12.03 (s, 1H). MS (ESI+) m/z 493.2 (M+H)$^+$.

Example 54 tert-butyl {1-[4-(2,4-difluorophenoxy)-3-(6-methyl-7-oxo-6,7-dihydro-1H-pyrrolo[2,3-c]pyridin-4-yl)benzoyl]pyrrolidin-3-yl}carbamate Example 54 was prepared according to the procedure used for the preparation of Example 13b, substituting Example 50c for Example 13a, and tert-butyl pyrrolidin-3-ylcarbamate for ethylamine, respectively, to provide the title compound. $^1$H NMR (500 MHz, DMSO-$d_6$) δ 1.33-1.40 (m, 9H), 1.74-1.83 (m, 1H), 2.01-2.0.3 (m, 1H), 3.27-3.31 (m, 1H), 3.56 (s, 3H), 3.62-3.56 (m, 1H), 3.93-4.07 (m, 1H), 6.24 (d, J=2.29 Hz, 1H), 6.83 (d, J=8.54 Hz, 1H), 7.0-7.13 (m, 1H), 7.20-7.33 (m, 3H), 7.41-7.52 (m, 2H), 7.60 (d, J=16.2 Hz, 1H), 12.03 (s, 1H). MS (ESI+) m/z 565.2 (M+H)$^+$.

Example 55

4-[2-(2,4-difluorophenoxy)-5-(pyrrolidin-1-ylcarbonyl)phenyl]-6-methyl-1,6-dihydro-7H-pyrrolo[2,3-c]pyridin-7-one Example 55 was prepared according to the procedure used for the preparation of Example 13b, substituting Example 50c for Example 13a, and pyrrolidine for ethylamine, respectively, to provide the title compound. $^1$H NMR (500 MHz, DMSO-$d_6$) δ 1.82-1.86 (m, 4H), 3.45-3.48 (m, 4H), 3.56 (s, 3H), 6.24-6.26 (m, 1H), 6.82 (d, J=8.24 Hz, 1H), 7.06-7.12 (m, 1H), 7.26-7.33 (m, 3H), 7.41-7.46 (m, 1H), 7.52 (dd, J=8.54, 2.14 Hz, 1H), 7.61 (d, J=2.14 Hz, 1H), 12.03 (s, 1H). MS (ESI+) m/z 450.3 (M+H)$^+$.

Example 56

4-[2-(2,4-difluorophenoxy)-5-(morpholin-4-ylcarbonyl)phenyl]-6-methyl-1,6-dihydro-7H-pyrrolo[2,3-c]pyridin-7-one Example 56 was prepared according to the procedure used for the preparation of Example 13b, substituting Example 50c for Example 13a, and morpholine for ethylamine, respectively, to provide the title compound. 1H NMR (500 MHz, DMSO-$d_6$) δ 3.56 (s, 3H), 3.60-3.68 (m, 8H), 6.24-6.25 (m, 1H), 6.84 (d, J=8.54 Hz, 1H), 7.06-7.12 (m, 1H), 7.26-7.33 (m, 3H), 7.40 dd, J=8.54, 2.14 Hz, 1H), 7.44-7.46 (m, 1H), 7.50 (dd, J=2.14 Hz, 1H), 12.03 (s, 1H). MS (ESI+) m/z 466.3 (M+H)$^+$.

Example 57

N-[4-(cyclohexyloxy)-3-(6-methyl-7-oxo-6,7-dihydro-1H-pyrrolo[2,3-c]pyridin-4-yl)phenyl]methanesulfonamide

Example 57a 4-(2-(cyclohexyloxy)-5-nitrophenyl)-6-methyl-1H-pyrrolo[2,3-c]pyridin-7(6H)-one Example 57a was prepared according to the procedure used for the preparation of Example 29a, substituting cyclohexanol for tetrahydro-2H-pyran-4-ol, to provide the title compound.

Example 57b 4-(5-amino-2-(cyclohexyloxy)phenyl)-6-methyl-1H-pyrrolo[2,3-c]pyridin-7(6H)-one Example 57b was prepared according to the procedure used for the preparation of Example 3, substituting the product of Example 57a for the product of Example 2b, to provide the title compound.

Example 57c

N-[4-(cyclohexyloxy)-3-(6-methyl-7-oxo-6,7-dihydro-1H-pyrrolo[2,3-c]pyridin-4-yl)phenyl]methanesulfonamide Example 57c was prepared according to the procedure used in method A of Example 4, substituting the product of Example 57b for the product of Example 3, to provide the title compound. $^1$H NMR (300 MHz, DMSO-$d_6$) δ 1.47-1.10 (m, 6H), 1.61-1.47 (m, 2H), 1.84-1.69 (m, 2H), 2.94 (s, 3H), 3.55

(s, 3H), 4.31-4.22 (m, 1H), 6.21 (t, J=2.3 Hz, 1H), 7.18-7.06 (m, 2H), 7.31-7.25 (m, 3H), 9.39 (s, 1H), 11.98 (bs, 1H). MS (ESI+) m/z 416.2 (M+H)$^+$.

Example 58

N-[4-(cyclopentyloxy)-3-(6-methyl-7-oxo-6,7-dihydro-1H-pyrrolo[2,3-c]pyridin-4-yl)phenyl]methanesulfonamide

Example 58a 4-(2-(cyclopentyloxy)-5-nitrophenyl)-6-methyl-1H-pyrrolo[2,3-c]pyridin-7(6H)-one Example 58a was prepared according to the procedure used for the preparation of Example 29a, substituting cyclopentanol for tetrahydro-2H-pyran-4-ol, to provide the title compound.

Example 58b 4-(5-amino-2-(cyclopentyloxy)phenyl)-6-methyl-1H-pyrrolo[2,3-c]pyridin-7(6H)-one Example 58b was prepared according to the procedure used for the preparation of Example 3, substituting the product of Example 58a for the product of Example 2b, to provide the title compound.

Example 58c

N-[4-(cyclopentyloxy)-3-(6-methyl-7-oxo-6,7-dihydro-1H-pyrrolo[2,3-c]pyridin-4-yl)phenyl]methanesulfonamide Example 58c was prepared according to the procedure used in method A of Example 4, substituting the product of Example 58b for the product of Example 3, to provide the title compound. $^1$H NMR (300 MHz, DMSO-d$_6$) δ 1.70-1.43 (m, 6H), 1.88-1.70 (m, 2H), 2.94 (s, 3H), 3.55 (s, 3H), 4.78-4.70 (m, 1H), 6.16 (t, J=2.3 Hz, 1H), 7.06 (d, J=8.8 Hz, 1H), 7.16 (dd, J=8.7, 2.7 Hz, 1H), 7.22 (s, 1H), 7.30-7.23 (m, 2H), 9.39 (s, 1H), 11.97 (bs, 1H). MS (ESI+) m/z 402.1 (M+H)$^+$.

Example 59

N-{4-[(4,4-difluorocyclohexyl)oxy]-3-(6-methyl-7-oxo-6,7-dihydro-1H-pyrrolo[2,3-c]pyridin-4-yl)phenyl}methanesulfonamide

Example 59a 4-(2-(4,4-difluorocyclohexyloxy)-5-nitrophenyl)-6-methyl-1H-pyrrolo[2,3-c]pyridin-7(6H)-one Example 59a was prepared according to the procedure used for the preparation of Example 29a, substituting 4,4-difluorocyclohexanol for tetrahydro-2H-pyran-4-ol, to provide the title compound.

Example 59b 4-(5-amino-2-(4,4-difluorocyclohexyloxy)phenyl)-6-methyl-1H-pyrrolo[2,3-c]pyridin-7(6H)-one Example 59b was prepared according to the procedure used for the preparation of Example 3, substituting the product of Example 59a for the product of Example 2b, to provide the title compound.

Example 59c

N-{4-[(4,4-difluorocyclohexyl)oxy]-3-(6-methyl-7-oxo-6,7-dihydro-1H-pyrrolo[2,3-c]pyridin-4-yl)phenyl}methanesulfonamide Example 59c was prepared according to the procedure used in method A of Example 4, substituting the product of Example 59b for the product of Example 3, to provide the title compound. $^1$H NMR (300 MHz, DMSO-d$_6$) δ 1.95-1.61 (m, 8H), 2.95 (s, 3H), 3.55 (s, 3H), 4.55-4.46 (m, 1H), 6.22-6.17 (m, 1H), 7.20-7.15 (m, 2H), 7.31-7.25 (m, 3H), 9.47 (s, 1H), 12.01 (bs, 1H). MS (ESI+) m/z 452.2 (M+H)$^+$.

Example 60

N-[3-(6-methyl-7-oxo-6,7-dihydro-1H-pyrrolo[2,3-c]pyridin-4-yl)-4-(tetrahydro-2H-pyran-3-yloxy)phenyl]methanesulfonamide

Example 60a 6-methyl-4-(5-nitro-2-(tetrahydro-2H-pyran-3-yloxy)phenyl)-1H-pyrrolo[2,3-c]pyridin-7(6H)-one Example 60a was prepared according to the procedure used for the preparation of Example 29a, substituting tetrahydro-2H-pyran-3-ol for tetrahydro-2H-pyran-4-ol, to provide the title compound.

Example 60b 4-(5-amino-2-(tetrahydro-2H-pyran-3-yloxy)phenyl)-6-methyl-1H-pyrrolo[2,3-c]pyridin-7(6H)-one Example 60b was prepared according to the procedure used for the preparation of Example 29b, substituting the product of Example 60a for the product of Example 29a, to provide the title compound.

Example 60c

N-[3-(6-methyl-7-oxo-6,7-dihydro-1H-pyrrolo[2,3-c]pyridin-4-yl)-4-(tetrahydro-2H-pyran-3-yloxy)phenyl]methanesulfonamide Example 60c was prepared according to the procedure used in method A of Example 4, substituting the product of Example 60b for the product of Example 3, to provide the title compound. $^1$H NMR (500 MHz, DMSO-d$_6$) δ 1.39-1.45 (m, 1H), 1.55-1.70 (m, 2H), 1.89-1.96 (m, 1H), 2.95 (s, 3H), 3.41-3.57 (m, 7H), 3.65-3.69 (m, 1H), 6.24-6.26 (m, 1H), 6.84 (d, J=8.54 Hz, 1H), 7.14 (m, 2H), 7.29-7.31 (m, 2H), 7.38 (s, 1H), 9.45 (s, 1H), 12.03 (s, 1H). MS (ESI+) m/z 418.2 (M+H)$^+$.

Example 61

6-methyl-4-[2-(morpholin-4-ylcarbonyl)phenyl]-1,6-dihydro-7H-pyrrolo[2,3-c]pyridin-7-one Example 61 was prepared according to the procedure used for the preparation of Example 1f, substituting morpholino (2-(4,4,5,5-tetramethyl-1,3,2-dioxaborolan-2-yl)phenyl) methanone for 2-phenoxyphenylboronic acid, followed by purification by preparative HPLC (C18, 10-100% acetonitrile in 0.1% TFA in water), to provide the title compound. $^1$H NMR (500 MHz, DMSO-$d_6$) δ 2.80-2.83 (m, 2H), 2.91-2.99 (m, 2H), 3.20-3.25 (m, 2H), 3.54-3.57 (m, 5H), 6.17-6.18 (m, 1H), 7.06 (s, 1H), 7.32 (t, J=2.9 Hz, 1H), 7.40 (d, J=7.32 Hz, 1H), 7.42-7.53 (m, 3H), 1H), 12.15 (s, 1H). MS (ESI+) m/z 338.1 (M+H)$^+$.

Example 62

N-[3-(6-methyl-7-oxo-6,7-dihydro-1H-pyrrolo[2,3-c]pyridin-4-yl)-4-(2,4,6-trifluorophenoxy)phenyl]ethanesulfonamide Example 62 was prepared according to the procedure used in method A of Example 4, substituting Example 33b for Example 3 and substituting ethanesulfonyl chloride for methanesulfonyl chloride respectively to provide the title compound. $^1$H NMR (300 MHz, DMSO-$d_6$) δ 1.22 (t, J=7.3 Hz, 3H), 3.09 (q, J=7.3 Hz, 2H), 3.56 (s, 3H), 6.22 (t, J=2.3 Hz, 1H), 6.79 (d, J=8.8 Hz, 1H), 7.15 (dd, J=8.8, 2.7 Hz, 1H), 7.44-7.27 (m, 5H), 9.72 (s, 1H), 12.06 (bs, 1H). MS (ESI+) m/z 478.1 (M+H)$^+$.

Example 63

N-[4-(benzyloxy)-3-(6-methyl-7-oxo-6,7-dihydro-1H-pyrrolo[2,3-c]pyridin-4-yl)phenyl]methanesulfonamide

Example 63a 4-(2-(benzyloxy)-5-nitrophenyl)-6-methyl-1H-pyrrolo[2,3-c]pyridin-7(6H)-one Example 63a was prepared according to the procedure used for the preparation of Example 29a, substituting phenylmethanol for tetrahydro-2H-pyran-4-ol, to provide the title compound.

Example 63b 4-(5-amino-2-(benzyloxy)phenyl)-6-methyl-1H-pyrrolo[2,3-c]pyridin-7(6H)-one Example 63b was prepared according to the procedure used for the preparation of Example 3, substituting the product of Example 63a for the product of Example 2b, to provide the title compound.

Example 63c

N-[4-(benzyloxy)-3-(6-methyl-7-oxo-6,7-dihydro-1H-pyrrolo[2,3-c]pyridin-4-yl)phenyl]methanesulfonamide Example 63c was prepared according to the procedure used in method A of Example 4, substituting the product of Example 63b for the product of Example 3, to provide the title compound. $^1$H NMR (300 MHz, DMSO-$d_6$) δ 2.94 (s, 3H), 3.51 (s, 3H), 5.07 (s, 2H), 6.24-6.18 (m, 1H), 7.22-7.16 (m, 2H), 7.37-7.24 (m, 8H), 9.45 (s, 1H), 12.00 (bs, 1H). MS (ESI+) m/z 424.2 (M+H)$^+$.

Example 64

N-[4-(2,4-difluorophenoxy)-3-(6-methyl-7-oxo-6,7-dihydro-1H-pyrrolo[2,3-c]pyridin-4-yl)phenyl]-2-fluoroethanesulfonamide Example 64 was prepared according to the procedure used for the preparation of Example 27c, substituting 2-fluoroethanesulfonyl chloride for methanesulfonyl chloride, and bypassing the sodium hydroxide hydrolysis step, to provide the title compound. $^1$H NMR (300 MHz, DMSO-$d_6$) δ 3.52 (s, 3H), 3.63 (t, J=6.0 Hz, 2H), 4.12 (q, J=6.0 Hz, 2H), 6.25-6.19 (m, 1H), 7.08-6.62 (m, 5H), 7.27-7.20 (m, 3H), 11.99-11.92 (m, 1H). MS (ESI+) m/z 478.2 (M+H)$^+$.

Example 65

N-[4-(2,4-difluorophenoxy)-3-(6-methyl-7-oxo-6,7-dihydro-1H-pyrrolo[2,3-c]pyridin-4-yl)phenyl]-N'-methylsulfuric diamide Example 65 was prepared according to the procedure used for the preparation of Example 27c, substituting methylsulfamoyl chloride for methanesulfonyl chloride, to provide the title compound. $^1$H NMR (300 MHz, DMSO-$d_6$) δ 2.50 (m, 3H solvent obscured), 3.52 (s, 3H), 6.28-6.22 (m, 1H), 7.08-6.86 (m, 3H), 7.15 (dd, J=8.8, 2.7 Hz, 1H), 7.39-7.21 (m, 5H), 9.65 (s, 1H), 12.02 (bs, 1H), MS (ESI+) m/z 461.1 (M+H)$^+$.

Example 66

N-[3-(6-methyl-7-oxo-6,7-dihydro-1H-pyrrolo[2,3-c]pyridin-4-yl)-4-(tetrahydrofuran-3-yloxy)phenyl]ethanesulfonamide Example 66 was prepared according to the procedure used in method A of Example 4, substituting the product of Example 31b for the product of Example 3, and ethanesulfonyl chloride for methanesulfonyl chloride, respectively, to provide the title compound. $^1$H NMR (300 MHz, DMSO-$d_6$) δ 1.22 (t, J=7.3 Hz, 3H), 1.93-1.80 (m, 1H), 2.20-2.04 (m, 1H), 3.02 (q, J=7.3 Hz, 2H), 3.55 (s, 3H), 3.65 (m, 3H), 3.82 (dd, J=10.0, 4.5 Hz, 1H), 5.00-4.91 (m, 1H), 6.16 (t, J=2.3 Hz, 1H), 7.06 (d, J=8.8 Hz, 1H), 7.16 (dd, J=8.7, 2.7 Hz, 1H), 7.24 (s, 1H), 7.31-7.25 (m, 3H), 9.53 (s, 1H), 12.01 (bs, 1H), MS (ESI+) m/z 418.1 (M+H)$^+$.

Example 67 methyl 6-methyl-7-oxo-4-(2-phenoxyphenyl)-6,7-dihydro-1H-pyrrolo[2,3-c]pyridine-2-carboxylate

Example 67a ethyl 4-bromo-6-methyl-7-oxo-1-tosyl-6,7-dihydro-1H-pyrrolo[2,3-c]pyridine-2-carboxylate Diisopropylamine (0.111 g, 1.102 mmol) in tetrahydrofuran (3 mL) was treated with BuLi (2.5 M, 0.44 mL, 1.102 mmol) at −78° C. The solution was stirred for 20 minutes at −78° C., and warmed up to room temperature for 5 minutes, and cooled down to −78° C. again. To this solution was added N¹,N¹,N²,N²-tetramethylethane-1,2-diamine (0.128 g, 1.102 mmol). Then Example 1e (0.30 g, 0.787 mmol) in tetrahydrofuran (3 mL) was added to the reaction mixture via cannula under nitrogen. The reaction mixture was stirred at −78° C. for 1 hour, warmed to 0° C. briefly, and cooled down to −78° C. To this suspension was added ethyl carbonochloridate (0.205 g, 1.889 mmol) via a syringe. The reaction mixture was allowed to warm to room temperature gradually overnight. The mixture was then partitioned between water and ethyl acetate. The aqueous layer was extracted with additional ethyl acetate three times. The combined organic layers were washed with brine, dried over MgSO$_4$, filtered, and concentrated. The residue was purified by flash chromatography on silica gel eluting with 30-50% ethyl acetate in hexanes to afford 0.074 g of the title compound.

Example 67b methyl 6-methyl-7-oxo-4-(2-phenoxyphenyl)-6,7-dihydro-1H-pyrrolo[2,3-c]pyridine-2-carboxylate Example 67b was prepared according to the procedure used for the preparation of Example 1f, substituting Example 67a for Example 1e, and bypassing the use of potassium carbonate, followed by purification by preparative HPLC (C18, 10-100% acetonitrile in 0.1% TFA in water), to provide the title compound. $^1$H NMR (500 MHz, DMSO-d$_6$) δ 3.50 (s, 3H), 3.80 (s, 3H), 6.80-6.82 (m, 3H), 7.00 (t, J=7.32 Hz, 1H), 7.06 (d, J=7.02 Hz, 1H), 7.23-7.32 (m, 4H), 7.40-7.42 (m, 1H), 7.52 (dd, J=7.48, 1.68 Hz, 1H), 12.85 (s, 1H). MS (ESI+) m/z 375 (M+H)$^+$.

Example 68 methyl 1,6-dimethyl-7-oxo-4-(2-phenoxyphenyl)-6,7-dihydro-1H-pyrrolo[2,3-c]pyridine-2-carboxylate The title compound was obtained as a by-product from the preparation of Example 67b. $^1$H NMR (500 MHz, DMSO-d$_6$) δ 3.48 (s, 3H), 3.81 (s, 3H), 4.38 (s, 3H), 6.81-6.84 (m, 3H), 6.98-7.07 (m, 2H), 7.25-7.31 (m, 3H), 7.34 (s, 1H), 7.41-7.47 (m, 1H), 7.48 (dd, J=7.48, 1.68 Hz, 1H). MS (ESI+) m/z 389 (M+H)$^+$.

Example 69 ethyl 4-(5-amino-2-phenoxyphenyl)-6-methyl-7-oxo-6,7-dihydro-1H-pyrrolo[2,3-c]pyridine-2-carboxylate Example 69a ethyl 1-benzyl-4-bromo-7-oxo-6,7-dihydro-1H-pyrrolo[2,3-c]pyridine-2-carboxylate Example 69a was prepared according to the procedure used for the preparation of Example 2a (Method B), substituting Example 67a for Example 1e, to provide the title compound.

Example 69b ethyl 6-methyl-4-(5-nitro-2-phenoxyphenyl)-7-oxo-6,7-dihydro-1H-pyrrolo[2,3-c]pyridine-2-carboxylate Example 69b was prepared according to the procedure used for the preparation of Example 2b, substituting Example 69a for Example 2a, to provide the title compound.

Example 69c ethyl 4-(5-amino-2-phenoxyphenyl)-6-methyl-7-oxo-6,7-dihydro-1H-pyrrolo[2,3-c]pyridine-2-carboxylate Example 69c was prepared according to the procedure used for the preparation of Example 29b, substituting Example 69b for Example 29a, and purified by preparative HPLC (C18, 10-100% acetonitrile in 0.1% TFA/water) to provide the TFA salt of the title compound. $^1$H NMR (500 MHz, DMSO-d$_6$) δ 1.30 (t, J=7.02 Hz, 3H), 3.49 (s, 3H), 4.27 (q, J=7.12 Hz, 2H), 6.77 (d, J=7.93 Hz, 2H), 6.86 (d, J=2.14 Hz, 1H), 6.93-7.03 (m, 3H), 7.11 (s, 1H), 7.20-7.24 (m, 2H), 7.31 (s, 1H), 12.86 (s, 1H). MS (ESI+) m/z 404.1 (M+H)$^+$.

Example 70

6-methyl-4-{5-[(methylsulfonyl)amino]-2-phenoxyphenyl}-7-oxo-6,7-dihydro-1H-pyrrolo[2,3-c]pyridine-2-carboxylic acid Example 70a (Z)-ethyl 3-(5-bromo-2-methoxy-3-nitropyridin-4-yl)-2-hydroxyacrylate To a solution of ethanol (15 mL) and ether (150 mL) were added 5-bromo-2-methoxy-4-methyl-3-nitropyridine (14.82 g, 60 mmol), diethyl oxalate (13.15 g, 90 mmol), and potassium ethoxide (6.06 g, 72 mmol). The reaction mixture was heated at 45° C. for 24 hours. During the reaction, the flask was shaken by hand several times. After cooling, the reaction mixture was partitioned between water and ethyl acetate. The aqueous layer was extracted with additional ethyl acetate three times. The combined organic layers were washed with brine, dried over MgSO$_4$, filtered, and concentrated. The residue was purified by flash chromatography on silica gel eluting with 10-20% ethyl acetate in hexanes to 9.5 g of the title compound (yield 46%).

Example 70b ethyl 4-bromo-7-methoxy-1H-pyrrolo[2,3-c]pyridine-2-carboxylate

A mixture Example 70a (9.5 g, 27.4 mmol) and iron (7.64 g, 137 mmol) in ethanol (60 mL) and acetic acid (60 mL) was heated at 100° C. for 1 hour. The solution turned from red to gray. The solid was filtered off, and then washed with additional ethyl acetate. The solvents were removed under reduced pressure to 20% of original volume, and it was partitioned between water and ethyl acetate. The aqueous layer was extracted with additional ethyl acetate several times. The combined organic layers were washed with brine, dried over MgSO$_4$, filtered, and concentrated. The residue was purified by flash chromatography on silica gel eluting with 20-40% ethyl acetate in hexanes to afford 6.05 g of the title compound.

Example 70c ethyl 1-benzyl-4-bromo-7-methoxy-1H-pyrrolo[2,3-c]pyridine-2-carboxylate Example 70b (0.88 g, 2.94 mmol) in dimethylformamide (15 mL) was treated with 60% sodium hydride (0.106 g, 4.41 mmol, 0.117 g of a 60% in oil dispersion). The solution was stirred at room temperature for 10 minutes. To this solution was added benzyl bromide (0.59 g, 3.45 mmol). The reaction mixture was stirred for another 2 hours. It was partitioned between water and ethyl acetate. The aqueous layer was extracted with additional ethyl acetate twice. The combined organic layers were washed with brine, dried over $MgSO_4$, filtered, and concentrated. The residue was purified by flash chromatography on silica gel eluting with 20-40% ethyl acetate in hexanes to afford 1.07 g of the title compound.

Example 70d ethyl 1-benzyl-4-bromo-7-oxo-6,7-dihydro-1H-pyrrolo[2,3-c]pyridine-2-carboxylate Example 70d was prepared according to the procedure used for the preparation of Example 1d, substituting Example 70c for Example 1c, to provide the title compound.

Example 70e ethyl 1-benzyl-4-bromo-6-methyl-7-oxo-6,7-dihydro-1H-pyrrolo[2,3-c]pyridine-2-carboxylat Example 70e was prepared according to the procedure used for the preparation of Example 1e, substituting Example 70d for Example 1d, to provide the title compound.

Example 70f ethyl 1-benzyl-4-(2-fluoro-5-nitrophenyl)-6-methyl-7-oxo-6,7-dihydro-1H-pyrrolo[2,3-c]pyridine-2-carboxylate Example 70f was prepared according to the procedure used for the preparation of Example 2a (Method B), substituting Example 70e for Example 1e, to provide the title compound.

Example 70g ethyl 1-benzyl-6-methyl-4-(5-nitro-2-phenoxyphenyl)-7-oxo-6,7-dihydro-1H-pyrrolo[2,3-c]pyridine-2-carboxylate Example 70g was prepared according to the procedure used for the preparation of Example 2b, substituting Example 70f for Example 2a, to provide the title compound.

Example 70h ethyl 4-(5-amino-2-phenoxyphenyl)-1-benzyl-6-methyl-7-oxo-6,7-dihydro-1H-pyrrolo[2,3-c]pyridine-2-carboxylate Example 70h was prepared according to the procedure used for the preparation of Example 29b, substituting Example 70g for Example 29a, to provide the title compound.

Example 70i ethyl 1-benzyl-6-methyl-4-(5-(N-(methylsulfonyl)methylsulfonamido)-2-phenoxyphenyl)-7-oxo-6,7-dihydro-1H-pyrrolo[2,3-c]pyridine-2-carboxylate Example 70i was prepared according to the procedure used in method A of Example 4, substituting Example 70h for Example 3, except the use of 1 M NaOH, to provide the title compound.

Example 70j ethyl 6-methyl-4-(5-(N-(methylsulfonyl)methylsulfonamido)-2-phenoxyphenyl)-7-oxo-6,7-dihydro-1H-pyrrolo[2,3-c]pyridine-2-carboxylate A mixture of Example 70i (0.53 g, 0.816 mmol), anisole (0.176 g, 1.631 mmol), and concentrated $H_2SO_4$ (0.5 mL) in TFA (10 mL) was heated at 90° C. for 4 hours. Excess TFA was removed under reduced pressure, and the residue was partitioned between water and ethyl acetate. The organic layer was separated, and the aqueous layer was extracted with additional ethyl acetate several times. The combined organic layers were washed with saturated aqueous sodium bicarbonate, followed by brine, dried over $MgSO_4$, filtered, and concentrated to afford 0.48 g of the title compound. The crude material was used directly for the next reaction.

Example 70k 6-methyl-4-{5-[(methylsulfonyl)amino]-2-phenoxyphenyl}-7-oxo-6,7-dihydro-1H-pyrrolo[2,3-c]pyridine-2-carboxylic acid Example 70j (0.4 g, 0.858 mmol) in dioxane (5 mL) was treated with 2.0 N NaOH (1.72 mL, 3.43 mmol). The reaction mixture was heated at 65° C. for 2 hours. The reaction mixture was cooled to room temperature and poured into water (100 mL). After addition of concentrated HCl (1 mL), the mixture was extracted with ethyl acetate three times (3×30 mL). The combined organic layers were washed with brine, dried over $MgSO_4$, filtered, and concentrated to afford 0.36 g (93%) of the title compound. A small amount of sample was purified by preparative HPLC (C18, 10-70% acetonitrile in 0.1% TFA/water) to provide the TFA salt of the title compound. $^1H$ NMR (500 MHz, DMSO-$d_6$) δ 3.03 (s, 3H), 3.49 (s, 3H), 6.81 (d, J=7.63 Hz, 2H), 6.84 (d, J=2.14 Hz, 1H), 6.96-7.00 (m, 1H), 7.08 (d, J=8.85 Hz, 1H), 7.22-7.27 (m, 3H), 7.34 (s, 1H), 7.37 (d, J=2.75 Hz, 1H), 9.77 (s, 1H), 12.62 (d, J=1.53 Hz, 1H), 13.00 (s, br, 1H). MS (ESI+) m/z 454.1 $(M+H)^+$.

Example 71 ethyl 6-methyl-4-{5-[(methylsulfonyl)amino]-2-phenoxyphenyl}-7-oxo-6,7-dihydro-1H-pyrrolo[2,3-c]pyridine-2-carboxylate Example 70k (0.2 g, 0.441 mmol) in ethanol (10 mL) was treated with concentrated $H_2SO_4$ (0.5 mL). The reaction mixture was heated under reflux overnight. The solvent was removed, and the remaining was partitioned between water and ethyl acetate. The organic layer was separated, and the aqueous layer was extracted with additional ethyl acetate several times. The combined organic layers were washed with sat. $NaHCO_3$, brine, dried over $MgSO_4$, filtered, and concentrated to afford 0.19 g of the title compound. A small amount of crude product was purified by preparative HPLC to provide clean product for biological testing. ¹H NMR (500 MHz, DMSO-d$_6$) δ 1.30 (t, J=7.17 Hz, 3H), 3.04 (s, 3H), 3.50 (s, 3H), 4.26 (q, J=7.22 Hz, 2H), 6.80 (d, J=7.63 Hz, 2H), 6.86 (d, J=2.14 Hz, 1H), 6.96-7.00 (m, 1H), 7.09 (d, J=8.85 Hz, 1H), 7.21-7.28 (m, 3H), 7.35 (s, 1H), 7.36 (d, J=2.75 Hz, 1H), 9.78 (s, 1H), 12.86 (s, 1H). (ESI+) m/z 482.1 (M+H)⁺.

Example 72

N-ethyl-6-methyl-4-{5-[(methylsulfonyl)amino]-2-phenoxyphenyl}-7-oxo-6,7-dihydro-1H-pyrrolo[2,3-c]pyridine-2-carboxamide Example 72a 6-methyl-4-(5-(methylsulfonamido)-2-phenoxyphenyl)-7-oxo-6,7-dihydro-1H-pyrrolo[2,3-c]pyridine-2-carbonyl chloride Example 72a was prepared according to the procedure used for the preparation of Example 13a, substituting Example 70k for Example 10, to provide the title compound.

Example 72b

N-ethyl-6-methyl-4-{5-[(methylsulfonyl)amino]-2-phenoxyphenyl}-7-oxo-6,7-dihydro-1H-pyrrolo[2,3-c]pyridine-2-carboxamide Example 72b was prepared according to the procedure used for the preparation of Example 13b, substituting Example 72a for Example 13a, to provide the title compound. ¹H NMR (500 MHz, DMSO-d$_6$) δ 1.12 (t, J=7.17 Hz, 3H), 3.03 (s, 3H), 3.23-3.30 (M, 2H), 3.49 (s, 3H), 6.81 (d, J=7.63 Hz, 2H), 6.86 (d, J=2.44 Hz, 1H), 6.96-7.00 (m, 1H), 7.07 (d, J=8.54 Hz, 1H), 7.22-7.28 (m, 3H), 7.30 (s, 1H), 7.34 (d, J=2.75 Hz, 1H), 8.34 (t, J=5.34 Hz, 1H), 9.79 (s, 1H), 12.22 (s, 1H). (ESI+) m/z 481.1 (M+H)⁺.

Example 73

6-methyl-4-{5-[(methylsulfonyl)amino]-2-phenoxyphenyl}-7-oxo-6,7-dihydro-1H-pyrrolo[2,3-c]pyridine-2-carboxamide Example 73 was prepared according to the procedure used for the preparation of Example 13b, substituting Example 72a for Example 13a, and aqueous ammonium hydroxide for ethyl amine, respectively, to provide the title compound. ¹H NMR (500 MHz, DMSO-d$_6$) δ 3.03 (s, 3H), 3.50 (s, 3H), 6.82 (d, J=7.63 Hz, 2H), 6.88 (d, J=2.44 Hz, 1H), 6.97-7.01 (m, 1H), 7.06 (d, J=8.54 Hz, 1H), 7.22-7.28 (m, 3H), 7.31 (s, 1H), 7.35 (d, J=2.75 Hz, 1H), 7.46 (s, 1H), 7.81 (s, 1H), 9.78 (s, 1H), 12.22 (s, 1H). MS (ESI+) m/z 453.1 (M+H)⁺.

Example 74 ethyl 4-(5-amino-2-phenoxyphenyl)-6-methyl-7-oxo-6,7-dihydro-1H-pyrrolo[2,3-d]pyridazine-2-carboxylate Example 74a 4-amino-6-chloro-2-methylpyridazin-3 (2H)-one A mixture of 4,6-dichloro-2-methylpyridazin-3(2H)-one (5.0 g, 27.9 mmol) and ammonium hydroxide (55 mL, 1412 mmol) was heated at 150° C. for 2 hours and then cooled to room temperature. The solvent was removed, and the residue was dissolved in ethyl acetate and washed with water. The aqueous layer was extracted with additional ethyl acetate three times. The combined organic layers were washed with brine, dried and concentrated. The residue was purified by flash chromatography (silica gel, eluted with 40% ethyl acetate in hexanes to afford 3.85 g (87%) of the title compound.

Example 74b 4-amino-6-chloro-5-iodo-2-methylpyridazin-3 (2H)-one

A mixture of Example 74a (2.12 g, 13.3 mmol) and N-iodosuccinimide (5.38 g, 23.9 mmol) in acetonitrile (30 mL) was heated under reflux for 6 hours. The reaction mixture was cooled to room temperature and partitioned between ethyl acetate and water. The aqueous layer was extracted with additional ethyl acetate twice. The combined organic layers were washed with brine, dried over anhydrous magnesium sulfate, filtered, and concentrated. The residue was purified by flash chromatography on silica gel eluting with 20-40% ethyl acetate in hexanes to afford 3.27 g (86%) of the title compound.

Example 74c 4-chloro-6-methyl-7-oxo-6,7-dihydro-1H-pyrrolo[3,2-d]pyridazine-2-carboxylic acid A mixture of Example 74b (0.59 g, 2.1 mmol), pyruvic acid (0.546 g, 6.2 mmol), 1,4-diazabicyclo[2.2.2]octane (0.695 g, 6.2 mmol), and palladium(II)acetate (0.046 g, 10 mol %) in dimethylformamide (8 mL) was degassed and back-filled with nitrogen three times. The reaction mixture was then heated at 105° C. overnight. The reaction mixture was cooled to room temperature and partitioned between ethyl acetate and water. The aqueous layer was extracted with additional ethyl acetate twice. The combined organic layers were washed with brine, dried over anhydrous magnesium sulfate, filtered, and concentrated. The residue was triturated in 30% ethyl acetate in hexanes to afford 0.25 g (53%) of the title compound.

Example 74d ethyl 4-chloro-6-methyl-7-oxo-6,7-dihydro-1H-pyrrolo[3,2-d]pyridazine-2-carboxylate Example 74c (0.45 g, 2.0 mmol) in ethanol (15 mL) was treated concentrated sulfuric acid (1 mL). The reaction mixture was heated under reflux for 16 hours. The reaction mixture was cooled to room temperature and partitioned between ethyl acetate and water. The aqueous layer was extracted with additional ethyl acetate twice. The combined organic layers were washed with brine, dried over anhydrous magnesium sulfate, filtered, and concentrated to afford 0.45 g (89%) of the title compound.

Example 74e ethyl 4-chloro-6-methyl-7-oxo-1-((2-(trimethylsilyl)ethoxy)methyl)-6,7-dihydro-1H-pyrrolo[3,2-d]pyridazine-2-carboxylate A solution of Example 74d (0.41 g, 1.6 mmol) in dimethylformamide (15 mL) was treated with 60% sodium hydride (0.096 g, 2.4 mmol) at room temperature. The reaction mixture was stirred for 30 min, and then was treated with (2-(chloromethoxy)ethyl)trimethylsilane (0.40 g, 2.4 mmol). The reaction mixture was then stirred for 2 hours. It was partitioned between ethyl acetate and water. The aqueous layer was extracted with additional ethyl acetate twice. The combined organic layers were washed with brine, dried over anhydrous magnesium sulfate, filtered, and concentrated. The residue was purified by flash chromatography on silica gel, eluting with 20% ethyl acetate to afford 0.50 g (81%) of the title compound.

Example 74f ethyl 4-(2-fluoro-5-nitrophenyl)-6-methyl-7-oxo-1-((2-(trimethylsilyl)ethoxy)methyl)-6,7-dihydro-1H-pyrrolo[3,2-d]pyridazine-2-carboxylate Example 74f was prepared according to the procedure used for the preparation of Example 2a (Method B), substituting Example 74e for Example 1e, to provide the title compound

Example 74g ethyl 6-methyl-4-(5-nitro-2-phenoxyphenyl)-7-oxo-6,7-dihydro-1H-pyrrolo[3,2-d]pyridazine-2-carboxylate A mixture of Example 74f (0.26 g, 0.53 mmol), phenol (0.060 g, 0.64 mmol) and cesium carbonate (0.21 g, 0.63 mmol) in dimethylsulfoxide (5 mL) was heated at 110° C. for 6 hours. After cooling to room temperature, the reaction mixture was partitioned between water and ethyl acetate. The aqueous layer was extracted with additional ethyl acetate three times. The combined organic layers were washed with brine, dried over anhydrous magnesium sulfate, filtered, and concentrated. The residue was then treated with 15 mL of ethanol and 1 mL of concentrated $H_2SO_4$. The mixture was heated under reflux overnight. The reaction mixture was cooled to room temperature and partitioned between ethyl acetate and water. The organic layer was washed with brine, dried over anhydrous magnesium sulfate, filtered, and concentrated. The residue was purified by flash chromatography on silica gel eluting with 40-80% ethyl acetate to afford 0.14 g (61%) of the title compound.

Example 74h ethyl 4-(5-amino-2-phenoxyphenyl)-6-methyl-7-oxo-6,7-dihydro-1H-pyrrolo[2,3-d]pyridazine-2-carboxylate Example 74h was prepared according to the procedure used for the preparation of Example 29b, substituting Example 74g for Example 29a, and ethanol for ethyl acetate, respectively, to provide the title compound. $^1$H NMR (500 MHz, DMSO-$d_6$) δ 1.29 (t, J=7.02 Hz, 3H), 3.61 (s, 3H), 4.28 (q, J=7.22 Hz, 2H), 5.22 (s, 2H), 6.65 (d, J=7.33 Hz, 2H), 6.74 (dd, J=8.85, 2.75 Hz, 1H), 6.79 (t, J=2.75 Hz, 1H), 6.87 (d, J=7.32 Hz, 1H), 6.91-6.93 (m, 2H), 7.13-7.17 (m, 2H), 13.37 (br s, 1H). MS (ESI+) m/z 405.1 (M+H)$^+$.

Example 75 ethyl 4-[5-(ethylamino)-2-phenoxyphenyl]-6-methyl-7-oxo-6,7-dihydro-1H-pyrrolo[2,3-d]pyridazine-2-carboxylate Example 75 was obtained as a by-product from the preparation of Example 74h $^1$H NMR (500 MHz, DMSO-$d_6$) δ 1.19 (t, J=7.17 Hz, 3H), 1.30 (t, J=7.02 Hz, 3H), 3.03-3.08 (m, 2H), 3.62 (s, 3H), 4.29 (q, J=7.02 Hz, 2H), 5.71 (t, J=5.19 Hz, 1H), 6.65 (d, J=7.63 Hz, 2H), 6.72-6.74 (m, 2H), 6.87 (t, J=7.32 Hz, 1H), 6.91 (s, 1H), 6.99 (d, J=9.16 Hz, 1H), 7.13-7.17 (m, 2H), 13.47 (br s, 1H). MS (ESI+) m/z 433.1 (M+H)$^+$.

Example 76 ethyl 4-{5-[ethyl(methylsulfonyl)amino]-2-phenoxyphenyl}-6-methyl-7-oxo-6,7-dihydro-1H-pyrrolo[2,3-d]pyridazine-2-carboxylate Example 76 was prepared according to the procedure used in method A of Example 4, substituting Example 75 for Example 3, except the use of NaOH, to provide the title compound. $^1$H NMR (500 MHz, DMSO-$d_6$) δ 1.07 (t, J=7.02 Hz, 3H), 1.30 (t, J=7.17 Hz, 3H), 3.02 (s, 3H), 3.67-3.72 (m, 5H), 4.23 (q, J=7.22 Hz, 2H), 6.93 (d, J=7.93 Hz, 2H), 6.99 (d, J=2.14 Hz, 1H), 7.07-7.12 (m, 2H), 7.30-7.34 (m, 2H), 7.52-7.55 (m, 1H), 7.85 (d, J=2.75 Hz, 1H). MS (ESI+) m/z 511.1 (M+H)$^+$.

Example 77

6-methyl-4-{5-[(methylsulfonyl)amino]-2-phenoxyphenyl}-7-oxo-6,7-dihydro-1H-pyrrolo[2,3-d]pyridazine-2-carboxylic acid Example 77 was prepared according to the procedure used in method A of Example 4, substituting Example 74h for Example 3, to provide the title compound. $^1$H NMR (500 MHz, DMSO-$d_6$) δ 3.04 (s, 3H), 3.66 (s, 3H), 6.39-6.40 (m, 1H), 6.81-6.83 (m, 2H), 6.93 (d, J=1.53 Hz, 1H), 6.98-7.01 (m, 1H), 7.14 (d, J=8.85 Hz, 1H), 7.23-7.27 (m, 2H), 7.37-7.42 (m, 1H), 7.43 (d, J=2.75 Hz, 1H), 9.82 (s, 1H), 13.35 (s, 1H). MS (ESI+) m/z 455.1 (M+H)$^+$.

Example 78

6-methyl-4-{5-[(methylsulfonyl)amino]-2-phenoxyphenyl}-7-oxo-6,7-dihydro-1H-pyrrolo[2,3-d]pyridazine-2-carboxamide

Example 78a 6-methyl-4-(5-(methylsulfonamido)-2-phenoxyphenyl)-7-oxo-6,7-dihydro-1H-pyrrolo[2,3-d]pyridazine-2-carbonyl chloride Example 78a was prepared according to the procedure used for the preparation of Example 13a, substituting Example 77 for Example 10, to provide the title compound.

Example 78b 6-methyl-4-{5-[(methylsulfonyl)amino]-2-phenoxyphenyl}-7-oxo-6,7-dihydro-1H-pyrrolo[2,3-d]pyridazine-2-carboxamide Example 78b was prepared according to the procedure used for the preparation of Example 13b, substituting Example 78a for Example 13a, and aqueous ammonium hydroxide for ethylamine, respectively, to provide the title compound. $^1$H NMR (500 MHz, DMSO-$d_6$) δ 3.03 (s, 3H), 3.67 (s, 3H), 6.85 (d, J=7.63 Hz, 2H), 6.99-7.04 (m, 2H), 7.10

(d, J=8.54 Hz, 1H), 7.23-7.28 (m, 2H), 7.37-7.40 (m, 2H), 7.57 (s, 1H), 7.91 (s, 1H), 9.82 (s, 1H), 12.95 (s, 1H). MS (ESI+) m/z 454.1 (M+H)$^+$.

Example 79

6-methyl-N-[2-(4-methylpiperazin-1-yl)ethyl]-4-{5-[(methylsulfonyl)amino]-2-phenoxyphenyl}-7-oxo-6,7-dihydro-1H-pyrrolo[2,3-d]pyridazine-2-carboxamide Example 79 was prepared according to the procedure used for the preparation of Example 13b, substituting Example 78a for Example 13a, and 2-(4-methylpiperazin-1-yl)ethanamine for ethylamine, respectively, to provide the TFA salt of the title compound. $^1$H NMR (500 MHz, DMSO-d$_6$) δ 2.67-2.80 (m, 6H), 3.04 (s, 3H), 3.49 (br, 8H), 3.67 (s, 3H), 6.82 (d, J=7.63 Hz, 2H), 6.99-7.03 (m, 2H), 7.13 (d, J=8.85 Hz, 1H), 7.24-7.28 (m, 2H), 7.37-7.40 (m, 2H), 8.50-8.52 (m, 1H), 9.85 (s, 1H), 13.03 (s, 1H). MS (ESI+) m/z 580.2 (M+H)$^+$.

Example 80

N-[3-(6-methyl-7-oxo-6,7-dihydro-1H-pyrrolo[2,3-d]pyridazin-4-yl)-4-phenoxyphenyl]methanesulfonamide Example 80a (E)-4-amino-6-chloro-5-(2-ethoxyvinyl)-2-methylpyridazin-3(2H)-one Example 80a was prepared according to the procedure used for the preparation of Example 2a (Method B), substituting Example 74b for Example 1e, and (E)-2-(2-ethoxyvinyl)-4,4,5,5-tetramethyl-1,3,2-dioxaborolane for 2-fluoro-5-nitrophenylboronic acid, respectively, to provide the title compound.

Example 80b 4-chloro-6-methyl-1H-pyrrolo[3,2-d]pyridazin-7(6H)-one

Example 80a (0.1 g, 0.435 mmol) in acetic acid (5 mL) was heated at 90° C. overnight. The solvent was evaporated under reduced pressure to afford 0.071 g of the title compound.

Example 80c 4-chloro-6-methyl-1-((2-(trimethylsilyl)ethoxy)methyl)-1H-pyrrolo[3,2-d]pyridazin-7(6H)-one Example 80c was prepared according to the procedure used for the preparation of Example 74e, substituting Example 80b for Example 74c, to provide the title compound.

Example 80d 4-(2-fluoro-5-nitrophenyl)-6-methyl-1-((2-(trimethylsilyl)ethoxy)methyl)-1H-pyrrolo[3,2-d]pyridazin-7(6H)-one Example 80d was prepared according to the procedure used for the preparation of Example 2a (Method B), substituting Example 80c for Example 1e, to provide the title compound.

Example 80e 6-methyl-4-(5-nitro-2-phenoxyphenyl)-1H-pyrrolo[3,2-d]pyridazin-7(6H)-one Example 80e was prepared according to the procedure used for the preparation of Example 2b, substituting Example 80d for Example 2a, to provide the title compound.

Example 80f 4-(5-amino-2-phenoxyphenyl)-6-methyl-1H-pyrrolo[3,2-d]pyridazin-7(6H)-one Example 80f was prepared according to the procedure used for the preparation of Example 29b, substituting Example 80e for Example 29a, to provide the title compound.

Example 80g

N-[3-(6-methyl-7-oxo-6,7-dihydro-1H-pyrrolo[2,3-d]pyridazin-4-yl)-4-phenoxyphenyl]methanesulfonamide Example 80g was prepared according to the procedure used in method A of Example 4, substituting Example 80f for Example 3, to provide the title compound. $^1$H NMR (500 MHz, DMSO-d$_6$) δ 3.03 (s, 3H), 3.67 (s, 3H), 6.39-6.40 (m, 1H), 6.87 (d, J=7.63 Hz, 2H), 7.01 (t, J=7.48 Hz, 1H), 7.08 (d, J=8.54 Hz, 1H), 7.24-7.28 (m, 2H), 7.35 (dd, J=8.85, 2.75 Hz, 1H), 7.42-7.43 (m, 2H), 9.80 (s, 1H), 12.67 (s, 1H). MS (ESI+) m/z 411.1 (M+H)$^+$.

Example 81

N-ethyl-6-methyl-4-{5-[(methylsulfonyl)amino]-2-phenoxyphenyl}-7-oxo-6,7-dihydro-1H-pyrrolo[2,3-d]pyridazine-2-carboxamide Example 81 was prepared according to the procedure used for the preparation of Example 13b, substituting Example 78a for Example 13a, to provide the title compound. $^1$H NMR (500 MHz, DMSO-d$_6$) δ 1.12 (t, J=7.17 Hz, 3H), 3.03 (s, 3H), 3.27-3.30 m, 2H), 3.66 (s, 3H), 6.82-6.84 (m, 2H), 6.98-7.02 (m, 2H), 6.97-7.01 (m, 1H), 7.12 (d, J=9.16 Hz, 1H), 7.23-7.28 (m, 2H), 7.37-7.40 (m, 2H), 8.44 (t, J=5.34 Hz, 1H), 9.83 (s, 1H), 12.97 (s, 1H). MS (ESI+) m/z 482.1 (M+H)$^+$.

Example 82

6-methyl-4-(2-phenoxyphenyl)-1,6-dihydro-7H-pyrrolo[2,3-d]pyridazin-7-one

Example 82 was prepared according to the procedure used for the preparation of Example 1f, substituting Example 80b for Example 1e, except for the use of potassium carbonate, followed by purification by preparative HPLC (C18, 10-100% acetonitrile in 0.1% TFA in water), to provide the title compound. $^1$H NMR (500 MHz, DMSO-d$_6$) δ 3.70 (s, 3H), 6.36-6.37 (m, 1H), 6.91-6.93 (m, 2H), 7.02-7.07 (m, 2H), 7.27-7.31 (m, 3H), 7.41 (t, J=2.75 Hz, 1H), 7.47-7.52 (m, 1H), 7.56 (dd, J=7.63, 1.83 Hz, 1H), 12.65 (s, 1H). MS (ESI+) m/z 318.1 (M+H)$^+$.

Example 83

N-ethyl-N,6-dimethyl-4-{5-[(methylsulfonyl)amino]-2-phenoxyphenyl}-7-oxo-6,7-dihydro-1H-pyrrolo[2,3-d]pyridazine-2-carboxamide Example 83 was prepared according to the procedure used for the preparation of Example 13b, substituting Example 78a for Example 13a, and N-methylethanamine for ethylamine, respectively, to provide the title compound. $^1$H NMR (500 MHz, DMSO-$d_6$) δ 1.07 (br, 3H), 2.94 (s, 3H), 3.03 (s, 3H), 3.45 (br, 2H), 3.68 (s, 3H), 6.88 (d, J=7.93 Hz, 2H), 7.01 (t, J=7.32 Hz, 1H), 7.12 (d, J=8.85 Hz, 1H), 7.24-7.28 (m, 2H), 7.36 (dd, J=8.85, 2.75 Hz, 1H), 7.43 (d, J=2.75 Hz, 1H), 9.81 (s, 1H), 13.01 (s, 1H). MS (ESI+) m/z 496.1 (M+H)$^+$.

Example 84

4-{4-[(ethylsulfonyl)amino]-2-(6-methyl-7-oxo-6,7-dihydro-1H-pyrrolo[2,3-c]pyridin-4-yl)phenoxy}benzamide To a mixture of Example 33b (50 mg, 0.14 mmol) and triethylamine (0.043 g, 0.42 mmol) in dichloromethane (4 mL) was added dropwise ethanesulfonyl chloride (0.072 g, 0.56 mmol), and the reaction mixture stirred at ambient temperature for 1 hour. The reaction mixture was concentrated under reduced pressure, dioxane (4 mL) and sodium hydroxide (10% w/v, 3 mL, 0.14 mmol) were added, and the reaction mixture was heated at 70° C. for 1 hour. The mixture was cooled to ambient temperature and then neutralized with saturated aqueous ammonium chloride (50 mL) to a pH of 7. The organic layer was separated and the aqueous phase was extracted with ethyl acetate (3×25 mL). The combined organic layers were washed with saturated aqueous sodium chloride, dried (anhydrous magnesium sulfate), filtered, and concentrated. The residue was purified by preparative HPLC (C18, 10-100% acetonitrile/water, 0.1% TFA) to afford the title compound (22 mg, 35%). $^1$H NMR (300 MHz, DMSO-$d_6$) ppm 12.01 (s, 1H) 9.86 (s, 1H) 7.77 (s, 1H) 7.74 (d, J=8.82 Hz, 2H) 7.42 (d, J=2.37 Hz, 1H) 7.22-7.30 (m, 3H) 7.18 (s, 1H) 7.11-7.16 (m, 1H) 6.83 (d, J=8.82 Hz, 2H) 6.23-6.28 (m, 1H) 3.47 (s, 3H) 3.15 (q, J=7.35 Hz, 2H) 1.21-1.29 (m, 3H). MS (ESI+) m/z 467.2 (M+H)$^+$.

Example 85

6-methyl-4-[5-(methylsulfonyl)-2-phenoxyphenyl]-1,6-dihydro-7H-pyrrolo[2,3-c]pyridin-7-one

Example 85a 4-(methylsulfonyl)-2-nitro-1-phenoxybenzene

Example 85a was prepared according to the procedure used for the preparation of Example 2b, substituting 1-fluoro-4-(methylsulfonyl)-2-nitrobenzene for Example 2a, to provide the title compound.

Example 85b 5-(methylsulfonyl)-2-phenoxyaniline

Example 85b was prepared according to the procedure used for the preparation of Example 29b, substituting 85a for Example 29a, to provide the title compound.

Example 85c 2-iodo-4-(methylsulfonyl)-1-phenoxybenzene

Example 85b (0.27 g, 1.025 mmol) in dioxane (1 mL) was treated with concentrated HCl (6 mL) at 0° C. The reaction mixture was stirred at 0° C. for 10 minutes. To this solution was added sodium nitrite (0.085 g, 1.23 mmol) in water (1 mL). The reaction was stirred at 0° C. for another 1 hour. To this solution was added potassium iodide (0.34 g, 1.051 mmol) in water (2 mL). The reaction was stirred for 1 hour at room temperature. The reaction mixture was partitioned between water and ethyl acetate. The organic layer was extracted with additional ethyl acetate twice. The combined organic layer were washed with brine, dried over MgSO$_4$, filtered and concentrated. The residue was purified by flash chromatography on silica gel eluting with 10-30% ethyl acetate in hexanes to afford 0.28 g of the title product.

Example 85d 6-methyl-4-[5-(methylsulfonyl)-2-phenoxyphenyl]-1,6-dihydro-7H-pyrrolo[2,3-c]pyridin-7-one Example 85d was prepared according to the procedure used for the preparation of Example 1f, substituting 85c for Example 1e, and Example 6a for 2-phenoxyphenylboronic acid, followed by purification by preparative HPLC (C18, 10-100% acetonitril/0.1% TFA in water), to provide the title compound. $^1$H NMR (500 MHz, DMSO-$d_6$) δ 3.26 (s, 3H), 3.57 (s, 3H), 6.29-6.30 (m, 1H), 7.03 (d, J=8.54 Hz, 1H), 7.11 (d, J=7.63 Hz, 2H), 7.20 (t, J=7.32 Hz, 1H), 7.30 (t, J=2.75 Hz, 1H), 7.40-7.44 (m, 3H), 7.88 (dd, J=8.54, 2.44 Hz, 1H), 8.00 (d, J=2.44 Hz, 1H), 12.07 (s, 1H). MS (ESI+) m/z 395.2 (M+H)$^+$.

Example 86

5-(6-methyl-7-oxo-6,7-dihydro-1H-pyrrolo[2,3-c]pyridin-4-yl)-6-(tetrahydrofuran-3-yloxy)pyridine-3-sulfonamide

Example 86a 5-bromo-6-chloropyridine-3-sulfonamide

5-Bromo-6-chloropyridine-3-sulfonyl chloride (8.2 g) in methanol (20 mL) was cooled to 0° C. To this solution was added 7N NH$_3$ in methanol (80 mL). The reaction mixture was stirred over night at room temperature. The solvent was removed at low temperature, and the residue was partitioned between ethyl acetate and water. The aqueous layer was extracted with ethyl acetate three times. The combined organic layers were washed with brine, dried (MgSO$_4$), filtered, and concentrated. The solid was purified by flash column chromatography on silica gel to afford 4.2 g of the clean product.

Example 86b 5-bromo-6-(tetrahydrofuran-3-yloxy)pyridine-3-sulfonamide

Example 86b was prepared according to the procedure used for the preparation of Example 29a, substituting 86a for

Example 2a, and tetrahydrofuran-3-ol for tetrahydro-2H-pyran-4-ol, to provide the title compound.

Example 86c 5-(6-methyl-7-oxo-6,7-dihydro-1H-pyrrolo[2,3-c] pyridin-4-yl)-6-(tetrahydrofuran-3-yloxy)pyridine-3-sulfonamide Example 86c was prepared according to the procedure used for the preparation of Example 1f, substituting 86b for Example 1e, and Example 6a for 2-phenoxyphenylboronic acid, followed by purification by preparative HPLC (C18, 10-100% acetonitrile in 0.1% TFA in water), to provide the title compound. $^1$H NMR (500 MHz, DMSO-$d_6$) δ 1.91-1.97 (m, 1H), 2.18-2.25 (m, 1H), 3.59 (s, 3H), 3.66-3.76 (m, 3H), 3.92-3.95 (m, 1H), 5.63-5.66 (m, 1H), 6.19-6.21 (m, 1H), 7.34 (t, J=2.75 Hz, 1H), 7.41 (s, 1H), 7.47 (s, 2H), 8.14 (d, J=2.44 Hz, 1H), 8.54 (d, J=2.44 Hz, 1H), 12.11 (s, 1H). MS (ESI+) m/z 391.1 (M+H)$^+$.

Example 87

N-methyl-5-(6-methyl-7-oxo-6,7-dihydro-1H-pyrrolo[2,3-c]pyridin-4-yl)-6-(tetrahydrofuran-3-yloxy) pyridine-3-sulfonamide Example 87 was obtained as a by-product from the preparation of Example 86c. $^1$H NMR (500 MHz, DMSO-$d_6$) δ 1.93-1.98 (m, 1H), 2.17-2.24 (m, 1H), 2.48 (d, J=5.19 Hz, 3H), 3.57 (s, 3H), 3.67-3.78 (m, 3H), 3.91-3.94 (m, 1H), 5.65-5.67 (m, 1H), 6.19 (t, J=2.29 Hz, 1H), 7.33 (t, J=2.75 Hz, 1H), 7.43 (s, 1H), 7.55 (q, J=4.88 Hz, 1H), 8.06 (d, J=2.44 Hz, 1H), 8.51 (d, J=2.44 Hz, 1H), 12.13 (s, 1H). MS (ESI+) m/z 405.1 (M+H)$^+$.

Example 88

6-methyl-4-(2-phenoxyphenyl)-2-phenyl-1,6-dihydro-7H-pyrrolo[2,3-c]pyridin-7-one 4-bromo-2-iodo-6-methyl-1-tosyl-1H-pyrrolo[2,3-c] pyridin-7(6H)-one

Example 88a

To a cold (−78° C., dry ice/acetone bath) solution of Example 1e (0.2 g, 0.525 mmol) in tetrahydrofuran (6 mL) was added a freshly prepared solution of lithium di-isopropyl amide (1.2 equivalents). The reaction mixture was stirred at −78° C. for 45 minutes. A solution of iodine (0.054 ml, 1.049 mmol) in tetrahydrofuran (0.5 mL) was added at −78° C. The cooling bath was removed, and the reaction mixture was allowed to warm to room temperature and stirred for 1 hour. The reaction was quenched by the addition of saturated aqueous sodium thiosulfate (20 mL). The reaction mixture was partitioned between water and ethyl acetate. The layers were separated, and the aqueous layer was extracted with additional ethyl acetate. The combined organics were washed with brine, dried with anhydrous MgSO$_4$, filtered and concentrated to dryness. The residue was purified by flash chromatography (silica gel, 1-100% ethyl acetate/hexane). The recovered material was further purified by reverse phase HPLC (C18, 10-100% acetonitrile in 0.1% TFA/water) to afford the title compound (55 mg, 21%).

Example 88b 4-bromo-6-methyl-2-phenyl-1-tosyl-1H-pyrrolo[2,3-c]pyridin-7(6H)-one A mixture of Example 88a (0.1 g, 0.197 mmol), phenylboronic acid (0.024 g, 0.197 mmol), Pd(PPh$_3$)$_4$ (0.011 g, 0.0096 mmol), and sodium hydrogencarbonate (0.041 g, 0.493 mmol) in dimethylformamide (2 mL) and water (0.6 mL) was heated at 85° C. for 4 hours. After cooling, the reaction mixture was partitioned between water and ethyl acetate. The aqueous layer was extracted with additional ethyl acetate twice. The combined organic layers were washed with brine, dried over MgSO$_4$, filtered, and concentrated. The residue was purified by flash chromatography on silica gel eluting with 30% ethyl acetate to afford 0.084 g of the title compound.

Example 88c 6-methyl-4-(2-phenoxyphenyl)-2-phenyl-1,6-dihydro-7H-pyrrolo[2,3-c]pyridin-7-one Example 88c was prepared according to the procedure used for the preparation of Example 1f, substituting 88b for Example 1e, followed by purification by preparative HPLC (C18, 10-100% acetonitrile in 0.1% TFA in water), to provide the title compound. $^1$H NMR (500 MHz, DMSO-$d_6$) δ 3.53 (s, 3H), 6.67 (d, J=1.22 Hz, 1H), 6.93 (d, J=7.63 Hz, 2H), 7.01-7.04 (m, 2H), 7.26-7.31 (m, 5H), 7.36-7.43 (m, 3H), 7.56 (dd, J=7.48, 1.68 Hz, 1H), 7.89 (d, J=7.32 Hz, 1H), 12.31 (s, 1H). MS (ESI+) m/z 393.3 (M+H)$^+$.

Example 89

N-{3-[2-(hydroxymethyl)-6-methyl-7-oxo-6,7-dihydro-1H-pyrrolo[2,3-c]pyridin-4-yl]-4-phenoxyphenyl}methanesulfonamide Example 89 was prepared according to the procedure used for the preparation of Example 20b, substituting Example 71 for Example 20a, to provide the title compound. $^1$H NMR (500 MHz, DMSO-$d_6$) δ 3.02 (s, 3H), 3.47 (s, 3H), 4.50 (s, 2H), 6.19 (d, J=1.83 Hz, 1H), 6.82 (d, J=7.63 Hz, 2H), 6.99 (t, J=7.32 Hz, 1H), 7.05 (d, J=8.85 Hz, 1H), 7.21-7.27 (m, 4H), 7.38 (d, J=2.75 Hz, 1H), 9.75 (s, 1H), 11.60 (s, 1H). MS (ESI+) m/z 440.1 (M+H)$^+$.

Example 90

N-[4-(4-cyanophenoxy)-3-(6-methyl-7-oxo-6,7-dihydro-1H-pyrrolo[2,3-c]pyridin-4-yl)phenyl]ethanesulfonamide

Example 90a 4-(2-bromo-4-nitrophenoxy)benzonitrile

Example 90a was prepared according to the procedure used for the preparation of Example 7a, substituting 4-hydroxybenzonitrile for phenol, to provide the title compound.

Example 90b 4-(4-amino-2-bromophenoxy)benzonitrile

To a 250 mL stainless steel pressure bottle were added Example 90a (3.21 g, 10.1 mmol), platinum (IV) oxide (0.642 g, 2.83 mmol) and tetrahydrofuran (70 mL) under a stream of nitrogen. The reaction flask was charged with hydrogen to 30 psi and stirred at ambient temperature for 45 minutes. The mixture was filtered through a nylon membrane. The filtrate was concentrated. The residue was purified by flash chromatography (silica gel, 1:1 ethyl acetate/hexanes) to provide the title compound (1.75 g, 60% yield).

Example 90c 4-(4-amino-2-(4,4,5,5-tetramethyl-1,3,2-dioxaborolan-2-yl)phenoxy)benzonitrile A mixture of example 90b (1.75 g, 6.05 mmol), 4,4,4',4', 5,5,5',5'-octamethyl-2,2'-bi(1,3,2-dioxaborolane) (3.07 g, 12.1 mmol), 1,3,5,7-tetramethyl-6-phenyl-2,4,8-trioxa-6-phosphaadamante (0.159 g, 0.545 mmol), potassium acetate (1.31 g, 13.3 mmol) and tris(dibenzylideneacetone)dipalladium(0) (0.166 g, 0.182 mmol) in dioxane (30 mL) was degassed and backfilled with nitrogen. The reaction mixture was heated at 80° C. for 20 hours and then cooled to ambient temperature. The mixture was concentrated and the residue was partitioned between ethyl acetate and water. The organic layer was separated and washed with saturated aqueous sodium chloride, dried over anhydrous magnesium sulfate, filtered, and concentrated. The residue was purified by flash chromatography (silica gel, hexane/ethyl acetate) to provide the title compound (2.0 g, 98% yield).

Example 90d 4-(4-amino-2-(6-methyl-7-oxo-6,7-dihydro-1H-pyrrolo[2,3-c]pyridin-4-yl)phenoxy)benzonitrile Example 90d was prepared according to the procedure used for the preparation of Example 1f, substituting Example 90c for 2-phenoxyphenylboronic acid, with purification by preparative HPLC (C18, 10-100% acetonitrile in 0.1% TFA in water), to provide the title compound.

Example 90e

N-[4-(4-cyanophenoxy)-3-(6-methyl-7-oxo-6,7-dihydro-1H-pyrrolo[2,3-c]pyridin-4-yl)phenyl]ethanesulfonamide Example 90e was prepared according to the procedure used for the preparation of Example 4, Method A, substituting ethanesulfonyl chloride for methanesulfonyl chloride, and Example 90d for Example 3, respectively, to provide the title compound. $^1$H NMR (300 MHz, DMSO-$d_6$) δ ppm 12.01-12.05 (m, 1H) 9.94 (s, 1H) 7.62-7.69 (m, 2H) 7.43 (d, J=2.75 Hz, 1H) 7.21-7.33 (m, 4H) 6.86-6.93 (m, 2H) 6.22 (dd, J=2.75, 2.14 Hz, 1H) 3.46 (s, 3H) 3.16 (q, J=7.32 Hz, 2H) 1.25 (t, J=7.32 Hz, 3H). MS (ESI+) m/z 449.1 (M+H)$^+$.

Example 91

2-fluoro-N-[3-(6-methyl-7-oxo-6,7-dihydro-1H-pyrrolo[2,3-c]pyridin-4-yl)-4-(tetrahydrofuran-3-yloxy)phenyl]ethanesulfonamide Example 91a 6-methyl-4-(5-nitro-2-(tetrahydrofuran-3-yloxy)phenyl)-1H-pyrrolo[2,3-c]pyridin-7(6H)-one Example 91a was prepared according to the procedure used for the preparation of Example 29a, substituting tetrahydrofuran-3-ol for tetrahydro-2H-pyran-4-ol, to provide the title compound.

Example 91b 4-(5-amino-2-(tetrahydrofuran-3-yloxy)phenyl)-6-methyl-1H-pyrrolo[2,3-c]pyridin-7(6H)-one Example 91b was prepared according to the procedure used for the preparation of Example 29b, substituting Example 91a for Example 29a, to provide the title compound.

Example 91c 2-fluoro-N-[3-(6-methyl-7-oxo-6,7-dihydro-1H-pyrrolo[2,3-c]pyridin-4-yl)-4-(tetrahydrofuran-3-yloxy)phenyl]ethanesulfonamide To a mixture of Example 91b (80.0 mg, 0.246 mmol) and triethylamine (74.6 mg, 0.738 mmol) in dichloromethane (4 mL) was added dropwise 2-fluoroethanesulfonyl chloride (144 mg, 0.984 mmol), and the reaction mixture was stirred at about ambient temperature for about 1 hour. The reaction mixture was neutralized with saturated aqueous ammonium chloride solution (50 mL) and the mixture was extracted with ethyl acetate (3×50 mL). The combined organic layers were washed with saturated aqueous sodium chloride solution, dried (anhydrous magnesium sulfate), filtered, and concentrated. The residue was purified by preparative HPLC (C18, 10-80% acetonitrile in 0.1% TFA/water) to provide the title compound (7.0 mg, 6.5% yield). $^1$H NMR (300 MHz, CDCl$_3$) ppm 11.54 (bs, 1H), 7.45 (t, J=2.8 Hz, 1H), 7.19 (s, 1H), 6.88 (d, J=8.7 Hz, 1H), 6.73 (d, J=2.7 Hz, 1H) 6.67 (dd, J=3.1, 8.8 Hz, 1H), 6.40 (dd, J=2.0, 2.7 Hz, 1H), 4.76 (m, 1H), 3.82 (s, 3H), 3.85-3.62 (m, 8H), 2.97 (bs, 1H), 2.24-1.85 (m, 2H). MS (ESI+) m/z 436.2 (M+H)$^+$.

Example 92

N-[3-(6-methyl-7-oxo-6,7-dihydro-1H-pyrrolo[2,3-c]pyridin-4-yl)-4-(tetrahydrofuran-3-yloxy)phenyl]propane-1-sulfonamide Example 92 was prepared according to the procedure used for the preparation of Example 4, (Method A), substituting Example 91b for Example 3 and substituting propane-1-sulfonyl chloride for methanesulfonyl chloride, to provide the title compound. $^1$H NMR (300 MHz, CDCl$_3$) ppm 10.63 (bs, 1H), 7.25 (m, 3H), 6.90 (d, J=8.7 Hz, 1H), 6.46 6.35 (m, 2H), 4.88 (bs, 1H), 4.01 3.66 (m, 7H), 3.12 3.03 (m, 2H), 2.2 (bs, 1H), 2.19 1.80 (m, 4H), 1.06 (t, J=7.4 Hz, 3H). MS (ESI+) m/z 432.2 (M+H)$^+$.

Example 93

N-[4-(4-cyanophenoxy)-3-(6-methyl-7-oxo-6,7-dihydro-1H-pyrrolo[2,3-c]pyridin-4-yl)phenyl]propane-1-sulfonamide Example 93 was prepared according to the procedure used for the preparation of Example 4, (Method A), substituting Example 33b for Example 3 and substituting propane-1-sulfonyl chloride for methanesulfonyl chloride, to provide the title compound. $^1$H NMR (300 MHz, DMSO-$d_6$) ppm 12.03 (bs, 1H), 9.91 (s, 1H), 7.70-7.63 (m, 2H), 7.42 (d, J=2.5 Hz, 1H), 7.32-7.17 (m, 4H), 6.93-6.86 (m, 2H), 6.22 (dd, J=2.8, 1.9 Hz, 1H), 3.46 (s, 3H), 3.18-3.09 (m, 2H), 1.92-1.65 (m, 2H), 0.98 (t, J=7.4 Hz, 3H). MS (ESI+) m/z 463.2 (M+H)$^+$.

Example 94

N-[3-(6-methyl-7-oxo-6,7-dihydro-1H-pyrrolo[2,3-c]pyridin-4-yl)-4-(2,4,6-trifluorophenoxy)phenyl]propane-1-sulfonamide

Example 94a 6-methyl-4-(5-nitro-2-(2,4,6-trifluorophenoxy)phenyl)-1H-pyrrolo[2,3-c]pyridin-7(6H)-one Example 94a was prepared according to the procedure used for the preparation of Example 2b, substituting 2,4,6-trifluorophenol for phenol, to provide the title compound.

Example 94b 4-(5-amino-2-(2,4,6-trifluorophenoxy)phenyl)-6-methyl-1H-pyrrolo[2,3-c]pyridin-7(6H)-one Example 94b was prepared according to the procedure used for the preparation of Example 3, substituting Example 94a for Example 2b, to provide the title compound.

Example 94c

N-[3-(6-methyl-7-oxo-6,7-dihydro-1H-pyrrolo[2,3-c]pyridin-4-yl)-4-(2,4,6-trifluorophenoxy)phenyl]propane-1-sulfonamide Example 94c was prepared according to the procedure used for the preparation of Example 4, (Method A), substituting Example 94b for Example 3 and substituting propane-1-sulfonyl chloride for methanesulfonyl chloride, to provide the title compound. $^1$H NMR (300 MHz, DMSO-$d_6$) ppm 12.07 (bs, 1H), 9.72 (s, 1H), 7.44 7.33 (m, 2H), 7.33 7.28 (m, 3H), 7.14 (dd, J=8.8, 2.7 Hz, 1H), 6.80 (d, J=8.8 Hz, 1H), 6.24 6.19 (m, 1H), 3.56 (s, 3H), 3.11 3.02 (m, 2H), 1.78 1.62 (m, 2H), 0.95 (t, J=7.4 Hz, 3H). MS (ESI+) m/z 492.1 (M+H)$^+$.

Example 95

3-(6-methyl-7-oxo-6,7-dihydro-1H-pyrrolo[2,3-c]pyridin-4-yl)-4-phenoxybenzenesulfonamide

Example 95a 3-nitro-4-phenoxybenzenesulfonamide

Phenol (1.282 g, 13.63 mmol) in dimethylformamide (20 mL) was treated with 60% sodium hydride (0.545 g, 13.63 mmol). The reaction mixture was stirred for 10 minutes. To this solution was added 4-fluoro-3-nitrobenzenesulfonamide (0.75 g, 3.41 mmol). The reaction mixture was stirred at ambient temperature for 2 hours. The reaction mixture was partitioned between water and ethyl acetate. The aqueous layer was neutralized with 10% HCl and extracted with additional ethyl acetate twice. The combined organic layers were washed with saturated aqueous sodium chloride, dried over anhydrous magnesium sulfate, filtered, and concentrated. The residue was purified by flash chromatography (1:1 ethyl acetate/hexanes) on silica gel to give 0.96 g of the title product.

Example 95b 3-amino-4-phenoxybenzenesulfonamide

Example 95b was prepared according to the procedure used for the preparation of Example 29b, substituting 95a for Example 29a, to provide the title compound.

Example 95c 3-iodo-4-phenoxybenzenesulfonamide

Example 95c was prepared according to the procedure used for the preparation of Example 85c, substituting 95b for Example 85b, to provide the title compound.

Example 95d 3-(6-methyl-7-oxo-6,7-dihydro-1H-pyrrolo[2,3-c]pyridin-4-yl)-4-phenoxybenzenesulfonamide A mixture of Example 6a (0.086 g, 0.20 mmol), Example 95c (0.083 g, 0.22 mmol), Pd(PPh$_3$)$_4$ (0.012 g, 5 mol %) and cesium fluoride (0.091 g, 0.6 mmol) in dimethoxyethane (2 mL) and methanol (1 mL) was heated under microwave conditions (110° C., 30 minutes). The reaction mixture was cooled to ambient temperature and portioned between ethyl acetate and water. The organic layer was separated and dried over anhydrous magnesium sulfate, filtered, and concentrated. The residue was purified by preparative HPLC (C18, 10-100% acetonitrile in 0.1% TFA/water) to provide the title compound (48 mg, 61% yield). $^1$H NMR (500 MHz, DMSO-$d_6$) δ ppm 12.08 (s, 1H), 7.95 (d, J=2.14 Hz, 1H), 7.79 (dd, J=8.54, 2.44 Hz, 1H), 7.36-7.39 (m, 5H), 7.16 (t, J=7.48 Hz, 1H), 7.03-7.05 (m, 3H), 6.28 (t, J=2.29 Hz, 1H), 3.55 (s, 3H). MS (ESI+) m/z 396.2 (M+H)$^+$.

Example 96

6-(cyclohexylamino)-5-(6-methyl-7-oxo-6,7-dihydro-1H-pyrrolo[2,3-c]pyridin-4-yl)pyridine-3-sulfonamide

Example 96a 5-bromo-6-(cyclohexylamino)pyridine-3-sulfonamide

A mixture of Example 86a (0.136 g, 0.5 mmol) and cyclohexanamine (0.198 g, 2.0 mmol) in dioxane (2 mL) was heated under microwave conditions (140° C., 1 hour). The solvent was removed, and the residue was purified by flash chromatography (3:2 ethyl acetate/hexanes) on silica gel to give 0.164 g of the title product.

Example 96b 6-(cyclohexylamino)-5-(6-methyl-7-oxo-6,7-dihydro-1H-pyrrolo[2,3-c]pyridin-4-yl)pyridine-3-sulfonamide Example 96b was prepared according to the procedure used for the preparation of Example 95d, substituting Example 96a for Example 95c, to provide the title compound. $^1$H NMR (500 MHz, DMSO-$d_6$) δ ppm 12.17 (s, 1H), 8.38 (d, J=2.44 Hz, 1H), 7.69 (d, J=2.44 Hz, 1H), 7.32 (t, J=2.75 Hz, 1H), 7.29 (s, 1H), 7.18 (br s, 2H), 6.04 (t, J=2.29 Hz, 1H), 5.97 (d, J=7.63 Hz, 1H), 3.56 (s, 3H), 1.81-1.82 (m, 2H), 1.54-1.65 (m, 3H), 1.01-1.33 (m, 5H) MS (ESI+) m/z 402.1 (M+H)$^+$.

Example 97

6-(cyclohexylamino)-N-methyl-5-(6-methyl-7-oxo-6,7-dihydro-1H-pyrrolo[2,3-c]pyridin-4-yl)pyridine-3-sulfonamide Example 97 was isolated as a minor product during the preparation of Example 96b. $^1$H NMR (500 MHz, DMSO-$d_6$) δ ppm 12.16 (s, 1H), 8.35 (d, J=2.44 Hz, 1H), 7.69 (d, J=2.44 Hz, 1H), 7.32 (t, J=2.75 Hz, 1H), 7.29 (s, 1H), 7.18 (q, J=4.88 Hz, 1H), 6.02 (t, J=2.29 Hz, 1H), 5.96 (d, J=7.24 Hz, 1H), 3.99-4.05 (m, 1H), 3.55 (s, 3H), 2.42 (d, J=4.88 Hz, 3H), 1.80-1.82 (m, 2H), 1.54-1.65 (m, 3H), 1.01-1.33 (m, 6H) MS (ESI+) m/z 416.1 (M+H)$^+$.

Example 98

N-methyl-N'-[3-(6-methyl-7-oxo-6,7-dihydro-1H-pyrrolo[2,3-c]pyridin-4-yl)-4-(2,4,6-trifluorophenoxy)phenyl]sulfuric diamide To a mixture of Example 94b (76.3 mg, 0.198 mmol) and triethylamine (60.1 mg, 0.594 mmol) in dichloromethane (4 mL) was added dropwise methylsulfamoyl chloride (103 mg, 0.792 mmol), and the reaction mixture was stirred at ambient temperature for 1 hour. The reaction mixture was concentrated under reduced pressure, and the residue was mixed with dioxane (5 mL) and 1M aqueous sodium hydroxide (3 mL, 0.2 mmol) and heated at 70° C. for 1 hour. The reaction mixture cooled to ambient temperate and then neutralized with saturated aqueous ammonium chloride (50 mL) and the aqueous extracted with ethyl acetate (3×50 mL). The combined organic layers were washed with saturated aqueous sodium chloride, dried (anhydrous magnesium sulfate), filtered, and concentrated. The residue was purified by preparative HPLC (C18, 10-80% acetonitrile in 0.1% TFA/water) to provide the title compound (11 mg, 11% yield). $^1$H NMR (300 MHz, DMSO-$d_6$) ppm 12.04 (bs, 1H), 9.58 (s, 1H), 7.43-7.32 (m, 6H), 7.32-7.16 (m, 1H), 7.10 (dd, J=8.8, 2.7 Hz, 1H), 6.75 (d, J=8.8 Hz, 1H), 6.23 (t, J=2.3 Hz, 1H), 3.57 (bs, 3H), 2.35 (d, J=4.9 Hz, 3H). MS (ESI+) m/z 479.1 (M+H)$^+$.

Example 99

N-[3-(6-methyl-7-oxo-6,7-dihydro-1H-pyrrolo[2,3-c]pyridin-4-yl)-4-(tetrahydro-2H-pyran-4-yloxy)phenyl]propane-1-sulfonamide

Example 99a 6-methyl-4-(5-nitro-2-(tetrahydro-2H-pyran-4-yloxy)phenyl)-1H-pyrrolo[2,3-c]pyridin-7(6H)-one To a solution of tetrahydro-2H-pyran-4-ol (231 mg, 2.265 mmol) in tetrahydrofuran (10 mL) was added sodium hydride (181 mg, 4.53 mmol) portion wise. After stirring for 10 minutes, Example 2a (500 mg, 1.133 mmol) was added. The mixture was heated at 50° C. for 2 hours. Upon cooling, the reaction mixture was quenched with saturated ammonium chloride solution (10 mL), diluted with 50% aqueous sodium chloride (80 mL) and extracted with ethyl acetate (75 mL, 2×50 mL). The combined organics were dried over anhydrous sodium sulfate, filtered, and concentrated. The residue was purified by flash column chromatography (silica gel, 0.5-4% methanol in dichloromethane) to provide the title compound (220 mg, 52.6% yield).

Example 99b 4-(5-amino-2-(tetrahydro-2H-pyran-4-yloxy)phenyl)-6-methyl-1H-pyrrolo[2,3-c]pyridin-7(6H)-one Example 99b was prepared according to the procedure used for the preparation of Example 29b, substituting Example 99a for Example 29a, to provide the title compound.

Example 99c

N-[3-(6-methyl-7-oxo-6,7-dihydro-1H-pyrrolo[2,3-c]pyridin-4-yl)-4-(tetrahydro-2H-pyran-4-yloxy)phenyl]propane-1-sulfonamide Example 99c was prepared according to the procedure used for the preparation of Example 4 (Method A), substituting Example 99b for Example 3 and propane-1-sulfonyl chloride for methanesulfonyl chloride with the exception that the reaction mixture was initially stirred for 18 hours at ambient temperature and then heated at 50° C. for 1 hour in the presence of sodium hydroxide, to provide the title compound. $^1$H NMR (300 MHz, DMSO-$d_6$) δ ppm 12.00 (s, 1H), 9.50 (s, 1H), 7.24-7.33 (m, 3H), 7.14 (s, 2H), 6.19 (t, J=2.37 Hz, 1H), 4.39-4.53 (m, 1H), 3.53-3.68 (m, 5H), 3.33-3.45 (m, 2H), 2.96-3.06 (m, 2H), 1.78-1.92 (m, 2H), 1.63-1.78 (m, 2H), 1.39-1.54 (m, 2H), 0.95 (t, J=7.46 Hz, 3H). MS (ESI+) m/z 446.1 (M+H)$^+$.

Example 100

2,2,2-trifluoro-N-[3-(6-methyl-7-oxo-6,7-dihydro-1H-pyrrolo[2,3-c]pyridin-4-yl)-4-(tetrahydro-2H-pyran-4-yloxy)phenyl]ethanesulfonamide To a solution of Example 99b (43.2 mg, 0.127 mmol) in dichloromethane (2 mL) was added 2,2,2-trifluoroethanesulfonyl chloride (0.015 mL, 0.140 mmol) and triethylamine (0.053 mL, 0.382 mmol). The mixture was stirred for 18 hours at ambient temperature. The reaction mixture was concentrated and the residue was purified by flash column chromatography (silica gel, 0.5-5% methanol in dichloromethane) to provide the title compound (20.8 mg, 33.7% yield). $^1$H NMR (300 MHz, DMSO-$d_6$) δ ppm 12.00 (s, 1H), 10.16 (s, 1H), 7.25-7.32 (m, 3H), 7.14-7.20 (m, 2H), 6.18-6.24 (m, 1H), 4.36-4.55 (m, 3H), 3.52-3.68 (m, 5H), 3.33-3.45 (m, 2H), 1.79-1.94 (m, 2H), 1.39-1.57 (m, 2H). MS (ESI+) m/z 486.1 (M+H)$^+$.

Example 101

N-{4-[(4,4-difluorocyclohexyl)oxy]-3-(6-methyl-7-oxo-6,7-dihydro-1H-pyrrolo[2,3-c]pyridin-4-yl)phenyl}ethanesulfonamide

Example 101a 4-(2-(4,4-difluorocyclohexyloxy)-5-nitrophenyl)-6-methyl-1H-pyrrolo[2,3-c]pyridin-7(6H)-one Example 101a was prepared according to the procedure used for the preparation of Example 99a, substituting 4,4-difluorocyclohexanol for tetrahydro-2H-pyran-4-ol, to provide the title compound.

Example 101b 4-(5-amino-2-(4,4-difluorocyclohexyloxy)phenyl)-6-methyl-1H-pyrrolo[2,3-c]pyridin-7(6H)-one Example 101b was prepared according to the procedure used for the preparation of Example 29b, substituting Example 101a for Example 29a, to provide the title compound.

Example 101c

N-{4-[(4,4-difluorocyclohexyl)oxy]-3-(6-methyl-7-oxo-6,7-dihydro-1H-pyrrolo[2,3-c]pyridin-4-yl)phenyl}ethanesulfonamide Example 101c was prepared according to the procedure used for the preparation of Example 4 (Method A), substituting Example 101b for Example 3 and ethanesulfonyl chloride for methanesulfonyl chloride with the exception that the reaction mixture was initially stirred for 18 hours at ambient temperature and then heated at 50° C. for 1 hour in the presence of sodium hydroxide to provide the title compound. $^1$H NMR (300 MHz, DMSO-$d_6$) δ ppm 12.02 (s, 1H), 9.56 (s, 1H), 7.24-7.34 (m, J=4.36 Hz, 3H), 7.17 (s, 2H), 6.15-6.23 (m, 1H), 4.48 (s, 1H), 3.49-3.61 (m, 3H), 3.05 (q, J=7.27 Hz, 2H), 1.62-1.88 (m, 8H), 1.22 (t, J=7.34 Hz, 3H). MS (ESI+) m/z 466.1 (M+H)$^+$.

Example 102

N-{4-[(4,4-difluorocyclohexyl)oxy]-3-(6-methyl-7-oxo-6,7-dihydro-1H-pyrrolo[2,3-c]pyridin-4-yl)phenyl}propane-1-sulfonamide Example 102 was prepared according to the procedure used for the preparation of Example 4 (Method A), substituting Example 101b for Example 3 and propane-1-sulfonyl chloride for methanesulfonyl chloride with the exception that the reaction mixture was initially stirred for 18 hours at ambient temperature and then heated at 50° C. for 1 hour in the presence of sodium hydroxide, to provide the title compound. $^1$H NMR (300 MHz, DMSO-$d_6$) δ ppm 12.02 (s, 1H), 9.54 (s, 1H), 7.25-7.31 (m, 3H), 7.17 (s, 2H), 6.14-6.22 (m, 1H), 4.44-4.56 (m, J=2.78 Hz, 1H), 3.51-3.57 (m, 3H), 2.96-3.08 (m, 2H), 1.61-1.89 (m, 10OH), 0.95 (t, J=7.54 Hz, 3H). MS (ESI+) m/z 480.2 (M+H)$^+$.

Example 103

N-{4-[(4,4-difluorocyclohexyl)oxy]-3-(6-methyl-7-oxo-6,7-dihydro-1H-pyrrolo[2,3-c]pyridin-4-yl)phenyl}-2,2,2-trifluoroethanesulfonamide Example 103 was prepared according to the procedure used for the preparation of Example 100, substituting Example 101b for Example 99b, to provide the title compound. $^1$H NMR (300 MHz, DMSO-$d_6$) δ ppm 12.00 (s, 1H), 10.19 (s, 1H), 7.25-7.32 (m, 3H), 7.19 (s, 2H), 6.17-6.24 (m, 1H), 4.36-4.60 (m, 3H), 3.55 (s, 3H), 1.60-1.88 (m, J=4.07 Hz, 8H). MS (ESI+) m/z 520.1 (M+H)$^+$.

Example 104

N-{4-[(4,4-difluorocyclohexyl)oxy]-3-(6-methyl-7-oxo-6,7-dihydro-1H-pyrrolo[2,3-c]pyridin-4-yl)phenyl}-N'-methylsulfuric diamide Example 104 was prepared according to the procedure used for the preparation of Example 100, substituting Example 101b for Example 99b and methylsulfamoyl chloride for 2,2,2-trifluoroethanesulfonyl chloride, to provide the title compound. $^1$H NMR (300 MHz, DMSO-$d_6$) δ ppm 11.98 (s, 1H), 9.41 (s, 1H), 7.21-7.30 (m, 3H), 7.06-7.17 (m, 3H), 6.15-6.24 (m, 1H), 4.44 (s, 1H), 3.55 (s, 3H), 2.51 (s, 3H), 1.59-1.86 (m, 8H). MS (ESI+) m/z 467.1 (M+H)+.

Example 105

N-[3-(6-methyl-7-oxo-6,7-dihydro-1H-pyrrolo[2,3-c]pyridin-4-yl)-4-(tetrahydro-2H-pyran-3-yloxy)phenyl]ethanesulfonamide

Example 105a 6-methyl-4-(5-nitro-2-(tetrahydro-2H-pyran-3-yloxy)phenyl)-1H-pyrrolo[2,3-c]pyridin-7(6H)-one Example 105a was prepared according to the procedure used for the preparation of Example 99a, substituting tetrahydro-2H-pyran-3-ol for tetrahydro-2H-pyran-4-ol, to provide the title compound.

Example 105b 4-(5-amino-2-(tetrahydro-2H-pyran-3-yloxy)phenyl)-6-methyl-1H-pyrrolo[2,3-c]pyridin-7(6H)-one Example 105b was prepared according to the procedure used for the preparation of Example 29b, substituting Example 105a for Example 29a, to provide the title compound.

Example 105c

N-[3-(6-methyl-7-oxo-6,7-dihydro-1H-pyrrolo[2,3-c]pyridin-4-yl)-4-(tetrahydro-2H-pyran-3-yloxy)phenyl]ethanesulfonamide Example 105c was prepared according to the procedure used for the preparation of Example 4 (Method A), substituting Example 105b for Example 3 and ethanesulfonyl chloride for methanesulfonyl chloride with the exception that the reaction mixture was initially stirred for 18 hours at ambient temperature and then heated at 50° C. for 1 hour in the presence of sodium hydroxide, to provide the title compound. $^1$H NMR (300 MHz, DMSO-$d_6$) δ ppm 12.02 (s, 1H), 9.53 (s, 1H), 7.37 (s, 1H), 7.27-7.33 (m, 2H), 7.09-7.17 (m, 2H), 6.23 (t, J=2.18 Hz, 1H), 4.23-4.34 (m, 1H), 3.67 (dd, J=11.70, 2.58 Hz, 1H), 3.37-3.59 (m, 6H), 3.04 (q, J=7.54 Hz, 2H), 1.85-2.00 (m, 1H), 1.51-1.73 (m, 2H), 1.33-1.49 (m, 1H), 1.21 (t, J=7.34 Hz, 3H). MS (ESI+) m/z 432.2 (M+H)$^+$.

Example 106

N-[3-(6-methyl-7-oxo-6,7-dihydro-1H-pyrrolo[2,3-c]pyridin-4-yl)-4-(tetrahydro-2H-pyran-3-yloxy)phenyl]propane-1-sulfonamide Example 106 was prepared according to the procedure used for the preparation of Example 4 (Method A), substituting Example 105b for Example 3 and propane-1-sulfonyl chloride for methanesulfonyl chloride with the exception that the reaction mixture was initially stirred for 18 hours at ambient temperature and then heated at 50° C. for 1 hour in the presence of sodium hydroxide, to provide the title compound. $^1$H NMR (300 MHz, DMSO-$d_6$) δ ppm 12.02 (s, 1H), 9.52 (s, 1H), 7.37 (s, 1H), 7.30 (s, 2H), 7.12 (s, 2H), 6.23 (t, J=2.18 Hz, 1H), 4.22-4.34 (m, 1H), 3.67 (dd, J=11.50, 2.78 Hz, 1H), 3.36-3.59 (m, 6H), 2.96-3.07 (m, 2H), 1.85-1.99 (m, 1H), 1.52-1.79 (m, 4H), 1.32-1.50 (m, 1H), 0.95 (t, J=7.54 Hz, 3H). MS (ESI+) m/z 446.2 (M+H)$^+$.

Example 107

2,2,2-trifluoro-N-[3-(6-methyl-7-oxo-6,7-dihydro-1H-pyrrolo[2,3-c]pyridin-4-yl)-4-(tetrahydro-2H-pyran-3-yloxy)phenyl]ethanesulfonamide Example 107 was prepared according to the procedure used for the preparation of Example 100, substituting Example 105b for Example 99b, to provide the title compound. $^1$H NMR (300 MHz, DMSO-$d_6$) δ ppm 12.02 (s, 1H), 10.17 (s, 1H), 7.38 (s, 1H), 7.26-7.33 (m, 2H), 7.12-7.18 (m, J=1.59 Hz, 2H), 6.26 (t, J=2.38 Hz, 1H), 4.43 (q, J=9.92 Hz, 2H), 4.27-4.36 (m, 1H), 3.68 (dd, J=11.50, 2.38 Hz, 1H), 3.39-3.59 (m, 6H), 1.86-2.01 (m, 1H), 1.53-1.73 (m, 2H), 1.36-1.49 (m, 1H). MS (ESI+) m/z 486.1 (M+H)$^+$.

Example 108

N-methyl-N'-[3-(6-methyl-7-oxo-6,7-dihydro-1H-pyrrolo[2,3-c]pyridin-4-yl)-4-(tetrahydro-2H-pyran-3-yloxy)phenyl]sulfuric diamide Example 108 was prepared according to the procedure used for the preparation of Example 100, substituting the Example 105b for Example 99b and methylsulfamoyl chloride for 2,2,2-trifluoroethanesulfonyl chloride, to provide the title compound. $^1$H NMR (300 MHz, DMSO-$d_6$) δ ppm 11.99 (s, 1H), 9.38 (s, 1H), 7.33 (s, 1H), 7.26-7.30 (m, J=2.54, 2.54 Hz, 2H), 7.05-7.13 (m, 3H), 6.22-6.27 (m, 1H), 4.16-4.27 (m, 1H), 3.65 (dd, J=11.53, 2.37 Hz, 1H), 3.37-3.59 (m, 6H), 2.50-2.53 (m, J=1.70 Hz, 3H), 1.84-1.96 (m, 1H), 1.50-1.71 (m, 2H), 1.35-1.47 (m, 1H). MS (ESI+) m/z 433.1 (M+H)$^+$.

Example 109

N-[3-(6-methyl-7-oxo-6,7-dihydro-1H-pyrrolo[2,3-c]pyridin-4-yl)-4-(tetrahydro-2H-pyran-4-yloxy)phenyl]ethanesulfonamide Example 109 was prepared according to the procedure used for the preparation of Example 4 (Method A), substituting Example 99b for Example 3 and ethanesulfonyl chloride for methanesulfonyl chloride with the exception that the reaction mixture was initially stirred for 18 hours at ambient temperature and then heated at 50° C. for 1 hour in the presence of sodium hydroxide, to provide the title compound. $^1$H NMR (300 MHz, DMSO-$d_6$) δ ppm 12.00 (s, 1H), 9.50 (s, 1H), 7.24-7.33 (m, 3H), 7.14 (s, 2H), 6.19 (t, J=2.37 Hz, 1H), 4.39-4.53 (m, 1H), 3.53-3.68 (m, 5H), 3.33-3.45 (m, 2H), 2.96-3.06 (m, 2H), 1.78-1.92 (m, 2H), 1.63-1.78 (m, 2H), 1.39-1.54 (m, 2H), 0.95 (t, J=7.46 Hz, 3H). MS (ESI+) m/z 432.1 (M+H)$^+$.

Example 110

N,N-dimethyl-5-(6-methyl-7-oxo-6,7-dihydro-1H-pyrrolo[2,3-c]pyridin-4-yl)-6-(tetrahydrofuran-3-yloxy)pyridine-3-sulfonamide Example 110a 5-bromo-6-chloro-N,N-dimethylpyridine-3-sulfonamide 5-Bromo-6-chloropyridine-3-sulfonyl chloride (1.455 g, 5 mmol) in methanol (20 mL) was treated with 2.0 N dimethylamine (6.25 mL, 12.50 mmol). The reaction mixture was stirred at ambient temperature for 16 hours. The solvent was removed, and the solid was washed with water several times. The solid was then purified by chromatography on silica gel eluting with 15% ethyl acetate in hexanes to give 0.8 g of the title compound.

Example 110b 5-bromo-N,N-dimethyl-6-(tetrahydrofuran-3-yloxy)pyridine-3-sulfonamide Example 110b was prepared according to the procedure used for the preparation of Example 29a, substituting 110a for Example 2a, and tetrahydrofuran-3-ol for tetrahydro-2H-pyran-4-ol, respectively, to provide the title compound.

Example 110c

N,N-dimethyl-5-(6-methyl-7-oxo-6,7-dihydro-1H-pyrrolo[2,3-c]pyridin-4-yl)-6-(tetrahydrofuran-3-yloxy)pyridine-3-sulfonamide Example 110c was prepared according to the procedure used for the preparation of Example 95d, substituting Example 110b for Example 95c, to provide the title compound. $^1$H NMR (500 MHz, DMSO-$d_6$) δ ppm 12.11 (s, 1H), 8.53 (d, J=2.44 Hz, 1H), 8.00 (d, J=2.44 Hz, 1H), 7.43 (s, 1H), 7.32 (d, J=2.75 Hz, 1H), 6.17 (t, J=2.29 Hz, 1H), 5.67 (d, J=1.53 Hz, 1H), 3.93 (dd, J=10.38, 4.58 Hz, 1H), 3.78 (d, J=10.07 Hz, 1H), 3.68-3.72 (m, 2H), 3.57 (s, 3H), 2.69 (s, 6H), 2.54-2.56 (m, 5H), 2.17-2.24 (m, 1H), 1.94-1.98 (m, 1H). MS (ESI+) m/z 419.2 (M+H)$^+$.

Example 111

5-(6-methyl-7-oxo-6,7-dihydro-1H-pyrrolo[2,3-c]pyridin-4-yl)-6-(phenylamino)pyridine-3-sulfonamide Example 111a 5-bromo-6-(phenylamino)pyridine-3-sulfonamide A mixture of Example 86a (0.136 g, 0.5 mmol), aniline (0.186 g, 2.0 mmol), and 60% sodium hydride (0.12 g, 3.0 mmol) in dioxane (2 mL) was stirred and heated at 60° C. for 16 hours. After cooling, the reaction mixture was partitioned between water and ethyl acetate. The aqueous layer was neutralized with 10% HCl and extracted with additional ethyl acetate twice. The combined organic layers were washed with saturated aqueous sodium chloride, dried over anhydrous magnesium sulfate, filtered, and concentrated. The residue was purified by flash chromatography on silica gel (2:3 ethyl acetate/hexanes) to give 0.095 g of the title product.

Example 111b 5-(6-methyl-7-oxo-6,7-dihydro-1H-pyrrolo[2,3-c] pyridin-4-yl)-6-(phenylamino)pyridine-3-sulfonamide Example 111b was prepared according to the procedure used for the preparation of Example 95d, substituting Example 111a for Example 95c, to provide the title compound. $^1$H NMR (500 MHz, DMSO-$d_6$) δ ppm 12.17 (s, 1H), 8.49 (d, J=2.44 Hz, 1H), 8.25 (s, 1H), 7.87 (d, J=2.44 Hz, 1H), 7.55 (d, J=7.63 Hz, 2H), 7.42 (s, 1H), 7.24-7.31 (m, 5H), 6.99 (t, J=7.32 Hz, 1H), 6.04 (m, 1H), 3.58 (s, 3H). MS (ESI+) m/z 396.2 (M+H)$^+$.

Example 112

N-methyl-5-(6-methyl-7-oxo-6,7-dihydro-1H-pyrrolo[2,3-c]pyridin-4-yl)-6-(phenylamino)pyridine-3-sulfonamide Example 112 was isolated as a minor product during the preparation of Example 111b. $^1$H NMR (500 MHz, DMSO-$d_6$) δ ppm 12.17 (s, 1H), 8.44 (d, J=2.44 Hz, 1H), 8.31 (s, 1H), 7.78 (d, J=2.44 Hz, 1H), 7.56 (d, J=7.63 Hz, 2H), 7.45 (s, 1H), 7.34-7.37 (m, 1H), 7.25-7.30 (m, 3H), 7.00 (t, J=7.32 Hz, 1H), 6.04 (m, 1H), 3.58 (s, 3H), 2.46 (d, J=4.88 Hz, 3H). MS (ESI+) m/z 410.2 (M+H)$^+$.

Example 113

N-[4-(4-cyanophenoxy)-3-(6-methyl-7-oxo-6,7-dihydro-1H-pyrrolo[2,3-c]pyridin-4-yl)phenyl]-2-fluoroethanesulfonamide Example 33b (50 mg, 0.140 mmol) and triethylamine (42.6 mg, 0.421 mmol) were combined in dichloromethane (4 mL). 2-Fluoroethanesulfonyl chloride (82 mg, 0.561 mmol) was added dropwise and reaction mixture was stirred for 1 hour at ambient temperature. The reaction mixture was then extracted with saturated aqueous sodium chloride, separated, dried over anhydrous magnesium sulfate, filtered, and concentrated. The residue was purified by preparative HPLC (C18, 10-100% acetonitrile/water, 0.1% TFA) to afford the title compound (1.4 mg, 2% yield). $^1$H NMR (300 MHz, DMSO-$d_6$) ppm 11.98-11.92 (m, 1H), 7.62-7.56 (m, 2H), 7.25 (t, J=2.7 Hz, 1H), 7.17 (s, 1H), 7.05 (d, J=8.6 Hz, 1H), 6.82-6.70 (m, 4H), 6.24-6.13 (m, 1H), 4.19-4.09 (m, 2H), 3.70-3.62 (m, 2H) 3.45 (s, 3H). MS (ESI+) m/z 467.1 (M+H)$^+$.

Example 114

2-fluoro-N-[3-(6-methyl-7-oxo-6,7-dihydro-1H-pyrrolo[2,3-c]pyridin-4-yl)-4-(2,4,6-trifluorophenoxy)phenyl]ethanesulfonamide Example 114 was prepared according to the procedure used for the preparation of Example 91c, substituting Example 94b for Example 91b, to provide the title compound. $^1$H NMR (300 MHz, DMSO-$d_6$) ppm 12.00-11.94 (m, 1H), 7.33 (d, J=8.8 Hz, 1H), 7.27 (m, 2H), 7.25 (s, 1H), 6.69 (d, J=2.5 Hz, 1H), 6.63-6.47 (m, 2H), 6.22 (dd, J=2.8, 2.0 Hz, 1H), 4.08 (q, J=6.3, 5.7, 6.0 Hz, 2H), 3.60 (t, J=6.3, 6.0 Hz, 2H), 3.55 (bs, 3H). MS (ESI+) m/z 496.2 (M+H)$^+$.

Example 115

N-[4-(2,4-difluorophenoxy)-3-(6-methyl-7-oxo-6,7-dihydro-1H-pyrrolo[2,3-c]pyridin-4-yl)phenyl]propane-1-sulfonamide Example 115 was prepared according to the procedure used for the preparation of Example 27c, substituting propane-1-sulfonyl chloride for methanesulfonyl chloride, to provide the title compound. $^1$H NMR (300 MHz, DMSO-$d_6$) ppm 12.04 (bs, 1H), 9.76 (s, 1H), 7.42-7.26 (m, 4H), 7.18 (dd, J=8.8, 2.7 Hz, 1H), 7.13-6.94 (m, 2H), 6.91 (d, J=8.7 Hz, 1H), 6.24 (t, J=2.3 Hz, 1H), 3.53 (s, 3H), 3.13-3.04 (m, 2H), 1.79-1.64 (m, 2H), 0.96 (t, J=7.4 Hz, 3H). MS (ESI+) m/z 474.1 (M+H)$^+$.

Example 116

4-(2,4-difluorophenoxy)-3-(6-methyl-7-oxo-6,7-dihydro-1H-pyrrolo[2,3-c]pyridin-4-yl)-N-(pyrimidin-2-yl)benzamide A solution of Example 50b (24 mg, 0.06 mmol) in a 4 mL vial was dissolved in anhydrous tetrahydrofuran (1.0 mL), followed by the addition of 1-chloro-N,N,2-trimethyl-1-propenylamine (65 μL, 0.48 mmol). This was capped and placed to shake for 2 hours at ambient temperature. Then, a solution of pyrimidin-2-amine (9 mg, 0.09 mmol) in anhydrous tetrahydrofuran (0.3 mL) was added, followed by a solution of 4-(dimethylamino)pyridine (37 mg, 0.3 mmol) in anhydrous tetrahydrofuran (0.5 mL). The mixture was stirred at 60° C. for 16 hours, cooled, and concentrated to dryness. The residues were dissolved in 1:1 DMSO/MeOH and purified by reverse phase HPLC (10-80% acetonitrile in 0.1% TFA water). $^1$H NMR (500 MHz, DMSO-$d_6$/D$_2$O, Temp=25° C.) δ ppm 8.73 (d, J=4.88 Hz, 2H) 8.09 (d, J=2.44 Hz, 1H) 7.95 (dd, J=8.70, 2.29 Hz, 1H) 7.42-7.48 (m, 1H) 7.41 (s, 1H) 7.32-7.38 (m, 2H) 7.27 (t, J=4.88 Hz, 1H) 7.11-7.17 (m, 1H) 6.90 (d, J=8.85 Hz, 1H) 6.32 (d, J=2.75 Hz, 1H) 3.60 (s, 3H); (ESI) m/z 474 (M+H)$^+$.

Example 117

4-(2,4-difluorophenoxy)-N-(2,6-dimethoxypyridin-3-yl)-3-(6-methyl-7-oxo-6,7-dihydro-1H-pyrrolo[2,3-c]pyridin-4-yl)benzamide Example 117 was prepared according to the procedure used for the preparation of Example 116, substituting 2,6-dimethoxypyridin-3-amine hydrochloride for pyrimidin-2-amine, to provide the TFA salt of the title compound. $^1$H NMR (500 MHz, DMSO-$d_6$/D$_2$O, Temp=25° C.) δ ppm 8.08 (d, J=1.53 Hz, 1H) 7.94 (dd, J=8.85, 2.14 Hz, 1H) 7.74-7.78 (m, 1H) 7.40-7.47 (m, 1H) 7.38 (s, 1H) 7.28-7.35 (m, 2H) 7.09-7.15 (m, 1H) 6.91 (d, J=8.54 Hz, 1H) 6.43 (d, J=8.24 Hz, 1H) 6.29 (d, J=2.75 Hz, 1H) 3.88 (d, J=9.46 Hz, 6H) 3.60 (s, 3H); (ESI) m/z 533 (M+H)$^+$.

Example 118

4-(2,4-difluorophenoxy)-N-(1H-indazol-6-yl)-3-(6-methyl-7-oxo-6,7-dihydro-1H-pyrrolo[2,3-c]pyridin-4-yl)benzamide Example 118 was prepared according to the procedure used for the preparation of Example 116, substituting 1H-indazol-6-amine for pyrimidin-2-amine, to provide the title compound. $^1$H NMR (500 MHz, DMSO-$d_6$/$D_2$O, Temp=25° C.) δ ppm 8.22 (s, 1H) 8.12 (d, J=2.44 Hz, 1H) 8.02 (s, 1H) 7.97 (dd, J=8.54, 2.44 Hz, 1H) 7.73 (d, J=8.54 Hz, 1H) 7.42-7.48 (m, 1H) 7.41 (s, 1H) 7.30-7.38 (m, 3H) 7.11-7.16 (m, 1H) 6.93 (d, J=8.54 Hz, 1H) 6.31 (d, J=2.75 Hz, 1H) 3.61 (s, 3H); (ESI) m/z 512 (M+H)$^+$.

Example 119

4-[2-(2,4-difluorophenoxy)-5-{[4-(pyrrolidin-1-ylcarbonyl)piperazin-1-yl]carbonyl}phenyl]-6-methyl-1,6-dihydro-7H-pyrrolo[2,3-c]pyridin-7-one Example 119 was prepared according to the procedure used for the preparation of Example 116, substituting piperazin-1-yl(pyrrolidin-1-yl)methanone for pyrimidin-2-amine, to provide the title compound. $^1$H NMR (500 MHz, DMSO-$d_6$/$D_2$O, Temp=25° C.) δ ppm 7.51 (d, J=2.14 Hz, 1H) 7.39-7.46 (m, 2H) 7.35 (s, 1H) 7.32-7.34 (m, J=2.90, 2.90 Hz, 1H) 7.25-7.31 (m, 1H) 7.07-7.13 (m, 1H) 6.87 (d, J=8.54 Hz, 1H) 6.28 (d, J=2.75 Hz, 1H) 3.59-3.71 (m, 1H) 3.56-3.58 (m, 4H) 3.40-3.55 (m, 2H) 3.18-3.33 (m, J=6.41, 6.41 Hz, 8H) 1.75 (t, J=6.26 Hz, 4H); (ESI) m/z 562 (M+H)$^+$.

Example 120

4-(2,4-difluorophenoxy)-N-[4-(dimethylamino)phenyl]-3-(6-methyl-7-oxo-6,7-dihydro-1H-pyrrolo[2,3-c]pyridin-4-yl)benzamide Example 120 was prepared according to the procedure used for the preparation of Example 116, substituting $N^1,N^1$-dimethylbenzene-1,4-diamine for pyrimidin-2-amine, to provide the TFA salt of the title compound. 1H NMR (500 MHz, DMSO-$d_6$/$D_2$O, Temp=25° C.) δ ppm 8.09 (d, J=2.44 Hz, 1H) 7.94 (dd, J=8.70, 2.29 Hz, 1H) 7.76 (d, J=9.16 Hz, 2H) 7.41-7.47 (m, 1H) 7.39 (s, 1H) 7.29-7.36 (m, 2H) 7.26 (d, J=8.85 Hz, 2H) 7.10-7.16 (m, 1H) 6.92 (d, J=8.54 Hz, 1H) 6.29 (d, J=3.05 Hz, 1H) 3.60 (s, 3H) 3.06 (s, 6H); (ESI) m/z 515 (M+H)$^+$.

Example 121

4-(2,4-difluorophenoxy)-3-(6-methyl-7-oxo-6,7-dihydro-1H-pyrrolo[2,3-c]pyridin-4-yl)-N-(pyridin-4-ylmethyl)benzamide Example 121 was prepared according to the procedure used for the preparation of Example 116, substituting pyridin-4-ylmethanamine for pyrimidin-2-amine, to provide the TFA salt of the title compound. 1H NMR (500 MHz, DMSO-$d_6$/$D_2$O, Temp=25° C.) δ ppm 8.79 (d, J=6.41 Hz, 2H) 8.05 (d, J=2.14 Hz, 1H) 7.87-7.96 (m, 3H) 7.41-7.47 (m, 1H) 7.28-7.38 (m, 3H) 7.09-7.16 (m, 1H) 6.91 (d, J=8.54 Hz, 1H) 6.28 (d, J=2.75 Hz, 1H) 4.73 (s, 2H) 3.59 (s, 3H); (ESI) m/z 487 (M+H)$^+$.

Example 122

4-(2,4-difluorophenoxy)-3-(6-methyl-7-oxo-6,7-dihydro-1H-pyrrolo[2,3-c]pyridin-4-yl)-N-[2-(2-oxopyrrolidin-1-yl)ethyl]benzamide Example 122 was prepared according to the procedure used for the preparation of Example 116, substituting 1-(2-aminoethyl)pyrrolidin-2-one for pyrimidin-2-amine, to provide the title compound. $^1$H NMR (500 MHz, DMSO-$d_6$/$D_2$O, Temp=25° C.) δ ppm 7.91 (d, J=2.44 Hz, 1H) 7.77 (dd, J=8.70, 2.29 Hz, 1H) 7.38-7.47 (m, 1H) 7.32-7.36 (m, 2H) 7.26-7.31 (m, 1H) 7.07-7.13 (m, 1H) 6.86 (d, J=8.54 Hz, 1H) 6.27 (d, J=2.75 Hz, 1H) 3.59 (s, 3H) 3.33-3.46 (m, 6H) 2.19 (t, J=8.09 Hz, 2H) 1.86-1.95 (m, 2H); (ESI) m/z 507 (M+H)$^+$.

Example 123

4-(2,4-difluorophenoxy)-N-(2-hydroxy-2-methylpropyl)-3-(6-methyl-7-oxo-6,7-dihydro-1H-pyrrolo[2,3-c]pyridin-4-yl)benzamide Example 123 was prepared according to the procedure used for the preparation of Example 116, substituting 1-amino-2-methylpropan-2-ol for pyrimidin-2-amine, to provide the title compound. $^1$H NMR (500 MHz, DMSO-$d_6$/$D_2$O, Temp=25° C.) δ ppm 7.98 (d, J=2.14 Hz, 1H) 7.85 (dd, J=8.70, 2.29 Hz, 1H) 7.39-7.45 (m, 1H) 7.35 (s, 1H) 7.32 (d, J=3.05 Hz, 1H) 7.25-7.31 (m, 1H) 7.07-7.13 (m, 1H) 6.86 (d, J=8.54 Hz, 1H) 6.26 (d, J=2.75 Hz, 1H) 3.58-3.60 (m, 3H) 3.27 (s, 2H) 1.11 (s, 6H); (ESI) m/z 468 (M+H)$^+$.

Example 124

4-(2,4-difluorophenoxy)-N-[2-(5-methoxy-1H-indol-3-yl)ethyl]-3-(6-methyl-7-oxo-6,7-dihydro-1H-pyrrolo[2,3-c]pyridin-4-yl)benzamide Example 124 was prepared according to the procedure used for the preparation of Example 116, substituting 2-(5-methoxy-1H-indol-3-yl)ethanamine for pyrimidin-2-amine, to provide the title compound. $^1$H NMR (500 MHz, DMSO-$d_6$/$D_2$O, Temp=25° C.) δ ppm 7.93 (d, J=2.14 Hz, 1H) 7.83 (dd, J=8.54, 2.14 Hz, 1H) 7.39-7.45 (m, 1H) 7.30-7.33 (m, 2H) 7.26-7.30 (m, 1H) 7.24 (d, J=8.85 Hz, 1H) 7.14 (s, 1H) 7.07-7.13 (m, 1H) 7.03 (d, J=2.44 Hz, 1H) 6.86 (d, J=8.54 Hz, 1H) 6.72 (dd, J=8.85, 2.44 Hz, 1H) 6.24 (d, J=2.75 Hz, 1H) 3.67 (s, 3H) 3.59 (s, 3H) 3.53 (t, J=7.32 Hz, 2H) 2.92 (t, J=7.32 Hz, 2H); (ESI) m/z 569 (M+H)$^+$.

Example 125

N-(3,4-difluorobenzyl)-4-(2,4-difluorophenoxy)-3-(6-methyl-7-oxo-6,7-dihydro-1H-pyrrolo[2,3-c]pyridin-4-yl)benzamide Example 125 was prepared according to the procedure used for the preparation of Example 116, substituting (3,4-difluorophenyl)methanamine for pyrimidin-2-amine, to provide the title compound. $^1$H NMR (500 MHz, DMSO-$d_6$/$D_2$O, Temp=25° C.) δ ppm 8.00 (d, J=2.14 Hz, 1H) 7.87 (dd, J=8.54, 2.14 Hz, 1H) 7.26-7.46 (m, 6H) 7.15-7.20 (m, 1H)

7.08-7.13 (m, 1H) 6.88 (d, J=8.54 Hz, 1H) 6.26 (d, J=2.75 Hz, 1H) 4.45 (s, 2H) 3.58 (s, 3H); (ESI) m/z 522 (M+H)+.

Example 126

4-(2,4-difluorophenoxy)-3-(6-methyl-7-oxo-6,7-dihydro-1H-pyrrolo[2,3-c]pyridin-4-yl)-N-[4-(trifluoromethoxy)benzyl]benzamide Example 126 was prepared according to the procedure used for the preparation of Example 116, substituting (4-(trifluoromethoxy)phenyl)methanamine for pyrimidin-2-amine, to provide the title compound. $^1$H NMR (500 MHz, DMSO-d$_6$/D$_2$O, Temp=25° C.) ppm 8.01 (d, J=2.44 Hz, 1H) 7.88 (dd, J=8.54, 2.14 Hz, 1H) 7.39-7.47 (m, 3H) 7.35 (s, 1H) 7.26-7.34 (m, 4H) 7.08-7.14 (m, 1H) 6.88 (d, J=8.54 Hz, 1H) 6.26 (d, J=2.75 Hz, 1H) 4.50 (s, 2H) 3.58 (s, 3H); (ESI) m/z 570 (M+H)+.

Example 127

2-{4-[4-(2,4-difluorophenoxy)-3-(6-methyl-7-oxo-6,7-dihydro-1H-pyrrolo[2,3-c]pyridin-4-yl)benzoyl]piperazin-1-yl}-N,N-dimethylacetamide Example 127 was prepared according to the procedure used for the preparation of Example 116, substituting N,N-dimethyl-2-(piperazin-1-yl)acetamide for pyrimidin-2-amine, to provide the TFA salt of the title compound. $^1$H NMR (500 MHz, DMSO-d$_6$/D$_2$O, Temp=25° C.) ppm 7.56 (d, J=2.14 Hz, 1H) 7.40-7.48 (m, 2H) 7.35 (s, 1H) 7.33 (d, J=2.75 Hz, 1H) 7.26-7.32 (m, 1H) 7.08-7.13 (m, 1H) 6.88 (d, J=8.24 Hz, 1H) 6.28 (d, J=2.75 Hz, 1H) 4.26 (s, 2H) 2.99-3.71 (m, 11H) 2.92 (d, J=5.49 Hz, 6H); (ESI) m/z 550 (M+H)+.

Example 128

4-(2,4-difluorophenoxy)-3-(6-methyl-7-oxo-6,7-dihydro-1H-pyrrolo[2,3-c]pyridin-4-yl)-N-(pyridin-3-ylmethyl)benzamide Example 128 was prepared according to the procedure used for the preparation of Example 116, substituting pyridin-3-ylmethanamine for pyrimidin-2-amine, to provide the TFA salt of the title compound. 1H NMR (500 MHz, DMSO-d$_6$/D$_2$O, Temp=25° C.) ppm 8.78 (s, 1H) 8.72 (d, J=5.19 Hz, 1H) 8.36 (d, J=7.93 Hz, 1H) 8.01 (d, J=2.14 Hz, 1H) 7.85-7.92 (m, 2H) 7.40-7.46 (m, 1H) 7.35 (s, 1H) 7.33 (t, J=3.36 Hz, 1H) 7.27-7.31 (m, 1H) 7.09-7.14 (m, 1H) 6.89 (d, J=8.54 Hz, 1H) 6.26 (d, 1H) 4.63 (s, 2H) 3.59 (s, 3H); (ESI) m/z 487 (M+H)+.

Example 129

4-(2,4-difluorophenoxy)-3-(6-methyl-7-oxo-6,7-dihydro-1H-pyrrolo[2,3-c]pyridin-4-yl)-N-(pyridin-2-ylmethyl)benzamide Example 129 was prepared according to the procedure used for the preparation of Example 116, substituting pyridin-2-ylmethanamine for pyrimidin-2-amine, to provide the TFA salt of the title compound. $^1$H NMR (500 MHz, DMSO-d$_6$/D$_2$O, Temp=25° C.) ppm 8.68 (d, J=5.49 Hz, 1H) 8.23-8.29 (m, 1H) 8.04 (d, J=2.44 Hz, 1H) 7.90 (dd, J=8.70, 2.29 Hz, 1H) 7.75 (d, J=7.93 Hz, 1H) 7.69-7.73 (m, 1H) 7.39-7.47 (m, 1H) 7.36 (s, 1H) 7.33 (d, J=2.75 Hz, 1H) 7.26-7.32 (m, 1H) 7.09-7.15 (m, 1H) 6.90 (d, J=8.85 Hz, 1H) 6.27 (d, J=2.75 Hz, 1H) 4.73 (s, 2H) 3.59 (s, 3H); (ESI) m/z 487 (M+H)+.

Example 130

4-(2,4-difluorophenoxy)-3-(6-methyl-7-oxo-6,7-dihydro-1H-pyrrolo[2,3-c]pyridin-4-yl)-N-(3,4,5-trimethoxybenzyl)benzamide Example 130 was prepared according to the procedure used for the preparation of Example 116, substituting (3,4,5-trimethoxyphenyl)methanamine for pyrimidin-2-amine, to provide the title compound. $^1$H NMR (500 MHz, DMSO-d$_6$/D$_2$O, Temp=25° C.) ppm 8.00 (d, J=2.14 Hz, 1H) 7.87 (dd, J=8.70, 2.29 Hz, 1H) 7.39-7.45 (m, 1H) 7.35 (s, 1H) 7.32 (d, J=2.75 Hz, 1H) 7.26-7.31 (m, 1H) 7.11 (m, 1H) 6.87 (d, J=8.54 Hz, 1H) 6.66 (s, 2H) 6.26 (d, J=2.75 Hz, 1H) 4.41 (s, 2H) 3.75 (s, 6H) 3.63 (s, 3H) 3.58 (s, 3H); (ESI) m/z 576 (M+H)+.

Example 131

4-(2,4-difluorophenoxy)-N-[2-(dimethylamino)ethyl]-3-(6-methyl-7-oxo-6,7-dihydro-1H-pyrrolo[2,3-c]pyridin-4-yl)benzamide Example 131 was prepared according to the procedure used for the preparation of Example 116, substituting $N^1,N^1$-dimethylethane-1,2-diamine for pyrimidin-2-amine, to provide the TFA salt of the title compound. 1H NMR (500 MHz, DMSO-d$_6$/D$_2$O, Temp=25° C.) ppm 7.97 (d, J=2.14 Hz, 1H) 7.85 (dd, J=8.70, 2.29 Hz, 1H) 7.39-7.46 (m, 1H) 7.31-7.35 (m, 2H) 7.25-7.31 (m, 1H) 7.09-7.15 (m, 1H) 6.90 (d, J=8.55 Hz, 1H) 6.25 (d, J=2.75 Hz, 1H) 3.62 (t, J=5.95 Hz, 2H) 3.59 (s, 3H) 3.26 (t, J=5.95 Hz, 2H) 2.84 (s, 6H); (ESI) m/z 467 (M+H)+.

Example 132

N-[2-(1,3-benzodioxol-5-yl)ethyl]-4-(2,4-difluorophenoxy)-3-(6-methyl-7-oxo-6,7-dihydro-1 H-pyrrolo[2,3-c]pyridin-4-yl)benzamide Example 132 was prepared according to the procedure used for the preparation of Example 116, substituting 2-(benzo[d][1,3]dioxol-5-yl)ethanamine for pyrimidin-2-amine, to provide the title compound. $^1$H NMR (500 MHz, DMSO-d$_6$/D$_2$O, Temp=25° C.) ppm 7.92 (d, J=2.14 Hz, 1H) 7.79 (dd, J=8.70, 2.29 Hz, 1H) 7.39-7.45 (m, 1H) 7.31-7.34 (m, 2H) 7.25-7.31 (m, 1H) 7.06-7.14 (m, 1H) 6.80-6.87 (m, 3H) 6.70 (d, J=7.02 Hz, 1H) 6.25 (d, J=3.05 Hz, 1H) 5.94 (s, 2H) 3.59 (s, 3H) 3.44 (t, J=7.32 Hz, 2H) 2.76 (t, J=7.32 Hz, 2H); (ESI) m/z 544 (M+H)+.

Example 133

4-(2,4-difluorophenoxy)-N-[2-(1H-indol-3-yl)ethyl]-3-(6-methyl-7-oxo-6,7-dihydro-1H-pyrrolo[2,3-c]pyridin-4-yl)benzamide Example 133 was prepared according to the procedure used for the preparation of Example 116, substituting 2-(1H-indol-3-yl)ethanamine for pyrimidin-2-amine, to provide the title compound. $^1$H NMR (500 MHz, DMSO-d$_6$/D$_2$O, Temp=25° C.) ppm 8.65 (t, J=5.49 Hz, 1H) 7.94 (d, J=2.14 Hz, 1H) 7.83 (dd, J=8.70, 2.29 Hz, 1H) 7.58 (d, J=7.93 Hz, 1H) 7.39-7.45 (m, 1H) 7.36 (d, J=7.93 Hz, 1H) 7.32-7.34 (m, 2H) 7.25-7.31 (m, 1H) 7.18 (s, 1H) 7.05-7.13 (m, 2H) 6.98 (t, J=7.32 Hz, 1H) 6.86 (d, J=8.54 Hz, 1H) 6.25 (d, J=2.75 Hz, 1H) 3.59 (s, 3H) 3.48-3.58 (m, 2H) 2.96 (t, J=7.48 Hz, 2H); (ESI) m/z 539 (M+H)+.

Example 134

4-[2-(2,4-difluorophenoxy)-5-{[4-(furan-2-ylcarbonyl)piperazin-1-yl]carbonyl}phenyl]-6-methyl-1,6-dihydro-7H-pyrrolo[2,3-c]pyridin-7-one Example 134 was prepared according to the procedure used for the preparation of Example 116, substituting furan-2-yl(piperazin-1-yl)methanone for pyrimidin-2-amine, to provide the title compound. $^1$H NMR (500 MHz, DMSO-d$_6$/D$_2$O, Temp=25° C.) ppm 7.82 (s, 1H) 7.55 (d, J=2.14 Hz, 1H) 7.39-7.48 (m, 2H) 7.25-7.37 (m, 3H) 7.07-7.13 (m, 1H) 7.05 (d, J=3.36 Hz, 1H) 6.88 (d, J=8.24 Hz, 1H) 6.64 (dd, J=3.36, 1.83 Hz, 1H) 6.29 (d, J=2.75 Hz, 1H) 3.74-3.89 (m, 4H) 3.41-3.70 (m, 7H); (ESI) m/z 559 (M+H)+.

Example 135 tert-butyl {1-[4-(2,4-difluorophenoxy)-3-(6-methyl-7-oxo-6,7-dihydro-1H-pyrrolo[2,3-c]pyridin-4-yl)benzoyl]piperidin-4-yl}carbamate Example 135 was prepared according to the procedure used for the preparation of Example 116, substituting tert-butyl piperidin-4-ylcarbamate for pyrimidin-2-amine, to provide the title compound. $^1$H NMR (500 MHz, DMSO-d$_6$/D$_2$O, Temp=25° C.) ppm 7.45 (d, J=1.83 Hz, 1H) 7.36-7.44 (m, 2H) 7.34 (s, 1H) 7.32 (d, J=2.75 Hz, 1H) 7.25-7.31 (m, 1H) 7.06-7.13 (m, 1H) 6.86 (d, J=8.54 Hz, 1H) 6.27 (d, J=2.75 Hz, 1H) 4.31 (s, 1H) 3.42-3.69 (m, 5H) 2.85-3.24 (m, 2H) 1.77 (s, 2H) 1.21-1.47 (m, 11H); (ESI) m/z 579 (M+H)+.

Example 136 tert-butyl 4-{[4-(2,4-difluorophenoxy)-3-(6-methyl-7-oxo-6,7-dihydro-1H-pyrrolo[2,3-c]pyridin-4-yl)benzoyl]amino}piperidine-1-carboxylate Example 136 was prepared according to the procedure used for the preparation of Example 116, substituting tert-butyl 4-aminopiperidine-1-carboxylate for pyrimidin-2-amine, to provide the title compound. $^1$H NMR (500 MHz, DMSO-d$_6$/D$_2$O, Temp=25° C.) ppm 7.95 (d, J=2.14 Hz, 1H) 7.83 (dd, J=8.54, 2.14 Hz, 1H) 7.43 (d, J=8.54 Hz, 1H) 7.31-7.35 (m, 2H) 7.24-7.51 (m, 1H) 7.10 (d, J=1.83 Hz, 1H) 6.86 (d, J=8.54 Hz, 1H) 6.24 (d, J=2.75 Hz, 1H) 3.87-4.08 (m, 3H) 3.58 (s, 3H) 2.91 (d, J=85.75 Hz, 2H) 1.78 (d, 2H) 1.34-1.45 (m, 11H); (ESI) m/z 579 (M+H)+.

Example 137

4-[2-(2,4-difluorophenoxy)-5-{[4-(ethylsulfonyl)piperazin-1-yl]carbonyl}phenyl]-6-methyl-1,6-dihydro-7H-pyrrolo[2,3-c]pyridin-7-one Example 137 was prepared according to the procedure used for the preparation of Example 116, substituting 1-(ethylsulfonyl)piperazine for pyrimidin-2-amine, to provide the title compound. $^1$H NMR (500 MHz, DMSO-d$_6$/D$_2$O, Temp=25° C.) ppm 7.53 (d, J=2.14 Hz, 1H) 7.38-7.47 (m, 2H) 7.35 (s, 1H) 7.33 (d, J=3.05 Hz, 1H) 7.26-7.32 (m, 1H) 7.07-7.13 (m, 1H) 6.87 (d, J=8.54 Hz, 1H) 6.28 (d, J=2.75 Hz, 1H) 3.43-3.70 (m, 7H) 3.25 (s, 4H) 3.07 (q, J=7.43 Hz, 2H) 1.22 (t, J=7.32 Hz, 3H); (ESI) m/z 557 (M+H)+.

Example 138

4-[2-(2,4-difluorophenoxy)-5-(methylsulfonyl)phenyl]-6-methyl-1,6-dihydro-7H-pyrrolo[2,3-c]pyridin-7-one Example 138a 4-(2-fluoro-5-(methylsulfonyl)phenyl)-6-methyl-1-tosyl-1H-pyrrolo[2,3-c]pyridin-7(6H)-one A mixture of Example 6a (0.642 g, 1.5 mmol), 2-bromo-1-fluoro-4-(methylsulfonyl)benzene (0.380 g, 1.500 mmol), 1,3,5,7-tetramethyl-6-phenyl-2,4,8-trioxa-6-phosphaadamantane (0.051 g, 0.176 mmol), tris(dibenzylideneacetone)dipalladium(0) (0.041 g, 0.045 mmol), and potassium phosphate (0.796 g, 3.75 mmol) in dioxane (10 mL) and water (2.500 mL) was degassed and back-filled with nitrogen several times. The reaction was heated at 60° C. for 16 hours. The reaction mixture was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The residue was purified by flash column chromatography on silica gel eluting with 30% ethyl acetate in hexanes to give the title compound (0.63 g, 1.328 mmol, 89% yield).

Example 138b

4-[2-(2,4-difluorophenoxy)-5-(methylsulfonyl)phenyl]-6-methyl-1,6-dihydro-7H-pyrrolo[2,3-c]pyridin-7-one A mixture of Example 138a (0.05 g, 0.105 mmol), 2,4-difluorophenol (0.016 g, 0.126 mmol), and cesium carbonate (0.069 g, 0.211 mmol) in DMSO (1 mL) was heated at 120° C. for 16 hours. The reaction mixture was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The residue was purified by reverse phase Preparative HPLC (10-80% acetonitrile in 0.1% TFA/water) to give the title compound (0.036 g, 0.084 mmol, 79% yield). $^1$H NMR (500 MHz, DMSO-d$_6$) δ ppm 12.10 (s, 1H), 7.99 (d, J=2.44 Hz, 1H), 7.86 (dd, J=8.54, 2.44 Hz, 1H), 7.40-7.56 (m, 3H), 7.31 (t, J=2.9 Hz, 1H), 7.14-7.20 (m, 1H), 6.98 (d, J=8.54 Hz, 1H), 6.28-6.30 (m, 1H), 3.59 (s, 3H), 3.26 (s, 3H). MS (ESI+) m/z 431.1 (M+H)+.

Example 139

4-[2-(4-chlorobenzoyl)phenyl]-6-methyl-1,6-dihydro-7H-pyrrolo[2,3-c]pyridin-7-one Example 139 was prepared according to the procedure used for the preparation of Example 95d, substituting (2-bromophenyl)(4-chlorophenyl)methanone for Example 95c, to provide the title compound. $^1$H NMR (500 MHz, DMSO-d$_6$) δ ppm 11.96 (s, 1H), 7.86-7.73 (m, 1H), 7.55-7.62 (m, 3H), 7.39-7.43 (m, 2H), 7.25-7.29 (m, 2H), 7.21 (t, J=2.75 Hz, 1H), 6.88 (s, 1H), 6.05-6.06 (m, 1H), 3.39 (s, 3H). MS (DCI+) m/z 363.0 (M+H)+.

Example 140

4-{2-[(4-chlorophenyl)(hydroxy)methyl]phenyl}-6-methyl-1,6-dihydro-7H-pyrrolo[2,3-c]pyridin-7-one A mixture of Example 139 (0.05 g, 0.138 mmol) and sodium tetrahydroborate (2) (5.21 mg, 0.138 mmol) in tetrahydrofuran (2 mL) was heated at 60° C. for 3 hours. The solvent was removed, and the residue was purified by reverse phase Preparative HPLC (10-80% acetonitrile in 0.1% TFA/water) to give the title compound (0.042 g, 0.115 mmol, 84% yield). $^1$H NMR (500 MHz, DMSO-d$_6$) δ ppm 11.70 (s, 1H), 7.56 (d, J=7.63 Hz, 1H), 7.35-7.39 (m, 1H), 7.27-7.31 (m, 1H), 7.21-7.23 (m, 4H), 7.00 (d, J=8.54 Hz, 2H), 6.79 (s, 1H), 5.94 (t, J=2.29 Hz, 1H), 5.75 (s, 1H), 3.47 (s, 3H). MS (DCI+) m/z 365.0 (M+H)$^+$.

Example 141

N-[3-(6-methyl-7-oxo-6,7-dihydro-1H-pyrrolo[2,3-c]pyridin-4-yl)-4-(pyrimidin-5-yloxy)phenyl]ethanesulfonamide

Example 141a 6-methyl-4-(5-nitro-2-(pyrimidin-5-yloxy)phenyl)-1H-pyrrolo[2,3-c]pyridin-7(6H)-one Example 141a was prepared according to the procedure used for the preparation of Example 2b, substituting pyrimidin-5-ol for phenol, to provide the title compound.

Example 141b 4-(5-amino-2-(pyrimidin-5-yloxy)phenyl)-6-methyl-1H-pyrrolo[2,3-c]pyridin-7(6H)-one Example 141b was prepared according to the procedure used for the preparation of Example 3, substituting Example 141a for Example 2b, to provide the title compound.

Example 141c

N-[3-(6-methyl-7-oxo-6,7-dihydro-1H-pyrrolo[2,3-c]pyridin-4-yl)-4-(pyrimidin-5-yloxy)phenyl]ethanesulfonamide Example 141c was prepared according to the procedure used for the preparation of Example 4 (Method A), substituting Example 141b for Example 3 and substituting ethanesulfonyl chloride for methanesulfonyl chloride, to provide the title compound. $^1$H NMR (300 MHz, DMSO-d$_6$) ppm 12.03 (bs, 1H), 9.90 (s, 1H), 8.35 (s, 2H), 7.40 (d, J=2.3 Hz, 1H), 7.31-7.22 (m, 4H), 6.25-6.20 (m, 1H), 3.49 (s, 3H), 3.17 (q, J=7.3 Hz, 2H), 1.24 (t, J=7.3 Hz, 3H). MS (ESI+) m/z 462.2 (M+H)$^+$.

Example 142

N-{3-(6-methyl-7-oxo-6,7-dihydro-1H-pyrrolo[2,3-c]pyridin-4-yl)-4-[(1-methyl-1H-pyrazol-5-yl)methoxy]phenyl}ethanesulfonamide

Example 142a 6-methyl-4-(2-((1-methyl-1H-pyrazol-5-yl)methoxy)-5-nitrophenyl)-1H-pyrrolo[2,3-c]pyridin-7(6H)-one Example 142a was prepared according to the procedure used for the preparation of Example 29a, substituting (1-methyl-1H-pyrazol-5-yl)methanol for tetrahydro-2H-pyran-4-ol, to provide the title compound.

Example 142b 4-(5-amino-2-((1-methyl-1H-pyrazol-5-yl)methoxy)phenyl)-6-methyl-1H-pyrrolo[2,3-c]pyridin-7(6H)-one Example 142b was prepared according to the procedure used for the preparation of Example 3, substituting Example 142a for Example 2b, to provide the title compound.

Example 142c

N-{3-(6-methyl-7-oxo-6,7-dihydro-1H-pyrrolo[2,3-c]pyridin-4-yl)-4-[(1-methyl-1H-pyrazol-5-yl)methoxy]phenyl}ethanesulfonamide Example 142c was prepared according to the procedure used for the preparation of Example 4 (Method A), substituting Example 142b for Example 3 and substituting ethanesulfonyl chloride for methanesulfonyl chloride, to provide the title compound. $^1$H NMR (300 MHz, DMSO-d$_6$) ppm 12.01 (bs, 1H), 9.58 (s, 1H), 7.32-7.14 (m, 6H), 6.20 (d, J=1.8 Hz, 1H), 6.10 (dd, J=2.8, 1.9 Hz, 1H), 5.10 (s, 2H), 3.63 (s, 3H), 3.50 (s, 3H), 3.04 (q, J=7.4 Hz, 2H), 1.21 (t, J=7.4 Hz, 3H). MS (ESI+) m/z 442.1 (M+H)$^+$.

Example 143

N-{4-[(1,3-dimethyl-1H-pyrazol-5-yl)methoxy]-3-(6-methyl-7-oxo-6,7-dihydro-1H-pyrrolo[2,3-c]pyridin-4-yl)phenyl}ethanesulfonamide

Example 143a 4-(2-((1,3-dimethyl-1H-pyrazol-5-yl)methoxy)-5-nitrophenyl)-6-methyl-1H-pyrrolo[2,3-c]pyridin-7(6H)-one Example 143a was prepared according to the procedure used for the preparation of Example 29a, substituting (1,3-dimethyl-1H-pyrazol-5-yl)methanol for tetrahydro-2H-pyran-4-ol, to provide the title compound.

Example 143b 4-(5-amino-2-((1,3-dimethyl-1H-pyrazol-5-yl)methoxy)phenyl)-6-methyl-1H-pyrrolo[2,3-c]pyridin-7(6H)-one Example 143b was prepared according to the procedure used for the preparation of Example 3, substituting Example 143a for Example 2b, to provide the title compound.

Example 143c

N-{4-[(1,3-dimethyl-1H-pyrazol-5-yl)methoxy]-3-(6-methyl-7-oxo-6,7-dihydro-1H-pyrrolo[2,3-c]pyridin-4-yl)phenyl}ethanesulfonamide Example 143c was prepared according to the procedure used for the preparation of Example 4 (Method A), substituting Example 143b for Example 3 and substituting ethanesulfonyl chloride for methanesulfonyl chloride, to provide the title compound. $^1$H NMR (300 MHz, DMSO-d$_6$) ppm 12.04-

11.99 (m, 1H), 9.57 (s, 1H), 7.29-7.13 (m, 5H), 6.12-6.07 (m, 1H), 5.98 (s, 1H), 5.03 (s, 2H), 3.54 (s, 3H), 3.50 (s, 3H), 3.04 (q, J=7.3 Hz, 2H), 2.05 (s, 3H), 1.21 (t, J=7.3 Hz, 3H). MS (ESI+) m/z 456.2 (M+H)$^+$.

Example 144

N-[4-(2,2-dimethylpropoxy)-3-(6-methyl-7-oxo-6,7-dihydro-1H-pyrrolo[2,3-c]pyridin-4-yl)phenyl]ethanesulfonamide

Example 144a 6-methyl-4-(2-(neopentyloxy)-5-nitrophenyl)-1H-pyrrolo[2,3-c]pyridin-7(6H)-one Example 144a was prepared according to the procedure used for the preparation of Example 29a, substituting 2,2-dimethylpropan-1-ol for tetrahydro-2H-pyran-4-ol, to provide the title compound.

Example 144b 4-(5-amino-2-(neopentyloxy)phenyl)-6-methyl-1H-pyrrolo[2,3-c]pyridin-7(6H)-one Example 144b was prepared according to the procedure used for the preparation of Example 3, substituting Example 144a for Example 2b, to provide the title compound.

Example 144c

Example 144c was prepared according to the procedure used for the preparation of Example 4 (Method A), substituting Example 144b for Example 3 and substituting ethanesulfonyl chloride for methanesulfonyl chloride, to provide the title compound. $^1$H NMR (300 MHz, DMSO-d$_6$) ppm 12.00 (s, 1H) 9.50 (s, 1H) 7.26-7.33 (m, 3H) 7.15 (dd, J=2.71, 8.82 Hz, 1H) 7.06 (d, J=9.16 Hz, 1H) 6.17-6.22 (m, 1H) 3.59 (s, 2H) 3.54 (s, 3H) 3.03 (q, J=7.23 Hz, 2H) 1.21 (t, J=7.29 Hz, 3H) 0.84 (s, 9H). MS (ESI+) m/z 416.5 (M−H)$^+$.

Example 145

N-[4-(cyclopropylmethoxy)-3-(6-methyl-7-oxo-6,7-dihydro-1H-pyrrolo[2,3-c]pyridin-4-yl)phenyl]ethanesulfonamide

Example 145a 4-(2-(cyclopropylmethoxy)-5-nitrophenyl)-6-methyl-1H-pyrrolo[2,3-c]pyridin-7(6H)-one Example 145a was prepared according to the procedure used for the preparation of Example 29a, substituting cyclopropylmethanol for tetrahydro-2H-pyran-4-ol, to provide the title compound.

Example 145b 4-(5-amino-2-(cyclopropylmethoxy)phenyl)-6-methyl-1H-pyrrolo[2,3-c]pyridin-7(6H)-one Example 145b was prepared according to the procedure used for the preparation of Example 3, substituting Example 145a for Example 2b, to provide the title compound.

Example 145c

N-[4-(cyclopropylmethoxy)-3-(6-methyl-7-oxo-6,7-dihydro-1H-pyrrolo[2,3-c]pyridin-4-yl)phenyl]ethanesulfonamide Example 145c was prepared according to the procedure used for the preparation of Example 4 (Method A), substituting Example 145b for Example 3 and substituting ethanesulfonyl chloride for methanesulfonyl chloride, to provide the title compound. $^1$H NMR (300 MHz, DMSO-d$_6$) ppm 12.02-11.97 (m, 1H), 9.49 (s, 1H), 7.32-7.24 (m, 3H), 7.14 (dd, J=8.7, 2.7 Hz, 1H), 7.05 (d, J=8.8 Hz, 1H), 6.21-6.16 (m, 1H), 3.80 (d, J=6.7 Hz, 2H), 3.56 (s, 3H), 3.02 (q, J=7.3 Hz, 2H), 1.21 (t, J=7.3 Hz, 3H), 1.08 (m, 1H), 0.50-0.39 (m, 2H), 0.27 0.18 (m, 2H). MS (ESI+) m/z 402.1 (M+H)$^+$.

Example 146

4-(2,4-difluorophenoxy)-3-(6-methyl-7-oxo-6,7-dihydro-1H-pyrrolo[2,3-c]pyridin-4-yl)benzenesulfonamide

Example 146a 4-(2,4-difluorophenoxy)-3-nitrobenzenesulfonamide

A solution of 2,4-difluorophenol (5.39 g, 41.4 mmol) in N,N-dimethylformamide (34.5 mL) was cooled to 10° C. and treated portionwise with sodium hydride (1.66 g, 41.4 mmol). After stirring 15 minutes, 4-fluoro-3-nitrobenzenesulfonamide (2.28 g, 10.36 mmol) was added portionwise. The reaction mixture was stirred at ambient temperature for 1.5 hours, diluted into ethyl acetate and quenched with 0.5 M HCl to pH 6. The organic layer was washed with saturated aqueous sodium chloride, dried over anhydrous magnesium sulfate, filtered, and concentrated to provide the title compound (3.24 g, 95%).

Example 146b 3-amino-4-(2,4-difluorophenoxy)benzenesulfonamide

Example 146a (3.24 g, 9.81 mmol), iron (2.74 g, 49.1 mmol), and ammonium chloride (0.787 g, 14.72 mmol) were stirred in a mixture of tetrahydrofuran (21 mL), ethanol (21 mL) and water (7 mL) at 95° C. for 3 hours. The mixture was filtered through a nylon membrane and concentrated. The residue partitioned between ethyl acetate and water. The organic layer was washed with saturated aqueous sodium chloride, dried over anhydrous sodium sulfate, filtered, and concentrated to provide the title compound (2.81 g, 95%).

Example 146c 4-(2,4-difluorophenoxy)-3-iodobenzenesulfonamide

To a solution of Example 146b (2.8 g, 9.32 mmol) in dioxane (20 mL) at 0° C. was added concentrated hydrochloric acid (40 mL, 9.32 mmol). The mixture was stirred 15 minutes and a solution of sodium nitrite (0.772 g, 11.19 mmol) in water (10 mL) was added. The mixture was stirred for 1 hour at 0° C. A solution of potassium iodide (3.10 g, 18.7 mmol) in water (10 mL) was added and stirring was continued 1 hour at ambient temperature. The mixture was partitioned between ethyl acetate and water. The organic layer was washed with saturated sodium thiosulfate, water, and saturated aqueous sodium chloride, dried over anhydrous magnesium sulfate, filtered, and concentrated. The residue was purified by flash column chromatography (silica gel, 0-60% ethyl acetate in hexane) to provide the title compound (2.24 g, 58.4% yield).

Example 146d 4-(2,4-difluorophenoxy)-3-(6-methyl-7-oxo-6,7-dihydro-1H-pyrrolo[2,3-c]pyridin-4-yl)benzenesulfonamide A suspension of Example 146c (111 mg, 0.270 mmol), Example 6a (150 mg, 0.351 mmol), tetrakis(triphenylphosphine)palladium (0) (31.2 mg, 0.027 mmol) and cesium fluoride (123 mg, 0.810 mmol) in a mixture of 1,2 dimethoxyethane (4.6 mL) and methanol (2.3 mL) was heated under microwave conditions at 150° C. for 5 minutes. The reaction mixture was partitioned between ethyl acetate (75 mL) and 50% aqueous sodium chloride (75 mL). The organic layer was dried over anhydrous sodium sulfate, filtered, and concentrated. To a solution of the residue in dioxane (4 mL) was added a solution of lithium hydroxide hydrate (113 mg, 2.7 mmol) in water (1 mL) and the mixture was heated under microwave conditions at 120° C. for 30 minutes. The reaction mixture was partitioned between ethyl acetate (75 mL) and water (75 mL). The organic layer was dried over anhydrous sodium sulfate, filtered, and concentrated. The residue was purified by flash column chromatography (silica gel, 0.5-10% methanol in dichloromethane) to provide the title compound (74 mg, 63.5% yield). $^1$H NMR (300 MHz, DMSO-$d_6$) δ ppm 12.09 (s, 1H), 7.92 (d, J=2.37 Hz, 1H), 7.76 (dd, J=8.82, 2.37 Hz, 1H), 7.43-7.53 (m, 1H), 7.28-7.40 (m, 5H), 7.08-7.18 (m, 1H), 6.95 (d, J=8.82 Hz, 1H), 6.27 (d, J=2.71 Hz, 1H), 3.58 (s, 3H). MS (ESI+) m/z 432.2 (M+H)$^+$.

Example 147

4-[2-(cyclohexylamino)-5-(methylsulfonyl)phenyl]-6-methyl-1,6-dihydro-7H-pyrrolo[2,3-c]pyridin-7-one Example 147a 2-bromo-N-cyclohexyl-4-(methylsulfonyl)aniline A mixture of 2-bromo-1-fluoro-4-(methylsulfonyl)benzene (0.05 g, 0.198 mmol) and cyclohexanamine (0.059 g, 0.593 mmol) in dioxane (1 mL) in a vial was capped and heated at 110° C. for three days. The reaction mixture was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by flash column chromatography on silica gel eluting with 40% ethyl acetate in hexanes to afford the title compound (0.044 g, 0.132 mmol, 67.0% yield).

Example 147b

4-[2-(cyclohexylamino)-5-(methylsulfonyl)phenyl]-6-methyl-1,6-dihydro-7H-pyrrolo[2,3-c]pyridin-7-one Example 147b was prepared according to the procedure used for the preparation of Example 95d, substituting Example 147a for Example 95c, to provide the title compound. $^1$H NMR (500 MHz, DMSO-$d_6$) δ ppm 12.13 (s, 1H), 7.66 (dd, J=8.7, 2.29 Hz, 1H), 7.51 (d, J=2.14 Hz, 1H), 7.30 (t, J=2.75 Hz, 1H), 7.26 (s, 1H), 6.86 (d, J=8.85 Hz, 1H), 6.00-6.01 (m, 1H), 4.83 (br, s, 1H), 3.56 (s, 3H), 3.35-3.44 (m, 1H), 1.84-1.87 (m, 2H), 1.53-1.62 (m, 3H), 1.27-1.37 (m, 2H), 1.03-1.12 (m, 3H). MS (APCI+) m/z 400.1 (M+H)$^+$.

Example 148

4-[5-amino-2-(2,4-difluorophenoxy)phenyl]-6-methyl-1,6-dihydro-7H-pyrrolo[2,3-d]pyridazin-7-one Example 148a Example 148a was prepared according to the procedure used for the preparation of Example 2b, substituting 2-bromo-1-fluoro-4-nitrobenzene for Example 2a, and 2,4-difluorophenol for phenol, respectively, to provide the title compound.

Example 148b 3-bromo-4-(2,4-difluorophenoxy)aniline

Example 148b was prepared according to the procedure used for the preparation of Example 3, substituting Example 148a for Example 2b, to provide the title compound.

Example 148c 4-(2,4-difluorophenoxy)-3-(4,4,5,5-tetramethyl-1,3,2-dioxaborolan-2-yl)aniline Example 148c was prepared according to the procedure used for the preparation of Example 6a, substituting Example 148b for Example 1e, to provide the title compound.

Example 148d

4-[5-amino-2-(2,4-difluorophenoxy)phenyl]-6-methyl-1,6-dihydro-7H-pyrrolo[2,3-d]pyridazin-7-one Example 148d was prepared according to the procedure used for the preparation of Example 95d, substituting Example 80b for Example 95c and Example 148c for Example 6a, respectively, to provide the TFA salt of the title compound. $^1$H NMR (500 MHz, DMSO-$d_6$) δ ppm 12.69 (s, 1H), 7.44 (t, J=2.59 Hz, 1H), 7.32-7.37 (m, 2H), 7.16 (d, J=2.75 Hz, 1H), 7.05-7.12 (m, 1H), 6.97-7.02 (m, 1H), 6.92 (d, J=8.54 Hz, 1H), 3.37-6.39 (m, 1H), 3.70 (s, 3H). MS (ESI+) m/z 369.4 (M+H)$^+$.

Example 149

4-[2-(2-fluorophenoxy)-5-(methylsulfonyl)phenyl]-6-methyl-1,6-dihydro-7H-pyrrolo[2,3-c]pyridin-7-one Example 149 was prepared according to the procedure used for the preparation of Example 138b, substituting 2-fluorophenol for 2,4-difluorophenol, to provide the title compound. $^1$H NMR (400 MHz, DMSO-$d_6$/$D_2$O) δ ppm 7.99 (d, J=2.4 Hz, 1H), 7.89 (dt, J=7.7, 3.9 Hz, 1H), 7.50-7.38 (m, 2H), 7.35-7.24 (m, 4H), 6.98 (d, J=8.6 Hz, 1H), 6.32 (d, J=2.8 Hz, 1H), 3.60 (s, 3H), 3.26 (s, 3H). MS (ESI+) m/z 413 (M+H)$^+$.

Example 150

4-[2-(3-fluorophenoxy)-5-(methylsulfonyl)phenyl]-6-methyl-1,6-dihydro-7H-pyrrolo[2,3-c]pyridin-7-one Example 150 was prepared according to the procedure used for the preparation of Example 138b, substituting 3-fluorophenol for 2,4-difluorophenol, to provide the title compound. $^1$H NMR (400 MHz, DMSO-d$_6$/D$_2$O) δ ppm 8.01 (t, J=3.4 Hz, 1H), 7.93 (dt, J=7.1, 3.5 Hz, 1H), 7.47-7.37 (m, 2H), 7.34 (t, J=3.3 Hz, 1H), 7.21 (t, J=6.3 Hz, 1H), 6.96 (dddd, J=26.2, 21.5, 8.3, 2.2 Hz, 3H), 6.30 (d, J=2.8 Hz, 1H), 3.57 (s, 3H), 3.27 (s, 3H). MS (ESI+) m/z 413 (M+H)$^+$.

Example 151

4-[2-(4-fluorophenoxy)-5-(methylsulfonyl)phenyl]-6-methyl-1,6-dihydro-7H-pyrrolo[2,3-c]pyridin-7-one Example 151 was prepared according to the procedure used for the preparation of Example 138b, substituting 4-fluorophenol for 2,4-difluorophenol, to provide the title compound. $^1$H NMR (400 MHz, DMSO-d$_6$/D$_2$O) δ ppm 7.98 (d, J=2.4 Hz, 1H), 7.89 (dd, J=8.7, 2.4 Hz, 1H), 7.43 (s, 1H), 7.34 (d, J=2.8 Hz, 1H), 7.31-7.22 (m, 2H), 7.22-7.10 (m, 2H), 7.04 (d, J=8.7 Hz, 1H), 6.31 (d, J=2.8 Hz, 1H), 3.59 (s, 3H), 3.25 (s, 3H). MS (ESI+) m/z 413 (M+H)$^+$.

Example 152

4-[2-(2-chlorophenoxy)-5-(methylsulfonyl)phenyl]-6-methyl-1,6-dihydro-7H-pyrrolo[2,3-c]pyridin-7-one Example 152 was prepared according to the procedure used for the preparation of Example 138b, substituting 2-chlorophenol for 2,4-difluorophenol, to provide the title compound. $^1$H NMR (400 MHz, DMSO-d$_6$/D$_2$O) δ ppm 8.02 (dd, J=7.0, 1.6 Hz, 1H), 7.96-7.85 (m, 1H), 7.65-7.57 (m, 1H), 7.47 (s, 1H), 7.44-7.34 (m, 2H), 7.33-7.21 (m, 2H), 6.92 (d, J=8.7 Hz, 1H), 6.37 (d, J=2.8 Hz, 1H), 3.59 (s, 3H), 3.26 (s, 3H). MS (ESI+) m/z 429 (M+H)$^+$.

Example 153

4-[2-(3-chlorophenoxy)-5-(methylsulfonyl)phenyl]-6-methyl-1,6-dihydro-7H-pyrrolo[2,3-c]pyridin-7-one Example 153 was prepared according to the procedure used for the preparation of Example 138b, substituting 3-chlorophenol for 2,4-difluorophenol, to provide the title compound. $^1$H NMR (400 MHz, DMSO-d$_6$/D$_2$O) δ ppm 8.01 (d, J=2.4 Hz, 1H), 7.99-7.88 (m, 1H), 7.43-7.37 (m, 2H), 7.35 (t, J=3.3 Hz, 1H), 7.27-7.19 (m, 2H), 7.16 (dd, J=10.2, 8.1 Hz, 1H), 7.08-6.93 (m, 1H), 6.30 (d, J=2.8 Hz, 1H), 3.57 (s, 3H), 3.27 (s, 3H). MS (ESI+) m/z 429 (M+H)$^+$.

Example 154

4-[2-(4-chlorophenoxy)-5-(methylsulfonyl)phenyl]-6-methyl-1,6-dihydro-7H-pyrrolo[2,3-c]pyridin-7-one Example 154 was prepared according to the procedure used for the preparation of Example 138b, substituting 4-chlorophenol for 2,4-difluorophenol, to provide the title compound. $^1$H NMR (400 MHz, DMSO-d$_6$/D$_2$O) δ ppm 8.00 (d, J=2.4 Hz, 1H), 7.91 (dd, J=8.3, 2.0 Hz, 1H), 7.56-7.38 (m, 3H), 7.34 (t, J=3.3 Hz, 1H), 7.19-7.07 (m, 3H), 6.29 (d, J=2.8 Hz, 1H), 3.58 (s, 3H), 3.26 (s, 3H). MS (ESI+) m/z 429 (M+H)$^+$.

Example 155

3-[2-(6-methyl-7-oxo-6,7-dihydro-1H-pyrrolo[2,3-c]pyridin-4-yl)-4-(methylsulfonyl)phenoxy]benzonitrile Example 155 was prepared according to the procedure used for the preparation of Example 138b, substituting 3-cyanophenol for 2,4-difluorophenol, to provide the title compound. $^1$H NMR (400 MHz, DMSO-d$_6$/D$_2$O) δ ppm 8.02 (d, J=2.4 Hz, 1H), 7.99-7.91 (m, 1H), 7.68-7.49 (m, 3H), 7.46-7.38 (m, 2H), 7.38-7.32 (m, 1H), 7.24 (d, J=8.6 Hz, 1H), 6.30 (d, J=2.8 Hz, 1H), 3.56 (s, 3H), 3.28 (s, 3H). MS (ESI+) m/z 420 (M+H)$^+$.

Example 156

4-[2-(6-methyl-7-oxo-6,7-dihydro-1H-pyrrolo[2,3-c]pyridin-4-yl)-4-(methylsulfonyl)phenoxy]benzonitrile Example 156 was prepared according to the procedure used for the preparation of Example 138b, substituting 4-cyanophenol for 2,4-difluorophenol, to provide the title compound. $^1$H NMR (400 MHz, DMSO-d$_6$/D$_2$O) δ ppm 8.05 (d, J=2.4 Hz, 1H), 8.02-7.94 (m, 1H), 7.80-7.73 (m, 2H), 7.38 (t, J=4.3 Hz, 2H), 7.33 (t, J=3.3 Hz, 1H), 7.17-7.03 (m, 2H), 6.25 (d, J=2.8 Hz, 1H), 3.54 (s, 3H), 3.29 (s, 3H). MS (ESI+) m/z 420 (M+H)$^+$.

Example 157

6-methyl-4-{5-(methylsulfonyl)-2-[3-(trifluoromethyl)phenoxy]phenyl}-1,6-dihydro-7H-pyrrolo[2,3-c]pyridin-7-one Example 157 was prepared according to the procedure used for the preparation of Example 138b, substituting 3-trifluorormethylphenol for 2,4-difluorophenol, to provide the title compound. $^1$H NMR (400 MHz, DMSO-d$_6$/D$_2$O) δ ppm 8.03 (d, J=2.4 Hz, 1H), 7.95 (dd, J=8.6, 2.4 Hz, 1H), 7.62-7.56 (m, 1H), 7.54-7.48 (m, 1H), 7.42 (d, J=7.1 Hz, 1H), 7.37-7.31 (m, 3H), 7.25 (d, J=8.6 Hz, 1H), 6.30 (d, J=2.8 Hz, 1H), 3.55 (s, 3H), 3.28 (s, 3H). MS (ESI+) m/z 463 (M+H)$^+$.

Example 158

4-[2-(cyclopropylmethoxy)-5-(methylsulfonyl)phenyl]-6-methyl-1,6-dihydro-7H-pyrrolo[2,3-c]pyridin-7-one Cyclopropylmethanol (0.014 g, 0.19 mmol) in tetrahydrofuran (2 mL) was treated with 60% sodium hydride (10.11 mg, 0.253 mmol). The reaction mixture was stirred at ambient temperature for 5 minutes. To this solution was added Example 138a (0.03 g, 0.063 mmol). The reaction mixture was heated at 60° C. for 16 hours. The solvent was removed, and the residue was purified by Preparative HPLC (C18, 10-80% CH$_3$CN/water (0.1% TFA)) to give the title compound (0.012 g, 0.032 mmol, 51.0% yield). $^1$H NMR (400

MHz, DMSO-d$_6$/D$_2$O) δ ppm 7.88 (dd, J=8.6, 2.5 Hz, 1H), 7.84 (d, J=2.4 Hz, 1H), 7.37 (s, 1H), 7.34 (d, J=2.4 Hz, 2H), 7.32 (d, J=3.5 Hz, 2H), 6.17 (d, J=2.8 Hz, 1H), 3.99 (d, J=6.8 Hz, 2H), 3.20 (s, 3H), 1.17-1.06 (m, 1H), 0.52-0.41 (m, 2H), 0.34-0.24 (m, 2H). MS (ESI+) m/z 373 (M+H)$^+$.

Example 159

N-[4-(2,4-difluorophenoxy)-3-(6-methyl-7-oxo-6,7-dihydro-1H-pyrrolo[2,3-d]pyridazin-4-yl)phenyl]methanesulfonamide Example 159 was prepared according to the procedure used for the preparation of Example 4 (Method A), substituting Example 148d for Example 3, to provide the title compound. $^1$H NMR (500 MHz, DMSO-d$_6$) δ ppm 12.72 (s, 1H), 9.79 (s, 1H), 7.45 (t, J=2.59 Hz, 1H), 7.40 (t, J=2.44 Hz, 1H), 7.31-7.38 (m, 2H), 7.11-7.17 (m, 1H), 6.89-7.03 (m, 1H), 6.39-6.40 (m, 1H), 3.70 (s, 3H), 3.02 (s, 3H). MS (ESI+) m/z 447.1 (M+H)$^+$.

Example 160

N-[4-(2,4-difluorophenoxy)-3-(6-methyl-7-oxo-6,7-dihydro-1H-pyrrolo[2,3-d]pyridazin-4-yl)phenyl]ethanesulfonamide Example 160 was prepared according to the procedure used for the preparation of Example 4 (Method A), substituting Example 148d for Example 3, and ethanesulfonyl chloride for methanesulfonyl chloride, respectively, to provide the title compound. $^1$H NMR (500 MHz, DMSO-d$_6$) δ ppm 12.72 (s, 1H), 9.86 (s, 1H), 7.45 (t, J=2.75 Hz, 1H), 7.41 (d, J=2.75 Hz, 1H), 7.31-7.40 (m, 2H), 7.10-7.16 (m, 1H), 6.98-7.03 (m, 1H), 6.38-6.39 (m, 1H), 3.70 (s, 3H), 3.11 (q, J=7.43 Hz, 2H), 1.23 (t, J=7.32 Hz, 3H). MS (ESI+) m/z 461.1 (M+H)$^+$.

Example 161

4-[2-(isoquinolin-5-yloxy)-5-(methylsulfonyl)phenyl]-6-methyl-1,6-dihydro-7H-pyrrolo[2,3-c]pyridin-7-one Example 161 was prepared according to the procedure used for the preparation of Example 138b, substituting isoquinolin-5-ol for 2,4-difluorophenol, to provide the TFA salt of the title compound. $^1$H NMR (400 MHz, DMSO-d$_6$/D$_2$O) δ ppm 9.68 (s, 1H), 8.58 (d, J=6.4 Hz, 1H), 8.30 (d, J=6.4 Hz, 1H), 8.11 (t, J=4.9 Hz, 2H), 8.00 (dd, J=8.6, 2.4 Hz, 1H), 7.78 (t, J=8.1 Hz, 1H), 7.55-7.46 (m, 2H), 7.40 (d, J=8.6 Hz, 1H), 7.33 (d, J=2.8 Hz, 1H), 6.39 (d, J=2.8 Hz, 1H), 3.97 (s, 1H), 3.47 (s, 3H), 3.31 (s, 3H). MS (ESI+) m/z 445 (M+H)$^+$.

Example 162

6-methyl-4-[5-(methylsulfonyl)-2-(quinolin-6-yloxy)phenyl]-1,6-dihydro-7H-pyrrolo[2,3-c]pyridin-7-one Example 162 was prepared according to the procedure used for the preparation of Example 138b, substituting quinolin-6-ol for 2,4-difluorophenol, to provide the TFA salt of the title compound. $^1$H NMR (400 MHz, DMSO-d$_6$/D$_2$O) δ ppm 9.03 (dd, J=4.8, 1.4 Hz, 1H), 8.71 (d, J=8.1 Hz, 1H), 8.15 (d, J=9.0 Hz, 1H), 8.08 (d, J=2.4 Hz, 1H), 7.99 (dd, J=8.6, 2.4 Hz, 1H), 7.88-7.80 (m, 1H), 7.74 (dt, J=3.7, 2.5 Hz, 2H), 7.45 (s, 1H), 7.37 (d, J=8.6 Hz, 1H), 7.32 (t, J=3.3 Hz, 1H), 6.34 (d, J=2.8 Hz, 1H), 3.53 (d, J=6.8 Hz, 3H), 3.30 (s, 3H). MS (ESI+) m/z 446 (M+H)$^+$.

Example 163

4-{2-[2-chloro-5-(trifluoromethyl)phenoxy]-5-(methylsulfonyl)phenyl}-6-methyl-1,6-dihydro-7H-pyrrolo[2,3-c]pyridin-7-one Example 163 was prepared according to the procedure used for the preparation of Example 138b, substituting 2-chloro-5-trifluoromethylphenol for 2,4-difluorophenol, to provide the title compound. $^1$H NMR (400 MHz, DMSO-d$_6$/D$_2$O) δ ppm 8.03 (d, J=2.4 Hz, 1H), 7.94 (dd, J=8.7, 2.4 Hz, 1H), 7.79 (d, J=8.3 Hz, 1H), 7.58 (dd, J=16.2, 8.4 Hz, 1H), 7.49 (d, J=1.8 Hz, 1H), 7.44 (s, 1H), 7.34 (d, J=2.8 Hz, 1H), 7.27-7.13 (m, 2H), 6.33 (d, J=2.9 Hz, 1H), 3.56 (s, 3H), 3.28 (s, 3H). MS (ESI+) m/z 496 (M+H)$^+$.

Example 164

4-{2-[2-fluoro-5-(trifluoromethyl)phenoxy]-5-(methylsulfonyl)phenyl}-6-methyl-1,6-dihydro-7H-pyrrolo[2,3-c]pyridin-7-one Example 164 was prepared according to the procedure used for the preparation of Example 138b, substituting 2-fluoro-5-trifluoromethylphenol for 2,4-difluorophenol, to provide the title compound. $^1$H NMR (400 MHz, DMSO-d$_6$/D$_2$O) δ ppm 8.01 (d, J=2.4 Hz, 1H), 7.93 (dd, J=8.6, 2.4 Hz, 1H), 7.67-7.55 (m, 3H), 7.43 (s, 1H), 7.34 (d, J=2.8 Hz, 1H), 7.23-7.15 (m, 2H), 6.29 (d, J=2.8 Hz, 1H), 3.57 (s, 3H), 3.27 (s, 3H). MS (ESI+) m/z 480 (M+H)$^+$.

Example 165

2-{4-[2-(6-methyl-7-oxo-6,7-dihydro-1H-pyrrolo[2,3-c]pyridin-4-yl)-4-(methylsulfonyl)phenoxy]phenyl}acetamide Example 165 was prepared according to the procedure used for the preparation of Example 138b, substituting 2-(4-hydroxyphenyl)acetamide for 2,4-difluorophenol, to provide the title compound. $^1$H NMR (400 MHz, DMSO-d$_6$/D$_2$O) δ ppm 7.97 (d, J=2.4 Hz, 1H), 7.88 (dd, J=8.6, 2.4 Hz, 1H), 7.43 (s, 1H), 7.36-7.30 (m, 3H), 7.09-7.00 (m, 3H), 6.31 (d, J=2.8 Hz, 1H), 3.59 (s, 3H), 3.39 (s, 2H), 3.24 (s, 3H). MS (ESI+) m/z 452 (M+H)$^+$.

Example 166

4-[2-(3-aminophenoxy)-5-(methylsulfonyl)phenyl]-6-methyl-1,6-dihydro-7H-pyrrolo[2,3-c]pyridin-7-one Example 166 was prepared according to the procedure used for the preparation of Example 138b, substituting 3-aminophenol for 2,4-difluorophenol, to provide the TFA salt of the title compound. $^1$H NMR (400 MHz, DMSO-d$_6$/D$_2$O) δ ppm 8.00 (d, J=2.4 Hz, 1H), 7.92 (dd, J=8.6, 2.4 Hz, 1H), 7.40 (s, 1H), 7.36-7.24 (m, 2H), 7.15 (d, J=8.6 Hz, 1H), 6.78 (dd, J=8.0, 1.9 Hz, 1H), 6.70-6.62 (m, 2H), 6.27 (d, J=2.8 Hz, 1H), 3.96 (s, 1H), 3.58 (s, 3H), 3.26 (s, 3H). MS (ESI+) m/z 410 (M+H)$^+$.

Example 167

6-methyl-4-[5-(methylsulfonyl)-2-(tetrahydrofuran-3-ylamino)phenyl]-1,6-dihydro-7H-pyrrolo[2,3-c]pyridin-7-one

Example 167a

N-(2-bromo-4-(methylsulfonyl)phenyl)tetrahydrofuran-3-amine

Example 167a was prepared according to the procedure used for the preparation of Example 147a, substituting tetrahydrofuran-3-amine for cyclohexanamine, to provide the title compound.

Example 167b

6-methyl-4-[5-(methylsulfonyl)-2-(tetrahydrofuran-3-ylamino)phenyl]-1,6-dihydro-7H-pyrrolo[2,3-c]pyridin-7-one Example 167b was prepared according to the procedure used for the preparation of Example 95d, substituting Example 167a for Example 95c, to provide the title compound. $^1$H NMR (500 MHz, DMSO-$d_6$) δ ppm 12.12 (s, 1H), 7.70 (dd, J=8.7, 2.29 Hz, 1H), 7.54 (d, J=2.44 Hz, 1H), 7.29 (t, J=2.75 Hz, 1H), 7.27 (s, 1H), 6.87 (d, J=8.85 Hz, 1H), 6.00 (t, J=2.29 Hz, 1H), 5.25 (br s, 1H), 4.17 (br s, 1H), 3.68 (q, J=7.32, Hz, 2H), 3.56 (s, 3H), 3.49 (dd, J=9, 3.51 Hz, 1H), 3.12 (s, 3H), 2.12-2.19 (m, 1H), 1.74-1.77 (m, 1H). MS (ESI+) m/z 388.2 (M+H)$^+$.

Example 168

4-[2-(2,4-difluorophenoxy)-5-(ethylsulfonyl)phenyl]-6-methyl-1,6-dihydro-7H-pyrrolo[2,3-c]pyridin-7-one

Example 168a

(3-bromo-4-fluorophenyl)(ethyl)sulfane

A mixture of 3-bromo-4-fluorobenzenethiol (3.89 g, 18.79 mmol) and sodium hydroxide (3.95 mL, 19.73 mmol) in MeOH was stirred at 0° C. for 10 minutes. To this solution was added iodoethane (1.803 mL, 22.54 mmol). The reaction mixture was stirred at ambient temperature for 6 hours. The solvent was removed, and the residue was partitioned between water and ethyl acetate. The aqueous layer was extracted with addition ethyl acetate three times. The combined organic layers were washed with saturated aqueous sodium chloride, dried over anhydrous magnesium sulfate, filtered, and concentrated to give the title compound (4.35 g, 18.50 mmol, 98% yield). It was used directly for the next reaction.

Example 168b

2-bromo-4-(ethylsulfonyl)-1-fluorobenzene

Example 168a (4.4 g, 18.71 mmol) in dichloromethane (250 mL) was cooled to 0° C. To this solution was treated with mCPBA (10.15 g, 41.2 mmol) portionwise. The reaction was stirred at ambient temperature for 6 hours. The solid from the reaction mixture was removed by filtration. The filtrate was washed with saturated aqueous sodium bicarbonate several times. The aqueous layer was then extracted with additional dichloromethane three times. The combined organic layers were washed with saturated aqueous sodium chloride, dried over anhydrous magnesium sulfate, filtered, and concentrated. The residue was purified by flash chromatography on silica gel eluting with 15% ethyl acetate/hexanes to afford the title compound (4.4 g, 16.47 mmol, 88% yield).

Example 168c

4-(5-(ethylsulfonyl)-2-fluorophenyl)-6-methyl-1-tosyl-1H-pyrrolo[2,3-c]pyridin-7(6H)-one Example 168c was prepared according to the procedure used for the preparation of Example 138a, substituting Example 168b for 2-bromo-1-fluoro-4-(methylsulfonyl)benzene, to provide the title compound.

Example 168d

4-[2-(2,4-difluorophenoxy)-5-(ethylsulfonyl)phenyl]-6-methyl-1,6-dihydro-7H-pyrrolo[2,3-c]pyridin-7-one Example 168d was prepared according to the procedure used for the preparation of Example 138b, substituting Example 168c for Example 138a, to provide the title compound. $^1$H NMR (500 MHz, DMSO-$d_6$) δ ppm 12.31 (s, 1H), 7.93 (d, J=2.44 Hz, 1H), 7.83 (dd, J=8.54, 2.44 Hz, 1H), 7.52-7.54 (m, 1H), 7.42-7.46 (m, 2H), 7.32 (t, J=2.75 Hz, 1H), 7.16-7.19 (m, 1H), 6.99 (d, J=8.54 Hz, 1H), 6.27-6.28 (m, 1H), 3.59 (s, 3H), 3.38 (q, J=7.32, Hz, 2H), 1.15 (t, J=7.32 Hz, 1H). MS (ESI+) m/z 445.2 (M+H)$^+$.

Example 169

4-{2-[(4,4-difluorocyclohexyl)oxy]-5-(ethylsulfonyl)phenyl}-6-methyl-1,6-dihydro-7H-pyrrolo[2,3-c]pyridin-7-one Example 169 was prepared according to the procedure used for the preparation of Example 158, substituting Example 168c for Example 138a, and 4,4-difluorocyclohexanol for cyclopropylmethanol, respectively, to provide the title compound. $^1$H NMR (500 MHz, DMSO-$d_6$) δ ppm 12.05 (s, 1H), 7.81-7.85 (m, 2H), 7.45 (d, J=8.85 Hz, 1H), 7.33 (s, 1H), 7.29 (t, J=2.75 Hz, 1H), 6.12-6.13 (m, 1H), 4.81 (s, 1H), 3.56 (s, 3H), 3.29 (q, J=7.32, Hz, 2H), 1.70-1.87 (m, 8H), 1.14 (t, J=7.32 Hz, 1H). MS (ESI+) m/z 451.2 (M+H)$^+$.

Example 170

4-{5-(ethylsulfonyl)-2-[(1-methylpiperidin-4-yl)oxy]phenyl}-6-methyl-1,6-dihydro-7H-pyrrolo[2,3-c]pyridin-7-one Example 170 was prepared according to the procedure used for the preparation of Example 158, substituting Example 168c for Example 138a, and 1-methylpiperidin-4-ol for cyclopropylmethanol, respectively, to provide the TFA salt of the title compound. $^1$H NMR (500 MHz, DMSO-$d_6$) δ ppm 12.13 (s, 1H), 7.81-7.87 (m, 2H), 7.46 (d, J=8.85 Hz, 1H), 7.34 (s, 1H), 7.32 (t, J=2.75 Hz, 1H), 6.11-6.12 (m, 1H), 4.86 (s, 1H), 3.56 (s, 3H), 3.30 (s, 3H), 3.29 (q, J=7.32, Hz, 2H), 3.24-3.29 (m, 1H), 3.04-3.10 (m, 1H), 2.25-2.29 (m, 2H), 1.91-2.05 (m, 2H), 1.14 (t, J=7.32 Hz, 1H). MS (ESI+) m/z 430.2 (M+H)$^+$.

Example 171

4-[2-(2,1,3-benzothiadiazol-4-yloxy)-5-(methylsulfonyl)phenyl]-6-methyl-1,6-dihydro-7H-pyrrolo[2,3-c]pyridin-7-one Example 171 was prepared according to the procedure used for the preparation of Example 138b, substituting benzo[c][1,2,5]thiadiazol-5-ol for 2,4-difluorophenol, to provide the title compound. $^1$H NMR (400 MHz, DMSO-$d_6$/$D_2$O) δ ppm 8.04 (d, J=2.4 Hz, 1H), 7.93 (d, J=8.4 Hz, 1H), 7.84 (dd, J=8.6, 2.4 Hz, 1H), 7.69 (dd, J=8.8, 7.5 Hz, 1H), 7.50 (s, 1H), 7.36 (d, J=7.1 Hz, 1H), 7.29 (d, J=2.8 Hz, 1H), 7.09 (d, J=8.7 Hz, 1H), 6.49 (d, J=2.8 Hz, 1H), 3.55 (s, 3H), 3.27 (s, 3H). MS (ESI$^+$) m/z 453 (M+H)$^+$.

Example 172

4-[2-(isoquinolin-7-yloxy)-5-(methylsulfonyl)phenyl]-6-methyl-1,6-dihydro-7H-pyrrolo[2,3-c]pyridin-7-one Example 172 was prepared according to the procedure used for the preparation of Example 138b, substituting isoquinolin-7-ol for 2,4-difluorophenol, to provide the title compound. $^1$H NMR (400 MHz, DMSO-$d_6$/$D_2$O) δ ppm 8.65 (s, 1H), 8.39 (s, 1H), 8.24 (d, J=8.9 Hz, 1H), 8.16-8.04 (m, 1H), 8.03 (dd, J=8.6, 2.4 Hz, 1H), 7.95-7.76 (m, 2H), 7.47 (dd, J=20.3, 11.7 Hz, 2H), 7.31 (t, J=5.9 Hz, 1H), 6.32 (d, J=2.8 Hz, 1H), 3.51 (s, 3H), 3.31 (s, 3H). MS (ESI+) m/z 446 (M+H)$^+$.

Example 173

4-[2-(2,5-difluorophenoxy)-5-(methylsulfonyl)phenyl]-6-methyl-1,6-dihydro-7H-pyrrolo[2,3-c]pyridin-7-one Example 173 was prepared according to the procedure used for the preparation of Example 138b, substituting 2,5-difluorophenol for 2,4-difluorophenol, to provide the title compound. $^1$H NMR (400 MHz, DMSO-$d_6$/$D_2$O) δ ppm 8.08-7.98 (m, 1H), 7.97-7.83 (m, 1H), 7.50-7.39 (m, 2H), 7.35 (t, J=3.3 Hz, 1H), 7.33-7.21 (m, 1H), 7.20-7.08 (m, 2H), 6.31 (d, J=2.8 Hz, 1H), 3.59 (s, 3H), 3.25 (d, J=6.7 Hz, 3H) MS (ESI+) m/z 431 (M+H)$^+$.

Example 174

4-[2-(3,4-difluorophenoxy)-5-(methylsulfonyl)phenyl]-6-methyl-1,6-dihydro-7H-pyrrolo[2,3-c]pyridin-7-one Example 174 was prepared according to the procedure used for the preparation of Example 138b, substituting 3,4-difluorophenol for 2,4-difluorophenol, to provide the title compound. $^1$H NMR (400 MHz, DMSO-$d_6$/$D_2$O) δ ppm 7.99 (d, J=2.4 Hz, 1H), 7.91 (dd, J=8.6, 2.4 Hz, 1H), 7.53-7.40 (m, 2H), 7.34 (d, J=2.8 Hz, 1H), 7.29 (ddd, J=11.4, 6.8, 2.9 Hz, 1H), 7.16 (d, J=8.7 Hz, 1H), 6.95 (dd, J=8.8, 5.0 Hz, 1H), 6.31 (d, J=2.8 Hz, 1H), 3.58 (s, 3H), 3.25 (s, 3H). MS (ESI+) m/z 431 (M+H)$^+$.

Example 175

6-methyl-4-{5-(methylsulfonyl)-2-[(1-oxo-2,3-dihydro-1H-inden-4-yl)oxy]phenyl}-1,6-dihydro-7H-pyrrolo[2,3-c]pyridin-7-one Example 175 was prepared according to the procedure used for the preparation of Example 138b, substituting 4-hydroxy-2,3-dihydro-1H-inden-1-one for 2,4-difluorophenol, to provide the title compound. $^1$H NMR (400 MHz, DMSO-$d_6$/$D_2$O) δ ppm 8.02 (d, J=2.4 Hz, 1H), 7.92 (dd, J=8.6, 2.4 Hz, 1H), 7.50-7.41 (m, 1H), 7.36 (d, J=2.8 Hz, 1H), 7.28 (dd, J=7.3, 1.4 Hz, 1H), 7.16 (d, J=8.6 Hz, 1H), 6.32 (d, J=2.8 Hz, 1H), 3.62-3.54 (m, 2H), 3.27 (s, 1H), 2.89-2.82 (m, 1H), 2.65-2.59 (m, 1H). MS (ESI+) m/z 449 (M+H)$^+$.

Example 176

4-[2-(3,5-difluorophenoxy)-5-(methylsulfonyl)phenyl]-6-methyl-1,6-dihydro-7H-pyrrolo[2,3-c]pyridin-7-one Example 176 was prepared according to the procedure used for the preparation of Example 138b, substituting 3,5-difluorophenol for 2,4-difluorophenol, to provide the title compound. $^1$H NMR (400 MHz, DMSO-$d_6$/$D_2$O) δ ppm 8.02 (d, J=2.4 Hz, 1H), 7.96 (dd, J=8.6, 2.4 Hz, 1H), 7.40 (s, 1H), 7.34 (dd, J=5.7, 2.8 Hz, 2H), 6.98 (tt, J=9.3, 2.3 Hz, 1H), 6.83-6.62 (m, 2H), 6.29 (d, J=2.8 Hz, 1H), 3.56 (s, 3H), 3.27 (s, 3H). MS (ESI+) m/z 431 (M+H)$^+$.

Example 177

6-methyl-4-[2-(4-methylphenoxy)-5-(methylsulfonyl)phenyl]-1,6-dihydro-7H-pyrrolo[2,3-c]pyridin-7-one Example 177 was prepared according to the procedure used for the preparation of Example 138b, substituting 4-methylphenol for 2,4-difluorophenol, to provide the title compound. $^1$H NMR (400 MHz, DMSO-$d_6$/$D_2$O) δ ppm 7.96 (d, J=2.4 Hz, 1H), 7.88-7.79 (m, 1H), 7.42 (s, 1H), 7.33 (d, J=2.8 Hz, 1H), 7.24 (d, J=8.4 Hz, 2H), 7.00 (dd, J=8.6, 4.3 Hz, 3H), 6.30 (d, J=2.8 Hz, 1H), 3.59 (s, 3H), 3.24 (s, 3H). MS (ESI+) m/z 409 (M+H)$^+$.

Example 178

4-[2-(2-methoxyphenoxy)-5-(methylsulfonyl)phenyl]-6-methyl-1,6-dihydro-7H-pyrrolo[2,3-c]pyridin-7-one Example 178 was prepared according to the procedure used for the preparation of Example 138b, substituting 2-methoxyphenol for 2,4-difluorophenol, to provide the title compound. $^1$H NMR (400 MHz, DMSO-$d_6$/$D_2$O) δ ppm 7.94 (d, J=2.4 Hz, 1H), 7.81 (dd, J=8.7, 2.4 Hz, 1H), 7.47 (s, 1H), 7.39-7.25 (m, 2H), 7.26-7.13 (m, 2H), 7.03 (td, J=7.6, 1.5 Hz, 1H), 6.75 (d, J=8.7 Hz, 1H), 6.43 (d, J=2.8 Hz, 1H), 3.61 (s, 3H), 3.23 (s, 3H). MS (ESI+) m/z 425 (M+H)$^+$.

Example 179

6-methyl-4-{2-[(2-methylpyridin-3-yl)oxy]-5-(methylsulfonyl)phenyl}-1,6-dihydro-7H-pyrrolo[2,3-c]pyridin-7-one Example 179 was prepared according to the procedure used for the preparation of Example 138b, substituting 2-methylpyridin-3-ol for 2,4-difluorophenol, to provide the title compound. ¹H NMR (400 MHz, DMSO-d₆/D₂O) δ ppm 8.38 (d, J=2.1 Hz, 1H), 8.05 (d, J=2.4 Hz, 1H), 7.98 (dd, J=8.5, 2.4 Hz, 1H), 7.73 (d, J=8.3 Hz, 1H), 7.53 (dd, J=8.4, 4.9 Hz, 1H), 7.43 (s, 1H), 7.35 (d, J=2.8 Hz, 1H), 7.28 (d, J=8.5 Hz, 1H), 6.30 (d, J=2.8 Hz, 1H), 3.56 (s, 3H), 3.28 (s, 3H), 2.41 (s, 3H). MS (ESI+) m/z 410 (M+H)⁺.

Example 180

4-{2-[3-(dimethylamino)phenoxy]-5-(methylsulfonyl)phenyl}-6-methyl-1,6-dihydro-7H-pyrrolo[2,3-c]pyridin-7-one Example 180 was prepared according to the procedure used for the preparation of Example 138b, substituting 3-(dimethylamino)phenol for 2,4-difluorophenol, to provide the title compound. ¹H NMR (400 MHz, DMSO-d₆/D₂O) δ ppm 7.97 (d, J=2.4 Hz, 1H), 7.88 (dd, J=8.6, 2.4 Hz, 1H), 7.42 (s, 1H), 7.34 (d, J=2.8 Hz, 1H), 7.26 (t, J=8.1 Hz, 1H), 7.08 (d, J=8.6 Hz, 1H), 6.68 (dd, J=8.3, 2.4 Hz, 1H), 6.52-6.43 (m, 2H), 6.31 (d, J=2.8 Hz, 1H), 3.58 (s, 3H), 3.24 (s, 3H), 2.90 (s, 6H). MS (ESI+) m/z 438 (M+H)⁺.

Example 181

6-methyl-4-{5-(methylsulfonyl)-2-[(1-oxo-2,3-dihydro-1H-inden-5-yl)oxy]phenyl}-1,6-dihydro-7H-pyrrolo[2,3-c]pyridin-7-one Example 181 was prepared according to the procedure used for the preparation of Example 138b, substituting 5-hydroxy-2,3-dihydro-1H-inden-1-one for 2,4-difluorophenol, to provide the title compound. ¹H NMR (400 MHz, DMSO-d₆/D₂O) δ ppm 8.04 (d, J=2.4 Hz, 1H), 7.98 (dd, J=8.6, 2.4 Hz, 1H), 7.60 (d, J=8.4 Hz, 1H), 7.40 (s, 1H), 7.34 (dd, J=6.9, 5.8 Hz, 2H), 7.11 (s, 1H), 7.08-6.97 (m, 1H), 6.28 (d, J=2.9 Hz, 1H), 3.54 (s, 3H), 3.29 (s, 3H), 3.00 (d, J=5.0 Hz, 2H), 2.62-2.58 (m, 2H). MS (ESI+) m/z 449 (M+H)

Example 182

6-methyl-4-{5-(methylsulfonyl)-2-[(3-oxo-2,3-dihydro-1H-inden-5-yl)oxy]phenyl}-1,6-dihydro-7H-pyrrolo[2,3-c]pyridin-7-one Example 182 was prepared according to the procedure used for the preparation of Example 138b, substituting 6-hydroxy-2,3-dihydro-1H-inden-1-one for 2,4-difluorophenol, to provide the title compound ¹H NMR (400 MHz, DMSO-d₆/D₂O) δ ppm 8.01 (d, J=2.5 Hz, 1H), 7.92 (d, J=8.6 Hz, 1H), 7.61 (d, J=8.7 Hz, 1H), 7.42 (d, J=14.0 Hz, 2H), 7.34 (d, J=2.8 Hz, 1H), 7.22-7.10 (m, 2H), 6.30 (d, J=2.8 Hz, 1H), 3.56 (s, 3H), 3.26 (s, 3H), 3.06 (s, 2H), 2.69 (s, 3H). MS (ESI+) m/z 449 (M+H)⁺.

Example 183

2-[2-(6-methyl-7-oxo-6,7-dihydro-1H-pyrrolo[2,3-c]pyridin-4-yl)-4-(methylsulfonyl)phenoxy]benzonitrile Example 183 was prepared according to the procedure used for the preparation of Example 138b, substituting 2-cyanophenol for 2,4-difluorophenol, to provide the title compound. ¹H NMR (400 MHz, DMSO-d₆/D₂O) δ ppm 8.06 (d, J=2.4 Hz, 1H), 7.99 (dd, J=8.5, 2.4 Hz, 1H), 7.81 (dd, J=7.7, 1.6 Hz, 1H), 7.67-7.59 (m, 1H), 7.41 (s, 1H), 7.39-7.24 (m, 3H), 7.09 (d, J=8.4 Hz, 1H), 6.30 (d, J=2.8 Hz, 1H), 3.56 (s, 3H), 3.29 (s, 3H). MS (ESI+) m/z 420 (M+H)⁺.

Example 184

4-[2-(3-chloro-2-fluorophenoxy)-5-(methylsulfonyl)phenyl]-6-methyl-1,6-dihydro-7H-pyrrolo[2,3-c]pyridin-7-one Example 184 was prepared according to the procedure used for the preparation of Example 138b, substituting 2-fluoro-3chlorophenol for 2,4-difluorophenol, to provide the title compound. ¹H NMR (400 MHz, DMSO-d₆/D₂O) δ ppm 8.00 (d, J=2.4 Hz, 1H), 7.92 (dd, J=8.6, 2.4 Hz, 1H), 7.47-7.41 (m, 2H), 7.35 (d, J=2.8 Hz, 1H), 7.28-7.23 (m, 2H), 7.13 (d, J=8.6 Hz, 1H), 6.28 (d, J=2.8 Hz, 1H), 3.59 (s, 3H), 3.26 (s, 3H). MS (ESI+) m/z 447 (M+H)⁺.

Example 185

6-methyl-4-[5-(methylsulfonyl)-2-(naphthalen-1-yloxy)phenyl]-1,6-dihydro-7H-pyrrolo[2,3-c]pyridin-7-one Example 185 was prepared according to the procedure used for the preparation of Example 138b, substituting naphthalen-1-ol for 2,4-difluorophenol, to provide the title compound. ¹H NMR (400 MHz, DMSO-d₆/D₂O) δ ppm 8.02 (d, J=2.4 Hz, 1H), 7.99 (d, J=8.9 Hz, 2H), 7.96-7.87 (m, 2H), 7.86 (d, J=8.0 Hz, 1H), 7.59-7.44 (m, 4H), 7.36-7.28 (m, 2H), 7.15 (d, J=8.6 Hz, 1H), 6.37 (d, J=2.8 Hz, 1H), 3.58 (s, 3H), 3.26 (s, 3H). MS (ESI+) m/z 445 (M+H)⁺.

Example 186

4-[2-(2-fluoro-5-methylphenoxy)-5-(methylsulfonyl)phenyl]-6-methyl-1,6-dihydro-7H-pyrrolo[2,3-c]pyridin-7-one Example 186 was prepared according to the procedure used for the preparation of Example 138b, substituting 2-fluoro-5methylphenol for 2,4-difluorophenol, to provide the title compound. ¹H NMR (400 MHz, DMSO-d₆/D₂O) δ ppm 7.98 (d, J=2.4 Hz, 1H), 7.89 (dd, J=8.6, 2.4 Hz, 1H), 7.43 (s, 1H), 7.35 (d, J=2.8 Hz, 1H), 7.27 (dd, J=10.9, 8.1 Hz, 1H), 7.14-7.06 (m, 2H), 6.98 (d, J=8.6 Hz, 1H), 6.31 (d, J=2.8 Hz, 1H), 3.60 (s, 3H), 3.25 (s, 3H), 2.27 (s, 3H). MS (ESI+) m/z 427 (M+H)⁺.

Example 187

4-[2-(5-fluoro-2-methylphenoxy)-5-(methylsulfonyl)phenyl]-6-methyl-1,6-dihydro-7H-pyrrolo[2,3-c]pyridin-7-one Example 187 was prepared according to the procedure used for the preparation of Example 138b, substituting 5-fluoro-2-methylphenol for 2,4-difluorophenol, to provide the title compound. ¹H NMR (400 MHz, DMSO-d₆/D₂O) δ ppm 8.11-7.96 (m, 1H), 7.91 (dt, J=5.1, 2.8 Hz, 1H), 7.43 (s, 1H), 7.38-7.28 (m, 2H), 7.07-6.91 (m, 2H), 6.91-6.81 (m, 1H), 6.31 (t, J=3.9 Hz, 1H), 3.58 (s, 3H), 3.26 (s, 3H), 2.04 (s, 3H). MS (ESI+) m/z 427 (M+H)+.

Example 188

6-methyl-4-[5-(methylsulfonyl)-2-(quinolin-7-yloxy) phenyl]-1,6-dihydro-7H-pyrrolo[2,3-c]pyridin-7-one Example 188 was prepared according to the procedure used for the preparation of Example 138b, substituting quinolin-7-ol for 2,4-difluorophenol, to provide the title compound. $^1$H NMR (400 MHz, DMSO-$d_6$/$D_2$O) δ ppm 8.97 (s, 1H), 8.67 (d, J=8.5 Hz, 1H), 8.12 (dd, J=12.8, 5.7 Hz, 2H), 8.02 (dd, J=8.6, 2.4 Hz, 1H), 7.69 (dd, J=8.3, 4.8 Hz, 1H), 7.55-7.41 (m, 4H), 7.32 (d, J=2.8 Hz, 1H), 6.32 (s, 1H), 3.50 (d, J=16.9 Hz, 3H), 3.30 (d, J=9.2 Hz, 3H). MS (ESI+) m/z 446 (M+H)+.

Example 189

4-[2-(4-chloro-3-fluorophenoxy)-5-(methylsulfonyl) phenyl]-6-methyl-1,6-dihydro-7H-pyrrolo[2,3-c] pyridin-7-one Example 189 was prepared according to the procedure used for the preparation of Example 138b, substituting 3-fluoro-4-chlorophenol for 2,4-difluorophenol, to provide the title compound. $^1$H NMR (400 MHz, DMSO-$d_6$/$D_2$O) δ ppm 8.01 (t, J=3.5 Hz, 1H), 7.99-7.90 (m, 1H), 7.68-7.52 (m, 1H), 7.40 (s, 1H), 7.33 (d, J=2.8 Hz, 1H), 7.29-7.24 (m, 1H), 7.20 (dd, J=10.3, 2.7 Hz, 1H), 7.00-6.86 (m, 1H), 6.29 (t, J=3.4 Hz, 1H), 3.57 (s, 3H), 3.27 (s, 3H). MS (ESI+) m/z 447 (M+H)+.

Example 190

6-methyl-4-[5-(methylsulfonyl)-2-(pyridin-3-yloxy) phenyl]-1,6-dihydro-7H-pyrrolo[2,3-c]pyridin-7-one Example 190 was prepared according to the procedure used for the preparation of Example 138b, substituting pyridin-3-ol for 2,4-difluorophenol, to provide the title compound. $^1$H NMR (400 MHz, DMSO-$d_6$/$D_2$O) δ ppm 8.03 (d, J=2.3 Hz, 1H), 8.01-7.90 (m, 1H), 7.72-7.64 (m, 1H), 7.42 (d, J=7.2 Hz, 1H), 7.37-7.30 (m, 1H), 7.30-7.15 (m, 1H), 6.36-6.24 (m, 1H), 3.56 (s, 3H), 3.27 (s, 3H). MS (ESI+) m/z 395 (M+H)+.

Example 191

4-[2-(2,3-dihydro-1H-inden-5-yloxy)-5-(methylsulfonyl)phenyl]-6-methyl-1,6-dihydro-7H-pyrrolo[2,3-c]pyridin-7-one Example 191 was prepared according to the procedure used for the preparation of Example 138b, substituting 2,3-dihydro-1H-inden-5-ol for 2,4-difluorophenol, to provide the title compound. $^1$H NMR (400 MHz, DMSO-$d_6$/$D_2$O) δ ppm 7.96 (d, J=2.4 Hz, 1H), 7.86 (dd, J=8.6, 2.4 Hz, 1H), 7.42 (s, 1H), 7.34 (d, J=2.8 Hz, 1H), 7.26 (d, J=8.1 Hz, 1H), 7.00 (d, J=8.7 Hz, 2H), 6.98 (d, J=2.2 Hz, 1H), 6.85 (dd, J=8.1, 2.3 Hz, 1H), 6.31 (d, J=2.8 Hz, 1H), 3.59 (s, 3H), 3.23 (s, 3H), 2.88-2.79 (m, 4H), 2.03 (p, J=7.4 Hz, 2H). MS (ESI+) m/z 435 (M+H)+.

Example 192

6-methyl-4-{5-(methylsulfonyl)-2-[4-(propan-2-yl) phenoxy]phenyl}-1,6-dihydro-7H-pyrrolo[2,3-c] pyridin-7-one Example 192 was prepared according to the procedure used for the preparation of Example 138b, substituting 4-isopropylphenol for 2,4-difluorophenol, to provide the title compound. $^1$H NMR (400 MHz, DMSO-$d_6$/$D_2$O) δ ppm 7.97 (d, J=2.4 Hz, 1H), 7.88 (dd, J=8.6, 2.4 Hz, 1H), 7.42 (s, 1H), 7.33 (d, J=2.8 Hz, 1H), 7.32-7.26 (m, 2H), 7.06-6.98 (m, 3H), 6.30 (d, J=2.8 Hz, 1H), 3.58 (s, 3H), 3.24 (s, 3H), 2.89 (p, J=6.9 Hz, 1H), 1.19 (d, J=6.9 Hz, 6H) MS (ESI+) m/z 437 (M+H)+.

Example 193

4-[2-(isoquinolin-8-yloxy)-5-(methylsulfonyl)phenyl]-6-methyl-1,6-dihydro-7H-pyrrolo[2,3-c]pyridin-7-one Example 193 was prepared according to the procedure used for the preparation of Example 138b, substituting isoquinolin-8-ol for 2,4-difluorophenol, to provide the title compound. $^1$H NMR (400 MHz, DMSO-$d_6$/$D_2$O) δ ppm 8.34 (bs, 1H), 8.12 (d, J=2.3 Hz, 1H), 8.05 (dd, J=8.4, 2.4 Hz, 1H), 7.86 (t, J=7.9 Hz, 1H), 7.79 (d, J=8.2 Hz, 1H), 7.55 (d, J=8.5 Hz, 1H), 7.48 (s, 1H), 7.32 (d, J=2.6 Hz, 1H), 7.17-7.11 (m, 1H), 6.40 (d, J=2.6 Hz, 1H), 3.44 (s, 3H), 3.32 (s, 3H). MS (ESI+) m/z 446 (M+H)+.

Example 194

6-methyl-4-[5-(methylsulfonyl)-2-(3,4,5-trifluorophenoxy)phenyl]-1,6-dihydro-7H-pyrrolo[2,3-c] pyridin-7-one Example 194 was prepared according to the procedure used for the preparation of Example 138b, substituting 3,4,5-trifluorophenol for 2,4-difluorophenol, to provide the title compound. $^1$H NMR (400 MHz, DMSO-$d_6$/$D_2$O) δ ppm 8.00 (d, J=2.4 Hz, 1H), 7.94 (dd, J=8.6, 2.4 Hz, 1H), 7.41 (s, 1H), 7.34 (d, J=2.8 Hz, 1H), 7.28 (d, J=8.6 Hz, 1H), 7.18-7.10 (m, 2H), 6.31 (d, J=2.8 Hz, 1H), 3.57 (s, 3H), 3.26 (s, 3H). MS (ESI+) m/z 449 (M+H)+.

Example 195

4-(2-benzylphenyl)-6-methyl-1,6-dihydro-7H-pyrrolo[2,3-c]pyridin-7-one

Example 195 was prepared according to the procedure used for the preparation of Example 95d, substituting 1-benzyl-2-bromobenzene for Example 95c, to provide the title compound. $^1$H NMR (500 MHz, DMSO-$d_6$) δ ppm 12.08 (s, 1H), 7.23-7.34 (m, 5H), 7.16-7.19 (m, 2H), 7.09-7.12 (m, 1H), 6.92-6.93 (m, 3H), 5.95 (t, J=2.29 Hz, 1H), 3.89 (s, 2H), 3.47 (s, 3H). MS (ESI+) m/z 315.3 (M+H)+.

Example 196

4-(biphenyl-2-yl)-6-methyl-1,6-dihydro-7H-pyrrolo [2,3-c]pyridin-7-one

Example 196 was prepared according to the procedure used for the preparation of Example 95d, substituting biphenyl-2-ylboronic acid for Example 6a and Example 1e for Example 95c, to provide the title compound. $^1$H NMR (500 MHz, DMSO-d$_6$) δ ppm 11.88 (s, 1H), 7.44-7.49 (m, 4H), 7.18-7.24 (m, 4H), 7.13-7.16 (m, 1H), 7.08 (t, J=2.75 Hz, 1H), 6.93 (s, 1H), 5.77-5.78 (m, 1H), 3.38 (s, 3H). MS (ESI+) m/z 301.2 (M+H)$^+$.

Example 197

4-[2-(1,4-dioxaspiro[4.5]dec-8-yloxy)-5-(ethylsulfonyl)phenyl]-6-methyl-1,6-dihydro-7H-pyrrolo[2,3-c]pyridin-7-one Example 197 was prepared according to the procedure used for the preparation of Example 158, substituting Example 168c for Example 138a, and 1,4-dioxaspiro[4.5]decan-8-ol for cyclopropylmethanol, respectively, to provide the title compound. $^1$H NMR (500 MHz, DMSO-d$_6$) δ ppm 12.05 (s, 1H), 7.79-7.81 (m, 2H), 7.40-7.42 (m, 1H), 7.28-7.34 (m, 2H), 6.6.12-6.13 (m, 1H), 4.70-4.73 (m, 1H), 3.79-3.34 (m, 3H), 3.65 (s, 3H), 3.26-3.31 (m, 2H), 1.99-2.21 (m, 1H), 1.67-1.99 (m, 2H), 1.48-1.52 (m, 3H), 1.14 (t, J=7.32 Hz, 3H). MS (ESI+) m/z 473.2 (M+H)$^+$.

Example 198

4-[2-(cyclopropylmethoxy)-5-(ethylsulfonyl)phenyl]-6-methyl-1,6-dihydro-7H-pyrrolo[2,3-c]pyridin-7-one Example 198 was prepared according to the procedure used for the preparation of Example 158, substituting Example 168c for Example 138a to provide the title compound. $^1$H NMR (500 MHz, DMSO-d$_6$) δ ppm 12.04 (s, 1H), 7.79-7.82 (m, 2H), 7.37 (s, 1H), 7.29-7.33 (m, 2H), 6.13-6.14 (m, 1H), 3.99 (d, J=6.71 Hz, 2H), 3.58 (s, 3H), 3.27 (q, J=7.32 Hz, 2H), 1.11-1.14 (m, 4H), 0.45-0.048 (m, 2H), 0.26-0.29 (m, 2H). MS (ESI+) m/z 387.2 (M+H)$^+$.

Example 199

4-{5-(ethylsulfonyl)-2-[(4-oxocyclohexyl)oxy]phenyl}-6-methyl-1,6-dihydro-7H-pyrrolo[2,3-c]pyridin-7-one Example 197 (0.192 g, 0.406 mmol) was treated with 4.0 N hydrogen chloride in dioxane (1.016 mL, 4.06 mmol), tetrahydrofuran (10 mL), and water (2 mL). The reaction mixture was heated at 60° C. for 2 hours. The solvent was removed, and the residue was purified by reverse phase HPLC (C18, 10-80% CH$_3$CN/water (0.1% TFA)) to give the title compound (0.154 g, 0.359 mmol, 88% yield). $^1$H NMR (500 MHz, DMSO-d$_6$) δ ppm 12.05 (s, 1H), 7.82-7.86 (m, 2H), 7.51 (d, J=8.85 Hz, 1H), 7.34 (s, 1H), 7.28 (t, J=2.75 Hz, 1H), 6.14 (t, J=2.29 Hz, 1H), 4.97-4.99 (m, 1H), 3.56 (s, 3H), 3.30 (q, J=7.32 Hz, 2H), 1.96-2.24 (m, 8H), 1.15 (t, J=7.48 Hz, 3H). MS (ESI+) m/z 429.2 (M+H)$^+$.

Example 200

4-{2-[(cyclopropylmethyl)amino]-5-(ethylsulfonyl)phenyl}-6-methyl-1,6-dihydro-7H-pyrrolo[2,3-c]pyridin-7-one Example 200a 2-bromo-N-(cyclopropylmethyl)-4-(ethylsulfonyl)aniline Example 200a was prepared according to the procedure used for the preparation of Example 147a, substituting cyclopropylmethanamine for cyclohexanamine, and Example 168b for 2-bromo-1-fluoro-4-(methylsulfonyl)benzene to provide the title compound.

Example 200b

4-{2-[(cyclopropylmethyl)amino]-5-(ethylsulfonyl)phenyl}-6-methyl-1,6-dihydro-7H-pyrrolo[2,3-c]pyridin-7-one Example 200b was prepared according to the procedure used for the preparation of Example 95d, substituting Example 200a for Example 95c, to provide the title compound. $^1$H NMR (500 MHz, DMSO-d$_6$) δ ppm 12.14 (s, 1H), 7.62 (dd, J=8.7, 2.29 Hz, 1H), 7.45 (d, J=2.14 Hz, 1H), 7.30 (t, J=2.75 Hz, 1H), 7.26 (s, 1H), 6.86 (J=8.85 Hz, 1H), 6.00-6.01 (m, 1H), 5.50 (br s, 1H), 3.56 (s, 3H), 3.16 (q, J=7.12 Hz, 2H), 3.04 (d, J=6.71 Hz, 2H), 1.15 (t, J=7.48 Hz, 3H), 0.97-1.04 (m, 1H), 0.36-0.41 (m, 2H), 0.14-0.18 (m, 2H). MS (ESI+) m/z 386.2 (M+H)$^+$.

Example 201

6-methyl-4-{5-(methylsulfonyl)-2-[(tetrahydrofuran-3-ylmethyl)amino]phenyl}-1,6-dihydro-7H-pyrrolo[2,3-c]pyridin-7-one Example 201a 2-bromo-4-(ethylsulfonyl)-N-((tetrahydrofuran-3-yl)methyl)aniline Example 200a was prepared according to the procedure used for the preparation of Example 147a, substituting (tetrahydrofuran-3-yl)methanamine for cyclohexanamine, and Example 168b for 2-bromo-1-fluoro-4-(methylsulfonyl)benzene to provide the title compound.

Example 201b 6-methyl-4-{5-(methylsulfonyl)-2-[(tetrahydrofuran-3-ylmethyl)amino]phenyl}-1,6-dihydro-7H-pyrrolo[2,3-c]pyridin-7-one Example 201b was prepared according to the procedure used for the preparation of Example 95d, substituting Example 201a for Example 95c, to provide the title compound. $^1$H NMR (500 MHz, DMSO-d$_6$) δ ppm 12.10 (s, 1H), 7.67 (dd, J=8.85, 2.44 Hz, 1H), 7.50 (d, J=2.14 Hz, 1H), 7.28 (t, J=2.9 Hz, 1H), 7.23 (s, 1H), 6.84 (J=8.85 Hz, 1H), 5.95-5.97 (m, 1H), 5.70 (br s, 1H), 3.55-3.70 (m, 7H), 3.38 (dd, J=8.54, 4.88 Hz, 2H), 3.10 (m, 5H), 1.84-1.92 (m, 1H), 1.47-1.55 (m, 1H). MS (ESI+) m/z 402.2 (M+H)$^+$.

Example 202

4-{5-(ethylsulfonyl)-2-[(cis-4-hydroxycyclohexyl)oxy]phenyl}-6-methyl-1,6-dihydro-7H-pyrrolo[2,3-c]pyridin-7-one A mixture of Example 199 (0.052 g, 0.121 mmol) and sodium tetrahydroborate (6.89 mg, 0.182 mmol) in tetrahydrofuran (5 mL) was heated at 60° C. for 2 hours. The solvent was removed, and the solid was treated with MeOH and a couple of drops of TFA. The resulting solution was purified by Preparative HPLC (C18, 10-80% CH$_3$CN/water (0.1% TFA)) to give the title compound (second eluting peak, 0.036 g, 0.084 mmol, 68.9% yield). $^1$H NMR (500 MHz, DMSO-$d_6$) δ ppm 12.06 (s, 1H), 7.78-7.82 (m, 2H), 7.36-7.38 (m, 2H), 7.30 (t, J=2.75 Hz, 1H), 6.14-6.16 (m, 1H), 4.62-4.63 (m, 1H), 3.51-3.58 (m, 5H), 3.25-3.31 (m, 2H), 1.75-1.81 (m, 2H), 1.50-1.64 (m, 4H), 1.32-1.40 (m, 2H), 1.14 (t, J=7.32 Hz, 3H). MS (ESI+) m/z 431.2 (M+H)$^+$.

Example 203

4-{5-(ethylsulfonyl)-2-[(trans-4-hydroxycyclohexyl)oxy]phenyl}-6-methyl-1,6-dihydro-7H-pyrrolo[2,3-c]pyridine-7-one The title compound (first eluting peak) was isolated as a minor product during the preparation of Example 202. $^1$H NMR (500 MHz, DMSO-$d_6$) δ ppm 12.02 (s, 1H), 7.77-7.81 (m, 2H), 7.40 (d, J=8.54 Hz, 1H), 7.31 (s, 1H), 7.28 (t, J=2.75 Hz, 1H), 6.09-6.11 (m, 1H), 4.53-4.55 (m, 1H), 3.56 (s, 3H), 3.27 (q, J=7.32 Hz, 2H), 1.95-2.00 (m, 2H), 1.68-1.71 (m, 4H), 1.27-1.38 (m, 4H), 1.13 (t, J=7.32 Hz, 3H). MS (ESI+) m/z 431.2 (M+H)$^+$.

Example 204

4-[2-(cyclopropylmethoxy)-5-(ethylsulfonyl)phenyl]-6-methyl-1,6-dihydro-7H-pyrrolo[2,3-d]pyridazin-7-one Example 204a 2-bromo-1-(cyclopropylmethoxy)-4-(ethylsulfonyl)benzene Example 204a was prepared according to the procedure used for the preparation of Example 158, substituting Example 168b for Example 138a, to provide the title compound.

Example 204b 2-(2-(cyclopropylmethoxy)-5-(ethylsulfonyl)phenyl)-4,4,5,5-tetramethyl-1,3,2-dioxaborolane Example 204b was prepared according to the procedure used for the preparation of Example 6a, substituting Example 204a for Example 1e, to provide the title compound.

Example 204c

4-[2-(cyclopropylmethoxy)-5-(ethylsulfonyl)phenyl]-6-methyl-1,6-dihydro-7H-pyrrolo[2,3-d]pyridazin-7-one Example 204c was prepared according to the procedure used for the preparation of Example 95d, substituting Example 80b for Example 95c, and Example 204b for Example 6a, respectively, to provide the title compound. $^1$H NMR (500 MHz, DMSO-$d_6$) δ ppm 12.67 (s, 1H), 7.92 (dd, J=8.85, 2.44 Hz, 1H), 7.83 (d, J=2.44 Hz, 1H), 7.43 (t, J=2.75 Hz, 1H), 7.40 (d, J=8.85 Hz, 1H), 6.29-6.30 (m, 1H), 4.02 (d, J=7.02 Hz, 2H), 3.80 (s, 3H), 3.29 (q, J=7.12 Hz, 2H), 1.12 (t, J=7.32 Hz, 3H), 1.01-1.08 (m, 1H), 0.40-0.45 (m, 2H), 0.21-0.25 (m, 2H). MS (ESI+) m/z 388.0 (M+H)$^+$.

Example 205

6-methyl-4-[5-(methylsulfonyl)-2-(tetrahydrofuran-3-yloxy)phenyl]-1,6-dihydro-7H-pyrrolo[2,3-c]pyridin-7-one Example 205 was prepared according to the procedure used for the preparation of Example 158, substituting tetrahydrofuran-3-ol for cyclopropylmethanol, to provide the title compound. $^1$H NMR (500 MHz, DMSO-$d_6$) δ ppm 12.03 (s, 1H), 7.85-7.89 (m, 2H), 7.31-7.33 (m, 1H), 7.28 (t, J=2.75 Hz, 1H), 6.11-6.12 (m, 1H), 5.17-5.20 (m, 1H), 3.89-3.91 (m, 2H), 3.63-3.70 (m, 3H), 3.57 (s, 3H), 3.22 (s, 3H), 2.17-2.26 (m, 1H), 1.85-1.91 (m, 1H). MS (ESI+) m/z 389.1 (M+H)$^+$.

Example 206

4-{2-[(3-fluorooxetan-3-yl)methoxy]-5-(methylsulfonyl)phenyl}-6-methyl-1,6-dihydro-7H-pyrrolo[2,3-c]pyridin-7-one Example 206 was prepared according to the procedure used for the preparation of Example 158, substituting (3-fluorooxetan-3-yl)methanol for cyclopropylmethanol, to provide the title compound. $^1$H NMR (500 MHz, DMSO-$d_6$) δ ppm 12.06 (s, 1H), 7.90-7.93 (m, 2H), 7.42 (d, J=8.54 Hz, 1H), 7.37 (s, 1H), 7.30 (t, J=2.75 Hz, 1H), 6.16-6.17 (m, 1H), 4.52-4.64 (m, 8H), 3.56 (s, 3H), 3.23 (s, 3H). MS (ESI+) m/z 407.1 (M+H)$^+$.

Example 207

6-(cyclopropylmethoxy)-5-(6-methyl-7-oxo-6,7-dihydro-1H-pyrrolo[2,3-c]pyridin-4-yl)pyridine-3-sulfonamide Example 207a 5-bromo-6-(cyclopropylmethoxy)pyridine-3-sulfonamide Example 207a was prepared according to the procedure used for the preparation of Example 29a, substituting 86a for Example 2a, and cyclopropylmethanol for tetrahydro-2H-pyran-4-ol, to provide the title compound.

Example 207b 6-(cyclopropylmethoxy)-5-(6-methyl-7-oxo-6,7-dihydro-1H-pyrrolo[2,3-c]pyridin-4-yl)pyridine-3-sulfonamide Example 207b was prepared according to the procedure used for the preparation of Example 95d, substituting Example 207a for Example 95c, to provide the title compound. $^1$H NMR (500 MHz, DMSO-$d_6$) δ ppm 12.12 (s, 1H), 8.52 (d, J=2.44 Hz, 1H), 8.12 (d, J=2.44 Hz, 1H), 7.44-7.45 (m, 3H), 7.33 (t, J=2.75 Hz, 1H), 6.22-6.24 (m, 1H), 4.23 (d, J=7.02 Hz, 2H), 3.58 (s, 3H), 1.14-1.24 (m, 1H), 0.47-0.52 (m, 2H), 0.29-0.33 (m, 2H). MS (ESI+) m/z 374.9 (M+H)+.

Example 208

6-(cyclopropylmethoxy)-N-methyl-5-(6-methyl-7-oxo-6,7-dihydro-1H-pyrrolo[2,3-c]pyridin-4-yl)pyridine-3-sulfonamide The title compound was isolated as a minor product during the preparation of Example 207b. $^1$H NMR (500 MHz, DMSO-d$_6$) δ ppm 12.12 (s, 1H), 8.49 (s, 1H), 8.05 (d, J=2.44 Hz, 1H), 7.53 (q, J=4.88 Hz, 1H), 7.46 (s, 1H), 7.33 (t, J=2.75 Hz, 1H), 6.21-6.22 (m, 1H), 4.25 (d, J=7.32 Hz, 2H), 3.58 (s, 3H), 2.47 (d, J=4.88 Hz, 3H), 1.14-1.24 (m, 1H), 0.47-0.52 (m, 2H), 0.29-0.33 (m, 2H). MS (ESI+) m/z 389.2 (M+H)+.

Example 209

6-[(cyclopropylmethyl)amino]-5-(6-methyl-7-oxo-6,7-dihydro-1H-pyrrolo[2,3-c]pyridin-4-yl)pyridine-3-sulfonamide Example 209a 5-bromo-6-(cyclopropylmethylamino)pyridine-3-sulfonamide Example 209a was prepared according to the procedure used for the preparation of Example 96a, substituting cyclopropylmethanamine for cyclohexanamine, to provide the title compound.

Example 209b

6-[(cyclopropylmethyl)amino]-5-(6-methyl-7-oxo-6,7-dihydro-1H-pyrrolo[2,3-c]pyridin-4-yl)pyridine-3-sulfonamide Example 209b was prepared according to the procedure used for the preparation of Example 95d, substituting Example 209a for Example 95c, to provide the title compound. $^1$H NMR (500 MHz, DMSO-d$_6$) δ ppm 12.17 (s, 1H), 8.38 (d, J=2.44 Hz, 1H), 7.69 (d, J=2.44 Hz, 1H), 7.32 (t, J=2.75 Hz, 1H), 7.30 (s, 1H), 7.18 (br s, 2H), 6.62 (s, 1H), 6.05-6.06 (m, 1H), 3.56 (s, 3H), 3.22 (d, J=3.97 Hz, 2H), 1.06-1.10 (m, 1H), 0.34-0.38 (m, 2H), 0.15-0.17 (m, 2H). MS (ESI+) m/z 374.2 (M+H)+.

Example 210

6-[(cyclopropylmethyl)amino]-N-methyl-5-(6-methyl-7-oxo-6,7-dihydro-1H-pyrrolo[2,3-c]pyridin-4-yl)pyridine-3-sulfonamide The title compound was isolated as a minor product during the preparation of Example 209b. $^1$H NMR (500 MHz, DMSO-d$_6$) δ ppm 12.17 (s, 1H), 8.35 (d, J=2.44 Hz, 1H), 7.60 (d, J=2.44 Hz, 1H), 7.31-7.32 (m, 2H), 7.21 (d, J=4.58 Hz, 1H), 6.55 (s, 1H), 6.04-6.05 (m, 1H), 3.56 (s, 3H), 3.22 (m, 1H), J=5.19 Hz, 2H), 2.43 (d, J=2.75 Hz, 3H), 1.05-1.12 (m, 1H), 0.34-0.39 (m, 2H), 0.15-0.19 (m, 2H). MS (ESI+) m/z 386.7 (M+H)+.

Example 211

4-{5-(ethylsulfonyl)-2-[(cis-4-hydroxy-4-methylcyclohexyl)oxy]phenyl}-6-methyl-1,6-dihydro-7H-pyrrolo[2,3-c]pyridin-7-one Example 199 (0.052 g, 0.121 mmol) in tetrahydrofuran was treated with 3.0 M methylmagnesium bromide in tetrahydrofuran (0.485 mL, 0.485 mmol). The reaction mixture was stirred at ambient temperature for 2 hours. The solvent was removed, and the solid was treated with MeOH and a few drops of TFA. The resulting solution was purified by reverse phase Preparative HPLC (C18, 10-80% CH$_3$CN/water (0.1% TFA)) to give the title compound (first eluting peak, 0.018 g, 0.040 mmol, 33.4% yield). $^1$H NMR (500 MHz, DMSO-d$_6$) δ ppm 12.04 (s, 1H), 7.78-7.80 (m, 2H), 7.38 (d, J=9.77 Hz, 1H), 7.33 (s, 1H), 7.29 (t, J=2.75 Hz, 1H), 6.11-6.12 (m, 1H), 4.46-4.49 (m, 1H), 3.57 (s, 3H), 3.27 (q, J=7.32 Hz, 2H), 1.39-1.76 (m, 8H), 1.13 (t, J=7.32 Hz, 3H), 1.10 (s, 3H). MS (ESI+) m/z 445.1 (M+H)+.

Example 212

4-{5-(ethylsulfonyl)-2-[(trans-4-hydroxy-4-methylcyclohexyl)oxy]phenyl}-6-methyl-1,6-dihydro-7H-pyrrolo[2,3-c]pyridin-7-one The title compound (second eluting peak) was isolated as a minor product in the preparation of Example 211. $^1$H NMR (500 MHz, DMSO-d$_6$) δ ppm 12.04 (s, 1H), 7.79-7.81 (m, 2H), 7.37 (d, J=9.46 Hz, 1H), 7.30 (s, 1H), 7.29 (t, J=2.75 Hz, 1H), 6.10-6.11 (m, 1H), 4.46-4.49 (m, 1H), 3.56 (s, 3H), 3.28 (q, J=7.32 Hz, 2H), 1.80-1.86 (m, 2H), 1.54-1.59 (m, 2H), 1.23-1.26 (m, 4H), 1.13 (t, J=7.32 Hz, 3H), 0.91 (s, 3H). MS (ESI+) m/z 445.1 (M+H)+.

Example 213

4-[2-(cyclobutyloxy)-5-(methylsulfonyl)phenyl]-6-methyl-1,6-dihydro-7H-pyrrolo[2,3-c]pyridin-7-one A 4 mL vial was charged with a stir bar, a solution of Example 138a (30 mg, 0.063 mmol) in tetrahydrofuran (1 mL), a solution of cyclobutanol (32 mg, 7 equivalents, 0.46 mmol) in tetrahydrofuran (1 mL) and neat sodium hydride (19 mg, 7 equivalents, 0.46 mmol). The reaction mixture was stirred at 60° C. for 16 hours. The crude material was filtered, concentrated, and purified by reverse phase HPLC (C18, 10-100% CH$_3$CN/water (0.1% TFA)) to afford the title compound. $^1$H NMR (400 MHz, DMSO-d$_6$/D$_2$O) δ ppm 7.98-7.75 (m, 2H), 7.33 (d, J=1.4 Hz, 2H), 7.16 (d, J=8.7 Hz, 1H), 6.15 (d, J=2.8 Hz, 1H), 4.82 (p, J=7.2 Hz, 1H), 3.59 (s, 3H), 3.19 (d, J=8.5 Hz, 3H), 2.47-2.38 (m, 2H), 1.96 (p, J=9.6 Hz, 2H), 1.81-1.72 (m, 1H), 1.72-1.57 (m, 1H). MS (ESI+) m/z 373 (M+H)+.

Example 214

4-[2-(cyclopentylmethoxy)-5-(methylsulfonyl)phenyl]-6-methyl-1,6-dihydro-7H-pyrrolo[2,3-c]pyridin-7-one Example 214 was prepared according to the procedure used for the preparation of Example 213, substituting cyclopentylmethanol for cyclobutanol, to provide the title compound. $^1$H NMR (400 MHz, DMSO-d$_6$/D$_2$O) δ ppm 7.93-7.81 (m, 2H), 7.40-7.29 (m, 3H), 6.14 (d, J=2.8 Hz, 1H), 3.99

(d, J=6.6 Hz, 2H), 3.58 (s, 3H), 3.20 (s, 3H), 2.18 (dt, J=14.6, 7.2 Hz, 1H), 1.59 (dt, J=17.2, 8.5 Hz, 2H), 1.44 (dd, J=10.1, 4.8 Hz, 4H), 1.31-1.16 (m, 2H). MS (ESI+) m/z 401 (M+H)+.

Example 215

4-[2-(cyclohexyloxy)-5-(methylsulfonyl)phenyl]-6-methyl-1,6-dihydro-7H-pyrrolo[2,3-c]pyridin-7-one Example 215 was prepared according to the procedure used for the preparation of Example 213, substituting cyclohexanol for cyclobutanol, to provide the title compound. $^1$H NMR (400 MHz, DMSO-$d_6$/D$_2$O) δ ppm 7.85 (dt, J=4.1, 2.4 Hz, 2H), 7.35 (dd, J=17.3, 5.9 Hz, 3H), 6.16 (d, J=2.8 Hz, 1H), 4.66-4.49 (m, 1H), 3.58 (s, 3H), 3.20 (s, 3H), 1.94-1.79 (m, 2H), 1.54 (d, J=5.1 Hz, 2H), 1.50-1.28 (m, 5H), 1.21 (d, J=8.9 Hz, 1H). MS (ESI+) m/z 401 (M+H)+.

Example 216

4-[2-(cyclopentyloxy)-5-(methylsulfonyl)phenyl]-6-methyl-1,6-dihydro-7H-pyrrolo[2,3-c]pyridin-7-one Example 216 was prepared according to the procedure used for the preparation of Example 213, substituting cyclopentanol for cyclobutanol, to provide the title compound. $^1$H NMR (400 MHz, DMSO-$d_6$/D$_2$O) δ ppm 7.88 (dd, J=8.7, 2.5 Hz, 1H), 7.82 (d, J=2.4 Hz, 1H), 7.32 (dd, J=10.3, 7.4 Hz, 3H), 6.10 (d, J=2.8 Hz, 1H), 4.96 (dt, J=8.3, 2.8 Hz, 1H), 3.58 (s, 3H), 3.19 (d, J=8.6 Hz, 3H), 2.53 (dd, J=3.5, 1.7 Hz, 2H), 1.98-1.82 (m, 2H), 1.69-1.56 (m, 2H), 1.56-1.46 (m, 4H) MS (ESI+) m/z 387 (M+H)+.

Example 217

6-methyl-4-[5-(methylsulfonyl)-2-(tetrahydrofuran-3-ylmethoxy)phenyl]-1,6-dihydro-7H-pyrrolo[2,3-c]pyridin-7-one Example 217 was prepared according to the procedure used for the preparation of Example 213, substituting (tetrahydrofuran-3-yl)methanol for cyclobutanol, to provide the title compound. $^1$H NMR (400 MHz, DMSO-$d_6$/D$_2$O) δ ppm 7.90 (dd, J=8.6, 2.5 Hz, 1H), 7.85 (d, J=2.4 Hz, 1H), 7.37 (d, J=8.7 Hz, 1H), 7.33 (d, J=2.8 Hz, 2H), 6.14 (d, J=2.8 Hz, 1H), 4.10 (dd, J=9.4, 6.2 Hz, 1H), 4.03 (dd, J=9.4, 7.5 Hz, 1H), 3.58 (s, 5H), 3.62-3.52 (m, 6H), 3.40 (dd, J=8.6, 5.8 Hz, 1H), 3.20 (s, 3H), 1.93-1.80 (m, 1H), 1.63-1.51 (m, 1H). MS (ESI+) m/z 403 (M+H)+.

Example 218

6-methyl-4-{5-(methylsulfonyl)-2-[2-(2-oxoimidazolidin-1-yl)ethoxy]phenyl}-1,6-dihydro-7H-pyrrolo[2,3-c]pyridin-7-one Example 218 was prepared according to the procedure used for the preparation of Example 213, substituting 1-(2-hydroxyethyl)imidazolidin-2-one for cyclobutanol, to provide the title compound. $^1$H NMR (400 MHz, DMSO-$d_6$/D$_2$O) δ ppm 7.90 (dd, J=8.6, 2.4 Hz, 1H), 7.86 (d, J=2.4 Hz, 1H), 7.39 (d, J=8.7 Hz, 1H), 7.34 (d, J=2.8 Hz, 2H), 6.15 (d, J=2.8 Hz, 1H), 4.20 (t, J=5.2 Hz, 2H), 3.58 (s, 3H), 3.35 (t, J=5.2 Hz, 2H), 3.21 (s, 3H), 3.07 (s, 4H). MS (ESI+) m/z 431 (M+H)+.

Example 219

4-[2-(2-cyclopropylethoxy)-5-(methylsulfonyl)phenyl]-6-methyl-1,6-dihydro-7H-pyrrolo[2,3-c]pyridin-7-one Example 219 was prepared according to the procedure used for the preparation of Example 213, substituting 2-cyclopropylethanol for cyclobutanol, to provide the title compound. $^1$H NMR (400 MHz, DMSO-$d_6$/D$_2$O) δ ppm 7.93 (dd, J=8.6, 2.4 Hz, 1H), 7.86 (d, J=2.4 Hz, 1H), 7.43-7.32 (m, 3H), 6.14 (d, J=2.8 Hz, 1H), 4.18 (t, J=6.3 Hz, 2H), 3.23 (s, 3H), 1.54 (q, J=6.5 Hz, 2H), 0.72-0.60 (m, 1H), 0.39-0.29 (m, 2H) MS (ESI+) m/z 387 (M+H)+.

Example 220

4-[2-(cycloheptyloxy)-5-(methylsulfonyl)phenyl]-6-methyl-1,6-dihydro-7H-pyrrolo[2,3-c]pyridin-7-one Example 220 was prepared according to the procedure used for the preparation of Example 213, substituting cycloheptanol for cyclobutanol, to provide the title compound. $^1$H NMR (400 MHz, DMSO-$d_6$/D$_2$O) δ ppm 7.91-7.80 (m, 2H), 7.32 (d, J=2.8 Hz, 2H), 7.34-7.27 (m, 3H), 6.14 (d, J=2.8 Hz, 1H), 4.77-4.67 (m, 1H), 3.20 (s, 3H), 1.98-1.84 (m, 2H), 1.69-1.57 (m, 2H), 1.57-1.30 (m, 8H). MS (ESI+) m/z 415 (M+H)+.

Example 221

6-methyl-4-[2-(2-methylpropoxy)-5-(methylsulfonyl)phenyl]-1,6-dihydro-7H-pyrrolo[2,3-c]pyridin-7-one Example 221 was prepared according to the procedure used for the preparation of Example 213, substituting 2-methylpropan-1-ol for cyclobutanol, to provide the title compound. $^1$H NMR (400 MHz, DMSO-$d_6$/D$_2$O) δ ppm 7.92-7.82 (m, 2H), 7.38-7.32 (m, 3H), 7.32 (d, J=2.8 Hz, 2H), 6.13 (d, J=2.8 Hz, 1H), 3.88 (d, J=6.3 Hz, 2H), 3.20 (s, 3H), 0.83 (d, J=6.7 Hz, 6H). MS (ESI+) m/z 375 (M+H)+.

Example 222

6-methyl-4-{2-{[(2S)-1-methylpyrrolidin-2-yl]methoxy}-5-(methylsulfonyl)phenyl]-1,6-dihydro-7H-pyrrolo[2,3-c]pyridin-7-one Example 222 was prepared according to the procedure used for the preparation of Example 213, substituting (S)-(1-methylpyrrolidin-2-yl)methanol for cyclobutanol, to provide the title compound. $^1$H NMR (400 MHz, DMSO-$d_6$/D$_2$O) δ ppm 7.96 (dd, J=8.6, 2.4 Hz, 1H), 7.89 (d, J=2.4 Hz, 1H), 7.43-7.33 (m, 3H), 6.20 (d, J=2.8 Hz, 1H), 4.49 (dd, J=11.0, 3.3 Hz, 1H), 4.27 (dd, J=10.9, 8.2 Hz, 1H), 3.59 (s, 3H), 3.44-3.34 (m, 1H), 3.25-3.16 (m, 3H), 3.07-2.95 (m, 1H), 2.32-2.09 (m, 1H), 2.01-1.83 (m, 1H), 1.85-1.62 (m, 2H). MS (ESI+) m/z 416 (M+H)+.

Example 223

6-methyl-4-{2-[(2-methylcyclopropyl)methoxy]-5-(methylsulfonyl)phenyl}-1,6-dihydro-7H-pyrrolo[2,3-c]pyridin-7-one Example 223 was prepared according to the procedure used for the preparation of Example 213, substituting (2-methylcyclopropyl)methanol for cyclobutanol, to provide the title compound. $^1$H NMR (400 MHz, DMSO-d$_6$/D$_2$O) δ ppm 7.94-7.79 (m, 2H), 7.41-7.28 (m, 3H), 6.16 (t, J=3.0 Hz, 1H), 4.10-3.97 (m, 1H), 3.91 (dd, J=10.3, 7.3 Hz, 1H), 3.59 (d, J=2.7 Hz, 3H), 3.19 (s, 3H), 0.91 (t, J=11.4 Hz, 3H), 0.89-0.75 (m, 1H), 0.77-0.63 (m, 1H), 0.48-0.36 (m, 1H), 0.29-0.19 (m, 1H). MS (ESI+) m/z 387 (M+H)$^+$.

Example 224

4-[2-(cyclohexylmethoxy)-5-(methylsulfonyl)phenyl]-6-methyl-1,6-dihydro-7H-pyrrolo[2,3-c]pyridin-7-one Example 224 was prepared according to the procedure used for the preparation of Example 213, substituting cyclohexylmethanol for cyclobutanol, to provide the title compound. $^1$H NMR (400 MHz, DMSO-d$_6$/D$_2$O) δ ppm 7.91-7.82 (m, 2H), 7.38-7.30 (m, 3H), 6.14 (d, J=2.8 Hz, 1H), 3.91 (d, J=5.7 Hz, 2H), 3.58 (s, 3H), 3.20 (s, 3H), 1.65-1.57 (m, 5H), 1.28-0.85 (m, 5H). MS (ESI+) m/z 415 (M+H)$^+$.

Example 225

6-methyl-4-{2-[2-(1-methylpyrrolidin-2-yl)ethoxy]-5-(methylsulfonyl)phenyl}-1,6-dihydro-7H-pyrrolo[2,3-c]pyridin-7-one Example 225 was prepared according to the procedure used for the preparation of Example 213, substituting 2-(1-methylpyrrolidin-2-yl)ethanol for cyclobutanol, to provide the title compound. $^1$H NMR (400 MHz, DMSO-d$_6$/D$_2$O) δ ppm 7.93 (dd, J=8.7, 2.4 Hz, 1H), 7.85 (d, J=2.4 Hz, 1H), 7.36 (dd, J=10.4, 7.7 Hz, 3H), 6.15 (d, J=2.8 Hz, 1H), 4.30-4.12 (m, 2H), 3.59 (s, 3H), 3.57-3.42 (m, 1H), 3.19 (d, J=14.3 Hz, 3H), 3.04 (dt, J=9.9, 5.0 Hz, 1H), 2.93 (dt, J=11.5, 8.5 Hz, 1H), 2.53 (dt, J=3.5, 1.7 Hz, 2H), 2.34-2.19 (m, 1H), 2.06 (dtd, J=12.9, 8.1, 5.0 Hz, 1H), 1.96-1.72 (m, 3H), 1.51 (ddd, J=16.7, 13.2, 9.3 Hz, 1H). MS (ESI+) m/z 430 (M+H)$^+$.

Example 226

6-methyl-4-[5-(methylsulfonyl)-2-{[(2R)-5-oxopyrrolidin-2-yl]methoxy}phenyl]-1,6-dihydro-7H-pyrrolo[2,3-c]pyridin-7-one Example 226 was prepared according to the procedure used for the preparation of Example 213, substituting (R)-5-(hydroxymethyl)pyrrolidin-2-one for cyclobutanol, to provide the title compound. $^1$H NMR (400 MHz, DMSO-d$_6$/D$_2$O) δ ppm 7.91 (dd, J=8.7, 2.4 Hz, 1H), 7.86 (d, J=2.4 Hz, 1H), 7.42-7.29 (m, 3H), 6.15 (d, J=2.8 Hz, 1H), 4.08 (qd, J=9.9, 4.2 Hz, 2H), 3.81 (dt, J=28.2, 14.1 Hz, 1H), 3.58 (s, 3H), 3.19 (d, J=11.5 Hz, 3H), 2.09-1.87 (m, 2H), 1.86-1.66 (m, 2H). MS (ESI+) m/z 416 (M+H)$^+$.

Example 227

6-methyl-4-{5-(methylsulfonyl)-2-[2-(morpholin-4-yl)ethoxy]phenyl}-1,6-dihydro-7H-pyrrolo[2,3-c]pyridin-7-one Example 227 was prepared according to the procedure used for the preparation of Example 213, substituting 2-morpholinoethanol for cyclobutanol, to provide the title compound. $^1$H NMR (400 MHz, DMSO-d$_6$/D$_2$O) δ ppm 7.97 (dd, J=8.6, 2.4 Hz, 1H), 7.87 (d, J=2.4 Hz, 1H), 7.42 (d, J=8.7 Hz, 1H), 7.35 (d, J=2.8 Hz, 2H), 6.12 (d, J=2.8 Hz, 1H), 4.48 (t, J=4.6 Hz, 2H), 3.96 (s, 1H), 3.59 (s, 3H), 3.57-3.36 (m, 3H), 3.22 (s, 3H), 3.18 (s, 1H), 3.10-2.68 (m, 2H). MS (ESI+) m/z 432 (M+H)$^+$.

Example 228

6-methyl-4-[5-(methylsulfonyl)-2-{[(2S)-5-oxopyrrolidin-2-yl]methoxy}phenyl]-1,6-dihydro-7H-pyrrolo[2,3-c]pyridin-7-one Example 228 was prepared according to the procedure used for the preparation of Example 213, substituting (S)-5-(hydroxymethyl)pyrrolidin-2-one for cyclobutanol, to provide the title compound. $^1$H NMR (400 MHz, DMSO-d$_6$/D$_2$O) δ ppm 7.88 (tt, J=15.3, 7.7 Hz, 2H), 7.46-7.27 (m, 3H), 6.15 (d, J=2.8 Hz, 1H), 4.08 (qd, J=9.9, 4.2 Hz, 2H), 3.83 (dd, J=8.1, 4.1 Hz, 1H), 3.57 (d, J=9.0 Hz, 3H), 3.20 (s, 3H), 2.09-1.90 (m, 2H), 1.85-1.69 (m, 2H) MS (ESI+) m/z 416 (M+H)$^+$.

Example 229

4-{2-[(1-tert-butoxypropan-2-yl)oxy]-5-(methylsulfonyl)phenyl}-6-methyl-1,6-dihydro-7H-pyrrolo[2,3-c]pyridin-7-one Example 229 was prepared according to the procedure used for the preparation of Example 213, substituting 1-tert-butoxypropan-2-ol for cyclobutanol, to provide the title compound. $^1$H NMR (400 MHz, DMSO-d$_6$/D$_2$O) δ ppm 7.92-7.80 (m, 2H), 7.45-7.24 (m, 3H), 6.19 (d, J=2.8 Hz, 1H), 4.74-4.62 (m, 1H), 3.58 (s, 3H), 3.38 (t, J=7.6 Hz, 2H), 3.19 (d, J=8.9 Hz, 3H), 1.20 (t, J=8.9 Hz, 3H), 1.02 (s, 9H). MS (ESI+) m/z 433 (M+H)$^+$.

Example 230

4-{2-[(1S,4R)-bicyclo[2.2.1]hept-2-ylmethoxy]-5-(methylsulfonyl)phenyl}-6-methyl-1,6-dihydro-7H-pyrrolo[2,3-c]pyridin-7-one Example 230 was prepared according to the procedure used for the preparation of Example 213, substituting (1S,4R)-bicyclo[2.2.1]heptan-2-ylmethanol for cyclobutanol, to provide the title compound. $^1$H NMR (400 MHz, DMSO-d$_6$/D$_2$O) δ ppm 7.92-7.81 (m, 2H), 7.43-7.28 (m, 3H), 6.14 (dd, J=8.3, 2.8 Hz, 1H), 4.15-4.07 (m, 1H), 4.01-3.78 (m, 2H), 3.20 (s, 3H), 2.18-2.00 (m, 2H), 1.50-1.34 (m, 2H), 1.32-1.15 (m, 3H), 1.14-0.95 (m, 2H). MS (ESI+) m/z 427 (M+H)$^+$.

Example 231

6-methyl-4-{2-[(1-methylcyclopropyl)methoxy]-5-(methylsulfonyl)phenyl}-1,6-dihydro-7H-pyrrolo[2,3-c]pyridin-7-one Example 231 was prepared according to the procedure used for the preparation of Example 213, substituting (1-methylcyclopropyl)methanol for cyclobutanol, to provide the title compound. $^1$H NMR (400 MHz, DMSO-d$_6$/D$_2$O) δ ppm 7.90-7.83 (m, 2H), 7.33 (d, J=2.9 Hz, 1H), 7.30 (d, J=8.9 Hz, 1H), 6.17 (d, J=2.8 Hz, 1H), 3.90 (s, 2H), 3.19 (s, 3H), 0.97 (s, 3H), 0.48-0.41 (m, 2H), 0.31-0.25 (m, 2H). MS (ESI+) m/z 387 (M+H)$^+$.

Example 232

6-methyl-4-{5-(methylsulfonyl)-2-[2-(2-oxopyrrolidin-1-yl)ethoxy]phenyl}-1,6-dihydro-7H-pyrrolo[2,3-c]pyridin-7-one Example 232 was prepared according to the procedure used for the preparation of Example 213, substituting 1-(2-hydroxyethyl)pyrrolidin-2-one for cyclobutanol, to provide the title compound. $^1$H NMR (400 MHz, DMSO-$d_6$/$D_2O$) δ ppm 7.91 (dd, J=8.6, 2.4 Hz, 1H), 7.84 (d, J=2.4 Hz, 1H), 7.41-7.30 (m, 3H), 6.10 (d, J=2.8 Hz, 1H), 4.21 (t, J=5.2 Hz, 2H), 3.58 (s, 3H), 3.45 (t, J=5.2 Hz, 2H), 3.23-3.16 (m, 3H), 3.01 (t, J=7.0 Hz, 2H), 2.08 (t, J=8.0 Hz, 2H), 1.67 (p, J=7.5 Hz, 2H). MS (ESI+) m/z 430 (M+H)$^+$.

Example 233

6-methyl-4-{2-[(4-methylcyclohexyl)oxy]-5-(methylsulfonyl)phenyl}-1,6-dihydro-7H-pyrrolo[2,3-c]pyridin-7-one Example 233 was prepared according to the procedure used for the preparation of Example 213, substituting 4-methylcyclohexanol for cyclobutanol, to provide the title compound. $^1$H NMR (400 MHz, DMSO-$d_6$/$D_2O$) δ ppm 7.89-7.83 (m, 2H), 7.39-7.31 (m, 3H), 6.17 (d, J=2.8 Hz, 1H), 4.78-4.71 (m, 1H), 3.20 (s, 3H), 1.86-1.75 (m, 2H), 1.57-1.45 (m, 2H), 1.41-1.22 (m, 3H), 0.96-0.82 (m, 2H), 0.68 (d, J=6.2 Hz, 3H). MS (ESI+) m/z 415 (M+H)$^+$.

Example 234

4-[2-(cyclobutylmethoxy)-5-(methylsulfonyl)phenyl]-6-methyl-1,6-dihydro-7H-pyrrolo[2,3-c]pyridin-7-one Example 234 was prepared according to the procedure used for the preparation of Example 213, substituting cyclobutylmethanol for cyclobutanol, to provide the title compound. $^1$H NMR (400 MHz, DMSO-$d_6$/$D_2O$) δ ppm 7.94-7.80 (m, 2H), 7.34 (dd, J=13.2, 5.7 Hz, 3H), 6.14 (d, J=2.8 Hz, 1H), 4.07 (d, J=6.2 Hz, 2H), 3.57 (s, 3H), 3.19 (d, J=9.2 Hz, 3H), 2.61 (d, J=7.1 Hz, 1H), 1.99-1.62 (m, 6H). MS (ESI+) m/z 387 (M+H)$^+$.

Example 235

N-[4-(2,4-difluorophenoxy)-3-(6-methyl-7-oxo-6,7-dihydro-1H-pyrrolo[2,3-c]pyridin-4-yl)phenyl]cyclopropanesulfonamide Example 235 was prepared according to the procedure used for the preparation of Example 4 (Method A), substituting Example 27c for Example 3, and cyclopropanesulfonyl chloride for methanesulfonyl chloride, respectively, to provide the title compound. $^1$H NMR (500 MHz, DMSO-$d_6$) δ ppm 12.05 (s, 1H), 9.70 (s, 1H), 7.35-7.38 (m, 2H), 7.29-7.30 (m, 2H), 7.22 (dd, J=8.7, 2.59 Hz, 1H), 7.06-7.10 (m, 1H), 6.98-7.01 (m, 1H), 6.92 (d, J=8.54 Hz, 1H), 6.25-6.26 (m, 1H), 3.54 (s, 3H), 2.61-2.66 (m, 1H), 0.90-0.98 (m, 4H). MS (ESI+) m/z 472.1 (M+H)$^+$.

Example 236

N-[4-(2,4-difluorophenoxy)-3-(6-methyl-7-oxo-6,7-dihydro-1H-pyrrolo[2,3-c]pyridin-4-yl)phenyl]-2-methoxyethanesulfonamide Example 236 was prepared according to the procedure used for the preparation of Example 4, Method A, substituting Example 27b for Example 3, and 2-methoxyethanesulfonyl chloride for methanesulfonyl chloride, respectively, to provide the title compound. $^1$H NMR (500 MHz, DMSO-$d_6$) δ ppm 12.05 (s, 1H), 9.76 (s, 1H), 7.34-7.39 (m, 2H), 7.28-7.30 (m, 2H), 7.19 (dd, J=8.85, 2.75 Hz, 1H), 7.05-7.10 (m, 1H), 6.98-7.01 (m, 1H), 6.91 (d, J=8.54 Hz, 1H), 6.25-6.26 (m, 1H), 3.68 (t, J=6.1 Hz, 2H), 3.53 (s, 3H), 3.37 (t, J=6.1 Hz, 2H), 3.20 (s, 3H). MS (ESI+) m/z 490.1 (M+H)$^+$.

Example 237

6-methyl-4-{5-(methylsulfonyl)-2-[tricyclo[3.3.1.1$^{3,7}$]dec-2-yloxy]phenyl}-1,6-dihydro-7H-pyrrolo[2,3-c]pyridin-7-one Example 237 was prepared according to the procedure used for the preparation of Example 158, substituting 2-adamantanol for cyclopropylmethanol, to provide the title compound. $^1$H NMR (500 MHz, DMSO-$d_6$) δ ppm 12.04 (s, 1H), 7.88 (d, J=2.44 Hz, 1H), 7.83 (dd, J=8.85, 2.44, HZ, 1H), 7.38 (s, 1H), 7.36 (d, J=8.85 Hz, 1H), 7.29 (t, J=2.75 Hz, 1H), 6.18-6.19 (m, 1H), 4.70 (s, 1H), 3.56 (s, 3H), 3.21 (s, 3H), 2.06 (s, 2H), 1.80 (s, 5H), 1.62-1.65 (m, 5H), 1.34 (d, J=11.29 Hz, 2H). MS (ESI+) m/z 453.2 (M+H)$^+$.

Example 238

4-[(cyclopropylmethyl)amino]-3-(6-methyl-7-oxo-6,7-dihydro-1H-pyrrolo[2,3-c]pyridin-4-yl)benzenesulfonamide

Example 238a 3-bromo-4-(cyclopropylmethylamino)benzenesulfonamide

Example 238a was prepared according to the procedure used for the preparation of Example 96a, substituting cyclopropylmethanamine for cyclohexanamine, and 3-bromo-4-fluorobenzenesulfonamide for Example 86a, respectively, to provide the title compound.

Example 238b

4-[(cyclopropylmethyl)amino]-3-(6-methyl-7-oxo-6,7-dihydro-1H-pyrrolo[2,3-c]pyridin-4-yl)benzenesulfonamide Example 238b was prepared according to the procedure used for the preparation of Example 95d, substituting Example 238a for Example 95c, to provide the title compound. 1H NMR (500 MHz, DMSO-$d_6$) δ ppm 12.13 (s, 1H), 7.61-7.63 (m, 1H), 7.50 (d, J=2.14 Hz, 1H), 7.30 (t, J=2.75 Hz, 1H), 7.20 (s, 1H), 6.97 (br s, 2H), 6.80 (d, J=8.85 Hz, 1H), 6.01 (s, 1H), 3.56 (s, 3H), 3.02 (d, J=6.71 Hz, 2H), 0.97-1.03 (m, 1H), 0.35-0.39 (m, 2H), 0.13-0.16 (m, 2H). MS (ESI+) m/z 373.2 (M+H)$^+$.

Example 239

4-[(cyclopropylmethyl)amino]-N-methyl-3-(6-methyl-7-oxo-6,7-dihydro-1H-pyrrolo[2,3-c]pyridin-4-yl)benzenesulfonamide The title compound was isolated as a minor product in the preparation of Example 238b. $^1$H NMR (500 MHz, DMSO-$d_6$) δ ppm 12.13 (s, 1H), 7.56 (dd, J=8.54, 2.44 Hz, 1H), 7.42 (d, J=2.14 Hz, 1H), 7.23 (s, 1H), 7.30 (t, J=2.75 Hz, 1H), 7.02 (d, J=4.88 Hz, 1H), 6.83 (d, J=8.54 Hz, 1H), 6.00-6.01 (m, 1H), 3.56 (s, 3H), 3.02 (d, J=6.71 Hz, 2H), 2.38 (d, J=4.58 Hz, 3H), 0.99-1.18 (m, 1H), 0.36-0.40 (m, 2H), 0.13-0.17 (m, 2H). MS (ESI+) m/z 387.2 (M+H)$^+$.

Example 240

4-{2-[(2,2-difluorocyclopropyl)methoxy]-5-(ethylsulfonyl)phenyl}-6-methyl-1,6-dihydro-7H-pyrrolo[2,3-c]pyridin-7-one

Example 240a 2-bromo-1-((2,2-difluorocyclopropyl)methoxy)-4-(ethylsulfonyl)benzene Example 240a was prepared according to the procedure used for the preparation of Example 158, substituting Example 168b for Example 138a, and (2,2-difluorocyclopropyl)methanol for cyclopropylmethanol, to provide the title compound.

Example 240b

4-{2-[(2,2-difluorocyclopropyl)methoxy]-5-(ethylsulfonyl)phenyl}-6-methyl-1,6-dihydro-7H-pyrrolo[2,3-c]pyridin-7-one Example 240b was prepared according to the procedure used for the preparation of Example 95d, substituting Example 240a for Example 95c, to provide the title compound. $^1$H NMR (500 MHz, DMSO-$d_6$) δ ppm 12.05 (s, 1H), 7.81-7.85 (m, 2H), 7.37-7.39 (m, 2H), 7.29 (t, J=2.75 Hz, 1H), 6.14-6.15 (m, 1H), 4.25-4.29 (m, 2H), 4.16-4.20 (m, 2H), 3.57 (s, 3H), 3.29 (q, J=7.43 Hz, 2H), 2.08-2.16 (m, 1H), 1.63-1.66 (m, 1H), 1.44-1.46 (m, 1H), 1.13 (t, J=7.32 Hz, 3H). MS (ESI+) m/z 423.1 (M+H)$^+$.

Example 241

4-(4-bromo-2-methoxyphenyl)-6-methyl-1,6-dihydro-7H-pyrrolo[2,3-c]pyridin-7-one

Example 241a 4-(4-bromo-2-methoxyphenyl)-6-methyl-1-tosyl-1H-pyrrolo[2,3-c]pyridin-7(6H)-one The product from Example 6a (0.2 g, 0.467 mmol), 4-bromo-1-iodo-2-methoxybenzene (0.16 g, 0.514 mmol), tris(dibenzylideneacetone)dipalladium(0) (0.013 g, 0.014 mmol), 1,3,5,7-tetramethyl-6-phenyl-2,4,8-trioxa-6-phosphaadamante (0.014 g, 0.047 mmol) and potassium phosphate tribasic (0.347 g, 1.634 mmol) were combined and sparged with argon for 15 minutes. Meanwhile a solution of 4:1 dioxane/water (7.5 mL) was sparged with nitrogen for 15 minutes and transferred by syringe into the reaction vessel under argon. The mixture was stirred at ambient temperature for 20 minutes and partitioned between ethyl acetate and water. The organic layer was washed with saturated aqueous sodium chloride, dried (Na$_2$SO$_4$), treated with 3-mercaptopropyl functionalized silica gel for twenty minutes, filtered, and concentrated. Purification by chromatography (silica gel, 10-80% ethyl acetate in heptanes) afforded the title compound (0.2 g, 88%)

Example 241b 4-(4-bromo-2-methoxyphenyl)-6-methyl-1,6-dihydro-7H-pyrrolo[2,3-c]pyridin-7-one The product from Example 241a (0.2 g, 0.410 mmol), potassium hydroxide (0.460 g, 8.21 mmol) and cetyltrimethylammonium bromide (7.48 mg, 0.021 mmol) were combined in dioxane (8 mL) and water (4 mL) and heated at 100° C. for 18 hours. The reaction mixture was partitioned between equal volumes of ethyl acetate and water and the pH was adjusted to pH 7 by careful addition of concentrated HCl. The organic layer was separated and washed three times with saturated aqueous sodium chloride, dried (Na$_2$SO$_4$), filtered, and concentrated. Purification by trituration in dichloromethane afforded the title compound (0.1 g, 73%). $^1$H NMR (300 MHz, DMSO-$d_6$) δ ppm 11.97 (s, 1H) 7.05-7.42 (m, 5H) 5.87-6.09 (m, 1H) 3.75 (s, 3H) 3.54 (s, 3H). MS (ESI+) m/z 333/335 (M+H)$^+$.

Example 242

6-(2,4-difluorophenoxy)-5-(6-methyl-7-oxo-6,7-dihydro-1H-pyrrolo[2,3-c]pyridin-4-yl)pyridine-3-sulfonamide

Example 242a 5-bromo-6-(2,4-difluorophenoxy)pyridine-3-sulfonamide

A mixture of Example 86a (0.543 g, 2 mmol), 2,4-difluorophenol (0.390 g, 3.00 mmol), and cesium carbonate (1.955 g, 6.00 mmol) in DMSO (10 mL) was heated at 110° C. for 16 hours. After cooling, the reaction mixture was partitioned between water and ethyl acetate. The aqueous layer was neutralized with 10% HCl and extracted with additional ethyl acetate twice. The combined organic layers were washed with saturated aqueous sodium chloride, dried over anhydrous magnesium sulfate, filtered, and concentrated. The residue was purified by flash chromatography (3:2 ethyl acetate/hexanes) on silica gel to give the title compound (0.53 g, 1.451 mmol, 72.6% yield).

Example 242b 6-(2,4-difluorophenoxy)-5-(6-methyl-7-oxo-6,7-dihydro-1H-pyrrolo[2,3-c]pyridin-4-yl)pyridine-3-sulfonamide Example 242b was prepared according to the procedure used for the preparation of Example 95d, substituting Example 242a for Example 95c, to provide the title compound. $^1$H NMR (500 MHz, DMSO-$d_6$) δ ppm 12.19 (s, 1H), 8.46 (d, J=2.44 Hz, 1H), 8.29 (d, J=2.14 Hz, 1H), 7.56 (s, 2H), 7.54 (s, 1H), 7.44-7.50 (m, 2H), 7.35 (t, J=2.75 Hz, 1H), 7.14-7.18 (m, 1H), 6.34 (t, J=2.44 Hz, 1H), 3.61 (s, 3H). MS (ESI+) m/z 433.2 (M+H)$^+$.

Example 243

4-{2-(cyclopropylmethoxy)-5-[(trifluoromethyl)sulfonyl]phenyl}-6-methyl-1,6-dihydro-7H-pyrrolo[2,3-c]pyridin-7-one

Example 243a (3-bromo-4-fluorophenyl)(trifluoromethyl)sulfane

3-Bromo-4-fluorobenzenethiol (2.071 g, 10 mmol) in dimethylformamide (10 mL) was treated with 60% sodium hydride (0.480 g, 12.00 mmol). The solution was stirred for 10 minutes at room temperature. Trifluoroiodomethane (2.74 g, 14.00 mmol) was released into a balloon with a three-way stopcock. The balloon was then put onto the flask and trifluoroiodomethane was released into the reaction. After 1 hour, all the content in the balloon was gone. And the balloon was filled with 2.74 g of trifluoroiodomethane again. The reaction mixture was stirred for 16 hours. The reaction mixture was poured into water, and extracted with ethyl acetate several times. The combined organic layers were washed with saturated aqueous sodium chloride, dried over anhydrous magnesium sulfate, filtered, and concentrated. The resulting oil was used directly in the next reaction.

Example 243b 2-bromo-1-fluoro-4-(trifluoromethylsulfonyl)benzene

Example 243a (2.75 g, 10.00 mmol) in acetonitrile (4 mL), carbon tetrachloride (4.00 mL), and water (16.00 mL) was treated with sodium periodate (6.42 g, 30.0 mmol) and ruthenium(III) chloride hydrate (0.023 g, 0.100 mmol). The reaction mixture was stirred at ambient temperature for 16 hours. Dichloromethane (100 mL) was added to the reaction mixture, which was then filtered through a pad of filtering agent. The filtrate was treated with saturated sodium bicarbonate (50 mL). And the organic layer was separated. The aqueous layer was then extracted with additional dichloromethane three times. The combined organic layers were washed with saturated aqueous sodium chloride, dried over anhydrous magnesium sulfate, filtered, and concentrated. The residue was purified by column chromatography on silica gel eluting with 5% ethyl acetate in hexanes to give 2.14 g of the title compound (7.85 mmol, 79% yield).

Example 243c 2-bromo-1-(cyclopropylmethoxy)-4-(trifluoromethylsulfonyl)benzene Example 243c was prepared according to the procedure used for the preparation of Example 158, substituting Example 243b for Example 138a, to provide the title compound.

Example 243d

4-{2-(cyclopropylmethoxy)-5-[(trifluoromethyl)sulfonyl]phenyl}-6-methyl-1,6-dihydro-7H-pyrrolo[2,3-c]pyridin-7-one Example 243d was prepared according to the procedure used for the preparation of Example 95d, substituting Example 243c for Example 95c, to provide the title compound. $^1$H NMR (500 MHz, DMSO-$d_6$) δ ppm 12.10 (s, 1H), 8.08 (dd, J=8.85, 2.44 Hz, 1H), 7.95 (d, J=2.44 Hz, 1H), 7.50 (d, J=8.85 Hz, 1H), 7.44 (s, 1H), 7.35 (t, J=2.75 Hz, 1H), 6.12-6.13 (m, 1H), 4.09 (d, J=7.02 Hz, 2H), 3.58 (s, 3H), 1.11-1.17 (m, 1H), 0.48-0.50 (m, 2H), 0.29-0.33 (m, 2H). MS (ESI+) m/z 427.0 (M+H)$^+$.

Example 244

4-{2-[(cyclopropylmethyl)amino]-5-[(trifluoromethyl)sulfonyl]phenyl}-6-methyl-1,6-dihydro-7H-pyrrolo[2,3-c]pyridin-7-one

Example 244a

Example 244a was prepared according to the procedure used for the preparation of Example 96a, substituting cyclopropylmethanamine for cyclohexanamine, and Example 243b for Example 86a, respectively, to provide the title compound.

Example 244b

4-{2-[(cyclopropylmethyl)amino]-5-[(trifluoromethyl)sulfonyl]phenyl}-6-methyl-1,6-dihydro-7H-pyrrolo[2,3-c]pyridin-7-one Example 244b was prepared according to the procedure used for the preparation of Example 95d, substituting Example 244a for Example 95c, to provide the title compound. $^1$H NMR (500 MHz, DMSO-$d_6$) δ ppm 12.16 (s, 1H), 7.80 (dd, J=8.85, 2.44 Hz, 1H), 7.53 (d, J=2.44 Hz, 1H), 7.29-7.31 (m, 2H), 7.02 (d, J=9.16 Hz, 1H), 6.41 (t, J=5.8 Hz, 1H), 5.96-5.97 (m, 1H), 3.56 (s, 3H), 3.10 (t, J=6.26 Hz, 2H), 1.01-1.06 (m, 1H), 0.39-0.43 (m, 2H), 0.16-0.20 (m, 2H). MS (ESI+) m/z 426.1 (M+H)$^+$.

Example 245

6-[(cyclopropylmethyl)amino]-N,N-dimethyl-5-(6-methyl-7-oxo-6,7-dihydro-1H-pyrrolo[2,3-c]pyridin-4-yl)pyridine-3-sulfonamide

Example 245a 5-bromo-6-(cyclopropylmethylamino)-N,N-dimethylpyridine-3-sulfonamide Example 245a was prepared according to the procedure used for the preparation of Example 96a, substituting cyclopropylmethanamine for cyclohexanamine, and Example 110a for Example 86a, respectively, to provide the title compound.

Example 245b

6-[(cyclopropylmethyl)amino]-N,N-dimethyl-5-(6-methyl-7-oxo-6,7-dihydro-1H-pyrrolo[2,3-c]pyridin-4-yl)pyridine-3-sulfonamide Example 245b was prepared according to the procedure used for the preparation of Example 95d, substituting Example 245a for Example 95c, to provide the title compound. $^1$H NMR (500 MHz, DMSO-$d_6$) δ ppm 12.16 (s, 1H), 8.35 (d, J=2.44 Hz, 1H), 7.51 (d, J=2.44 Hz, 1H), 7.20-7.32 (m, 2H), 6.69 (t, J=5.34 Hz, 1H), 6.03-6.04 (m, 1H), 3.58 (s, 3H), 3.24 (t, J=5.95 Hz, 2H), 2.62 (s, 6H), 1.05-1.12 (m, 1H), 0.34-0.39 (m, 2H), 0.15-0.19 (m, 2H). MS (ESI+) m/z 402.1 (M+H)$^+$.

Example 246

6-(2,4-difluorophenoxy)-N-methyl-5-(6-methyl-7-oxo-6,7-dihydro-1H-pyrrolo[2,3-c]pyridin-4-yl)pyridine-3-sulfonamide The title compound was isolated as a minor product in the preparation of Example 242b. $^1$H NMR (500 MHz, DMSO-d$_6$) δ ppm 12.19 (s, 1H), 8.45 (d, J=2.44 Hz, 1H), 8.22 (d, J=2.44 Hz, 1H), 7.60 (q, J=4.78 Hz, 1H), 7.57 (s, 1H), 7.46-7.52 (m, 3H), 7.36 (t, J=2.75 Hz, 1H), 7.14-7.19 (m, 1H), 6.34-6.35 (m, 1H), 3.61 (s, 3H), 2.50 (d, J=4.88 Hz, 3H). MS (ESI+) m/z 477.1 (M+H)$^+$.

Example 247

4-[2-(cyclopropylmethoxy)-6-methylphenyl]-6-methyl-1,6-dihydro-7H-pyrrolo[2,3-c]pyridin-7-one

Example 247a 2-bromo-1-(cyclopropylmethoxy)-3-methylbenzene

A 250 mL flask with stirbar was charged with 2-bromo-3-methylphenol (2.86 g, 15.3 mmol), (bromomethyl)cyclopropane (1.80 mL, 18.6 mmol) and cesium carbonate (7.46 g, 22.9 mmol) in dimethylformamide (50 mL). The mixture was stirred for 16 hours at ambient temperature and then heated at 50° C. for 3 hours. The mixture was cooled to ambient temperature and partitioned between ethyl acetate (200 mL) and saturated aqueous sodium chloride (200 mL). The organics were washed twice with saturated aqueous sodium chloride, dried over anhydrous sodium sulfate, filtered, and concentrated to provide the title compound (3.7 g, 100%).

Example 247b 4-(2-(cyclopropylmethoxy)-6-methylphenyl)-6-methyl-1-tosyl-1H-pyrrolo[2,3-c]pyridin-7(6H)-one Example 247b was prepared according to the procedure used for the preparation of Example 7d, substituting the product of Example 247a for the product of Example 7c and stirring at 65° C. for 2.5 hours, to provide the title compound.

Example 247c 4-(2-(cyclopropylmethoxy)-6-methylphenyl)-6-methyl-1H-pyrrolo[2,3-c]pyridin-7(6H)-one Example 247c was prepared according to the procedure used for the preparation of Example 4b, substituting the product of Example 247b for the product of Example 4a to provide the title compound. $^1$H NMR (400 MHz, DMSO-d$_6$) ppm 11.91 (bds, 1H), 7.23-7.18 (m, 2H), 6.99 (s, 1H), 6.91 (d, J=3.1 Hz, 1H), 6.89 (m, 1H), 5.79 (m, 1H), 3.74 (dd, J=6.6, 2.3 Hz, 2H), 3.54 (s, 3H), 2.06 (s, 3H) 0.99 (m, 1H), 0.33 (m, 2H), 0.08 (m, 2H). MS (DCI+) m/z 309.1 (M+H)$^+$.

Example 248

4-{5-(ethylsulfonyl)-2-[(cis-4-methoxycyclohexyl)oxy]phenyl}-6-methyl-1,6-dihydro-7H-pyrrolo[2,3-c]pyridin-7-one

Example 248a 2-bromo-4-(ethylsulfonyl)-1-(4-methoxycyclohexyloxy)benzene

4-Methoxycyclohexanol (a mixture of 70% cis and 30% trans isomers) (0.521 g, 4.00 mmol) in dioxane (20 mL) was treated with sodium hydride (0.240 g, 6.00 mmol). The reaction mixture was stirred for 10 minutes. To this solution was added Example 168b (0.534 g, 2 mmol). The reaction was heated at 60° C. for 16 hours. After cooling, the reaction mixture was partitioned between water and ethyl acetate. The aqueous layer was extracted with additional ethyl acetate two more times. The combined organic layers were washed with saturated aqueous sodium chloride, dried over anhydrous magnesium sulfate, filtered, and concentrated. The residue was purified by flash chromatography (silica gel, 70:30 ethyl acetate/hexanes) to give the title compound (0.29 g, 38.4% yield).

Example 248b

4-{5-(ethylsulfonyl)-2-[(cis-4-methoxycyclohexyl)oxy]phenyl}-6-methyl-1,6-dihydro-7H-pyrrolo[2,3-c]pyridin-7-one Example 248b (second eluting peak) was prepared according to the procedure used for the preparation of Example 95d, substituting Example 248a for Example 95c, to provide the title compound. $^1$H NMR (500 MHz, DMSO-d$_6$) δ ppm 12.05 (s, 1H), 7.78-7.80 (m, 2H), 7.38-7.40 (m, 1H), 7.34 (s, 1H), 7.29 (t, J=2.75 Hz, 1H), 6.12-6.13 (m, 1H), 4.63-4.66 (m, 1H), 3.56 (s, 3H), 3.28 (t, J=7.32 Hz, 2H), 3.19-3.23 (m, 1H), 3.15 (s, 3H), 1.65-1.72 (m, 6H), 1.42-1.48 (m, 2H), 1.13 (t, J=7.32, 3H). MS (ESI+) m/z 445.0 (M+H)$^+$.

Example 249

4-(cyclopropylmethoxy)-3-(6-methyl-7-oxo-6,7-dihydro-1H-pyrrolo[2,3-c]pyridin-4-yl)benzenesulfonamide

Example 249a 3-bromo-4-(cyclopropylmethoxy)benzenesulfonamide

Example 249a was prepared according to the procedure used for the preparation of Example 29a, substituting 3-bromo-4-fluorobenzenesulfonamide for Example 2a, and cyclopropylmethanol for tetrahydro-2H-pyran-4-ol, to provide the title compound.

Example 249b 4-(cyclopropylmethoxy)-3-(6-methyl-7-oxo-6,7-dihydro-1H-pyrrolo[2,3-c]pyridin-4-yl)benzenesulfonamide Example 249b was prepared according to the procedure used for the preparation of Example 95d, substituting Example 249a for Example 95c, to provide the title compound. ¹H NMR (500 MHz, DMSO-d$_6$) δ ppm 12.03 (s, 1H), 7.80 (d, J=2.44 Hz, 1H), 7.76 (dd, J=8.54, 2.44 Hz, 1H), 7.31 (s, 1H), 7.30 (t, J=2.9 Hz, 1H), 7.22-7.25 (m, 3H), 6.15-6.16 (m, 1H), 3.93 (d, J=6.71 Hz, 2H), 3.57 (s, 3H), 1.08-1.13 (m, 1H), 0.44-0.49 (m, 2H), 0.25-0.28 (m, 2H). MS (ESI+) m/z 374.1 (M+H)$^+$.

Example 250

4-(cyclopropylmethoxy)-N-methyl-3-(6-methyl-7-oxo-6,7-dihydro-1H-pyrrolo[2,3-c]pyridin-4-yl)benzenesulfonamide The title compound was isolated as a minor product in the preparation of Example 249b. ¹H NMR (500 MHz, DMSO-d$_6$) δ ppm 12.05 (s, 1H), 7.70-7.74 (m, 2H), 7.35 (s, 1H), 7.30 (t, J=2.9 Hz, 1H), 7.26-7.32 (m, 3H), 6.14 (t, J=2.44 Hz, 1H), 3.95 (d, J=6.71 Hz, 2H), 3.58 (s, 3H), 2.41 (d, J=4.88 Hz, 3H), 1.07-1.15 (m, 1H), 0.45-0.50 (m, 2H), 0.26-0.29 (m, 2H). MS (ESI+) m/z 388.1 (M+H)$^+$.

Example 251

N-[4-(cyclopropylmethoxy)-2-methyl-3-(6-methyl-7-oxo-6,7-dihydro-1H-pyrrolo[2,3-c]pyridin-4-yl)phenyl]ethanesulfonamide Example 251a 2-bromo-1-(cyclopropylmethoxy)-3-methyl-4-nitrobenzene Example 251a was prepared according to the procedure used for the preparation of Example 247a, substituting 2-bromo-3-methyl-4-nitrophenol for 2-bromo-3-methylphenol, to provide the title compound.

Example 251b 4-(6-(cyclopropylmethoxy)-2-methyl-3-nitrophenyl)-6-methyl-1-tosyl-1H-pyrrolo[2,3-c]pyridin-7(6H)-one Example 251b was prepared according to the procedure used for the preparation of Example 7d, substituting the product of Example 251a for the product of Example 7c and stirring at 65° C. for 2.5 hours, to provide the title compound.

Example 251c 4-(3-amino-6-(cyclopropylmethoxy)-2-methylphenyl)-6-methyl-1-tosyl-1H-pyrrolo[2,3-c]pyridin-7(6H)-one Example 251c was prepared according to the procedure used for the preparation of Example 3, substituting the product of Example 251b for the product of Example 2b to provide the title compound.

Example 251d

N-(4-(cyclopropylmethoxy)-2-methyl-3-(6-methyl-7-oxo-6,7-dihydro-1H-pyrrolo[2,3-c]pyridin-4-yl)phenyl)ethanesulfonamide Example 251d was prepared according to the procedure used for the preparation of Example 4 (Method A), substituting Example 251c for Example 3, and ethanesulfonyl chloride for methanesulfonyl chloride, respectively, to provide the title compound. ¹H NMR (400 MHz, DMSO-d$_6$) ppm 11.93 (bds, 1H), 8.89 (bds, 1H), 7.23-7.19 (m, 2H), 6.99 (s, 1H), 6.91 (d, J=3.1 Hz, 1H), 5.75 (m, 1H), 3.74 (dd, J=6.6, 2.3 Hz, 2H), 3.54 (s, 3H), 3.07 (m, 2H), 2.06 (s, 3H), 1.27 (m, 3H), 0.99 (m, 1H), 0.33 (m, 2H), 0.08 (m, 2H). MS (ESI+) m/z 416.1 (M+H)$^+$.

Example 252

4-[2-(2,4-difluorophenoxy)-5-(methylsulfonyl)phenyl]-6-methyl-7-oxo-6,7-dihydro-1H-pyrrolo[2,3-c]pyridine-2-carboxamide Example 252a 1-(2,4-difluorophenoxy)-4-(methylsulfonyl)-2-nitrobenzene A mixture of 1-fluoro-4-(methylsulfonyl)-2-nitrobenzene (20 g, 91 mmol), 2,4-difluorophenol (11.87 g, 91 mmol) and potassium carbonate (12.6 g, 91 mmol) in DMSO (90 mL) was heated at 120° C. for 2 hours. The reaction mixture was quenched with water and extracted with ethyl acetate. The combined organic layers were washed with saturated aqueous sodium chloride, dried over anhydrous magnesium sulfate, filtered, and concentrated. The residue was purified by flash chromatography (silica gel, 1:1 ethyl acetate/hexanes) to provide the title compound (28 g, 89% yield).

Example 252b 2-(2,4-difluorophenoxy)-5-(methylsulfonyl)aniline

A solution of Example 252a (10.0 g, 30.4 mmol) in tetrahydrofuran (150 mL) was added to 10% Pd/C (1.616 g, 15.18 mmol) in a 250 mL bottle and the mixture was stirred for 24 hour under a 30 psi hydrogen atmosphere at 40° C. The mixture was filtered through a nylon membrane and concentrated. The residue was purified flash chromatography (silica gel, 70:30 ethyl acetate/hexanes) to provide the title compound (8.6 g, 55% yield).

Example 252c 1-(2,4-difluorophenoxy)-2-iodo-4-(methylsulfonyl)benzene

Example 252b (5.00 g, 16.7 mmol) in dioxane (30 mL) was treated with concentrated HCl (150 mL) at 0° C. The reaction mixture was stirred at 0° C. for 10 minutes. To this solution was added sodium nitrite (1.383 g, 20.05 mmol) in water (6 mL). The reaction mixture was stirred at 0° C. for one hour. To this solution was added potassium iodide (5.55 g, 33.4 mmol) in water (20 mL). The reaction mixture was stirred for two hours at 10° C. The reaction mixture was then partitioned between water and ethyl acetate. The organic layer was extracted with additional ethyl acetate twice. The combined organic layer was washed with saturated aqueous sodium chloride, dried (anhydrous magnesium sulfate), filtered, and concentrated. The residue was purified by flash chromatography (silica gel, 2:3 ethyl acetate/hexanes) to provide the title compound (8.9 g, 89% yield)

Example 252d ethyl 1-benzyl-6-methyl-7-oxo-4-(4,4,5,5-tetramethyl-1,3,2-dioxaborolan-2-yl)-6,7-dihydro-1H-pyrrolo[2,3-c]pyridine-2-carboxylate A mixture of Example 70e (2 g, 5.14 mmol), bis(pinacolato)diboron (2.61 g, 10.3 mmol), potassium acetate (1.11 g, 11.3 mmol tris(dibenzylideneacetone)dipalladium(0) (0.235 g, 0.257 mmol) and 2-dicyclohexylphosphino-2',4',6'-triisopropylbiphenyl (0.245 g, 0.514 mmol) in dioxane (50 mL) was stirred at 90° C. for 16 hour under an argon atmosphere. The mixture was filtered through Celite, washed with ethyl acetate several times and concentrated. The residue was purified by flash chromatography (silica gel, 50-75% ethyl acetate/petroleum ether gradient) to afford the title compound (1.15 g, 40% yield).

Example 252e ethyl 1-benzyl-4-(2-(2,4-difluorophenoxy)-5-(methylsulfonyl)phenyl)-6-methyl-7-oxo-6,7-dihydro-1H-pyrrolo[2,3-c]pyridine-2-carboxylate Example 252d (2.3 g, 5.27 mmol), Example 252c (2.270 g, 5.54 mmol), 1,3,5,7-tetramethyl-6-phenyl-2,4,8-trioxa-6-phosphaadamantane (0.154 g, 0.527 mmol), tris(dibenzylideneacetone)dipalladium(0) (0.121 g, 0.132 mmol) and potassium phosphate (1.119 g, 5.27 mmol) were combined and sparged with argon for 30 minutes. A mixture of degassed dioxane (30 mL) and water (7.5 mL) was added and the reaction mixture was stirred at 60° C. for 16 hours. The reaction mixture was cooled to ambient temperature and partitioned between ethyl acetate and water. The organic layer was washed with saturated aqueous sodium chloride, dried (anhydrous sodium sulfate), filtered, and concentrated. The residue was purified by flash chromatography (silica gel, 20-100% ethyl acetate in petroleum ether) to afford the title compound (1.77 g, 33.4% yield).

Example 252f ethyl 4-(2-(2,4-difluorophenoxy)-5-(methylsulfonyl)phenyl)-6-methyl-7-oxo-6,7-dihydro-1 H-pyrrolo[2,3-c]pyridine-2-carboxylate A mixture of Example 252e, anisole (1.585 mL, 14.51 mmol) and concentrated sulfuric acid (4.3 mL, 81 mmol) in trifluoroacetic acid (20 mL, 260 mmol) was heated at 90° C. for 4 hours. Excess trifluoroacetic acid was removed under reduced pressure, and the residue was partitioned between water (100 mL) and ethyl acetate (200 mL). The organic layer was separated, and the aqueous layer was extracted with additional ethyl acetate (2×200 mL). The combined organic layers were washed with saturated aqueous sodium bicarbonate (100 mL), followed by saturated aqueous sodium chloride (100 mL), dried over anhydrous magnesium sulfate, filtered, and concentrated. The crude material was taken into methanol (50 mL) and the resulting solid was filtered, rinsed with methanol, and dried to provide the title compound (3.1 g, 63% yield).

Example 252g 4-(2-(2,4-difluorophenoxy)-5-(methylsulfonyl)phenyl)-6-methyl-7-oxo-6,7-dihydro-1H-pyrrolo[2,3-c]pyridine-2-carboxylic acid Example 252f (1.1 g, 2.2 mmol) in dioxane (60 mL) was treated with 2.0 M aqueous lithium hydroxide (4.38 mL, 8.76 mmol). The reaction mixture was heated at 65° C. for two hours. The reaction mixture was cooled to ambient temperature and the solvent was removed under reduced pressure. The residue was dissolved in water (50 mL) and the pH adjusted to 5 with HCl (3M). The resulting solid was filtered and dissolved in ethyl acetate (200 mL). The solution was dried over anhydrous sodium sulfate, filtered, and concentrated to provide the title compound (0.85 g, 77% yield).

Example 252h

4-[2-(2,4-difluorophenoxy)-5-(methylsulfonyl)phenyl]-6-methyl-7-oxo-6,7-dihydro-1H-pyrrolo[2,3-c]pyridine-2-carboxamide To a solution of Example 252g (0.10 g, 0.21 mmol) in anhydrous dichloromethane (5 mL) was added oxalyl chloride (0.037 mL, 0.42 mmol) and dimethylformamide (0.816 µl, 10.5 µmol) The reaction mixture was stirred at ambient temperature for 2 hours. The reaction mixture was concentrated. The residue was redissolved in dichloromethane (5 mL) and treated with ammonium hydroxide (2 mL, 92 mmol) and the reaction mixture was stirred at ambient temperature for 16 hours. The reaction mixture was partitioned between water (15 mL) and ethyl acetate (25 mL). The aqueous layer was extracted with additional ethyl acetate (2×15 mL). The combined organic layers were dried over anhydrous sodium sulfate, filtered, and concentrated. The residue was triturated with ethyl acetate and the resulting solid was filtered, washed with dichloromethane and dried under vacuo to provide the title compound (48 mg, 47% yield). $^1$H NMR (400 MHz, DMSO-$d_6$) δ ppm 12.33 (s, 1H), 7.98 (s, 1H), 7.98-7.88 (m, 1H), 7.82 (s, 1H), 7.56-7.40 (m, 4H), 7.19 (m, 1H), 7.00 (d, J=8.8 Hz, 1H), 6.87 (s, 1H), 3.59 (s, 3H), 3.27 (s, 3H). MS (ESI+) m/z 474.1 (M+H)$^+$

Example 253

4-[2-(2,4-difluorophenoxy)-5-(methylsulfonyl)phenyl]-N-ethyl-6-methyl-7-oxo-6,7-dihydro-1 H-pyrrolo[2,3-c]pyridine-2-carboxamide Example 253 was prepared according to the procedure used for the preparation of Example 252h, substituting ethanamine for ammonium hydroxide, to provide the title compound. $^1$H NMR (400 MHz, DMSO-$d_6$) δ ppm 12.32 (s, 1H), 8.35-8.32 (m, 1H), 7.98 (s, 1H), 7.89 (dd, J=2.4, 6.4 Hz, 1H), 7.56-7.21 (m, 3H), 7.20-7.16 (m, 1H), 7.01 (d, J=8.4 Hz, 1H), 6.85 (s, 1H), 3.59 (s, 3H), 3.30-3.23 (m, 5H), 1.11 (t, J=7.2 Hz, 3H). MS (ESI+) m/z 502.1 (M+H)$^+$.

Example 254

4-[2-(2,4-difluorophenoxy)-5-(methylsulfonyl)phenyl]-6-methyl-7-oxo-N-(2,2,2-trifluoroethyl)-6,7-dihydro-1H-pyrrolo[2,3-c]pyridine-2-carboxamide Example 254 was prepared according to the procedure used for the preparation of Example 252h, substituting 2,2,2-trifluoroethanamine for ammonium hydroxide, to provide the title compound. $^1$H NMR (400 MHz, DMSO-$d_6$) δ ppm 12.56 (s, 1H), 8.94 (t, J=6 Hz, 1H), 7.99 (s, 1H), 7.98-7.89 (m, 1H), 7.52-7.50 (m, 2H), 7.42-7.40 (m, 1H), 7.17 (m, 1H), 7.03-7.00 (m, 2H), 4.13-4.08 (m, 2H), 3.59 (s, 3H), 3.26 (s, 3H). MS (ESI+) m/z 556.1 (M+H)$^+$.

Example 255

4-[2-(2,4-difluorophenoxy)-5-(methylsulfonyl)phenyl]-6-methyl-2-(morpholin-4-ylcarbonyl)-1,6-dihydro-7H-pyrrolo[2,3-c]pyridin-7-one Example 255 was prepared according to the procedure used for the preparation of Example 252h, substituting morpholine for ammonium hydroxide, to provide the title compound. $^1$H NMR (400 MHz, DMSO-$d_6$) δ ppm 7.99 (s, 1H), 7.88 (dd, J=2.4, 6 Hz, 1H), 7.59-7.42 (m, 3H), 7.22-7.17 (m, 1H), 6.98 (d, J=8.4 Hz, 1H), 6.50 (s, 1H), 3.59 (s, 3H), 3.55 (m, 8H), 3.27 (s, 3H). MS (ESI+) m/z 544.2 (M+H)$^+$.

Example 256

4-[2-(2,4-difluorophenoxy)-5-(methylsulfonyl)phenyl]-6-methyl-2-[(4-methylpiperazin-1-yl)carbonyl]-1,6-dihydro-7H-pyrrolo[2,3-c]pyridin-7-one Example 256 was prepared according to the procedure used for the preparation of Example 252h, substituting 1-methylpiperazine for ammonium hydroxide, to provide the title compound. $^1$H NMR (400 MHz, DMSO-$d_6$) δ ppm 7.97 (d, J=2 Hz, 1H), 7.84 (dd, J=2.4, 6 Hz, 1H), 7.32 (s, 1H), 7.13-7.10 (m, 2H), 6.94-6.91 (m, 2H), 6.51 (s, 1H), 3.68-3.65 (m, 4H), 3.60 (s, 3H), 3.08 (s, 3H), 2.38 (m, 4H), 2.24 (s, 3H). MS (ESI+) m/z 557.2 (M+H)$^+$.

Example 257

4-[2-(2,4-difluorophenoxy)-5-(methylsulfonyl)phenyl]-6-methyl-7-oxo-N-(1,3-thiazol-2-yl)-6,7-dihydro-1H-pyrrolo[2,3-c]pyridine-2-carboxamide Example 257 was prepared according to the procedure used for the preparation of Example 252h, substituting thiazol-2-amine for ammonium hydroxide, to provide the title compound. $^1$H NMR (400 MHz, DMSO-$d_6$) δ ppm 12.82 (s, 1H), 12.49 (s, 1H), 8.01 (s, 1H), 7.92 (dd, J=2.4, 6.4 Hz, 1H), 7.56-7.45 (m, 4H), 7.34-7.29 (m, 2H), 7.22-7.18 (m, 1H), 7.03 (d, J=8.4 Hz, 1H), 3.61 (s, 3H), 3.28 (s, 3H). MS (ESI+) m/z 557.1 (M+H)$^+$.

Example 258 ethyl 4-[2-(6-methyl-7-oxo-6,7-dihydro-1H-pyrrolo[2,3-c]pyridin-4-yl)-4-(methylsulfonyl)phenoxy]piperidine-1-carboxylate Example 258 was prepared according to the procedure used for the preparation of Example 158, substituting ethyl 4-hydroxypiperidine-1-carboxylate for cyclopropylmethanol, to provide the title compound. $^1$H NMR (500 MHz, DMSO-$d_6$) δ ppm 12.01 (s, 1H), 7.84-7.87 (m, 2H), 7.41 (d, J=9.46 Hz, 1H), 7.31 (s, 1H), 7.27 (t, J=2.59 Hz, 1H), 6.12 (s, 1H), 4.75-4.79 (m, 1H), 3.98 (q, J=7.02 Hz, 2H), 3.56 (s, 3H), 3.22-3.26 (m, 2H), 3.20 (s, 3H), 2.10 (s, 1H), 1.83-1.88 (m, 2H), 1.43-1.55 (M, 2H), 1.13 (t, J=7.02 Hz, 3H). MS (ESI+) m/z 474.1 (M+H)$^+$.

Example 259

4-[2-ethoxy-5-(methylsulfonyl)phenyl]-6-methyl-1,6-dihydro-7H-pyrrolo[2,3-c]pyridin-7-one The title compound was isolated as a minor product in the preparation of Example 258. $^1$H NMR (500 MHz, DMSO-$d_6$) δ ppm 12.02 (s, 1H), 7.88 (dd, J=8.54, 2.44 Hz, 1H), 7.82 (d, J=2.44 Hz, 1H), 7.32-7.34 (m, 2H), 7.28 (t, J=2.75 Hz, 1H), 6.10-6.11 (m, 1H), 4.17 (q, J=6.92 Hz, 2H), 3.57 (s, 3H), 3.21 (s, 3H), 3.20 (s, 3H), 1.22 (t, J=7.02 Hz, 3H). MS (ESI+) m/z 347.1 (M+H)$^+$.

Example 260

4-{5-(ethylsulfonyl)-2-[(trans-4-methoxycyclohexyl)oxy]phenyl}-6-methyl-1,6-dihydro-7H-pyrrolo[2,3-c]pyridin-7-one The title compound (first eluting peak) was isolated as a second product in the preparation of Example 248b. $^1$H NMR (500 MHz, DMSO-$d_6$) δ ppm 12.03 (s, 1H), 7.78-7.81 (m, 2H), 7.40 (d, J=8.54 Hz, 1H), 7.31 (s, 1H), 7.28 (t, J=2.75 Hz, 1H), 6.10-6.11 (m, 1H), 4.57-4.61 (m, 1H), 3.56 (s, 3H), 3.28 (t, J=7.32 Hz, 2H), 3.19 (s, 3H), 3.14-3.18 (m, 1H), 1.93-1.97 (m, 2H), 1.73-1.77 (m, 2H), 1.31-1.42 (m, 4H), 1.13 (t, J=7.32, 3H). MS (ESI+) m/z 445.0 (M+H)$^+$.

Example 261

4-{2-[(cyclopropylmethyl)amino]-5-(propan-2-ylsulfonyl)phenyl}-6-methyl-1,6-dihydro-7H-pyrrolo[2,3-c]pyridin-7-one

Example 261a (3-bromo-4-fluorophenyl)(isopropyl)sulfane

Example 261a was prepared according to the procedure used for the preparation of Example 168a, substituting 2-iodopropane for iodoethane, to provide the title compound.

Example 261b 2-bromo-1-fluoro-4-(isopropylsulfonyl)benzene

Example 261b was prepared according to the procedure used for the preparation of Example 168b, substituting Example 261a for Example 168a, to provide the title compound.

Example 261c 2-bromo-N-(cyclopropylmethyl)-4-(isopropylsulfonyl)aniline

Example 261c was prepared according to the procedure used for the preparation of Example 147a, substituting cyclopropylmethanamine for cyclohexanamine, and Example 261b for 2-bromo-1-fluoro-4-(methylsulfonyl)benzene to provide the title compound.

Example 261d

4-{2-[(cyclopropylmethyl)amino]-5-(propan-2-ylsulfonyl)phenyl}-6-methyl-1,6-dihydro-7H-pyrrolo[2,3-c]pyridin-7-one Example 261d was prepared according to the procedure used for the preparation of Example 95d, substituting Example 261c for Example 95c, to provide the title compound. $^1$H NMR (500 MHz, DMSO-$d_6$) δ ppm 12.12 (s, 1H), 7.59 (dd, J=8.7, 2.29 Hz, 1H), 7.40 (d, J=2.44 Hz, 1H), 7.30 (t, J=2.9 Hz, 1H), 7.25 (s, 1H), 6.88 (d, J=8.85 Hz, 1H), 5.98-5.99 (m, 1H), 5.61 (br s, 1H), 3.56 (s, 3H), 3.22-3.30 (m, 2H), 3.03 (d, J=6.71 Hz, 2H), 1.16 (d, J=7.02 Hz, 6H), 0.98-1.14 (m, 1H), 0.36-0.41 (m, 2H), 0.14-0.18 (m, 2H). MS (ESI+) m/z 400.1 (M+H)$^+$.

Example 262

N-[4-(cyclopropylmethoxy)-2-methyl-3-(6-methyl-7-oxo-6,7-dihydro-1H-pyrrolo[2,3-c]pyridin-4-yl)phenyl]methanesulfonamide Example 262 was prepared according to the procedure used for the preparation of Example 4 (Method A), substituting Example 251c for Example 3, to provide the title compound. $^1$H NMR (500 MHz, CD$_3$OD) ppm 7.34 (d, J=8.9 Hz, 1H), 7.28 (d, J=2.8 Hz, 1H), 6.98 (s, 1H), 6.93 (d, J=8.9 Hz, 1H), 5.93 (d, J=2.8 Hz, 1H), 3.78 (m, 2H), 3.69 (s, 3H), 2.98 (s, 3H), 2.13 (m, 3H), 0.99 (m, 1H), 0.35 (m, 2H), 0.08 (m, 2H). MS (ESI+) m/z 402.1 (M+H)$^+$.

Example 263

N-[4-(cyclopropylmethoxy)-2-methyl-5-(6-methyl-7-oxo-6,7-dihydro-1H-pyrrolo[2,3-c]pyridin-4-yl)phenyl]methanesulfonamide

Example 263a 1-bromo-2-(cyclopropylmethoxy)-4-methyl-5-nitrobenzene

Example 263a was prepared according to the procedure used for the preparation of Example 247a, substituting 2-bromo-5-methyl-4-nitrophenol for 2-bromo-3-methylphenol to provide the title compound.

Example 263b 4-(2-(cyclopropylmethoxy)-4-methyl-5-nitrophenyl)-6-methyl-1-tosyl-1H-pyrrolo[2,3-c]pyridin-7(6H)-one Example 263b was prepared according to the procedure used for the preparation of Example 7d, substituting the product of Example 263a for the product of Example 7c and stirring at 65° C. for 2.5 hours, to provide the title compound.

Example 263c 4-(5-amino-2-(cyclopropylmethoxy)-4-methylphenyl)-6-methyl-1-tosyl-1H-pyrrolo[2,3-c]pyridin-7(6H)-one Example 263c was prepared according to the procedure used for the preparation of Example 3, substituting the product of Example 263b for the product of Example 2b to provide the title compound.

Example 263d

N-(4-(cyclopropylmethoxy)-2-methyl-5-(6-methyl-7-oxo-6,7-dihydro-1H-pyrrolo[2,3-c]pyridin-4-yl)phenyl)methanesulfonamide Example 263d was prepared according to the procedure used for the preparation of Example 4 (Method A), substituting Example 263c for Example 3, to provide the title compound. $^1$H NMR (500 MHz, CD$_3$OD) ppm 7.36 (s, 1H), 7.31 (d, J=2.8 Hz, 1H), 7.28 (s, 1H), 6.96 (s, 1H), 6.35 (d, J=2.8 Hz, 1H), 3.84 (d, J=6.7 Hz, 2H), 3.69 (s, 3H), 3.11 (s, 3H), 2.41 (s, 3H), 1.11 (m, 1H), 0.47 (m, 2H), 0.24 (m, 2H). MS (ESI+) m/z 402.1 (M+H)$^+$.

Example 264

4-[5-(ethylsulfonyl)-2-(tetrahydro-2H-thiopyran-4-yloxy)phenyl]-6-methyl-1,6-dihydro-7H-pyrrolo[2,3-c]pyridin-7-one

Example 264a 4-(2-bromo-4-(ethylsulfonyl)phenoxy)tetrahydro-2H-thiopyran

Example 264a was prepared according to the procedure used for the preparation of Example 158, substituting Example 168b for Example 138a, and tetrahydro-2H-thiopyran-4-ol for cyclopropylmethanol, respectively, to provide the title compound.

Example 264b

4-[5-(ethylsulfonyl)-2-(tetrahydro-2H-thiopyran-4-yloxy)phenyl]-6-methyl-1,6-dihydro-7H-pyrrolo[2,3-c]pyridin-7-one Example 264b was prepared according to the procedure used for the preparation of Example 95d, substituting Example 264a for Example 95c, to provide the title compound. $^1$H NMR (500 MHz, DMSO-d$_6$) δ ppm 12.05 (s, 1H), 7.79-7.82 (m, 2H), 7.40 (d, J=9.77 Hz, 1H), 7.34 (s, 1H), 7.30 (t, J=2.75 Hz, 1H), 6.12-6.13 (m, 1H), 4.69-4.72 (m, 1H), 3.58 (s, 3H), 3.28 (d, J=7.32 Hz, 2H), 2.50-2.62 (m, 4H), 2.06-2.12 (m, 2H), 1.74-1.81 (m, 2H), 1.13 (d, J=7.32 Hz, 6H). MS (ESI+) m/z 433.1 (M+H)$^+$.

Example 265

4-{2-[(1,1-dioxidotetrahydro-2H-thiopyran-4-yl)oxy]-5-(ethylsulfonyl)phenyl}-6-methyl-1,6-dihydro-7H-pyrrolo[2,3-c]pyridin-7-one Example 265 was prepared according to the procedure used for the preparation of Example 168b, substituting 264b for Example 168a, to provide the title compound. $^1$H NMR (500 MHz, DMSO-d$_6$) δ ppm 12.09 (s, 1H), 7.83-7.87 (m, 2H), 7.48 (d, J=8.85 Hz, 1H), 7.35 (s, 1H), 7.29 (t, J=2.75 Hz, 1H), 6.14-6.15 (m, 1H), 4.90-4.93 (m, 1H), 3.58 (s, 3H), 3.30 (q, J=7.43 Hz, 2H), 3.01-3.04 (m, 2H), 2.76-2.82 (m, 2H), 2.12-2.18 (m, 4H), 1.14 (t, J=7.32 Hz, 3H). MS (ESI+) m/z 465.1 (M+H)$^+$.

Example 266

6-(2,4-difluorophenoxy)-N,N-dimethyl-5-(6-methyl-7-oxo-6,7-dihydro-1H-pyrrolo[2,3-c]pyridin-4-yl)pyridine-3-sulfonamide

Example 266a 5-bromo-6-(2,4-difluorophenoxy)-N,N-dimethylpyridine-3-sulfonamide Example 242a (0.365 g, 1 mmol) in dimethylformamide (5 mL) was treated with 60% sodium hydride (0.120 g, 3.00 mmol). The solution was stirred for 10 minutes. To this solution was added iodomethane (0.355 g, 2.500 mmol). The reaction mixture was stirred at ambient temperature for 2 hours. The reaction mixture was partitioned between water and ethyl acetate. The aqueous layer was extracted with additional ethyl acetate two more times. The combined organic layers were washed with saturated aqueous sodium chloride, dried over anhydrous magnesium sulfate, filtered, and concentrated. The residue was purified by flash chromatography on silica gel to give the title compound (0.365 g, 0.928 mmol, 93% yield).

Example 266b 6-(2,4-difluorophenoxy)-N,N-dimethyl-5-(6-methyl-7-oxo-6,7-dihydro-1H-pyrrolo[2,3-c]pyridin-4-yl)pyridine-3-sulfonamide Example 266b was prepared according to the procedure used for the preparation of Example 95d, substituting Example 266a for Example 95c, to provide the title compound. $^1$H NMR (500 MHz, DMSO-$d_6$) δ ppm 12.17 (s, 1H), 8.50 (d, J=2.44 Hz, 1H), 8.18 (d, J=2.44 Hz, 1H), 7.57 (s, 1H), 7.46-7.51 (m, 2H), 7.35 (t, J=2.75 Hz, 1H), 7.15-7.18 (m, 1H), 6.33-6.34 (m, 1H), 3.61 (s, 3H), 2.71 (s, 6H). MS (ESI+) m/z 461.1 (M+H)$^+$.

Example 267

4-[2-(cyclopropylamino)-5-(ethylsulfonyl)phenyl]-6-methyl-1,6-dihydro-7H-pyrrolo[2,3-c]pyridin-7-one

Example 267a 2-bromo-N-cyclopropyl-4-(ethylsulfonyl)aniline

Example 267a was prepared according to the procedure used for the preparation of Example 147a, substituting cyclopropylamine for cyclohexanamine, and Example 168b for 2-bromo-1-fluoro-4-(methylsulfonyl)benzene to provide the title compound.

Example 267b

4-[2-(cyclopropylamino)-5-(ethylsulfonyl)phenyl]-6-methyl-1,6-dihydro-7H-pyrrolo[2,3-c]pyridin-7-one Example 267b was prepared according to the procedure used for the preparation of Example 95d, substituting Example 267a for Example 95c, to provide the title compound. $^1$H NMR (500 MHz, DMSO-$d_6$) δ ppm 12.32 (s, 1H), 7.92 (dd, J=8.7, 2.29 Hz, 1H), 7.68 (d, J=2.44 Hz, 1H), 7.51 (t, J=2.75 Hz, 1H), 7.45 (s, 1H), 7.40 (d, J=8.54 Hz, 1H), 6.14-6.15 (m, 1H), 6.11 (s, 1H), 3.77 (s, 3H), 3.40 (q, J=7.32 Hz, 2H), 2.63-2.67 (m, 1H), 1.35 (t, J=7.32 Hz, 3H), 0.95-0.97 (m, 2H), 0.62-0.68 (m 2H). MS (ESI+) m/z 372.1 (M+H)$^+$.

Example 268

4-(5-(ethylsulfonyl)-2-(cis-4-methoxy-4-methylcyclohexyloxy)phenyl)-6-methyl-1H-pyrrolo[2,3-c]pyridin-7(6H)-one

Example 268a 8-(2-bromo-4-(ethylsulfonyl)phenoxy)-1,4-dioxaspiro[4.5]decane

Example 268a was prepared according to the procedure used for the preparation of Example 158, substituting Example 168b for Example 138a, and 1,4-dioxaspiro[4.5]decan-8-ol for cyclopropylmethanol, respectively, to provide the title compound.

Example 268b 4-(2-bromo-4-(ethylsulfonyl)phenoxy)cyclohexanone

Example 268b was prepared according to the procedure used for the preparation of Example 199, substituting Example 268a for Example 197, to provide the title compound.

Example 268c (cis)-4-(2-bromo-4-(ethylsulfonyl)phenoxy)-1-methylcyclohexanol Example 268b (0.95 g, 2.63 mmol) in THF (15 mL) was cooled to 0° C. This solution was treated with 3.0 M methylmagnesium bromide (2.63 ml, 7.89 mmol) and stirred at room temperature overnight. The reaction mixture was quenched with saturated NH$_4$Cl solution and partitioned between water and ethyl acetate. The aqueous layer was extracted with additional ethyl acetate twice. The combined organic layers were washed with brine, dried over MgSO$_4$, filtered, and concentrated. The residue was purified by flash column chromatography on silica gel eluting with 1:1 ethyl acetate/hexanes to give two fractions. Example 268c was the first fraction to elute from the column.

Example 268d 2-bromo-4-(ethylsulfonyl)-1-((cis)-4-methoxy-4-methylcyclohexyloxy)benzene Example 268c (0.43 g, 1.140 mmol) in tetrahydrofuran (5 mL) was treated with 60% sodium hydride (0.182 g, 4.5 mmol). The reaction was stirred at ambient temperature for 10 minutes. To this solution was added iodomethane (2) (0.65 g, 4.5 mmol). The reaction mixture was heated at 40° C. for 16 ours. The reaction mixture was partitioned between water and ethyl acetate. The aqueous layer was extracted with additional ethyl acetate two more times. The combined organic layers were washed with saturated aqueous sodium chloride, dried over anhydrous magnesium sulfate, filtered, and concentrated. The residue was purified by flash chromatography on silica gel to give the title compound (0.356 g, 0.910 mmol, 80% yield).

Example 268e 4-(5-(ethylsulfonyl)-2-(cis-4-methoxy-4-methylcyclohexyloxy)phenyl)-6-methyl-1H-pyrrolo[2,3-c]pyridin-7(6H)-one Example 268e was prepared according to the procedure used for the preparation of Example 95d, substituting Example 268d for Example 95c, to provide the title compound. $^1$H NMR (500 MHz, DMSO-$d_6$) δ ppm 12.04 (s, 1H), 7.77-7.81 (m, 2H), 7.39 (d, J=8.85 Hz, 1H), 7.31 (s, 1H), 7.29 (t, J=2.75 Hz, 1H), 6.10-6.11 (m, 1H), 4.50-4.55 (m, 1H), 3.57 (s, 3H), 3.28 (q, J=7.32 Hz, 2H), 1.69-1.78 (m, 4H), 1.46-1.53 (m, 2H), 1.33-1.38 (m, 2H), 1.13 (t, J=7.32 Hz, 3H), 1.05 (s, 3H). MS (ESI+) m/z 459.1 (M+H)$^+$.

Example 269

4-[2-(2,4-difluorophenoxy)-5-(methylsulfonyl)phenyl]-N,N,6-trimethyl-7-oxo-6,7-dihydro-1H-pyrrolo[2,3-c]pyridine-2-carboxamide Example 269 was prepared according to the procedure used for the preparation of Example 252h, substituting dimethylamine for ammonium hydroxide, to provide the title compound. $^1$H NMR (400 MHz, DMSO-$d_6$) δ ppm 8.08 (s, 1H), 7.95 (dd, J=2.4, 6 Hz, 1H), 7.43 (s, 1H), 7.26-7.15 (m, 2H), 7.05-6.99 (m, 2H), 6.69 (s, 1H), 3.72 (s, 3H), 3.25 (s, 3H), 3.19 (s, 3H), 3.12 (s, 1H). MS (ESI+) m/z 502.0 (M+H)$^+$.

Example 270

6-methyl-4-{5-(methylsulfonyl)-2-[4-(methylsulfonyl)phenoxy]phenyl}-1,6-dihydro-7H-pyrrolo[2,3-c]pyridin-7-one Example 270 was prepared according to the procedure used for the preparation of Example 138b, substituting 4-(methylsulfonyl)phenol for 2,4-difluorophenol, to provide the title compound. $^1$H NMR (500 MHz, DMSO-$d_6$) δ ppm 12.08 (s, 1H), 8.06 (d, J=2.44 Hz, 1H), 7.97 (dd, J=8.7, 2.29 Hz, 1H), 7.85-7.88 (m, 2H), 7.40 (s, 1H), 7.35 (d, J=8.54 Hz, 1H), 7.29 (t, J=2.75 Hz, 1H), 7.20-7.23 (m, 2H), 6.24-6.25 (m, 1H), 3.54 (s, 3H), 3.30 (s, 3H), 3.17 (s, 3H). MS (ESI+) m/z 471.2 (M+H)$^+$.

Example 271

4-[2-(2,4-difluorophenoxy)-5-(propan-2-ylsulfonyl)phenyl]-6-methyl-1,6-dihydro-7H-pyrrolo[2,3-c]pyridin-7-one

Example 271a 2-bromo-1-(2,4-difluorophenoxy)-4-(isopropylsulfonyl)benzene

Example 271a was prepared according to the procedure used for the preparation of Example 138b, substituting Example 261b for Example 138a, to provide the title compound.

Example 271b

4-[2-(2,4-difluorophenoxy)-5-(propan-2-ylsulfonyl)phenyl]-6-methyl-1,6-dihydro-7H-pyrrolo[2,3-c]pyridin-7-one Example 271b was prepared according to the procedure used for the preparation of Example 95d, substituting Example 271a for Example 95c, to provide the title compound. $^1$H NMR (500 MHz, DMSO-$d_6$) δ ppm 12.11 (s, 1H), 7.88 (d, J=2.44 Hz, 1H), 7.80 (dd, J=8.85, 2.44 Hz, 1H), 7.50-7.54 (m, 1H), 7.42-7.49 (m, 2H), 7.31 (t, J=2.75 Hz, 1H), 7.15-7.19 (m, 1H), 7.00 (d, J=8.54, Hz, 1H), 6.25-6.26 (m, 1H), 3.59 (s, 3H), 3.44-3.48 (m, 1H), 1.20 (d, J=7.02 Hz, 6H). MS (ESI+) m/z 459.0 (M+H)$^+$.

Example 272

6-(cyclopropylmethoxy)-N,N-diethyl-5-(6-methyl-7-oxo-6,7-dihydro-1H-pyrrolo[2,3-c]pyridin-4-yl)pyridine-3-sulfonamide

Example 272a 5-bromo-6-(cyclopropylmethoxy)-N,N-diethylpyridine-3-sulfonamide Example 272a was prepared according to the procedure used for the preparation of Example 266a, substituting Example 207a for Example 242a, and ethyl iodide for iodomethane, respectively, to provide the title compound.

Example 272b 6-(cyclopropylmethoxy)-N,N-diethyl-5-(6-methyl-7-oxo-6,7-dihydro-1H-pyrrolo[2,3-c]pyridin-4-yl)pyridine-3-sulfonamide Example 272b was prepared according to the procedure used for the preparation of Example 95d, substituting Example 272a for Example 95c, to provide the title compound. $^1$H NMR (500 MHz, DMSO-$d_6$) δ ppm 12.10 (s, 1H), 8.54 (d, J=2.44 Hz, 1H), 8.01 (d, J=2.44 Hz, 1H), 7.44 (s, 1H), 7.32 (t, J=2.75 Hz, 1H), 6.15-6.16 (m, 1H), 4.24 (d, J=7.02 Hz, 2H), 3.58 (s, 3H), 3.21 (q, J=7.02 Hz, 4H), 1.17-1.20 (m, 4H), 1.08 (t, J=7.02 Hz, 6H), 0.47-0.51 (m, 2H), 0.29-0.32 (m, 2H). MS (ESI+) m/z 431.1 (M+H)$^+$.

Example 273

4-(cyclopropylmethoxy)-N,N-dimethyl-3-(6-methyl-7-oxo-6,7-dihydro-1H-pyrrolo[2,3-c]pyridin-4-yl)benzenesulfonamide

Example 273a 3-bromo-4-(cyclopropylmethoxy)-N,N-dimethylbenzenesulfonamide

Example 273a was prepared according to the procedure used for the preparation of Example 266a, substituting Example 249a for Example 242a, to provide the title compound.

Example 273b 4-(cyclopropylmethoxy)-N,N-dimethyl-3-(6-methyl-7-oxo-6,7-dihydro-1H-pyrrolo[2,3-c]pyridin-4-yl)benzenesulfonamide Example 273b was prepared according to the procedure used for the preparation of Example 95d, substituting Example 273a for Example 95c, to provide the title compound. $^1$H NMR (500 MHz, DMSO-$d_6$) δ ppm 12.05 (s, 1H), 7.70 (dd, J=8.54, 2.44 Hz, 1H), 7.66 (d, J=2.44 Hz, 1H), 7.37 (s, 1H), 7.29-7.32 (m, 2H), 6.12-6.13 (m, 1H), 3.98 (d, J=6.71

Hz, 2H), 3.57 (s, 3H), 2.62 (s, 6H), 3.21 (q, J=7.02 Hz, 4H), 1.11-1.15 (m, 1H), 0.46-0.49 (m, 2H), 0.27-0.30 (m, 2H). MS (ESI+) m/z 402.1 (M+H)$^+$.

Example 274

4-[2-(cyclopropylmethoxy)-5-fluorophenyl]-6-methyl-1,6-dihydro-7H-pyrrolo[2,3-c]pyridin-7-one Example 274a 2-bromo-1-(cyclopropylmethoxy)-4-fluorobenzene To a solution of 2-bromo-4-fluorophenol (0.50 g, 2.6 mmol) in tetrahydrofuran (13 mL) were added cyclopropanemethanol (0.209 mL, 2.62 mmol), triphenylphosphine (0.687 g, 2.62 mmol), and DIAD (0.509 mL, 2.62 mmol). The reaction mixture was stirred for 16 hours at ambient temperature. The solvent was removed under reduced pressure. The residue was triturated with hexanes. The mixture was filtered, and the filtrate containing the product was concentrated by under reduced pressure. The residue was purified by flash chromatography (silica gel, hexanes) to provide the title compound (400 mg, 62% yield).

Example 274b (2-(cyclopropylmethoxy)-5-fluorophenyl)boronic acid

To a solution of Example 274a (0.1 g, 0.408 mmol) in tetrahydrofuran (2 mL) at −20° C. was added nBuLi (0.180 mL of a 2.5 M solution in hexanes, 0.449 mmol). The reaction mixture was stirred for 2 hours, then cooled to −40° C. 2-Isopropoxy-4,4,5,5-tetramethyl-1,3,2-dioxaborolane (0.092 mL, 0.449 mmol) was added dropwise. The reaction mixture was stirred for 30 minutes. The reaction mixture was quenched with 1M citric acid at 0° C. The mixture was stirred at ambient temperature for 1 hour and then extracted with ethyl acetate. The layers were separated, and the organic layer was dried over anhydrous sodium sulfate, filtered, and concentrated. The crude material was purified by flash chromatography (silica gel, 10-33% ethyl acetate/hexanes gradient) to provide the title compound (23 mg, 20% yield).

Example 274c

4-[2-(cyclopropylmethoxy)-5-fluorophenyl]-6-methyl-1,6-dihydro-7H-pyrrolo[2,3-c]pyridin-7-one Nitrogen was bubbled through a 4:1 dimethoxyethane/ethanol solution for 20 minutes. A microwave vial was charged with Example 1e (0.05 g, 0.131 mmol), Example 274b (0.046 g, 0.144 mmol), Pd(Ph$_3$P)$_4$ (7.58 mg, 6.56 μmol), and cesium fluoride (0.060 g, 0.393 mmol). The vial was sealed and flushed with nitrogen. The 4:1 dimethoxyethane/ethanol mixture (0.5 mL) was added. The reaction mixture was heated in a microwave reactor at 120° C. for 40 minutes. The reaction mixture was partitioned between water and ethyl acetate. The layers were separated. The aqueous layer was extracted with ethyl acetate. The combined organics were dried over anhydrous sodium sulfate, filtered, and concentrated. The crude material was purified by flash chromatography (silica gel, 20-80% ethyl acetate/hexanes gradient) to provide the title compound (5 mg, 23% yield). $^1$H NMR (300 MHz, DMSO-d$_6$) ppm 11.98 (s, 1H), 7.29 (s, 1H), 7.26 (t, J=2.71 Hz, 1H), 7.05-7.18 (m, 3H), 6.14 (dd, J=2.71, 2.03 Hz, 1H), 3.80 (d, J=6.78 Hz, 2H), 3.55 (s, 3H), 0.98-1.09 (m, 1H), 0.39-0.46 (m, 2H), 0.17-0.22 (m, 2H). MS (ESI+) m/z 313.1 (M+H)$^+$.

Example 275

4-[2-(2,4-difluorophenoxy)-5-(trifluoromethyl)phenyl]-6-methyl-1,6-dihydro-7H-pyrrolo[2,3-c]pyridin-7-one Example 275a 2-bromo-1-(2,4-difluorophenoxy)-4-(trifluoromethyl)benzene A mixture of 3-bromo-4-fluorobenzotrifluoride (0.5 mL, 3.52 mmol), 2,4-difluorophenol (0.337 mL, 3.52 mmol), and potassium carbonate (0.486 g, 3.52 mmol) in dimethylformamide (7 mL) was heated at 80° C. for 16 hours. The reaction mixture was cooled to ambient temperature and partitioned between ethyl acetate and water. The layers were separated, and the aqueous layer was extracted with ethyl acetate. The combined organics were washed with water and saturated aqueous sodium chloride, dried over anhydrous sodium sulfate, filtered, and concentrated. The crude material was purified by flash chromatography (silica gel, 0-10% ethyl acetate/hexanes gradient) to provide the title compound (1.0 g, 80% yield).

Example 275b (2-(2,4-difluorophenoxy)-5-(trifluoromethyl)phenyl)boronic acid

To a suspension of magnesium (0.083 g, 3.42 mmol) in tetrahydrofuran (1.00 mL) was added 0.5 mL of a solution of Example 275a (1.099 g, 3.11 mmol) in tetrahydrofuran (1.5 mL). The reaction mixture was warmed (about 40-50° C.) until reaction commenced. The remaining solution of starting bromide was added dropwise. The reaction mixture was stirred at ambient temperature for 1 hour. The resulting solution was added dropwise to a solution of trimethyl borate (0.696 mL, 6.23 mmol) in tetrahydrofuran (1.5 mL) at 0° C. The reaction mixture was stirred at ambient temperature for 1 hour, quenched with ice water and then neutralized with 2 M HCl. The mixture was extracted with ethyl acetate. The combined organics were washed with saturated aqueous sodium chloride, dried over anhydrous sodium sulfate, filtered, and concentrated. The residue was purified by flash chromatography (silica gel, 10-33% ethyl acetate/hexanes gradient) to provide the title compound (650 mg, 66% yield).

Example 275c

4-[2-(2,4-difluorophenoxy)-5-(trifluoromethyl)phenyl]-6-methyl-1,6-dihydro-7H-pyrrolo[2,3-c]pyridin-7-one Example 275c was prepared according to the procedure used for the preparation of Example 274c, substituting example 275b for example 274b, to provide the title compound. $^1$H NMR (300 MHz, DMSO-d$_6$) ppm 12.06 (s, 1H), 7.78 (d, J=2.37 Hz, 1H), 7.70 (dd, J=8.48, 1.70 Hz, 1H), 7.49 (td, J=11.36, 8.65, 3.05 Hz, 1H), 7.40 (s, 1H), 7.34-7.43 (m, 1H), 7.28 (t, J=2.71 Hz, 1H), 7.10-7.17 (m, 1H), 6.95 (d, J=8.48 Hz, 1H), 6.24 (dd, J=2.71, 2.03 Hz, 1H), 3.57 (s, 3H). MS (ESI+) m/z 421.1 (M+H)⁺.

Example 276

4-[2-(2,4-difluorophenoxy)-5-(methylsulfonyl)phenyl]-2-(hydroxymethyl)-6-methyl-1,6-dihydro-7H-pyrrolo[2,3-c]pyridin-7-one To a suspension of Example 252f (0.20 g, 0.40 mmol) in tetrahydrofuran (5 mL) stirring at 0° C. was added lithium aluminum hydride (1M in tetrahydrofuran, 0.398 mL, 0.398 mmol) and the mixture was stirred at 0° C. for two hours. The solvent was evaporated under reduced pressure and the residue was partitioned between ethyl acetate (30 mL) and water (20 mL). The mixture was filtered to remove the undissolved materials. The aqueous layer was extracted with ethyl acetate (2×30 mL). The combined organic layers were dried over anhydrous sodium sulfate, filtered, and concentrated. The residue was triturated with dichloromethane and the resulting solid was filtered and dried to provide the title compound (0.10 g, 55% yield). $^1$H NMR (400 MHz, DMSO-$d_6$) δ ppm 11.91 (s, 1H), 7.97 (d, J=2.4 Hz, 1H), 7.86 (dd, J=2.4, 6.4 Hz, 1H), 7.56-7.38 (m, 3H), 7.20-7.15 (m, 1H), 6.97 (d, J=8.4 Hz, 1H), 6.18 (s, 1H), 5.11 (t, J=5.6 Hz, 1H), 4.50 (d, J=5.6 Hz, 2H), 3.57 (s, 3H), 3.16 (s, 3H). MS (ESI+) m/z 461.2 (M+H)⁺.

Example 277

4-[2-(2,3-dihydro-1H-inden-2-yloxy)-5-(methylsulfonyl)phenyl]-6-methyl-1,6-dihydro-7H-pyrrolo[2,3-c]pyridin-7-one Example 277 was prepared according to the procedure used for the preparation of Example 158, substituting 2,3-dihydro-1H-inden-2-ol for cyclopropylmethanol, to provide the title compound. $^1$H NMR (500 MHz, DMSO-$d_6$) δ ppm 11.97 (s, 1H), 7.91 (dd, J=8.54, 2.44 Hz, 1H), 7.85 (d, J=2.44 Hz, 1H), 7.47 (d, J=8.85 Hz, 1H), 7.20-7.23 (m, 2H), 7.12-7.17 (m, 3H), 7.07 (s, 1H), 6.00-6.01 (m, 1H), 5.41-5.44 (m, 1H), 3.36-3.42 (m, 2H), 3.56 (s, 3H), 3.23 (s, 3H), 3.20 (s, 3H), 2.97 (dd, J=16.94, 1.98 Hz, 2H). MS (ESI+) m/z 435.1 (M+H)⁺.

Example 278

4-[2-(2,4-difluorophenoxy)-5-(methylsulfonyl)phenyl]-2-(1-hydroxyethyl)-6-methyl-1,6-dihydro-7H-pyrrolo[2,3-c]pyridin-7-one Example 278a 4-(2-(2,4-difluorophenoxy)-5-(methylsulfonyl)phenyl)-6-methyl-7-oxo-6,7-dihydro-1H-pyrrolo[2,3-c]pyridine-2-carbaldehyde To the solution of Example 276 (1.0 g, 2.2 mmol) in dichloromethane (50 mL) at 0° C. was added Dess-MartinPeriodinane (1.84 g, 4.34 mmol) and the reaction mixture was stirred at 0° C. for 30 minutes. The reaction mixture was then stirred at ambient temperature for three hours. A solution of sodium bisulfite (0.9 g, 9 mmol) in saturated aqueous sodium bicarbonate (5 mL) was added, and the reaction mixture was stirred for 15 minutes and extracted with ethyl acetate. The organic layer was dried (anhydrous sodium sulfate), filtered, and concentrated to provide the title compound (0.80 g, 70% yield).

Example 278b

4-[2-(2,4-difluorophenoxy)-5-(methylsulfonyl)phenyl]-2-(1-hydroxyethyl)-6-methyl-1,6-dihydro-7H-pyrrolo[2,3-c]pyridin-7-one To a solution of Example 278a (0.20 g, 0.44 mmol) in tetrahydrofuran (6 mL) at 0° C. was added methylmagnesium bromide (1.0 M in tetrahydrofuran, 0.873 mL, 0.873 mmol). The reaction mixture was stirred at 0° C. for one hour, and then 1M aqueous HCl (2 mL) was added. The reaction mixture was concentrated and partitioned between saturated aqueous sodium chloride (10 mL) and ethyl acetate (2×30 mL). The combined organic phase was washed with saturated aqueous sodium chloride (30 mL), dried over anhydrous sodium sulfate, filtered, and concentrated. The residue was purified by preparative thin layer chromatography (silica gel, dichloromethane/methanol, 15/1) to provide the title compound (51 mg, 24% yield). $^1$H NMR (400 MHz, DMSO-$d_6$) δ ppm 11.83 (s, 1H), 7.96 (d, J=2.4 Hz, 1H), 7.86 (dd, J=2.4, 6.4 Hz, 1H), 7.55-7.50 (m, 1H), 7.42-7.36 (m, 2H), 7.20-7.15 (m, 1H), 6.97 (d, J=8.8 Hz, 1H), 6.15 (d, J=2 Hz, 1H), 5.13 (d, J=5.2 Hz, 1H), 4.80-4.77 (m, 1H), 3.57 (s, 3H), 3.25 (s, 3H), 1.38 (d, J=6.4 Hz, 3H). MS (ESI+) m/z 475.1 (M+1)⁺.

Example 279

4-[2-(2,4-difluorophenoxy)-5-(methylsulfonyl)phenyl]-2-[(dimethylamino)methyl]-6-methyl-1,6-dihydro-7H-pyrrolo[2,3-c]pyridin-7-one To a solution of Example 278a (0.20 g, 0.44 mmol) and dimethylamine hydrochloride (0.071 g, 0.873 mmol) in methanol (6 mL) was added zinc chloride (0.059 g, 0.436 mmol) at ambient temperature. The reaction mixture was stirred at ambient temperature for one hour, and then sodium cyanoborohydride (0.055 g, 0.873 mmol) was added and the reaction mixture was stirred at ambient temperature for three days. The resulting solid was filtered and washed with methanol (10 mL), and the eluant was concentrated. The residue was purified by preparative thin layer chromatography (silica gel, dichloromethane/methanol, 15/1) to provide the title compound (75 mg, 34% yield). $^1$H NMR (400 MHz, CD$_3$OD) δ ppm 8.07 (d, J=2.4 Hz, 1H), 7.94 (dd, J=2.4, 6.4 Hz, 1H), 7.38 (s, 1H), 7.25-7.06 (m, 2H), 7.04-6.98 (m, 2H), 6.31 (s, 1H), 3.71 (s, 3H), 3.67 (s, 2H), 3.19 (s, 3H), 2.28 (s, 6H). MS (ESI+) m/z 488.1 (M+H)⁺.

Example 280

4-[2-(2,4-difluorophenoxy)-5-(methylsulfonyl)phenyl]-6-methyl-2-(morpholin-4-ylmethyl)-1,6-dihydro-7H-pyrrolo[2,3-c]pyridin-7-one Example 280 was prepared according to the procedure used for the preparation of Example 279, substituting morpholine for dimethylamine hydrochloride, to provide the title compound. $^1$H NMR (400 MHz, DMSO-$d_6$) δ ppm 11.98 (s, 1H), 7.98 (d, J=2.4 Hz, 1H), 7.87 (dd, J=2.4, 6.4 Hz, 1H), 7.56-7.50 (m, 1H), 7.44-7.38 (m, 2H), 7.19-7.16 (m, 1H), 6.99 (d, J=8.4 Hz, 1H), 6.15 (s, 1H), 3.58 (s, 3H), 3.55 (s, 2H), 3.49-3.47 (m, 4H), 3.26 (s, 3H), 2.31 (m, 4H). MS (ESI+) m/z 530.2 (M+H)⁺.

Example 281

4-[2-(2,4-difluorophenoxy)-5-(methylsulfonyl)phenyl]-6-methyl-2-[(4-methylpiperazin-1-yl)methyl]-1,6-dihydro-7H-pyrrolo[2,3-c]pyridin-7-one Example 281 was prepared according to the procedure used for the preparation of Example 279, substituting 1-methylpiperazine for dimethylamine hydrochloride, to provide the title compound. $^1$H NMR (400 MHz, DMSO-$d_6$) δ ppm 11.94 (s, 1H), 7.98 (d, J=2.4 Hz, 1H), 7.87 (dd, J=2.4, 6.4 Hz, 1H), 7.55-7.49 (m, 1H), 7.43-7.37 (m, 2H), 7.18-7.13 (m, 1H), 6.99 (d, J=8.4 Hz, 1H), 6.12 (s, 1H), 3.57 (s, 3H), 3.52 (s, 2H), 3.26 (s, 3H), 2.32-2.21 (m, 8H), 2.09 (s, 3H). MS (ESI+) m/z 543.2 (M+H)$^+$.

Example 282

4-[2-(2,4-difluorophenoxy)-5-(methylsulfonyl)phenyl]-6-methyl-2-[(phenylamino)methyl]-1,6-dihydro-7H-pyrrolo[2,3-c]pyridin-7-one Example 282 was prepared according to the procedure used for the preparation of Example 279, substituting aniline for dimethylamine hydrochloride, to provide the title compound. $^1$H NMR (400 MHz, DMSO-$d_6$) δ ppm 11.95 (s, 1H), 7.93 (d, J=2.4 Hz, 1H), 7.84 (dd, J=2.4, 6.8 Hz, 1H), 7.48 (m, 1H), 7.40 (s, 1H), 7.29-7.28 (m, 1H), 7.12 (m, 1H), 6.99-6.91 (m, 3H), 6.58 (d, J=7.6 Hz, 2H), 6.49 (t, J=7.2 Hz, 1H), 6.19 (d, J=2.0 Hz, 1H), 5.94 (m, 1H), 4.31 (d, J=6.4 Hz, 2H), 3.56 (s, 3H), 3.23 (s, 3H). MS (ESI+) m/z 536.2 (M+H)$^+$.

Example 283

4-[2-(2,4-difluorophenoxy)-5-(methylsulfonyl)phenyl]-6-methyl-2-[(1,3-thiazol-2-ylamino)methyl]-1,6-dihydro-7H-pyrrolo[2,3-c]pyridin-7-one Example 283 was prepared according to the procedure used for the preparation of Example 279, substituting thiazol-2-amine for dimethylamine hydrochloride, to provide the title compound. $^1$H NMR (400 MHz, DMSO-$d_6$) δ ppm 11.99 (s, 1H), 7.94 (d, J=2.4 Hz, 1H), 7.86-7.83 (m, 2H), 7.51-7.45 (m, 1H), 7.42 (s, 1H), 7.30-7.26 (m, 1H), 7.14-7.13 (m, 1H), 6.99-6.92 (m, 2H), 6.62 (d, J=3.6 Hz, 1H), 6.18 (s, 1H), 5.94 (m, 1H), 4.49 (d, J=5.6 Hz, 2H), 3.58 (s, 3H), 3.24 (s, 3H). MS (ESI+) m/z 543.2 (M+H)$^+$.

Example 284

4-[2-(2,4-difluorophenoxy)-5-(methylsulfonyl)phenyl]-6-methyl-2-[(tetrahydrofuran-3-ylamino)methyl]-1,6-dihydro-7H-pyrrolo[2,3-c]pyridin-7-one Example 284 was prepared according to the procedure used for the preparation of Example 279, substituting tetrahydrofuran-3-amine for dimethylamine hydrochloride, to provide the title compound. $^1$H NMR (400 MHz, DMSO-$d_6$) δ ppm 11.86 (s, 1H), 7.97 (d, J=2.4 Hz, 1H), 7.87-7.85 (m, 2H), 7.54-7.39 (m, 3H), 7.18-7.16 (m, 1H), 6.98 (d, J=8.4 Hz, 1H), 6.17 (s, 1H), 3.72-3.66 (m, 3H), 3.57-3.53 (m, 5H), 3.25 (s, 3H), 3.14-3.13 (m, 1H), 2.27-2.26 (m, 1H), 1.82-1.77 (m, 1H), 1.58-1.57 (m, 1H). MS (ESI+) m/z 530.2 (M+H)$^+$.

Example 285

4-[2-(cyclopropylmethoxy)-5-(phenylsulfonyl)phenyl]-6-methyl-1,6-dihydro-7H-pyrrolo[2,3-c]pyridin-7-one Example 285a 1-(cyclopropylmethoxy)-4-(phenylsulfonyl)benzene Example 285a was prepared according to the procedure used for the preparation of Example 158, substituting 1-fluoro-4-(phenylsulfonyl)benzene for Example 138a, to provide the title compound.

Example 285b 2-bromo-1-(cyclopropylmethoxy)-4-(phenylsulfonyl) benzene

Example 285a (0.087 g, 0.3 mmol) in acetic acid (5 mL) was cooled to 0° C. To this solution was added 1-bromopyrrolidine-2,5-dione (2) (0.059 g, 0.330 mmol). The reaction mixture was heated at 80° C. for 16 hours. After cooling, the reaction mixture was partitioned between water and ethyl acetate. The aqueous layer was extracted with additional ethyl acetate two more times. The combined organic layers were washed with saturated aqueous sodium chloride, dried over anhydrous magnesium sulfate, filtered, and concentrated. The residue was purified by flash chromatography on silica gel to give the title compound (0.032 g, 0.087 mmol, 29% yield).

Example 285c

4-[2-(cyclopropylmethoxy)-5-(phenylsulfonyl)phenyl]-6-methyl-1,6-dihydro-7H-pyrrolo[2,3-c]pyridin-7-one Example 285c was prepared according to the procedure used for the preparation of Example 95d, substituting Example 285b for Example 95c, to provide the title compound. $^1$H NMR (500 MHz, DMSO-$d_6$) δ ppm 11.80 (s, 1H), 7.63-7.74 (m, 4H), 7.36-7.46 (m, 3H), 7.12 (s, 1H), 7.04-7.06 (m, 2H), 5.80-5.81 (m, 1H), 3.72 (d, J=6.71 Hz, 2H), 3.34 (s, 3H), 0.82-0.89 (m, 1H), 0.29-0.24 (m, 2H), 0.00-0.04 (m, 2H). MS (ESI+) m/z 434.9 (M−H)$^+$.

Example 286

4-[2-(cyclopropylmethoxy)-5-(morpholin-4-ylsulfonyl)phenyl]-6-methyl-1,6-dihydro-7H-pyrrolo[2,3-c]pyridin-7-one Example 286a 4-(3-bromo-4-fluorophenylsulfonyl)morpholine 3-Bromo-4-fluorobenzene-1-sulfonyl chloride (0.44 g, 1.609 mmol) in tetrahydrofuran (10 mL) was treated with morpholine (0.294 g, 3.38 mmol). The reaction mixture was stirred for 16 hours at ambient temperature. The solvent was removed, and the residue was loaded onto a silica gel column and eluted with 20% ethyl acetate in hexanes to give the title compound (0.45 g, 1.388 mmol, 86% yield).

Example 286b 4-(3-bromo-4-(cyclopropylmethoxy)phenylsulfonyl) morpholine

Example 286b was prepared according to the procedure used for the preparation of Example 158, substituting Example 286a for Example 138a, to provide the title compound.

Example 286c

4-[2-(cyclopropylmethoxy)-5-(morpholin-4-ylsulfonyl)phenyl]-6-methyl-1,6-dihydro-7H-pyrrolo[2,3-c]pyridin-7-one Example 286c was prepared according to the procedure used for the preparation of Example 95d, substituting Example 286b for Example 95c, to provide the title compound. $^1$H NMR (500 MHz, DMSO-d$_6$) δ ppm 12.03 (s, 1H), 7.69 (dd, J=8.85, 2.44 Hz, 1H), 7.64 (d, J=2.44 Hz, 1H), 7.37 (s, 1H), 7.33 (d, J=8.85 Hz, 1H), 7.29 (t, J=2.75 Hz, 1H), 6.11-6.13 (m, 1H), 3.97 (d, J=6.71 Hz, 2H), 3.62-3.65 (m, 4H), 3.57 (s, 3H), 2.86-2.88 (m, 4H), 0.45-0.48 (m, 2H), 0.27-0.29 (m, 2H). MS (ESI+) m/z 444.1 (M+H)$^+$.

Example 287

4-{2-(2,4-difluorophenoxy)-5-[(methylsulfonyl)methyl]phenyl}-6-methyl-1,6-dihydro-7H-pyrrolo[2,3-c]pyridin-7-one

Example 287a 3-bromo-4-(2,4-difluorophenoxy)benzaldehyde

A mixture of 3-bromo-4-fluorobenzaldehyde (4.06 g, 20 mmol), 2,4-difluorophenol (2.60 g, 20 mmol) and cesium carbonate (7.17 g, 22 mmol) in dimethyl sulfoxide (20 mL) was heated at 100° C. for 1 hour. The reaction mixture was partitioned with ethyl acetate and water. The organic layer was washed with saturated aqueous sodium chloride twice, dried with anhydrous sodium sulfate, filtered, and concentrated. The residue was purified by flash chromatography (silica gel, 20% ethyl acetate in heptanes) to provide the title compound (5.94 g, 95%).

Example 287b (3-bromo-4-(2,4-difluorophenoxy)phenyl)methanol

To a solution of Example 287a (3.76 g, 12 mmol) in the mixture of ethanol (10 mL) and tetrahydrofuran (10 mL) was added sodium borohydride (0.136 g, 3.60 mmol). The reaction mixture was stirred at ambient temperature for 1 hour. The solvent was evaporated and the residue was partitioned with ethyl acetate and water. The organic layer was washed with saturated aqueous sodium chloride, dried with anhydrous sodium sulfate, filtered, and concentrated to provide the title compound (3.72 g, 98%).

Example 287c 2-bromo-4-(bromomethyl)-1-(2,4-difluorophenoxy) benzene

To a solution of Example 287b (3.70 g, 11.74 mmol) in dichloromethane (20 mL) was added phosphorus tribromide (1.11 mL, 11.7 mmol) dropwise. The reaction mixture was stirred at ambient temperature for 3 hours, and poured into ice water. The pH was adjusted to basic by the careful addition of saturated aqueous sodium bicarbonate and the mixture was extracted with dichloromethane. The organic layer was washed with saturated aqueous sodium chloride, dried with anhydrous sodium sulfate, filtered, and concentrated to provide the title compound (4.15 g, 93%).

Example 287d (3-bromo-4-(2,4-difluorophenoxy)benzyl)(methyl) sulfane

A mixture of Example 287c (1.512 g, 4.00 mmol) and sodium thiomethoxide (0.280 g, 4.00 mmol) in dimethylformamide (8 mL) was stirred at ambient temperature for 6 hours. The reaction mixture was partitioned with ethyl acetate and water. The organic layer was washed with saturated aqueous sodium chloride twice, dried with anhydrous sodium sulfate, filtered, and concentrated to provide the title compound (1.38 g, 100%).

Example 287e 2-bromo-1-(2,4-difluorophenoxy)-4-(methylsulfonylmethyl)benzene To a solution of Example 287d (1.38 g, 4.00 mmol) in methanol (15 mL) was added oxone (5.16 g, 8.40 mmol) in water (15 mL) at 0° C. The reaction mixture was stirred at ambient temperature for 1 hour. The reaction mixture was partitioned with ethyl acetate and water. The organic layer was washed with saturated aqueous sodium chloride, dried with anhydrous sodium sulfate, filtered, and concentrated. The residue was purified by flash chromatography (silica gel, 20 to 40% ethyl acetate in heptanes) to provide the title compound (1.49 g, 98%).

Example 287f 4-(2-(2,4-difluorophenoxy)-5-(methylsulfonylmethyl)phenyl)-6-methyl-1-tosyl-1H-pyrrolo[2,3-c]pyridin-7(6H)-one Example 287e (94 mg, 0.25 mmol), Example 6a (107 mg, 0.250 mmol), potassium phosphate (186 mg, 0.875 mmol), tris(dibenzylideneacetone)dipalladium (6.9 mg, 7.5 µmol) and 1,3,5,7-tetramethyl-6-phenyl-2,4,8-trioxa-6-phosphaadamante (6.6 mg, 0.023 mmol) were combined in a microwave tube and purged with nitrogen for 15 minutes. A mixture of dioxane (2 mL) and water (0.5 mL) was purged with nitrogen for 15 minutes and transferred to the microwave tube. The reaction mixture was heated at 60° C. for 1 hour. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 1 to 2% methanol in dichloromethane) to provide the title compound (62 mg, 41%).

Example 287g

4-{2-(2,4-difluorophenoxy)-5-[(methylsulfonyl)methyl]phenyl}-6-methyl-1,6-dihydro-7H-pyrrolo[2,3-c]pyridin-7-one Example 287f (59.9 mg, 0.100 mmol), potassium hydroxide (84 mg, 1.5 mmol) and cetyltrimethylammonium bromide (1.8 mg, 5.0 μmol) were combined in a mixture of tetrahydrofuran (4 mL) and water (2 mL). The reaction mixture was heated at 100° C. for 44 hours and then cooled to ambient temperature. To this mixture was added water, and the pH was adjusted to pH 7 by the addition of 1M HCl. The mixture was extracted with ethyl acetate and the organic layer was washed with saturated aqueous sodium chloride twice, dried with anhydrous sodium sulfate, filtered, and concentrated. The residue was purified by flash chromatography (silica gel, 2 to 4% methanol in dichloromethane) to provide the title compound (31 mg, 70%). $^1$H NMR (300 MHz, DMSO-$d_6$) δ ppm 12.04 (s, 1H) 7.57 (d, J=2.37 Hz, 1H) 7.26-7.48 (m, 4H) 7.16-7.26 (m, 1H) 7.00-7.11 (m, 1H) 6.88 (d, J=8.48 Hz, 1H) 6.23-6.33 (m, 1H) 4.51 (s, 2H) 3.55 (s, 3H) 2.94 (s, 3H). MS (ESI+) m/z 445 (M+H)$^+$.

Example 288

4-[2-(2,4-difluorophenoxy)-5-(methylsulfonyl)pyridin-3-yl]-6-methyl-1,6-dihydro-7H-pyrrolo[2,3-c]pyridin-7-one

Example 288a 2-fluoro-5-(methylthio)pyridine

A mixture of 5-bromo-2-fluoropyridine (2.05 g, 11.7 mmol) and $N^1,N^1,N^2,N^2$-tetramethylethane-1,2-diamine (2.27 mL, 15.1 mmol) was purged with nitrogen for 45 minutes. Toluene (116 mL) was added and the reaction mixture was cooled to −78° C. N-butyllithium (2.5 M in hexanes, 5.59 mL, 14.0 mmol) was added dropwise over 6 minutes. The reaction mixture was stirred at −78° C. for 1 hour. Dimethyl disulfide (1.26 mL, 14.0 mmol) was added. The reaction mixture was stirred at −78° C. for 1 hour. The reaction mixture was warmed to 0° C., then immediately quenched with saturated aqueous ammonium chloride. The layers were separated, and the organic layer was washed with saturated aqueous sodium chloride, dried over anhydrous magnesium sulfate, filtered, and concentrated. The residue was purified by flash chromatography (10% ethyl acetate/heptane) to provide the title compound (1.00 g, 60%).

Example 288b 2-fluoro-5-(methylsulfonyl)pyridine

To a solution of Example 288a (2.17 g, 15.2 mmol) in dichloromethane (50.5 mL) was added 3-chlorobenzoperoxoic acid (7.15 g, 31.1 mmol) portionwise over 10 minutes. The reaction mixture was stirred at ambient temperature for 4 hours. Additional 3-chlorobenzoperoxoic acid (2.62 g, 15.16 mmol) was added and the reaction mixture was stirred at ambient temperature for 1 hour. The reaction mixture was quenched with saturated aqueous sodium carbonate, and the layers were separated. The aqueous layer was extracted with dichloromethane. The combined organic layers were washed with saturated aqueous sodium chloride, dried over anhydrous magnesium sulfate, filtered, and concentrated. The residue was purified by flash chromatography (silica gel, 0-10% methanol/dichloromethane) to provide the title compound (1.81 g, 68%).

Example 288c 5-(methylsulfonyl)pyridin-2(1H)-one

Example 288b (0.679 g, 3.88 mmol) was treated with acetic acid (35.2 mL) and water (3.52 mL) at 110° C. for 16 hours. The reaction mixture was cooled to ambient temperature and the solvent was removed to provide the title compound (0.700 g, 100%).

Example 288d 3-bromo-5-(methylsulfonyl)pyridin-2(1H)-one

To a solution of Example 288c (0.671 g, 3.87 mmol) and sodium acetate (0.318 g, 3.87 mmol) in acetic acid (8.50 mL) was added bromine (0.201 mL, 3.91 mmol) dropwise as a solution in acetic acid (1.7 mL). The reaction mixture was stirred at 40° C. for 3 hours. Bromine (0.05 mL) was added, and the reaction mixture was stirred at 40° C. for 2 hours. The reaction mixture was cooled to ambient temperature and quenched with 100 mL of 10% aqueous sodium thiosulfate. The resulting suspension was filtered, and the solid collected and dried for 16 hours to provide the title compound (0.64 g, 66%).

Example 288e 3-bromo-2-chloro-5-(methylsulfonyl)pyridine

Example 288d (0.6395 g, 2.54 mmol) was treated with phosphorus oxychloride (12.7 mL) at 110° C. for 4 hours. The reaction mixture was cooled to ambient temperature and poured onto ice. The resulting suspension was filtered and rinsed with water, and the off white solid was collected and dried in a 60° C. vacuum oven for 16 hours to provide the title compound (0.244 g, 35%).

Example 288f 3-bromo-2-(2,4-difluorophenoxy)-5-(methylsulfonyl)pyridine

Example 288f was prepared according to the procedure used for the preparation of Example 2b, substituting 2,4-difluorophenol for phenol, and Example 288e for Example 2a, respectively, to provide the title compound.

Example 288g 4-(2-(2,4-difluorophenoxy)-5-(methylsulfonyl)pyridin-3-yl)-6-methyl-1-tosyl-1H-pyrrolo[2,3-c]pyridin-7(6H)-one Example 288g was prepared according to the procedure used for the preparation of Example 4a, substituting Example 288f for Example 7c to provide the title compound.

Example 288h 4-(2-(2,4-difluorophenoxy)-5-(methylsulfonyl)pyridin-3-yl)-6-methyl-1H-pyrrolo[2,3-c]pyridin-7(6H)-one Example 288h was prepared according to the procedure used for the preparation of Example 4b, substituting Example 288g for Example 4a to provide the title compound. $^1$H NMR (300 MHz, DMSO-$d_6$) ppm 12.16 (s, 1H) 8.59 (d, J=2.37 Hz, 1H) 8.37 (d, J=2.37 Hz, 1H) 7.58 (s, 1H) 7.48 (m, 2H) 7.34 (t, J=2.71 Hz, 1H) 7.16 (m, 1H) 6.36 (dd, J=2.71, 2.03 Hz, 1H) 3.61 (s, 3H) 3.35 (s, 3H). MS (ESI+) m/z 432.4 (M+H)$^+$.

Example 289

4-[2-(2,4-difluorophenoxy)-5-(methylsulfonyl)phenyl]-6-methyl-2-[(pyridin-3-yloxy)methyl]-1,6-dihydro-7H-pyrrolo[2,3-c]pyridin-7-one

Example 289a 2-(chloromethyl)-4-(2-(2,4-difluorophenoxy)-5-(methylsulfonyl)phenyl)-6-methyl-1H-pyrrolo[2,3-c]pyridin-7(6H)-one A mixture of Example 276 (0.50 g, 1.09 mmol) and thionyl chloride (5.0 mL, 69 mmol) was heated under reflux for 2 hours. The solvent was removed under reduced pressure and the residue was dried under vacuo for 1 hour to provide the title compound.

Example 289b

4-[2-(2,4-difluorophenoxy)-5-(methylsulfonyl)phenyl]-6-methyl-2-[(pyridin-3-yloxy)methyl]-1,6-dihydro-7H-pyrrolo[2,3-c]pyridin-7-one To a solution of pyridin-3-ol (0.039 g, 0.407 mmol) in tetrahydrofuran (5 mL) was added sodium hydride (16 mg, 0.407 mmol) at 0° C., and the mixture was stirred for 30 minutes. To this solution was added Example 289a (0.25 g, 0.204 mmol) and the reaction mixture was heated under reflux for 16 hours. The reaction mixture was poured into a mixture of ethyl acetate (30 mL) and saturated aqueous sodium chloride (20 mL). The aqueous layer was extracted with ethyl acetate (20 mL). The combined organic layers were dried over anhydrous magnesium sulfate, filtered, and concentrated. The residue was purified by reverse phase HPLC (C18, water (10 mM NH$_4$HCO$_3$):acetonitrile, 25-50% gradient) to provide the title compound (18 mg, 16% yield). $^1$H NMR (400 MHz, DMSO-$d_6$) δ ppm 12.52 (s, 1H), 7.95 (d, J=2.4 Hz, 1H), 7.87 (dd, J=2.4, 6.4 Hz, 1H), 7.56-7.38 (m, 5H), 7.22-7.18 (m, 2H), 6.97 (d, J=8.4 Hz, 1H), 6.84-6.82 (m, 1H), 6.48 (s, 1H), 5.38 (s, 2H), 3.58 (s, 3H), 3.25 (s, 3H). MS (ESI+) m/z 538.1 (M+1)$^+$.

Example 290

4-[5-(cyclopropylsulfonyl)-2-(2,4-difluorophenoxy)phenyl]-6-methyl-1,6-dihydro-7H-pyrrolo[2,3-c]pyridin-7-one

Example 290a (3-bromo-4-fluorophenyl)(cyclopropyl)sulfane

Example 290a was prepared according to the procedure used for the preparation of Example 168a, substituting bromocyclopropane for iodoethane, to provide the title compound

Example 290b 2-bromo-4-(cyclopropylsulfonyl)-1-fluorobenzene

Example 290b was prepared according to the procedure used for the preparation of Example 168b, substituting Example 290a for Example 168a, to provide the title compound.

Example 290c 2-bromo-4-(cyclopropylsulfonyl)-1-(2,4-difluorophenoxy)benzene Example 290c was prepared according to the procedure used for the preparation of Example 138b, substituting Example 290b for Example 138a, to provide the title compound.

Example 290d

4-[5-(cyclopropylsulfonyl)-2-(2,4-difluorophenoxy)phenyl]-6-methyl-1,6-dihydro-7H-pyrrolo[2,3-c]pyridin-7-one Example 290d was prepared according to the procedure used for the preparation of Example 95d, substituting Example 290c for Example 95c, to provide the title compound. $^1$H NMR (500 MHz, DMSO-$d_6$) δ ppm 12.11 (s, 1H), 7.94 (d, J=2.44 Hz, 1H), 7.83 (dd, J=8.54, 2.44 Hz, 1H), 7.42-7.55 (m, 3H), 7.32 (t, J=2.75 Hz, 1H), 7.15-7.20 (m, 1H), 6.97 (d, J=8.54 Hz, 1H), 6.28-6.29 (m, 1H), 3.59 (s, 3H), 2.90-2.96 (m, 1H), 1.12-1.15 (m, 2H), 1.03-1.09 (m, 2H). MS (ESI+) m/z 457.1 (M+H)$^+$.

Example 291

4-[2-(2,4-difluorophenoxy)-5-(methylsulfonyl)phenyl]-6-methyl-2-(prop-1-en-2-yl)-1,6-dihydro-7H-pyrrolo[2,3-c]pyridin-7-one To a solution of Example 252f (0.10 g, 0.20 mmol) in tetrahydrofuran (6 mL) stirring at 0° C. was added methylmagnesium bromide (0.498 mL, 0.498 mmol). The reaction mixture was stirred at 0° C. for 1 hour, and then aqueous HCl (1 M, 2 mL) was added. The reaction mixture was concentrated and partitioned between saturated aqueous sodium chloride (10 mL) and ethyl acetate. The organic phase was washed with saturated aqueous sodium chloride (30 mL), dried over anhydrous sodium sulfate, filtered, and concentrated. The residue was purified by reverse phase-HPLC (C 18 40-90% gradient acetonitrile:water (0.1% TFA)) to provide the title compound (25 mg, 25% yield). $^1$H NMR (400 MHz, DMSO-d$_6$) δ ppm 12.05 (s, 1H), 7.98 (d, J=2.4 Hz, 1H), 7.87 (dd, J=8.7, 2.4 Hz, 1H), 7.61-7.36 (m, 3H), 7.18 (t, J=8.6 Hz, 1H), 6.98 (d, J=8.3 Hz, 1H), 6.34 (d, J=2.2 Hz, 1H), 5.85 (s, 1H), 5.07 (s, 1H), 3.60 (s, 3H), 3.26 (s, 3H), 2.02 (s, 3H). MS (ESI+) m/z 471.1 (M+1)$^+$.

Example 292

4-[2-(2,4-difluorophenoxy)-5-(methylsulfonyl)phenyl]-6-methyl-2-(phenoxymethyl)-1,6-dihydro-7H-pyrrolo[2,3-c]pyridin-7-one Example 292 was prepared according to the procedure used for the preparation of Example 289b, substituting phenol for pyridin-3-ol, to provide the title compound. $^1$H NMR (400 MHz, DMSO-d$_6$) δ ppm 12.32 (s, 1H), 7.96 (d, J=2.4 Hz, 1H), 7.86 (dd, J=2.4, 6.4 Hz, 1H), 7.55-7.50 (m, 1H), 7.49 (s, 1H), 7.45-7.36 (m, 1H), 7.26-7.16 (m, 3H), 6.98-6.89 (m, 4H), 6.37 (s, 1H), 5.11 (s, 2H), 3.59 (s, 3H), 3.23 (s, 3H). MS (ESI+) m/z 537.2 (M+1)$^+$ Example 293

4-[2-(2,4-difluorophenoxy)-5-(morpholin-4-ylsulfonyl)phenyl]-6-methyl-1,6-dihydro-7H-pyrrolo[2,3-c]pyridin-7-one Example 293a 4-((3-bromo-4-(2,4-difluorophenoxy)phenyl)sulfonyl)morpholine Example 293a was prepared according to the procedure used for the preparation of Example 138b, substituting Example 286a for Example 138a, to provide the title compound.

Example 293b

4-[2-(2,4-difluorophenoxy)-5-(morpholin-4-ylsulfonyl)phenyl]-6-methyl-1,6-dihydro-7H-pyrrolo[2,3-c]pyridin-7-one Example 293b was prepared according to the procedure used for the preparation of Example 95d, substituting Example 293a for Example 95c, to provide the title compound. $^1$H NMR (500 MHz, DMSO-d$_6$) δ ppm 12.10 (s, 1H), 7.76 (d, J=2.44 Hz, 1H), 7.83 (dd, J=8.7, 2.44 Hz, 1H), 7.42-7.54 (m, 3H), 7.30 (t, J=2.75 Hz, 1H), 7.14-7.16 (m, 1H), 7.01 (d, J=8.54 Hz, 1H), 6.25-6.27 (m, 1H), 3.64-3.66 (m, 4H), 3.59 (s, 3H), 2.88-2.92 (m, 4H). MS (ESI+) m/z 502.2 (M+H)$^+$.

Example 294

4-[2-(2,4-difluorophenoxy)-5-(ethylsulfonyl)pyridin-3-yl]-6-methyl-1,6-dihydro-7H-pyrrolo[2,3-c]pyridin-7-one Example 294a 3-bromo-2-chloro-5-(ethylsulfonyl)pyridine Sodium sulfite (1.755 g, 13.92 mmol) and sodium bicarbonate (1.231 g, 14.65 mmol) were dissolved in water (37 mL) to give a colorless solution. The mixture was heated at 75° C. 3-Bromo-2-chloropyridine-5-sulfonyl chloride (2.132 g, 7.33 mmol) was added portionwise over 1 hour. The reaction mixture was stirred at 75° C. for 1 hour. The mixture was concentrated and N,N-dimethylformamide (13.88 mL) was added. Sodium bicarbonate (1.231 g, 14.65 mmol) and iodoethane (0.589 mL, 7.33 mmol) were added. The resulting mixture was heated to 75° C. for 2 hours and then cooled to ambient temperature. The mixture was partitioned between ethyl acetate and water. The organic layer was washed with saturated aqueous sodium chloride, dried over anhydrous magnesium sulfate, filtered, and concentrated. The residue was purified by flash chromatography (silica gel, 0-100% ethyl acetate/heptane) to provide the title compound.

Example 294b 4-(2-chloro-5-(ethylsulfonyl)pyridin-3-yl)-6-methyl-1-tosyl-1H-pyrrolo[2,3-c]pyridin-7(6H)-one Example 294b was prepared according to the procedure used for the preparation of Example 4a, substituting Example 294a for Example 7c to provide the title compound.

Example 294c 4-(2-(2,4-difluorophenoxy)-5-(ethylsulfonyl)pyridin-3-yl)-6-methyl-1H-pyrrolo[2,3-c]pyridin-7(6H)-one Example 294c was prepared according to the procedure used for the preparation of Example 2b, substituting 2,4-difluorophenol for phenol, and Example 294b for Example 2a, respectively, to provide the title compound. $^1$H NMR (400 MHz, DMSO-d$_6$) δ ppm 12.17 (bs, 1H), 8.56 (d, J=2.4 Hz, 1H), 8.32 (d, J=2.4 Hz, 1H), 7.58 (s, 1H), 7.54-7.43 (m, 2H), 7.34 (t, J=2.7 Hz, 1H), 7.21-7.12 (m, 1H), 6.35 (t, J=2.1 Hz, 1H), 3.61 (s, 3H), 3.44 (q, J=7.3 Hz, 2H), 1.18 (t, J=7.3 Hz, 1H). MS (ESI+) m/z 446.2 (M+H)$^+$.

Example 295

N-[4-(2,4-difluorophenoxy)-3-(6-methyl-7-oxo-6,7-dihydro-1H-pyrrolo[2,3-c]pyridin-4-yl)phenyl]-2-(morpholin-4-yl)ethanesulfonamide Example 295a 4-(5-amino-2-(2,4-difluorophenoxy)phenyl)-6-methyl-1-tosyl-1H-pyrrolo[2,3-c]pyridin-7(6H)-one Example 295a was prepared according to the procedure used for the preparation of Example 138a, substituting Example 1e for 2-bromo-1-fluoro-4-(methylsulfonyl)benzene, and Example 148c for Example 6a, respectively, to provide the title compound.

Example 295b

N-[4-(2,4-difluorophenoxy)-3-(6-methyl-7-oxo-6,7-dihydro-1H-pyrrolo[2,3-c]pyridin-4-yl)phenyl]-2-(morpholin-4-yl)ethanesulfonamide A mixture of Example 295a, 2-chloroethanesulfonyl chloride (0.098 g, 0.600 mmol), and triethylamine (0.081 g, 0.800 mmol) in dichloromethane (3 mL) was stirred at ambient temperature for 2 hours. The solvent was removed, and the residue was redissolved in MeOH (5 mL). To this solution was added morpholine (0.697 g, 8.00 mmol). The reaction mixture was heated at 50° C. for 2 hours. To this solution was added 2.0 N sodium hydroxide (2.00 mL, 4.00 mmol). The reaction mixture was heated at 85° C. for 2 hours. After cooling, the reaction mixture was partitioned between ethyl acetate and 1.0 N HCl. The aqueous layer was extracted with additional ethyl acetate several times. The combined organic layers were washed with saturated aqueous sodium chloride, dried over anhydrous magnesium sulfate, filtered, and concentrated. The residue was purified by preparative HPLC (10-80% acetonitrile in 0.1% TFA water) to give the TFA salt of the title compound (0.077 g, 0.117 mmol, 58.5% yield). $^1$H NMR (500 MHz, DMSO-$d_6$) δ ppm 12.08 (s, 1H), 10.18 (s, 1H), 7.37-7.43 (m, 2H), 7.30-7.31 (m, 2H), 7.22 (dd, J=8.85, 2.75 Hz, 1H), 7.08-7.14 (m, 1H), 7.00-7.04 (m, 1H), 6.91 (d, J=8.54 Hz, 1H), 6.28-6.29 (m, 1H), 3.51-3.62 (m, 11H), 3.24 (br s, 4H). MS (ESI+) m/z 545.1 (M+H)$^+$.

Example 296

N-[4-(2,4-difluorophenoxy)-3-(6-methyl-7-oxo-6,7-dihydro-1H-pyrrolo[2,3-c]pyridin-4-yl)phenyl]-N-[2-(dimethylamino)ethyl]ethanesulfonamide A mixture of Example 36e (0.15 g, 0.326 mmol), 2-(dimethylamino)ethanol (0.029 g, 0.326 mmol), and triphenylphosphine (0.128 g, 0.490 mmol) in tetrahydrofuran (3 mL) was stirred at ambient temperature for 10 minutes. To this solution was added (E)-di-tert-butyl diazene-1,2-dicarboxylate (0.113 g, 0.490 mmol). The solution was stirred for three hours at ambient temperature. The solvent was removed, and the residue was purified by preparative HPLC (10-80% acetonitrile in 0.1% TFA water) to give the title compound (0.055 g, 0.104 mmol, 31.8% yield). $^1$H NMR (500 MHz, DMSO-$d_6$) δ ppm 12.06 (s, 1H), 7.51 (d, J=2.44 Hz, 1H), 7.41-7.47 (m, 1H), 7.35-7.37 (m, 2H), 7.23-7.31 (m, 2H), 7.06-7.11 (m, 1H), 6.85 (d, J=8.85 Hz, 1H), 3.57 (t, J=6.71 Hz, 2H), 3.56 (s, 3H), 3.17 (q, J=7.32 Hz, 1H), 2.25 (m, 2H), 2.13 (s, 6H), 1.25 (q, J=7.48 Hz, 3H). MS (ESI+) m/z 531.2 (M+H)$^+$.

Example 297

4-{2-(2,4-difluorophenoxy)-5-[(ethylsulfonyl)methyl]phenyl}-6-methyl-1,6-dihydro-7H-pyrrolo[2,3-c]pyridin-7-one Example 297a (3-bromo-4-(2,4-difluorophenoxy)benzyl)(ethyl)sulfane Example 297a was prepared according to the procedure used for the preparation of Example 287d, substituting sodium ethanethiolate for sodium thiomethoxide, to provide the title compound (1.04 g, 99%).

Example 297b 2-bromo-1-(2,4-difluorophenoxy)-4-(ethylsulfonylmethyl)benzene

Example 297b was prepared according to the procedure used for the preparation of Example 287e, substituting Example 297a for Example 287d, to provide the title compound (1.01 g, 89%).

Example 297c 4-(2-(2,4-difluorophenoxy)-5-(ethylsulfonylmethyl)phenyl)-6-methyl-1-tosyl-1H-pyrrolo[2,3-c]pyridin-7(6H)-one Example 297c was prepared according to the procedure used for the preparation of Example 287f, substituting Example 297b for Example 287e. Purification by flash chromatography (silica gel, 0 to 2% methanol in dichloromethane) afforded the title compound (63 mg, 51%).

Example 297d

4-{2-(2,4-difluorophenoxy)-5-[(ethylsulfonyl)methyl]phenyl}-6-methyl-1,6-dihydro-7H-pyrrolo[2,3-c]pyridin-7-one Example 297d was prepared according to the procedure used for the preparation of Example 287g, substituting Example 297c for Example 287f, to provide the title compound (34 mg, 75%). $^1$H NMR (300 MHz, DMSO-$d_6$) ppm 12.04 (s, 1H) 7.56 (d, J=2.37 Hz, 1H) 7.15-7.48 (m, 5H) 6.99-7.11 (m, 1H) 6.87 (d, J=8.14 Hz, 1H) 6.25-6.35 (m, 1H) 4.49 (s, 2H) 3.55 (s, 3H) 3.07 (q, J=7.23 Hz, 2H) 1.23 (t, J=7.46 Hz, 3H). MS (ESI+) m/z 459 (M+H)$^+$.

Example 298

4-{2-(2,4-difluorophenoxy)-5-[2-(ethylsulfonyl)propan-2-yl]phenyl}-6-methyl-1,6-dihydro-7H-pyrrolo[2,3-c]pyridin-7-one Example 298a 2-bromo-1-(2,4-difluorophenoxy)-4-(2-(ethylsulfonyl)propan-2-yl)benzene To a solution of Example 297b (469 mg, 1.20 mmol) in tetrahydrofuran (10 mL) was added 60% sodium hydride in mineral oil (240 mg, 6.00 mmol) at 0° C. The reaction mixture was stirred at ambient temperature under nitrogen for 10 minutes. Iodomethane (0.750 mL, 12.0 mmol) was added. The reaction mixture was stirred at ambient temperature for 20 hours. The reaction mixture was partitioned with ethyl acetate and water. The organic layer was washed with saturated aqueous sodium chloride, dried with anhydrous sodium sulfate, filtered, and concentrated. The residue was purified by flash chromatography (silica gel, 20 to 40% ethyl acetate in heptanes) to provide the title compound (442 mg, 88%).

Example 298b 4-(2-(2,4-difluorophenoxy)-5-(2-(ethylsulfonyl)propan-2-yl)phenyl)-6-methyl-1-tosyl-1H-pyrrolo[2,3-c]pyridin-7(6H)-one Example 298b was prepared according to the procedure used for the preparation of Example 287f, substituting Example 298a for Example 287e. Purification by flash chromatography (silica gel, 0 to 2% methanol in dichloromethane) afforded the title compound (80 mg, 62%).

Example 298c

4-{2-(2,4-difluorophenoxy)-5-[2-(ethylsulfonyl)propan-2-yl]phenyl}-6-methyl-1,6-dihydro-7H-pyrrolo[2,3-c]pyridin-7-one Example 298c was prepared according to the procedure used for the preparation of Example 287g, substituting Example 298b for Example 287f and the reaction time was 16 hours instead of 44 hours, to provide the title compound (52 mg, 88%). $^1$H NMR (400 MHz, DMSO-d$_6$) ppm 12.06 (s, 1H) 7.71 (d, J=2.44 Hz, 1H) 7.55 (dd, J=8.70, 2.59 Hz, 1H) 7.38-7.48 (m, 1H) 7.33 (s, 1H) 7.19-7.31 (m, 2H) 7.02-7.12 (m, 1H) 6.85 (d, J=8.24 Hz, 1H) 6.29 (d, J=2.14 Hz, 1H) 3.56 (s, 3H) 2.90 (q, J=7.43 Hz, 2H) 1.77 (s, 6H) 1.06 (t, J=7.48 Hz, 3H). MS (ESI+) m/z 487 (M+H)$^+$.

Example 299

4-[2-(2,4-difluorophenoxy)-5-(pyrrolidin-1-ylsulfonyl)phenyl]-6-methyl-1,6-dihydro-7H-pyrrolo[2,3-c]pyridin-7-one

Example 299a 1-((3-bromo-4-fluorophenyl)sulfonyl)pyrrolidine

To a solution of 3-bromo-4-fluorobenzene-1-sulfonyl chloride (1.0 g, 3.66 mmol) in 20 mL dichloromethane at 0° C. was added pyrrolidine (0.635 mL, 7.68 mmol). The mixture was stirred at 0° C. for 30 minutes and then at room temperature overnight. The reaction mixture was diluted with dichloromethane, washed with 1% HCl solution and water, dried over anhydrous magnesium sulfate, filtered, and concentrated to give the title compound (0.86 g, 76% yield)

Example 299b 1-((3-bromo-4-(2,4-difluorophenoxy)phenyl)sulfonyl)pyrrolidine

A mixture of Example 299a (250 mg, 0.811 mmol), 2,4-difluorophenol (106 mg, 0.811 mmol) and cesium carbonate (317 mg, 0.973 mmol) in 5 mL dimethylsulfoxide was heated at 110° C. for 2 hours. Water was added and the mixture was extracted with ethyl acetate. The organic phase was washed with water (2×), saturated aqueous sodium chloride, dried over anhydrous magnesium sulfate, and filtered. The filtrate was concentrated to give the title compound (278 mg, 82% yield), which was used without further purification.

Example 299c

4-[2-(2,4-difluorophenoxy)-5-(pyrrolidin-1-ylsulfonyl)phenyl]-6-methyl-1,6-dihydro-7H-pyrrolo[2,3-c]pyridin-7-one A mixture of Example 299b (100 mg, 0.239 mmol), Example 6a (102 mg, 0.239 mmol), tetrakis(triphenylphosphine)palladium(0) (13.81 mg, 0.012 mmol) and cesium fluoride (109 mg, 0.717 mmol) in 2 mL dimethoxyethane and 1 mL methanol was heated at 120° C. in a microwave oven (Biotage Initiator) for 40 minutes. The mixture was then treated with 4 N NaOH (1 mL) and stirred at ambient temperature for 2 hours. Water was added and the mixture was extracted with ethyl acetate (2×). The organic phase was washed with saturated aqueous sodium chloride, dried over anhydrous magnesium sulfate, and filtered. The filtrate was concentrated and the residue was purified by flash chromatography (silica gel, 60-100% ethyl acetate/heptanes gradient) to give the title compound (75 mg, 64.6% yield). $^1$H NMR (400 MHz, DMSO-d$_6$) δ ppm 12.06 (s, 1H), 12.06 (s, 1H), 7.81 (d, J=2.4 Hz, 1H), 7.81 (d, J=2.4 Hz, 1H), 7.77-7.72 (m, 1H), 7.79-7.72 (m, 1H), 7.47 (ddd, J=11.5, 8.8, 3.0 Hz, 1H), 7.47 (ddd, J=17.8, 10.4, 6.0 Hz, 1H), 7.42-7.39 (m, 1H), 7.43-7.35 (m, 2H), 7.30 (t, J=2.8 Hz, 1H), 7.30 (t, J=2.8 Hz, 1H), 7.28-7.09 (m, 1H), 7.17-7.09 (m, 1H), 6.98-6.93 (m, 1H), 6.99-6.93 (m, 1H), 6.24 (ddd, J=23.2, 2.6, 2.2 Hz, 1H), 6.22 (dd, J=2.6, 2.2 Hz, 1H), 3.57 (s, 3H), 3.57 (s, 3H), 3.22-3.09 (m, 4H), 3.19-3.11 (m, 4H), 1.72-1.64 (m, 4H), 1.75-1.61 (m, 4H), 1.17 (dd, J=18.8, 11.7 Hz, 1H), 0.87-0.74 (m, 1H). MS (ESI+) m/z 464.2 (M+H)$^+$.

Example 300

N-[4-(2,4-difluorophenoxy)-3-(6-methyl-7-oxo-6,7-dihydro-1H-pyrrolo[2,3-c]pyridin-4-yl)phenyl]-2-(dimethylamino)ethanesulfonamide Example 300 was prepared according to the procedure used for the preparation of Example 295b, substituting N,N-dimethylamine for morpholine, to provide the TFA salt of the title compound. $^1$H NMR (500 MHz, DMSO-d$_6$) δ ppm 12.07 (s, 1H), 10.18 (s, 1H), 9.86 (br s, 1H), 7.37-7.42 (m, 2H), 7.29-7.31 (m, 2H), 7.22 (dd, J=8.54, 2.75 Hz, 1H), 7.09-7.14 (m, 1H), 7.01-7.07 (m, 1H), 6.91 (d, J=8.85 Hz, 1H), 6.28 (t, J=2.29 Hz, 1H), 3.62-3.65 (m, 2H), 3.54 (s, 3H), 3.48-3.51 (m, 2H), 2.83 (s, 6H). MS (ESI+) m/z 503.1 (M+H)$^+$.

Example 301 ethyl 4-[4-(ethylsulfonyl)-2-(6-methyl-7-oxo-6,7-dihydro-1H-pyrrolo[2,3-c]pyridin-4-yl)phenoxy]piperidine-1-carboxylate

Example 301a ethyl 4-(2-bromo-4-(ethylsulfonyl)phenoxy)piperidine-1-carboxylate Example 301a was prepared according to the procedure used for the preparation of Example 158, substituting Example 138a for Example 168b, and ethyl 4-hydroxypiperidine-1-carboxylate for cyclopropylmethanol, respectively, to provide the title compound.

Example 301b ethyl 4-[4-(ethylsulfonyl)-2-(6-methyl-7-oxo-6,7-dihydro-1H-pyrrolo[2,3-c]pyridin-4-yl)phenoxy]piperidine-1-carboxylate Example 301b was prepared according to the procedure used for the preparation of Example 95d, substituting Example 301a for Example 95c, to provide the title compound. $^1$H NMR (500 MHz, DMSO-d$_6$) δ ppm 12.04 (s, 1H), 7.80-7.83 (m, 2H), 7.44 (d, J=8.54 Hz, 1H), 7.33 (s, 1H), 7.29 (t, J=2.75 Hz, 1H), 6.12-6.13 (m, 1H), 4.76-4.81 (m, 1H), 3.99 (q, J=7.02 Hz, 2H), 3.57 (s, 3H), 3.24-3.39 (m, 6H), 1.86-1.90 (m, 2H), 1.49-1.53 (m, 2H), 1.12-1.16 (M, 6H). MS (ESI+) m/z 488.1 (M+H)$^+$.

Example 302

4-[2-(cyclopropylmethoxy)-5-(pyrrolidin-1-ylsulfonyl)phenyl]-6-methyl-1,6-dihydro-7H-pyrrolo[2,3-c]pyridin-7-one

Example 302a

1-((3-bromo-4-(cyclopropylmethoxy)phenyl)sulfonyl)pyrrolidine

To a solution of cyclopropylmethanol (115 µL, 1.460 mmol) in dioxane (8 mL) at room temperature was added sodium hydride (78 mg, 1.947 mmol). After stirring at ambient temperature for 10 minutes, Example 299a (300 mg, 0.973 mmol) was added as a solid. The mixture was then heated at 65° C. overnight. Water was added. The mixture was extracted with ethyl acetate, washed with water (2×), saturated aqueous sodium chloride, dried over anhydrous magnesium sulfate, filtered, and concentrated. The residue was purified by flash chromatography (silica gel, 0-50% ethyl acetate/heptanes gradient) to give the title compound (156 mg, 44.5% yield)

Example 302b

4-[2-(cyclopropylmethoxy)-5-(pyrrolidin-1-ylsulfonyl)phenyl]-6-methyl-1,6-dihydro-7H-pyrrolo[2,3-c]pyridin-7-one A mixture of Example 302a (84 mg, 0.233 mmol), Example 6a (100 mg, 0.233 mmol), tetrakis(triphenylphosphine)palladium(0) (13.49 mg, 0.012 mmol) and cesium fluoride (106 mg, 0.700 mmol) in 2 mL dimethoxyethane and 1 mL methanol was purged with nitrogen gas and heated at 130° C. under microwave conditions (Biotage Initiator) for 40 minutes. The mixture was then treated with 4 N NaOH (1 mL) and stirred at room temperature for 2 hours. Water was added and the mixture was extracted with ethyl acetate, washed with saturated aqueous sodium chloride, dried over anhydrous magnesium sulfate, filtered, and concentrated. The residue was absorbed on silica gel and purified by flash chromatography (silica gel, 0-10% methanol/dichloromethane gradient) to give the title compound (64 mg, 64.1% yield). $^1$H NMR (400 MHz, DMSO-$d_6$) δ ppm 12.10-11.92 (m, 1H), 7.77-7.70 (m, 2H), 7.37 (s, 1H), 7.30 (dd, J=6.9, 4.1 Hz, 2H), 6.17-6.03 (m, 1H), 3.97 (d, J=6.8 Hz, 2H), 3.58 (s, 3H), 3.14 (t, J=6.7 Hz, 4H), 1.71-1.64 (m, 4H), 1.15-1.08 (m, 1H), 0.50-0.44 (m, 2H), 0.30-0.24 (m, 2H). MS (ESI+) m/z 482.2 (M+H)$^+$.

Example 303

4-{2-[(1-acetylpiperidin-4-yl)oxy]-5-(ethylsulfonyl)phenyl}-6-methyl-1,6-dihydro-7H-pyrrolo[2,3-c]pyridin-7-one

Example 303a

1-(4-(2-bromo-4-(ethylsulfonyl)phenoxy)piperidin-1-yl)ethanone

Example 303a was prepared according to the procedure used for the preparation of Example 158, substituting Example 168b for Example 138a, and substituting 1-(4-hydroxypiperidin-1-yl)ethanone for cyclopropylmethanol, respectively, to provide the title compound.

Example 303b

4-{2-[(1-acetylpiperidin-4-yl)oxy]-5-(ethylsulfonyl)phenyl}-6-methyl-1,6-dihydro-7H-pyrrolo[2,3-c]pyridin-7-one Example 303b was prepared according to the procedure used for the preparation of Example 95d, substituting Example 303a for Example 95c, to provide the title compound. $^1$H NMR (500 MHz, DMSO-$d_6$) δ ppm 12.04 (s, 1H), 7.80-7.84 (m, 2H), 7.45 (d, J=8.54 Hz, 1H), 7.33 (s, 1H), 7.29 (t, J=2.75 Hz, 1H), 6.12-6.13 (m, 1H), 4.81-4.84 (m, 1H), 3.57 (s, 3H), 3.24-3.39 (m, 6H), 2.09 (s, 3H), 1.49-1.53 (m, 2H), 1.12-1.16 (m, 3H). MS (ESI+) m/z 458.2 (M+H)$^+$.

Example 304

4-[4-(ethylsulfonyl)-2-(6-methyl-7-oxo-6,7-dihydro-1H-pyrrolo[2,3-c]pyridin-4-yl)phenoxy]benzonitrile Example 304 was prepared according to the procedure used for the preparation of Example 138b, substituting Example 168c for Example 138a, and 4-cyanophenol for 2,4-difluorophenol, respectively, to provide the title compound. $^1$H NMR (500 MHz, DMSO-$d_6$) δ ppm 12.09 (s, 1H), 8.00 (d, J=2.44 Hz, 1H), 7.92 (dd, J=8.54, 2.54 Hz, 1H), 7.79-7.82 (m, 2H), 7.39 (s, 1H), 7.35 (d, J=8.54 Hz, 1H), 7.29 (t, J=2.75 Hz, 1H), 7.14-7.17 (m, 2H), 6.22-6.23 (m, 1H), 3.54 (s, 3H), 3.38 (q, J=7.32 Hz, 2H), 1.17 (t, J=7.32 Hz, 3H). MS (ESI+) m/z 434.2 (M+H)$^+$.

Example 305

4-[2-(cyclopropylmethoxy)-5-(2,3-dihydro-1H-indol-1-ylsulfonyl)phenyl]-6-methyl-1,6-dihydro-7H-pyrrolo[2,3-c]pyridin-7-one

Example 305a

1-(3-bromo-4-fluorophenylsulfonyl)indoline

A solution of 3-bromo-4-fluorobenzene-1-sulfonyl chloride (Aldrich) (2.53 g, 8.33 mmol), indoline (0.99 g, 8.33 mmol), N,N-diisopropylethylamine (1.60 mL, 9.16 mmol) and tetrahydrofuran (20 mL) was stirred at ambient temperature for 16 hours. The reaction mixture was partitioned between water and ethyl acetate. The aqueous layer was extracted twice with additional ethyl acetate. The combined organic layers were washed with saturated aqueous sodium chloride, dried over anhydrous magnesium sulfate, filtered, and concentrated to afford a brown oil which solidified upon standing. The crude product was recrystallized from ether/heptane to afford the title compound (1.99 g, 5.59 mmol, 67% yield).

Example 305b

1-(3-bromo-4-(cyclopropylmethoxy)phenylsulfonyl)indoline

Example 305b was prepared according to the procedure used for the preparation of Example 29a, substituting cyclopropylmethanol for tetrahydro-2H-pyran-4-ol and substituting Example 305a for Example 2a to afford the title compound.

Example 305c 4-(2-(cyclopropylmethoxy)-5-(indolin-1-ylsulfonyl)phenyl)-6-methyl-1-tosyl-1H-pyrrolo[2,3-c]pyridin-7(6H)-one Example 305c was prepared according to the procedure used for the preparation of Example 6c, substituting Example 305b for Example 6b to afford the title compound.

Example 305d 4-(2-(cyclopropylmethoxy)-5-(indolin-1-ylsulfonyl)phenyl)-6-methyl-1H-pyrrolo[2,3-c]pyridin-7(6H)-one Example 305d was prepared according to the procedure used for the preparation of Example 6d, substituting Example 305c for Example 6c to afford the title compound. $^1$H NMR (300 MHz, DMSO-$d_6$) 0.24 (tt, J=13.4, 6.6 Hz, 2H) 0.35-0.50 (m, 2H) 1.01-1.18 (m, 1H) 2.90 (t, J=8.3 Hz, 2H) 3.54 (s, 3H) 3.90 (t, J=8.4 Hz, 2H) 3.92 (d, J=6.8 Hz, 2H) 5.80-5.86 (m, 1H) 7.04 (td, J=7.4, 1.0 Hz, 1H) 7.14-7.36 (m, 5H) 7.50 (d, J=8.0 Hz, 1H) 7.66 (d, J=2.4 Hz, 1H) 7.77 (dd, J=8.7, 2.5 Hz, 1H) 12.02 (bs, 1H). MS (ESI+) m/z 476 [M+H]$^+$.

Example 306

4-{2-(2,4-difluorophenoxy)-5-[(phenylsulfonyl)methyl]phenyl}-6-methyl-1,6-dihydro-7H-pyrrolo[2,3-c]pyridin-7-one

Example 306a (3-bromo-4-(2,4-difluorophenoxy)benzyl)(phenyl)sulfane

Example 306a was prepared according to the procedure used for the preparation of Example 287d, substituting sodium thiophenoxide for sodium thiomethoxide, to provide the title compound (815 mg, 100%).

Example 306b 2-bromo-1-(2,4-difluorophenoxy)-4-(phenylsulfonylmethyl)benzene Example 306b was prepared according to the procedure used for the preparation of Example 287e, substituting Example 306a for Example 287d, to provide the title compound (867 mg, 99%).

Example 306c 4-(2-(2,4-difluorophenoxy)-5-(phenylsulfonylmethyl)phenyl)-6-methyl-1-tosyl-1H-pyrrolo[2,3-c]pyridin-7(6H)-one Example 306c was prepared according to the procedure used for the preparation of Example 287f, substituting Example 306b for Example 287e. Purification by flash chromatography (silica gel, 0 to 2% methanol in dichloromethane) afforded the title compound (51 mg, 52%).

Example 306d

4-{2-(2,4-difluorophenoxy)-5-[(phenylsulfonyl)methyl]phenyl}-6-methyl-1,6-dihydro-7H-pyrrolo[2,3-c]pyridin-7-one Example 306d was prepared according to the procedure used for the preparation of Example 287g, substituting Example 306c for Example 287f, to provide the title compound (30 mg, 80%). $^1$H NMR (300 MHz, DMSO-$d_6$) ppm 12.02 (s, 1H) 7.69-7.81 (m, 3H) 7.55-7.67 (m, 2H) 7.34-7.46 (m, 1H) 7.20-7.29 (m, 2H) 6.98-7.18 (m, 4H) 6.80 (d, J=8.48 Hz, 1H) 6.09 (dd, J=2.37, 1.70 Hz, 1H) 4.71 (s, 2H) 3.52 (s, 3H). MS (ESI+) m/z 507 (M+H)$^+$.

Example 307

4-{2-[(2,2-difluorocyclopropyl)methoxy]-5-(pyrrolidin-1-ylsulfonyl)phenyl}-6-methyl-1,6-dihydro-7H-pyrrolo[2,3-c]pyridin-7-one

Example 307a 1-((3-bromo-4-((2,2-difluorocyclopropyl)methoxy)phenyl)sulfonyl)pyrrolidine Example 307a was prepared according to the procedure used for the preparation of Example 302a, substituting (2,2-difluorocyclopropyl)methanol for cyclopropylmethanol, to provide the title compound.

Example 307b

4-{2-[(2,2-difluorocyclopropyl)methoxy]-5-(pyrrolidin-1-ylsulfonyl)phenyl}-6-methyl-1,6-dihydro-7H-pyrrolo[2,3-c]pyridin-7-one Example 307b was prepared according to the procedure used for the preparation of Example 302b, substituting 307a for 302a, to provide the title compound. $^1$H NMR (300 MHz, DMSO-$d_6$) δ ppm 12.05 (s, 1H), 12.05 (s, 1H), 7.76 (tt, J=6.9, 3.5 Hz, 2H), 7.81-7.71 (m, 2H), 7.35 (d, J=8.4 Hz, 2H), 7.38-7.27 (m, 3H), 7.30 (t, J=2.6 Hz, 1H), 6.12 (dd, J=2.5, 1.6 Hz, 1H), 6.12 (dd, J=2.5, 1.6 Hz, 1H), 4.21 (dt, J=18.8, 9.6 Hz, 2H), 3.57 (s, 3H), 3.57 (s, 3H), 3.15 (t, J=6.7 Hz, 4H), 3.15 (t, J=6.7 Hz, 4H), 2.21-2.04 (m, 1H), 2.19-1.98 (m, 1H), 1.74-1.57 (m, 5H), 1.77-1.57 (m, 5H), 1.52-1.36 (m, 1H), 1.53-1.38 (m, 1H). MS (ESI+) m/z 464.2 (M+H)$^+$.

Example 308

4-{2-(cyclopropylmethoxy)-5-[(3,3-difluoroazetidin-1-yl)sulfonyl]phenyl}-6-methyl-1,6-dihydro-7H-pyrrolo[2,3-c]pyridin-7-one

Example 308a 1-((3-bromo-4-fluorophenyl)sulfonyl)-3,3-difluoroazetidine

To a suspension of 3,3-difluoroazetidine hydrochloric acid (0.947 g, 7.31 mmol) in 20 mL dichloromethane at 0° C. was added N-ethyl-N-isopropylpropan-2-amine (2.80 mL, 16.1 mmol) followed by the addition of a solution of 3-bromo-4- fluorobenzene-1-sulfonyl chloride (2.0 g, 7.3 mmol) in 4 mL dichloromethane. The mixture was stirred at room temperature overnight and then heated at 55° C. for 5 hours, diluted with dichloromethane, washed with water, dried over anhydrous magnesium sulfate, and filtered. The filtrate was concentrated and the residue was purified by flash chromatography (silica gel, 10-50% ethyl acetate/heptanes gradient) to give the title compound (1.5 g, 62.1% yield)

Example 308b 1-((3-bromo-4-(cyclopropylmethoxy)phenyl)sulfonyl)-3,3-difluoroazetidine Example 308b was prepared according to the procedure used for the preparation of Example 302a, substituting Example 308a for Example 299a to provide the title compound.

Example 308c

4-{2-(cyclopropylmethoxy)-5-[(3,3-difluoroazetidin-1-yl)sulfonyl]phenyl}-6-methyl-1,6-dihydro-7H-pyrrolo[2,3-c]pyridin-7-one Example 308c was prepared according to the procedure used for the preparation of Example 302b, substituting Example 308b for Example 302a to provide the title compound. $^1$H NMR (400 MHz, DMSO-$d_6$) δ ppm 12.04 (s, 1H), 7.87 (dd, J=8.7, 2.4 Hz, 1H), 7.78 (d, J=2.4 Hz, 1H), 7.40 (s, 1H), 7.36 (d, J=8.8 Hz, 1H), 7.29 (t, J=2.7 Hz, 1H), 6.12-6.08 (m, 1H), 4.26 (t, J=12.7 Hz, 4H), 4.01 (d, J=6.8 Hz, 2H), 3.58 (s, 3H), 1.14-1.08 (m, 1H), 0.50-0.43 (m, 2H), 0.30-0.25 (m, 2H). MS (DCI+) m/z 491.4 (M+CH3CN)$^+$.

Example 309

4-{2-[2-(2-hydroxyethyl)phenoxy]-5-(methylsulfonyl)phenyl}-6-methyl-1,6-dihydro-7H-pyrrolo[2,3-c]pyridin-7-one Example 304 was prepared according to the procedure used for the preparation of Example 138b, substituting 2-(2-hydroxyethyl)phenol for 2,4-difluorophenol, to provide the title compound. $^1$H NMR (500 MHz, DMSO-$d_6$) δ ppm 12.11 (s, 1H), 8.00 (d, J=2.44 Hz, 1H), 7.85 (dd, J=8.85, 2.44 Hz, 1H), 7.45 (s, 1H), 7.36 (dd, J=7.63, 1.53 Hz, 1H), 7.32 (t, J=2.9 Hz, 1H), 7.24-7.28 (m, 1H), 7.14-7.18 (m, 1H), 6.98-7.01 (m, 1H), 6.89 (d, J=8.54 Hz, 1H), 6.29-6.31 (m, 1H), 3.57 (s, 3H), 3.46 (t, J=7.02 Hz, 2H), 3.25 (s, 3H), 2.63 (t, J=7.02 Hz, 2H). MS (ESI+) m/z 439.1 (M+H)$^+$.

Example 310

4-[2-(cyclopropylmethoxy)-5-{[3-(dimethylamino)pyrrolidin-1-yl]sulfonyl}phenyl]-6-methyl-1,6-dihydro-7H-pyrrolo[2,3-c]pyridin-7-one

Example 310a 1-(3-bromo-4-fluorophenylsulfonyl)-N,N-dimethylpyrrolidin-3-amine A solution of 3-bromo-4-fluorobenzene-1-sulfonyl chloride (Combi-blocks) (250 mg, 0.91 mmol), N,N-dimethylpyrrolidin-3-amine (218 mg, 1.9 mmol) in tetrahydrofuran (5.7 mL) was stirred at ambient temperature for 16 hours. The solvent was evaporated and residue was purified by flash chromatography (silica gel, dichloromethane/gradient with MeOH) to afford the title compound (220 mg, 69% yield).

Example 310b 1-(3-bromo-4-(cyclopropylmethoxy)phenylsulfonyl-N,N-dimethyl-3-amine Example 310b was prepared according to the procedure used for the preparation of Example 29a, substituting cyclopropylmethanol for tetrahydro-2H-pyran-4-ol and substituting Example 310a for Example 2a to afford the title compound.

Example 310c 4-(2-(cyclopropylmethoxy)-5-(3-(dimethylamino)pyrrolidin-1-ylsulfonyl)phenyl)-6-methyl-1-tosyl-1H-pyrrolo[2,3-c]pyridin-7(6H)-one Example 310c was prepared according to the procedure used for the preparation of Example 6c, substituting Example 310b for Example 6b, to afford the title compound.

Example 310d 4-(2-(cyclopropylmethoxy)-5-(3-(dimethylamino)pyrrolidin-1-ylsulfonyl)phenyl)-6-methyl-1H-pyrrolo[2,3-c]pyridin-7(6H)-one Example 310d was prepared according to the procedure used for the preparation of Example 6d, substituting Example 310c for Example 6c, to afford the title compound. $^1$H NMR (300 MHz, DMSO-$d_6$) ppm 0.25-0.31 (m, 2H) 0.44-0.51 (m, 2H) 1.06-1.17 (m, 1H) 1.45-1.59 (m, 1H) 1.86-1.97 (m, 1H) 2.04 (s, 6H) 2.52-2.57 (m, 1H) 2.82-2.90 (m, 1H) 3.07-3.18 (m, 1H) 3.25-3.28 (m, 1H) 3.34-3.42 (m, 1H) 3.57 (s, 3H) 3.98 (d, J=6.78 Hz, 2H) 6.12 (t, J=2.71, 2.03 Hz, 1H) 7.28-7.33 (m, 2H) 7.35 (s, 1H) 7.71-7.79 (m, 2H) 12.04 (s, 1H). MS (ESI+) m/z 471 [M+H]$^+$.

Example 311

4-{2-(2,4-difluorophenoxy)-5-[(methylsulfonyl)methyl]pyridin-3-yl}-6-methyl-1,6-dihydro-7H-pyrrolo[2,3-c]pyridin-7-one

Example 311a 5-bromo-6-(2,4-difluorophenoxy)nicotinic acid 5-bromo-6-chloronicotinic acid (3 g, 12.69 mmol), 2,4-difluorophenol (3.30 g, 25.4 mmol) and cesium carbonate (16.54 g, 50.8 mmol) were combined in DMSO (25.4 mL), heated at 100° C. for 6 hours, cooled, diluted with 150 mL of iced water and the pH was adjusted to pH 3 with 12M HCl. The resulting solid was collected by filtration, washed with cold water and dried to constant mass to afford the title compound (2.84 g, 64%).

Example 311b (5-bromo-6-(2,4-difluorophenoxy)pyridin-3-yl)methanol

The product from Example 311a (1.0 g, 3.03 mmol) and borane tetrahydrofuran complex (6.06 mL, 6.06 mmol) were combined in tetrahydrofuran (15.15 mL) and heated at 50° C. for 2 hours, cooled, treated with 10 mL of methanol, heated at 50° C. for 1 hour, cooled and concentrated. The residue was partitioned between ethyl acetate and water. The organic layer was washed with saturated aqueous sodium chloride, dried ($Na_2SO_4$), filtered, and concentrated. Purification by chromatography (silica gel, 0-50% ethyl acetate in heptanes) afforded the title compound (0.73 g, 76%).

Example 311c 3-bromo-5-(bromomethyl)-2-(2,4-difluorophenoxy) pyridine

A solution of the product from Example 311b (0.73 g, 2.309 mmol) in dichloromethane (11.55 mL) under nitrogen was treated dropwise with tribromophosphine (0.218 mL, 2.309 mmol), stirred for one hour at ambient temperature and poured into ice water and the pH was adjusted to pH 9 by addition of solid sodium bicarbonate added portionwise. An emulsion formed that was partially removed by filtration. The aqueous layer was extracted with dichloromethane and the organics were combined, washed with saturated aqueous sodium chloride, dried ($Na_2SO_4$) filtered, and concentrated to afford the title compound (0.75 g, 86%).

Example 311d 3-bromo-2-(2,4-difluorophenoxy)-5-(methylthiomethyl)pyridine

The product from Example 311c (0.75 g, 1.979 mmol) and sodium thiomethoxide (0.139 g, 1.979 mmol) were combined in dimethylformamide (3.96 mL), stirred for 4 hours at ambient temperature, and partitioned into ethyl acetate and cold water. The organic layer was washed with saturated aqueous sodium chloride, dried ($Na_2SO_4$), filtered, and concentrated to afford the title compound (0.66 g, 96%).

Example 311e 3-bromo-2-(2,4-difluorophenoxy)-5-(methylsulfonylmethyl)pyridine

A solution of the product from Example 311d (0.66 g, 1.906 mmol) at 0° C. in methanol (7.33 mL) was treated with a solution of Oxone (2.461 g, 4.00 mmol) in water (7.33 mL), stirred at ambient temperature for two hours and partitioned between ethyl acetate and water. The organic layer was washed with saturated aqueous sodium chloride, dried ($Na_2SO_4$), filtered, and concentrated. Purification by chromatography (silica gel, 0-5% methanol in dichloromethane) afforded the title compound (0.433 g, 60%).

Example 311f 4-(2-(2,4-difluorophenoxy)-5-((methylsulfonyl)methyl)pyridin-3-yl)-6-methyl-1-tosyl-1H-pyrrolo[2,3-c]pyridin-7(6H)-one The product from Example 311e (0.075 g, 0.198 mmol), the product from Example 6a (0.085 g, 0.198 mmol), tris(dibenzylideneacetone)dipalladium(0) (5.45 mg, 5.95 µmol), 1,3,5,7-tetramethyl-6-phenyl-2,4,8-trioxa-6-phosphaadamante (5.80 mg, 0.020 mmol) and potassium phosphate (0.126 g, 0.595 mmol) were combined and sparged with argon for 15 minutes. Meanwhile a solution of 4:1 dioxane/water (2 mL) was sparged with nitrogen for 15 minutes and transferred by syringe into the reaction vessel under argon. The mixture was stirred for 2 hours at 60° C. and partitioned between ethyl acetate and water. The organic layer was washed with saturated aqueous sodium chloride, dried ($Na_2SO_4$), treated with 3-mercaptopropyl functionalized silica gel, filtered, and concentrated. Purification by trituration in dichloromethane afforded the title compound (0.083 g, 70%).

Example 311g

4-{2-(2,4-difluorophenoxy)-5-[(methylsulfonyl)methyl]pyridin-3-yl}-6-methyl-1,6-dihydro-7H-pyrrolo[2,3-c]pyridin-7-one The product from Example 311f (0.083 g, 0.138 mmol), potassium hydroxide (0.194 g, 3.46 mmol) and N,N,N-trimethylhexadecan-1-aminium bromide (2.52 mg, 6.92 µmol) were combined in dioxane (1.8 mL)/water (0.9 mL) and heated at 100° C. for 4 hours, cooled, and partitioned into ethyl acetate adjusting the pH to 7 with 1 M HCl. The organic layer was washed with saturated aqueous sodium chloride, dried ($Na_2SO_4$), filtered, and concentrated. Purification by chromatography (silica gel, 0-4% methanol in dichloromethane) afforded the title compound (0.035 g, 57%). $^1$H NMR (400 MHz, DMSO-$d_6$) δ ppm 12.14 (s, 1H) 8.03 (dd, J=22.74, 2.29 Hz, 2H) 7.30-7.51 (m, 4H) 7.03-7.17 (m, 1H) 6.39 (d, J=2.14 Hz, 1H) 4.57 (s, 2H) 3.60 (s, 3H) 3.00 (s, 3H). MS (ESI+) m/z 446 [M+H]$^+$.

Example 312 tert-butyl 4-[4-(ethylsulfonyl)-2-(6-methyl-7-oxo-6,7-dihydro-1H-pyrrolo[2,3-c]pyridin-4-yl)phenoxy]piperidine-1-carboxylate Example 312a tert-butyl 4-(2-bromo-4-(ethylsulfonyl)phenoxy)piperidine-1-carboxylate Example 312a was prepared according to the procedure used for the preparation of Example 158, substituting Example 168b for Example 138a, and tert-butyl 4-hydroxypiperidine-1-carboxylate for cyclopropylmethanol, respectively, to provide the title compound.

Example 312b tert-butyl 4-[4-(ethylsulfonyl)-2-(6-methyl-7-oxo-6,7-dihydro-1H-pyrrolo[2,3-c]pyridin-4-yl)phenoxy]piperidine-1-carboxylate Example 312b was prepared according to the procedure used for the preparation of Example 95d, substituting Example 312a for Example 95c, to provide the title compound. $^1$H NMR (500 MHz, DMSO-$d_6$) δ ppm 12.02 (s, 1H), 7.79-7.842 (m, 2H), 7.42 (d, J=8.54 Hz, 1H), 7.31 (s, 1H), 7.27 (t, J=2.75 Hz, 1H), 6.10-6.11 (m, 1H), 4.74-4.78 (m, 1H), 3.55 (s, 3H), 3.14-3.32 (m, 6H), 1.82-1.87 (m, 2H), 1.43-1.51 (m, 2H), 1.35 (s, 9H), 1.12 (t, J=7.32 Hz, 3H). MS (ESI+) m/z 515.9 (M+H)$^+$.

Example 313

4-(cyclopropylmethoxy)-3-(6-methyl-7-oxo-6,7-dihydro-1H-pyrrolo[2,3-c]pyridin-4-yl)-N-phenyl-benzenesulfonamide

Example 313a 3-bromo-4-fluoro-N-phenylbenzenesulfonamide

Example 313a was prepared according to the procedure used for the preparation of Example 305a, substituting aniline for indoline. The crude product was purified by flash chromatography (silica gel, eluted with 10% ethyl acetate in heptane) to afford title compound

Example 313b 3-bromo-4-(cyclopropylmethoxy)-N-phenylbenzenesulfonamide

Example 313b was prepared according to the procedure used for the preparation of Example 29a, substituting cyclopropylmethanol for tetrahydro-2H-pyran-4-ol and substituting Example 313a for Example 2a to afford the title compound.

Example 313c 4-(cyclopropylmethoxy)-3-(6-methyl-7-oxo-1-tosyl-6,7-dihydro-1H-pyrrolo[2,3-c]pyridin-4-yl)-N-phenylbenzenesulfonamide Example 313c was prepared according to the procedure used for the preparation of Example 6c, substituting Example 313b for Example 6b to afford the title compound.

Example 313d 4-(cyclopropylmethoxy)-3-(6-methyl-7-oxo-6,7-dihydro-1H-pyrrolo[2,3-c]pyridin-4-yl)-N-phenyl-benzenesulfonamide Example 313d was prepared according to the procedure used for the preparation of Example 6d, substituting Example 313c for Example 6c to afford the title compound. $^1$H NMR (300 MHz, DMSO-$d_6$) 0.25 (tt, J=15.6, 7.6 Hz, 2H) 0.39-0.50 (m, 2H) 1.01-1.18 (m, 1H) 3.55 (s, 3H) 3.91 (d, J=6.8 Hz, 2H) 5.91 (dd, J=2.8, 2.0 Hz, 1H) 7.01-7.15 (m, 3H) 7.15-7.34 (m, 5H) 7.65-7.72 (m, 2H) 10.12 (s, 1H) 12.02 (bs, 1H). MS (ESI+) m/z 450 [M+H]$^+$.

Example 314

4-[2-(cyclopropylmethoxy)-5-(pyrrolidin-1-ylmethyl)phenyl]-6-methyl-1,6-dihydro-7H-pyrrolo[2,3-c]pyridin-7-one

Example 314a 4-bromo-1-(cyclopropylmethoxy)-2-iodobenzene

A mixture of 4-bromo-2-iodophenol (5.00 g, 16.7 mmol), bromomethylcyclopropane (2.26 g, 16.7 mmol) and cesium carbonate (6.54 g, 20.1 mmol) in 15 mL dimethylformamide was stirred at 50° C. overnight. Water was added and the mixture was extracted with ethyl acetate. The organic phase was washed with water, saturated aqueous sodium chloride, dried over anhydrous magnesium sulfate, and filtered. The filtrate was concentrated to the provide title compound (5.84 g, 99% yield).

Example 314b 4-(5-bromo-2-(cyclopropylmethoxy)phenyl)-6-methyl-1-tosyl-1H-pyrrolo[2,3-c]pyridin-7(6H)-one A mixture of Example 6a (1.1 g, 2.57 mmol), Example 314a (0.907 g, 2.57 mmol), 1,3,5,7-tetramethyl-6-phenyl-2,4,8-trioxa-6-phosphaadamantane (0.060 g, 0.21 mmol), tris(dibenzylideneacetone)dipalladium(0) (0.094 g, 0.103 mmol), and potassium phosphate (1.635 g, 7.70 mmol) in 15 mL dioxane and 5 mL water was purged with nitrogen gas and then heated at 55° C. for 3 hours. Saturated aqueous sodium chloride was added and the mixture was extracted with ethyl acetate (2×). The combined organic phases were dried over anhydrous magnesium sulfate, filtered, and concentrated. The residue was purified by flash chromatography (silica gel, 0-80% ethyl acetate/heptanes gradient) to give the title compound (1.24 g, 92% yield).

Example 314c

4-[2-(cyclopropylmethoxy)-5-(pyrrolidin-1-ylmethyl)phenyl]-6-methyl-1,6-dihydro-7H-pyrrolo[2,3-c]pyridin-7-one A mixture of Example 314b (100 mg, 0.190 mmol), potassium trifluoro(pyrrolidin-1-ylmethyl)borate (36.2 mg, 0.190 mmol), palladium(II) acetate (2.55 mg, 0.011 mmol), dicyclohexyl(2',4',6'-triisopropylbiphenyl-2-yl)phosphine (10.85 mg, 0.023 mmol), and cesium carbonate (185 mg, 0.569 mmol) in 4 mL dioxane/water (9:1) was purged with nitrogen gas and then heated under microwave conditions (Biotage Initiator) at 140° C. for 40 minutes. The reaction mixture was then treated with 2 mL of 4 N NaOH and heated in a microwave oven (Biotage Initiator) at 100° C. for 30 minutes. Water was added. The mixture was extracted with ethyl acetate, washed with saturated aqueous sodium chloride, dried over anhydrous magnesium sulfate, and filtered. The filtrate was concentrated and the residue was purified by flash chromatography (silica gel, 2-14% methanol/dichloromethane gradient) to give the title compound (8.0 mg, 11% yield). $^1$H NMR (300 MHz, DMSO-$d_6$) δ ppm 11.93 (s, 1H), 7.29-7.17 (m, 4H), 7.00 (d, J=8.4 Hz, 1H), 6.11 (dd, J=2.6, 2.2 Hz, 1H), 3.81 (d, J=6.7 Hz, 2H), 3.56 (s, 3H), 3.53 (s, 2H), 2.43 (s, 4H), 1.68 (s, 4H), 1.13-0.98 (m, 1H), 0.48-0.36 (m, 2H), 0.26-0.16 (m, 2H). MS (ESI+) m/z 378.0 (M+H)$^+$.

Example 315

4-[2-(cyclopropylmethoxy)-5-(pyridin-3-yl)phenyl]-6-methyl-1,6-dihydro-7H-pyrrolo[2,3-c]pyridin-7-one A suspension of Example 314b (100 mg, 0.190 mmol), pyridin-3-ylboronic acid (23.31 mg, 0.190 mmol), sodium carbonate (60.3 mg, 0.569 mmol), and tris(dibenzylideneacetone)-dipalladium(0) (15.48 mg, 0.019 mmol) in 4 mL dioxane-water (3:1) was heated under nitrogen under microwave conditions (Biotage Initiator) at 120° C. for 30 minutes. The reaction mixture was the treated with 1 mL aqueous 4 N NaOH and heated at 120° C. under microwave conditions again for 30 minutes. The mixture was diluted with water and extracted with ethyl acetate (2×), washed with saturated aqueous sodium chloride, dried over anhydrous magnesium sulfate, and filtered. The filtrate was concentrated and the residue was purified by flash chromatography (silica gel, 0-10% methanol/dichloromethane gradient) to give the title compound (53 mg, 75% yield). $^1$H NMR (300 MHz, DMSO-$d_6$) δ ppm 11.95 (s, 1H), 8.90 (dd, J=2.4, 0.7 Hz, 1H), 8.56-8.49 (m, 1H), 8.07 (ddd, J=8.0, 2.4, 1.7 Hz, 1H), 7.71-7.64 (m, 2H), 7.45 (ddd, J=7.9, 4.8, 0.8 Hz, 1H), 7.34 (s, 1H), 7.26 (t, J=2.7 Hz, 1H), 7.21 (d, J=8.5 Hz, 1H), 6.18 (dd, J=2.6, 2.2 Hz, 1H), 3.91 (d, J=6.7 Hz, 2H), 3.58 (s, 3H), 1.15-1.04 (m, 1H), 0.49-0.42 (m, 2H), 0.28-0.21 (m, 2H). MS (ESI+) m/z 372.2 (M+H)$^+$.

Example 316

4-[2-(cyclopropylmethoxy)-5-(morpholin-4-ylmethyl)phenyl]-6-methyl-1,6-dihydro-7H-pyrrolo[2,3-c]pyridin-7-one Example 316 was prepared according to the procedure used for the preparation of Example 314c, substituting potassium trifluoro(morpholinomethyl)borate for potassium trifluoro(pyrrolidin-1-ylmethyl)borate to afford the title compound. $^1$H NMR (300 MHz, DMSO-$d_6$) δ ppm 12.01 (s, 1H), 7.50 (d, J=1.9 Hz, 1H), 7.43 (d, J=8.4 Hz, 1H), 7.28 (dd, J=4.9, 2.0 Hz, 2H), 7.18 (d, J=8.5 Hz, 1H), 6.21-6.14 (m, 1H), 4.32 (s, 2H), 3.97 (d, J=12.4 Hz, 2H), 3.89 (d, J=6.7 Hz, 2H), 3.63 (d, J=11.7 Hz, 2H), 3.57 (s, 3H), 3.29 (d, J=12.8 Hz, 2H), 3.10 (d, J=10.4 Hz, 2H), 1.17-1.02 (m, 1H), 0.51-0.42 (m, 2H), 0.28-0.21 (m, 2H). MS (ESI+) m/z 394.0 (M+H)$^+$.

Example 317

4-{5-(ethylsulfonyl)-2-[3-(hydroxymethyl)phenoxy]phenyl}-6-methyl-1,6-dihydro-7H-pyrrolo[2,3-c]pyridin-7-one Example 317 was prepared according to the procedure used for the preparation of Example 138b, substituting 3-(hydroxymethyl)phenol for 2,4-difluorophenol, and Example 168c for Example 138a, respectively, to provide the title compound. $^1$H NMR (500 MHz, DMSO-$d_6$) δ 12.07 (s, 1H), 7.93 (d, J=2.44 Hz, 1H), 7.83 (dd, J=8.7, 2.29 Hz, 1H), 7.42 (s, 1H), 7.35 (t, J=7.93 Hz, 1H), 7.30 (t, J=2.75 Hz, 1H), 7.15 (d, J=7.63 Hz, 1H), 7.02-7.05 (m, 2H), 6.97 (dd, J=7.93, 2.14 Hz, 1H), 6.26 (t, J=2.44 Hz, 1H), 4.48 (s, 2H), 3.57 (s, 3H), 3.34 (q, J=7.32 Hz, 2H), 1.15 (t, J=7.32 Hz, 3H). MS (ESI+) m/z 439.0 (M+H)$^+$.

Example 318

4-[2-(cyclopropylmethoxy)-5-(1-methyl-1H-pyrazol-4-yl)phenyl]-6-methyl-1,6-dihydro-7H-pyrrolo[2,3-c]pyridin-7-one Example 318 was prepared according to the procedure used for the preparation of Example 315, substituting 1-methyl-4-(4,4,5,5-tetramethyl-1,3,2-dioxaborolan-2-yl)-1H-pyrazole for pyridin-3-ylboronic acid to afford the title compound. $^1$H NMR (400 MHz, DMSO-$d_6$) δ ppm 11.93 (s, 1H), 8.05 (d, J=7.4 Hz, 1H), 7.77 (dd, J=6.3, 0.6 Hz, 1H), 7.48 (q, J=2.2 Hz, 2H), 7.28-7.24 (m, 2H), 7.06 (d, J=8.3 Hz, 1H), 6.21-6.05 (m, 1H), 3.83 (d, J=4.9 Hz, 5H), 3.56 (d, J=5.7 Hz, 3H), 1.06-1.02 (m, 1H), 0.46-0.40 (m, 2H), 0.24-0.19 (m, 2H). MS (ESI+) m/z 375.2 (M+H)$^+$.

Example 319

4-[2-(2,4-difluorophenoxy)-5-(2,3-dihydro-1H-indol-1-ylsulfonyl)phenyl]-6-methyl-1,6-dihydro-7H-pyrrolo[2,3-c]pyridin-7-one Example 319a 1-(3-bromo-4-(2,4-difluorophenoxy)phenylsulfonyl)indoline Example 319a was prepared according to the procedure used for the preparation of Example 2b, substituting 2,4-difluorophenol for phenol and substituting Example 305a for Example 2a, to provide the title compound.

Example 319b 4-(2-(2,4-difluorophenoxy)-5-(indolin-1-ylsulfonyl)phenyl)-6-methyl-1-tosyl-1H-pyrrolo[2,3-c]pyridin-7(6H)-one Example 319b was prepared according to the procedure used for the preparation of Example 6c, substituting Example 319a for Example 6b, to afford the title compound.

Example 319c

4-[2-(2,4-difluorophenoxy)-5-(2,3-dihydro-1H-indol-1-ylsulfonyl)phenyl]-6-methyl-1,6-dihydro-7H-pyrrolo[2,3-c]pyridin-7-one Example 319c was prepared according to the procedure used for the preparation of Example 6d, and substituting Example 319b for Example 6c to afford the title compound. $^1$H NMR (300 MHz, DMSO-d6) 2.92 (t, J=8.3 Hz, 2H) 3.55 (s, 3H) 3.93 (t, J=8.3 Hz, 2H) 5.98 (dd, J=2.8, 1.9 Hz, 1H) 6.91 (dd, J=9.3, 1.0 Hz, 1H) 6.98-7.29 (m, 6H) 7.34-7.58 (m, 3H) 7.74-7.91 (m, 2H) 12.08 (bs, 1H). MS (ESI+) m/z 534 [M+H]$^+$.

Example 320

N-[4-(2,4-difluorophenoxy)-3-(6-methyl-7-oxo-6,7-dihydro-1H-pyrazolo[3,4-c]pyridin-4-yl)phenyl]ethanesulfonamide Example 320a 5-bromo-1,4-dimethyl-3-nitropyridin-2(1H)-one Example 320a was prepared according to the procedure used for the preparation of Example 1e, substituting Example 1d for 5-bromo-4-methyl-3-nitropyridin-2-ol, to provide the title compound.

Example 320b 3-amino-5-bromo-1,4-dimethylpyridin-2(1H)-one

Example 320b was prepared according to the procedure used for the preparation of Example 7b, substituting Example 320a for Example 7a, to provide the title compound.

Example 320c

4-bromo-6-methyl-1H-pyrazolo[3,4-c]pyridin-7 (6H)-one

Example 320b (1 g, 4.61 mmol), acetic anhydride (1.304 mL, 13.82 mmol), and potassium acetate (0.543 g, 5.53 mmol) were stirred in toluene (25 mL) for 18 hours. Isoamyl nitrite (0.930 mL, 6.91 mmol) was added dropwise and the solution heated at 80° C. for 24 hours. The solution was cooled, water added, and the aqueous extracted with ethyl acetate. The combined organics were washed with saturated aqueous sodium chloride, dried (anhydrous magnesium sulfate), filtered, and concentrated. The residue was triturated with 30% ethyl acetate in hexanes to afford 0.415 g of the title compound.

Example 320d

4-bromo-6-methyl-1-((2-(trimethylsilyl)ethoxy)methyl)-1H-pyrazolo[3,4-c]pyridin-7(6H)-one Example 320c (0.228 g, 1.000 mmol) in dimethylformamide (5 mL) was treated with sodium hydride (0.060 g, 1.500 mmol). The reaction mixture was stirred at ambient temperature for 10 minutes. To this solution was added (2-(chloromethoxy)ethyl)trimethylsilane (0.200 g, 1.200 mmol). The reaction mixture was stirred at ambient temperature for 2 hours. The reaction mixture was partitioned between ethyl acetate and water, and the organic phase separated, washed with saturated aqueous sodium chloride, dried over anhydrous magnesium sulfate, filtered, and concentrated. The residue was purified by flash chromatography (silica gel, ethyl acetate/heptane gradient) to afford the title compound (0.301 g, 0.840 mmol, 84% yield).

Example 320e

4-(5-amino-2-(2,4-difluorophenoxy)phenyl)-6-methyl-1-((2-(trimethylsilyl)ethoxy)methyl)-1H-pyrazolo[3,4-c]pyridin-7(6H)-one Example 320e was prepared according to the procedure used for the preparation of Example 138a, substituting Example 320d for 2-bromo-1-fluoro-4-(methylsulfonyl)benzene, and Example 148c for Example 6a, respectively, to provide the title compound.

Example 320f

N-(4-(2,4-difluorophenoxy)-3-(6-methyl-7-oxo-1-((2-(trimethylsilyl)ethoxy)methyl)-6,7-dihydro-1H-pyrazolo[3,4-c]pyridin-4-yl)phenyl)-N-(ethylsulfonyl)ethanesulfonamide A mixture of Example 320e (0.1 g, 0.201 mmol), ethanesulfonyl chloride (0.077 g, 0.602 mmol), and triethylamine (0.081 g, 0.802 mmol) in dichloromethane was stirred for 2 hours at room temperature. The solvent was removed, and the residue was purified by flash chromatography on silica gel (4:1 ethyl acetate/hexanes) to give the title compound (0.11 g, 0.161 mmol, 80% yield).

Example 320g

N-[4-(2,4-difluorophenoxy)-3-(6-methyl-7-oxo-6,7-dihydro-1H-pyrazolo[3,4-c]pyridin-4-yl)phenyl]ethanesulfonamide Example 320f in dichloromethane (3 mL) was treated with 2,2,2-trifluoroacetic acid (1.837 g, 16.11 mmol). The reaction mixture was stirred for 16 hours at ambient temperature. The solvent was removed, and the residue was put on high vacuum for 1 hour. It was then treated with dioxane (5 mL) and 2.0 N sodium hydroxide (1.611 mL, 3.22 mmol). The reaction mixture was heated at 85° C. for 2 hours. After cooling, the reaction mixture was partitioned between 0.1% HCl and ethyl acetate. The aqueous layer was extracted with additional ethyl acetate twice. The combined organic layers were washed with saturated aqueous sodium chloride, dried over anhydrous magnesium sulfate, filtered, and concentrated. The residue was then purified by reverse phase preparative HPLC (10-80% acetonitrile in 0.1% TFA water) to afford the TFA salt of the title compound (0.055 g, 0.119 mmol, 74.1% yield). $^1$H NMR (500 MHz, DMSO-$d_6$) δ ppm 9.80 (s, 1H), 7.86 (s, 1H), 7.36-7.42 (m, 3H), 7.22 (dd, J=8.85, 2.75 Hz, 1H), 7.13-7.15 (m, 1H), 6.99-7.04 (m, 1H), 6.92 (d, J=8.85 Hz, 1H), 3.56 (s, 3H), 3.13 (t, J=7.32 Hz, 2H), 1.23 (t, J=7.32 Hz, 3H). MS (ESI+) m/z 461.0 (M+H)$^+$.

Example 321

4-{2-(2,4-difluorophenoxy)-5-[(methylsulfonyl)methyl]phenyl}-6-methyl-1,6-dihydro-7H-pyrazolo[3,4-c]pyridin-7-one

Example 321a

2-(2-(2,4-difluorophenoxy)-5-((methylsulfonyl)methyl)phenyl)-4,4,5,5-tetramethyl-1,3,2-dioxaborolane Example 287e (1.13 g, 3 mmol), 4,4,4',4',5,5,5',5'-octamethyl-2,2'-bi(1,3,2-dioxaborolane) (1.52 g, 6 mmol), potassium acetate (1.18 g, 12 mmol), and bis(triphenylphosphine)palladium(II) chloride (0.126 g, 0.18 mmol) were combined in a 20-mL microwave vial and sparged with nitrogen for 30 minutes. To this mixture was added nitrogen-sparged dioxane (15 mL). The reaction mixture was heated at 90° C. for 8 hours. The reaction mixture was partitioned between water and ethyl acetate. The organic layer was washed with saturated aqueous sodium chloride, dried over anhydrous sodium sulfate, treated with 3-mercaptopropyl-functionalized silica gel, filtered, and concentrated. The residue was purified by flash chromatography (silica gel, 0 to 10% ethyl acetate in dichloromethane) and then triturated with heptane to provide the title compound (0.64 g, 50%).

Example 321b

4-(2-(2,4-difluorophenoxy)-5-((methylsulfonyl)methyl)phenyl)-6-methyl-1-((2-(trimethylsilyl)ethoxy)methyl)-1H-pyrazolo[3,4-c]pyridin-7(6H)-one Example 320d (0.04 g, 0.112 mmol), Example 321a (0.052 g, 0.123 mmol), tris(dibenzylideneacetone)dipalladium(0) (0.0031 g, 3.35 µmol), (1S,3R,5R,7S)-1,3,5,7-tetramethyl-8-phenyl-2,4,6-trioxa-8-phosphaadamantane (0.0033 g, 0.011 mmol) and sodium carbonate (0.051 g, 0.48 mmol) were combined in a 5-mL microwave vial and sparged with nitrogen for 30 minutes. To this mixture was added nitrogen-sparged dioxane (0.8 mL) and water (0.2 mL). The reaction mixture was stirred at 60° C. for 4.5 hours. The reaction mixture was cooled to ambient temperature and then partitioned between ethyl acetate and water. The organic layer was washed with saturated aqueous sodium chloride, treated with 3-mercaptopropyl-functionalized silica gel, dried over anhydrous magnesium sulfate, filtered, and concentrated. The residue was purified by flash chromatography (silica gel, 0 to 10% methanol in dichloromethane) to provide the title compound (0.06 g, 93%).

Example 321c

4-{2-(2,4-difluorophenoxy)-5-[(methylsulfonyl)methyl]phenyl}-6-methyl-1,6-dihydro-7H-pyrazolo[3,4-c]pyridin-7-one Example 321b (0.06 g, 0.104 mmol) was treated with 2,2,2-trifluoroacetic acid (2 mL, 26.1 mmol), stirred at ambient temperature for 30 minutes and then concentrated to dryness. The residue was purified by reverse phase HPLC (C18, $CH_3CN$/water (0.1% TFA), 20-80%) to provide the title compound (0.03 g, 65%). $^1$H NMR (400 MHz, DMSO-$d_6$) ppm 7.91 (s, 1H), 7.60 (d, J=2.14 Hz, 1H), 7.42 (m, 3H), 7.29 (m, J=9.23, 9.23, 5.65 Hz, 1H), 7.09 (m, 1H), 6.89 (d, J=8.54 Hz, 1H), 4.53 (s, 2H), 3.58 (s, 3H), 2.96 (s, 3H). MS (ESI+) m/z 446.1 $(M+H)^+$.

Example 322

4-[2-(2,4-difluorophenoxy)-5-(ethylsulfonyl)phenyl]-6-methyl-1,6-dihydro-7H-pyrazolo[3,4-c]pyridin-7-one Example 322a ethyl(4-fluorophenyl)sulfane Triethylamine (5.44 mL, 39 mmol) was added to a solution of 4-fluorobenzenethiol (5 g, 39 mmol) and iodoethane (3.78 mL, 46.8 mmol) in tetrahydrofuran (50 mL). The resulting mixture was stirred at ambient temperature for 2 hours and then filtered. The filtrate was concentrated, triturated with hexane, and dried under vacuum to afford the title compound (4.8 g, 76%).

Example 322b 1-(ethylsulfonyl)-4-fluorobenzene

Example 322a (5 g, 32 mmol) in dichloromethane (200 mL) was treated with 3-chloroperoxybenzoic acid (14.3 g, 70.4 mmol) and stirred at ambient temperature for 6 hours. The solid formed during the reaction mixture was removed by filtration and washed with additional dichloromethane. The combined filtrate was washed with 10% aqueous sodium hydroxide solution (50 mL, twice) and saturated aqueous sodium bicarbonate solution, dried over anhydrous sodium sulfate, filtered, and concentrated. The residue was purified by flash chromatography (silica gel, 15% ethyl acetate in petroleum ether) to afford the title compound (4.6 g, 76%).

Example 322c 2-bromo-4-(ethylsulfonyl)-1-fluorobenzene

Example 322b (1 g, 5.31 mmol) in sulfuric acid (6 mL, 113 mmol) was treated with N-bromosuccinimide (1.04 g, 5.84 mmol), stirred at ambient temperature for 6 hours and then at 50° C. for 16 hours. The reaction mixture was then poured into ice water and the resulting solid was collected by filtration, washed with cold water three times, and dried in a vacuum oven for 16 hours. The solid was then purified by flash chromatography (silica gel, 9-20% ethyl acetate in petroleum ether) to afford the title compound (1.1 g, 78%).

Example 322d 2-(5-(ethylsulfonyl)-2-fluorophenyl)-4,4,5,5-tetramethyl-1,3,2-dioxaborolane 4,4,4',4',5,5,5',5'-octamethyl-2,2'-bi(1,3,2-dioxaborolane) (0.665 g, 2.62 mmol), Example 322c (0.5 g, 1.9 mmol), potassium acetate (0.367 g, 3.74 mmol) and [1,1'-bis(diphenylphosphino)ferrocene]dichloropalladium(II) (0.041 g, 0.056 mmol) were combined in an argon-sparged mixture of dioxane (10 mL)/dimethyl sulfoxide (0.3 mL) and heated at 90° C. under argon for 24 hours. The reaction mixture was partitioned between ethyl acetate and water and filtered through a plug of Celite to remove elemental palladium. The layers were separated and the organic layer was washed with saturated aqueous sodium chloride, dried over anhydrous sodium sulfate, treated with 3-mercaptopropyl-functionalized silica gel for 15 minutes, filtered, and concentrated. The residue was triturated in a minimal amount of heptane/diethyl ether (20:1) and filtered to give crude product. This material was then dissolved in ethyl acetate, treated again with 3-mercaptopropyl-functionalized silica gel, filtered, and concentrated. The residue was recrystallized from heptane/ethyl acetate (9:1) to afford the title compound (0.3 g, 77%).

Example 322e 4-(5-(ethylsulfonyl)-2-fluorophenyl)-6-methyl-1-((2-(trimethylsilyl)ethoxy)methyl)-1H-pyrazolo[3,4-c]pyridin-7(6H)-one Example 322e was prepared according to the procedure used for the preparation of Example 321b, substituting Example 322d for Example 321a, to provide the title compound (0.0635 g, 55%).

Example 322f 4-(2-(2,4-difluorophenoxy)-5-(ethylsulfonyl)phenyl)-6-methyl-1-((2-(trimethylsilyl)ethoxy)methyl)-1H-pyrazolo[3,4-c]pyridin-7(6H)-one Example 322e (0.0635 g, 0.136 mmol), 2,4-difluorophenol (0.021 g, 0.164 mmol) and cesium carbonate (0.089 g, 0.273 mmol) were combined in a 4-mL vial with dimethyl sulfoxide (1.5 mL), stirred at 60° C. for 8 hours and then at ambient temperature for 16 hours. The reaction mixture was partitioned between ethyl acetate and water. The organic layer was washed with saturated aqueous sodium chloride, dried over anhydrous magnesium sulfate, filtered, and concentrated. The residue was purified by flash chromatography (silica gel, 0 to 8% methanol in dichloromethane) to provide the title compound (0.0574 g, 73%).

Example 322g 4-(2-(2,4-difluorophenoxy)-5-(ethylsulfonyl)phenyl)-6-methyl-1H-pyrazolo[3,4-c]pyridin-7(6H)-one Example 322g was prepared according to the procedure used for the preparation of Example 321c, substituting Example 322f for Example 321b, to provide the title compound (0.0299 g, 67%). $^1$H NMR (400 MHz, DMSO-$d_6$) ppm 7.96 (d, J=2.14 Hz, 1H), 7.91 (s, 1H), 7.85 (dd, J=8.70, 2.29 Hz, 1H), 7.54 (m, 3H), 7.20 (m, 1H), 7.00 (d, J=8.85 Hz, 1H), 3.61 (s, 3H), 3.35 (q, J=7.32 Hz, 2H), 1.15 (t, J=7.32 Hz, 3H). MS (ESI+) m/z 446.2 (M+H)$^+$.

Example 323

4-[2-(cyclopropylmethoxy)-5-(ethylsulfonyl)phenyl]-6-methyl-1,6-dihydro-7H-pyrazolo[3,4-c]pyridin-7-one Example 323a 4-(2-(cyclopropylmethoxy)-5-(ethylsulfonyl)phenyl)-6-methyl-1-((2-(trimethylsilyl)ethoxy)methyl)-1H-pyrazolo[3,4-c]pyridin-7(6H)-one Cyclopropylmethanol (0.018 g, 0.25 mmol) in dioxane (0.75 mL) was treated with sodium hydride (60% oil dispersion) (0.023 g, 0.587 mmol) and stirred at ambient temperature for 10 minutes. A solution of Example 322e (0.0683 g, 0.147 mmol) in dioxane (0.75 mL) was added and the mixture was stirred at 60° C. for 8 hours and then at ambient temperature for 16 hours. Additional cyclopropylmethanol (0.018 g, 0.249 mmol) and sodium hydride (60% oil dispersion) (0.023 g, 0.587 mmol) were added and the mixture was heated at 70° C. for 9 hours. The reaction mixture was cooled to ambient temperature and then partitioned between ethyl acetate and water. The organic layer was washed with saturated aqueous sodium chloride, dried over anhydrous magnesium sulfate, filtered, and concentrated. The residue was purified by flash chromatography (silica gel, 0 to 30% ethyl acetate in dichloromethane) to provide the title compound (0.0685 g, 90%).

Example 323b 4-(2-(cyclopropylmethoxy)-5-(ethylsulfonyl)phenyl)-6-methyl-1H-pyrazolo[3,4-c]pyridin-7(6H)-one Example 323b was prepared according to the procedure used for the preparation of Example 321c, substituting Example 323a for Example 321b, to provide the title compound (0.0302 g, 59%). $^1$H NMR (400 MHz, DMSO-$d_6$) ppm 14.07 (s, 1H), 7.85 (dd, J=8.70, 2.29 Hz, 1H), 7.80 (d, J=2.14 Hz, 1H), 7.78 (m, 1H), 7.41 (s, 1H), 7.34 (d, J=8.54 Hz, 1H), 4.01 (d, J=7.02 Hz, 2H), 3.60 (s, 3H), 3.29 (q, J=7.32 Hz, 2H), 1.13 (t, J=7.32 Hz, 3H), 1.06 (m, 1H), 0.45 (m, 2H), 0.27 (m, 2H). MS (ESI+) m/z 388.2 (M+H)$^+$.

Example 324

N-[2-cyano-4-(2,4-difluorophenoxy)-5-(6-methyl-7-oxo-6,7-dihydro-1H-pyrrolo[2,3-c]pyridin-4-yl)phenyl]ethanesulfonamide Example 324a 4-bromo-5-(2,4-difluorophenoxy)-2-nitrobenzoic acid Example 324a was prepared according to the procedure used for the preparation of Example 7a, substituting 4-bromo-5-fluoro-2-nitrobenzoic acid for 2-bromo-1-fluoro-4-nitrobenzene (Combi Blocks) and substituting 2,4-difluorophenol for phenol to afford the title compound.

Example 324b methyl 4-bromo-5-(2,4-difluorophenoxy)-2-nitrobenzoate

Oxalyl chloride (1.4 mL, 16.6 mmol) was added dropwise to a 0° C. suspension of Example 324a (5.47 g, 14.6 mmol) and dichloromethane (65 mL). 3 drops dimethylformamide was added and the reaction mixture was stirred at ambient temperature for 2 hours. After cooling to 0° C., methanol (12 mL, 296 mmol) was added dropwise. The solution was stirred for 15 minutes at 0° C. and for 2.5 hours at ambient temperature. The solution was diluted with dichloromethane and was washed with water, saturated aqueous sodium bicarbonate, saturated aqueous sodium chloride, dried over anhydrous sodium sulfate, filtered and concentrated to afford the title compound (5.42 g, 96% yield).

Example 324c methyl 2-amino-4-bromo-5-(2,4-difluorophenoxy)benzoate

Example 324c was prepared according to the procedure used for the preparation of Example 7b, substituting Example 324b for Example 7a to afford the title compound.

Example 324d 4-bromo-5-(2,4-difluorophenoxy)-2-(ethylsulfonamido)benzoic acid

Example 324d was prepared according to the procedure used for the preparation of Example 7c, substituting Example 324c for Example 7b to afford the title compound.

Example 324e 4-bromo-5-(2,4-difluorophenoxy)-2-(ethylsulfonamido)benzamide

Oxalyl chloride (0.046 mL, 0.54 mmol) was added dropwise to a suspension of Example 324d (214 mg, 0.49 mmol) and dichloromethane (2.2 mL). 1 Drop dimethylformamide was added and the reaction mixture was stirred at ambient temperature for 2 hours. The solvent was evaporated and the residue was dried (in-vacuo). The resulting acid chloride was suspended in tetrahydrofuran (1.0 mL) and was cooled to 0° C. as ammonium hydroxide (0.65 mL, 4.7 mmol) was added dropwise. The reaction mixture was stirred at ambient temperature for 2 hours. Ethyl acetate was added and the solution was washed with water, saturated aqueous sodium chloride, dried over anhydrous magnesium sulfate, filtered, and concentrated. The residue was purified by flash chromatography (silica gel, 1-8% methanol/dichloromethane gradient) to afford the title compound (176 mg, 82% yield).

Example 324f

N-(5-bromo-2-cyano-4-(2,4-difluorophenoxy)phenyl)ethanesulfonamide

To a suspension of Example 324e (230 mg, 0.53 mmol) and dioxane (1.5 mL) was added pyridine (0.14 mL, 1.7 mmol)

followed by 2,2,2-trifluoroacetic anhydride (0.14 mL, 0.99 mmol). The reaction mixture was stirred at ambient temperature for 1 hour. Water was added and the solution was extracted with ethyl acetate. The organic layer was washed with water, saturated aqueous sodium chloride, dried over anhydrous magnesium sulfate, filtered, and concentrated. The residue was purified by flash chromatography (silica gel, 5-40% ethyl acetate/heptane gradient) to afford the title compound (135 mg, 61% yield).

Example 324g

N-(2-cyano-4-(2,4-difluorophenoxy)-5-(6-methyl-7-oxo-1-tosyl-6,7-dihydro-1H-pyrrolo[2,3-c]pyridin-4-yl)phenyl)ethanesulfonamide Example 324g was prepared according to the procedure used for the preparation of Example 6c, substituting Example 324f for Example 6b to afford the title compound.

Example 324h

N-(2-cyano-4-(2,4-difluorophenoxy)-5-(6-methyl-7-oxo-6,7-dihydro-1H-pyrrolo[2,3-c]pyridin-4-yl)phenyl)ethanesulfonamide Example 324h was prepared according to the procedure used for the preparation of Example 6d, substituting Example 324g for Example 6c to afford the title compound. $^1$H NMR (300 MHz, DMSO-$d_6$) ppm 1.32 (t, J=7.12 Hz, 3H) 3.20 (q, J=7.46, 5.76 Hz, 2H) 3.54-3.57 (m, 3H) 6.32 (t, J=2.71, 2.03 Hz, 1H) 7.03-7.11 (m, 1H) 7.24-7.32 (m, 1H) 7.32 (t, J=2.71 Hz, 1H) 7.37 (s, 1H) 7.38-7.48 (m, 1H) 7.46 (s, 1H) 7.59 (s, 1H) 10.07 (s, 1H) 12.13 (brs, 1H). MS (ESI+) m/z 485 [M+H]$^+$.

Example 325 tert-butyl 4-[4-(cyclopropylmethoxy)-3-(6-methyl-7-oxo-6,7-dihydro-1H-pyrrolo[2,3-c]pyridin-4-yl)phenyl]-3,6-dihydropyridine-1(2H)-carboxylate Example 325 was prepared according to the procedure used for the preparation of Example 315, substituting tert-butyl 4-(4,4,5,5-tetramethyl-1,3,2-dioxaborolan-2-yl)-5,6-dihydropyridine-1(2H)-carboxylate for pyridin-3-ylboronic acid to afford the title compound. $^1$H NMR (400 MHz, DMSO-$d_6$) δ ppm 11.93 (s, 1H), 7.40-7.34 (m, 2H), 7.27-7.22 (m, 2H), 7.04 (d, J=9.0 Hz, 1H), 6.13-6.09 (m, 1H), 6.07 (s, 1H), 3.97 (s, 2H), 3.83 (d, J=6.7 Hz, 2H), 3.56 (s, 3H), 3.52 (dd, J=9.1, 3.4 Hz, 2H), 2.45 (s, 2H), 1.42 (d, J=5.3 Hz, 9H), 1.06-0.97 (m, 1H), 0.46-0.38 (m, 2H), 0.26-0.17 (m, 2H). MS (ESI+) m/z 476.2 (M+H)$^+$.

Example 326

4-[5-(6-aminopyridin-3-yl)-2-(cyclopropylmethoxy)phenyl]-6-methyl-1,6-dihydro-7H-pyrrolo[2,3-c]pyridin-7-one Example 326 was prepared according to the procedure used for the preparation of Example 315, substituting 5-(4,4,5,5-tetramethyl-1,3,2-dioxaborolan-2-yl)pyridin-2-amine for pyridin-3-ylboronic acid to afford the title compound. $^1$H NMR (300 MHz, DMSO-$d_6$) δ ppm 11.93 (s, 1H), 8.21 (d, J=2.4 Hz, 1H), 7.67 (dd, J=8.6, 2.5 Hz, 1H), 7.49 (dd, J=6.3, 2.4 Hz, 2H), 7.30 (s, 1H), 7.25 (t, J=2.7 Hz, 1H), 7.14-7.07 (m, 1H), 6.49 (t, J=7.5 Hz, 1H), 6.16 (t, J=2.4 Hz, 1H), 5.94 (s, 2H), 3.86 (d, J=6.7 Hz, 2H), 3.57 (s, 3H), 1.14-1.00 (m, 1H), 0.51-0.38 (m, 2H), 0.27-0.14 (m, 2H). MS (ESI+) m/z 387.2 (M+H)$^+$.

Example 327

4-{2-[(2,2-difluorocyclopropyl)methoxy]-5-(ethylsulfonyl)phenyl}-6-methyl-7-oxo-N-(2,2,2-trifluoroethyl)-6,7-dihydro-1H-pyrrolo[2,3-c]pyridine-2-carboxamide Example 327a ethyl 1-benzyl-6-methyl-7-oxo-4-(4,4,5,5-tetramethyl-1,3,2-dioxaborolan-2-yl)-6,7-dihydro-1H-pyrrolo[2,3-c]pyridine-2-carboxylate Example 327a was prepared according to the procedure used for the preparation of Example 6a, substituting Example 70e for Example 1e, to provide the title compound.

Example 327b ethyl 1-benzyl-4-(5-(ethylsulfonyl)-2-fluorophenyl)-6-methyl-7-oxo-6,7-dihydro-1H-pyrrolo[2,3-c]pyridine-2-carboxylate Example 327b was prepared according to the procedure used for the preparation of Example 138a, substituting Example 327a for Example 6a, and Example 168b for 2-bromo-1-fluoro-4-(methylsulfonyl)benzene, respectively, to provide the title compound.

Example 327c ethyl 4-(5-(ethylsulfonyl)-2-fluorophenyl)-6-methyl-7-oxo-6,7-dihydro-1H-pyrrolo[2,3-c]pyridine-2-carboxylate Example 327c was prepared according to the procedure used for the preparation of Example 70j, substituting Example 327b for Example 70i, to provide the title compound.

Example 327d 4-(2-((2,2-difluorocyclopropyl)methoxy)-5-(ethylsulfonyl)phenyl)-6-methyl-7-oxo-6,7-dihydro-1H-pyrrolo[2,3-c]pyridine-2-carboxylic acid To the solution of Example 327c (1 g, 2.460 mmol) and (2,2-difluorocyclopropyl) methanol (0.532 g, 4.92 mmol) in dimethylsulfoxide (10 mL) was added cesium carbonate (1.203 g, 3.69 mmol). The reaction mixture was sealed in a microwave tube and heated at 110° C. for 5 days. During the 5 days, three additional batches of (2,2-difluorocyclopropyl) methanol (0.532 g, 4.92 mmol) were added into the reaction mixture. The reaction mixture was poured into ethyl acetate (150 mL) and water (150 mL). The aqueous layer was extracted with ethyl acetate (100 mL×2). The combined organic layers were dried over anhydrous sodium sulfate, filtered, and concentrated to give the corresponding ethyl ester (1.2 g, 1.869 mmol, 76% yield). The aqueous layer was adjusted pH to about 3 with 1N HCl and the resulting solid was filtered and dried to give the title compound (0.30 g, 0.64 mmol).

Example 327e

4-{2-[(2,2-difluorocyclopropyl)methoxy]-5-(ethylsulfonyl)phenyl}-6-methyl-7-oxo-N-(2,2,2-trifluoroethyl)-6,7-dihydro-1H-pyrrolo[2,3-c]pyridine-2-carboxamide To a solution of Example 327d (0.070 g, 0.15 mmol) in anhydrous dichloromethane (5 mL) were added oxalyl chloride (0.026 mL, 0.300 mmol) and dimethylformamide (0.581 µl, 7.50 µmol). The reaction mixture was stirred at ambient temperature for 2 hours and then evaporated. The residue was dissolved in dichloromethane (5 mL) and treated with 2,2,2-trifluoroethylamine (0.048 mL, 0.600 mmol) and the mixture was stirred at ambient temperature overnight. The reaction mixture was partitioned between water (15 mL) and ethyl acetate (25 mL). The aqueous layer was extracted with additional ethyl acetate (15 mL) twice. The combined organic layers were dried over anhydrous sodium sulfate, filtered, and concentrated. The residue was purified by reverse phase HPLC (C18, mobile phase A:water (10 mM $NH_4HCO_3$); B: acetonitrile, Gradient 25-60% B in A) to give the title compound (70 mg, 85%). $^1$H NMR (400 MHz, $CD_3OD$) δ ppm 7.96-7.90 (m, 2H), 7.66-7.25 (m, 2H), 6.92 (s, 1H), 4.29 (t, J=7.5 Hz, 1H), 4.16 (t, J=9.2 Hz, 1H), 4.05 (tt, J=9.2, 4.5 Hz, 2H), 3.72 (s, 3H), 3.22 (q, J=7.4 Hz, 2H), 2.00 (td, J=12.0, 7.3 Hz, 1H), 1.58-1.46 (m, 1H), 1.32-1.25 (m, 4H). MS (ESI+) m/z 548.1 (M+H)$^+$.

Example 328

4-{2-[(cyclopropylmethyl)amino]-5-[(methylsulfonyl)methyl]phenyl}-6-methyl-1,6-dihydro-7H-pyrrolo[2,3-c]pyridin-7-one

Example 328a 1-((methylsulfonyl)methyl)-4-nitrobenzene

To a solution of 4-nitrobenzyl bromide (10.02 g, 46.4 mmol) in N,N-dimethylformamide (25 mL) was added sodium methanesulfinate (7.10 g, 69.6 mmol). The reaction mixture was stirred at 65° C. for 1 hour. The reaction mixture was cooled to ambient temperature and diluted with water. The resulting suspension was stirred for 10 minutes and filtered through a medium frit to provide the title compound.

Example 328b 4-((methylsulfonyl)methyl)aniline

Example 328a (8.2 g, 38.1 mmol) and tetrahydrofuran (200 mL) were added to 5% Pd/C, wet (1.6 g, 0.376 mmol) in a 50 mL pressure bottle and stirred for 2 hours at 30 psi and 50° C. The mixture was filtered through a nylon membrane and washed with a small amount of tetrahydrofuran and methanol. The solvent was evaporated to provide the title compound.

Example 328c 2-iodo-4-((methylsulfonyl)methyl)aniline

To a solution of Example 328b (3.80 g, 20.5 mmol) in N,N-dimethylformamide (103 mL) was added N-iodosuccinimide (5.08 g, 22.56 mmol). The reaction mixture was stirred at ambient temperature for 1 hour. The reaction mixture was quenched with 150 mL 10% aqueous sodium thiosulfate and 100 mL saturated aqueous sodium bicarbonate. The reaction mixture was extracted with ethyl acetate. The combined organic layers were washed with saturated aqueous sodium chloride and concentrated. Water was added, and the resulting suspension was stirred at ambient temperature 10 minutes. The suspension was filtered, and the solids collected was rinsed with water, and dried overnight to provide the title compound.

Example 328d

N-(cyclopropylmethyl)-2-iodo-4-((methylsulfonyl)methyl)aniline

Example 328c (0.200 g, 0.643 mmol) and cyclopropanecarbaldehyde (0.062 mL, 0.836 mmol) were suspended in dichloromethane (3.21 mL) and methanol (3.21 mL). Acetic acid (0.368 mL, 6.43 mmol) was added. The reaction mixture was heated at 50° C. for 30 minutes and then cooled to ambient temperature. Polymer supported cyanoborohydride (0.817 g, 1.928 mmol) was added. The reaction mixture was stirred at ambient temperature overnight. Cyclopropanecarbaldehyde (0.062 mL, 0.836 mmol) was added, and the reaction mixture was stirred at ambient temperature for 2 hours. The reaction mixture was filtered, thoroughly rinsed with dichloromethane, and concentrated. The residue was purified by flash chromatography (silica gel, 20-100% ethyl acetate/heptane gradient) to provide the title compound.

Example 328e 4-(2-((cyclopropylmethyl)amino)-5-((methylsulfonyl)methyl)phenyl)-6-methyl-1-tosyl-1H-pyrrolo[2,3-c]pyridin-7(6H)-one Example 328e was prepared according to the procedure used for the preparation of Example 4a, substituting Example 328d for Example 7c to provide the title compound.

Example 328f

4-{2-[(cyclopropylmethyl)amino]-5-[(methylsulfonyl)methyl]phenyl}-6-methyl-1,6-dihydro-7H-pyrrolo[2,3-c]pyridin-7-one Example 328f was prepared according to the procedure used for the preparation of Example 4b, substituting Example 328e for Example 4a to provide the title compound. $^1$H NMR (400 MHz, DMSO-d$_6$) δ ppm 12.08 (bs, 1H), 7.29 (t, J=2.3 Hz, 1H), 7.21 (dd, J=8.3, 2.1 Hz, 1H), 7.17 (s, 1H), 7.12 (d, J=2.1 Hz, 1H), 6.73 (d, J=8.3 Hz, 1H), 6.05 (d, J=2.7 Hz, 1H), 4.67 (t, J=5.7 Hz, 1H), 4.30 (bs, 2H), 3.55 (s, 3H), 2.96 (t, J=6.1 Hz, 2H), 2.86 (s, 3H), 1.05-0.92 (m, 1H), 0.41-0.29 (m, 2H), 0.19-0.10 (m, 2H). MS (ESI+) m/z 386.0 (M+H)$^+$

Example 329

4-{2-[(cyclopropylmethyl)amino]-5-(methylsulfonyl)phenyl}-6-methyl-1,6-dihydro-7H-pyrrolo[2,3-c]pyridin-7-one

Example 329a 2-bromo-N-(cyclopropylmethyl)-4-(methylsulfonyl)aniline

Example 329a was prepared according to the procedure used for the preparation of Example 147a, substituting cyclopropylmethanamine for cyclohexanamine to provide the title compound.

Example 329b 4-(2-((cyclopropylmethyl)amino)-5-(methylsulfonyl)phenyl)-6-methyl-1-tosyl-1H-pyrrolo[2,3-c]pyridin-7(6H)-one Example 329b was prepared according to the procedure used for the preparation of Example 7d, substituting the product of Example 329a for the product of Example 7c and stirring at 100° C. for 30 minutes, to provide the title compound.

Example 329c

4-{2-[(cyclopropylmethyl)amino]-5-(methylsulfonyl)phenyl}-6-methyl-1,6-dihydro-7H-pyrrolo[2,3-c]pyridin-7-one Example 329c was prepared according to the procedure used for the preparation of Example 4 (Method B), substituting the product of Example 329b for the product of Example 7d, and purified by Preparative HPLC (C18, 10-100% acetonitrile in 0.1% TFA/water) to provide the TFA salt of the title compound. $^1$H NMR (300 MHz, DMSO-$d_6$) ppm 12.12 (bds, 1H), 7.67 (dd, J=2.4, 8.8 Hz, 1H), 7.51 (d, J=2.4 Hz, 1H), 7.29 (t, J=3.1 Hz, 1H), 7.26 (s, 1H), 6.86 (d, J=8.8 Hz, 1H), 6.02 (t, J=2.2 Hz, 1H), 5.45 (m, 1H), 3.56 (s, 3H), 3.10 (m, 2H), 3.04 (m, 2H), 1.01 (m, 1H), 0.37 (m, 2H), 0.16 (m, 2H). MS (ESI+) m/z 372.1 (M+H)$^+$.

Example 330

4-[5-(ethylsulfonyl)-2-(pyrrolidin-1-yl)phenyl]-6-methyl-1,6-dihydro-7H-pyrrolo[2,3-c]pyridin-7-one

Example 330a 4-(5-(ethylsulfonyl)-2-fluorophenyl)-6-methyl-1H-pyrrolo[2,3-c]pyridin-7(6H)-one A mixture of Example 168b (0.935 g, 3.50 mmol), Example 6a (1.5 g, 3.5 mmol), tetrakis(triphenylphosphine)palladium(0) (0.202 g, 0.175 mmol) and cesium fluoride (1.596 g, 10.51 mmol) in 12 mL dimethoxyethane and 4 mL methanol was heated at 120° C. under microwave conditions for 40 minutes. The mixture was concentrated and the residue was absorbed on silica gel and purified by flash chromatography (SiO$_2$, 0-10% methanol/dichloromethane gradient) to give the title compound (1.01 g, 86% yield).

Example 330b

4-[5-(ethylsulfonyl)-2-(pyrrolidin-1-yl)phenyl]-6-methyl-1,6-dihydro-7H-pyrrolo[2,3-c]pyridin-7-one A mixture of Example 330a (90 mg, 0.27 mmol) and pyrrolidine (668 µL, 8.08 mmol) in 1 mL DMSO was heated at 160° C. under microwave conditions for 30 minutes. The product was purified by preparative HPLC (C18, 10-80% CH$_3$CN/water (0.1% TFA)) to give the title compound (37 mg, 35.7% yield). $^1$H NMR (300 MHz, DMSO-$d_6$) δ ppm 12.07 (s, 1H), 7.61 (dd, J=8.8, 2.4 Hz, 1H), 7.48 (d, J=2.4 Hz, 1H), 7.26 (t, J=2.8 Hz, 1H), 7.20 (s, 1H), 6.95 (d, J=8.9 Hz, 1H), 5.99-5.94 (m, 1H), 3.56 (s, 3H), 3.16 (q, J=7.3 Hz, 2H), 3.06 (s, 4H), 1.69 (t, J=6.3 Hz, 4H), 1.10 (t, J=7.4 Hz, 3H). MS (ESI+) m/z 386.1 (M+H)$^+$.

Example 331

4-[5-(ethylsulfonyl)-2-(4-methylpiperazin-1-yl)phenyl]-6-methyl-1,6-dihydro-7H-pyrrolo[2,3-c]pyridin-7-one Example 331 was prepared according to the procedure used for the preparation of Example 330b, substituting N-methylpiperazine for pyrrolidine, to afford the TFA salt of the title compound. $^1$H NMR (300 MHz, DMSO-$d_6$) δ ppm 12.12 (s, 1H), 9.57 (s, 1H), 7.80 (dd, J=8.5, 2.3 Hz, 1H), 7.71 (d, J=2.3 Hz, 1H), 7.45 (s, 1H), 7.32 (dd, J=8.6, 5.7 Hz, 2H), 6.17 (t, J=2.3 Hz, 1H), 3.60 (s, 3H), 3.49 (t, J=6.7 Hz, 2H), 3.28 (q, J=7.4 Hz, 4H), 2.94 (t, J=11.8 Hz, 2H), 2.71 (s, 3H), 2.68-2.53 (m, 2H), 1.13 (t, J=7.3 Hz, 3H). MS (ESI+) m/z 415.2 (M+H)$^+$.

Example 332

4-{2-[(4-fluorophenyl)amino]-5-(methylsulfonyl)phenyl}-6-methyl-1,6-dihydro-7H-pyrrolo[2,3-c]pyridin-7-one

Example 332a 4-(2-amino-5-(methylsulfonyl)phenyl)-6-methyl-1-tosyl-1H-pyrrolo[2,3-c]pyridin-7(6H)-one Example 6a (1.71 g, 4.00 mmol), 2-bromo-4-(methylsulfonyl)aniline (1.00 g, 4.00 mmol), tris(dibenzylideneacetone)dipalladium (0.110 g, 0.120 mmol), 1,3,5,7-tetramethyl-6-phenyl-2,4,8-trioxa-6-phosphaadamante (0.117 g, 0.400 mmol) and sodium carbonate (1.48 g, 14.0 mmol) were combined and purged with argon for 15 minutes. A mixture of dioxane (21.3 mL) and water (5.3 mL) was purged with nitrogen for 15 minutes and transferred to the reaction vessel. The reaction mixture was heated at 60° C. for 3 hours, cooled to ambient temperature and diluted with water. The resulting solid was filtered, washed with water and dried to afford the title compound (2.06 g, quantitative yield).

Example 332b 4-(2-((4-fluorophenyl)amino)-5-(methylsulfonyl)phenyl)-6-methyl-1-tosyl-1H-pyrrolo[2,3-c]pyridin-7(6H)-one Example 332a (47.2 mg, 0.100 mmol), 1-bromo-4-fluorobenzene (17.5 mg, 0.100 mmol), diacetoxypalladium (0.9 mg, 4 µmol), dicyclohexyl(2',4',6'-triisopropyl-[1,1'-biphenyl]-2-yl)phosphine (3.8 mg, 8.0 μmol) and cesium carbonate (45.6 mg, 0.140 mmol) were combined in a mixture of toluene (1.6 mL) and tert-butanol (0.4 mL). The reaction mixture was heated in a microwave reactor at 150° C. for 15 minutes. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 2 to 4% methanol in dichloromethane) to provide the title compound (30 mg, 53%).

Example 332c

4-{2-[(4-fluorophenyl)amino]-5-(methylsulfonyl)phenyl}-6-methyl-1,6-dihydro-7H-pyrrolo[2,3-c]pyridin-7-one Example 332b (28 mg, 0.050 mmol), potassium hydroxide (41.7 mg, 0.743 mmol) and cetyltrimethylammonium bromide (0.90 mg, 2.5 μmol) were combined in a mixture of tetrahydrofuran (2 mL) and water (1 mL). The reaction mixture was heated at 100° C. for 20 hours and then cooled to ambient temperature. To this mixture was added water, and the pH was adjusted to pH 7 by the addition of 1M HCl. The mixture was extracted with ethyl acetate and the organic layer was washed with saturated aqueous sodium chloride twice, dried with anhydrous sodium sulfate, filtered, and concentrated. The residue was purified by flash chromatography (silica gel, 2 to 4% methanol in dichloromethane) to provide the title compound (13 mg, 64%). $^1$H NMR (300 MHz, DMSO-$d_6$) δ ppm 12.04 (s, 1H) 7.57-7.71 (m, 3H) 7.34 (s, 1H) 7.08-7.27 (m, 6H) 6.06 (t, J=2.20 Hz, 1H) 3.57 (s, 3H) 3.15 (s, 3H). MS (ESI+) m/z 412 (M+H)+.

Example 333

4-(cyclopropylmethoxy)-3-(6-methyl-7-oxo-6,7-dihydro-1H-pyrrolo[2,3-c]pyridin-4-yl)-N-(pyridin-3-ylmethyl)benzenesulfonamide Example 333a 3-bromo-4-fluoro-N-(pyridin-3-ylmethyl)benzenesulfonamide Example 333a was prepared according to the procedure used for the preparation of Example 305a, substituting pyridin-3-ylmethanamine for indoline. The crude product was purified by crystallization from ethyl acetate/ethyl ether to afford title compound Example 333b 3-bromo-4-(cyclopropylmethoxy)-N-(pyridin-3-ylmethyl)benzenesulfonamide Example 333b was prepared according to the procedure used for the preparation of Example 29a, substituting cyclopropylmethanol for tetrahydro-2H-pyran-4-ol and substituting Example 333a for Example 2a to afford the title compound.

Example 333c 4-(cyclopropylmethoxy)-3-(6-methyl-7-oxo-1-tosyl-6,7-dihydro-1H-pyrrolo[2,3-c]pyridin-4-yl)-N-(pyridin-3-ylmethyl)benzenesulfonamide Example 333c was prepared according to the procedure used for the preparation of Example 6c, substituting Example 333b for Example 6b to afford the title compound.

Example 333d 4-(cyclopropylmethoxy)-3-(6-methyl-7-oxo-6,7-dihydro-1H-pyrrolo[2,3-c]pyridin-4-yl)-N-(pyridin-3-ylmethyl)benzenesulfonamide Example 333d was prepared according to the procedure used for the preparation of Example 6d, substituting Example 333c for Example 6c, and purified by Preparative HPLC (C18, 10-100% acetonitrile in 0.1% TFA/water) to provide the TFA salt of the title compound. $^1$H NMR (300 MHz, DMSO-$d_6$) ppm 12.03 (s, 1H) 8.55 (s, 2H) 8.17 (t, J=6.44 Hz, 1H) 7.88 (d, J=7.80 Hz, 1H) 7.70-7.76 (m, 2H) 7.50 (dd, J=7.12, 4.75 Hz, 1H) 7.27-7.32 (m, 2H) 7.20-7.26 (m, 1H) 6.10-6.16 (m, 1H) 4.11 (d, J=6.44 Hz, 2H) 3.95 (d, J=6.78 Hz, 2H) 3.58 (s, 3H) 1.03-1.19 (m, 1H) 0.44-0.52 (m, 2H) 0.24-0.31 (m, 2H). MS (ESI+) m/z 465.0 [M+H]$^+$.

Example 334

4-[4-(cyclopropylmethoxy)-3'-fluorobiphenyl-3-yl]-6-methyl-1,6-dihydro-7H-pyrrolo[2,3-c]pyridin-7-one Example 334a 4-(5-bromo-2-(cyclopropylmethoxy)phenyl)-6-methyl-1-tosyl-1H-pyrrolo[2,3-c]pyridin-7(6H)-one Example 334a was prepared according to the procedure used for the preparation of Example 6c, substituting Example 314a for Example 6b to afford the title compound.

Example 334b 4-(4-(cyclopropylmethoxy)-3'-fluorobiphenyl-3-yl)-6-methyl-1-tosyl-1H-pyrrolo[2,3-c]pyridin-7(6H)-one Example 334b was prepared according to the procedure used for the preparation of Example 6c, substituting Example 334a for Example 6b and substituting (3-fluorophenyl)boronic acid for Example 6a to afford the title compound.

Example 334c 4-(4-(cyclopropylmethoxy)-3'-fluorobiphenyl-3-yl)-6-methyl-1H-pyrrolo[2,3-c]pyridin-7(6H)-one Example 334c was prepared according to the procedure used for the preparation of Example 6d, substituting Example 334b for Example 6c to afford the title compound. $^1$H NMR (300 MHz, DMSO-$d_6$) ppm 0.22-0.28 (m, 2H) 0.42-0.49 (m, 2H) 1.03-1.14 (m, 1H) 3.58 (s, 3H) 3.90 (d, J=6.78 Hz, 2H) 6.17 (t, J=2.71, 2.03 Hz, 1H) 7.09-7.20 (m, 2H) 7.27 (t, J=3.05

Hz, 1H) 7.34 (s, 1H) 7.42-7.55 (m, 3H) 7.62-7.69 (m, 2H) 11.98 (brs, 1H). MS (ESI+) m/z 389 [M+H]+.

Example 335

4-{2-[(4-fluorophenyl)amino]-5-[(methylsulfonyl) methyl]phenyl}-6-methyl-1,6-dihydro-7H-pyrrolo[2,3-c]pyridin-7-one Example 335a 4-(2-amino-5-((methylsulfonyl)methyl)phenyl)-6-methyl-1-tosyl-1H-pyrrolo[2,3-c]pyridin-7(6H)-one Example 335a was prepared according to the procedure used for the preparation of Example 4a, substituting Example 328c for Example 7c to provide the title compound.

Example 335b 4-(2-((4-fluorophenyl)amino)-5-((methylsulfonyl) methyl)phenyl)-6-methyl-1-tosyl-1H-pyrrolo[2,3-c] pyridin-7(6H)-one 4-Bromofluorobenzene (0.027 mL, 0.25 mmol), Example 335a (0.100 g, 0.206 mmol), palladium (II) acetate (1.849 mg, 8.24 µmol), dicyclohexyl(2',4',6'-triisopropyl-[1,1'-biphenyl]-2-yl)phosphine (7.85 mg, 0.016 mmol), and cesium carbonate (0.094 g, 0.29 mmol) were suspended in toluene (1.37 mL) and t-butanol (0.69 mL). The reaction mixture was heated at 150° C. for 30 minutes under microwave conditions. The reaction mixture was filtered through a 2.5 g Celite column and rinsed thoroughly with ethyl acetate. The filtrate was washed with saturated aqueous sodium chloride, dried over anhydrous magnesium sulfate and mercaptopropyl silica gel, filtered, and concentrated. The residue was purified by flash chromatography (silica gel, 0-4% methanol/dichloromethane gradient) to provide the title compound.

Example 335c

4-{2-[(4-fluorophenyl)amino]-5-[(methylsulfonyl) methyl]phenyl}-6-methyl-1,6-dihydro-7H-pyrrolo[2,3-c]pyridin-7-one Example 335c was prepared according to the procedure used for the preparation of Example 4b, substituting Example 335b for Example 4a to provide the title compound. $^1$H NMR (500 MHz, DMSO-$d_6$) δ ppm 11.99 (bs, 1H), 7.32 (d, J=2.1 Hz, 1H), 7.25 (dd, J=8.3, 2.0 Hz, 1H), 7.18-7.23 (m, 4H), 6.97-7.07 (m, 4H), 6.06 (t, J=2.0 Hz, 1H), 4.40 (bs, 2H), 3.53 (s, 3H), 2.91 (s, 3H). MS (ESI+) m/z 426.2 (M+H)+

Example 336

[4-(cyclopropylmethoxy)-3-(6-methyl-7-oxo-6,7-dihydro-1H-pyrrolo[2,3-c]pyridin-4-yl)phenyl]acetonitrile A mixture of Example 314b (100 mg, 0.190 mmol), 4-(4,4,5,5-tetramethyl-1,3,2-dioxaborolan-2-yl)isoxazole (44.4 mg, 0.228 mmol), [1,1'-bis(diphenylphosphino)ferrocene]dichloropalladium (II), complex with dichloromethane (1:1) (15.5 mg, 0.019 mmol), and potassium fluoride (44.1 mg, 0.758 mmol) in dimethylsulfoxide (1.9 mL) and water (0.75 mL) was purged with nitrogen gas and heated under microwave conditions at 130° C. at for 1.5 hours. The mixture was then treated with 1 mL 4N NaOH and stirred at ambient temperature for 2 hours. The reaction mixture was partitioned between water and ethyl acetate, and the aqueous layers was extracted with ethyl acetate. The combined organic phases were washed with water (2×), saturated aqueous sodium chloride, dried over anhydrous magnesium sulfate, and filtered. The filtrate was concentrated and the residue was purified by flash chromatography (silica gel, 0-8% methanol/dichloromethane gradient) to give the title compound (30 mg, 48% yield). $^1$H NMR (300 MHz, DMSO-$d_6$) δ ppm 12.00 (s, 1H), 12.00 (s, 1H), 7.32 (d, J=2.4 Hz, 1H), 7.34-7.25 (m, 4H), 7.30-7.25 (m, 3H), 7.10 (d, J=8.4 Hz, 1H), 7.10 (d, J=8.4 Hz, 1H), 6.14 (dd, J=2.6, 2.2 Hz, 1H), 6.14 (dd, J=2.6, 2.2 Hz, 1H), 3.99 (s, 2H), 3.99 (s, 2H), 3.84 (d, J=6.7 Hz, 2H), 3.84 (d, J=6.7 Hz, 2H), 3.56 (s, 3H), 3.56 (s, 3H), 1.11-1.02 (m, 1H), 1.12-1.02 (m, 1H), 0.48-0.39 (m, 2H), 0.49-0.35 (m, 2H), 0.31-0.18 (m, 2H), 0.26-0.19 (m, 2H). MS (ESI+) m/z 334.1 (M+H)+.

Example 337

N-{4-(2,4-difluorophenoxy)-3-[2-(hydroxymethyl)-6-methyl-7-oxo-6,7-dihydro-1H-pyrrolo[2,3-c]pyridin-4-yl]phenyl}ethanesulfonamide Example 337a ethyl 4-(5-amino-2-(2,4-difluorophenoxy)phenyl)-1-benzyl-6-methyl-7-oxo-6,7-dihydro-1H-pyrrolo[2,3-c]pyridine-2-carboxylate Example 337a was prepared according to the procedure used for the preparation of Example 138a, substituting Example 70e for 2-bromo-1-fluoro-4-(methylsulfonyl)benzene, and Example 148c for Example 6a, respectively, to provide the title compound.

Example 337b ethyl 1-benzyl-4-(2-(2,4-difluorophenoxy)-5-(N-(ethylsulfonyl)ethylsulfonamido)phenyl)-6-methyl-7-oxo-6,7-dihydro-1H-pyrrolo[2,3-c]pyridine-2-carboxylate Example 337b was prepared according to the procedure used for the preparation of Example 320f, substituting Example 337a for Example 320e, to provide the title compound.

Example 337c ethyl 4-(2-(2,4-difluorophenoxy)-5-(N-(ethylsulfonyl)ethylsulfonamido)phenyl)-6-methyl-7-oxo-6,7-dihydro-1H-pyrrolo[2,3-c]pyridine-2-carboxylate Example 337c was prepared according to the procedure used for the preparation of Example 70j, substituting Example 337b for Example 70i, to provide the title compound.

Example 337d 4-(2-(2,4-difluorophenoxy)-5-(ethylsulfonamido) phenyl)-6-methyl-7-oxo-6,7-dihydro-1H-pyrrolo[2,3-c]pyridine-2-carboxylic acid Example 337d was prepared according to the procedure used for the preparation of Example 70k, substituting Example 337c for Example 70j, to provide the title compound.

Example 337e

N-{4-(2,4-difluorophenoxy)-3-[2-(hydroxymethyl)-6-methyl-7-oxo-6,7-dihydro-1H-pyrrolo[2,3-c]pyridin-4-yl]phenyl}ethanesulfonamide Example 337d (0.060 g, 0.12 mmol) in tetrahydrofuran (5 mL) was treated with 1.0 N borane (0.119 mL, 0.119 mmol). The reaction mixture was heated at 60° C. for 2 hours. The reaction mixture was partitioned between water and ethyl acetate. The organic layer was extracted with additional ethyl acetate twice. The combined organic layer were washed with saturated aqueous sodium chloride, dried over anhydrous magnesium sulfate, filtered, and concentrated. The residue was purified by reverse phase HPLC (C18, 10-100% acetonitrile in 0.1% TFA/water) to give the title product. (0.035 g, 60% yield). $^1$H NMR (500 MHz, DMSO-$d_6$) δ ppm 11.81 (s, 1H), 9.78 (s, 1H), 7.33-7.39 (m, 2H), 7.28 (s, 1H), 7.20 (dd, J=8.7, 2.59 Hz, 1H), 6.97-7.08 (m, 2H), 6.91 (d, J=8.85 Hz, 1H), 6.15 (d, J=2.14 Hz, 1H), 4.50 (s, 2H), 3.52 (s, 3H), 3.10 (q, J=7.32 Hz, 2H), 1.23 (t, J=7.32 Hz, 3H). MS (ESI+) m/z 490.2 (M+H)$^+$.

Example 338

N-[4-(2,4-difluorophenoxy)-3-{6-methyl-2-[(4-methylpiperazin-1-yl)carbonyl]-7-oxo-6,7-dihydro-1H-pyrrolo[2,3-c]pyridin-4-yl}phenyl]ethanesulfonamide

Example 338a 4-(2-(2,4-difluorophenoxy)-5-(ethylsulfonamido) phenyl)-6-methyl-7-oxo-6,7-dihydro-1H-pyrrolo[2,3-c]pyridine-2-carbonyl chloride Example 338a was prepared according to the procedure used for the preparation of Example 13a, substituting Example 337d for Example 10, to provide the title compound.

Example 338b

N-[4-(2,4-difluorophenoxy)-3-{6-methyl-2-[(4-methylpiperazin-1-yl)carbonyl]-7-oxo-6,7-dihydro-1H-pyrrolo[2,3-c]pyridin-4-yl}phenyl]ethanesulfonamide Example 338b was prepared according to the procedure used for the preparation of Example 13b, substituting Example 338a for Example 13a, and 1-methylpiperazine for ethylamine, respectively, to provide the TFA salt of the title compound. $^1$H NMR (500 MHz, DMSO-$d_6$) δ ppm 12.53 (s, 1H), 10.14 (br s, 1H), 9.81 (s, 1H), 7.34-7.40 (m, 3H), 7.20 (dd, J=8.85, 2.75 Hz, 1H), 7.06-7.12 (m, 1H), 6.98-7.04 (m, 1H), 6.93 (d, J=8.54 Hz, 1H), 6.53 (d, J=2.14 Hz, 1H), 3.55 (s, 3H), 3.02-3.43 (m, 6H), 2.84 (s, 3H), 1.24 (t, J=7.32 Hz, 3H). MS (ESI+) m/z 586.2 (M+H)$^+$.

Example 339

N-[4-(2,4-difluorophenoxy)-3-{6-methyl-2-[(4-methylpiperazin-1-yl)methyl]-7-oxo-6,7-dihydro-1H-pyrrolo[2,3-c]pyridin-4-yl}phenyl]ethanesulfonamide Example 339 was prepared according to the procedure used for the preparation of Example 337e, substituting Example 338b for Example 337d, to provide the TFA salt of the title compound. $^1$H NMR (500 MHz, DMSO-$d_6$) δ ppm 12.01 (s, 1H), 9.80 (s, 1H), 7.34-7.39 (m, 2H), 7.31 (s, 1H), 7.19 (dd, J=8.85, 2.75 Hz, 1H), 7.05-7.11 (m, 1H), 6.98-7.04 (m, 1H), 6.91 (d, J=8.85 Hz, 1H), 6.19 (d, J=2.14 Hz, 1H), 3.75 (s, 2H), 3.11 (q, J=7.32 Hz, 2H), 2.95 (br s, 2H), 2.76 (s, 3H), 2.35 (br s, 2H), 1.24 (t, J=7.32 Hz, 3H). MS (ESI+) m/z 572.0 (M+H)$^+$.

Example 340

4-[2-(cyclopropylmethoxy)-5-(1,2,3,6-tetrahydropyridin-4-yl)phenyl]-6-methyl-1,6-dihydro-7H-pyrrolo[2,3-c]pyridin-7-one Example 325 (100 mg, 0.210 mmol) in 2 mL dichloromethane was treated with 1 mL trifluoroacetic acid. The mixture was stirred at ambient temperature for 2 hours. The solvent was evaporated. The residue was treated with saturated aqueous sodium carbonate solution and then extracted with ethyl acetate (4×). The organic phase was dried over anhydrous magnesium sulfate, filtered, and concentrated to give the title compound (26 mg, 32.9% yield). $^1$H NMR (300 MHz, DMSO-$d_6$) δ ppm 11.94 (s, 1H), 7.37-7.31 (m, 1H), 7.25 (dd, J=5.3, 3.0 Hz, 2H), 7.18 (d, J=2.2 Hz, 1H), 7.13 (dd, J=8.4, 2.3 Hz, 1H), 7.00 (d, J=8.4 Hz, 1H), 6.12 (m, 2H), 3.80 (d, J=6.7 Hz, 2H), 3.56 (s, 3H), 3.09 (d, J=12.1 Hz, 2H), 2.73-2.53 (m, 2H), 1.76 (d, J=11.0 Hz, 1H), 1.55 (qd, J=12.4, 3.8 Hz, 2H), 1.12-1.01 (m, 1H), 0.49-0.38 (m, 2H), 0.25-0.17 (m, 2H). MS ((DCI+) m/z 376.5 (M+H)$^+$.

Example 341

N-[4-(2,4-difluorophenoxy)-3-(6-methyl-7-oxo-6,7-dihydro-1H-pyrrolo[2,3-c]pyridin-4-yl)phenyl]-N-(2-methoxyethyl)ethanesulfonamide To a 4 mL vial was added (azidocarbonyl) dipiperidine (ADDP) (25.9 mg, 0.102 mmol) in anhydrous toluene. The vial was introduced into a dry box and tributylphosphine (41.5 mg, 3 eq, 0.205 mmol) was added to the vial. This mixture was shaken until the solution turned clear. To this solution was added a solution of 2-methoxyethanol in anhydrous tetrahydrofuran (1.2 equivalents, 0.082 mmol, 6.24 mg). This mixture was stirred for 10 minutes at ambient temperature. To this mixture was added a solution of Example 36e (0.068 mmol, 31.4 mg) in anhydrous toluene/anhydrous tetrahydrofuran (1:1 v/v) (1 mL). The reaction mixture was stirred at room temperature overnight in the dry box. The reaction mixture was concentrated to dryness and the residue purified by reverse phase HPLC (C18, 10-100% acetonitrile in 0.1% TFA/water) to provide the title compound (4.24%, 1.5 mg). $^1$H NMR (400 MHz, DMSO $d_6$/$D_2$O) δ ppm 7.49 (d, J=2.75 Hz, 1H), 7.38-7.43 (m, 1H), 7.37 (d, J=2.75 Hz, 1H), 7.35-7.36 (m, 1H), 7.34 (d, J=2.75 Hz, 1H), 7.22-7.27 (m, 1H), 7.05-7.11 (m, 1H), 6.87 (d, J=8.54 Hz, 1H), 6.30 (d, J=2.75 Hz, 1H), 3.78-3.81 (m, 2H), 3.57 (s, 3H), 3.37 (t, J=5.65 Hz, 2H), 3.20 (s, 3H), 3.16 (t, J=7.32 Hz, 2H), 1.26 (t, J=7.48 Hz, 3H). ESI$^+$ m/z=518.0 (M+H)$^+$.

Example 342

N-[4-(2,4-difluorophenoxy)-3-(6-methyl-7-oxo-6,7-dihydro-1H-pyrrolo[2,3-c]pyridin-4-yl)phenyl]-N-(pyridin-2-ylmethyl)ethanesulfonamide Example 342 was prepared according to the procedure used for the preparation of Example 341, substituting pyridin-2-ylmethanol for 2-methoxyethanol, to provide the TFA salt of the title compound. $^1$H NMR (400 MHz, DMSO d$_6$/D$_2$O) δ ppm 8.60 (d, J=4.58 Hz, 1H), 8.07 (t, J=7.78 Hz, 1H), 7.70 (d, J=7.93 Hz, 1H), 7.56 (d, J=2.44 Hz, 1H), 7.53 (dd, J=7.02, 5.80 Hz, 1H), 7.45 (dd, J=8.85, 2.75 Hz, 1H), 7.35-7.41 (m, 1H), 7.33 (d, J=2.75 Hz, 1H), 7.29 (s, 1H), 7.17-7.23 (m, 1H), 7.03-7.09 (m, 1H), 6.81 (d, J=8.85 Hz, 1H), 6.17 (d, J=2.75 Hz, 1H), 5.10 (s, 2H), 3.56 (s, 3H), 3.33 (q, J=7.43 Hz, 2H), 1.31 (t, J=7.32 Hz, 3H). ESI$^+$ m/z=551.0 (M+H)$^+$.

Example 343

N-(cyclopropylmethyl)-N-[4-(2,4-difluorophenoxy)-3-(6-methyl-7-oxo-6,7-dihydro-1H-pyrrolo[2,3-c]pyridin-4-yl)phenyl]ethanesulfonamide Example 343 was prepared according to the procedure used for the preparation of Example 341, substituting cyclopropylmethanol for 2-methoxyethanol, to provide the title compound. $^1$H NMR (400 MHz, DMSO d$_6$/D$_2$O) δ ppm 7.51 (d, J=2.44 Hz, 1H), 7.36-7.42 (m, 2H), 7.35 (s, 1H), 7.34 (d, J=2.75 Hz, 1H), 7.20-7.27 (m, 1H), 7.04-7.10 (m, 1H), 6.88 (d, J=8.85 Hz, 1H), 6.29 (d, J=2.75 Hz, 1H), 3.57 (s, 3H), 3.52 (d, J=7.02 Hz, 2H), 3.12-3.18 (m, 2H), 1.26 (t, J=7.32 Hz, 3H), 0.83-0.93 (m, 1H), 0.40-0.45 (m, 2H), 0.08-0.13 (m, 2H). ESI$^+$ m/z=514.0 (M+H)$^+$.

Example 344

N-[4-(2,4-difluorophenoxy)-3-(6-methyl-7-oxo-6,7-dihydro-1H-pyrrolo[2,3-c]pyridin-4-yl)phenyl]-N-[2-(2-oxopyrrolidin-1-yl)ethyl]ethanesulfonamide Example 344 was prepared according to the procedure used for the preparation of Example 341, substituting 1-(2-hydroxyethyl)pyrrolidin-2-one for 2-methoxyethanol, to provide the title compound. $^1$H NMR (400 MHz, DMSO d$_6$/D$_2$O) δ ppm 7.50 (d, J=2.44 Hz, 1H), 7.38-7.43 (m, 2H), 7.37 (s, 1H), 7.33 (d, J=2.75 Hz, 1H), 7.22-7.28 (m, 1H), 7.05-7.11 (m, 1H), 6.84 (d, J=8.54 Hz, 1H), 6.34 (d, J=2.75 Hz, 1H), 3.83 (t, J=5.65 Hz, 2H), 3.58 (s, 3H), 3.27-3.32 (m, 4H), 3.14 (q, J=7.32 Hz, 2H), 2.11 (t, J=8.09 Hz, 2H), 1.74-1.82 (m, 2H), 1.25 (t, J=7.32 Hz, 3H). ESI$^+$ m/z=571.1 (M+H)$^+$.

Example 345

N-[4-(2,4-difluorophenoxy)-3-(6-methyl-7-oxo-6,7-dihydro-1H-pyrrolo[2,3-c]pyridin-4-yl)phenyl]-N-(tetrahydrofuran-2-ylmethyl)ethanesulfonamide Example 345 was prepared according to the procedure used for the preparation of Example 341, substituting (tetrahydrofuran-2-yl)methanol for 2-methoxyethanol, to provide the title compound. $^1$H NMR (400 MHz, DMSO d$_6$/D$_2$O) δ ppm 7.51 (d, J=2.75 Hz, 1H), 7.37-7.43 (m, 2H), 7.36 (s, 1H), 7.34 (d, J=2.75 Hz, 1H), 7.21-7.27 (m, 1H), 7.04-7.11 (m, 1H), 6.86 (d, J=8.85 Hz, 1H), 6.31 (d, J=2.75 Hz, 1H), 3.78-3.84 (m, 1H), 3.58-3.70 (m, 4H), 3.57 (s, 3H), 3.13-3.19 (m, 2H), 1.73-1.93 (m, 3H), 1.51-1.59 (m, 1H), 1.25 (t, J=7.32 Hz, 3H). ESI$^+$ m/z=544.0 (M+H)$^+$.

Example 346

N-[4-(2,4-difluorophenoxy)-3-(6-methyl-7-oxo-6,7-dihydro-1H-pyrrolo[2,3-c]pyridin-4-yl)phenyl]-N-(3,3,3-trifluoropropyl)ethanesulfonamide Example 346 was prepared according to the procedure used for the preparation of Example 341, substituting 3,3,3-trifluoropropan-1-ol for 2-methoxyethanol, to provide the title compound. $^1$H NMR (400 MHz, DMSO-d$_6$/D$_2$O) δ ppm 7.54 (d, J=2.75 Hz, 1H), 7.31-7.44 (m, 4H), 7.23-7.30 (m, 1H), 7.05-7.11 (m, 1H), 6.89 (d, J=8.54 Hz, 1H), 6.31 (d, J=2.75 Hz, 1H), 3.93-3.98 (m, 2H), 3.57 (s, 3H), 3.18 (q, J=7.32 Hz, 2H), 2.41-2.51 (m, 2H), 1.25 (t, J=7.32 Hz, 3H). ESI$^+$ m/z=556.0 (M+H)$^+$.

Example 347

4-(cyclopropylmethoxy)-N-(4-fluorophenyl)-3-(6-methyl-7-oxo-6,7-dihydro-1H-pyrrolo[2,3-c]pyridin-4-yl)benzenesulfonamide Example 347a 3-bromo-4-fluoro-N-(4-fluorophenyl)benzenesulfonamide Example 347a was prepared according to the procedure used for the preparation of Example 305a, substituting 4-fluoroaniline for indoline. The crude product was purified by flash chromatography (silica gel, 10% ethyl acetate in heptane) to afford title compound Example 347b 3-bromo-4-(cyclopropylmethoxy)-N-(4-fluorophenyl)benzenesulfonamide Example 347b was prepared according to the procedure used for the preparation of Example 29a, substituting cyclopropylmethanol for tetrahydro-2H-pyran-4-ol and substituting Example 347a for Example 2a to afford the title compound.

Example 347c 4-(cyclopropylmethoxy)-N-(4-fluorophenyl)-3-(6-methyl-7-oxo-1-tosyl-6,7-dihydro-1H-pyrrolo[2,3-c]pyridin-4-yl)benzenesulfonamide Example 347c was prepared according to the procedure used for the preparation of Example 6c, substituting Example 347b for Example 6b to afford the title compound.

Example 347d 4-(cyclopropylmethoxy)-N-(4-fluorophenyl)-3-(6-methyl-7-oxo-6,7-dihydro-1H-pyrrolo[2,3-c]pyridin-4-yl)benzenesulfonamide Example 347d was prepared according to the procedure used for the preparation of Example 6d, substituting Example 347c for Example 6c to afford the title compound. ¹H NMR (300 MHz, DMSO-$d_6$) ppm 12.04 (s, 1H) 10.07 (s, 1H) 7.60-7.68 (m, 2H) 7.23-7.31 (m, 2H) 7.20 (d, J=9.16 Hz, 1H) 7.12 (d, J=6.78 Hz, 4H) 5.88-5.95 (m, 1H) 3.92 (d, J=6.78 Hz, 2H) 3.55 (s, 3H) 1.02-1.17 (m, 1H) 0.43-0.50 (m, 2H) 0.22-0.30 (m, 2H). MS (ESI+) m/z 468.1 [M+H]⁺.

Example 348

4-[2-(cyclopropylmethoxy)-5-(6-fluoropyridin-3-yl) phenyl]-6-methyl-1,6-dihydro-7H-pyrrolo[2,3-c] pyridin-7-one Example 348a 4-(2-(cyclopropylmethoxy)-5-(6-fluoropyridin-3-yl) phenyl)-6-methyl-1-tosyl-1H-pyrrolo[2,3-c]pyridin-7 (6H)-one Example 348a was prepared according to the procedure used for the preparation of Example 6c, substituting Example 334a for Example 6b and substituting (6-fluoropyridin-3-yl) boronic acid for Example 6a to afford the title compound.

Example 348b 4-(2-(cyclopropylmethoxy)-5-(6-fluoropyridin-3-yl) phenyl)-6-methyl-1H-pyrrolo[2,3-c]pyridin-7(6H)-one Example 348b was prepared according to the procedure used for the preparation of Example 6d, substituting Example 348a for Example 6c to afford the title compound. ¹H NMR (300 MHz, DMSO-$d_6$) ppm 0.21-0.28 (m, 2H) 0.41-0.49 (m, 2H) 1.03-1.15 (m, 1H) 3.57 (s, 3H) 3.91 (d, J=6.78 Hz, 2H) 6.17 (t, J=2.71, 2.03 Hz, 1H) 7.17-7.28 (m, 3H) 733 (s, 1H) 7.63-7.69 (m, 2H) 8.23-8.32 (m, 1H) 8.54 (d, J=2.37 Hz, 1H) 11.95 (brs, 1H). MS (ESI+) m/z 390 [M+H]⁺.

Example 349

N-[4-(2,4-difluorophenoxy)-3-(3-formyl-6-methyl-7-oxo-6,7-dihydro-1H-pyrrolo[2,3-c]pyridin-4-yl)phenyl]ethanesulfonamide Example 349a 4-bromo-6-methyl-1H-pyrrolo[2,3-c]pyridin-7(6H)-one A mixture of Example 1e (7 g, 18.36 mmol) and lithium hydroxide monohydrate (3.08 g, 73.4 mmol) in tetrahydrofuran (50 mL) and water (20 mL) was heated at 80° C. overnight. After cooling to ambient temperature, the reaction mixture was poured into 300 mL of water. The resulting solid was collected by vacuum filtration to give the title compound (3.92 g, 17.26 mmol, 94% yield).

Example 349b 4-bromo-6-methyl-1-((2-(trimethylsilyl)ethoxy)methyl)-1H-pyrrolo[2,3-c]pyridin-7(6H)-one Example 349a (3.92 g, 17.26 mmol) in tetrahydrofuran (100 mL) was treated with 60% sodium hydride (1.036 g, 25.9 mmol). The reaction was stirred at ambient temperature for 10 minutes. To this solution was added (2-(chloromethoxy)ethyl)trimethylsilane (4.58 mL, 25.9 mmol). The reaction mixture was stirred overnight. The resulting solid was filtered off, and the filtrate was concentrated. The residue was purified by flash chromatography (silica gel, 20% ethyl acetate in heptanes) to give the title compound (5.84 g, 95% yield).

Example 349c 4-bromo-6-methyl-7-oxo-1-((2-(trimethylsilyl) ethoxy)methyl)-6,7-dihydro-1H-pyrrolo[2,3-c]pyridine-3-carbaldehyde Example 349b (3.92 g, 17.3 mmol) in dimethylformamide (15 mL) was treated with phosphorus oxychloride (9.66 mL, 104 mmol) dropwise at 0° C. After the addition was complete, the solution was heated at 80° C. for 6 hours. After cooling to ambient temperature, the reaction mixture was partitioned between water and ethyl acetate. The organic layer was extracted with additional ethyl acetate twice. The combined organic layers were washed with saturated aqueous sodium chloride, dried over anhydrous magnesium sulfate, filtered, and concentrated. The residue was purified by flash chromatography (silica gel, 50-100% ethyl acetate/heptanes) to give the title compound (1.35 g, 20.3% yield).

Example 349d 4-(5-amino-2-(2,4-difluorophenoxy)phenyl)-6-methyl-7-oxo-1-((2-(trimethylsilyl)ethoxy)methyl)-6,7-dihydro-1H-pyrrolo[2,3-c]pyridine-3-carbaldehyde Example 349d was prepared according to the procedure used for the preparation of Example 138a, substituting Example 349c for 2-bromo-1-fluoro-4-(methylsulfonyl)benzene, and Example 148c for Example 6a, respectively, to provide the title compound. After aqueous workup, the crude product was used for the next reaction without purification.

Example 349e

N-[4-(2,4-difluorophenoxy)-3-(3-formyl-6-methyl-7-oxo-6,7-dihydro-1H-pyrrolo[2,3-c]pyridin-4-yl)phenyl]ethanesulfonamide A mixture of Example 349d (0.5 g, 0.951 mmol), ethanesulfonyl chloride (0.226 mL, 2.38 mmol) and triethylamine (0.817 mL, 5.71 mmol) in dichloromethane (10 mL) was stirred at ambient temperature for 2 hours. The solvent was evaporated under reduced pressure, and the residue was treated with dichloromethane (3 mL) and trifluoroacetic acid (3 mL). The reaction mixture was stirred at ambient temperature for 3 hours. The solvent was removed under reduced pressure, and the residue was treated with dixoane (10 mL) and 2.0 N NaOH (5 mL). The reaction mixture was heated at 90° C. for 2 hours. After cooling to ambient temperature, the reaction mixture was partitioned between water and ethyl acetate. The organic layer was extracted with additional ethyl acetate twice. The combined organic layers were washed with saturated aqueous sodium chloride, dried over anhydrous magnesium sulfate, filtered, and concentrated. The residue was purified by flash chromatography (silica gel, ethyl acetate) to give the title compound (0.42 g, 0.862 mmol, 91% yield). ¹H NMR (500 MHz, DMSO-$d_6$) δ ppm 13.07 (s, 1H), 9.78 (s, 1H), 9.40, (s, 1H), 7.99 (d, J=3.36 Hz, 1H), 7.38 (s, 1H), 7.23-7.31 (m, 3H), 6.89-6.97 (m, 3H), 3.55 (s, 3H), 3.10 (q, J=7.32 Hz, 2H), 1.21 (t, J=7.32 Hz, 3H). MS (ESI+) m/z 488.0 (M+H)⁺.

Example 350

N-{4-(2,4-difluorophenoxy)-3-[6-methyl-3-(morpholin-4-ylmethyl)-7-oxo-6,7-dihydro-1H-pyrrolo[2,3-c]pyridin-4-yl]phenyl}ethanesulfonamide A mixture of Example 349e (0.04 g, 0.082 mmol), morpholine (0.014 g, 0.164 mmol), and sodium triacetoxyhydroborate (0.035 g, 0.164 mmol) in 1,2-dichloroethane (2 mL) was stirred at ambient temperature overnight. The solvent was evaporated under reduced pressure, and the residue was purified by reverse phase HPLC (C18, 10-100% acetonitrile in 0.1% TFA/water) to give the TFA salt of the title compound (0.035 g, 0.052 mmol, 63.4% yield). ¹H NMR (500 MHz, DMSO-d₆) δ ppm 12.59 (s, 1H), 9.86 (s, 1H), 9.58, (s, 1H), 7.56 (s, 1H), 7.26-7.38 (m, 4H), 7.00-7.09 (m, 2H), 6.93 (d, J=8.85 Hz, 1H), 4.23-4.29 (m, 1H), 3.75-3.81 (m, 3H), 3.52 (s, 3H), 3.16 (q, J=7.32 Hz, 2H), 2.37-2.71 (m 4H), 1.24 (t, J=7.32 Hz, 3H). MS (ESI+) m/z 558.9 (M+H)⁺.

Example 351

N-[4-(2,4-difluorophenoxy)-3-{6-methyl-3-[(4-methylpiperazin-1-yl)methyl]-7-oxo-6,7-dihydro-1H-pyrrolo[2,3-c]pyridin-4-yl}phenyl]ethanesulfonamide Example 351 was prepared according to the procedure used for the preparation of Example 350, substituting 1-methylpiperazine for morpholine, to provide the TFA salt of the title compound. ¹H NMR (500 MHz, DMSO-d₆) δ ppm 12.11 (s, 1H), 9.86 (s, 1H), 9.58, (s, 1H), 7.29-7.35 (m, 2H), 7.20-7.22 (m, 2H), 7.11 (s, 1H), 6.97-7.06 (m, 2H), 6.91 (d, J=9.46 Hz, 1H), 3.85 (br s, 4H), 3.48 (s, 3H), 3.12-3.40 (m, 4H), 2.69 (s, 3H), 1.25 (t, J=7.32 Hz, 3H). MS (ESI+) m/z 571.9 (M+H)⁺.

Example 352

4-{2-[(cyclopropylmethyl)amino]phenyl}-6-methyl-1,6-dihydro-7H-pyrrolo[2,3-c]pyridin-7-one Example 352a 2-bromo-N-(cyclopropylmethyl)aniline A solution of 2-bromoaniline (1.720 g, 10.00 mmol), cyclopropanecarbaldehyde (0.374 mL, 5.00 mmol), and acetic acid (2.86 mL, 50.0 mmol) in dichloromethane (50 mL) was heated at 50° C. for 1 hour. The solution was cooled in an ice bath and sodium triacetoxyborohydride (2.119 g, 10.00 mmol) was added. This mixture was stirred for 2 hours while warming to ambient temperature and then partitioned between saturated sodium bicarbonate solution (100 mL) and ethyl acetate (100 mL). The organic layer was dried over anhydrous sodium sulfate, filtered, and concentrated. The residue was purified by flash column chromatography (silica gel, 0-10% ethyl acetate in heptane) to provide the title compound (1.05 g, 93% yield).

Example 352b 4-(2-((cyclopropylmethyl)amino)phenyl)-6-methyl-1-tosyl-1H-pyrrolo[2,3-c]pyridin-7(6H)-one Example 352b was prepared according to the procedure used for the preparation of Example 4a, substituting Example 352a for Example 7c with the exception that the reaction mixture was heated at 90° C. for 2.5 hours and the material was purified by flash column chromatography (silica gel, 0-5% methanol in dichloromethane) to provide the title compound.

Example 352c

4-{2-[(cyclopropylmethyl)amino]phenyl}-6-methyl-1,6-dihydro-7H-pyrrolo[2,3-c]pyridin-7-one Example 352c was prepared according to the procedure used for the preparation of Example 4b, substituting Example 352b for Example 4a with the exception that the reaction was heated at 90° C. for 2.5 hours and the material was purified by flash column chromatography (silica gel, 0-5% methanol in dichloromethane) to provide the title compound. ¹H NMR (400 MHz, CDCl₃) δ ppm 10.99 (s, 1H) 7.24-7.31 (m, 2H) 7.15 (dd, J=7.32, 1.53 Hz, 1H) 6.97 (s, 1H) 6.70-6.78 (m, 2H) 6.20-6.25 (m, 1H) 3.99 (s, 1H) 3.73 (s, 3H) 2.97 (d, J=6.41 Hz, 2H) 0.90-1.02 (m, 1H) 0.38-0.45 (m, 2H) 0.09-0.15 (m, 2H). MS (ESI+) m/z 294.0 (M+H)⁺.

Example 353

4'-(cyclopropylmethoxy)-3'-(6-methyl-7-oxo-6,7-dihydro-1H-pyrrolo[2,3-c]pyridin-4-yl)biphenyl-3-carbonitrile Example 353a 4'-(cyclopropylmethoxy)-3'-(6-methyl-7-oxo-1-tosyl-6,7-dihydro-1H-pyrrolo[2,3-c]pyridin-4-yl)biphenyl-3-carbonitrile Example 353a was prepared according to the procedure used for the preparation of Example 6c, substituting Example 334a for Example 6b and substituting (3-cyanophenyl)boronic acid for Example 6a to afford the title compound.

Example 353b

4'-(cyclopropylmethoxy)-3'-(6-methyl-7-oxo-6,7-dihydro-1H-pyrrolo[2,3-c]pyridin-4-yl)biphenyl-3-carbonitrile Example 353b was prepared according to the procedure used for the preparation of Example 6d, substituting Example 353a for Example 6c to afford the title compound. ¹H NMR (300 MHz, DMSO-d₆) ppm 0.21-0.28 (m, 2H) 0.41-0.49 (m, 2H) 1.00-1.15 (m, 1H) 3.58 (s, 3H) 3.91 (d, J=6.78 Hz, 2H) 6.17 (t, J=2.03 Hz, 1H) 7.20 (d, J=8.48 Hz, 1H) 7.26 (t, J=2.71 Hz, 1H) 7.33 (s, 1H) 7.63 (t, J=7.80 Hz, 1H) 7.67-7.79 (m, 3H) 8.03 (d, J=8.14 Hz, 1H) 8.16 (t, J=1.70 Hz, 1H) 11.94 (brs, 1H). MS (ESI+) m/z 396 [M+H]⁺.

Example 354

4-{2-(cyclopropylmethoxy)-5-[(4-hydroxypiperidin-1-yl)sulfonyl]phenyl}-6-methyl-1,6-dihydro-7H-pyrrolo[2,3-c]pyridin-7-one

Example 354a 1-(3-bromo-4-fluorophenylsulfonyl)piperidin-4-ol

Example 354a was prepared according to the procedure described for the preparation of Example 310a, substituting piperidin-4-ol for N,N-dimethylpyrrolidin-3-amine to afford the title compound.

Example 354b 1-(3-bromo-4-fluorophenylsulfonyl)-4-(tetrahydro-2H-pyran-2-yloxy)piperidine 3,4-Dihydro-2H-pyran (0.28 mL, 3.1 mmol) was added dropwise to a 0° C. solution of Example 354a (0.51 g, 1.5 mmol), 4-methylbenzenesulfonic acid hydrate (0.59 g, 3.1 mmol), and dichloromethane (28 mL). The reaction mixture was stirred at ambient temperature for 5 hours. Water was added and the mixture was extracted with dichloromethane. The organic layer was washed with water, saturated aqueous sodium chloride, dried over anhydrous sodium sulfate, filtered and concentrated. The residue was purified by flash chromatography (silica gel, dichloromethane/gradient with methanol) to afford the title compound (420 mg, 65.9% yield).

Example 354c 1-(3-bromo-4-(cyclopropylmethoxy)phenylsulfonyl)-4-(tetrahydro-2H-pyran-2-yloxy)piperidine Example 354c was prepared according to the procedure used for the preparation of Example 29a, substituting cyclopropylmethanol for tetrahydro-2H-pyran-4-ol and substituting Example 354b for Example 2a to afford the title compound.

Example 354d 4-(2-(cyclopropylmethoxy)-5-(4-(tetrahydro-2H-pyran-2-yloxy)piperidin-1-ylsulfonyl)phenyl)-6-methyl-1-tosyl-1H-pyrrolo[2,3-c]pyridin-7(6H)-one Example 354d was prepared according the to procedure used for the preparation of Example 6c, substituting Example 354c for Example 6b to afford the title compound.

Example 354e 4-(2-(cyclopropylmethoxy)-5-(4-(tetrahydro-2H-pyran-2-yloxy)piperidin-1-ylsulfonyl)phenyl)-6-methyl-1H-pyrrolo[2,3-c]pyridin-7(6H)-one Example 354e was prepared according to the procedure used for the preparation of Example 6d, substituting Example 354d for Example 6c to afford the title compound.

Example 354f 4-(2-(cyclopropylmethoxy)-5-(4-hydroxypiperidin-1-ylsulfonyl)phenyl)-6-methyl-1H-pyrrolo[2,3-c]pyridin-7(6H)-one A solution of Example 354e (54 mg, 0.10 mmol), acetic acid (4 mL, 69.9 mmol), tetrahydrofuran (2 mL) and water (1 mL) was stirred at 45° C. for 2.5 hours. The reaction mixture was concentrated to dryness and the residue was dried overnight (in-vacuo). The crude product was triturated with diethyl ether, filtered and dried (in-vacuo) to afford the title compound (30 mg, 66% yield). $^1$H NMR (300 MHz, DMSO-$d_6$) ppm 0.25-0.31 (m, 2H) 0.44-0.51 (m, 2H) 1.08-1.17 (m, 1H) 1.38-1.51 (m, 2H) 1.70-1.80 (m, 2H) 2.70-2.80 (m, 2H) 3.10-3.18 (m, 2H) 3.51-3.56 (m, 1H) 3.57 (s, 3H) 3.97 (d, J=6.78 Hz, 2H) 4.66 (d, J=4.07 Hz, 1H) 6.12 (t, J=2.71, 2.03 Hz, 1H) 7.27-7.32 (m, 2H) 7.36 (s, 1H) 7.64-7.70 (m, 2H) 12.04 (brs, 1H). MS (ESI+) m/z 458 [M+H]$^+$.

Biological Examples

Bromodomain Domain Binding Assay

A time-resolved fluorescence resonance energy transfer (TR-FRET) assay was used to determine the affinities of compounds of the Examples listed in Table 1 for each bromodomain of human BRD4. His-tagged first (BD1: amino acids K57-E168) and second (BD2: amino acids E352-E168) bromodomains of human BRD4 were expressed and purified. An Alexa647-labeled BET-inhibitor was used as the fluorescent probe in the assay.

Synthesis of Alexa647-labeled bromodomain inhibitor compound 2-((6S,Z)-4-(4-chlorophenyl)-2,3,9-trimethyl-6H-thieno[3,2-f][1,2,4]triazolo[4,3-a][1,4]diazepin-6-yl)acetic acid Methyl 2-((6S,Z)-4-(4-chlorophenyl)-2,3,9-trimethyl-6H-thieno[3,2-f][1,2,4]triazolo[4,3-a][1,4]diazepin-6-yl)acetate (see e.g., WO 2006129623) (100.95 mg, 0.243 mmol was suspended in 1 mL methanol to which was added a freshly prepared solution of lithium hydroxide monohydrate (0.973 mL, 0.5 M, 0.487 mmol) and shaken at ambient temperature for 3 hours. The methanol was evaporated and the pH adjusted with aqueous hydrochloric acid (1 M, 0.5 mL, 0.5 mmol) and extracted four times with ethyl acetate. The combined ethyl acetate layers were dried over magnesium sulfate and concentrated to afford 2-((6S,Z)-4-(4-chlorophenyl)-2,3,9-trimethyl-6H-thieno[3,2-f][1,2,4]triazolo[4,3-a][1,4]diazepin-6-yl)acetic acid (85.3 mg, 87.0%); ESI-MS m/z=401.1 [(M+H)$^+$] which was used directly in the next reaction.

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis (2,2,2-trifluoroacetate)

2-((6S,Z)-4-(4-chlorophenyl)-2,3,9-trimethyl-6H-thieno[3,2-f][1,2,4]triazolo[4,3-a][1,4]diazepin-6-yl)acetic acid (85.3 mg, 0.213 mmol) was combined with 2,2'-(ethane-1,2-diylbis(oxy))diethanamine (Sigma-Aldrich, 0.315 mg, 2.13 mmol) were combined in 5 mL anhydrous dimethylformamide. (1H-benzo[d][1,2,3]triazol-1-yloxy)tripyrrolidin-1-ylphosphonium hexafluorophosphate(V) (PyBOB, CSBio, Menlo Park Calif.; 332 mg, 0.638 mmol) was added and the reaction shaken at ambient temperature for 16 hours. The reaction mixture was diluted to 6 mL with dimethylsulfoxide: water (9:1, v:v) and purified in two injections with time collection Waters Deltapak C18 200×25 mm column eluted with a gradient of 0.1% trifluoroacetic acid (v/v) in water and acetonitrile. The fractions containing the two purified products were lyophilized to afford N-(2-(2-(2-aminoethoxy) ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (134.4 mg, 82.3%); ESI-MS m/z=531.1 [(M+H)$^+$]; 529.1 [(M−H)$^-$] and (S,Z)—N,N'-(2,2'-(ethane-1,2-diylbis(oxy))bis(ethane-2,1-diyl))bis (2-((6S,Z)-4-(4-chlorophenyl)-2,3,9-trimethyl-6H-thieno[3,2-f][1,2,4]triazolo[4,3-a][1,4]diazepin-6-yl)acetamide)bis (2,2,2-trifluoroacetate) (3.0 mg, 1.5%); ESI-MS m/z=913.2 [(M+H)+]; 911.0 [(M−H)$^-$].

N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl) acetamide(2,2,2-trifluoroacetate)

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (5.4 mg, 0.0071 mmol) was combined with Alexa Fluor® 647 carboxylic Acid, succinimidyl ester (Life Technologies, Grand Island, N.Y.; 3 mg, 0.0024 mmol) were combined in 1 mL anhydrous dimethylsulfoxide containing diisopropylethylamine (1% v/v) and shaken at ambient temperature for 16 hours. The reaction was diluted to 3 mL with dimethylsulfoxide:water (9:1, v:v) and purified in one injection with time collection Waters Deltapak C18 200×25 mm column eluted with a gradient of 0.1% trifluoroacetic acid (v/v) in water and acetonitrile. The fractions containing the purified product were lyophilized to afford N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate) (1.8 mg); MALDI-MS m/z=1371.1, 1373.1 [(M+H)$^+$] as a dark blue powder.

Assay

Compound dilution series were prepared in DMSO via a 3-fold serial dilution from 2.5 mM to 42 nM. Compounds were then diluted 6:100 in assay buffer (20 mM Sodium Phosphate, pH 6.0, 50 mM NaCl, 1 mM Ethylenediaminetetraacetic acid disodium salt dihydrate, 0.01% Triton X-100, 1 mM DL-Dithiothreitol) to yield 3× working solutions. Six microliters (L) of the working solution was then transferred to white, low-volume assay plates (Costar #3673). A 1.5× assay mixture containing His-tagged bromodomain, Europium-conjugated anti-His antibody (Invitrogen PV5596) and the Alexa-647-conjugated probe molecule was also prepared. Twelve L of this solution were added to the assay plate to reach a final volume of 18 L. The final concentration of 1× assay buffer contains 2% DMSO, 50 M-0.85 nM compound, 8 nM His-tagged bromodomain, 1 nM Europium-conjugated anti-His-tag antibody and 100 nM or 30 nM probe (for BDI or BDII, respectively). After a one-hour incubation at room temperature, TR-FRET ratios were determined using an Envision multilabel plate reader (Ex 340, Em 495/520).

TR-FRET data were normalized to the means of 24 no-compound controls ("high") and 8 controls containing 1 μM un-labeled probe ("low"). Percent inhibition was plotted as a function of compound concentration and the data were fit with the 4 parameter logistic equation to obtain $IC_{50}$s. Inhibition constants ($K_i$) were calculated from the $IC_{50}$s, probe $K_d$ and probe concentration. Typical Z' values were between 0.65 and 0.75. The minimum significant ratio was determined to evaluate assay reproducibility (Eastwood et al., (2006) J Biomol Screen, 11: 253-261). The MSR was determined to be 2.03 for BDI and 1.93 for BDII, and a moving MSR (last six run MSR overtime) for both BDI and BDII was typically <3. The $K_i$ values are reported in Table 1.

MX-1 Cell Line Proliferation Assay

The impact of compounds of the Examples on cancer cell proliferation was determined using the breast cancer cell line MX-1 (ATCC) in a 3-day proliferation assay. MX-1 cells were maintained in RPMI 1640 medium (Sigma) supplemented with 10% FBS (Fetal Bovine Serum) at 37° C. and an atmosphere of 5% $CO_2$. For compound testing, MX-1 cells were plated in 96-well black bottom plates at a density of 5000 cells/well in 90 μL of culture media and incubated at 370 overnight to allow cell adhesion and spreading. Compound dilution series were prepared in DMSO via a 3-fold serial dilution from 3 mM to 0.1 M. The DMSO dilution series were then diluted 1:100 in phosphate buffered saline, and 10 L of the resulted solution were added to the appropriate wells of the MX-1 cell plate. The final compound concentrations in the wells were 3, 1, 0.3, 0.1, 0.03, 0.01, 0.003, 0.001, 0.0003 and 0.0001 M. After the addition of compounds, the cells were incubated for 72 more hours and the amounts of viable cells were determined using the Cell Titer Glo assay kit (Promega) according to manufacturer suggested protocol. Luminescence readings from the Cell Titer Glo assay were normalized to the DMSO treated cells and analyzed using the GraphPad Prism software with sigmoidal curve fitting to obtain $EC_{50}$s. The minimum significant ratio (MSR) was determined to evaluate assay reproducibility (Eastwood et al., (2006) J Biomol Screen, 11: 253-261). The overall MSR was determined to be 2.1 and a moving MSR (last six run MSR overtime) has been <2.

Proliferation Panel Assay

The compounds of Examples 4 and 78 were tested for their impact on proliferation of a panel of cancer cell lines types (with specific cell line tested) as set out in (Table 2). Cells were plated in 96-well plates at 1500 cells/well in the appropriate culture media without test compound and incubated overnight at 37° C. and an atmosphere of 5% $CO_2$. Series dilution of compounds were prepared and added to the wells as in the MX-1 proliferation assay. After the addition of compounds, cells were incubated for another 3 days at 37° C. and an atmosphere of 5% $CO_2$. The amounts of viable cells were determined using the Cell Titer Glo assay kit (Promega) according to manufacturer suggested protocol. Cell proliferation data were analyzed as described above in the MX-1 proliferation assay to obtain the $EC_{50}$ for the compounds of Examples 4 and 78 and reported in Table 2.

TABLE 1

| Compound of Ex. No. | TR-FRET Binding Ki: BRD4 (BDI_K57-E168) (μM) | TR-FRET Binding Ki: BRD4 (BDII_E352-M457) (μM) | Cellular proliferation: $EC_{50}$ (μM) |
|---|---|---|---|
| 1 | 0.136* | 0.0410* | 0.137 |
| 2 | 0.529* | 0.178* | 0.860 |
| 3 | 0.0646 | 0.0736 | 0.185 |
| 4 | 0.0014* | 0.0020* | 0.0164 |
| 5 | 0.0150 | 0.0064 | 0.0310 |
| 6 | 0.0053 | 0.0058 | 0.0460 |
| 7 | 0.119 | 0.0773 | >3.0 |
| 8 | 0.0026 | 0.0039 | 0.0244* |
| 9 | 0.0180 | 0.0101 | 0.113* |
| 10 | 0.0154 | 0.0086 | >3.0 |
| 11 | 0.0018 | 0.0024 | 0.0342 |

TABLE 1-continued

| Compound of Ex. No. | TR-FRET Binding Ki: BRD4 (BDI_K57-E168) (µM) | TR-FRET Binding Ki: BRD4 (BDII_E352-M457) (µM) | Cellular proliferation: EC$_{50}$ (µM) |
|---|---|---|---|
| 12 | 1.8 | 4.33 | >3.0 |
| 13 | 0.0037 | 0.0034 | 0.128 |
| 14 | 0.0055 | 0.0123 | 0.170 |
| 15 | 0.0042 | 0.0075 | 0.140 |
| 16 | 0.0043 | 0.0053 | 0.0946 |
| 17 | 0.0171* | 0.0322* | 0.283 |
| 18 | 0.0102* | 0.0103* | 0.209 |
| 19 | 0.0074 | 0.0042 | 0.123 |
| 20 | 0.0109 | 0.00068 | 0.190 |
| 21 | 0.00039 | 0.00025 | 0.0139* |
| 22 | 0.0022 | 0.0010 | 0.0652 |
| 23 | 0.0012 | 0.00075 | 0.0459 |
| 24 | 0.0025 | 0.0021 | 0.0126 |
| 25 | 0.0030 | 0.0036 | 0.0562 |
| 26 | 0.0021 | 0.0033 | 0.0171 |
| 27 | 0.0025* | 0.0022* | 0.0317 |
| 28 | 0.0017 | 0.0020 | 0.0239 |
| 29 | 0.0011 | 0.0067 | 0.0718 |
| 30 | 0.0177 | 0.0104 | 0.562 |
| 31 | 0.0018 | 0.0134 | 0.0398 |
| 32 | 0.0160 | 0.0075 | 0.0833 |
| 33 | 0.0026 | 0.0048 | 0.0417 |
| 34 | 0.0035 | 0.0021 | 0.0268 |
| 35 | 0.661 | 1.14 | NA |
| 36 | 0.0035* | 0.0014* | 0.0174* |
| 37 | 0.0113 | 0.0108 | 0.0593 |
| 38 | 0.148 | 0.257 | NA |
| 39 | 0.112 | 0.124 | NA |
| 40 | 0.0145 | 0.0439 | 0.167 |
| 41 | 0.0028 | 0.00051 | 0.0298 |
| 42 | 0.0546 | 0.0934 | >3.0 |
| 43 | 0.0017 | 0.0012 | 0.0169 |
| 44 | 0.286 | 0.236 | 0.828 |
| 45 | 0.0128 | 0.0190 | 0.233 |
| 46 | 0.0516 | 0.0169 | 0.588 |
| 47 | 0.235 | 0.205 | 1.1 |
| 48 | 0.0023 | 0.0033 | 0.0235 |
| 49 | 0.0017* | 0.0015* | 0.0196* |
| 50 | 0.0215 | 0.0081 | 0.206* |
| 51 | 0.0097 | 0.0161 | 0.101 |
| 52 | 0.0241 | 0.0260 | 0.309 |
| 53 | 0.0622 | 0.0054 | 0.0765 |
| 54 | 0.0951 | 0.0375 | 0.266 |
| 55 | 0.0555 | 0.0336 | 0.200 |
| 56 | 0.0122 | 0.0024 | 0.251 |
| 57 | 0.00088 | 0.0020 | 0.0138* |
| 58 | 0.0021 | 0.0081 | 0.0451 |
| 59 | 0.00084 | 0.0016 | 0.0187* |
| 60 | 0.00075 | 0.0066 | 0.0142* |
| 61 | >13.0 | >22.2 | NA |
| 62 | 0.0030* | 0.0019* | 0.0079* |
| 63 | 0.0180 | 0.0427 | 0.105 |
| 64 | 0.0531* | 0.0633* | 0.773 |
| 65 | 0.0116* | 0.0049* | 0.0255 |
| 66 | 0.00074 | 0.0034 | 0.0332 |
| 67 | 0.0561* | 0.0938* | 0.341 |
| 68 | 1.7 | 2.55 | 5.9 |
| 69 | 0.0390 | 0.0123 | 0.140 |
| 70 | 0.0118 | 0.0468 | >3.0 |
| 71 | 0.00081* | 0.0012* | 0.0175* |
| 72 | 0.0015* | 0.0011* | 0.0457* |
| 73 | 0.00098 | 0.00050 | 0.0207 |
| 74 | 0.0961 | 0.101 | 0.275 |
| 75 | 0.137 | 0.0594 | 0.478 |
| 76 | 0.0658 | 0.0297 | 0.290 |
| 77 | 0.0124 | 0.0157 | >3.0 |
| 78 | 0.0025 | 0.0018 | 0.400 |
| 79 | 0.0062 | 0.0018 | 0.887 |
| 80 | 0.0091 | 0.0061 | 0.0620 |
| 81 | 0.0095 | 0.00099 | 0.103 |
| 82 | 0.519 | 0.183 | 0.767 |
| 83 | 0.0209 | 0.0422 | 0.424 |
| 84 | 0.00167 | 0.00065 | 0.231 |
| 85 | 0.0064 | 0.0017 | 0.0520 |
| 86 | 0.0043 | 0.0024 | 0.182 |
| 87 | 0.0056 | 0.0067 | 0.0534 |
| 88 | 0.635 | 0.236 | >3.0 |
| 89 | 0.0016 | 0.0021 | 0.0252* |
| 90 | 0.0040 | 0.0068 | 0.0168 |
| 91 | 0.0122 | 0.0874 | 0.240 |
| 92 | 0.0025 | 0.0253 | 0.0840 |
| 93 | 0.0076 | 0.0322 | 0.120 |
| 94 | 0.0162 | 0.0100 | 0.110 |
| 95 | 0.0087 | 0.0011 | 0.0560 |
| 96 | 0.00063 | 0.0011 | 0.0160 |
| 97 | 0.0023 | 0.0028 | 0.0140 |
| 98 | 0.0065 | 0.0027 | 0.0529 |
| 99 | 0.0035 | 0.0247 | 0.0977 |
| 100 | 0.0014 | 0.0027 | 0.107 |
| 101 | 0.0012 | 0.0043 | 0.0112 |
| 102 | 0.0034 | 0.0242 | 0.0615 |
| 103 | 0.0019 | 0.0038 | 0.0338 |
| 104 | 0.0044 | 0.0179 | 0.0653 |
| 105 | 0.00052 | 0.0015 | 0.0160 |
| 106 | 0.0013 | 0.0109 | 0.0468 |
| 107 | 0.00050 | 0.00087 | 0.0310 |
| 108 | 0.0014 | 0.0053 | 0.0380 |
| 109 | 0.00072 | 0.0034 | 0.0320 |
| 110 | 0.0031 | 0.0051 | 0.0324 |
| 111 | 0.0087 | 0.0103 | 0.199 |
| 112 | 0.0169 | 0.0206 | 0.240 |
| 113 | 0.0474 | 0.381 | >3.0 |
| 114 | 0.136 | 0.121 | >3.0 |
| 115 | 0.0671 | 0.0269 | 0.0550 |
| 116 | 0.105 | 0.0891 | NA |
| 117 | 2.3 | 0.486 | NA |
| 118 | NA | NA | NA |
| 119 | 0.0444 | 0.0225 | NA |
| 120 | 0.190 | 0.304 | NA |
| 121 | 0.0155 | 0.0334 | 0.251 |
| 122 | NA | NA | NA |
| 123 | 0.0271 | 0.0361 | 0.118 |
| 124 | 0.320 | 0.169 | NA |
| 125 | 0.215 | 0.274 | NA |
| 126 | 2.0 | 0.768 | NA |
| 127 | NA | NA | NA |
| 128 | 0.0725 | 0.112 | NA |
| 129 | 0.0379 | 0.0456 | 0.118 |
| 130 | 0.183 | 0.174 | NA |
| 131 | 0.0986 | 0.0600 | NA |
| 132 | 0.238 | 0.344 | NA |
| 133 | NA | NA | NA |
| 134 | 0.0435 | 0.0073 | 0.137* |
| 135 | 0.274 | 0.0774 | NA |
| 136 | 0.234 | 0.295 | NA |
| 137 | 0.0687 | 0.0089 | 0.303* |
| 138 | 0.0167 | 0.0095 | 0.0851 |
| 139 | 7.1 | 3.89 | NA |
| 140 | 3.6 | 1.58 | NA |
| 141 | 0.0054 | 0.0152 | 0.125 |
| 142 | 0.0065 | 0.0794 | 0.138 |
| 143 | 0.0223 | 0.107 | 0.370 |
| 144 | 0.0136 | 0.0178 | 0.0769 |
| 145 | 0.0027 | 0.0056 | 0.0264 |
| 146 | 0.0075 | 0.0019 | 0.0609 |
| 147 | 0.0021 | 0.0011 | 0.0148 |
| 148 | 0.205 | 0.152 | 0.740 |
| 149 | 0.0115 | 0.0030 | 0.0297 |
| 150 | 0.0097 | 0.0042 | 0.0665 |
| 151 | 0.0107 | 0.0081 | 0.0549 |
| 152 | 0.0246 | 0.0048 | 0.105 |
| 153 | 0.0228 | 0.0082 | 0.0933 |
| 154 | 0.0208 | 0.0131 | 0.0655 |
| 155 | 0.0193 | 0.0148 | 0.117 |
| 156 | 0.0113 | 0.0209 | 0.114 |
| 157 | 0.0308 | 0.0218 | 0.150 |
| 158 | 0.0041* | 0.0097* | 0.0243* |
| 159 | 0.0370 | 0.0207 | 0.0624 |
| 160 | 0.0416 | 0.0065 | 0.119 |
| 161 | 0.0204 | 0.0055 | 0.104 |

TABLE 1-continued

| Compound of Ex. No. | TR-FRET Binding Ki: BRD4 (BDI_K57-E168) (µM) | TR-FRET Binding Ki: BRD4 (BDII_E352-M457) (µM) | Cellular proliferation: EC$_{50}$ (µM) |
|---|---|---|---|
| 162 | 0.0111 | 0.0046 | 0.127 |
| 163 | 0.0857 | 0.0235 | 0.295 |
| 164 | NA | NA | NA |
| 165 | 0.0050 | 0.0022 | 0.104 |
| 166 | 0.0109 | 0.0036 | 0.0482 |
| 167 | 0.0065 | 0.0122 | 0.0430 |
| 168 | 0.0054 | 0.0013 | 0.0277 |
| 169 | 0.00088* | 0.00086* | 0.0053 |
| 170 | 0.0228 | 0.0940 | 0.332 |
| 171 | 0.0138 | 0.0103 | NA |
| 172 | 0.0133 | 0.0059 | NA |
| 173 | 0.0157 | 0.0066 | NA |
| 174 | 0.0192 | 0.0143 | NA |
| 175 | 0.0258 | 0.0178 | NA |
| 176 | 0.0213 | 0.0060 | NA |
| 177 | 0.0113 | 0.0044 | 0.0535 |
| 178 | 0.0105 | 0.0032 | 0.0362 |
| 179 | 0.0225 | 0.0165 | NA |
| 180 | 0.0179 | 0.0071 | 0.115 |
| 181 | 0.0305 | 0.0224 | NA |
| 182 | 0.0190 | 0.0097 | NA |
| 183 | 0.0412 | 0.0198 | NA |
| 184 | 0.0166 | 0.0045 | 0.0788 |
| 185 | 0.0345 | 0.0122 | NA |
| 186 | 0.0101 | 0.0033 | 0.0484 |
| 187 | 0.0248 | 0.0082 | NA |
| 188 | 0.0294 | 0.0180 | NA |
| 189 | 0.0304 | 0.0230 | NA |
| 190 | 0.0346 | 0.0181 | NA |
| 191 | 0.0178 | 0.0088 | NA |
| 192 | 0.0513 | 0.0096 | NA |
| 193 | 0.0704 | 0.0136 | NA |
| 194 | 0.0289 | 0.0191 | NA |
| 195 | 5.5 | 1.02 | NA |
| 196 | 9.5 | 0.479 | NA |
| 197 | 0.0015 | 0.00079 | 0.0117 |
| 198 | 0.0013 | 0.0016 | 0.0093* |
| 199 | 0.0019 | 0.0035 | NA |
| 200 | 0.00086 | 0.0011 | 0.0113 |
| 201 | 0.0102 | 0.0407 | 0.135 |
| 202 | 0.0017 | 0.0014 | 0.0228* |
| 203 | 0.00069 | 0.00075 | 0.0047 |
| 204 | 0.0205 | 0.0102 | 0.0829 |
| 205 | 0.0062 | 0.0102 | 0.0391* |
| 206 | 0.0116 | 0.0228 | 0.0777 |
| 207 | 0.0031 | 0.0018 | 0.0251* |
| 208 | 0.0056 | 0.0060 | 0.0235 |
| 209 | 0.0046 | 0.0036 | 0.0368 |
| 210 | 0.0045 | 0.0053 | 0.0367 |
| 211 | 0.0014 | 0.0021 | 0.0119 |
| 212 | 0.0018 | 0.0013 | 0.0073 |
| 213 | 0.0032 | 0.0048 | 0.0287 |
| 214 | 0.0024 | 0.0017 | 0.0105 |
| 215 | 0.00083 | 0.00046 | 0.0019 |
| 216 | 0.0018 | 0.0018 | 0.0066 |
| 217 | 0.0033 | 0.0081 | 0.0342 |
| 218 | 0.0693 | 0.0689 | NA |
| 219 | 0.0036 | 0.0029 | 0.0177 |
| 220 | 0.0028 | 0.0012 | 0.0213 |
| 221 | 0.0066 | 0.0050 | 0.0061 |
| 222 | 0.225 | 0.969 | NA |
| 223 | 0.0024 | 0.0050 | 0.0133 |
| 224 | 0.0069 | 0.0070 | 0.0076 |
| 225 | 0.264 | 0.845 | NA |
| 226 | 0.141 | 0.438 | >3.0 |
| 227 | 0.0739 | 0.211 | 0.658 |
| 228 | 0.0390 | 0.108 | >3.0 |
| 229 | 0.0343 | 0.0613 | 0.288 |
| 230 | 0.0026 | 0.0015 | 0.0236 |
| 231 | 0.0037 | 0.0067 | 0.0063 |
| 232 | 0.213 | 0.443 | NA |
| 233 | 0.0022* | 0.0015* | 0.0069* |
| 234 | 0.0030 | 0.0034 | 0.0159 |
| 235 | 0.0174 | 0.0070 | 0.0665 |
| 236 | 0.0145 | 0.0051 | 0.0250 |
| 237 | 0.0030 | 0.0035 | 0.0350 |
| 238 | 0.0011 | 0.00078 | 0.0033 |
| 239 | 0.0028 | 0.0024 | 0.0101 |
| 240 | 0.0020 | 0.0028 | 0.0115 |
| 241 | 0.332 | 0.603 | NA |
| 242 | 0.0365 | 0.0058 | 0.289 |
| 243 | 0.0115 | 0.0382 | 0.249 |
| 244 | 0.0232 | 0.0737 | 0.254 |
| 245 | 0.0025 | 0.0037 | 0.0269 |
| 246 | 0.0180 | 0.0046 | 0.0975 |
| 247 | 1.1 | 3.00 | NA |
| 248 | 0.0019 | 0.0013 | 0.0264* |
| 249 | 0.0015 | 0.00083 | 0.0144* |
| 250 | 0.0015* | 0.0015* | 0.0180* |
| 251 | 0.0631 | 0.171 | 0.573 |
| 252 | 0.0101 | 0.0017 | 0.246 |
| 253 | 0.0204 | 0.0012 | 0.145 |
| 254 | 0.0796 | 0.0087 | 0.0751 |
| 255 | 0.0105 | 0.154 | 0.265 |
| 256 | 0.0061 | 0.0840 | 0.405 |
| 257 | 0.0588 | 0.0030 | 0.360 |
| 258 | 0.0059 | 0.0124 | 0.0765 |
| 259 | 0.0242 | 0.0203 | 0.123 |
| 260 | 0.0010 | 0.0012 | 0.0063 |
| 261 | 0.0015 | 0.0016 | 0.0072 |
| 262 | 0.125 | 0.489 | NA |
| 263 | 0.0088 | 0.0163 | 0.0769 |
| 264 | 0.0012 | 0.0012 | 0.0178 |
| 265 | 0.0090 | 0.0356 | >3.0 |
| 266 | 0.0215 | 0.0078 | 0.0564 |
| 267 | 0.0044 | 0.0042 | 0.0436 |
| 268 | 0.00076 | 0.00057 | 0.0062 |
| 269 | 0.0124 | 0.0569 | 0.329 |
| 270 | 0.0487 | 0.0226 | 0.421 |
| 271 | 0.0029 | 0.0019 | 0.0213 |
| 272 | 0.0102 | 0.0116 | 0.112 |
| 273 | 0.0012 | 0.0013 | 0.0090 |
| 274 | 0.0933 | 0.310 | NA |
| 275 | 0.526 | 1.13 | NA |
| 276 | 0.0114 | 0.0171 | 0.149 |
| 277 | 0.0063 | 0.0143 | 0.0211 |
| 278 | 0.0121 | 0.0112 | 0.135 |
| 279 | 0.0314 | 0.131 | 0.364 |
| 280 | 0.0192 | 0.0920 | 0.292 |
| 281 | 0.0018 | 0.108 | 0.191 |
| 282 | 0.0173 | 0.0723 | 0.204 |
| 283 | 0.0189 | 0.0346 | 0.138 |
| 284 | 0.0183 | 0.130 | 0.131 |
| 285 | 0.0108 | 0.0075 | 0.111 |
| 286 | 0.0121 | 0.0054 | 0.0746 |
| 287 | 0.0089 | 0.0095 | 0.0195* |
| 288 | 0.0719 | 0.0539 | 0.173 |
| 289 | 0.0124 | 0.310 | >3.0 |
| 290 | 0.0050 | 0.0019 | 0.0362 |
| 291 | 0.0329 | 0.0237 | NA |
| 292 | 0.0532 | 0.0558 | 0.366 |
| 293 | 0.180 | 0.0193 | 0.381 |
| 294 | 0.0479 | 0.0217 | 0.332 |
| 295 | 0.0279 | 0.0307 | 0.223 |
| 296 | 0.705 | 0.101 | 0.535 |
| 297 | 0.0142 | 0.0052 | 0.0186 |
| 298 | 0.0029 | 0.0031 | 0.0061 |
| 299 | 0.0801 | 0.0050 | 0.0360 |
| 300 | 0.389 | 0.190 | 0.176 |
| 301 | 0.0179 | 0.0155 | 0.0421 |
| 302 | 0.0058 | 0.0035 | 0.0169 |
| 303 | 0.0039 | 0.0071 | 0.335* |
| 304 | 0.0090 | 0.0218 | 0.0323 |
| 305 | 0.327 | 0.0257 | 0.110 |
| 306 | 0.0822 | 0.0639 | 0.0516 |
| 307 | 0.0024 | 0.0029 | 0.122 |
| 308 | 0.0499 | 0.0065 | 0.0293 |
| 309 | 0.0306 | 0.0169 | 0.0859 |
| 310 | 0.0409 | 0.0711 | 0.103 |
| 311 | 0.0148 | 0.0045 | 0.0224 |

TABLE 1-continued

| Compound of Ex. No. | TR-FRET Binding Ki: BRD4 (BDI_K57-E168) (μM) | TR-FRET Binding Ki: BRD4 (BDII_E352-M457) (μM) | Cellular proliferation: EC$_{50}$ (μM) |
|---|---|---|---|
| 312 | 0.0141 | 0.0190 | 0.0675 |
| 313 | 0.0158 | 0.0061 | 0.0509 |
| 314 | 1.6 | 1.29 | NA |
| 315 | 0.0376 | 0.231 | 0.160 |
| 316 | >2.4 | 3.07 | NA |
| 317 | 0.0067 | 0.0036 | 0.0168 |
| 318 | 0.346 | 0.625 | >3.0 |
| 319 | 0.372 | 0.0099 | 0.435 |
| 320 | 0.0030 | 0.0037 | 0.0187 |
| 321 | 0.0334 | 0.0321 | 0.0344 |
| 322 | 0.181 | 0.0456 | 0.0668 |
| 323 | 0.0231 | 0.0255 | 0.0377 |
| 324 | 0.0032 | 0.0012 | NA |
| 325 | 0.155 | 0.199 | 0.703 |
| 326 | 0.145 | 0.272 | 0.286 |
| 327 | 0.0085 | 0.0042 | 0.0354 |
| 328 | 0.0245 | 0.0797 | 0.0426 |
| 329 | 0.0089 | 0.0126 | 0.0171 |
| 330 | 0.0509 | 0.0046 | 0.0306 |
| 331 | 0.561 | 0.311 | 0.481 |
| 332 | 0.0304 | 0.0306 | 0.0531 |
| 333 | 0.0369 | 0.0327 | 0.0740 |
| 334 | 0.661 | 1.17 | 0.515 |
| 335 | 0.0111 | 0.0536 | 0.0224 |
| 336 | 0.0762 | 0.152 | 0.115 |
| 337 | 0.0043 | 0.0042 | 0.0158 |
| 338 | 0.00086 | 0.0127 | 0.0779 |
| 339 | 0.00080 | 0.0316 | 0.0774 |
| 340 | 0.942 | 1.25 | NA |
| 341 | 0.295 | 0.0817 | 0.622 |
| 342 | 0.0719 | 0.0115 | 0.510 |
| 343 | 0.0427 | 0.0048 | 0.224 |
| 344 | 0.430 | 0.136 | 0.636 |
| 345 | 0.129 | 0.0326 | 0.479 |
| 346 | 0.0962 | 0.0160 | 0.213 |
| 347 | 0.0156 | 0.0040 | 0.0839 |
| 348 | 0.157 | 0.422 | 1.0 |
| 349 | 0.0066 | 0.0031 | 0.0321 |
| 350 | 1.4 | 0.505 | NA |
| 351 | 0.223 | 0.153 | 1.1 |
| 352 | 0.404 | 0.625 | NA |
| 353 | 0.158 | 0.256 | 0.786 |
| 354 | 0.066 | 0.0129 | 0.0954 |

*indicates average value of multiple experiments
NA means not determined

TABLE 2

| Cell line Type | Cell Line | Compound of Example 4 Cellular Proliferation EC$_{50}$ (μM) | Compound of Example 78 Cellular Proliferation EC$_{50}$ (μM) |
|---|---|---|---|
| AML | SKM1 | 0.005 | 0.058 |
| AML | Raji | 0.006 | 0.084 |
| Bladder | EJ-1 | 0.202 | 2.090 |
| Breast | MDAMB231 | 0.22 | 1.22 |
| Breast | MDAMB453 | 0.02 | 0.24 |
| Colon | GEO | 0.08 | 1.29 |
| Colon | DLD-1 | 0.20 | 4.97 |
| Glioblastoma | D54MG | 0.038 | 2.299 |
| Head & Neck | FaDu | 0.02 | 0.39 |
| Hepatocellular | HepG2 | 0.074565 | 0.8851 |
| Melanoma | A-375 | 0.020 | 3.606 |
| Multiple Myeloma | OPM2 | 0.001 | 0.039 |
| Multiple Myeloma | RPMI-8226 | 0.011 | 1.402 |
| Multiple Myeloma | NCI-H929 | 0.003 | 0.154 |
| NHL | Ramos | 0.02 | 0.32 |
| NHL | Ly18 | 0.02 | 0.42 |
| NSCLC | H1299 | 0.06 | 2.57 |
| NSCLC | H1975 | 0.02 | 1.37 |
| NSCLC | H460 | 3.77 | >10 |
| Pancreas | HPAC | 0.05 | 1.19 |
| Pancreas | BxPC3FP5 | 0.01 | 0.74 |
| Prostate | PC3M | 0.07 | 8.11 |
| RCC | 786-0 | 0.011 | 0.884 |
| Sarcoma | SK-LMS-1 | 0.025 | 0.934 |

Human, Rat, and Mouse Microsome Stability Assay

Microsome stability assays were carried out on compounds of the Examples listed in Table 3 ("test compounds"). Human, rat, and mouse liver microsomal incubations were carried out at 37° C. with a final incubation volume of 135 μL. Human liver microsomes (mixed gender, Catalog No. H2610) were obtained from XenoTech. Rat liver microsomes (male Sprague-Dawley, Catalog No. 42501) were obtained from BD Gentest. Mouse liver microsomes (male CD1, Catalog No. 452701) were obtained from BD Gentest. Incubations were conducted using a test compound (initially dissolved in DMSO at 5 μM concentration) concentration of 0.5 μM and 0.25 mg/mL microsomal protein in 50 mM phosphate buffer at pH 7.4. Time zero samples were prepared by transferring 13.5 μL of compound-microsomal mix to the quench plates containing 45 μL of quench solution made of 10 nM Buspirone (Sigma) or 50 nM Carbutamide (Princeton Bio) as internal standard in 1:1 methanol:acetonitrile. An aliquot of 1.5 μL Nicotinamide adenine dinucleotide phosphate reduced tetrasodium salt (NADPH) was also added to the time zero plates. The reaction was then initiated by the addition of 13.5 μL NADPH to the compound-microsomal mix. At each of the remaining time points (5, 10, 15, 20 and 30 min) 15 μL of incubation mixture was added to 45 μL of quench solution. Samples were centrifuged for 15-30 minutes at 3800 rpm. Samples were then pooled for 6 per group. An aliquot of 60 μL of supernatant was transferred to 384-well plate, and a 5 μL aliquot was injected and analyzed by LC-MS/MS (Applied Biosystems API 5500 QTrap). The intrinsic clearance of a compound was calculated by converting the peak area ratios (analyte peak area/IS peak area) to % parent remaining using the area ratio at time 0 as 100%. The slope (k) was determined from the plot of the % parent remaining versus incubation time, from which the half life ($t_{1/2}$; minutes), intrinsic clearance ($CL_{int}$; μL/min/mg protein for liver microsomes and μL/min/million cells for hepatocytes) and scaled intrinsic clearance (scaled $CL_{int}$; L/h/kg) were then derived. The $t_{1/2}$ values are reported in Table 3. The term "N/A" means not determined.

TABLE 3

| Compound of Ex. No. | Stability in human liver microsomes ($t_{1/2}$ in minutes) | Stability in rat liver microsomes ($t_{1/2}$ in minutes) | Stability in mouse liver microsomes ($t_{1/2}$ in minutes) |
|---|---|---|---|
| 1 | 9 | 1 | 1 |
| 4 | 59 | 4 | 57 |
| 5 | 100 | 6 | 24 |
| 6 | 30 | 7 | 3 |
| 7 | 12 | 2 | 4 |
| 8 | 19 | 1 | 9 |
| 9 | NA | 1 | 1 |

TABLE 3-continued

| Compound of Ex. No. | Stability in human liver microsomes ($t_{1/2}$ in minutes) | Stability in rat liver microsomes ($t_{1/2}$ in minutes) | Stability in mouse liver microsomes ($t_{1/2}$ in minutes) |
| --- | --- | --- | --- |
| 10 | 78 | >120 | >120 |
| 11 | 48 | 19 | 27 |
| 12 | 51 | 10 | 33 |
| 13 | 66 | 2 | 22 |
| 14 | 37 | 6 | 8 |
| 15 | 10 | 4 | 7 |
| 16 | >120 | 4 | 22 |
| 17 | 31 | 18 | 16 |
| 18 | 31 | 11 | 15 |
| 19 | 92 | 13 | 33 |
| 20 | 18 | 1 | 7 |
| 21 | >120 | 3 | 22 |
| 22 | 32 | 3 | 10.7 |
| 23 | 64 | 11 | >120 |
| 24 | 29 | 5 | 55 |
| 27 | 32 | >120 | 59 |
| 28 | 21 | 9 | NA |
| 29 | >120 | 26 | >120 |
| 31 | 56 | >120 | 19 |
| 32 | 24 | 82 | 32 |
| 33 | >120 | >120 | 46 |
| 34 | 37 | 42 | 35 |
| 35 | 37 | >120 | 42 |
| 36 | >120 | >120 | 41 |
| 37 | 88.9 | 54 | 3 |
| 38 | 16.8 | 25 | NA |
| 39 | 09.7 | 8 | NA |
| 40 | 13.1 | 1 | 6 |
| 41 | 13.6 | 1 | 10 |
| 42 | >120 | >120 | >120 |
| 43 | 34.9 | 2 | 5 |
| 44 | 33.7 | 6 | 27 |
| 45 | NA | 2 | 3 |
| 46 | 10 | 4 | 13 |
| 47 | 8 | 3 | 5 |
| 48 | 37 | 32 | 35 |
| 49 | 71 | 51 | 46 |
| 50 | 35 | 88 | 46 |
| 51 | 6 | 63 | >120 |
| 54 | 3 | 30 | 2 |
| 55 | 25 | 9 | 13 |
| 56 | 39 | 30 | 36 |
| 57 | 13 | 6 | 5 |
| 58 | >120 | 1 | 4 |
| 59 | >120 | 40 | 23 |
| 60 | 68 | 64 | 34 |
| 61 | >120 | >120 | >120 |
| 62 | 64 | 45 | 25 |
| 63 | 39 | 13 | 18 |
| 64 | NA | 3 | 4 |
| 65 | 88 | >120 | 11 |
| 66 | >120 | >120 | NA |
| 67 | 6 | 5 | 6 |
| 69 | 6 | 2 | 3 |
| 70 | 41 | 9 | 68 |
| 71 | 2 | 1 | 6 |
| 72 | 34 | 1 | 70 |
| 73 | 36 | 2 | 31 |
| 74 | 17 | 3 | 5 |
| 75 | 9 | 3 | 4 |
| 80 | 62 | 2 | 31 |
| 82 | 19 | 2 | 2 |
| 83 | NA | 3 | 43 |
| 84 | 112 | 92 | >120 |
| 85 | 43 | 6 | 34 |
| 86 | >120 | >120 | 43 |
| 87 | >120 | 23 | NA |
| 88 | 23 | 12 | NA |
| 91 | 17 | 7 | 7 |
| 92 | 97 | 20 | 11 |
| 93 | 54 | 102 | 25 |
| 94 | 47 | 28 | 25 |
| 95 | >120 | 7 | 36 |
| 96 | 24 | 13 | 33 |
| 97 | 26 | 9 | 28 |
| 98 | 26 | 33 | 10 |
| 99 | >120 | 22 | 35 |
| 100 | 77 | 71 | 60 |
| 101 | 92 | 12 | 20 |
| 102 | 36 | 3 | 8 |
| 103 | 47 | 16 | 37 |
| 104 | 27 | 8 | 7 |
| 105 | >120 | 13 | 7 |
| 106 | 39 | 8 | 4 |
| 107 | 71 | 16 | 8 |
| 108 | 37 | 33 | 13 |
| 109 | 71 | 61 | >120 |
| 111 | >120 | 42 | 63 |
| 112 | 49 | 28 | 51 |
| 114 | 13 | 5 | 8 |
| 115 | 41 | 38 | 55 |
| 117 | 34 | 36 | 1 |
| 118 | 81 | 34 | 18 |
| 119 | 14 | 24 | 2 |
| >120 | 19 | 12 | 10 |
| 121 | 21 | 25 | 24 |
| 122 | 8 | 16 | 2 |
| 123 | >120 | >120 | 45 |
| 124 | 2 | 4 | NA |
| 125 | 45 | 23 | 12 |
| 126 | 100 | 21 | 25 |
| 127 | 44 | 71 | 20 |
| 128 | 11 | 21 | 4 |
| 129 | 54 | 38 | 12 |
| 131 | >120 | 71 | 83 |
| 133 | 4 | 5 | 3 |
| 134 | 15 | 21 | 2 |
| 135 | 8 | 24 | 5 |
| 137 | 38 | 31 | 10 |
| 138 | 52 | 51 | 45 |
| 139 | 13 | 8 | 7 |
| 140 | 19 | 13 | 18 |
| 141 | >120 | 110 | 49 |
| 142 | 112 | 35 | 32 |
| 144 | 18 | 19 | 17 |
| 145 | >120 | 12 | 16 |
| 146 | >120 | 52 | 55 |
| 147 | 11 | 8 | 32 |
| 148 | 58 | 2 | 6 |
| 152 | 51 | 10 | 22 |
| 153 | 33 | 8 | 11 |
| 154 | 42 | 66 | 18 |
| 155 | >120 | >120 | 25 |
| 156 | >120 | >120 | 33 |
| 157 | 27 | 53 | 12 |
| 158 | >120 | >120 | >120 |
| 159 | 89 | 107 | 59 |
| 160 | 67 | 119 | 21 |
| 161 | 5 | 10 | 4 |
| 162 | 96 | 41 | 11 |
| 165 | >120 | 111 | 27 |
| 166 | 85 | 23 | 22 |
| 168 | 66 | 82 | 25 |
| 169 | 86 | 34 | 38 |
| 170 | >120 | 113 | 27 |
| 171 | 15 | 13 | 9 |
| 172 | 9 | 15 | 7 |
| 173 | 38 | 5 | 16 |
| 174 | 40 | 46 | 14 |
| 176 | 48 | 8 | 29 |
| 177 | 16 | 6 | 18 |
| 178 | 27 | 7 | 10 |
| 179 | 80 | 55 | 34 |
| 180 | 12 | 7 | 5 |
| 186 | 9 | 3 | 8 |
| 187 | 9 | 4 | 5 |
| 188 | 26 | 22 | 6 |
| 189 | 34 | 55 | NA |
| 190 | 27 | 66 | 8 |
| 191 | 7 | 6 | 2 |
| 192 | 9 | 5 | 3 |
| 193 | 11 | 7 | 2 |

TABLE 3-continued

| Compound of Ex. No. | Stability in human liver microsomes ($t_{1/2}$ in minutes) | Stability in rat liver microsomes ($t_{1/2}$ in minutes) | Stability in mouse liver microsomes ($t_{1/2}$ in minutes) |
| --- | --- | --- | --- |
| 194 | 41 | 38 | 49 |
| 195 | 13 | 1 | 1 |
| 196 | 59 | 5 | 3 |
| 197 | 16 | 15 | 10 |
| 198 | NA | NA | 55 |
| 199 | 94 | 1 | 3 |
| 200 | >120 | 31 | >120 |
| 201 | 56 | 117 | >120 |
| 202 | NA | >120 | NA |
| 203 | NA | >120 | NA |
| 204 | >120 | 81 | 68 |
| 205 | >120 | 81 | 118 |
| 206 | >120 | 118 | 95 |
| 207 | 102 | 78 | 100 |
| 208 | 88 | 23 | 37 |
| 209 | >120 | 105 | 116 |
| 210 | 104 | >120 | >120 |
| 211 | 65 | 48 | 63 |
| 212 | 69 | 67 | 53 |
| 213 | 79 | 38 | 89 |
| 214 | 27 | 9 | 8 |
| 215 | 12 | 6 | 11 |
| 217 | 70 | 101 | 68 |
| 218 | >120 | >120 | >120 |
| 220 | 5 | 5 | 4 |
| 221 | 63 | 24 | 43 |
| 222 | 65 | 80 | 98 |
| 223 | 54 | 24 | 48 |
| 224 | 6 | 8 | 5 |
| 225 | 52 | 59 | >120 |
| 226 | 105 | >120 | >120 |
| 227 | 50 | 70 | >120 |
| 228 | >120 | 107 | >120 |
| 229 | 25 | 33 | 9 |
| 230 | 6 | 8 | 7 |
| 231 | 33 | >120 | 72 |
| 232 | 57 | >120 | >120 |
| 235 | 81 | 49 | 22 |
| 236 | 33 | 32 | 15 |
| 237 | 3 | 7 | 2 |
| 238 | 103 | >120 | 63 |
| 240 | >120 | >120 | 47 |
| 241 | 39 | 9 | 4 |
| 242 | >120 | 86 | >120 |
| 243 | >120 | 20 | 109 |
| 244 | 53 | 6 | 87 |
| 245 | 32 | 24 | 12 |
| 246 | 52 | 53 | 56 |
| 248 | 13 | 16 | 5 |
| 249 | >120 | >120 | >120 |
| 250 | 56 | 36 | 37 |
| 251 | 118 | 23 | 44 |
| 252 | 68 | >120 | >120 |
| 253 | 72 | 110 | 90 |
| 254 | 74 | >120 | 91 |
| 255 | 70 | >120 | >120 |
| 256 | 58 | 58 | 71 |
| 257 | 18 | 56 | 20.3 |
| 258 | 42 | 91 | 69.8 |
| 259 | 117 | 87 | NA |
| 260 | 34 | 58 | 29 |
| 261 | 25 | 5 | 16 |
| 262 | >120 | 25 | NA |
| 263 | 70 | 72 | NA |
| 264 | 14 | 6 | NA |
| 265 | >120 | >120 | NA |
| 266 | 8 | 20 | NA |
| 267 | 95 | 18 | >120 |
| 268 | 10 | 26 | NA |
| 269 | 79 | 83 | 58 |
| 270 | >120 | >120 | >120 |
| 271 | 23 | 12 | 11 |
| 272 | 2 | 4 | 1 |
| 273 | 9 | 12 | 8 |
| 276 | >120 | 82 | 71 |
| 277 | 4 | 5 | 1 |
| 278 | >120 | >120 | >120 |
| 279 | NA | 41 | 91 |
| 280 | 17 | 84 | 36 |
| 281 | 25 | 119 | 116 |
| 282 | 9 | 21 | 7 |
| 283 | 7 | 22 | 12 |
| 284 | 12 | 108 | >120 |
| 285 | 19 | 10 | 12 |
| 286 | 10 | 19 | 11 |
| 287 | >120 | 116 | 29 |
| 288 | 85 | >120 | >120 |
| 290 | 73 | 48 | 52 |
| 291 | 16 | 8 | 16 |
| 292 | 8 | 22 | 12 |
| 293 | 4 | 9 | 3 |
| 294 | >120 | >120 | >120 |
| 295 | 7 | 15 | 3 |
| 296 | 7 | 13 | 6 |
| 297 | 83 | 43 | NA |
| 298 | 9 | 47 | 3 |
| 299 | 1 | 2 | 1 |
| 300 | 30 | 21 | 17 |
| 301 | 20 | 82 | 13 |
| 302 | 5 | 4 | 3 |
| 303 | 42 | 69 | >120 |
| 304 | >120 | 65 | 72 |
| 305 | 1 | 2 | 2 |
| 306 | 11 | 9 | 3 |
| 307 | 3 | 3 | 2 |
| 308 | 20 | 10 | 16 |
| 309 | >120 | >120 | >120 |
| 310 | 8 | 5 | 9 |
| 311 | >120 | 83 | >120 |
| 312 | 56 | 32 | 9 |
| 313 | 5 | 4 | 3 |
| 314 | 81 | 4 | 6 |
| 315 | 34 | 4 | 11 |
| 316 | 47 | 3 | 12 |
| 317 | 88 | 115 | 83 |
| 318 | 35 | 24 | 13 |
| 319 | 2 | 2 | 2 |
| 320 | >120 | 57 | 116 |
| 321 | >120 | 103 | >120 |
| 322 | >120 | 57 | >120 |
| 323 | >120 | >120 | >120 |
| 324 | >120 | >120 | >120 |
| 325 | 21 | 10 | 8 |
| 326 | 112 | 5 | 27 |
| 327 | >120 | >120 | >120 |
| 328 | >120 | 36 | >120 |
| 329 | >120 | >120 | >120 |
| 330 | 29.9 | 12 | 28 |
| 331 | >120 | >120 | >120 |
| 332 | 65 | 70 | >120 |
| 333 | 0.8 | 3 | 1 |
| 334 | 34 | NA | 21 |
| 335 | 35 | 34 | 54 |
| 336 | 44 | 5 | 17 |
| 337 | >120 | >120 | >120 |
| 338 | 39 | 29 | 20 |
| 339 | 100 | 76 | 67 |
| 340 | >120 | 4 | 9 |
| 342 | 2 | 5 | 1 |
| 343 | 2 | 7 | 1 |
| 344 | NA | NA | 1 |
| 345 | 2 | 4 | 2 |
| 346 | 4 | 5 | 2 |
| 347 | 4 | 6 | NA |
| 348 | >120 | 2 | 25 |
| 349 | >120 | 39 | 36 |
| 350 | 59 | 32 | 23 |
| 351 | 76 | 66 | 30 |
| 353 | 40 | 8 | 10 |
| 354 | 23 | 41 | 24 |

LPS (Lipopolysaccharide) Induced IL-6 Production Mouse Assay

Compounds of the Examples listed in Table 4 were assayed for their ability to inhibit LPS (lipopolysaccharide) induced IL-6 production in mice. Fox Chase SCID® female mice (Charles Rivers Labs, 8 per group) received an intraperitoneal challenge of lipopolysaccharide (2.5 mg/kg, L2630 E. coli 0111:B4) one hour after oral administration of compounds. Mice were euthanized 2 hours after lipopolysaccharide injection, blood was removed by cardiac puncture, and then the serum harvested from the blood samples was frozen at −80° C. On the day of the assay the serum samples were brought to room temperature and then diluted 1:20 in phosphate-buffered saline containing 2% bovine serum albumin. Interleukin-6 measurements were performed using a cytokine assay from Meso Scale Discovery (Gaithersburg, Md.) for mouse serum analysis according to the manufacturer's protocol and read on a SECTOR Imager 6000 (Meso Scale Discovery, Gaithersburg, Md.) instrument. Statistical analysis was performed using Prism software (version 5.0) incorporating Dunnett's one way ANOVA. The IL-6 mean and standard deviation of the group of vehicle treated animals were compared with the IL-6 mean and standard deviation of the group treated with test compound. A p value<0.05 means that there is less than a 5% probability that the mean values in the two groups are equal. The % inhibition values in Table 4 all exhibited a p value less than 0.05.

TABLE 4

Inhibition of LPS induced IL-6 production in Mice

| Example # | % inhibition at 3 mg/kg |
|---|---|
| 4 | 69* |
| 5 | 74% at 50 mg/kg |
| 11 | 34 |
| 24 | 58 |
| 26 | 60 |
| 27 | 89 |
| 28 | 52 |
| 32 | 69 |
| 34 | 78 |
| 36 | 78* |
| 48 | 62 |
| 49 | 57 |
| 56 | 28 |
| 59 | 54 |
| 62 | 67 |
| 65 | 63 |
| 80 | 69% at 30 mg/kg |
| 84 | 69 |
| 85 | 80 |
| 86 | 55 |
| 87 | 57 |
| 138 | 72 |
| 144 | 48 |
| 146 | 80 |
| 147 | 61 |
| 149 | 69 |
| 150 | 54 |
| 151 | 66 |
| 154 | 73 |
| 159 | 58 |
| 160 | 51 |

TABLE 4-continued

Inhibition of LPS induced IL-6 production in Mice

| Example # | % inhibition at 3 mg/kg |
|---|---|
| 162 | 41 |
| 166 | 44 |
| 167 | 64 |
| 168 | 70 |
| 169 | 67 |
| 197 | 59 |
| 198 | 66 |
| 200 | 75 |
| 202 | 68 |
| 203 | 78 |
| 204 | 35 |
| 205 | 48 |
| 207 | 62 |
| 210 | 78 |
| 212 | 47 |
| 231 | 51 |
| 238 | 69 |
| 240 | 62 |
| 242 | 46 |
| 245 | 71 |
| 246 | 71 |
| 248 | 82 |
| 249 | 59 |
| 260 | 66 |
| 267 | 74 |
| 273 | 47 |
| 276 | 25 |
| 278 | 51 |
| 286 | 57 |
| 287 | 73 |
| 288 | 60 |
| 290 | 64 |
| 294 | 79 |
| 304 | 67 |
| 308 | 48 |
| 311 | 74 |
| 321 | 63 |
| 328 | 40 |
| 329 | 63 |
| 330 | 45 |

*indicates average value of multiple experiments

Xenograft Tumor Growth Inhibition Assay

The effect of the compound of Example 36 to inhibit the growth of OPM-2 and MX-1 xenograft tumors implanted in mice was evaluated. Briefly, $5 \times 10^6$ human cancer cells (OPM-2) or 1:10 tumor brie (MX-1) (in S-MEM (MEM, Suspension, no Calcium, no Glutamine))(Life Technologies Corporation) was inoculated subcutaneously into the right hind flank of female SCID-beige or female Fox Chase SCID® (Charles River Labs) mice respectively on study day 0. Administration of compound (in (2% EtOH, 5% Tween-80, 20% PEG-400, 73% HPMC))(PO, QDx14) was initiated at the time of size match on day 17 (OPM-2) or day 12 (MX-1). The tumors were measured by a pair of calipers twice a week starting at the time of size match and tumor volumes were calculated according to the formula $V = L \times W^2/2$ (V: volume, mm$^3$; L: length, mm. W: width, mm). Tumor volume was measured for the duration of the experiment until the mean tumor volume in each group reached an endpoint of >1000 mm$^3$ for OPM-2 or until day 27 post inoculation for MX-1. Results are shown in Tables 5 and 6.

TABLE 5

OPM-2 human multiple myeloma cancer xenograft model.

| Group | Treatment | Dose route, regimen | % TGI[a] | % TGD[b] |
|---|---|---|---|---|
| 1 | Vehicle | 0 mg/kg/day IP, QDx14 | — | — |
| 2 | Compound of Example 36 | 3 mg/kg/day PO, QDx14 | 90*** | 78*** |

[a] Tumor growth inhibition, % TGI = 100 − mean tumor volume of treatment group/mean tumor volume of control group × 100. Number of mice per treatment group = 10. The p values (as indicated by asterisks) are derived from Student's T test comparison of treatment group vs. control group. Based on day 31.
*p < 0.05,
**p < 0.01,
***p < 0.001.

[b] Tumor growth delay, % TGD = (T − C)/C × 100, where T = median time to endpoint of treatment group and C = median time to endpoint of control group. The p values (as indicated by asterisks) derived from Kaplan Meier log-rank comparison of treatment group vs. treatment control group. Based on an endpoint of 1000 mm$^3$.
*p < 0.05,
**p < 0.01,
***p < 0.001.

TABLE 6

Efficacy of BET inhibitor in the MX-1 human breast cancer xenograft model.

| Group | Treatment | Dose route, regimen | % TGI[a] |
|---|---|---|---|
| 1 | Vehicle | 0 mg/kg/day PO, QDx14 | — |
| 2 | Compound of Example 36 | 0.3 mg/kg/day PO, QDx14 | 43** |
| 3 | Compound of Example 36 | 1 mg/kg/day PO, QDx14 | 60*** |
| 4 | Compound of Example 36 | 3 mg/kg/day PO, QDx14 | 76*** |

[a] Tumor growth inhibition, % TGI = 100 − mean tumor volume of treatment group/tumor volume of control group × 100. p values (as indicated by asterisks) are derived from Student's T test comparison of treatment group vs. control group. Based on day 27.
*p < 0.05,
**p < 0.01,
***p < 0.001.

Xenograft efficacy studies were conducted with additional example compounds using OPM-2, MX-1, HT1080, MV4-11, SKM1 and Ramos human cancer cells. Cancer cells were prepared from culture or from tumor brie (MX-1) as described above and inoculated subcutaneously into the right hind flank of female SCID-beige mice (OPM-2, HT1080, MV4-11) or female Fox Chase SCID (Charles River Labs) mice (MX-1, SKM1, Ramos). Administration of compound was initiated at the time of size match. Tumors were measured by a pair of calipers twice a week starting at the time of size match and tumor volumes were calculated according to the formula V=L×W$^2$/2 (V: volume, mm$^3$; L: length, mm. W: width, mm). Tumor volume was measured for the duration of the experiment until the mean tumor volume in each group reached a model-dependent endpoint of 500-2000 mm$^3$. Results are shown in Table 7.

TABLE 7

Efficacy of BET inhibitors in human xenograft models.

| Compound of Ex. No. | model | dose mg/kg/day | route, regimen | vehicle[a] | % TGI[b] | % TGD[c] | % removed from study |
|---|---|---|---|---|---|---|---|
| 4 | MX-1 | 12.5 | PO, BID (5 on, 3 off)x2 | F | 73*** | 70*** | 10 |
| 4 | MX-1 | 25 | PO, BID (5 on, 3 off)x2 | F | 77*** | 81*** | 30 |
| 4 | Ramos | 3.125 | PO, BID (5 d on, 3 d off)x2 | F | 19 | 27* | 0 |
| 4 | Ramos | 6.25 | PO, BID (5 d on, 3 d off)x2 | F | 24* | 28* | 0 |
| 27 | MX-1 | 0.3 | PO, QD | F | 38** | 35 | 0 |
| 27 | MX-1 | 1 | PO, QD | F | 57*** | 13 | 0 |
| 27 | MX-1 | 3 | PO, QD (5 on, 3 off, 5 on) | F | 69*** | ND | 0 |
| 27 | OPM-2 | 1 | PO, QDx14 | A | 59 | −2 | 0 |
| 27 | OPM-2 | 3 | PO, QD (5 on, 3 off, 5 on) | A | 67 | 7* | 0 |
| 36 | HT1080 | 0.3 | PO, QDx14 | H | 26 | −1 | 30 |
| 36 | HT1080 | 1 | PO, QDx14 | H | 41* | 3 | 10 |

TABLE 7-continued

Efficacy of BET inhibitors in human xenograft models.

| Compound of Ex. No. | model | dose mg/kg/day | route, regimen | vehicle[a] | % TGI[b] | % TGD[c] | % removed from study |
|---|---|---|---|---|---|---|---|
| 36 | HT1080 | 3 | PO, QDx14 | H | 47** | 46*** | 10 |
| 36 | MV4-11 | 0.2 | PO, QDx21 | D | 22* | 16*** | 0 |
| 36 | MV4-11 | 0.67 | PO, QDx21 | D | 57*** | 59*** | 0 |
| 36 | MV4-11 | 2 | PO, QDx21 | D | 81*** | 94* | 0 |
| cytarabine | MV4-11 | 250 | IP, BID Q7Dx3 | C | 47*** | 37*** | 0 |
| 36/ cytarabine | MV4-11 | 0.67/250 | PO/IP, QDx21/ BID Q7Dx3 | E | 64*** | 53*** | 0 |
| 36/ cytarabine | MV4-11 | 2/250 | PO/IP, QDx21/ BID Q7Dx3 | E | 90*** | 102*** | 0 |
| 36 | MX-1 | 0.3 | PO, QD | F | 43** | 40 | 0 |
| 36 | MX-1 | 1 | PO, QD | F | 60*** | ND | 0 |
| 36 | MX-1 | 3 | PO, QD | F | 76*** | ND | 0 |
| 36 | OPM-2 | 0.25 | PO, QDx21 | A | 19 | 29 | 0 |
| 36 | OPM-2 | 0.25 | IP, QDx21 | F | 45 | 55* | 0 |
| 36 | OPM-2 | 0.5 | PO, QDx21 | A | 75*** | 101*** | 0 |
| 36 | OPM-2 | 0.5 | IP, QDx21 | F | 49* | 52** | 0 |
| 36 | OPM-2 | 1 | PO, QDx21 | A | 75*** | 107*** | 10 |
| 36 | OPM-2 | 1 | PO, QDx21 | A | 72** | 64* | 10 |
| 36 | OPM-2 | 1 | PO, QDx21 | A | 79*** | 140*** | 0 |
| 36 | OPM-2 | 1 | PO, BIDx21 | A | 74*** | 140*** | 10 |
| 36 | OPM-2 | 1 | PO, QDx21 | A | 70** | 85** | 0 |
| 36 | OPM-2 | 1 | IV, Q4Dx3 | C | 69** | 66** | 0 |
| 36 | OPM-2 | 1 | IP, Q4DX3 | F | 61* | 80*** | 0 |
| 36 | OPM-2 | 1 | IV, Q4Dx3 | C | 80** | 112*** | 0 |
| 36 | OPM-2 | 2 | PO, QDx21 | A | | | 60 |
| 36 | OPM-2 | 3 | PO, QDx14 | A | 90*** | 21*** | 10 |
| 36 | OPM-2 | 3 | PO, QDx21 | A | 88*** | 131*** | 30 |
| 36 | OPM-2 | 3 | PO, BIDx21 d | A | | | 70 |
| 36 | OPM-2 | 3 | IP, QDx21 | F | | | 40 |
| 36 | OPM-2 | 3 | IP, QDx21 | F | | | 70 |
| 36 | OPM-2 | 4.2 | PO, QD(5 on 2 off)x3 | A | | | 50 |
| 36 | OPM-2 | 5.25 | PO, QD(4 on 3 off)x3 | A | | | 40 |
| 36 | OPM-2 | 6 | PO, Q2D x21 d | A | 82* | 84** | 20 |
| 36 | OPM-2 | 6 | IP, QDx21 | F | | | 100 |

TABLE 7-continued

Efficacy of BET inhibitors in human xenograft models.

| Compound of Ex. No. | model | dose mg/kg/day | route, regimen | vehicle[a] | % TGI[b] | % TGD[c] | % removed from study |
|---|---|---|---|---|---|---|---|
| 36 | OPM-2 | 7 | PO, QD(3 on 4 off)x3 | A | 81*** | 97*** | 0 |
| 36 | OPM-2 | 7 | PO, BID (3 on 4 off)x3 | A | | | 90 |
| 36 | OPM-2 | 10.5 | PO, QD(2 on 5 off)x3 | A | 75*** | 94*** | 0 |
| Bortezomib | OPM-2 | 1 | IV, Q4Dx3 | B | 80** | 93*** | 10 |
| 36/Bortezomib | OPM-2 | 0.25/1 | IP/IV, QDx21/Q4Dx3 | B | 94** | 195*** | 20 |
| 36/Bortezomib | OPM-2 | 0.5/1 | IP/IV, QDx21/Q4Dx3 | B | | | 40 |
| 36/Bortezomib | OPM-2 | 1/1 | PO/IV, QDx21/Q4Dx3 | B | | | 100 |
| 36/Bortezomib | OPM-2 | 1/1 | IP/IV, QDx21/Q4Dx3 | G | | | 40 |
| 36 | SKM1 | 0.2 | PO, QDx21 | A | 41* | 93 | 0 |
| 36 | SKM1 | 0.67 | PO, QDx21 | A | 58* | 444*** | 0 |
| 36 | SKM1 | 2 | PO, QDx21 | A | 86** | 721*** | 0 |
| azacitidine | SKM1 | 6 | IV, Q7Dx3 | C | 54** | 98* | 0 |
| 36/azacitidine | SKM1 | 0.67/6 | PO/IV, QDx21/Q7Dx3 | B | 86** | 649*** | 10 |
| 36/azacitidine | SKM1 | 2/6 | PO/IV, QDx21/Q7Dx3 | B | 91** | 958*** | 10 |
| cytarabine | SKM1 | 250 | IP, BID Q7Dx3 | C | 20 | 30 | 0 |
| 36/cytarabine | SKM1 | 0.67/250 | PO/IP, QDx21/BID Q7Dx3 | B | 69** | 514*** | 0 |
| 36/cytarabine | SKM1 | 2/250 | PO/IP, QDx21/BID Q7Dx3 | B | 87** | 739*** | 0 |
| 146 | OPM-2 | 1 | PO, QDx21 | A | 39 | 35 | 10 |
| 146 | OPM-2 | 3 | PO, QDx21 | A | 76* | 78** | 0 |
| 158 | OPM-2 | 6 | PO, QDx21 | A | 53 | 34 | 10 |
| 158 | OPM-2 | 20 | PO, QDx21 | A | 78* | 72** | 30 |
| 169 | OPM-2 | 3 | PO, QDx21 | A | 69* | 77* | 10 |
| 169 | OPM-2 | 10 | PO, QDx21 | A | | | 100 |
| 200 | OPM-2 | 1 | PO, QDx21 | A | 50 | 44 | 10 |
| 200 | OPM-2 | 3 | PO, QDx21 | A | 80** | 82** | 20 |
| 250 | OPM-2 | 3 | PO, QDx21 | A | 42** | 29 | 0 |
| 250 | OPM-2 | 10 | PO, QDx21 | A | | | 40 |
| 287 | OPM-2 | 10 | PO, QDx21 | A | | | 50 |

TABLE 7-continued

Efficacy of BET inhibitors in human xenograft models.

| Compound of Ex. No. | model | dose mg/kg/day | route, regimen | vehicle[a] | % TGI[b] | % TGD[c] | % removed from study |
|---|---|---|---|---|---|---|---|
| 287 | OPM-2 | 20 | PO, QDx21 | A | | | 70 |
| 311 | OPM-2 | 1.25 | PO, QDx21 | A | 60* | 90* | 0 |
| 311 | OPM-2 | 2.5 | PO, QDx21 | A | | | 56 |

[a]Compounds were formulated in the following vehicles: A: 10% EtOH, 30% PEG 400, 60% Phosol 53 MCT (Lipoid AG) B: 10% EtOH, 30% PEG 400, 60% Phosol 53 MCT (Lipoid AG)/0.9% Saline C: 0.9% Saline D: 10% EtOH, 27.5% PEG 400, 60% Phosol 53 MCT (Lipoid AG) E: 10% EtOH, 27.5% PEG 400, 60% Phosol 53 MCT (Lipoid AG)/0.9% Saline F: 2% EtOH, 5% Tween-80, 20% PEG400, 73% 0.2% HPMC G: 2% EtOH, 5% Tween-80, 20% PEG400, 73% 0.2% HPMC/0.9% Saline and H: 5% EtOH, 30% PEG 400, 60% Phosol 53 MCT (Lipoid AG)
[b]Tumor growth inhibition, % TGI = 100 − mean tumor volume of treatment group/mean tumor volume of control group × 100. Number of mice per treatment group = 8 (MX-1, MV4-11, SKM1) or 10 (OPM-2). The p values (as indicated by asterisks) are derived from Student's T test comparison of treatment group vs. control group. Based on day 31. *p < 0.05, p < 0.01, *p < 0.001. % TGI values are not presented if mortality 40%.
[c]Tumor growth delay, % TGD = (T − C)/C × 100, where T = median time to endpoint of treatment group and C = median time to endpoint of control group. The p values (as indicated by asterisks) derived from Kaplan Meier log-rank comparison of treatment group vs. treatment control group. *p < 0.05, p < 0.01, *p < 0.001. % TGD values are not presented if mortality 40%.
ND = Not determined

In Vivo Rat Collagen Induced Arthritis Model

Compound of Example 36 inhibits paw swelling in a rat collagen induced arthritis (rCIA) model of inflammation. On day 0 of the rCIA model female Lewis rats (n=9/group) were immunized intradermally (id) with 600 µg of bovine type II collagen in an emulsion with incomplete Freund's adjuvant (IFA). Immunization was given over three sites receiving a 100 µL intradermal injection at each site. On day 6 rats were boosted with 600 µg of bovine type II collagen in a manner identical to the initial immunization protocol. A control group of rats received the same volume of IFA alone, also on day 0 and day 6. Using a plethysmograph water displacement system paw volume was measured on day 7 (baseline measurement) and on days 10, 12, 14 and 17. Dose groups included IFA immunized non-arthritic rats, PBS vehicle treated, prednisolone treated (3 mg/kg positive control), compound vehicle treated (10% EtOH/30% PEG400/60% Phosal 53) and Example 36 dosed orally at 1.0, 0.3, 0.1, and 0.03 mg/kg. Dosing began on day 10 and animals were treated once daily through day 17 via oral dosing with a 1.0 mL volume. Paw swelling is reported as change in paw volume from baseline and area under the curve (AUC) was calculated for the paw swelling in each dose group. Example 36 inhibited inflammation in the arthritic paw in a dose dependent manner with an $ED_{50}$ of 0.21 mg/kg and an $ED_{80}$ of 0.69 mg/kg corresponding to maximum plasma concentrations of 6.8 ng/mL and 22.3 ng/mL at the $ED_{50}$ and $ED_{80}$, respectively.

TABLE 8

| | AUC of Paw Swelling (ml-day) | |
|---|---|---|
| Treatment group | MEAN | SEM |
| IFA immunized (non-arthritic) | 0.13** | 0.06 |
| PBS Vehicle | 4.33 | 0.49 |
| Compound vehicle | 4.90 | 0.32 |
| Example 36 dosed at 1.0 mg/kg | 0.70** | 0.16 |
| Example 36 dosed at 0.3 mg/kg | 1.84** | 0.23 |
| Example 36 dosed at 0.1 mg/kg | 3.66* | 0.21 |
| Example 36 dosed at 0.03 mg/kg | 4.19 | 0.34 |
| Prednisolone dosed at 3 mg/kg | 0.67** | 0.20 |

One way Anova (vs. compound vehicle)
*p < 0.05
**p < 0.001

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All publications, patents, and patent applications cited herein are hereby incorporated by reference in their entirety for all purposes.

The invention claimed is:

1. A compound of formula (I) or a pharmaceutically acceptable salt thereof

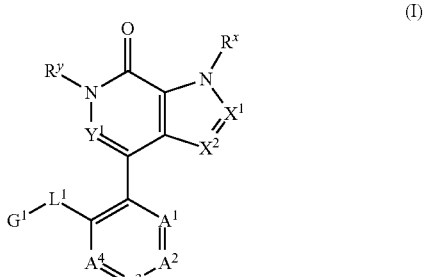

wherein $R^x$ is hydrogen or $C_1$-$C_3$ alkyl;

$R^y$ is $C_1$-$C_3$ alkyl, —($C_2$-$C_3$ alkylenyl)-OH, or $C_1$-$C_3$ haloalkyl;

$X^1$ is N or $CR^{x1}$ wherein $R^{x1}$ is hydrogen, $C_2$-$C_6$ alkenyl, $C_2$-$C_6$ alkynyl, —C(O)OR$^{ax1}$, —C(O)NR$^{bx1}$R$^{cx1}$, —C(O)R$^{dx1}$, S(O)$_2$R$^{dx1}$, —S(O)$_2$NR$^{bx1}$R$^{cx1}$, $G^{x1}$, $C_1$-$C_6$ haloalkyl, or $C_1$-$C_6$ alkyl; wherein the $C_1$-$C_6$ alkyl is optionally substituted with one substituent selected from the group consisting of OR$^{ax1}$, SR$^{ax1}$, S(O)R$^{dx1}$, S(O)$_2$R$^{dx1}$ NR$^{bx1}$R$^{cx1}$, —C(O)R$^{ax1}$, —C(O)OR$^{ax1}$, —C(O)NR$^{bx1}$R$^{cx1}$, —S(O)$_2$NR$^{bx1}$R$^{cx1}$, and $G^{x1}$;

$R^{ax1}$, $R^{bx1}$, and $R^{cx1}$, at each occurrence, are each independently hydrogen, $C_1$-$C_6$ alkyl, $C_1$-$C_6$ haloalkyl, $G^a$, or —($C_1$-$C_6$ alkylenyl)-$G^a$;

$R^{dx1}$, at each occurrence, is each independently $C_1$-$C_6$ alkyl, $C_1$-$C_6$ haloalkyl, $G^a$, or —($C_1$-$C_6$ alkylenyl)-$G^a$;

$X^2$ is N or $CR^{x2}$; wherein $R^{x2}$ is hydrogen, $C_2$-$C_6$ alkenyl, $C_2$-$C_6$ alkynyl, —C(O)OR$^{ax2}$, —C(O)NR$^{bx2}$R$^{cx2}$, —C(O)R$^{dx2}$, —C(O)H, S(O)$_2$R$^{dx2}$, —S(O)$_2$NR$^{bx2}$R$^{cx2}$, $G^{x2}$, $C_1$-$C_6$ haloalkyl, or $C_1$-$C_6$ alkyl; wherein the $C_1$-$C_6$ alkyl is optionally substituted with one substituent selected from the group consisting of OR$^{ax2}$, SR$^{ax2}$, S(O)R$^{dx2}$, S(O)$_2$R$^{dx2}$, NR$^{bx2}$R$^{cx2}$, —C(O)R$^{ax2}$, —C(O)OR$^{ax2}$, —C(O)NR$^{bx2}$, —S(O)$_2$NR$^{bx2}$R$^{cx2}$, and $G^{x2}$;

$R^{ax2}$, $R^{bx2}$, and $R^{cx2}$, at each occurrence, are each independently hydrogen, $C_1$-$C_6$ alkyl, $C_1$-$C_6$ haloalkyl, $G^b$, or —($C_1$-$C_6$ alkylenyl)-$G^b$;

$R^{dx2}$, at each occurrence, is independently $C_1$-$C_6$ alkyl, $C_1$-$C_6$ haloalkyl, $G^b$, or —($C_1$-$C_6$ alkylenyl)-$G^b$;

$Y^1$ is N or $CR^u$; wherein $R^u$ is hydrogen, $C_1$-$C_6$ alkyl, halogen, or $C_1$-$C_6$ haloalkyl;

$A^1$ is N or $CR^1$, $A^2$ is N or $CR^2$, $A^3$ is N or $CR^3$; and $A^4$ is N or $CR^4$; with a proviso that zero, one, two, or three of $A^1$, $A^2$, $A^3$, and $A^4$ are N;

$R^1$, $R^3$, and $R^4$ are each independently hydrogen, $C_1$-$C_6$ alkyl, $C_2$-$C_6$ alkenyl, $C_2$-$C_6$ alkynyl, halogen, $C_1$-$C_6$ haloalkyl, CN, or NO$_2$;

$R^2$ is hydrogen, $C_1$-$C_6$ alkyl, $C_2$-$C_6$ alkenyl, $C_2$-$C_6$ alkynyl, halogen, $C_1$-$C_6$ haloalkyl, —CN, NO$_2$, $G^{2a}$, —OR$^{2a}$, —OC(O)R$^{2d}$, —OC(O)NR$^{2b}$R$^{2c}$, —SR$^{2a}$, —S(O)$_2$R$^{2d}$, —S(O)$_2$NR$^{2b}$R$^{2c}$, —C(O)R$^{2d}$, —C(O)OR$^{2a}$, —C(O)NR$^{2b}$R$^{2c}$, —NR$^{2b}$R$^{2c}$, —N(R$^{2e}$)C(O)R$^{2d}$, —N(R$^{2e}$)S(O)$_2$R$^{2d}$, —N(R$^{2e}$)C(O)O(R$^{2d}$), —N(R$^{2e}$)C(O)NR$^{2b}$R$^{2c}$, —N(R$^{2e}$)S(O)$_2$NR$^{2b}$R$^{2c}$, —($C_1$-$C_6$ alkylenyl)-$G^{2a}$, —($C_1$-$C_6$ alkylenyl)-OR$^{2a}$, —($C_1$-$C_6$ alkylenyl)-OC(O)R$^{2d}$, —($C_1$-$C_6$ alkylenyl)-OC(O)NR$^{2b}$R$^{2c}$, —($C_1$-$C_6$ alkylenyl)-S(O)$_2$R$^{2d}$, —($C_1$-$C_6$ alkylenyl)-S(O)$_2$NR$^{2b}$R$^{2c}$, —($C_1$-$C_6$ alkylenyl)-C(O)R$^{2d}$, —($C_1$-$C_6$ alkylenyl)-C(O)OR$^{2a}$, —($C_1$-$C_6$ alkylenyl)-C(O)NR$^{2b}$R$^{2c}$, —($C_1$-$C_6$ alkylenyl)-NR$^{2b}$R$^{2c}$, —($C_1$-$C_6$ alkylenyl)-N(R$^{2e}$)C(O)R$^{2d}$, —($C_1$-$C_6$ alkylenyl)-N(R$^{2e}$)S(O)$_2$R$^{2d}$, —($C_1$-$C_6$ alkylenyl)-N(R$^{2e}$)C(O)O(R$^{2a}$), —($C_1$-$C_6$ alkylenyl)-N(R$^{2e}$)C(O)NR$^{2b}$R$^{2c}$, —($C_1$-$C_6$ alkylenyl)-N(R$^{2e}$)S(O)$_2$NR$^{2b}$R$^{2c}$, and —($C_1$-$C_6$ alkylenyl)-CN;

$R^{2a}$, $R^{2b}$, $R^{2c}$, and $R^{2e}$, at each occurrence, are each independently hydrogen, $C_2$-$C_6$ alkenyl, $C_2$-$C_6$ alkynyl, $C_1$-$C_6$ haloalkyl, $G^{2b}$, or $C_1$-$C_6$ alkyl wherein the $C_1$-$C_6$ alkyl is optionally substituted with one substituent selected from the group consisting of —OR$^{z1}$, NR$^{z1}$R$^{z2}$, —C(O)OR$^{z1}$, —C(O)NR$^{z1}$R$^{z2}$, —S(O)$_2$R$^{z1}$, —S(O)$_2$NR$^{z1}$R$^{z2}$, and $G^{2b}$;

$R^{2d}$, at each occurrence, is independently $C_2$-$C_6$ alkenyl, $C_2$-$C_6$ alkynyl, $C_1$-$C_6$ haloalkyl, $G^{2b}$, or $C_1$-$C_6$ alkyl wherein the $C_1$-$C_6$ alkyl is optionally substituted with one substituent selected from the group consisting of —OR$^{z1}$, NR$^{z1}$R$^{z2}$, —C(O)OR$^{z1}$, —C(O)NR$^{z1}$R$^{z2}$, —S(O)$_2$R$^{z1}$, —S(O)$_2$NR$^{z1}$R$^{z2}$, and $G^{2b}$;

$R^{z1}$ and $R^{z2}$, at each occurrence, are each independently hydrogen, $C_1$-$C_6$ alkyl, or $C_1$-$C_6$ haloalkyl;

$G^{x1}$, $G^{x2}$, $G^a$, $G^b$, $G^{2a}$, and $G^{2b}$, at each occurrence, are each independently aryl, heteroaryl, heterocycle, cycloalkyl, or cycloalkenyl, and each of which is independently unsubstituted or substituted with 1, 2, 3, 4, or 5 of $R^v$;

$L^1$ is absent, CH$_2$, C(O), C(H)(OH), (CH$_2$)$_m$O, (CH$_2$)$_m$S(O)$_n$ wherein n is 0, 1, or 2; or (CH$_2$)$_m$N(R$^z$) wherein R$^z$ is hydrogen, $C_1$-$C_3$ alkyl, $C_1$-$C_3$ haloalkyl, ($C_2$-$C_3$ alkylenyl)-OH, or unsubstituted cyclopropyl;

m is 0 or 1;

$G^1$ is $C_1$-$C_6$ alkyl, alkoxyalkyl, $G^{1a}$ or —($C_1$-$C_6$ alkylenyl)-$G^{1a}$; wherein each $G^{1a}$ is independently aryl, heteroaryl, heterocycle, cycloalkyl, or cycloalkenyl, and each $G^{1a}$ is independently unsubstituted or substituted with 1, 2, 3, 4, or 5 of $R^w$;

$R^v$ and $R^w$, at each occurrence, are each independently $C_1$-$C_6$ alkyl, $C_2$-$C_6$ alkenyl, $C_2$-$C_6$ alkynyl, halogen, $C_1$-$C_6$ haloalkyl, —CN, oxo, —OR$^h$, —OC(O)R$^i$, —OC(O)NR$^j$R$^k$, —SR$^h$, —S(O)$_2$R$^h$, —S(O)$_2$NR$^j$R$^k$, —C(O)R$^h$, —C(O)-monocyclic heterocycle, —C(O)-monocyclic heteroaryl, —C(O)OR$^h$, —C(O)NR$^j$R$^k$, —NR$^j$R$^k$, —N(R$^h$)C(O)R$^i$, —N(R$^h$)S(O)$_2$R$^i$, —N(R$^h$)C(O)O(R$^i$), —N(R$^h$)C(O)NR$^j$R$^k$, —($C_1$-$C_6$ alkylenyl)-OR$^h$, —($C_1$-$C_6$ alkylenyl)-OC(O)R$^i$, —($C_1$-$C_6$ alkylenyl)-OC(O)NR$^j$R$^k$, —($C_1$-$C_6$ alkylenyl)-S(O)$_2$R$^h$, —($C_1$-$C_6$ alkylenyl)-S(O)$_2$NR$^j$R$^k$, —($C_1$-$C_6$ alkylenyl)-C(O)R$^h$, —($C_1$-$C_6$ alkylenyl)-C(O)OR$^h$, —($C_1$-$C_6$ alkylenyl)-C(O)NR$^j$R$^k$, —($C_1$-$C_6$ alkylenyl)-NR$^j$R$^k$, —($C_1$-$C_6$ alkylenyl)-N(R$^h$)C(O)R$^i$, —($C_1$-$C_6$ alkylenyl)-N(R$^h$)S(O)$_2$R$^i$, —($C_1$-$C_6$ alkylenyl)-N(R$^h$)C(O)O(R$^1$), —($C_1$-$C_6$ alkylenyl)-N(R$^h$)C(O)NR$^j$R$^k$, or —($C_1$-$C_6$ alkylenyl)-CN;

$R^h$, $R^j$, $R^k$, at each occurrence, are each independently hydrogen, $C_1$-$C_6$ alkyl, or $C_1$-$C_6$ haloalkyl; and $R^i$, at each occurrence, is independently $C_1$-$C_6$ alkyl or $C_1$-$C_6$ haloalkyl.

2. A compound of formula (I) or a pharmaceutically acceptable salt thereof wherein $R^x$ is hydrogen or $C_1$-$C_3$ alkyl;

$R^y$ is $C_1$-$C_3$ alkyl, —($C_2$-$C_3$ alkylenyl)-OH, or $C_1$-$C_3$ haloalkyl;

$X^1$ is N or $CR^{x1}$ wherein $R^{x1}$ is hydrogen, $C_2$-$C_6$ alkenyl, $C_2$-$C_6$ alkynyl, —C(O)OR$^{ax1}$, —C(O)NR$^{bx1}$R$^{cx1}$, —C(O)R$^{dx1}$, S(O)$_2$R$^{dx1}$, —S(O)$_2$NR$^{bx1}$R$^{cx1}$, G$^{x1}$, C$_1$-C$_6$ haloalkyl, or C$_1$-C$_6$ alkyl; wherein the C$_1$-C$_6$ alkyl is optionally substituted with one substituent selected from the group consisting of OR$^{ax1}$, SR$^{ax1}$, S(O)R$^{dx1}$, S(O)$_2$R$^{dx1}$, NR$^{bx1}$R$^{cx1}$, —C(O)R$^{ax1}$, —C(O)OR$^{ax1}$, —C(O)NR$^{bx1}$R$^{cx1}$, —S(O)$_2$NR$^{bx1}$R$^{cx1}$ and G$^{x1}$;

R$^{ax1}$, R$^{bx1}$, and R$^{cx1}$, at each occurrence, are each independently hydrogen, C$_1$-C$_6$ alkyl, C$_1$-C$_6$ haloalkyl, G$^a$, or —(C$_1$-C$_6$ alkylenyl)-G$^a$;

R$^{dx1}$, at each occurrence, is each independently C$_1$-C$_6$ alkyl, C$_1$-C$_6$ haloalkyl, G$^a$, or —(C$_1$-C$_6$ alkylenyl)-G$^a$;

X$^2$ is N or CR$^{x2}$; wherein

R$^{x2}$ is hydrogen, C$_2$-C$_6$ alkenyl, C$_2$-C$_6$ alkynyl, —C(O)OR$^{ax2}$, —C(O)NR$^{bx2}$R$^{cx2}$, —C(O)R$^{dx2}$, S(O)$_2$R$^{dx2}$, —S(O)$_2$NR$^{bx2}$R$^{cx2}$, G$^{x2}$, C$_1$-C$_6$ haloalkyl, or C$_1$-C$_6$ alkyl; wherein the C$_1$-C$_6$ alkyl is optionally substituted with one substituent selected from the group consisting of OR$^{ax2}$, SR$^{ax2}$, S(O)R$^{dx2}$, S(O)$_2$R$^{dx2}$, NR$^{bx2}$R$^{cx2}$, —C(O)R$^{ax2}$, —C(O)OR$^{ax2}$, —C(O)NR$^{bx2}$R$^{cx2}$, —S(O)$_2$NR$^{bx2}$R$^{cx2}$, and G$^{x2}$;

R$^{ax2}$, R$^{bx2}$, and R$^{cx2}$, at each occurrence, are each independently hydrogen, C$_1$-C$_6$ alkyl, C$_1$-C$_6$ haloalkyl, G$^b$, or —(C$_1$-C$_6$ alkylenyl)-G$^b$;

R$^{dx2}$, at each occurrence, is independently C$_1$-C$_6$ alkyl, C$_1$-C$_6$ haloalkyl, G$^b$, or —(C$_1$-C$_6$ alkylenyl)-G$^b$;

Y$^1$ is N or CR$^u$; wherein R$^u$ is hydrogen, C$_1$-C$_6$ alkyl, halogen, or C$_1$-C$_6$ haloalkyl;

A$^1$ is N or CR$^1$, A$^2$ is N or CR$^2$, A$^3$ is N or CR$^3$; and A$^4$ is N or CR$^4$; with a proviso that zero, one, two, or three of A$^1$, A$^2$, A$^3$, and A$^4$ are N;

R$^1$, R$^3$, and R$^4$ are each independently hydrogen, C$_1$-C$_6$ alkyl, C$_2$-C$_6$ alkenyl, C$_2$-C$_6$ alkynyl, halogen, C$_1$-C$_6$ haloalkyl, CN, or NO$_2$;

R$^2$ is hydrogen, C$_1$-C$_6$ alkyl, C$_2$-C$_6$ alkenyl, C$_2$-C$_6$ alkynyl, halogen, C$_1$-C$_6$ haloalkyl, —CN, NO$_2$, G$^{2a}$, —OR$^{2a}$, —OC(O)R$^{2d}$, —OC(O)NR$^{2b}$R$^{2c}$, —SR$^{2a}$, —S(O)$_2$R$^{2d}$, —S(O)$_2$NR$^{2b}$R$^{2c}$, —C(O)R$^{2d}$, —C(O)OR$^{2a}$, —C(O)NR$^{2b}$R$^{2c}$, —NR$^{2b}$R$^{2c}$, —N(R$^{2e}$)C(O)R$^{2d}$, —N(R$^{2e}$)S(O)$_2$R$^{2d}$, —N(R$^{2e}$)C(O)O(R$^{2d}$), —N(R$^{2e}$)C(O)NR$^{2b}$R$^{2c}$, —N(R$^{2e}$)S(O)$_2$NR$^{2b}$R$^{2c}$, —(C$_1$-C$_6$ alkylenyl)-G$^{2a}$, —(C$_1$-C$_6$ alkylenyl)-OR$^{2a}$, —(C$_1$-C$_6$ alkylenyl)-OC(O)R$^{2d}$, —(C$_1$-C$_6$ alkylenyl)-OC(O)NR$^{2b}$R$^{2c}$, —(C$_1$-C$_6$ alkylenyl)-S(O)$_2$R$^{2d}$, —(C$_1$-C$_6$ alkylenyl)-S(O)$_2$NR$^{2b}$R$^{2c}$, —(C$_1$-C$_6$ alkylenyl)-C(O)R$^{2d}$, —(C$_1$-C$_6$ alkylenyl)-C(O)OR$^{2a}$, —(C$_1$-C$_6$ alkylenyl)-C(O)NR$^{2b}$R$^{2c}$, —(C$_1$-C$_6$ alkylenyl)-NR$^{2b}$R$^{2c}$, —(C$_1$-C$_6$ alkylenyl)-N(R$^{2e}$)C(O)R$^{2d}$, —(C$_1$-C$_6$ alkylenyl)-N(R$^{2e}$)S(O)$_2$R$^{2d}$, —(C$_1$-C$_6$ alkylenyl)-N(R$^{2e}$)C(O)O(R$^{2a}$), —(C$_1$-C$_6$ alkylenyl)-N(R$^{2e}$)C(O)NR$^{2b}$R$^{2c}$, —(C$_1$-C$_6$ alkylenyl)-N(R$^{2e}$)S(O)$_2$NR$^{2b}$R$^{2c}$, and —(C$_1$-C$_6$ alkylenyl)-CN;

R$^{2a}$, R$^{2b}$, R$^{2c}$, and R$^{2e}$, at each occurrence, are each independently hydrogen, C$_2$-C$_6$ alkenyl, C$_2$-C$_6$ alkynyl, C$_1$-C$_6$ haloalkyl, G$^{2b}$, or C$_1$-C$_6$ alkyl wherein the C$_1$-C$_6$ alkyl is optionally substituted with one substituent selected from the group consisting of —OR$^{z1}$, NR$^{z1}$R$^{z2}$, —C(O)OR$^{z1}$, —C(O)NR$^{z1}$R$^{z2}$, —S(O)$_2$R$^{z1}$, —S(O)$_2$NR$^{z1}$R$^{z2}$, and G$^{2b}$;

R$^{2d}$, at each occurrence, is independently C$_2$-C$_6$ alkenyl, C$_2$-C$_6$ alkynyl, C$_1$-C$_6$ haloalkyl, G$^{2b}$, or C$_1$-C$_6$ alkyl wherein the C$_1$-C$_6$ alkyl is optionally substituted with one substituent selected from the group consisting of —OR$^{z1}$, NR$^{z1}$R$^{z2}$, —C(O)OR$^{z1}$, —C(O)NR$^{z1}$R$^{z2}$, —S(O)$_2$R$^{z1}$, —S(O)$_2$NR$^{z1}$R$^{z2}$, and G$^{2b}$;

R$^{z1}$ and R$^{z2}$, at each occurrence, are each independently hydrogen, C$_1$-C$_6$ alkyl, or C$_1$-C$_6$ haloalkyl;

G$^{x1}$, G$^{x2}$, G$^a$, G$^{2a}$, and G$^{2b}$, at each occurrence, are each independently aryl, heteroaryl, heterocycle, cycloalkyl, or cycloalkenyl, and each of which is independently unsubstituted or substituted with 1, 2, 3, 4, or 5 of R$^v$;

L$^1$ is absent, CH$_2$, C(O), (CH$_2$)$_m$O, (CH$_2$)$_m$S(O)$_n$ wherein n is 0, 1, or 2; or (CH$_2$)$_m$N(R$^z$) wherein R$^z$ is hydrogen, C$_1$-C$_3$ alkyl, C$_1$-C$_3$ haloalkyl, (C$_2$-C$_3$ alkylenyl)-OH, or unsubstituted cyclopropyl;

m is 0 or 1;

G$^1$ is G$^{1a}$ or —(C$_1$-C$_6$ alkylenyl)-G$^{1a}$; wherein each G$^{1a}$ is independently aryl, heteroaryl, heterocycle, cycloalkyl, or cycloalkenyl, and each G$^{1a}$ is independently unsubstituted or substituted with 1, 2, 3, 4, or 5 of R$^w$;

R$^v$ and R$^w$, at each occurrence, are each independently C$_1$-C$_6$ alkyl, C$_2$-C$_6$ alkenyl, C$_2$-C$_6$ alkynyl, halogen, C$_1$-C$_6$ haloalkyl, —CN, oxo, —OR$^h$, —OC(O)R$^i$, —OC(O)NR$^j$R$^k$, —SR$^h$, —S(O)$_2$R$^h$, —S(O)$_2$NR$^j$R$^k$, —C(O)R$^h$, —C(O)OR$^h$, —C(O)NR$^j$R$^k$, —NR$^j$R$^k$, —N(R$^h$)C(O)R$^i$, —N(R$^h$)S(O)$_2$R$^i$, —N(R$^h$)C(O)O(R$^i$), —N(R$^h$)C(O)NR$^j$R$^k$, —(C$_1$-C$_6$ alkylenyl)-OR$^h$, —(C$_1$-C$_6$ alkylenyl)-OC(O)R$^i$, —(C$_1$-C$_6$ alkylenyl)-OC(O)NR$^j$R$^k$, —(C$_1$-C$_6$ alkylenyl)-S(O)$_2$R$^h$, —(C$_1$-C$_6$ alkylenyl)-S(O)$_2$NR$^j$R$^k$, —(C$_1$-C$_6$ alkylenyl)-C(O)R$^h$, —(C$_1$-C$_6$ alkylenyl)-C(O)OR$^h$, —(C$_1$-C$_6$ alkylenyl)-C(O)NR$^j$R$^k$, —(C$_1$-C$_6$ alkylenyl)-NR$^j$R$^k$, —(C$_1$-C$_6$ alkylenyl)-N(R$^h$)C(O)R$^i$, —(C$_1$-C$_6$ alkylenyl)-N(R$^h$)S(O)$_2$R$^i$, —(C$_1$-C$_6$ alkylenyl)-N(R$^h$)C(O)O(R$^i$), —(C$_1$-C$_6$ alkylenyl)-N(R$^h$)C(O)NR$^j$R$^k$, or —(C$_1$-C$_6$ alkylenyl)-CN;

R$^h$, R$^j$, R$^k$, at each occurrence, are each independently hydrogen, C$_1$-C$_6$ alkyl, or C$_1$-C$_6$ haloalkyl; and R$^i$, at each occurrence, is independently C$_1$-C$_6$ alkyl or C$_1$-C$_6$ haloalkyl.

3. The compound of claim 1 or a pharmaceutically acceptable salt thereof,
wherein R$^y$ is C$_1$-C$_3$ alkyl.

4. The compound of claim 1 or a pharmaceutically acceptable salt thereof,
wherein R$^y$ is methyl.

5. The compound of claim 1 or a pharmaceutically acceptable salt thereof,
wherein X$^1$ is CR$^{x1}$; and
X$^2$ is CR$^{x2}$.

6. The compound of claim 1 or a pharmaceutically acceptable salt thereof,
wherein Y$^1$ is N.

7. The compound of claim 1 or a pharmaceutically acceptable salt thereof,
wherein Y$^1$ is CR$^u$.

8. The compound of claim 7 or a pharmaceutically acceptable salt thereof, wherein
R$^u$ is hydrogen or C$_1$-C$_3$ alkyl.

9. The compound of claim 1 or a pharmaceutically acceptable salt thereof,
wherein L$^1$ is CH$_2$, C(O), (CH$_2$)$_m$O, or (CH$_2$)$_m$N(R$^z$).

10. The compound of claim 1 or a pharmaceutically acceptable salt thereof,
wherein L$^1$ is (CH$_2$)$_m$O and G$^1$ is G$^{1a}$.

11. The compound of claim 1 or a pharmaceutically acceptable salt thereof,
wherein A$^1$ is CR$^1$;
A$^2$ is CR$^2$;
A$^3$ is CR$^3$; and
A$^4$ is CR$^4$.

12. The compound of claim 1 or a pharmaceutically acceptable salt thereof,
wherein one of A$^1$, A$^2$, A$^3$, and A$^4$ is N.

13. The compound of claim 1 or a pharmaceutically acceptable salt thereof,
wherein
$R^2$ is hydrogen, $C_1$-$C_6$ alkyl, $NO_2$, $G^{2a}$, —$S(O)_2R^{2d}$, —$S(O)_2NR^{2b}R^{2c}$, —$C(O)R^{2d}$, —$C(O)OR^{2a}$, —$C(O)NR^{2b}R^{2c}$, —$NR^{2b}R^{2c}$, —$N(R^{2e})C(O)R^{2d}$, —$N(R^{2e})S(O)_2R^{2d}$, —$N(R^{2e})S(O)_2NR^{2b}R^{2c}$, —($C_1$-$C_6$ alkylenyl)-$G^{2a}$, —($C_1$-$C_6$ alkylenyl)-$OR^{2a}$, —($C_1$-$C_6$ alkylenyl)-$S(O)_2R^{2d}$, —($C_1$-$C_6$ alkylenyl)-$S(O)_2NR^{2b}R^{2c}$, —($C_1$-$C_6$ alkylenyl)-$C(O)R^{2d}$, —($C_1$-$C_6$ alkylenyl)-$C(O)OR^{2a}$, —($C_1$-$C_6$ alkylenyl)-$C(O)NR^{2b}R^{2c}$, —($C_1$-$C_6$ alkylenyl)-$NR^{2b}R^{2c}$, —($C_1$-$C_6$ alkylenyl)-$N(R^{2e})C(O)R^{2d}$, —($C_1$-$C_6$ alkylenyl)-$N(R^{2e})S(O)_2R^{2d}$, or —($C_1$-$C_6$ alkylenyl)-$N(R^{2e})S(O)_2NR^{2b}R^{2c}$.

14. The compound of claim 1 or a pharmaceutically acceptable salt thereof,
wherein
$R^2$ is —$S(O)_2R^{2d}$, —$S(O)_2NR^{2b}R^{2c}$, —$C(O)R^{2d}$, —$C(O)NR^{2b}R^{2c}$, —$N(R^{2e})C(O)R^{2d}$, —$N(R^{2e})S(O)_2R^{2d}$, —$N(R^{2e})S(O)_2NR^{2b}R^{2c}$, —($C_1$-$C_6$ alkylenyl)-$S(O)_2R^{2d}$, —($C_1$-$C_6$ alkylenyl)-$S(O)_2NR^{2b}R^{2c}$, —($C_1$-$C_6$ alkylenyl)-$C(O)R^{2d}$, —($C_1$-$C_6$ alkylenyl)-$C(O)NR^{2b}R^{2c}$, —($C_1$-$C_6$ alkylenyl)-$N(R^{2e})C(O)R^{2d}$, —($C_1$-$C_6$ alkylenyl)-$N(R^{2e})S(O)_2R^{2d}$, or —($C_1$-$C_6$ alkylenyl)-$N(R^{2e})S(O)_2NR^{2b}R^{2c}$.

15. The compound of claim 1 or a pharmaceutically acceptable salt thereof,
wherein
$R^2$ is —$S(O)_2R^{2d}$, —$S(O)_2NR^{2b}R^{2c}$, —$N(R^{2e})S(O)_2R^{2d}$ or —$N(R^{2e})S(O)_2NR^{2b}R^{2c}$.

16. The compound of claim 1 or a pharmaceutically acceptable salt thereof, wherein
$Y^1$ is N;
$X^1$ is $CR^{x1}$; and
$X^2$ is $CR^{x2}$.

17. The compound of claim 16 or a pharmaceutically acceptable salt thereof, wherein the compound is selected from the group consisting of:
ethyl 4-(5-amino-2-phenoxyphenyl)-6-methyl-7-oxo-6,7-dihydro-1H-pyrrolo[2,3-d]pyridazine-2-carboxylate;
ethyl 4-[5-(ethylamino)-2-phenoxyphenyl]-6-methyl-7-oxo-6,7-dihydro-1H-pyrrolo[2,3-d]pyridazine-2-carboxylate;
ethyl 4-{5-[ethyl(methylsulfonyl)amino]-2-phenoxyphenyl}-6-methyl-7-oxo-6,7-dihydro-1H-pyrrolo[2,3-d]pyridazine-2-carboxylate;
6-methyl-4-{5-[(methylsulfonyl)amino]-2-phenoxyphenyl}-7-oxo-6,7-dihydro-1H-pyrrolo[2,3-d]pyridazine-2-carboxylic acid;
6-methyl-4-{5-[(methylsulfonyl)amino]-2-phenoxyphenyl}-7-oxo-6,7-dihydro-1H-pyrrolo[2,3-d]pyridazine-2-carboxamide;
6-methyl-N-[2-(4-methylpiperazin-1-yl)ethyl]-4-{5-[(methylsulfonyl)amino]-2-phenoxyphenyl}-7-oxo-6,7-dihydro-1H-pyrrolo[2,3-d]pyridazine-2-carboxamide;
N-[3-(6-methyl-7-oxo-6,7-dihydro-1H-pyrrolo[2,3-d]pyridazin-4-yl)-4-phenoxyphenyl]methanesulfonamide;
N-ethyl-6-methyl-4-{5-[(methylsulfonyl)amino]-2-phenoxyphenyl}-7-oxo-6,7-dihydro-1H-pyrrolo[2,3-d]pyridazine-2-carboxamide;
6-methyl-4-(2-phenoxyphenyl)-1,6-dihydro-7H-pyrrolo[2,3-d]pyridazin-7-one;
N-ethyl-N,6-dimethyl-4-{5-[(methylsulfonyl)amino]-2-phenoxyphenyl}-7-oxo-6,7-dihydro-1H-pyrrolo[2,3-d]pyridazine-2-carboxamide;
4-[5-amino-2-(2,4-difluorophenoxy)phenyl]-6-methyl-1,6-dihydro-7H-pyrrolo[2,3-d]pyridazin-7-one;
N-[4-(2,4-difluorophenoxy)-3-(6-methyl-7-oxo-6,7-dihydro-1H-pyrrolo[2,3-d]pyridazin-4-yl)phenyl]methanesulfonamide;
N-[4-(2,4-difluorophenoxy)-3-(6-methyl-7-oxo-6,7-dihydro-1H-pyrrolo[2,3-d]pyridazin-4-yl)phenyl]ethanesulfonamide; and
4-[2-(cyclopropylmethoxy)-5-(ethylsulfonyl)phenyl]-6-methyl-1,6-dihydro-7H-pyrrolo[2,3-d]pyridazin-7-one.

18. The compound of claim 16 or a pharmaceutically acceptable salt thereof, wherein
$R^y$ is methyl.

19. The compound of claim 18 or a pharmaceutically acceptable salt thereof, wherein
$L^1$ is $CH_2$, $C(O)$, $(CH_2)_mO$, or $(CH_2)_mN(R^z)$.

20. The compound of claim 18, or a pharmaceutically acceptable salt thereof, wherein
$L^1$ is $(CH_2)_mO$.

21. The compound of claim 20 or a pharmaceutically acceptable salt thereof, wherein
$G^1$ is $G^{1a}$.

22. The compound of claim 21 or a pharmaceutically acceptable salt thereof, wherein
$G^{1a}$ is optionally substituted aryl.

23. The compound of claim 21 or a pharmaceutically acceptable salt thereof, wherein $G^{1a}$ is optionally substituted phenyl.

24. The compound of claim 21 or a pharmaceutically acceptable salt thereof, wherein
$G^{1a}$ is optionally substituted cycloalkyl.

25. The compound of claim 21 or a pharmaceutically acceptable salt thereof, wherein
$G^{1a}$ is optionally substituted monocyclic cycloalkyl.

26. The compound of claim 21 or a pharmaceutically acceptable salt thereof, wherein
$G^{1a}$ is optionally substituted heterocycle.

27. The compound of claim 21 or a pharmaceutically acceptable salt thereof, wherein
$G^{1a}$ is optionally substituted monocyclic heterocycle.

28. The compound of claim 1 or a pharmaceutically acceptable salt thereof, wherein
$Y^1$ is $CR^u$;
$X^1$ is $CR^{x1}$; and
$X^2$ is $CR^{x2}$.

29. The compound of claim 28 or a pharmaceutically acceptable salt thereof, wherein the compound is selected from the group consisting of
6-methyl-4-(2-phenoxyphenyl)-1,6-dihydro-7H-pyrrolo[2,3-c]pyridin-7-one;
6-methyl-4-(5-nitro-2-phenoxyphenyl)-1,6-dihydro-7H-pyrrolo[2,3-c]pyridin-7-one;
4-(5-amino-2-phenoxyphenyl)-6-methyl-1,6-dihydro-7H-pyrrolo[2,3-c]pyridin-7-one;
N-[3-(6-methyl-7-oxo-6,7-dihydro-1H-pyrrolo[2,3-c]pyridin-4-yl)-4-phenoxyphenyl]methanesulfonamide;
2,2,2-trifluoro-N-[3-(6-methyl-7-oxo-6,7-dihydro-1H-pyrrolo[2,3-c]pyridin-4-yl)-4-phenoxyphenyl]ethanesulfonamide;
N-[3-(6-methyl-7-oxo-6,7-dihydro-1H-pyrrolo[2,3-c]pyridin-4-yl)-4-phenoxyphenyl]acetamide;
N-methyl-N-[3-(6-methyl-7-oxo-6,7-dihydro-1H-pyrrolo[2,3-c]pyridin-4-yl)-4-phenoxyphenyl]methanesulfonamide;
ethyl 3-(6-methyl-7-oxo-6,7-dihydro-1H-pyrrolo[2,3-c]pyridin-4-yl)-4-phenoxybenzoate;

3-(6-methyl-7-oxo-6,7-dihydro-1H-pyrrolo[2,3-c]pyridin-4-yl)-4-phenoxybenzoic acid;
N-[3-(6-methyl-7-oxo-6,7-dihydro-1H-pyrrolo[2,3-c]pyridin-4-yl)-4-(pyridin-3-yloxy)phenyl]methanesulfonamide;
6-methyl-4-[2-(morpholin-4-ylmethyl)phenyl]-1,6-dihydro-7H-pyrrolo[2,3-c]pyridin-7-one;
N-ethyl-3-(6-methyl-7-oxo-6,7-dihydro-1H-pyrrolo[2,3-c]pyridin-4-yl)-4-phenoxybenzamide;
3-(6-methyl-7-oxo-6,7-dihydro-1H-pyrrolo[2,3-c]pyridin-4-yl)-4-phenoxy-N-(tetrahydrofuran-2-ylmethyl)benzamide;
N-cyclopentyl-3-(6-methyl-7-oxo-6,7-dihydro-1H-pyrrolo[2,3-c]pyridin-4-yl)-4-phenoxybenzamide;
N-(2,2-difluoroethyl)-3-(6-methyl-7-oxo-6,7-dihydro-1H-pyrrolo[2,3-c]pyridin-4-yl)-4-phenoxybenzamide;
3-(6-methyl-7-oxo-6,7-dihydro-1H-pyrrolo[2,3-c]pyridin-4-yl)-4-phenoxy-N-(1,3-thiazol-2-yl)benzamide;
N-(1,1-dioxidotetrahydrothiophen-3-yl)-3-(6-methyl-7-oxo-6,7-dihydro-1H-pyrrolo[2,3-c]pyridin-4-yl)-4-phenoxybenzamide;
3-(6-methyl-7-oxo-6,7-dihydro-1H-pyrrolo[2,3-c]pyridin-4-yl)-4-phenoxybenzamide;
4-[5-(hydroxymethyl)-2-phenoxyphenyl]-6-methyl-1,6-dihydro-7H-pyrrolo[2,3-c]pyridin-7-one;
N-[3-(6-methyl-7-oxo-6,7-dihydro-1H-pyrrolo[2,3-c]pyridin-4-yl)-4-phenoxyphenyl]ethanesulfonamide;
N,N-dimethyl-N'-[3-(6-methyl-7-oxo-6,7-dihydro-1H-pyrrolo[2,3-c]pyridin-4-yl)-4-phenoxyphenyl]sulfuric diamide;
N-[5-(6-methyl-7-oxo-6,7-dihydro-1H-pyrrolo[2,3-c]pyridin-4-yl)-6-phenoxypyridin-3-yl]methanesulfonamide;
N-[3-fluoro-5-(6-methyl-7-oxo-6,7-dihydro-1H-pyrrolo[2,3-c]pyridin-4-yl)-4-phenoxyphenyl]methanesulfonamide;
N-[4-(2-cyanophenoxy)-3-(6-methyl-7-oxo-6,7-dihydro-1H-pyrrolo[2,3-c]pyridin-4-yl)phenyl]methanesulfonamide;
N-[4-(4-fluorophenoxy)-3-(6-methyl-7-oxo-6,7-dihydro-1H-pyrrolo[2,3-c]pyridin-4-yl)phenyl]methanesulfonamide;
N-[4-(2,4-difluorophenoxy)-3-(6-methyl-7-oxo-6,7-dihydro-1H-pyrrolo[2,3-c]pyridin-4-yl)phenyl]methanesulfonamide;
N-[3-chloro-5-(6-methyl-7-oxo-6,7-dihydro-1H-pyrrolo[2,3-c]pyridin-4-yl)-4-phenoxyphenyl]methanesulfonamide;
N-[3-(6-methyl-7-oxo-6,7-dihydro-1H-pyrrolo[2,3-c]pyridin-4-yl)-4-(tetrahydro-2H-pyran-4-yloxy)phenyl]methanesulfonamide;
6-methyl-4-[2-phenoxy-5-(1H-pyrazol-1-ylmethyl)phenyl]-1,6-dihydro-7H-pyrrolo[2,3-c]pyridin-7-one;
N-[3-(6-methyl-7-oxo-6,7-dihydro-1H-pyrrolo[2,3-c]pyridin-4-yl)-4-(tetrahydrofuran-3-yloxy)phenyl]methanesulfonamide;
N-{3-(6-methyl-7-oxo-6,7-dihydro-1H-pyrrolo[2,3-c]pyridin-4-yl)-4-[2-(trifluoromethyl)phenoxy]phenyl}methanesulfonamide;
N-[4-(4-cyanophenoxy)-3-(6-methyl-7-oxo-6,7-dihydro-1H-pyrrolo[2,3-c]pyridin-4-yl)phenyl]methanesulfonamide;
N-[4-(2-chloro-4-fluorophenoxy)-3-(6-methyl-7-oxo-6,7-dihydro-1H-pyrrolo[2,3-c]pyridin-4-yl)phenyl]methanesulfonamide;
[4-(benzyloxy)-3-(6-methyl-7-oxo-6,7-dihydro-1H-pyrrolo[2,3-c]pyridin-4-yl)phenyl]acetic acid;
N-[4-(2,4-difluorophenoxy)-3-(6-methyl-7-oxo-6,7-dihydro-1H-pyrrolo[2,3-c]pyridin-4-yl)phenyl]ethanesulfonamide;
N-[4-(2,4-difluorophenoxy)-3-(6-methyl-7-oxo-6,7-dihydro-1H-pyrrolo[2,3-c]pyridin-4-yl)phenyl]acetamide;
N-[4-(2,4-difluorophenoxy)-3-(6-methyl-7-oxo-6,7-dihydro-1H-pyrrolo[2,3-c]pyridin-4-yl)phenyl]-3,3,3-trifluoropropanamide;
N-[4-(2,4-difluorophenoxy)-3-(6-methyl-7-oxo-6,7-dihydro-1H-pyrrolo[2,3-c]pyridin-4-yl)phenyl]-2,2-dimethylpropanamide;
ethyl 4-(cyclopentylamino)-3-(6-methyl-7-oxo-6,7-dihydro-1H-pyrrolo[2,3-c]pyridin-4-yl)benzoate;
4-{5-[(1,1-dioxido-1,2-thiazolidin-2-yl)methyl]-2-phenoxyphenyl}-6-methyl-1,6-dihydro-7H-pyrrolo[2,3-c]pyridin-7-one;
4-{[3-(6-methyl-7-oxo-6,7-dihydro-1H-pyrrolo[2,3-c]pyridin-4-yl)-4-phenoxybenzyl]amino}-4-oxobutanoic acid;
4-[2-(2,4-difluorophenoxy)-5-(1,1-dioxido-1,2-thiazolidin-2-yl)phenyl]-6-methyl-1,6-dihydro-7H-pyrrolo[2,3-c]pyridin-7-one;
4-[2-(benzyloxy)-5-(2-hydroxyethyl)phenyl]-6-methyl-1,6-dihydro-7H-pyrrolo[2,3-c]pyridin-7-one;
methyl [4-(benzyloxy)-3-(6-methyl-7-oxo-6,7-dihydro-1H-pyrrolo[2,3-c]pyridin-4-yl)phenyl]acetate;
2-[4-(benzyloxy)-3-(6-methyl-7-oxo-6,7-dihydro-1H-pyrrolo[2,3-c]pyridin-4-yl)phenyl]-N-ethylacetamide;
2-[4-(benzyloxy)-3-(6-methyl-7-oxo-6,7-dihydro-1H-pyrrolo[2,3-c]pyridin-4-yl)phenyl]-N,N-dimethylacetamide;
N-[4-(3,4-difluorophenoxy)-3-(6-methyl-7-oxo-6,7-dihydro-1H-pyrrolo[2,3-c]pyridin-4-yl)phenyl]methanesulfonamide;
N-[3-(6-methyl-7-oxo-6,7-dihydro-1H-pyrrolo[2,3-c]pyridin-4-yl)-4-(2,4,6-trifluorophenoxy)phenyl]methanesulfonamide;
4-(2,4-difluorophenoxy)-3-(6-methyl-7-oxo-6,7-dihydro-1H-pyrrolo[2,3-c]pyridin-4-yl)benzamide;
4-(2,4-difluorophenoxy)-3-(6-methyl-7-oxo-6,7-dihydro-1H-pyrrolo[2,3-c]pyridin-4-yl)-N-(tetrahydrofuran-3-yl)benzamide;
4-{2-(2,4-difluorophenoxy)-5-[(1,1-dioxidothiomorpholin-4-yl)carbonyl]phenyl}-6-methyl-1,6-dihydro-7H-pyrrolo[2,3-c]pyridin-7-one;
4-(2,4-difluorophenoxy)-3-(6-methyl-7-oxo-6,7-dihydro-1H-pyrrolo[2,3-c]pyridin-4-yl)-N-(1-methyl-2-oxopyrrolidin-3-yl)benzamide;
tert-butyl {1-[4-(2,4-difluorophenoxy)-3-(6-methyl-7-oxo-6,7-dihydro-1H-pyrrolo[2,3-c]pyridin-4-yl)benzoyl]pyrrolidin-3-yl}carbamate;
4-[2-(2,4-difluorophenoxy)-5-(pyrrolidin-1-ylcarbonyl)phenyl]-6-methyl-1,6-dihydro-7H-pyrrolo[2,3-c]pyridin-7-one;
4-[2-(2,4-difluorophenoxy)-5-(morpholin-4-ylcarbonyl)phenyl]-6-methyl-1,6-dihydro-7H-pyrrolo[2,3-c]pyridin-7-one;
N-[4-(cyclohexyloxy)-3-(6-methyl-7-oxo-6,7-dihydro-1H-pyrrolo[2,3-c]pyridin-4-yl)phenyl]methanesulfonamide;
N-[4-(cyclopentyloxy)-3-(6-methyl-7-oxo-6,7-dihydro-1H-pyrrolo[2,3-c]pyridin-4-yl)phenyl]methanesulfonamide;
N-{4-[(4,4-difluorocyclohexyl)oxy]-3-(6-methyl-7-oxo-6,7-dihydro-1H-pyrrolo[2,3-c]pyridin-4-yl)phenyl}methanesulfonamide;

N-[3-(6-methyl-7-oxo-6,7-dihydro-1H-pyrrolo[2,3-c]pyridin-4-yl)-4-(tetrahydro-2H-pyran-3-yloxy)phenyl]methanesulfonamide;
6-methyl-4-[2-(morpholin-4-ylcarbonyl)phenyl]-1,6-dihydro-7H-pyrrolo[2,3-c]pyridin-7-one;
N-[3-(6-methyl-7-oxo-6,7-dihydro-1H-pyrrolo[2,3-c]pyridin-4-yl)-4-(2,4,6-trifluorophenoxy)phenyl]ethanesulfonamide;
N-[4-(benzyloxy)-3-(6-methyl-7-oxo-6,7-dihydro-1H-pyrrolo[2,3-c]pyridin-4-yl)phenyl]methanesulfonamide;
N-[4-(2,4-difluorophenoxy)-3-(6-methyl-7-oxo-6,7-dihydro-1H-pyrrolo[2,3-c]pyridin-4-yl)phenyl]-2-fluoroethanesulfonamide;
N-[4-(2,4-difluorophenoxy)-3-(6-methyl-7-oxo-6,7-dihydro-1H-pyrrolo[2,3-c]pyridin-4-yl)phenyl]-N'-methylsulfuric diamide;
N-[3-(6-methyl-7-oxo-6,7-dihydro-1H-pyrrolo[2,3-c]pyridin-4-yl)-4-(tetrahydrofuran-3-yloxy)phenyl]ethanesulfonamide;
methyl 6-methyl-7-oxo-4-(2-phenoxyphenyl)-6,7-dihydro-1H-pyrrolo[2,3-c]pyridine-2-carboxylate;
methyl 1,6-dimethyl-7-oxo-4-(2-phenoxyphenyl)-6,7-dihydro-1H-pyrrolo[2,3-c]pyridine-2-carboxylate;
ethyl 4-(5-amino-2-phenoxyphenyl)-6-methyl-7-oxo-6,7-dihydro-1H-pyrrolo[2,3-c]pyridine-2-carboxylate;
6-methyl-4-(5-(methylsulfonamido)-2-phenoxyphenyl)-7-oxo-6,7-dihydro-1H-pyrrolo[2,3-c]pyridine-2-carboxylic acid;
ethyl 6-methyl-4-{5-[(methylsulfonyl)amino]-2-phenoxyphenyl}-7-oxo-6,7-dihydro-1H-pyrrolo[2,3-c]pyridine-2-carboxylate;
N-ethyl-6-methyl-4-{5-[(methylsulfonyl)amino]-2-phenoxyphenyl}-7-oxo-6,7-dihydro-1H-pyrrolo[2,3-c]pyridine-2-carboxamide;
6-methyl-4-{5-[(methylsulfonyl)amino]-2-phenoxyphenyl}-7-oxo-6,7-dihydro-1H-pyrrolo[2,3-c]pyridine-2-carboxamide;
4-{4-[(ethylsulfonyl)amino]-2-(6-methyl-7-oxo-6,7-dihydro-1H-pyrrolo[2,3-c]pyridin-4-yl)phenoxy}benzamide;
6-methyl-4-[5-(methylsulfonyl)-2-phenoxyphenyl]-1,6-dihydro-7H-pyrrolo[2,3-c]pyridin-7-one;
5-(6-methyl-7-oxo-6,7-dihydro-1H-pyrrolo[2,3-c]pyridin-4-yl)-6-(tetrahydrofuran-3-yloxy)pyridine-3-sulfonamide;
N-methyl-5-(6-methyl-7-oxo-6,7-dihydro-1H-pyrrolo[2,3-c]pyridin-4-yl)-6-(tetrahydrofuran-3-yloxy)pyridine-3-sulfonamide;
6-methyl-4-(2-phenoxyphenyl)-2-phenyl-1,6-dihydro-7H-pyrrolo[2,3-c]pyridin-7-one;
N-{3-[2-(hydroxymethyl)-6-methyl-7-oxo-6,7-dihydro-1H-pyrrolo[2,3-c]pyridin-4-yl]-4-phenoxyphenyl}methanesulfonamide;
N-[4-(4-cyanophenoxy)-3-(6-methyl-7-oxo-6,7-dihydro-1H-pyrrolo[2,3-c]pyridin-4-yl)phenyl]ethanesulfonamide;
2-fluoro-N-[3-(6-methyl-7-oxo-6,7-dihydro-1H-pyrrolo[2,3-c]pyridin-4-yl)-4-(tetrahydrofuran-3-yloxy)phenyl]ethanesulfonamide;
N-[3-(6-methyl-7-oxo-6,7-dihydro-1H-pyrrolo[2,3-c]pyridin-4-yl)-4-(tetrahydrofuran-3-yloxy)phenyl]propane-1-sulfonamide;
N-[4-(4-cyanophenoxy)-3-(6-methyl-7-oxo-6,7-dihydro-1H-pyrrolo[2,3-c]pyridin-4-yl)phenyl]propane-1-sulfonamide;
N-[3-(6-methyl-7-oxo-6,7-dihydro-1H-pyrrolo[2,3-c]pyridin-4-yl)-4-(2,4,6-trifluorophenoxy)phenyl]propane-1-sulfonamide;
3-(6-methyl-7-oxo-6,7-dihydro-1H-pyrrolo[2,3-c]pyridin-4-yl)-4-phenoxybenzenesulfonamide;
6-(cyclohexylamino)-5-(6-methyl-7-oxo-6,7-dihydro-1H-pyrrolo[2,3-c]pyridin-4-yl)pyridine-3-sulfonamide;
6-(cyclohexylamino)-N-methyl-5-(6-methyl-7-oxo-6,7-dihydro-1H-pyrrolo[2,3-c]pyridin-4-yl)pyridine-3-sulfonamide;
N-methyl-N'-[3-(6-methyl-7-oxo-6,7-dihydro-1H-pyrrolo[2,3-c]pyridin-4-yl)-4-(2,4,6-trifluorophenoxy)phenyl]sulfuric diamide;
N-[3-(6-methyl-7-oxo-6,7-dihydro-1H-pyrrolo[2,3-c]pyridin-4-yl)-4-(tetrahydro-2H-pyran-4-yloxy)phenyl]propane-1-sulfonamide;
2,2,2-trifluoro-N-[3-(6-methyl-7-oxo-6,7-dihydro-1H-pyrrolo[2,3-c]pyridin-4-yl)-4-(tetrahydro-2H-pyran-4-yloxy)phenyl]ethanesulfonamide;
N-{4-[(4,4-difluorocyclohexyl)oxy]-3-(6-methyl-7-oxo-6,7-dihydro-1H-pyrrolo[2,3-c]pyridin-4-yl)phenyl}ethanesulfonamide;
N-{4-[(4,4-difluorocyclohexyl)oxy]-3-(6-methyl-7-oxo-6,7-dihydro-1H-pyrrolo[2,3-c]pyridin-4-yl)phenyl}propane-1-sulfonamide;
N-{4-[(4,4-difluorocyclohexyl)oxy]-3-(6-methyl-7-oxo-6,7-dihydro-1H-pyrrolo[2,3-c]pyridin-4-yl)phenyl}-2,2,2-trifluoroethanesulfonamide;
N-{4-[(4,4-difluorocyclohexyl)oxy]-3-(6-methyl-7-oxo-6,7-dihydro-1H-pyrrolo[2,3-c]pyridin-4-yl)phenyl}-N'-methylsulfuric diamide;
N-[3-(6-methyl-7-oxo-6,7-dihydro-1H-pyrrolo[2,3-c]pyridin-4-yl)-4-(tetrahydro-2H-pyran-3-yloxy)phenyl]ethanesulfonamide;
N-[3-(6-methyl-7-oxo-6,7-dihydro-1H-pyrrolo[2,3-c]pyridin-4-yl)-4-(tetrahydro-2H-pyran-3-yloxy)phenyl]propane-1-sulfonamide;
2,2,2-trifluoro-N-[3-(6-methyl-7-oxo-6,7-dihydro-1H-pyrrolo[2,3-c]pyridin-4-yl)-4-(tetrahydro-2H-pyran-3-yloxy)phenyl]ethanesulfonamide;
N-methyl-N'-[3-(6-methyl-7-oxo-6,7-dihydro-1H-pyrrolo[2,3-c]pyridin-4-yl)-4-(tetrahydro-2H-pyran-3-yloxy)phenyl]sulfuric diamide;
N-[3-(6-methyl-7-oxo-6,7-dihydro-1H-pyrrolo[2,3-c]pyridin-4-yl)-4-(tetrahydro-2H-pyran-4-yloxy)phenyl]ethanesulfonamide;
N,N-dimethyl-5-(6-methyl-7-oxo-6,7-dihydro-1H-pyrrolo[2,3-c]pyridin-4-yl)-6-(tetrahydrofuran-3-yloxy)pyridine-3-sulfonamide;
5-(6-methyl-7-oxo-6,7-dihydro-1H-pyrrolo[2,3-c]pyridin-4-yl)-6-(phenylamino)pyridine-3-sulfonamide;
N-methyl-5-(6-methyl-7-oxo-6,7-dihydro-1H-pyrrolo[2,3-c]pyridin-4-yl)-6-(phenylamino)pyridine-3-sulfonamide;
N-[4-(4-cyanophenoxy)-3-(6-methyl-7-oxo-6,7-dihydro-1H-pyrrolo[2,3-c]pyridin-4-yl)phenyl]-2-fluoroethanesulfonamide;
2-fluoro-N-[3-(6-methyl-7-oxo-6,7-dihydro-1H-pyrrolo[2,3-c]pyridin-4-yl)-4-(2,4,6-trifluorophenoxy)phenyl]ethanesulfonamide;
N-[4-(2,4-difluorophenoxy)-3-(6-methyl-7-oxo-6,7-dihydro-1H-pyrrolo[2,3-c]pyridin-4-yl)phenyl]propane-1-sulfonamide;
4-(2,4-difluorophenoxy)-3-(6-methyl-7-oxo-6,7-dihydro-1H-pyrrolo[2,3-c]pyridin-4-yl)-N-(pyrimidin-2-yl)benzamide;

4-(2,4-difluorophenoxy)-N-(2,6-dimethoxypyridin-3-yl)-3-(6-methyl-7-oxo-6,7-dihydro-1H-pyrrolo[2,3-c]pyridin-4-yl)benzamide;

4-(2,4-difluorophenoxy)-N-(1H-indazol-6-yl)-3-(6-methyl-7-oxo-6,7-dihydro-1H-pyrrolo[2,3-c]pyridin-4-yl)benzamide;

4-[2-(2,4-difluorophenoxy)-5-{[4-(pyrrolidin-1-ylcarbonyl)piperazin-1-yl]carbonyl}phenyl]-6-methyl-1,6-dihydro-7H-pyrrolo[2,3-c]pyridin-7-one;

4-(2,4-difluorophenoxy)-N-[4-(dimethylamino)phenyl]-3-(6-methyl-7-oxo-6,7-dihydro-1H-pyrrolo[2,3-c]pyridin-4-yl)benzamide;

4-(2,4-difluorophenoxy)-3-(6-methyl-7-oxo-6,7-dihydro-1H-pyrrolo[2,3-c]pyridin-4-yl)-N-(pyridin-4-ylmethyl)benzamide;

4-(2,4-difluorophenoxy)-3-(6-methyl-7-oxo-6,7-dihydro-1H-pyrrolo[2,3-c]pyridin-4-yl)-N-[2-(2-oxopyrrolidin-1-yl)ethyl]benzamide;

4-(2,4-difluorophenoxy)-N-(2-hydroxy-2-methylpropyl)-3-(6-methyl-7-oxo-6,7-dihydro-1H-pyrrolo[2,3-c]pyridin-4-yl)benzamide;

4-(2,4-difluorophenoxy)-N-[2-(5-methoxy-1H-indol-3-yl)ethyl]-3-(6-methyl-7-oxo-6,7-dihydro-1H-pyrrolo[2,3-c]pyridin-4-yl)benzamide;

N-(3,4-difluorobenzyl)-4-(2,4-difluorophenoxy)-3-(6-methyl-7-oxo-6,7-dihydro-1H-pyrrolo[2,3-c]pyridin-4-yl)benzamide;

4-(2,4-difluorophenoxy)-3-(6-methyl-7-oxo-6,7-dihydro-1H-pyrrolo[2,3-c]pyridin-4-yl)-N-[4-(trifluoromethoxy)benzyl]benzamide;

2-{4-[4-(2,4-difluorophenoxy)-3-(6-methyl-7-oxo-6,7-dihydro-1H-pyrrolo[2,3-c]pyridin-4-yl)benzoyl]piperazin-1-yl}-N,N-dimethylacetamide;

4-(2,4-difluorophenoxy)-3-(6-methyl-7-oxo-6,7-dihydro-1H-pyrrolo[2,3-c]pyridin-4-yl)-N-(pyridin-3-ylmethyl)benzamide;

4-(2,4-difluorophenoxy)-3-(6-methyl-7-oxo-6,7-dihydro-1H-pyrrolo[2,3-c]pyridin-4-yl)-N-(pyridin-2-ylmethyl)benzamide;

4-(2,4-difluorophenoxy)-3-(6-methyl-7-oxo-6,7-dihydro-1H-pyrrolo[2,3-c]pyridin-4-yl)-N-(3,4,5-trimethoxybenzyl)benzamide;

4-(2,4-difluorophenoxy)-N-[2-(dimethylamino)ethyl]-3-(6-methyl-7-oxo-6,7-dihydro-1H-pyrrolo[2,3-c]pyridin-4-yl)benzamide;

N-[2-(1,3-benzodioxol-5-yl)ethyl]-4-(2,4-difluorophenoxy)-3-(6-methyl-7-oxo-6,7-dihydro-1H-pyrrolo[2,3-c]pyridin-4-yl)benzamide;

4-(2,4-difluorophenoxy)-N-[2-(1H-indol-3-yl)ethyl]-3-(6-methyl-7-oxo-6,7-dihydro-1H-pyrrolo[2,3-c]pyridin-4-yl)benzamide;

4-[2-(2,4-difluorophenoxy)-5-{[4-(furan-2-ylcarbonyl)piperazin-1-yl]carbonyl}phenyl]-6-methyl-1,6-dihydro-7H-pyrrolo[2,3-c]pyridin-7-one;

tert-butyl {1-[4-(2,4-difluorophenoxy)-3-(6-methyl-7-oxo-6,7-dihydro-1H-pyrrolo[2,3-c]pyridin-4-yl)benzoyl]piperidin-4-yl}carbamate;

tert-butyl 4-{[4-(2,4-difluorophenoxy)-3-(6-methyl-7-oxo-6,7-dihydro-1H-pyrrolo[2,3-c]pyridin-4-yl)benzoyl]amino}piperidine-1-carboxylate;

4-[2-(2,4-difluorophenoxy)-5-{[4-(ethylsulfonyl)piperazin-1-yl]carbonyl}phenyl]-6-methyl-1,6-dihydro-7H-pyrrolo[2,3-c]pyridin-7-one;

4-[2-(2,4-difluorophenoxy)-5-(methylsulfonyl)phenyl]-6-methyl-1,6-dihydro-7H-pyrrolo[2,3-c]pyridin-7-one;

4-[2-(4-chlorobenzoyl)phenyl]-6-methyl-1,6-dihydro-7H-pyrrolo[2,3-c]pyridin-7-one;

4-{2-[(4-chlorophenyl)(hydroxy)methyl]phenyl}-6-methyl-1,6-dihydro-7H-pyrrolo[2,3-c]pyridin-7-one;

N-[3-(6-methyl-7-oxo-6,7-dihydro-1H-pyrrolo[2,3-c]pyridin-4-yl)-4-(pyrimidin-5-yloxy)phenyl]ethanesulfonamide;

N-{3-(6-methyl-7-oxo-6,7-dihydro-1H-pyrrolo[2,3-c]pyridin-4-yl)-4-[(1-methyl-1H-pyrazol-5-yl)methoxy]phenyl}ethanesulfonamide;

N-{4-[(1,3-dimethyl-1H-pyrazol-5-yl)methoxy]-3-(6-methyl-7-oxo-6,7-dihydro-1H-pyrrolo[2,3-c]pyridin-4-yl)phenyl}ethanesulfonamide;

N-[4-(2,2-dimethylpropoxy)-3-(6-methyl-7-oxo-6,7-dihydro-1H-pyrrolo[2,3-c]pyridin-4-yl)phenyl]ethanesulfonamide;

N-[4-(cyclopropylmethoxy)-3-(6-methyl-7-oxo-6,7-dihydro-1H-pyrrolo[2,3-c]pyridin-4-yl)phenyl]ethanesulfonamide;

4-(2,4-difluorophenoxy)-3-(6-methyl-7-oxo-6,7-dihydro-1H-pyrrolo[2,3-c]pyridin-4-yl)benzenesulfonamide;

4-[2-(cyclohexylamino)-5-(methylsulfonyl)phenyl]-6-methyl-1,6-dihydro-7H-pyrrolo[2,3-c]pyridin-7-one;

4-[2-(2-fluorophenoxy)-5-(methylsulfonyl)phenyl]-6-methyl-1,6-dihydro-7H-pyrrolo[2,3-c]pyridin-7-one;

4-[2-(3-fluorophenoxy)-5-(methylsulfonyl)phenyl]-6-methyl-1,6-dihydro-7H-pyrrolo[2,3-c]pyridin-7-one;

4-[2-(4-fluorophenoxy)-5-(methylsulfonyl)phenyl]-6-methyl-1,6-dihydro-7H-pyrrolo[2,3-c]pyridin-7-one;

4-[2-(2-chlorophenoxy)-5-(methylsulfonyl)phenyl]-6-methyl-1,6-dihydro-7H-pyrrolo[2,3-c]pyridin-7-one;

4-[2-(3-chlorophenoxy)-5-(methylsulfonyl)phenyl]-6-methyl-1,6-dihydro-7H-pyrrolo[2,3-c]pyridin-7-one;

4-[2-(4-chlorophenoxy)-5-(methylsulfonyl)phenyl]-6-methyl-1,6-dihydro-7H-pyrrolo[2,3-c]pyridin-7-one;

3-[2-(6-methyl-7-oxo-6,7-dihydro-1H-pyrrolo[2,3-c]pyridin-4-yl)-4-(methylsulfonyl)phenoxy]benzonitrile;

4-[2-(6-methyl-7-oxo-6,7-dihydro-1H-pyrrolo[2,3-c]pyridin-4-yl)-4-(methylsulfonyl)phenoxy]benzonitrile;

6-methyl-4-{5-(methylsulfonyl)-2-[3-(trifluoromethyl)phenoxy]phenyl}-1,6-dihydro-7H-pyrrolo[2,3-c]pyridin-7-one;

4-[2-(cyclopropylmethoxy)-5-(methylsulfonyl)phenyl]-6-methyl-1,6-dihydro-7H-pyrrolo[2,3-c]pyridin-7-one;

4-[2-(isoquinolin-5-yloxy)-5-(methylsulfonyl)phenyl]-6-methyl-1,6-dihydro-7H-pyrrolo[2,3-c]pyridin-7-one;

6-methyl-4-[5-(methylsulfonyl)-2-(quinolin-6-yloxy)phenyl]-1,6-dihydro-7H-pyrrolo[2,3-c]pyridin-7-one;

4-{2-[2-chloro-5-(trifluoromethyl)phenoxy]-5-(methylsulfonyl)phenyl}-6-methyl-1,6-dihydro-7H-pyrrolo[2,3-c]pyridin-7-one;

4-{2-[2-fluoro-5-(trifluoromethyl)phenoxy]-5-(methylsulfonyl)phenyl}-6-methyl-1,6-dihydro-7H-pyrrolo[2,3-c]pyridin-7-one;

2-{4-[2-(6-methyl-7-oxo-6,7-dihydro-1H-pyrrolo[2,3-c]pyridin-4-yl)-4-(methylsulfonyl)phenoxy]phenyl}acetamide;

4-[2-(3-aminophenoxy)-5-(methylsulfonyl)phenyl]-6-methyl-1,6-dihydro-7H-pyrrolo[2,3-c]pyridin-7-one;

6-methyl-4-[5-(methylsulfonyl)-2-(tetrahydrofuran-3-ylamino)phenyl]-1,6-dihydro-7H-pyrrolo[2,3-c]pyridin-7-one;

4-[2-(2,4-difluorophenoxy)-5-(ethylsulfonyl)phenyl]-6-methyl-1,6-dihydro-7H-pyrrolo[2,3-c]pyridin-7-one;

4-{2-[(4,4-difluorocyclohexyl)oxy]-5-(ethylsulfonyl)phenyl}-6-methyl-1,6-dihydro-7H-pyrrolo[2,3-c]pyridin-7-one;

4-{5-(ethylsulfonyl)-2-[(1-methylpiperidin-4-yl)oxy]phenyl}-6-methyl-1,6-dihydro-7H-pyrrolo[2,3-c]pyridin-7-one;

4-[2-(2,1,3-benzothiadiazol-4-yloxy)-5-(methylsulfonyl)phenyl]-6-methyl-1,6-dihydro-7H-pyrrolo[2,3-c]pyridin-7-one;

4-[2-(isoquinolin-7-yloxy)-5-(methylsulfonyl)phenyl]-6-methyl-1,6-dihydro-7H-pyrrolo[2,3-c]pyridin-7-one;

4-[2-(2,5-difluorophenoxy)-5-(methylsulfonyl)phenyl]-6-methyl-1,6-dihydro-7H-pyrrolo[2,3-c]pyridin-7-one;

4-[2-(3,4-difluorophenoxy)-5-(methylsulfonyl)phenyl]-6-methyl-1,6-dihydro-7H-pyrrolo[2,3-c]pyridin-7-one;

6-methyl-4-{5-(methylsulfonyl)-2-[(1-oxo-2,3-dihydro-1H-inden-4-yl)oxy]phenyl}-1,6-dihydro-7H-pyrrolo[2,3-c]pyridin-7-one;

4-[2-(3,5-difluorophenoxy)-5-(methylsulfonyl)phenyl]-6-methyl-1,6-dihydro-7H-pyrrolo[2,3-c]pyridin-7-one;

6-methyl-4-[2-(4-methylphenoxy)-5-(methylsulfonyl)phenyl]-1,6-dihydro-7H-pyrrolo[2,3-c]pyridin-7-one;

4-[2-(2-methoxyphenoxy)-5-(methylsulfonyl)phenyl]-6-methyl-1,6-dihydro-7H-pyrrolo[2,3-c]pyridin-7-one;

6-methyl-4-{2-[(2-methylpyridin-3-yl)oxy]-5-(methylsulfonyl)phenyl}-1,6-dihydro-7H-pyrrolo[2,3-c]pyridin-7-one;

4-{2-[3-(dimethylamino)phenoxy]-5-(methylsulfonyl)phenyl}-6-methyl-1,6-dihydro-7H-pyrrolo[2,3-c]pyridin-7-one;

6-methyl-4-{5-(methylsulfonyl)-2-[(1-oxo-2,3-dihydro-1H-inden-5-yl)oxy]phenyl}-1,6-dihydro-7H-pyrrolo[2,3-c]pyridin-7-one;

6-methyl-4-{5-(methylsulfonyl)-2-[(3-oxo-2,3-dihydro-1H-inden-5-yl)oxy]phenyl}-1,6-dihydro-7H-pyrrolo[2,3-c]pyridin-7-one;

2-[2-(6-methyl-7-oxo-6,7-dihydro-1H-pyrrolo[2,3-c]pyridin-4-yl)-4-(methylsulfonyl)phenoxy]benzonitrile;

4-[2-(3-chloro-2-fluorophenoxy)-5-(methylsulfonyl)phenyl]-6-methyl-1,6-dihydro-7H-pyrrolo[2,3-c]pyridin-7-one;

6-methyl-4-[5-(methylsulfonyl)-2-(naphthalen-1-yloxy)phenyl]-1,6-dihydro-7H-pyrrolo[2,3-c]pyridin-7-one;

4-[2-(2-fluoro-5-methylphenoxy)-5-(methylsulfonyl)phenyl]-6-methyl-1,6-dihydro-7H-pyrrolo[2,3-c]pyridin-7-one;

4-[2-(5-fluoro-2-methylphenoxy)-5-(methylsulfonyl)phenyl]-6-methyl-1,6-dihydro-7H-pyrrolo[2,3-c]pyridin-7-one;

6-methyl-4-[5-(methylsulfonyl)-2-(quinolin-7-yloxy)phenyl]-1,6-dihydro-7H-pyrrolo[2,3-c]pyridin-7-one;

4-[2-(4-chloro-3-fluorophenoxy)-5-(methylsulfonyl)phenyl]-6-methyl-1,6-dihydro-7H-pyrrolo[2,3-c]pyridin-7-one;

6-methyl-4-[5-(methylsulfonyl)-2-(pyridin-3-yloxy)phenyl]-1,6-dihydro-7H-pyrrolo[2,3-c]pyridin-7-one;

4-[2-(2,3-dihydro-1H-inden-5-yloxy)-5-(methylsulfonyl)phenyl]-6-methyl-1,6-dihydro-7H-pyrrolo[2,3-c]pyridin-7-one;

6-methyl-4-{5-(methylsulfonyl)-2-[4-(propan-2-yl)phenoxy]phenyl}-1,6-dihydro-7H-pyrrolo[2,3-c]pyridin-7-one;

4-[2-(isoquinolin-8-yloxy)-5-(methylsulfonyl)phenyl]-6-methyl-1,6-dihydro-7H-pyrrolo[2,3-c]pyridin-7-one;

6-methyl-4-[5-(methylsulfonyl)-2-(3,4,5-trifluorophenoxy)phenyl]-1,6-dihydro-7H-pyrrolo[2,3-c]pyridin-7-one;

4-(2-benzylphenyl)-6-methyl-1,6-dihydro-7H-pyrrolo[2,3-c]pyridin-7-one;

4-(biphenyl-2-yl)-6-methyl-1,6-dihydro-7H-pyrrolo[2,3-c]pyridin-7-one;

4-[2-(1,4-dioxaspiro[4.5]dec-8-yloxy)-5-(ethylsulfonyl)phenyl]-6-methyl-1,6-dihydro-7H-pyrrolo[2,3-c]pyridin-7-one;

4-[2-(cyclopropylmethoxy)-5-(ethylsulfonyl)phenyl]-6-methyl-1,6-dihydro-7H-pyrrolo[2,3-c]pyridin-7-one;

4-{5-(ethylsulfonyl)-2-[(4-oxocyclohexyl)oxy]phenyl}-6-methyl-1,6-dihydro-7H-pyrrolo[2,3-c]pyridin-7-one;

4-{2-[(cyclopropylmethyl)amino]-5-(ethylsulfonyl)phenyl}-6-methyl-1,6-dihydro-7H-pyrrolo[2,3-c]pyridin-7-one;

6-methyl-4-{5-(methylsulfonyl)-2-[(tetrahydrofuran-3-ylmethyl)amino]phenyl}-1,6-dihydro-7H-pyrrolo[2,3-c]pyridin-7-one;

4-{5-(ethylsulfonyl)-2-[(cis-4-hydroxycyclohexyl)oxy]phenyl}-6-methyl-1,6-dihydro-7H-pyrrolo[2,3-c]pyridin-7-one;

4-{5-(ethylsulfonyl)-2-[(trans-4-hydroxycyclohexyl)oxy]phenyl}-6-methyl-1,6-dihydro-7H-pyrrolo[2,3-c]pyridin-7-one;

6-methyl-4-[5-(methylsulfonyl)-2-(tetrahydrofuran-3-yloxy)phenyl]-1,6-dihydro-7H-pyrrolo[2,3-c]pyridin-7-one;

4-{2-[(3-fluorooxetan-3-yl)methoxy]-5-(methylsulfonyl)phenyl}-6-methyl-1,6-dihydro-7H-pyrrolo[2,3-c]pyridin-7-one;

6-(cyclopropylmethoxy)-5-(6-methyl-7-oxo-6,7-dihydro-1H-pyrrolo[2,3-c]pyridin-4-yl)pyridine-3-sulfonamide;

6-(cyclopropylmethoxy)-N-methyl-5-(6-methyl-7-oxo-6,7-dihydro-1H-pyrrolo[2,3-c]pyridin-4-yl)pyridine-3-sulfonamide;

6-[(cyclopropylmethyl)amino]-5-(6-methyl-7-oxo-6,7-dihydro-1H-pyrrolo[2,3-c]pyridin-4-yl)pyridine-3-sulfonamide;

6-[(cyclopropylmethyl)amino]-N-methyl-5-(6-methyl-7-oxo-6,7-dihydro-1H-pyrrolo[2,3-c]pyridin-4-yl)pyridine-3-sulfonamide;

4-{5-(ethylsulfonyl)-2-[(cis-4-hydroxy-4-methylcyclohexyl)oxy]phenyl}-6-methyl-1,6-dihydro-7H-pyrrolo[2,3-c]pyridin-7-one;

4-{5-(ethylsulfonyl)-2-[(trans-4-hydroxy-4-methylcyclohexyl)oxy]phenyl}-6-methyl-1,6-dihydro-7H-pyrrolo[2,3-c]pyridin-7-one;

4-[2-(cyclobutyloxy)-5-(methylsulfonyl)phenyl]-6-methyl-1,6-dihydro-7H-pyrrolo[2,3-c]pyridin-7-one;

4-[2-(cyclopentylmethoxy)-5-(methylsulfonyl)phenyl]-6-methyl-1,6-dihydro-7H-pyrrolo[2,3-c]pyridin-7-one;

4-[2-(cyclohexyloxy)-5-(methylsulfonyl)phenyl]-6-methyl-1,6-dihydro-7H-pyrrolo[2,3-c]pyridin-7-one;

4-[2-(cyclopentyloxy)-5-(methylsulfonyl)phenyl]-6-methyl-1,6-dihydro-7H-pyrrolo[2,3-c]pyridin-7-one;

6-methyl-4-[5-(methylsulfonyl)-2-(tetrahydrofuran-3-ylmethoxy)phenyl]-1,6-dihydro-7H-pyrrolo[2,3-c]pyridin-7-one;

6-methyl-4-{5-(methylsulfonyl)-2-[2-(2-oxoimidazolidin-1-yl)ethoxy]phenyl}-1,6-dihydro-7H-pyrrolo[2,3-c]pyridin-7-one;

4-[2-(2-cyclopropylethoxy)-5-(methylsulfonyl)phenyl]-6-methyl-1,6-dihydro-7H-pyrrolo[2,3-c]pyridin-7-one;

4-[2-(cycloheptyloxy)-5-(methylsulfonyl)phenyl]-6-methyl-1,6-dihydro-7H-pyrrolo[2,3-c]pyridin-7-one;

6-methyl-4-[2-(2-methylpropoxy)-5-(methylsulfonyl)phenyl]-1,6-dihydro-7H-pyrrolo[2,3-c]pyridin-7-one;

6-methyl-4-[2-{[(2S)-1-methylpyrrolidin-2-yl]methoxy}-5-(methylsulfonyl)phenyl]-1,6-dihydro-7H-pyrrolo[2,3-c]pyridin-7-one;

6-methyl-4-{2-[(2-methylcyclopropyl)methoxy]-5-(methylsulfonyl)phenyl}-1,6-dihydro-7H-pyrrolo[2,3-c]pyridin-7-one;

4-[2-(cyclohexylmethoxy)-5-(methylsulfonyl)phenyl]-6-methyl-1,6-dihydro-7H-pyrrolo[2,3-c]pyridin-7-one;

6-methyl-4-{2-[2-(1-methylpyrrolidin-2-yl)ethoxy]-5-(methylsulfonyl)phenyl}-1,6-dihydro-7H-pyrrolo[2,3-c]pyridin-7-one;

6-methyl-4-[5-(methylsulfonyl)-2-{[(2R)-5-oxopyrrolidin-2-yl]methoxy}phenyl]-1,6-dihydro-7H-pyrrolo[2,3-c]pyridin-7-one;

6-methyl-4-{5-(methylsulfonyl)-2-[2-(morpholin-4-yl)ethoxy]phenyl}-1,6-dihydro-7H-pyrrolo[2,3-c]pyridin-7-one;

6-methyl-4-[5-(methylsulfonyl)-2-{[(2S)-5-oxopyrrolidin-2-yl]methoxy}phenyl]-1,6-dihydro-7H-pyrrolo[2,3-c]pyridin-7-one;

4-{2-[(1-tert-butoxypropan-2-yl)oxy]-5-(methylsulfonyl)phenyl}-6-methyl-1,6-dihydro-7H-pyrrolo[2,3-c]pyridin-7-one;

4-{2-[(1S,4R)-bicyclo[2.2.1]hept-2-ylmethoxy]-5-(methylsulfonyl)phenyl}-6-methyl-1,6-dihydro-7H-pyrrolo[2,3-c]pyridin-7-one;

6-methyl-4-{2-[(1-methylcyclopropyl)methoxy]-5-(methylsulfonyl)phenyl}-1,6-dihydro-7H-pyrrolo[2,3-c]pyridin-7-one;

6-methyl-4-{5-(methylsulfonyl)-2-[2-(2-oxopyrrolidin-1-yl)ethoxy]phenyl}-1,6-dihydro-7H-pyrrolo[2,3-c]pyridin-7-one;

6-methyl-4-{2-[(4-methylcyclohexyl)oxy]-5-(methylsulfonyl)phenyl}-1,6-dihydro-7H-pyrrolo[2,3-c]pyridin-7-one;

4-[2-(cyclobutylmethoxy)-5-(methylsulfonyl)phenyl]-6-methyl-1,6-dihydro-7H-pyrrolo[2,3-c]pyridin-7-one;

N-[4-(2,4-difluorophenoxy)-3-(6-methyl-7-oxo-6,7-dihydro-1H-pyrrolo[2,3-c]pyridin-4-yl)phenyl]cyclopropanesulfonamide;

N-[4-(2,4-difluorophenoxy)-3-(6-methyl-7-oxo-6,7-dihydro-1H-pyrrolo[2,3-c]pyridin-4-yl)phenyl]-2-methoxyethanesulfonamide;

6-methyl-4-{5-(methylsulfonyl)-2-[tricyclo[3.3.1.1$^{3,7}$]dec-2-yloxy]phenyl}-1,6-dihydro-7H-pyrrolo[2,3-c]pyridin-7-one;

4-[(cyclopropylmethyl)amino]-3-(6-methyl-7-oxo-6,7-dihydro-1H-pyrrolo[2,3-c]pyridin-4-yl)benzenesulfonamide;

4-[(cyclopropylmethyl)amino]-N-methyl-3-(6-methyl-7-oxo-6,7-dihydro-1H-pyrrolo[2,3-c]pyridin-4-yl)benzenesulfonamide;

4-{2-[(2,2-difluorocyclopropyl)methoxy]-5-(ethylsulfonyl)phenyl}-6-methyl-1,6-dihydro-7H-pyrrolo[2,3-c]pyridin-7-one;

4-(4-bromo-2-methoxyphenyl)-6-methyl-1,6-dihydro-7H-pyrrolo[2,3-c]pyridin-7-one;

6-(2,4-difluorophenoxy)-5-(6-methyl-7-oxo-6,7-dihydro-1H-pyrrolo[2,3-c]pyridin-4-yl)pyridine-3-sulfonamide;

4-{2-(cyclopropylmethoxy)-5-[(trifluoromethyl)sulfonyl]phenyl}-6-methyl-1,6-dihydro-7H-pyrrolo[2,3-c]pyridin-7-one;

4-{2-[(cyclopropylmethyl)amino]-5-[(trifluoromethyl)sulfonyl]phenyl}-6-methyl-1,6-dihydro-7H-pyrrolo[2,3-c]pyridin-7-one;

6-[(cyclopropylmethyl)amino]-N,N-dimethyl-5-(6-methyl-7-oxo-6,7-dihydro-1H-pyrrolo[2,3-c]pyridin-4-yl)pyridine-3-sulfonamide;

6-(2,4-difluorophenoxy)-N-methyl-5-(6-methyl-7-oxo-6,7-dihydro-1H-pyrrolo[2,3-c]pyridin-4-yl)pyridine-3-sulfonamide;

4-[2-(cyclopropylmethoxy)-6-methylphenyl]-6-methyl-1,6-dihydro-7H-pyrrolo[2,3-c]pyridin-7-one;

4-{5-(ethylsulfonyl)-2-[(cis-4-methoxycyclohexyl)oxy]phenyl}-6-methyl-1,6-dihydro-7H-pyrrolo[2,3-c]pyridin-7-one;

4-(cyclopropylmethoxy)-3-(6-methyl-7-oxo-6,7-dihydro-1H-pyrrolo[2,3-c]pyridin-4-yl)benzenesulfonamide;

4-(cyclopropylmethoxy)-N-methyl-3-(6-methyl-7-oxo-6,7-dihydro-1H-pyrrolo[2,3-c]pyridin-4-yl)benzenesulfonamide;

N-[4-(cyclopropylmethoxy)-2-methyl-3-(6-methyl-7-oxo-6,7-dihydro-1H-pyrrolo[2,3-c]pyridin-4-yl)phenyl]ethanesulfonamide;

4-[2-(2,4-difluorophenoxy)-5-(methylsulfonyl)phenyl]-6-methyl-7-oxo-6,7-dihydro-1H-pyrrolo[2,3-c]pyridine-2-carboxamide;

4-[2-(2,4-difluorophenoxy)-5-(methylsulfonyl)phenyl]-N-ethyl-6-methyl-7-oxo-6,7-dihydro-1H-pyrrolo[2,3-c]pyridine-2-carboxamide;

4-[2-(2,4-difluorophenoxy)-5-(methylsulfonyl)phenyl]-6-methyl-7-oxo-N-(2,2,2-trifluoroethyl)-6,7-dihydro-1H-pyrrolo[2,3-c]pyridine-2-carboxamide;

4-[2-(2,4-difluorophenoxy)-5-(methylsulfonyl)phenyl]-6-methyl-2-(morpholin-4-ylcarbonyl)-1,6-dihydro-7H-pyrrolo[2,3-c]pyridin-7-one;

4-[2-(2,4-difluorophenoxy)-5-(methylsulfonyl)phenyl]-6-methyl-2-[(4-methylpiperazin-1-yl)carbonyl]-1,6-dihydro-7H-pyrrolo[2,3-c]pyridin-7-one;

4-[2-(2,4-difluorophenoxy)-5-(methylsulfonyl)phenyl]-6-methyl-7-oxo-N-(1,3-thiazol-2-yl)-6,7-dihydro-1H-pyrrolo[2,3-c]pyridine-2-carboxamide;

ethyl 4-[2-(6-methyl-7-oxo-6,7-dihydro-1H-pyrrolo[2,3-c]pyridin-4-yl)-4-(methylsulfonyl)phenoxy]piperidine-1-carboxylate;

4-[2-ethoxy-5-(methylsulfonyl)phenyl]-6-methyl-1,6-dihydro-7H-pyrrolo[2,3-c]pyridin-7-one;

4-{5-(ethylsulfonyl)-2-[(trans-4-methoxycyclohexyl)oxy]phenyl}-6-methyl-1,6-dihydro-7H-pyrrolo[2,3-c]pyridin-7-one;

4-{2-[(cyclopropylmethyl)amino]-5-(propan-2-ylsulfonyl)phenyl}-6-methyl-1,6-dihydro-7H-pyrrolo[2,3-c]pyridin-7-one;

N-[4-(cyclopropylmethoxy)-2-methyl-3-(6-methyl-7-oxo-6,7-dihydro-1H-pyrrolo[2,3-c]pyridin-4-yl)phenyl]methanesulfonamide;

N-[4-(cyclopropylmethoxy)-2-methyl-5-(6-methyl-7-oxo-6,7-dihydro-1H-pyrrolo[2,3-c]pyridin-4-yl)phenyl]methanesulfonamide;

4-[5-(ethylsulfonyl)-2-(tetrahydro-2H-thiopyran-4-yloxy)phenyl]-6-methyl-1,6-dihydro-7H-pyrrolo[2,3-c]pyridin-7-one;

4-{2-[(1,1-dioxidotetrahydro-2H-thiopyran-4-yl)oxy]-5-(ethylsulfonyl)phenyl}-6-methyl-1,6-dihydro-7H-pyrrolo[2,3-c]pyridin-7-one;

6-(2,4-difluorophenoxy)-N,N-dimethyl-5-(6-methyl-7-oxo-6,7-dihydro-1H-pyrrolo[2,3-c]pyridin-4-yl)pyridine-3-sulfonamide;

4-[2-(cyclopropylamino)-5-(ethylsulfonyl)phenyl]-6-methyl-1,6-dihydro-7H-pyrrolo[2,3-c]pyridin-7-one;

4-(5-(ethylsulfonyl)-2-(cis-4-methoxy-4-methylcyclohexyloxy)phenyl)-6-methyl-1H-pyrrolo[2,3-c]pyridin-7(6H)-one;

4-[2-(2,4-difluorophenoxy)-5-(methylsulfonyl)phenyl]-N,N,6-trimethyl-7-oxo-6,7-dihydro-1H-pyrrolo[2,3-c]pyridine-2-carboxamide;

6-methyl-4-{5-(methylsulfonyl)-2-[4-(methylsulfonyl)phenoxy]phenyl}-1,6-dihydro-7H-pyrrolo[2,3-c]pyridin-7-one;

4-[2-(2,4-difluorophenoxy)-5-(propan-2-ylsulfonyl)phenyl]-6-methyl-1,6-dihydro-7H-pyrrolo[2,3-c]pyridin-7-one;

6-(cyclopropylmethoxy)-N,N-diethyl-5-(6-methyl-7-oxo-6,7-dihydro-1H-pyrrolo[2,3-c]pyridin-4-yl)pyridine-3-sulfonamide;

4-(cyclopropylmethoxy)-N,N-dimethyl-3-(6-methyl-7-oxo-6,7-dihydro-1H-pyrrolo[2,3-c]pyridin-4-yl)benzenesulfonamide;

4-[2-(cyclopropylmethoxy)-5-fluorophenyl]-6-methyl-1,6-dihydro-7H-pyrrolo[2,3-c]pyridin-7-one;

4-[2-(2,4-difluorophenoxy)-5-(trifluoromethyl)phenyl]-6-methyl-1,6-dihydro-7H-pyrrolo[2,3-c]pyridin-7-one;

4-[2-(2,4-difluorophenoxy)-5-(methylsulfonyl)phenyl]-2-(hydroxymethyl)-6-methyl-1,6-dihydro-7H-pyrrolo[2,3-c]pyridin-7-one;

4-[2-(2,3-dihydro-1H-inden-2-yloxy)-5-(methylsulfonyl)phenyl]-6-methyl-1,6-dihydro-7H-pyrrolo[2,3-c]pyridin-7-one;

4-[2-(2,4-difluorophenoxy)-5-(methylsulfonyl)phenyl]-2-(1-hydroxyethyl)-6-methyl-1,6-dihydro-7H-pyrrolo[2,3-c]pyridin-7-one;

4-[2-(2,4-difluorophenoxy)-5-(methylsulfonyl)phenyl]-2-[(dimethylamino)methyl]-6-methyl-1,6-dihydro-7H-pyrrolo[2,3-c]pyridin-7-one;

4-[2-(2,4-difluorophenoxy)-5-(methylsulfonyl)phenyl]-6-methyl-2-(morpholin-4-ylmethyl)-1,6-dihydro-7H-pyrrolo[2,3-c]pyridin-7-one;

4-[2-(2,4-difluorophenoxy)-5-(methylsulfonyl)phenyl]-6-methyl-2-[(4-methylpiperazin-1-yl)methyl]-1,6-dihydro-7H-pyrrolo[2,3-c]pyridin-7-one;

4-[2-(2,4-difluorophenoxy)-5-(methylsulfonyl)phenyl]-6-methyl-2-[(phenylamino)methyl]-1,6-dihydro-7H-pyrrolo[2,3-c]pyridin-7-one;

4-[2-(2,4-difluorophenoxy)-5-(methylsulfonyl)phenyl]-6-methyl-2-[(1,3-thiazol-2-ylamino)methyl]-1,6-dihydro-7H-pyrrolo[2,3-c]pyridin-7-one;

4-[2-(2,4-difluorophenoxy)-5-(methylsulfonyl)phenyl]-6-methyl-2-[(tetrahydrofuran-3-ylamino)methyl]-1,6-dihydro-7H-pyrrolo[2,3-c]pyridin-7-one;

4-[2-(cyclopropylmethoxy)-5-(phenylsulfonyl)phenyl]-6-methyl-1,6-dihydro-7H-pyrrolo[2,3-c]pyridin-7-one;

4-[2-(cyclopropylmethoxy)-5-(morpholin-4-ylsulfonyl)phenyl]-6-methyl-1,6-dihydro-7H-pyrrolo[2,3-c]pyridin-7-one;

4-{2-(2,4-difluorophenoxy)-5-[(methylsulfonyl)methyl]phenyl}-6-methyl-1,6-dihydro-7H-pyrrolo[2,3-c]pyridin-7-one;

4-[2-(2,4-difluorophenoxy)-5-(methylsulfonyl)pyridin-3-yl]-6-methyl-1,6-dihydro-7H-pyrrolo[2,3-c]pyridin-7-one;

4-[2-(2,4-difluorophenoxy)-5-(methylsulfonyl)phenyl]-6-methyl-2-[(pyridin-3-yloxy)methyl]-1,6-dihydro-7H-pyrrolo[2,3-c]pyridin-7-one;

4-[5-(cyclopropylsulfonyl)-2-(2,4-difluorophenoxy)phenyl]-6-methyl-1,6-dihydro-7H-pyrrolo[2,3-c]pyridin-7-one;

4-[2-(2,4-difluorophenoxy)-5-(methylsulfonyl)phenyl]-6-methyl-2-(prop-1-en-2-yl)-1,6-dihydro-7H-pyrrolo[2,3-c]pyridin-7-one;

4-[2-(2,4-difluorophenoxy)-5-(methylsulfonyl)phenyl]-6-methyl-2-(phenoxymethyl)-1,6-dihydro-7H-pyrrolo[2,3-c]pyridin-7-one;

4-[2-(2,4-difluorophenoxy)-5-(morpholin-4-ylsulfonyl)phenyl]-6-methyl-1,6-dihydro-7H-pyrrolo[2,3-c]pyridin-7-one;

4-[2-(2,4-difluorophenoxy)-5-(ethylsulfonyl)pyridin-3-yl]-6-methyl-1,6-dihydro-7H-pyrrolo[2,3-c]pyridin-7-one;

N-[4-(2,4-difluorophenoxy)-3-(6-methyl-7-oxo-6,7-dihydro-1H-pyrrolo[2,3-c]pyridin-4-yl)phenyl]-2-(morpholin-4-yl)ethanesulfonamide;

N-[4-(2,4-difluorophenoxy)-3-(6-methyl-7-oxo-6,7-dihydro-1H-pyrrolo[2,3-c]pyridin-4-yl)phenyl]-N-[2-(dimethylamino)ethyl]ethanesulfonamide;

4-{2-(2,4-difluorophenoxy)-5-[(ethylsulfonyl)methyl]phenyl}-6-methyl-1,6-dihydro-7H-pyrrolo[2,3-c]pyridin-7-one;

4-{2-(2,4-difluorophenoxy)-5-[2-(ethylsulfonyl)propan-2-yl]phenyl}-6-methyl-1,6-dihydro-7H-pyrrolo[2,3-c]pyridin-7-one;

4-[2-(2,4-difluorophenoxy)-5-(pyrrolidin-1-ylsulfonyl)phenyl]-6-methyl-1,6-dihydro-7H-pyrrolo[2,3-c]pyridin-7-one;

N-[4-(2,4-difluorophenoxy)-3-(6-methyl-7-oxo-6,7-dihydro-1H-pyrrolo[2,3-c]pyridin-4-yl)phenyl]-2-(dimethylamino)ethanesulfonamide;

ethyl 4-[4-(ethylsulfonyl)-2-(6-methyl-7-oxo-6,7-dihydro-1H-pyrrolo[2,3-c]pyridin-4-yl)phenoxy]piperidine-1-carboxylate;

4-[2-(cyclopropylmethoxy)-5-(pyrrolidin-1-ylsulfonyl)phenyl]-6-methyl-1,6-dihydro-7H-pyrrolo[2,3-c]pyridin-7-one;

4-{2-[(1-acetylpiperidin-4-yl)oxy]-5-(ethylsulfonyl)phenyl}-6-methyl-1,6-dihydro-7H-pyrrolo[2,3-c]pyridin-7-one;

4-[4-(ethylsulfonyl)-2-(6-methyl-7-oxo-6,7-dihydro-1H-pyrrolo[2,3-c]pyridin-4-yl)phenoxy]benzonitrile;

4-[2-(cyclopropylmethoxy)-5-(2,3-dihydro-1H-indol-1-ylsulfonyl)phenyl]-6-methyl-1,6-dihydro-7H-pyrrolo[2,3-c]pyridin-7-one;

4-{2-(2,4-difluorophenoxy)-5-[(phenylsulfonyl)methyl]phenyl}-6-methyl-1,6-dihydro-7H-pyrrolo[2,3-c]pyridin-7-one;

4-{2-[(2,2-difluorocyclopropyl)methoxy]-5-(pyrrolidin-1-ylsulfonyl)phenyl}-6-methyl-1,6-dihydro-7H-pyrrolo[2,3-c]pyridin-7-one;

4-{2-(cyclopropylmethoxy)-5-[(3,3-difluoroazetidin-1-yl)sulfonyl]phenyl}-6-methyl-1,6-dihydro-7H-pyrrolo[2,3-c]pyridin-7-one;

4-{2-[2-(2-hydroxyethyl)phenoxy]-5-(methylsulfonyl)phenyl}-6-methyl-1,6-dihydro-7H-pyrrolo[2,3-c]pyridin-7-one;

4-[2-(cyclopropylmethoxy)-5-{[3-(dimethylamino)pyrrolidin-1-yl]sulfonyl}phenyl]-6-methyl-1,6-dihydro-7H-pyrrolo[2,3-c]pyridin-7-one;

4-{2-(2,4-difluorophenoxy)-5-[(methylsulfonyl)methyl]pyridin-3-yl}-6-methyl-1,6-dihydro-7H-pyrrolo[2,3-c]pyridin-7-one;

tert-butyl 4-[4-(ethylsulfonyl)-2-(6-methyl-7-oxo-6,7-dihydro-1H-pyrrolo[2,3-c]pyridin-4-yl)phenoxy]piperidine-1-carboxylate;

4-(cyclopropylmethoxy)-3-(6-methyl-7-oxo-6,7-dihydro-1H-pyrrolo[2,3-c]pyridin-4-yl)-N-phenylbenzenesulfonamide;

4-[2-(cyclopropylmethoxy)-5-(pyrrolidin-1-ylmethyl)phenyl]-6-methyl-1,6-dihydro-7H-pyrrolo[2,3-c]pyridin-7-one;

4-[2-(cyclopropylmethoxy)-5-(pyridin-3-yl)phenyl]-6-methyl-1,6-dihydro-7H-pyrrolo[2,3-c]pyridin-7-one;

4-[2-(cyclopropylmethoxy)-5-(morpholin-4-ylmethyl)phenyl]-6-methyl-1,6-dihydro-7H-pyrrolo[2,3-c]pyridin-7-one;

4-{5-(ethylsulfonyl)-2-[3-(hydroxymethyl)phenoxy]phenyl}-6-methyl-1,6-dihydro-7H-pyrrolo[2,3-c]pyridin-7-one;

4-[2-(cyclopropylmethoxy)-5-(1-methyl-1H-pyrazol-4-yl)phenyl]-6-methyl-1,6-dihydro-7H-pyrrolo[2,3-c]pyridin-7-one;

4-[2-(2,4-difluorophenoxy)-5-(2,3-dihydro-1H-indol-1-ylsulfonyl)phenyl]-6-methyl-1,6-dihydro-7H-pyrrolo[2,3-c]pyridin-7-one;

N-[2-cyano-4-(2,4-difluorophenoxy)-5-(6-methyl-7-oxo-6,7-dihydro-1H-pyrrolo[2,3-c]pyridin-4-yl)phenyl]ethanesulfonamide;

tert-butyl 4-[4-(cyclopropylmethoxy)-3-(6-methyl-7-oxo-6,7-dihydro-1H-pyrrolo[2,3-c]pyridin-4-yl)phenyl]-3,6-dihydropyridine-1(2H)-carboxylate;

4-[5-(6-aminopyridin-3-yl)-2-(cyclopropylmethoxy)phenyl]-6-methyl-1,6-dihydro-7H-pyrrolo[2,3-c]pyridin-7-one;

4-{2-[(2,2-difluorocyclopropyl)methoxy]-5-(ethylsulfonyl)phenyl}-6-methyl-7-oxo-N-(2,2,2-trifluoroethyl)-6,7-dihydro-1H-pyrrolo[2,3-c]pyridine-2-carboxamide;

4-{2-[(cyclopropylmethyl)amino]-5-[(methylsulfonyl)methyl]phenyl}-6-methyl-1,6-dihydro-7H-pyrrolo[2,3-c]pyridin-7-one;

4-{2-[(cyclopropylmethyl)amino]-5-(methylsulfonyl)phenyl}-6-methyl-1,6-dihydro-7H-pyrrolo[2,3-c]pyridin-7-one;

4-[5-(ethylsulfonyl)-2-(pyrrolidin-1-yl)phenyl]-6-methyl-1,6-dihydro-7H-pyrrolo[2,3-c]pyridin-7-one;

4-[5-(ethylsulfonyl)-2-(4-methylpiperazin-1-yl)phenyl]-6-methyl-1,6-dihydro-7H-pyrrolo[2,3-c]pyridin-7-one;

4-{2-[(4-fluorophenyl)amino]-5-(methylsulfonyl)phenyl}-6-methyl-1,6-dihydro-7H-pyrrolo[2,3-c]pyridin-7-one;

4-(cyclopropylmethoxy)-3-(6-methyl-7-oxo-6,7-dihydro-1H-pyrrolo[2,3-c]pyridin-4-yl)-N-(pyridin-3-ylmethyl)benzenesulfonamide;

4-[4-(cyclopropylmethoxy)-3'-fluorobiphenyl-3-yl]-6-methyl-1,6-dihydro-7H-pyrrolo[2,3-c]pyridin-7-one;

4-{2-[(4-fluorophenyl)amino]-5-[(methylsulfonyl)methyl]phenyl}-6-methyl-1,6-dihydro-7H-pyrrolo[2,3-c]pyridin-7-one;

[4-(cyclopropylmethoxy)-3-(6-methyl-7-oxo-6,7-dihydro-1H-pyrrolo[2,3-c]pyridin-4-yl)phenyl]acetonitrile;

N-{4-(2,4-difluorophenoxy)-3-[2-(hydroxymethyl)-6-methyl-7-oxo-6,7-dihydro-1H-pyrrolo[2,3-c]pyridin-4-yl]phenyl}ethanesulfonamide;

N-[4-(2,4-difluorophenoxy)-3-{6-methyl-2-[(4-methylpiperazin-1-yl)carbonyl]-7-oxo-6,7-dihydro-1H-pyrrolo[2,3-c]pyridin-4-yl}phenyl]ethanesulfonamide;

N-[4-(2,4-difluorophenoxy)-3-{6-methyl-2-[(4-methylpiperazin-1-yl)methyl]-7-oxo-6,7-dihydro-1H-pyrrolo[2,3-c]pyridin-4-yl}phenyl]ethanesulfonamide;

4-[2-(cyclopropylmethoxy)-5-(1,2,3,6-tetrahydropyridin-4-yl)phenyl]-6-methyl-1,6-dihydro-7H-pyrrolo[2,3-c]pyridin-7-one;

N-[4-(2,4-difluorophenoxy)-3-(6-methyl-7-oxo-6,7-dihydro-1H-pyrrolo[2,3-c]pyridin-4-yl)phenyl]-N-(2-methoxyethyl)ethanesulfonamide;

N-[4-(2,4-difluorophenoxy)-3-(6-methyl-7-oxo-6,7-dihydro-1H-pyrrolo[2,3-c]pyridin-4-yl)phenyl]-N-(pyridin-2-ylmethyl)ethanesulfonamide;

N-(cyclopropylmethyl)-N-[4-(2,4-difluorophenoxy)-3-(6-methyl-7-oxo-6,7-dihydro-1H-pyrrolo[2,3-c]pyridin-4-yl)phenyl]ethanesulfonamide;

N-[4-(2,4-difluorophenoxy)-3-(6-methyl-7-oxo-6,7-dihydro-1H-pyrrolo[2,3-c]pyridin-4-yl)phenyl]-N-[2-(2-oxopyrrolidin-1-yl)ethyl]ethanesulfonamide;

N-[4-(2,4-difluorophenoxy)-3-(6-methyl-7-oxo-6,7-dihydro-1H-pyrrolo[2,3-c]pyridin-4-yl)phenyl]-N-(tetrahydrofuran-2-ylmethyl)ethanesulfonamide;

N-[4-(2,4-difluorophenoxy)-3-(6-methyl-7-oxo-6,7-dihydro-1H-pyrrolo[2,3-c]pyridin-4-yl)phenyl]-N-(3,3,3-trifluoropropyl)ethanesulfonamide;

4-(cyclopropylmethoxy)-N-(4-fluorophenyl)-3-(6-methyl-7-oxo-6,7-dihydro-1H-pyrrolo[2,3-c]pyridin-4-yl)benzenesulfonamide;

4-[2-(cyclopropylmethoxy)-5-(6-fluoropyridin-3-yl)phenyl]-6-methyl-1,6-dihydro-7H-pyrrolo[2,3-c]pyridin-7-one;

N-[4-(2,4-difluorophenoxy)-3-(3-formyl-6-methyl-7-oxo-6,7-dihydro-1H-pyrrolo[2,3-c]pyridin-4-yl)phenyl]ethanesulfonamide;

N-{4-(2,4-difluorophenoxy)-3-[6-methyl-3-(morpholin-4-ylmethyl)-7-oxo-6,7-dihydro-1H-pyrrolo[2,3-c]pyridin-4-yl]phenyl}ethanesulfonamide;

N-[4-(2,4-difluorophenoxy)-3-{6-methyl-3-[(4-methylpiperazin-1-yl)methyl]-7-oxo-6,7-dihydro-1H-pyrrolo[2,3-c]pyridin-4-yl}phenyl]ethanesulfonamide;

4-{2-[(cyclopropylmethyl)amino]phenyl}-6-methyl-1,6-dihydro-7H-pyrrolo[2,3-c]pyridin-7-one;

4'-(cyclopropylmethoxy)-3'-(6-methyl-7-oxo-6,7-dihydro-1H-pyrrolo[2,3-c]pyridin-4-yl)biphenyl-3-carbonitrile; and 4-{2-(cyclopropylmethoxy)-5-[(4-hydroxypiperidin-1-yl)sulfonyl]phenyl}-6-methyl-1,6-dihydro-7H-pyrrolo[2,3-c]pyridin-7-one.

30. The compound of claim 28 or a pharmaceutically acceptable salt thereof, wherein
$R^y$ is methyl.

31. The compound of claim 30 or a pharmaceutically acceptable salt thereof, wherein
$L^1$ is $CH_2$, $C(O)$, $(CH_2)_mO$, or $(CH_2)_mN(R^z)$.

32. The compound of claim 30 or a pharmaceutically acceptable salt thereof, wherein
$L^1$ is $(CH_2)_mO$.

33. The compound of claim 32 or a pharmaceutically acceptable salt thereof, wherein
$G^1$ is $G^{1a}$.

34. The compound of claim 33 or a pharmaceutically acceptable salt thereof, wherein
$G^{1a}$ is optionally substituted aryl.

35. The compound of claim 33 or a pharmaceutically acceptable salt thereof, wherein
$G^{1a}$ is optionally substituted phenyl.

36. The compound of claim 33 or a pharmaceutically acceptable salt thereof, wherein
$G^{1a}$ is optionally substituted cycloalkyl.

37. The compound of claim 33 or a pharmaceutically acceptable salt thereof, wherein
$G^{1a}$ is optionally substituted monocyclic cycloalkyl.

38. The compound of claim 33 or a pharmaceutically acceptable salt thereof, wherein
$G^{1a}$ is optionally substituted heterocycle.

39. The compound of claim 33 or a pharmaceutically acceptable salt thereof, wherein
$G^{1a}$ is optionally substituted monocyclic heterocycle.

40. The compound of claim 1 or a pharmaceutically acceptable salt thereof, wherein
$Y^1$ is $CR^u$;
$X^1$ is N;
$X^2$ is $CR^{x2}$; and
$R^y$ is methyl.

41. The compound of claim 40 or a pharmaceutically acceptable salt thereof, wherein the compound is selected from the group consisting of
N-[4-(2,4-difluorophenoxy)-3-(6-methyl-7-oxo-6,7-dihydro-1H-pyrazolo[3,4-c]pyridin-4-yl)phenyl]ethanesulfonamide;
4-{2-(2,4-difluorophenoxy)-5-[(methylsulfonyl)methyl]phenyl}-6-methyl-1,6-dihydro-7H-pyrazolo[3,4-c]pyridin-7-one;
4-[2-(2,4-difluorophenoxy)-5-(ethylsulfonyl)phenyl]-6-methyl-1,6-dihydro-7H-pyrazolo[3,4-c]pyridin-7-one; and
4-[2-(cyclopropylmethoxy)-5-(ethylsulfonyl)phenyl]-6-methyl-1,6-dihydro-7H-pyrazolo[3,4-c]pyridin-7-one;
or a pharmaceutically acceptable salt thereof.

42. The compound of claim 28, or a pharmaceutically acceptable salt thereof, wherein
$A^1$ is $CR^1$, $A^2$ is $CR^2$, $A^3$ is $CR^3$, and $A^4$ is $CR^4$; or one of $A^1$, $A^2$, $A^3$, and $A^4$ is N.

43. The compound of claim 42 or a pharmaceutically acceptable salt thereof,
wherein $R^2$ is hydrogen, $C_1$-$C_6$ alkyl, $NO_2$, $G^{2a}$, —S(O)$_2$R$^{2d}$, —S(O)$_2$NR$^{2b}$R$^{2c}$, —C(O)R$^{2d}$, —C(O)OR$^{2a}$, —C(O)NR$^{2b}$R$^{2c}$, —NR$^{2b}$R$^{2c}$, —N(R$^{2e}$)C(O)R$^{2d}$, —N(R$^{2e}$)S(O)$_2$R$^{2d}$, —N(R$^{2e}$)S(O)$_2$NR$^{2b}$R$^{2c}$, —(C$_1$-C$_6$ alkylenyl)-G$^{2a}$, —(C$_1$-C$_6$ alkylenyl)-OR$^{2a}$, —(C$_1$-C$_6$ alkylenyl)-S(O)$_2$R$^{2d}$, —(C$_1$-C$_6$ alkylenyl)-S(O)$_2$NR$^{2b}$R$^{2c}$, —(C$_1$-C$_6$ alkylenyl)-C(O)R$^{2d}$, —(C$_1$-C$_6$ alkylenyl)-C(O)OR$^{2a}$, —(C$_1$-C$_6$ alkylenyl)-C(O)NR$^{2b}$R$^{2c}$, —(C$_1$-C$_6$ alkylenyl)-NR$^{2b}$R$^{2c}$, —(C$_1$-C$_6$ alkylenyl)-N(R$^{2e}$)C(O)R$^{2d}$, —(C$_1$-C$_6$ alkylenyl)-N(R$^{2e}$)S(O)$_2$R$^{2d}$, or —(C$_1$-C$_6$ alkylenyl)-N(R$^{2e}$)S(O)$_2$NR$^{2b}$R$^{2c}$.

44. The compound of claim 42 or a pharmaceutically acceptable salt thereof,
wherein $R^2$ is —S(O)$_2$R$^{2d}$, —S(O)$_2$NR$^{2b}$R$^{2c}$, —N(R$^{2e}$)S(O)$_2$R$^{2d}$ or —N(R$^{2e}$)S(O)$_2$NR$^{2b}$R$^{2c}$.

45. The compound of claim 44 or a pharmaceutically acceptable salt thereof,
wherein
$R^x$ is hydrogen or methyl.

46. The compound of claim 44 or a pharmaceutically acceptable salt thereof,
wherein
$R^x$ is hydrogen.

47. The compound of claim 46 or a pharmaceutically acceptable salt thereof, wherein
$R^{x1}$ is hydrogen, —C(O)OR$^{ax1}$, —C(O)NR$^{bx1}$R$^{cx1}$, G$^{x1}$, or $C_1$-$C_6$ alkyl wherein the $C_1$-$C_6$ alkyl is optionally substituted with OR$^{ax1}$.

48. The compound of claim 46 or a pharmaceutically acceptable salt thereof,
wherein $R^{x1}$ is hydrogen, —C(O)OR$^{ax1}$, or —C(O)NR$^{bx1}$R$^{cx1}$.

49. The compound of claim 48 or a pharmaceutically acceptable salt thereof,
wherein $R^{x2}$ is hydrogen.

50. The compound of claim 1 or a pharmaceutically acceptable salt thereof,
wherein
$R^x$ is hydrogen;
$R^y$ is methyl;
$Y^1$ is $CR^u$ wherein $R^u$ is hydrogen;
$X^1$ is $CR^{x1}$ wherein $R^{x1}$ is hydrogen or —C(O)NR$^{bx1}$R$^{cx1}$;
$X^2$ is $CR^{x2}$ wherein $R^{x2}$ is hydrogen;
$L^1$ is (CH$_2$)$_m$O wherein m is 0;
$G^1$ is $G^{1a}$ or —(C$_1$-C$_6$ alkylenyl)-G$^{1a}$, wherein $G^{1a}$ is optionally substituted phenyl or optionally substituted cycloalkyl; and
$R^2$ is —S(O)$_2$R$^{2d}$, —S(O)$_2$NR$^{2b}$R$^{2c}$, —N(R$^{2e}$)S(O)$_2$R$^{2c}$, or —(C$_1$-C$_6$ alkylenyl)-S(O)$_2$R$^{2d}$.

51. The compound of claim 50 or a pharmaceutically acceptable salt thereof, wherein
$A^1$ is $CR^1$, $A^2$ is $CR^2$, $A^3$ is $CR^3$, and $A^4$ is $CR^4$.

52. The compound of claim 50 or a pharmaceutically acceptable salt thereof,
wherein
$A^1$ is $CR^1$, $A^2$ is $CR^2$, $A^3$ is $CR^3$, and $A^4$ is N.

53. The compound of claim 1 or a pharmaceutically acceptable salt thereof,
wherein
$R^x$ is hydrogen;
$R^y$ is methyl;
$Y^1$ is $CR^u$ wherein $R^u$ is hydrogen;
$X^1$ is $CR^{x1}$ wherein $R^{x1}$ is hydrogen;
$X^2$ is $CR^{x2}$ wherein $R^{x2}$ is hydrogen;
$L^1$ is (CH$_2$)$_m$N(R$^z$) wherein m is 0 and $R^z$ is hydrogen;
$G^1$ is —(C$_1$-C$_6$ alkylenyl)-G$^{1a}$, wherein $G^{1a}$ is optionally substituted cycloalkyl; and
$R^2$ is —S(O)$_2$R$^{2d}$, —S(O)$_2$NR$^{2b}$R$^{2c}$, —N(R$^{2e}$)S(O)$_2$R$^{2d}$, or —(C$_1$-C$_6$ alkylenyl)-S(O)$_2$R$^{2d}$.

54. The compound of claim 53 or a pharmaceutically acceptable salt thereof, wherein
$A^1$ is $CR^1$, $A^2$ is $CR^2$, $A^3$ is $CR^3$, and $A^4$ is $CR^4$.

55. A pharmaceutical composition comprising a therapeutically effective amount of a compound of formula (I) according to claim 1, or a pharmaceutically acceptable salt thereof, in combination with a pharmaceutically acceptable carrier.

56. The compound of claim 1, which is N-[3-(6-methyl-7-oxo-6,7-dihydro-1H-pyrrolo[2,3-c]pyridin-4-yl)-4-phenoxyphenyl]methanesulfonamide, or a pharmaceutically acceptable salt thereof.

57. The compound of claim 1, which is N-[4-(2,4-difluorophenoxy)-3-(6-methyl-7-oxo-6,7-dihydro-1H-pyrrolo[2,3-c]pyridin-4-yl)phenyl]methanesulfonamide, or a pharmaceutically acceptable salt thereof.

58. The compound of claim 1, which is N-[4-(2,4-difluorophenoxy)-3-(6-methyl-7-oxo-6,7-dihydro-1H-pyrrolo[2,3-c]pyridin-4-yl)phenyl]ethanesulfonamide, or a pharmaceutically acceptable salt thereof.

59. The compound of claim 1, which is 4-(2,4-difluorophenoxy)-3-(6-methyl-7-oxo-6,7-dihydro-1H-pyrrolo[2,3-c]pyridin-4-yl)benzenesulfonamide, or a pharmaceutically acceptable salt thereof.

60. The compound of claim 1, which is 4-[2-(cyclopropylmethoxy)-5-(methylsulfonyl)phenyl]-6-methyl-1,6-dihydro-7H-pyrrolo[2,3-c]pyridin-7-one, or a pharmaceutically acceptable salt thereof.

61. The compound of claim 1, which is 4-{2-[(cyclopropylmethyl)amino]-5-(ethylsulfonyl)phenyl}-6-methyl-1,6-dihydro-7H-pyrrolo[2,3-c]pyridin-7-one, or a pharmaceutically acceptable salt thereof.

* * * * *